US010454043B2

(12) United States Patent
Kim et al.

(10) Patent No.: US 10,454,043 B2
(45) Date of Patent: Oct. 22, 2019

(54) HETEROCYCLIC COMPOUND AND ORGANIC LIGHT-EMITTING ELEMENT USING SAME

(71) Applicant: HEESUNG MATERIAL LTD., Yongin, Gyeonggi-do (KR)

(72) Inventors: Mi-Jin Kim, Ulsan (KR); Kee-Yong Kim, Suwon (KR); Yang-Soo Ha, Osan (KR); Jin-Seok Choi, Suwon (KR); Dae-Hyuk Choi, Yongin (KR); Sung-Jin Eum, Yongin (KR); Joo-Dong Lee, Seongnam (KR)

(73) Assignee: HEESUNG MATERIAL LTD., Yongin (KR)

( * ) Notice: Subject to any disclaimer, the term of this patent is extended or adjusted under 35 U.S.C. 154(b) by 98 days.

(21) Appl. No.: 15/522,927

(22) PCT Filed: Oct. 30, 2015

(86) PCT No.: PCT/KR2015/011552
§ 371 (c)(1),
(2) Date: Apr. 28, 2017

(87) PCT Pub. No.: WO2016/068640
PCT Pub. Date: May 6, 2016

(65) Prior Publication Data
US 2017/0324046 A1 Nov. 9, 2017

(30) Foreign Application Priority Data
Oct. 31, 2014 (KR) ................. 10-2014-0150750

(51) Int. Cl.
| | | |
|---|---|---|
| *H01L 51/54* | (2006.01) | |
| *C09K 11/06* | (2006.01) | |
| *H01L 51/00* | (2006.01) | |
| *C07D 471/04* | (2006.01) | |
| *H01L 51/50* | (2006.01) | |
| *C07D 471/14* | (2006.01) | |
| *C07D 519/00* | (2006.01) | |
| *C07F 9/6561* | (2006.01) | |

(52) U.S. Cl.
CPC ........ *H01L 51/0072* (2013.01); *C07D 471/04* (2013.01); *C07D 471/14* (2013.01); *C07D 519/00* (2013.01); *C07F 9/6561* (2013.01); *C09K 11/06* (2013.01); *H01L 51/0052* (2013.01); *H01L 51/0054* (2013.01); *H01L 51/0058* (2013.01); *H01L 51/0061* (2013.01); *H01L 51/0067* (2013.01); *H01L 51/0073* (2013.01); *H01L 51/0074* (2013.01); *H01L 51/50* (2013.01); *H01L 51/5072* (2013.01)

(58) Field of Classification Search
CPC ... C07F 9/6561; C07D 417/00; C07D 417/02; C07D 417/04; C07D 417/10; C07D 417/12; C07D 417/14; C07D 519/00; H01L 51/0032; H01L 51/005; H01L 51/0058; H01L 51/0061; H01L 51/0067; H01L 51/0072; H01L 51/0073; H01L 51/0074; H01L 51/50; H01L 51/5012; H01L 51/5016; H01L 50/56; H01L 51/5072; C09K 11/06; C09K 2211/00; C09K 2211/10; C09K 2211/1018; C09K 2211/1022; C09K 2211/1029; C09K 2211/1044; C09K 2211/1059
USPC ....... 428/690, 691, 411.4, 336, 917; 427/58, 427/66; 313/500–512; 257/40, 88–104, 257/E51.001–E51.052; 252/301.16–301.35
See application file for complete search history.

(56) References Cited

U.S. PATENT DOCUMENTS

| | | | |
|---|---|---|---|
| 4,356,429 A | 10/1982 | Tang | |
| 9,331,290 B2 | 5/2016 | Stoessel et al. | |
| 9,382,253 B2 | 7/2016 | Stoessel et al. | |
| 2013/0112920 A1 | 5/2013 | Stoessel et al. | |
| 2014/0138659 A1 | 5/2014 | Shin et al. | |
| 2015/0263297 A1 | 9/2015 | Stoessel et al. | |
| 2016/0365520 A1 | 12/2016 | Stoessel et al. | |

FOREIGN PATENT DOCUMENTS

| | | |
|---|---|---|
| EP | 2 719 741 A2 | 4/2014 |
| KR | 10-2010-0137243 A | 12/2010 |
| KR | 10-1121677 B1 | 2/2012 |
| KR | 10-2013-0095258 A | 8/2013 |
| KR | 10-2013-0095259 A | 8/2013 |
| WO | WO 2014/008982 A1 | 1/2014 |
| WO | WO 2015/104045 A1 | 7/2015 |

OTHER PUBLICATIONS

Sharma et al. J. Comb. Chem. 2007, 9, 783-792. (Year: 2007).*
Chavignon et al. Heterocycles 1995, 41, 2019-2026. (Year: 1995).*
Chavignon et al., "Reactions of (Vinylimino)phosphoranes and Related Compounds: Access to the Azacarbolines and -aplysinopsines", J. Org. Chem., 1994, vol. 59, No. 21, pp. 6413-6418, see Abstract and scheme (Scheme) 3.
International Search Report, issued in PCT/KR2015/011552, dated Jul. 28, 2016.
Kuwabara et al., "Thermally Stable Multilayered Organic Electroluminescent Devices Using Novel Starburst Molecules, 4,4',4"-Tri(N-carbazolyl)triphenylamine (TCTA) and 4,4' ,4" -Tris(3-methylphenylphenylamino)triphenylamine (m-MTDATA), as Hole-Transport Materials", Advanced Materials, 1994, vol. 6, No. 9, pp. 677-679.
Maleki et al., "Synthesis of pyrido[2',1':2,3]imidazo[4,5-c]isoquinolines via a one-pot, three-component reaction", Tetrahedron Letters, Mar. 5, 2014, vol. 55, No. 10, pp. 1848-1850, see Abstract and Table 1.

(Continued)

*Primary Examiner* — Andrew K Bohaty
(74) *Attorney, Agent, or Firm* — Birch, Stewart, Kolasch & Birch, LLP

(57) ABSTRACT

The present specification relates to a novel hetero-cyclic compound and an organic light emitting device using the same.

6 Claims, 16 Drawing Sheets

(56) References Cited

OTHER PUBLICATIONS

Pandey et al., "Synthesis of biologically active pyridoimidazole/imidazobenzothiazole annulated polyheterocycles using cyanuric chloride in water", RSC Adv., May 29, 2014, vol. 4, pp. 26757-26770, see Abstract and Tables 1, 2.
Boganyi, B., et al, "Syntheses of New Quinoline-Containing Heterocyclic Scaffolds Using Inter- and Intramolecular Pd-Catalyzed Amination," J. Heterocyclic Chem., Jan. 1, 2009, vol. 46, No. 1, pp. 33-38.
European Search Report for Appl. No. 15854996.4 dated Mar. 9, 2018.
Fan, X.S., et al, "One-pot Sequential Reactions Featuring a Copper-catalyzed Amination Leading to Pyrido[2',1':2,3,]imidazo[4,5-c]quinolines and Dihydropyrido[2',1':2,3]imidazo[4,5-c]quinolines," Chemistry—An Asian Journal, Jun. 5, 2015, vol. 10, No. 6, pp. 1281-1285.

\* cited by examiner

[Figure 1]
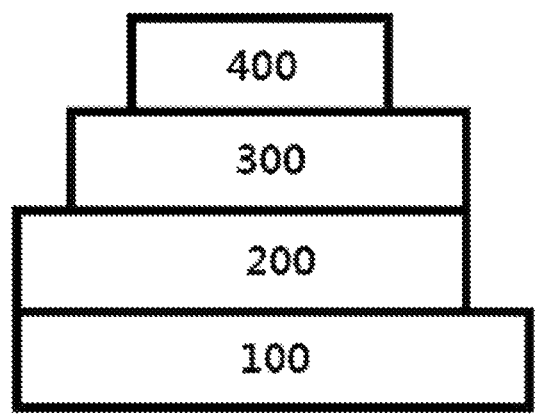
[Figure 2]
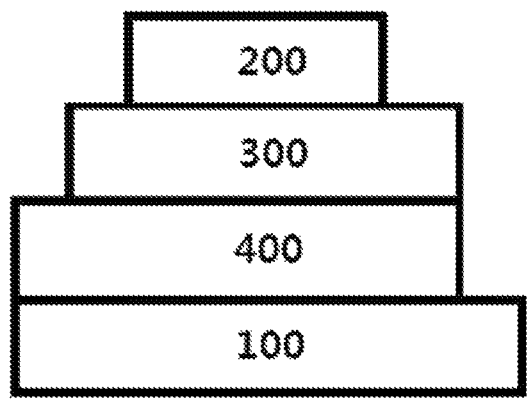

[Figure 3]
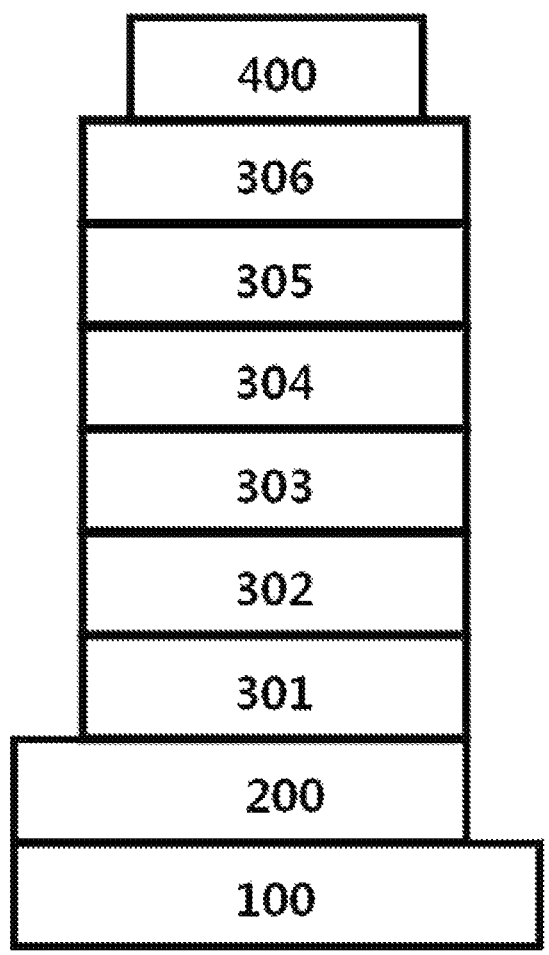

[Figure 4]
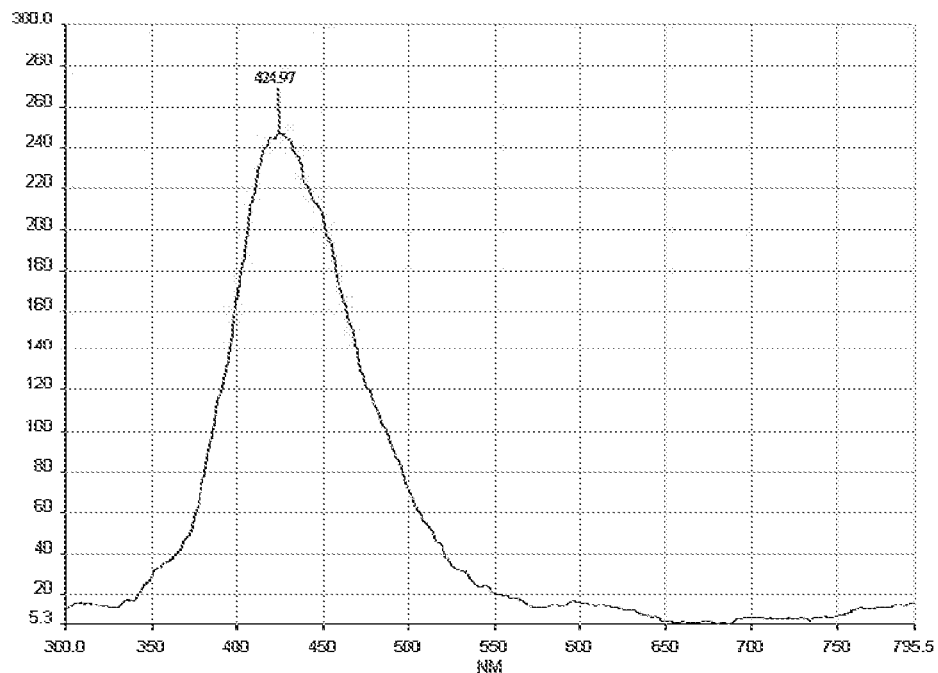
[Figure 5]
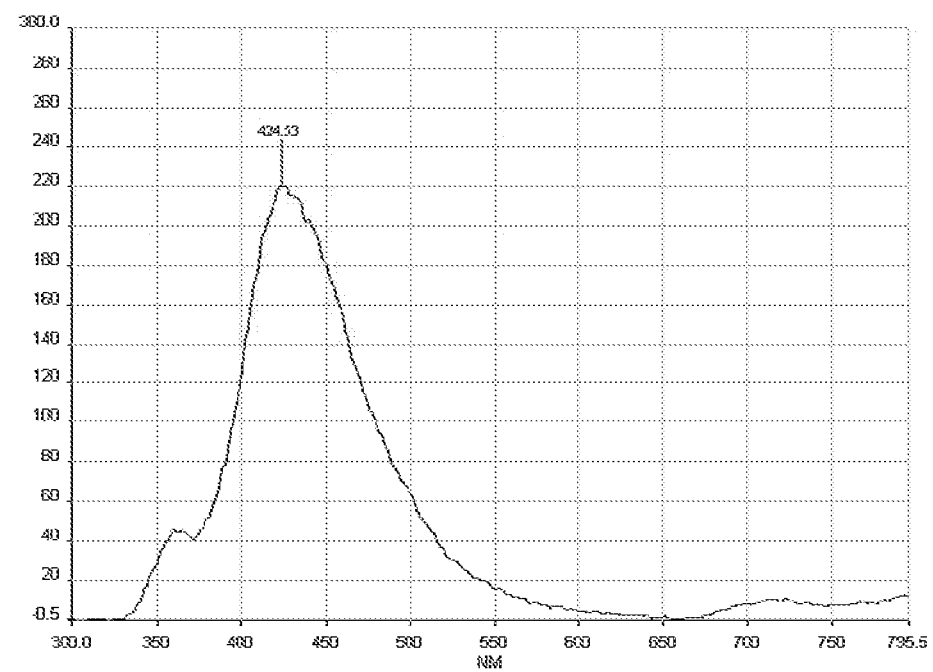

[Figure 6]
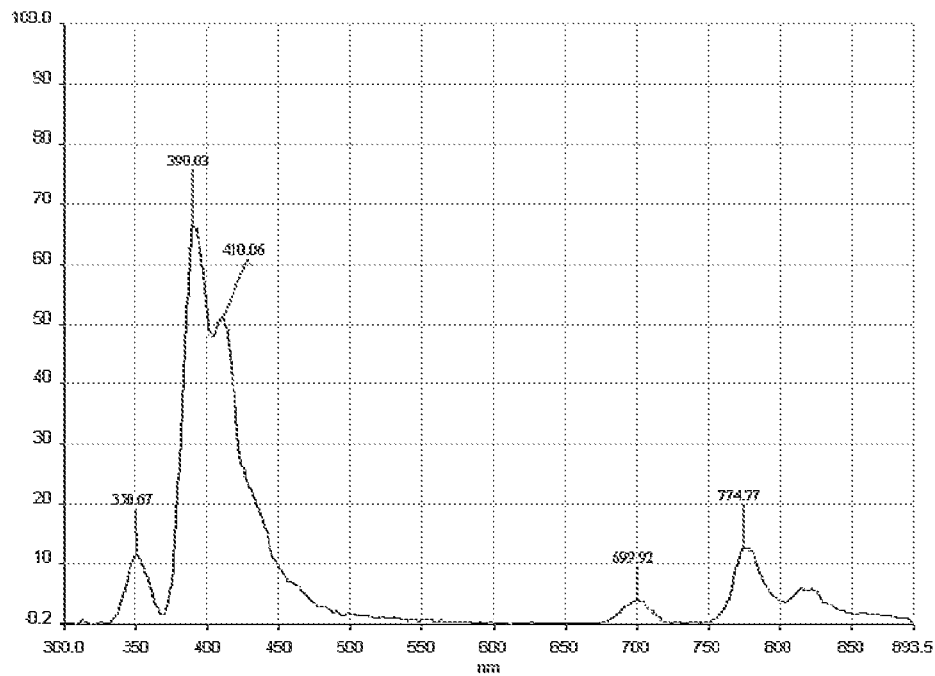
[Figure 7]
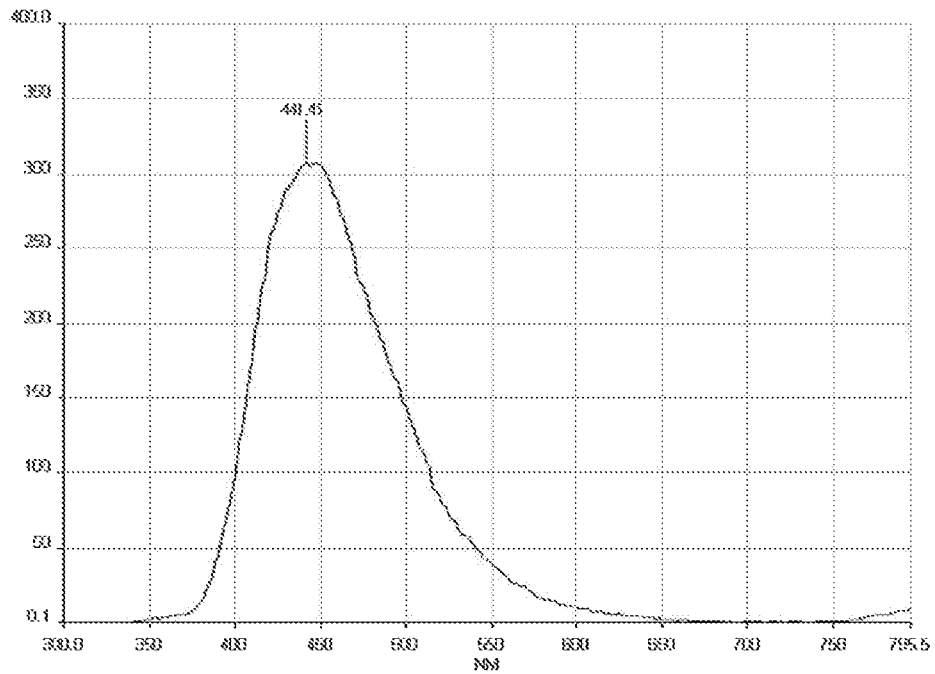

[Figure 8]
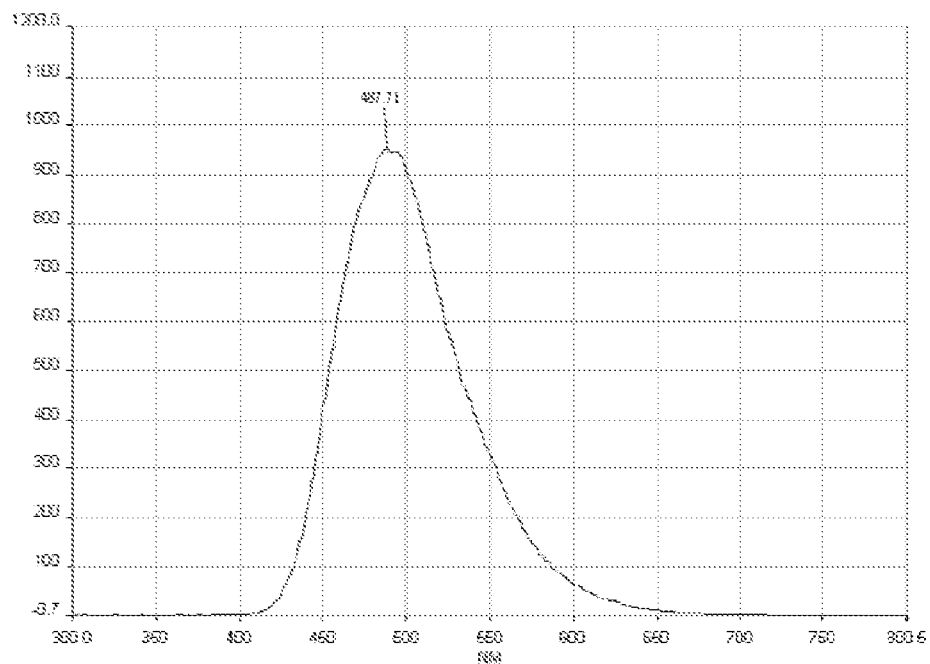
[Figure 9]
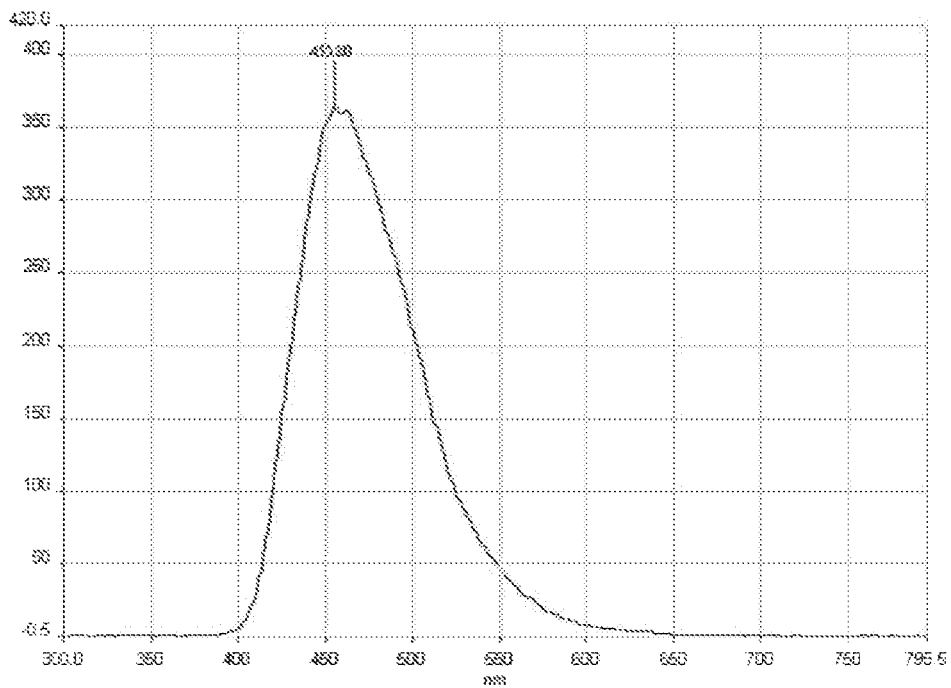

[Figure 10]
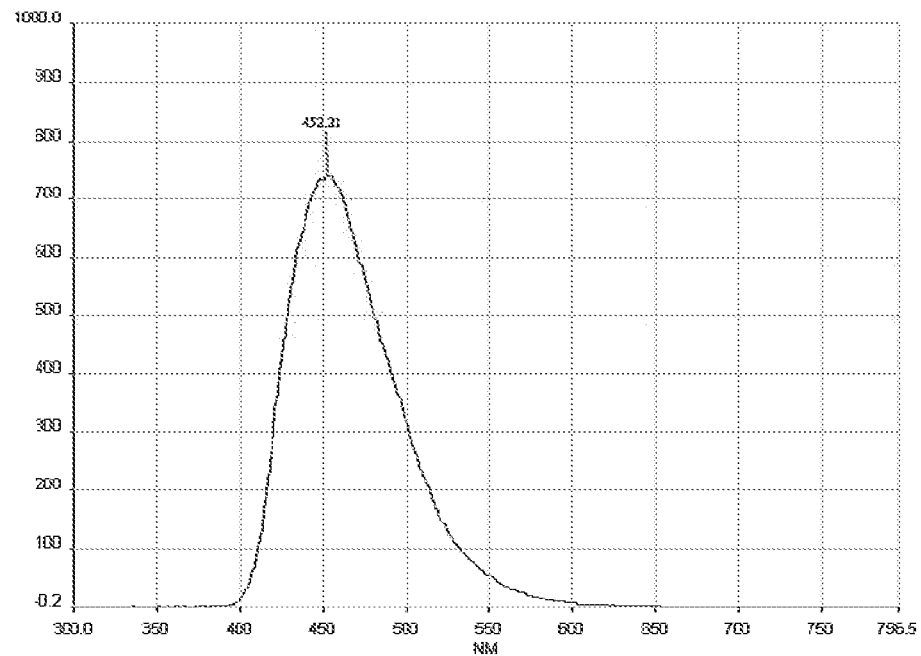
[Figure 11]
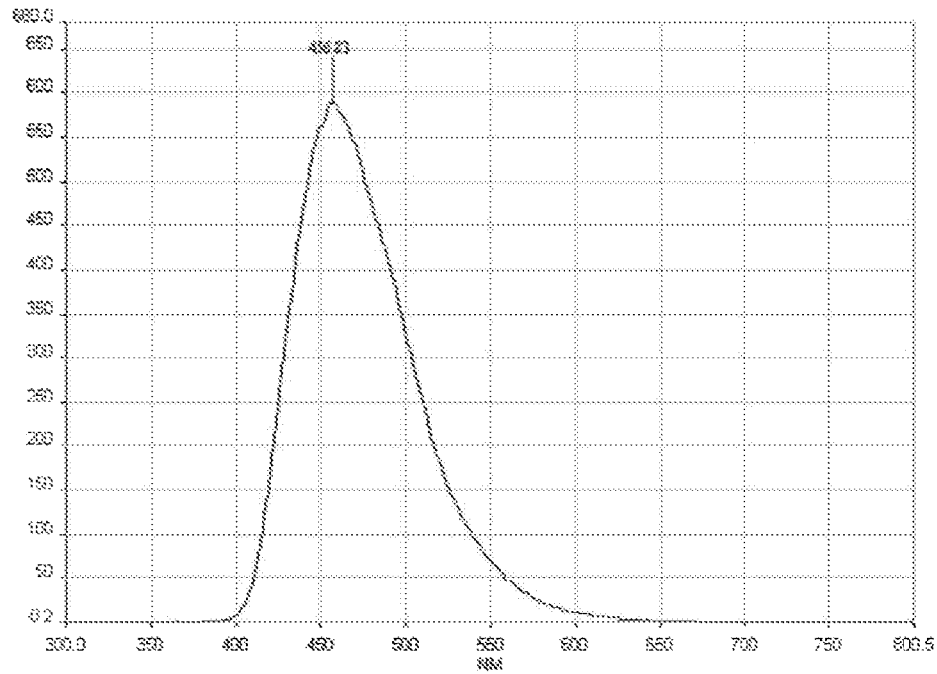

[Figure 12]
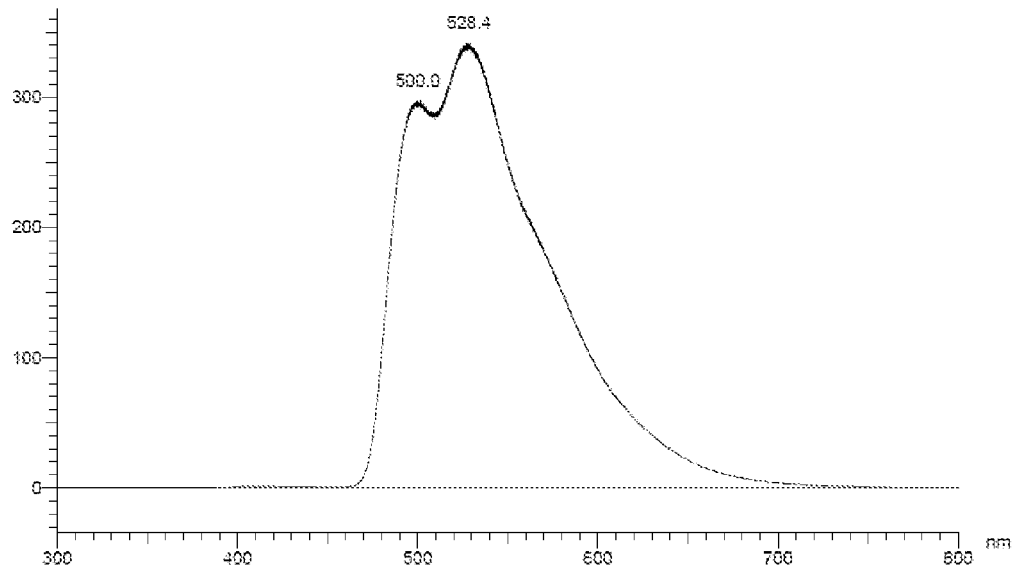
[Figure 13]
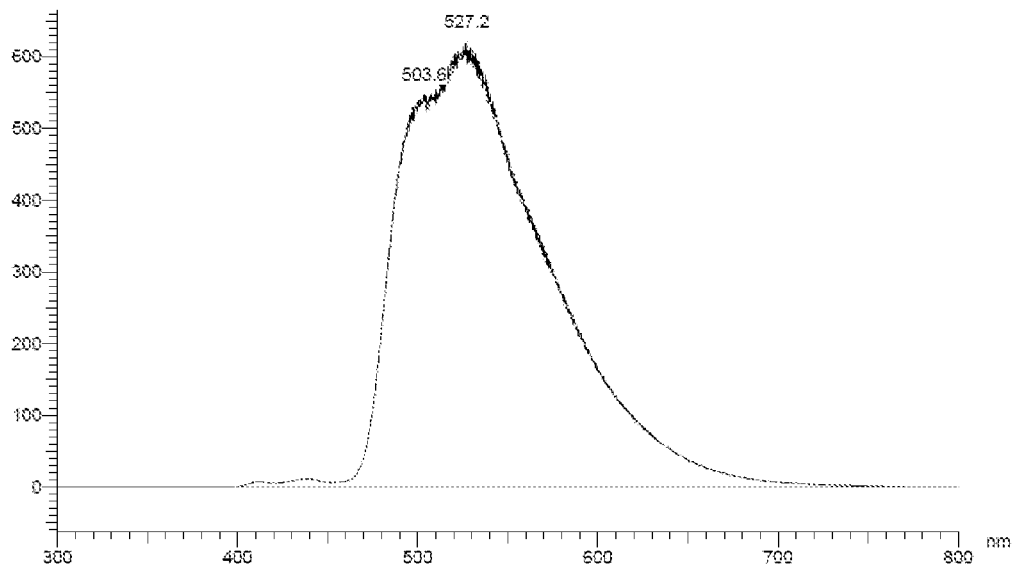

[Figure 14]
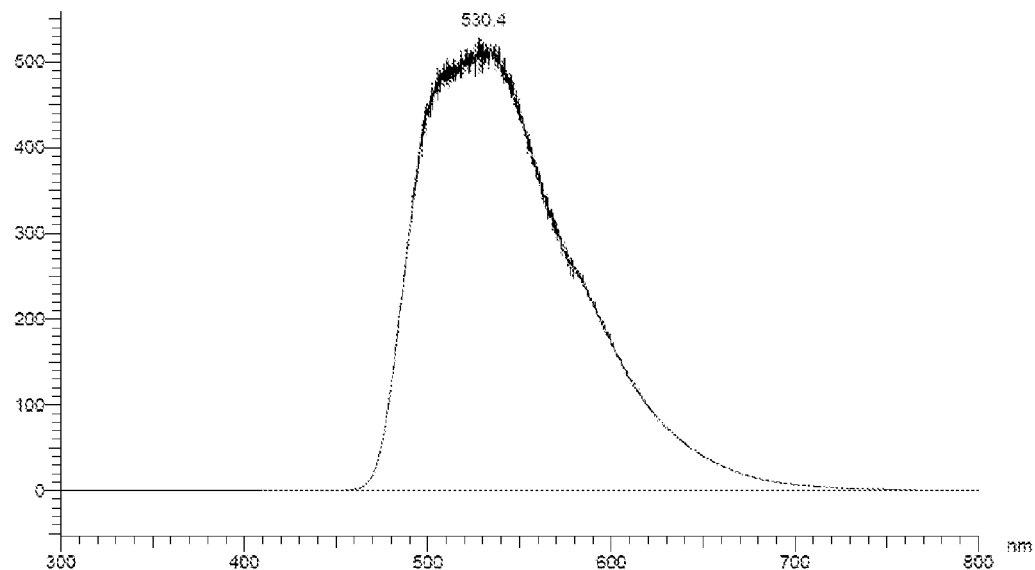
[Figure 15]
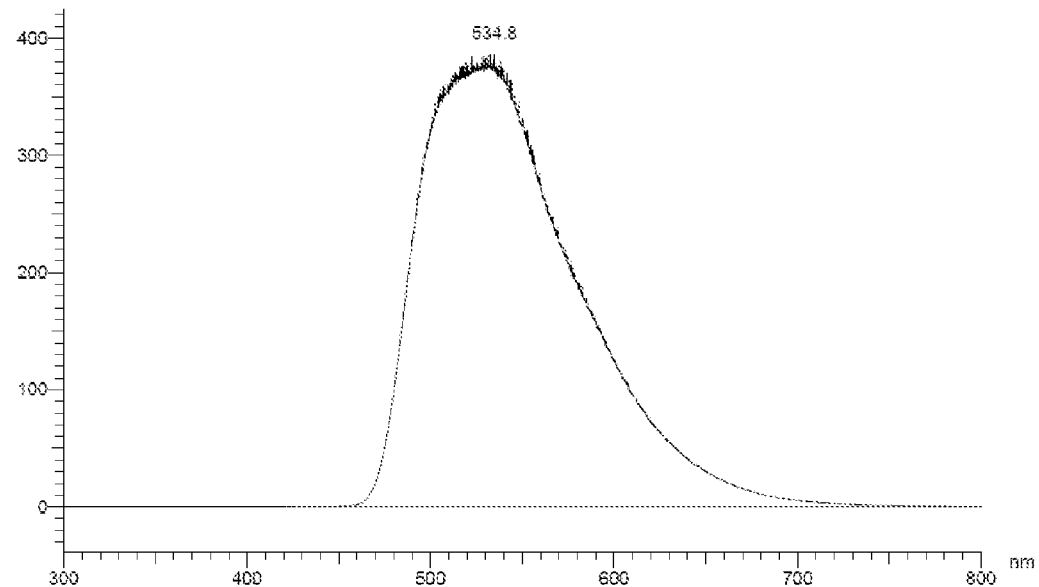

[Figure 16]
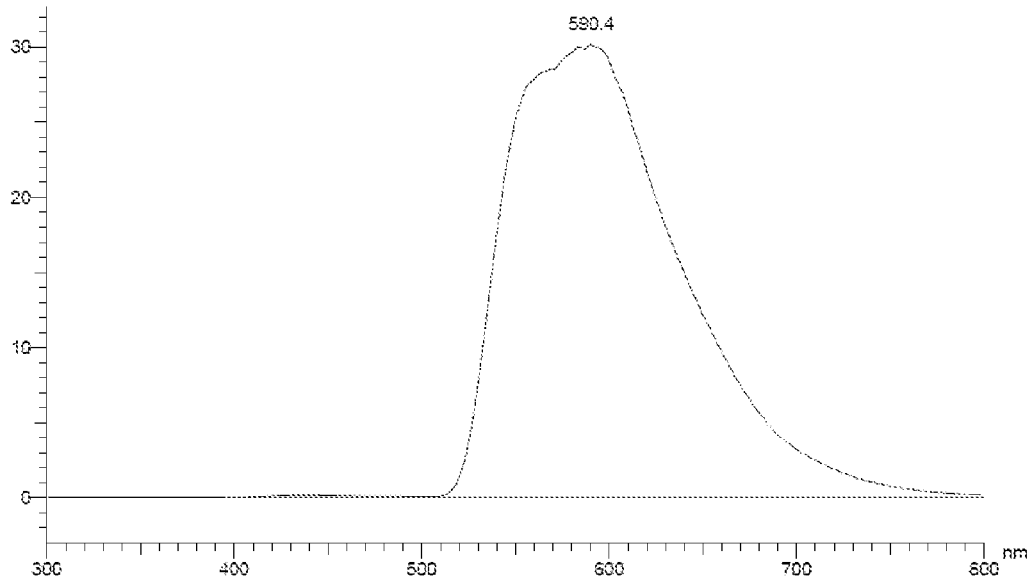
[Figure 17]
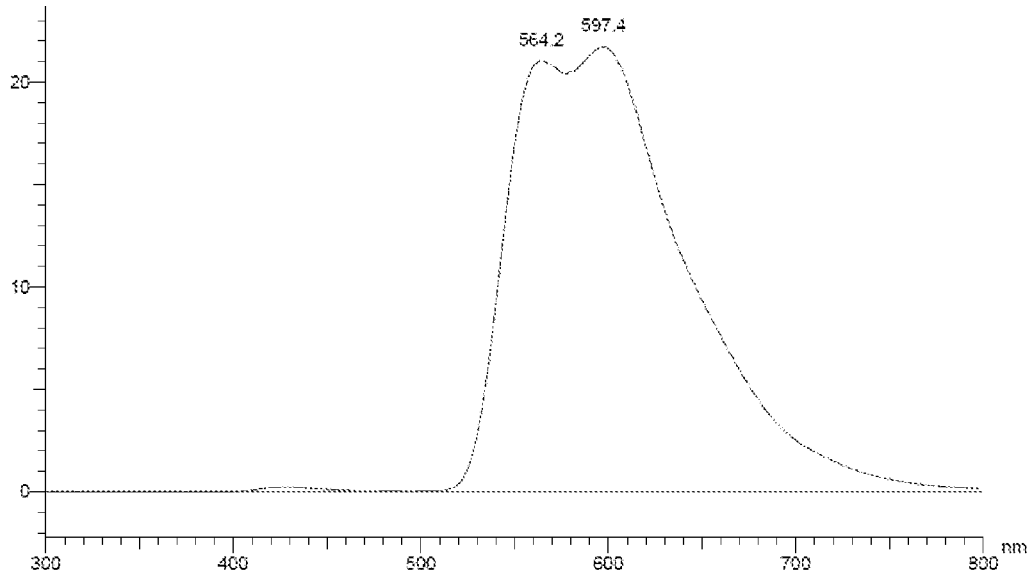

[Figure 18]
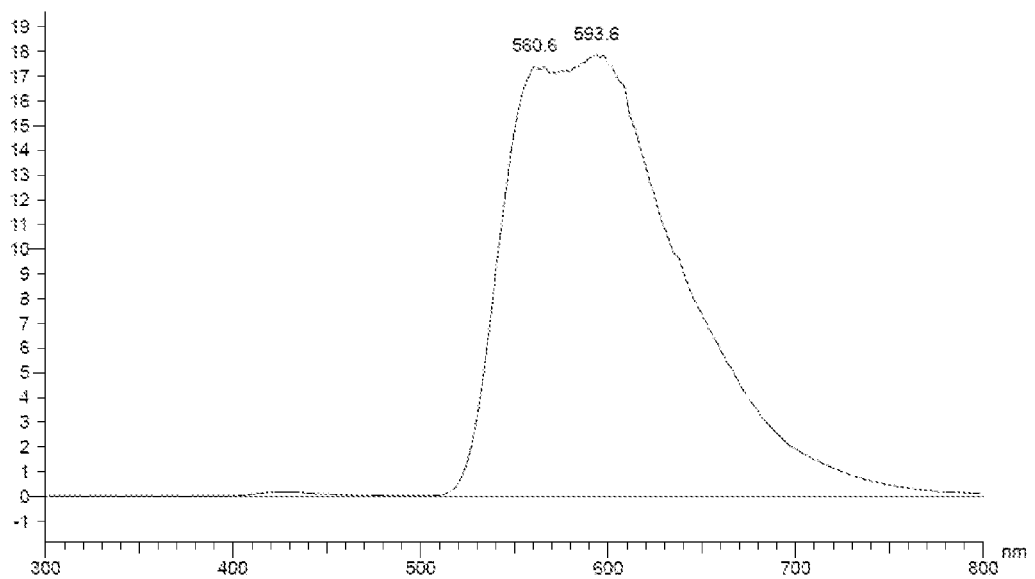
[Figure 19]
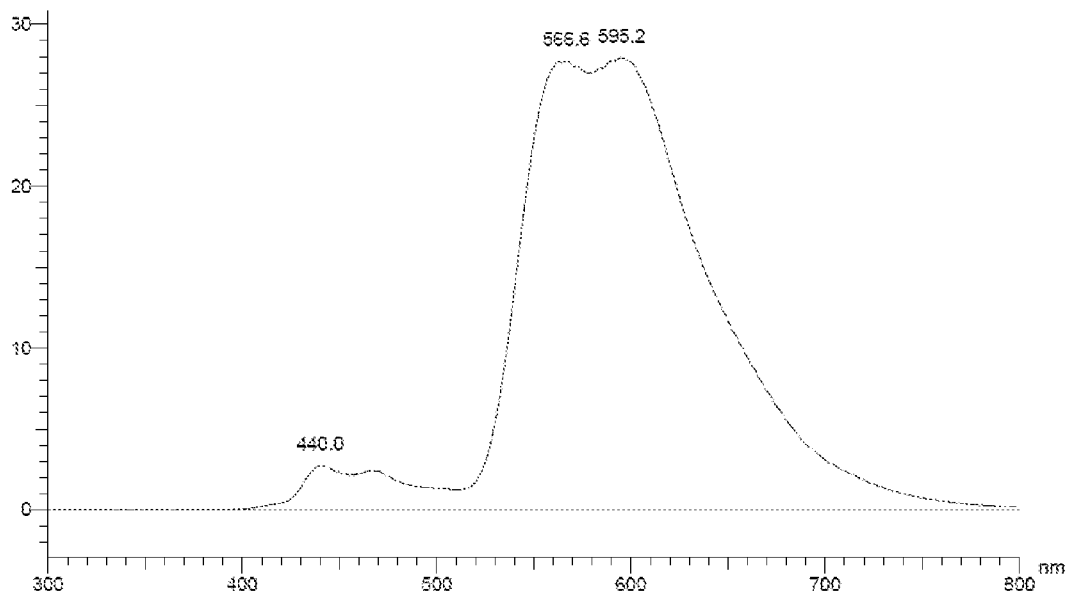

[Figure 20]
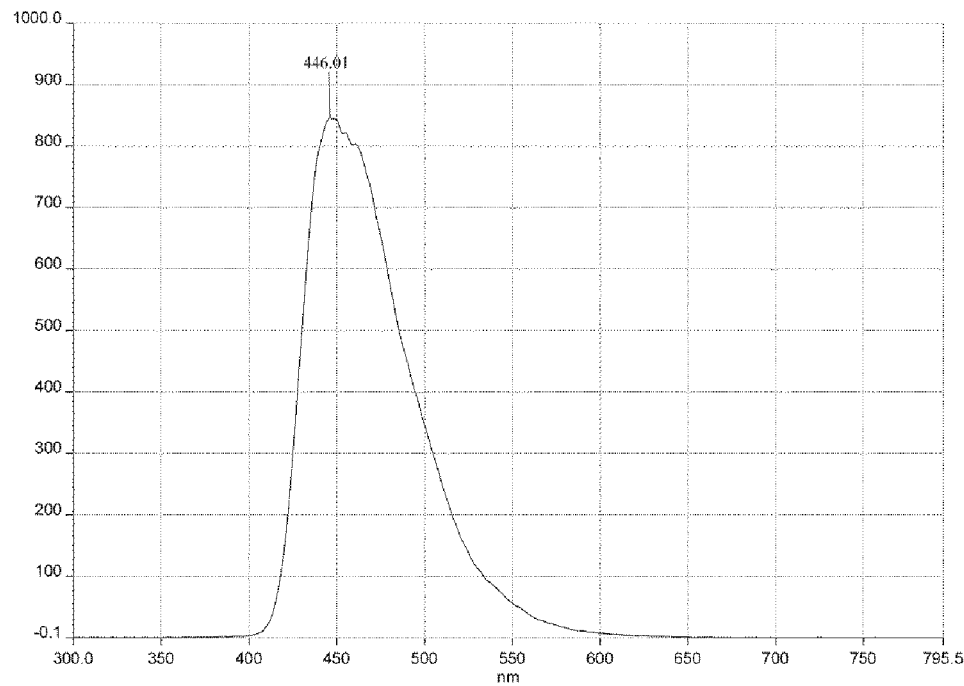
[Figure 21]
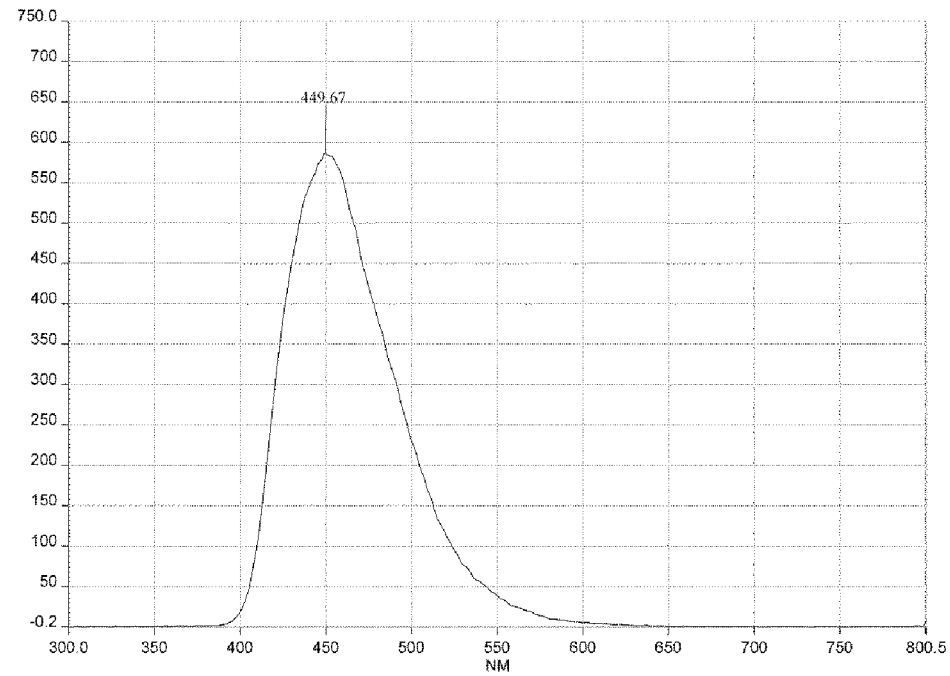

[Figure 22]
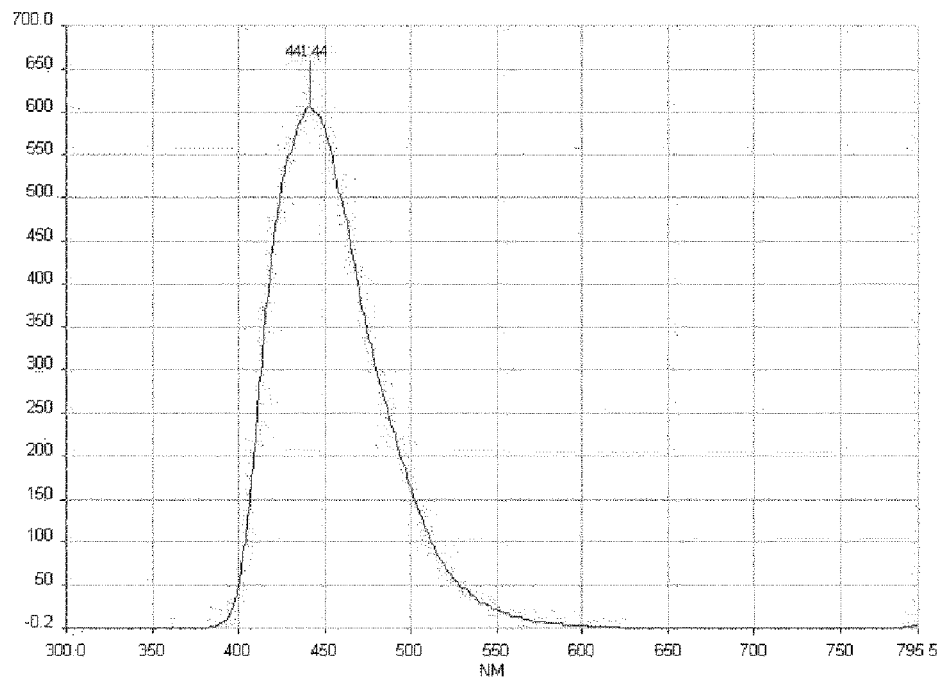
[Figure 23]
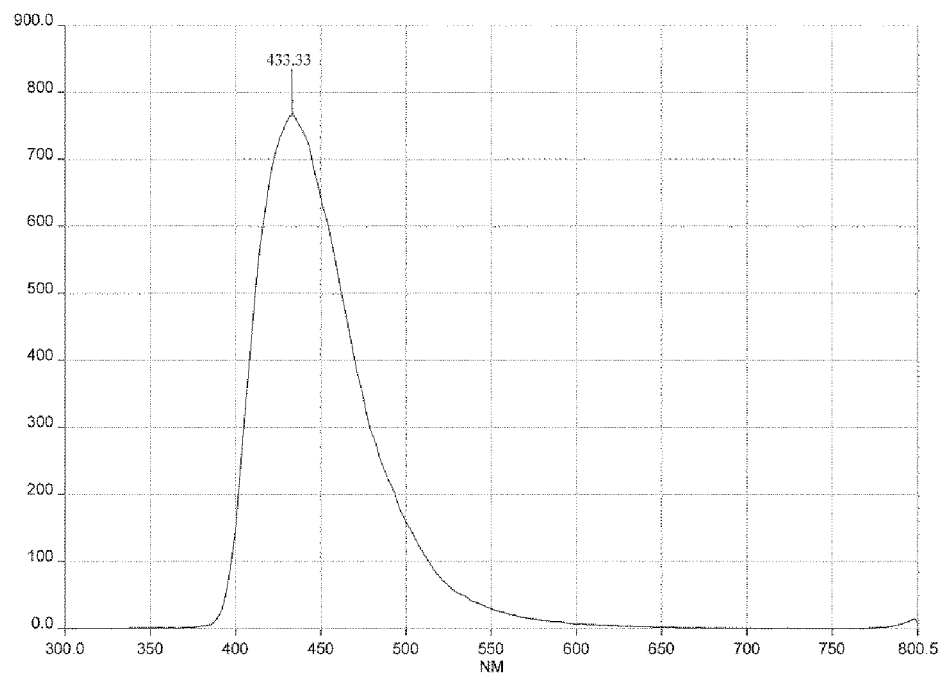

[Figure 24]
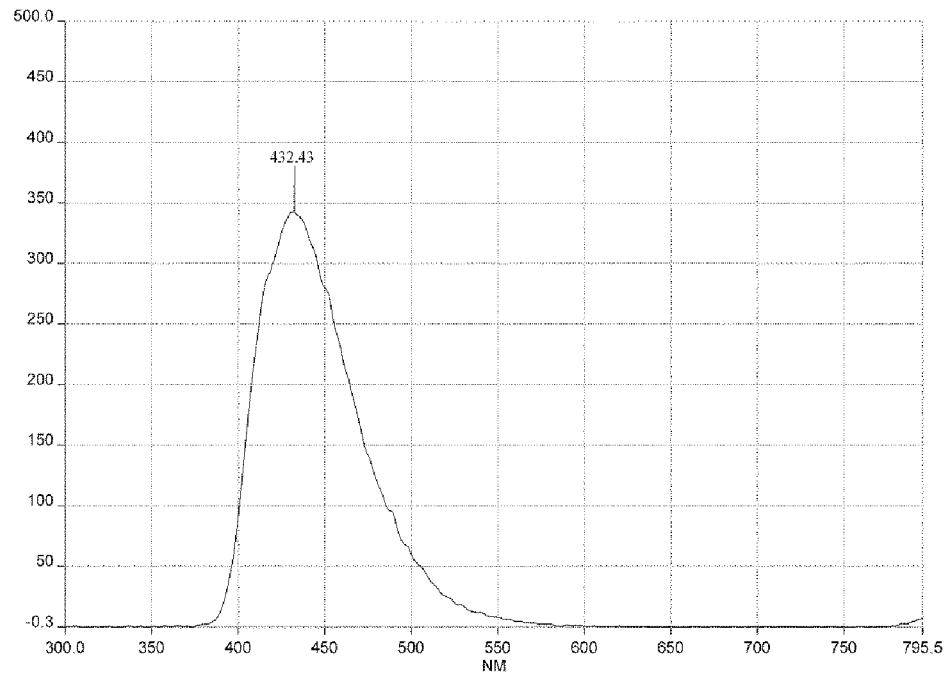
[Figure 25]
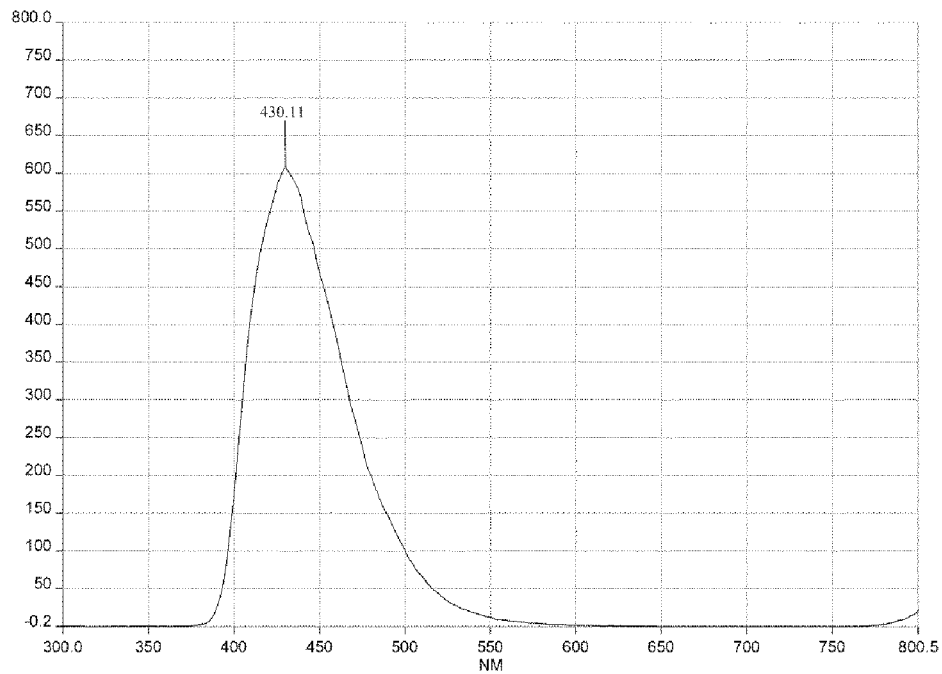

[Figure 26]
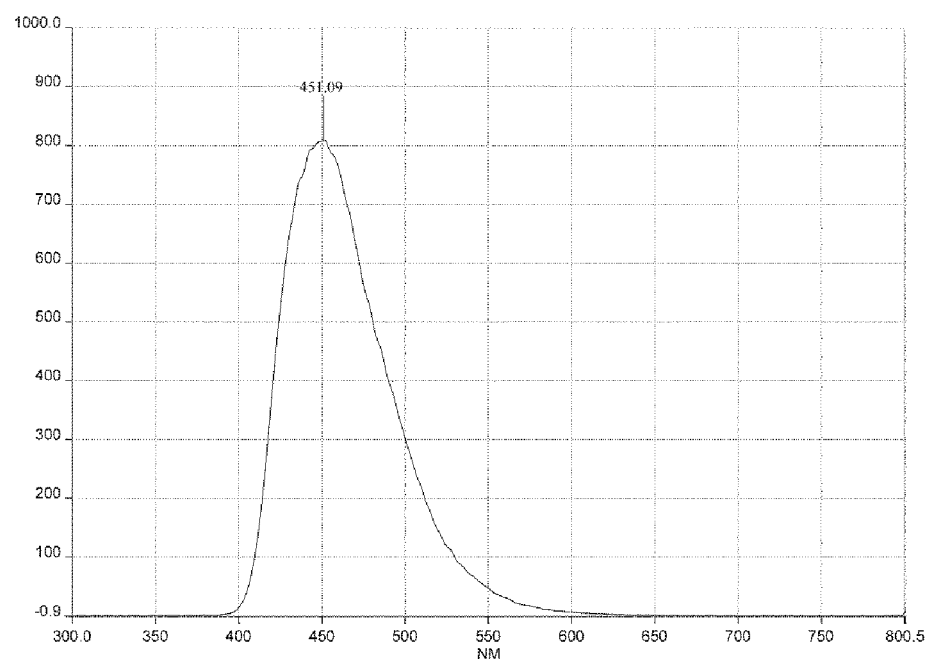
[Figure 27]
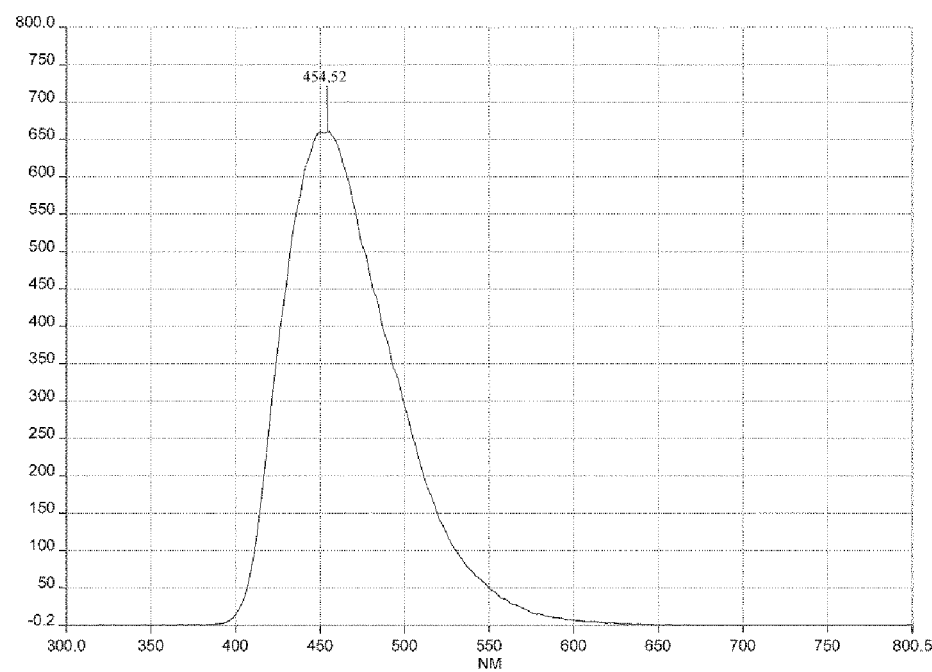

[Figure 28]
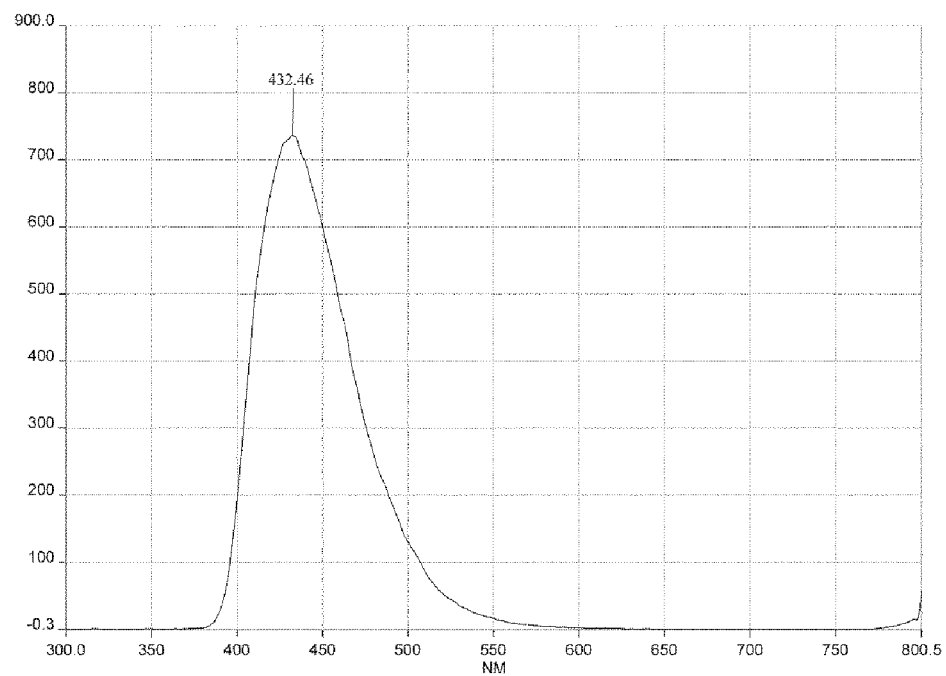
[Figure 29]
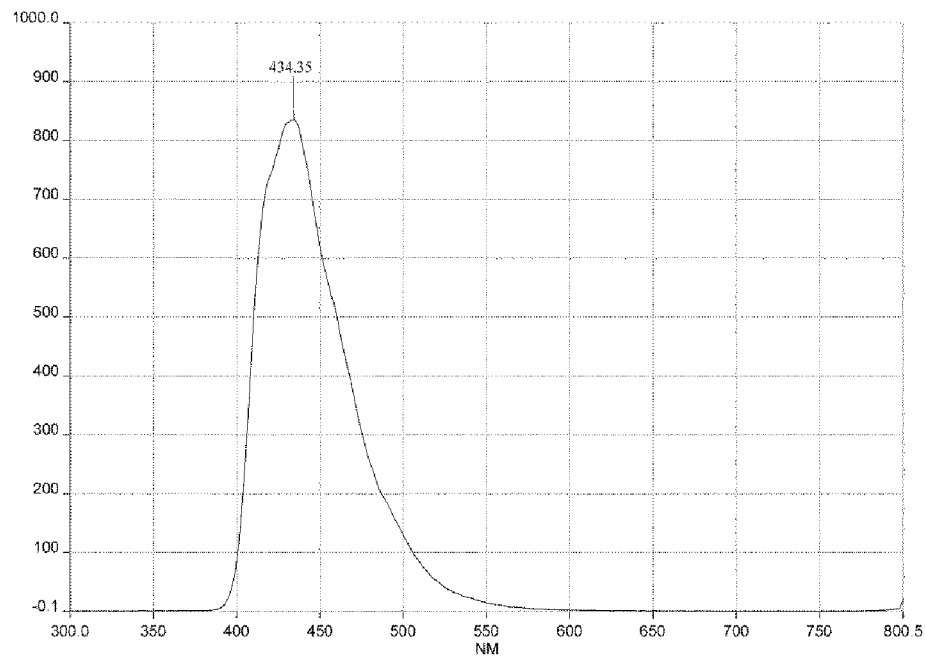

[Figure 30]
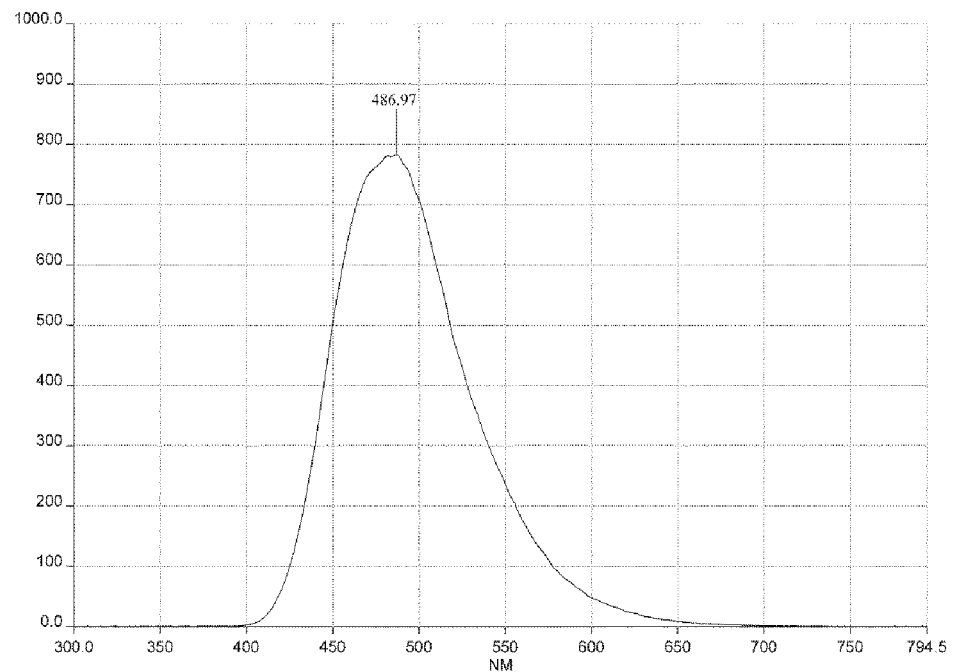

HETEROCYCLIC COMPOUND AND ORGANIC LIGHT-EMITTING ELEMENT USING SAME

TECHNICAL FIELD

This application claims priority to and the benefit of Korean Patent Application No. 10-2014-0150750 filed in the Korean Intellectual Property Office on Oct. 31, 2014, the entire contents of which are incorporated herein by reference.

The present specification relates to a hetero-cyclic compound and an organic light emitting device using the same.

BACKGROUND ART

An organic light emitting device is a kind of self-emitting type display device, and has an advantage in that the viewing angle is wide, the contrast is excellent, and the response speed is fast.

An organic light emitting device has a structure in which an organic thin film is disposed between two electrodes. When a voltage is applied to an organic light emitting device having the structure, electrons and holes injected from the two electrodes combine with each other in an organic thin film to make a pair, and then, emit light while being extinguished. The organic thin film may be composed of a single layer or multi layers, if necessary.

A material for the organic thin film may have a light emitting function, if necessary. For example, as the material for the organic thin film, it is also possible to use a compound, which may itself constitute a light emitting layer alone, or it is also possible to use a compound, which may serve as a host or a dopant of a host-dopant-based light emitting layer. In addition, as a material for the organic thin film, it is also possible to use a compound, which may serve as hole injection, hole transport, electron blocking, hole blocking, electron transport or electron injection.

In order to improve the performance, service life, or efficiency of the organic light emitting device, there is a continuous need for developing a material for an organic thin film.

DETAILED DESCRIPTION OF THE INVENTION

Technical Problem

The present specification provides a novel hetero-cyclic compound and an organic light emitting device using the same.

Technical Solution

According to an exemplary embodiment of the present application, provided is a hetero-cyclic compound represented by the following Chemical Formula 1.

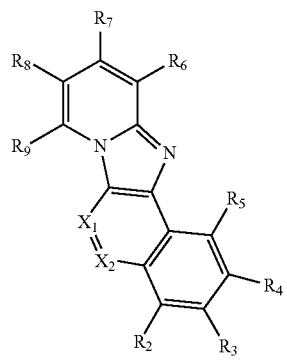

[Chemical Formula 1]

In Chemical Formula 1, $X_1$ and $X_2$ are the same as or different from each other, and are each independently N or $CR_1$, $R_1$ to $R_9$ are the same as or different from each other, and are each independently selected from the group consisting of hydrogen; deuterium; halogen; $-SiR_{10}R_{11}R_{12}$; $-P(=O)R_{13}R_{14}$; a substituted or unsubstituted $C_1$ to $C_{60}$ alkyl; a substituted or unsubstituted $C_6$ to $C_{60}$ aryl; a substituted or unsubstituted $C_2$ to $C_{60}$ heteroaryl; and an amine which is unsubstituted or substituted with one or more substituents selected from a substituted or unsubstituted $C_1$ to $C_{60}$ alkyl, a substituted or unsubstituted $C_6$ to $C_{60}$ aryl, and a substituted or unsubstituted $C_2$ to $C_{60}$ heteroaryl, and $R_{10}$ to $R_{14}$ are the same as or different from each other, and are each independently hydrogen; deuterium; a substituted or unsubstituted $C_1$ to $C_{60}$ alkyl; a substituted or unsubstituted $C_6$ to $C_{60}$ aryl; or a substituted or unsubstituted $C_2$ to $C_{60}$ heteroaryl.

Further, according to an exemplary embodiment of the present specification, provided is an organic light emitting device including a positive electrode, a negative electrode, and one or more organic material layers provided between the positive electrode and the negative electrode, in which one or more layers of the organic material layers include the above-described hetero-cyclic compound.

Advantageous Effects

The compound described in the present specification may be used as a material for the organic material layer of the organic light emitting device. The organic material layer including the compound may serve as a hole injection layer, a hole transporting layer, a light emitting layer, an electron transporting material, an electron injection layer, and the like in the organic light emitting device.

In particular, the hetero-cyclic compound represented by Chemical Formula 1 may be used as a material for the electron transporting layer of the organic light emitting device.

BRIEF DESCRIPTION OF DRAWINGS

FIGS. 1 to 3 exemplify the stacking sequence of electrodes and organic material layers of an organic light emitting device according to exemplary embodiments of the present application.

FIG. 4 illustrates a measurement graph of PL of Compound 6 at a wavelength of 254 nm.

FIG. 5 illustrates a measurement graph of PL of Compound 19 at a wavelength of 240 nm.

FIG. 6 illustrates a measurement graph of PL of Compound 109 at a wavelength of 349 nm.
FIG. 7 illustrates a measurement graph of PL of Compound 111 at a wavelength of 255 nm.
FIG. 8 illustrates a measurement graph of PL of Compound 373 at a wavelength of 272 nm.
FIG. 9 illustrates a measurement graph of PL of Compound 478 at a wavelength of 257 nm.
FIG. 10 illustrates a measurement graph of PL of Compound 601 at a wavelength of 255 nm.
FIG. 11 illustrates a measurement graph of PL of Compound 642 at a wavelength of 257 nm.
FIG. 12 illustrates a measurement graph of LTPL of Compound 6 at a wavelength of 279 nm.
FIG. 13 illustrates a measurement graph of LTPL of Compound 19 at a wavelength of 338 nm.
FIG. 14 illustrates a measurement graph of LTPL of Compound 109 at a wavelength of 349 nm.
FIG. 15 illustrates a measurement graph of LTPL of Compound 111 at a wavelength of 323 nm.
FIG. 16 illustrates a measurement graph of LTPL of Compound 373 at a wavelength of 385 nm.
FIG. 17 illustrates a measurement graph of LTPL of Compound 478 at a wavelength of 374 nm.
FIG. 18 illustrates a measurement graph of LTPL of Compound 601 at a wavelength of 375 nm.
FIG. 19 illustrates a measurement graph of LTPL of Compound 642 at a wavelength of 376 nm.
FIG. 20 illustrates a measurement graph of PL of Compound 353 at a wavelength of 275 nm.
FIG. 21 illustrates a measurement graph of PL of Compound 365 at a wavelength of 257 nm.
FIG. 22 illustrates a measurement graph of PL of Compound 367 at a wavelength of 253 nm.
FIG. 23 illustrates a measurement graph of PL of Compound 370 at a wavelength of 252 nm.
FIG. 24 illustrates a measurement graph of PL of Compound 372 at a wavelength of 241 nm.
FIG. 25 illustrates a measurement graph of PL of Compound 574 at a wavelength of 279 nm.
FIG. 26 illustrates a measurement graph of PL of Compound 577 at a wavelength of 254 nm.
FIG. 27 illustrates a measurement graph of PL of Compound 711 at a wavelength of 256 nm.
FIG. 28 illustrates a measurement graph of PL of Compound 719 at a wavelength of 260 nm.
FIG. 29 illustrates a measurement graph of PL of Compound 722 at a wavelength of 320 nm.
FIG. 30 illustrates a measurement graph of PL of Compound 724 at a wavelength of 314 nm.

EXPLANATION OF REFERENCE NUMERALS AND SYMBOLS

100 Substrate
200 Positive electrode
300 Organic material layer
301 Hole injection layer
302 Hole transporting layer
303 Light emitting layer
304 Hole blocking layer
305 Electron transporting layer
306 Electron injection layer
400 Negative electrode

BEST MODE

Hereinafter, the present specification will be described in detail.

The hetero-cyclic compound described in the present specification may be represented by Chemical Formula 1.

Specifically, the hetero-cyclic compound represented by Formula 1 may be used as a material for an organic material layer of an organic light emitting device by the structural characteristics of the core structure and the substituent as described above.

In the present specification, "substituted or unsubstituted" means being unsubstituted or substituted with one or more substituents selected from the group consisting of deuterium; halogen; —CN; a $C_1$ to $C_{60}$ alkyl; a $C_2$ to $C_{60}$ alkenyl; a $C_2$ to $C_{60}$ alkynyl; a $C_3$ to $C_{60}$ cycloalkyl; a $C_2$ to $C_{60}$ heterocycloalkyl; a $C_6$ to $C_{60}$ aryl; a $C_2$ to $C_{60}$ heteroaryl; —SiRR'R"; —P(=O)RR'; a $C_1$ to $C_{20}$ alkylamine; a $C_6$ to $C_{60}$ arylamine; and a $C_2$ to $C_{60}$ heteroarylamine, being unsubstituted or substituted with a substituent to which two or more substituents among the substituents are linked, or being unsubstituted or substituted with a substituent to which two or more substituents selected among the exemplified substituents are linked. For example, "the substituent to which two or more substituents are linked" may be a biphenyl group.

That is, the biphenyl group may also be an aryl group, and may be interpreted as a substituent to which two phenyl groups are linked. The additional substituents may also be additionally substituted.

R, R', and R" are the same as or different from each other, and are each independently hydrogen; deuterium; a substituted or unsubstituted $C_1$ to $C_{60}$ alkyl; a substituted or unsubstituted $C_6$ to $C_{60}$ aryl; or a substituted or unsubstituted $C_2$ to $C_{60}$ heteroaryl.

According to an exemplary embodiment of the present specification, the "substituted or unsubstituted" means being unsubstituted or substituted with one or more substituents selected from the group consisting of deuterium, halogen, —SiRR'R", —P(=O)RR', a $C_1$ to $C_{60}$ alkyl, a $C_6$ to $C_{60}$ aryl, and $C_2$ to $C_{60}$ heteroaryl.

R, R', and R" are the same as or different from each other, and are each independently hydrogen; deuterium; a $C_1$ to $C_{60}$ alkyl which is unsubstituted or substituted with one or more substituents selected from the group consisting of deuterium, halogen, a $C_1$ to $C_{60}$ alkyl, a $C_6$ to $C_{60}$ aryl, and a $C_2$ to $C_{60}$ heteroaryl; a $C_6$ to $C_{60}$ aryl which is unsubstituted or substituted with one or more substituents selected from the group consisting of deuterium, halogen, a $C_1$ to $C_{60}$ alkyl, a $C_6$ to $C_{60}$ aryl, and a $C_2$ to $C_{60}$ heteroaryl; or a $C_2$ to $C_{60}$ heteroaryl which is unsubstituted or substituted with one or more substituents selected from the group consisting of deuterium, halogen, a $C_1$ to $C_{60}$ alkyl, a $C_6$ to $C_{60}$ aryl, and a $C_2$ to $C_{60}$ heteroaryl.

In the present specification, the halogen may be fluorine, chlorine, bromine or iodine.

In the present specification, the alkyl includes a straight-chain or branched chain having 1 to 60 carbon atoms, and may be additionally substituted with another substituent. The number of carbon atoms of the alkyl may be 1 to 60, specifically 1 to 40, and more specifically 1 to 20.

In the present specification, the alkenyl includes a straight-chain or branched chain having 2 to 60 carbon atoms, and may be additionally substituted with another substituent. The number of carbon atoms of the alkenyl may be 2 to 60, specifically 2 to 40, and more specifically 2 to 20.

In the present specification, the alkynyl includes a straight-chain or branched chain having 2 to 60 carbon atoms, and may be additionally substituted with another substituent. The number of carbon atoms of the alkynyl may be 2 to 60, specifically 2 to 40, and more specifically 2 to 20.

In the present specification, the cycloalkyl includes a monocycle or polycycle having 3 to 60 carbon atoms, and may be additionally substituted with another substituent.

Here, the polycycle means a group in which cycloalkyl is directly linked to or fused with another cyclic group.

Here, another cyclic group may also be cycloalkyl, but may also be another kind of cyclic group, for example, heterocycloalkyl, aryl, heteroaryl, and the like. The number of carbon atoms of the cycloalkyl may be 3 to 60, specifically 3 to 40, and more specifically 5 to 20.

In the present specification, the heterocycloalkyl includes O, S, Se, N, and Si as a heteroatom, includes a monocycle or polycycle having 2 to 60 carbon atoms, and may be additionally substituted with another substituent. Here, the polycycle means a group in which heterocycloalkyl is directly linked to or fused with another cyclic group.

Here, another cyclic group may also be heterocycloalkyl, but may also be another kind of cyclic group, for example, cycloalkyl, aryl, heteroaryl, and the like. The number of carbon atoms of the heterocycloalkyl may be 2 to 60, specifically 2 to 40, and more specifically 3 to 20.

In the present specification, the aryl includes a monocycle or polycycle having 6 to 60 carbon atoms, and may be additionally substituted with another substituent. Here, the polycycle means a group in which aryl is directly linked to or fused with another cyclic group. Here, another cyclic group may also be aryl, but may also be another kind of cyclic group, for example, cycloalkyl, heterocycloalkyl, heteroaryl, and the like. The aryl includes a spiro group. The number of carbon atoms of the aryl may be 6 to 60, specifically 6 to 40, and more specifically 6 to 25. Specific examples of the aryl include phenyl, biphenyl, triphenyl, naphthyl, terphenyl, anthryl, chrysenyl, phenanthrenyl, perylenyl, fluoranthenyl, triphenylenyl, phenalenyl, pyrenyl, tetracenyl, pentacenyl, fluorenyl, indenyl, acenaphthylenyl, benzofluorenyl, spirobifluorenyl, 2,3-dihydro-1H-indenyl, and the like, or fused rings thereof, but are not limited thereto.

In the present specification, the spiro group is a group including a spiro structure, and may have 15 to 60 carbon atoms. For example, the spiro group may include a structure in which a 2,3-dihydro-1H-indene group or a cyclohexane group is spiro-bonded to a fluorene group.

Specifically, the spiro group includes a group of the following structural formulae.

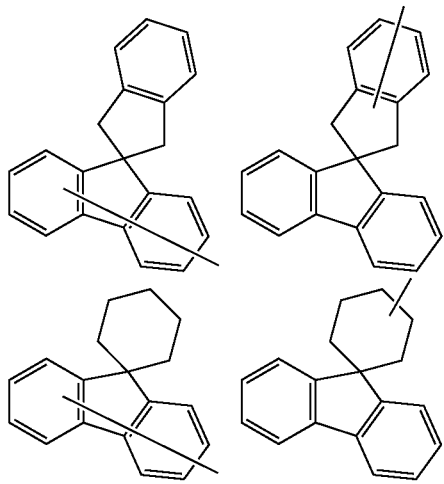

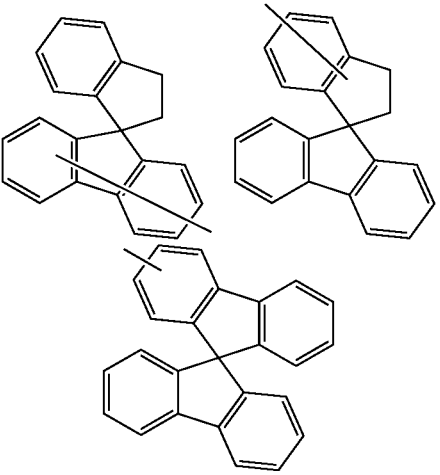

-continued

In the present specification, the heteroaryl includes S, O, Se, N, or Si as a heteroatom, includes a monocycle or a polycycle having 2 to 60 carbon atoms, and may be additionally substituted with another substituent. Here, the polycycle means a group in which heteroaryl is directly linked to or fused with another cyclic group. Here, another cyclic group may also be heteroaryl, but may also be another kind of cyclic group, for example, cycloalkyl, heterocycloalkyl, aryl, and the like. The number of carbon atoms of the heteroaryl may be 2 to 60, specifically 2 to 40, and more specifically 3 to 25. Specific examples of the heteroaryl include pyridyl, pyrrolyl, pyrimidyl, pyridazinyl, furanyl, a thiophene group, imidazolyl, pyrazolyl, oxazolyl, isoxazolyl, thiazolyl, isothiazolyl, triazolyl, furazanyl, oxadiazolyl, thiadiazolyl, dithiazolyl, tetrazolyl, pyranyl, thiopyranyl, diazinyl, oxazinyl, thiazinyl, dioxynyl, triazinyl, tetrazinyl, quinolyl, isoquinolyl, quinazolinyl, isoquinazolinyl, quinozolinyl, naphthyridyl, acridinyl, phenanthridinyl, imidazopyridyl, diazanaphthalenyl, triazaindene, indolyl, indolyzinyl, benzothiazolyl, benzoxazolyl, benzimidazolyl, a benzothiophene group, a benzofuran group, a dibenzothiophene group, a dibenzofuran group, carbazolyl, benzocarbazolyl, dibenzocarbazolyl, phenazinyl, dibenzosilole, spirobi(dibenzosilole), dihydrophenazinyl, phenoxazinyl, phenanthridyl, thienyl, indolecarbazolyl, indolinyl, phenanthrazinyl, phenothiathiazinyl, phthalazinyl, naphthylidinyl, phenanthrolinyl, benzothiadiazolyl, dibenzoazasilinyl, pyrazoloquinazolinyl, pyridoindazolyl, pyridoimidazoindolinyl, dihydroindenocarbazolyl, a dibenzoselenophene group, and the like, or fused rings thereof, but are not limited thereto.

In the present specification, the amine may be selected from the group consisting of monoalkylamine; monoarylamine; monoheteroarylamine; —NH$_2$; dialkylamine; diarylamine; diheteroarylamine; alkylarylamine; alkylheteroarylamine; and arylheteroarylamine, and the number of carbon atoms thereof is not particularly limited, but is preferably 1 to 30. Specific examples of the amine include methylamine, dimethylamine, ethylamine, diethylamine, phenylamine, naphthylamine, biphenylamine, dibiphenylamine, anthracenylamine, 9-methyl-anthracenylamine, diphenylamine, phenylnaphthylamine, ditolylamine, phenyltolylamine, triphenylamine, biphenylnaphthylamine, phenylbiphenylamine, biphenylfluorenylamine, phenyltriphenylenylamine, biphenyltriphenylenylamine, diphenylcarbazolylamine, and the like, but are not limited thereto.

According to an exemplary embodiment of the present specification, in Chemical Formula 1, at least one of $R_1$ to $R_9$ is -(L)$_m$-(Z)$_n$, L is selected from the group consisting of a direct bond; a substituted or unsubstituted $C_6$ to $C_{60}$ arylene; and a substituted or unsubstituted $C_2$ to $C_{60}$ heteroarylene, m is an integer of 1 to 3, n is an integer of 1 to 3, Z is selected from the group consisting of hydrogen; deuterium; —P(=O)$R_{15}R_{16}$; —Si$R_{17}R_{18}R_{19}$; a substituted or unsubstituted $C_1$ to $C_{60}$ alkyl; a substituted or unsubstituted $C_6$ to $C_{60}$ aryl; a substituted or unsubstituted $C_2$ to $C_{60}$ heteroaryl; and an amine which is unsubstituted or substituted with one or more substituents selected from a substituted or unsubstituted $C_1$ to $C_{60}$ alkyl, a substituted or unsubstituted $C_6$ to $C_{60}$ aryl, and a substituted or unsubstituted $C_2$ to $C_{60}$ heteroaryl, and when m is 2 or more, L's are the same as or different from each other, when n is 2 or more, Z's are the same as or different from each other, and $R_{15}$ to $R_{19}$ are the same as or different from each other, and are each independently hydrogen; deuterium; a substituted or unsubstituted $C_1$ to $C_{60}$ alkyl; a substituted or unsubstituted $C_6$ to $C_{60}$ aryl; or a substituted or unsubstituted $C_2$ to $C_{60}$ heteroaryl.

According to an exemplary embodiment of the present specification, in Chemical Formula 1, at least one of $R_1$ to $R_9$ is -(L)$_m$-(Z)$_n$, L is selected from the group consisting of a direct bond; a $C_6$ to $C_{60}$ arylene which is unsubstituted or substituted with one or more substituents selected from the group consisting of deuterium, halogen, —SiRR'R", —P(=O)RR', a $C_1$ to $C_{60}$ alkyl, a $C_6$ to $C_{60}$ aryl, and a $C_2$ to $C_{60}$ heteroaryl; and a $C_2$ to $C_{60}$ heteroarylene which is unsubstituted or substituted with one or more substituents selected from the group consisting of deuterium, halogen, —SiRR'R", —P(=O)RR', a $C_1$ to $C_{60}$ alkyl, a $C_6$ to $C_{60}$ aryl, and a $C_2$ to $C_{60}$ heteroaryl, m is an integer of 1 to 3, n is an integer of 1 to 3, Z is selected from the group consisting of hydrogen; deuterium; —P(=O) $R_{15}R_{16}$; —Si$R_{17}R_{18}R_{19}$; a $C_1$ to $C_{60}$ alkyl which is unsubstituted or substituted with one or more substituents selected from the group consisting of deuterium, halogen, —SiRR'R", —P(=O)RR', a $C_1$ to $C_{60}$ alkyl, a $C_6$ to $C_{60}$ aryl, and a $C_2$ to $C_{60}$ heteroaryl; a $C_6$ to $C_{60}$ aryl which is unsubstituted or substituted with one or more substituents selected from the group consisting of deuterium, halogen, —SiRR'R", —P(=O)RR', a $C_1$ to $C_{60}$ alkyl, a $C_6$ to $C_{60}$ aryl, and a $C_2$ to $C_{60}$ heteroaryl; a $C_2$ to $C_{60}$ heteroaryl which is unsubstituted or substituted with one or more substituents selected from the group consisting of deuterium, halogen, —SiRR'R", —P(=O)RR', a $C_1$ to $C_{60}$ alkyl, a $C_6$ to $C_{60}$ aryl, and a $C_2$ to $C_{60}$ heteroaryl; and an amine which is unsubstituted or substituted with one or more substituents selected from a substituted or unsubstituted $C_1$ to $C_{60}$ alkyl, a substituted or unsubstituted $C_6$ to $C_{60}$ aryl, and a substituted or unsubstituted $C_2$ to $C_{60}$ heteroaryl, when m is 2 or more, L's are the same as or different from each other, when n is 2 or more, Z's are the same as or different from each other, and R, R', R", and $R_{15}$ to $R_{19}$ are the same as or different from each other, and are each independently hydrogen; deuterium; a $C_1$ to $C_{60}$ alkyl which is unsubstituted or substituted with one or more substituents selected from the group consisting of deuterium, halogen, —SiRR'R", —P(=O)RR', a $C_1$ to $C_{60}$ alkyl, a $C_6$ to $C_{60}$ aryl, and a $C_2$ to $C_{60}$ heteroaryl; a $C_6$ to $C_{60}$ aryl which is unsubstituted or substituted with one or more substituents selected from the group consisting of deuterium, halogen, —SiRR'R", —P(=O)RR', a $C_1$ to $C_{60}$ alkyl, a $C_6$ to $C_{60}$ aryl, and a $C_2$ to $C_{60}$ heteroaryl; or a $C_2$ to $C_{60}$ heteroaryl which is unsubstituted or substituted with one or more substituents selected from the group consisting of deuterium, halogen, —SiRR'R", —P(=O)RR', a $C_1$ to $C_{60}$ alkyl, a $C_6$ to $C_{60}$ aryl, and a $C_2$ to $C_{60}$ heteroaryl.

According to an exemplary embodiment of the present specification, in Chemical Formula 1, $R_1$ is -(L)$_m$-(Z)$_n$, and L, Z, m, and n are the same as those described above.

According to an exemplary embodiment of the present specification, in Chemical Formula 1, $R_3$ is -(L)$_m$-(Z)$_n$, and L, Z, m, and n are the same as those described above.

According to an exemplary embodiment of the present specification, in Chemical Formula 1, $R_1$ and $R_3$ are each independently -(L)$_m$-(Z)$_n$, and L, Z, m, and n are the same as those described above.

According to another exemplary embodiment of the present specification, L is selected from the group consisting of a direct bond; a substituted or unsubstituted phenylene; a substituted or unsubstituted biphenylene; a substituted or unsubstituted terphenylene; a substituted or unsubstituted naphthylene; a substituted or unsubstituted anthrylene; a substituted or unsubstituted fluorenylene; a substituted or unsubstituted pyridylene; a substituted or unsubstituted triazinylene; a substituted or unsubstituted pyrimidylene; a substituted or unsubstituted quinazolinylene; a substituted or unsubstituted imidazopyridylene; a substituted or unsubstituted benzimidazolylene; a substituted or unsubstituted benzothiazolylene; and a substituted or unsubstituted carbazolylene, when L is substituted, the substituent is one or more substituents selected from the group consisting of deuterium, halogen, —SiRR'R", —P(=O)RR', a substituted or unsubstituted $C_1$ to $C_{60}$ alkyl, a substituted or unsubstituted $C_6$ to $C_{60}$ aryl, and a substituted or unsubstituted $C_2$ to $C_{60}$ heteroaryl, and R, R', and R" are the same as or different from each other, and are each independently hydrogen; deuterium; a substituted or unsubstituted $C_1$ to $C_{60}$ alkyl; a substituted or unsubstituted $C_6$ to $C_{60}$ aryl; or a substituted or unsubstituted $C_2$ to $C_{60}$ heteroaryl.

According to another exemplary embodiment of the present specification, L is selected from the group consisting of a direct bond; phenylene; biphenylene; terphenylene; naphthylene; anthrylene; fluorenylene; pyridylene; triazinylene; pyrimidylene; quinazolinylene; imidazopyridylene; benzimidazolylene; benzothiazolylene; and carbazolylene.

According to still another exemplary embodiment of the present specification, Z is selected from the group consisting of hydrogen; deuterium; halogen; —P(=O)$R_{15}R_{16}$; —Si$R_{17}R_{18}R_{19}$; a substituted or unsubstituted methyl; a substituted or unsubstituted ethyl; a substituted or unsubstituted phenyl; a substituted or unsubstituted naphthyl; a substituted or unsubstituted biphenyl; a substituted or unsubstituted phenanthrenyl; a substituted or unsubstituted pyridyl; a substituted or unsubstituted carbazolyl; a substituted or unsubstituted pyrenyl; a substituted or unsubstituted triphenylenyl; a substituted or unsubstituted phenanthrolinyl; a substituted or unsubstituted imidazopyridyl; a substituted or unsubstituted benzothiazolyl; a substituted or unsubstituted fluorenyl; a substituted or unsubstituted dimethylfluorenyl; a substituted or unsubstituted benzofluorenyl; a substituted or unsubstituted dimethylbenzofluorenyl; a substituted or unsubstituted dibenzoselenophene group; a substituted or unsubstituted dibenzothiophene group; a substituted or unsubstituted dibenzofuran group; a substituted or unsubstituted spirobifluorenyl; a substituted or unsubstituted quinolyl; a substituted or unsubstituted diarylamine; and a substituted or unsubstituted arylheteroarylamine, when Z is substituted, the substituent is one or more substituents selected from the group consisting of deuterium, halogen, —SiRR'R", —P(=O)RR', a substituted or unsubstituted $C_1$ to $C_{60}$ alkyl, a substituted or unsubstituted $C_6$ to $C_{60}$ aryl, and a substituted or unsubstituted $C_2$ to $C_{60}$ heteroaryl, and R, R', R", and $R_{15}$ to $R_{19}$ are the same as or different from each other, and are each independently hydrogen; deuterium; a substituted or unsubstituted $C_1$ to $C_{60}$ alkyl; a substituted or unsubstituted $C_6$ to $C_{60}$ aryl; or a substituted or unsubstituted $C_2$ to $C_{60}$ heteroaryl.

According to yet another exemplary embodiment of the present specification, Z is selected from the group consisting of hydrogen; deuterium; halogen; —P(=O)$R_{15}R_{16}$; —Si$R_{17}R_{18}R_{19}$; a substituted or unsubstituted methyl; a substituted or unsubstituted ethyl; a substituted or unsubstituted phenyl; a substituted or unsubstituted naphthyl; a substituted or unsubstituted biphenyl; a substituted or unsubstituted phenanthrenyl; a substituted or unsubstituted pyridyl; a substituted or unsubstituted carbazolyl; a substituted or unsubstituted pyrenyl; a substituted or unsubstituted triphenylenyl; a substituted or unsubstituted phenanthrolinyl; a substituted or unsubstituted imidazopyridyl; a substituted or unsubstituted benzothiazolyl; a substituted or unsubstituted fluorenyl; a substituted or unsubstituted dimethylfluorenyl; a substituted or unsubstituted benzofluorenyl; a substituted or unsubstituted dimethylbenzofluorenyl; a substituted or unsubstituted dibenzoselenophene group; a substituted or unsubstituted dibenzothiophene group; a substituted or unsubstituted dibenzofuran group; a substituted or unsubstituted spirobifluorenyl; a substituted or unsubstituted quinolyl; a substituted or unsubstituted biphenylcarbazolylamine; a substituted or unsubstituted biphenylfluorenylamine; a substituted or unsubstituted diphenylamine; and a substituted or unsubstituted dibiphenylamine, when Z is substituted, the substituent is selected among one or more substituents selected from the group consisting of deuterium, halogen, —SiRR'R", —P(=O)RR', a substituted or unsubstituted $C_1$ to $C_{60}$ alkyl, a substituted or unsubstituted $C_6$ to $C_{60}$ aryl, and a substituted or unsubstituted $C_2$ to $C_{60}$ heteroaryl, and R, R', R", and $R_{15}$ to $R_{19}$ are the same as or different from each other, and are each independently hydrogen; deuterium; a substituted or unsubstituted $C_1$ to $C_{60}$ alkyl; a substituted or unsubstituted $C_6$ to $C_{60}$ aryl; or a substituted or unsubstituted $C_2$ to $C_{60}$ heteroaryl.

According to still yet another exemplary embodiment of the present specification, Z is selected from the group consisting of hydrogen; deuterium; halogen; —P(=O)$R_{15}R_{16}$; —Si$R_{17}R_{18}R_{19}$; methyl; ethyl; phenyl; naphthyl; biphenyl; phenanthrenyl; pyridyl; carbazolyl; pyrenyl; triphenylenyl; phenanthrolinyl; imidazopyridyl; benzothiazolyl; fluorenyl; dimethylfluorenyl; benzofluorenyl; dimethylbenzofluorenyl; a dibenzoselenophene group; a dibenzothiophene group; a dibenzofuran group; spirobifluorenyl; quinolyl; biphenylcarbazolylamine; biphenylfluorenylamine; diphenylamine; and dibiphenylamine, and $R_{15}$ to $R_{19}$ are the same as or different from each other, and are each independently hydrogen; deuterium; a substituted or unsubstituted $C_1$ to $C_{60}$ alkyl; a substituted or unsubstituted $C_6$ to $C_{60}$ aryl; or a substituted or unsubstituted $C_2$ to $C_{60}$ heteroaryl.

According to further another exemplary embodiment of the present specification, $R_{15}$ to $R_{19}$ are the same as or different from each other, and each independently hydrogen; deuterium; or a substituted or unsubstituted phenyl.

According to still further another exemplary embodiment of the present specification, $R_{15}$ to $R_{19}$ are the same as or different from each other, and each independently hydrogen; deuterium; or phenyl.

According to an exemplary embodiment of the present specification, Chemical Formula 1 may be represented by the following Chemical Formula 2 or 3.

[Chemical Formula 2]

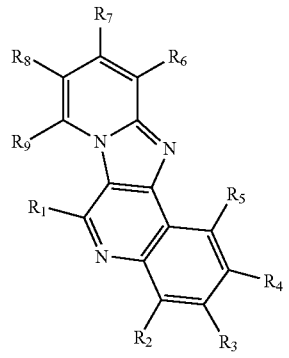

[Chemical Formula 3]

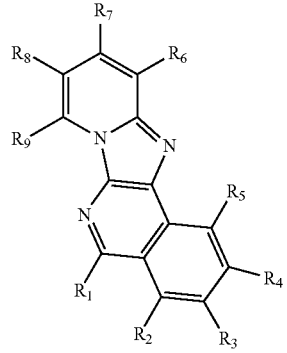

In Chemical Formulae 2 and 3, the definitions of $R_1$ to $R_9$ are the same as those defined in Chemical Formula 1.

According to an exemplary embodiment of the present specification, Chemical Formula 1 may be represented by any one of the following Formulae 4 to 6.

[Chemical Formula 4]

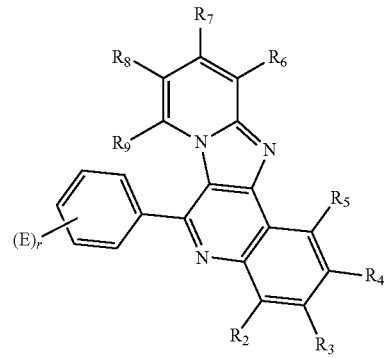

[Chemical Formula 5]

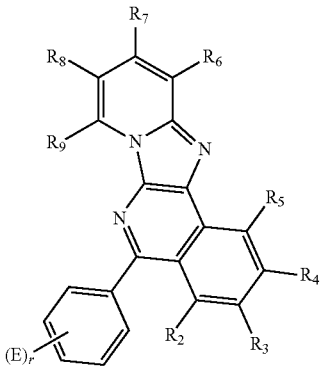

[Chemical Formula 6]

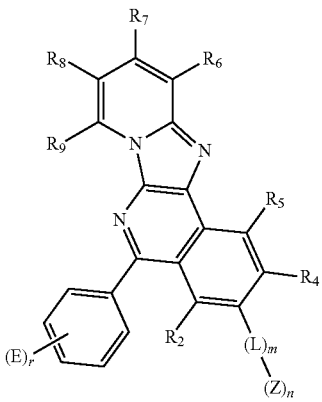

In Chemical Formulae 4 to 6,

E is selected from the group consisting of hydrogen; deuterium; —$SiR_{20}R_{21}R_{22}$; —$P(=O)R_{23}R_{24}$; a substituted or unsubstituted $C_1$ to $C_{60}$ alkyl; a substituted or unsubstituted $C_6$ to $C_{60}$ aryl; a substituted or unsubstituted $C_2$ to $C_{60}$ heteroaryl; and an amine which is unsubstituted or substituted with one or more substituents selected from a substituted or unsubstituted $C_1$ to $C_{60}$ alkyl, a substituted or unsubstituted $C_6$ to $C_{60}$ aryl, and a substituted or unsubstituted $C_2$ to $C_{60}$ heteroaryl, r is an integer of 1 to 5, when r is 2 or more, E's are the same as or different from each other, $R_{20}$ to $R_{24}$ are the same as or different from each other, and are each independently hydrogen; deuterium; a substituted or unsubstituted $C_1$ to $C_{60}$ alkyl; a substituted or unsubstituted $C_6$ to $C_{60}$ aryl; or a substituted or unsubstituted $C_2$ to $C_{60}$ heteroaryl, L is selected from the group consisting of a direct bond; a substituted or unsubstituted $C_6$ to $C_{60}$ arylene; and a substituted or unsubstituted $C_2$ to $C_{60}$ heteroarylene, m is an integer of 1 to 3, n is an integer of 1 to 3, Z is selected from the group consisting of hydrogen; deuterium; —$P(=O)R_{15}R_{16}$; —$SiR_{17}R_{18}R_{19}$; a substituted or unsubstituted $C_1$ to $C_{60}$ alkyl; a substituted or unsubstituted $C_6$ to $C_{60}$ aryl; a substituted or unsubstituted $C_2$ to $C_{60}$ heteroaryl; and an amine which is unsubstituted or substituted with one or more substituents selected from a substituted or unsubstituted $C_1$ to $C_{60}$ alkyl, a substituted or unsubstituted $C_6$ to $C_{60}$ aryl, and a substituted or unsubstituted $C_2$ to $C_{60}$ heteroaryl, when m is 2 or more, L's are the same as or different from each other, when n is 2 or more, Z's are the same as or different from each other, $R_{15}$ to $R_{19}$ are the same as or different from each other, and are each independently hydrogen; deuterium; a substituted or unsubstituted $C_1$ to $C_{60}$ alkyl; a substituted or unsubstituted $C_6$ to $C_{60}$ aryl; or a substituted or unsubstituted $C_2$ to $C_{60}$ heteroaryl, and the definitions of $R_2$ and $R_4$ to $R_9$ are the same as those defined in Formula 1.

According to an exemplary embodiment of the present specification, Chemical Formula 1 may be represented by the following Chemical Formula 7.

[Chemical Formula 7]

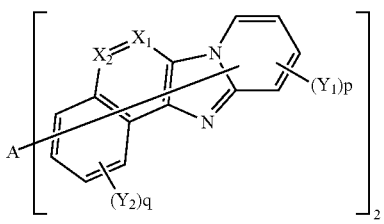

In Chemical Formula 7,

A is a direct bond; or a substituted or unsubstituted $C_6$ to $C_{60}$ arylene, $Y_1$ and $Y_2$ are the same as or different from each other, and are each independently selected from the group consisting of hydrogen; deuterium; halogen; $SiR_{25}R_{26}R_{27}$; —$P(=O)R_{28}R_{29}$; a substituted or unsubstituted $C_1$ to $C_{60}$ alkyl; a substituted or unsubstituted $C_6$ to $C_{60}$ aryl; a substituted or unsubstituted $C_2$ to $C_{60}$ heteroaryl; and an amine which is unsubstituted or substituted with one or more substituents selected from a substituted or unsubstituted $C_1$ to $C_{60}$ alkyl, a substituted or unsubstituted $C_6$ to $C_{60}$ aryl, and a substituted or unsubstituted $C_2$ to $C_{60}$ heteroaryl, p and q are the same as or different from each other, and are each an integer of 1 to 4, when p is 2 or more, $Y_1$'s are the same as or different from each other, when q is 2 or more, $Y_2$'s are the same as or different from each other, at least one of $Y_1$ and $Y_2$ is linked to A, $R_{25}$ to $R_{29}$ are the same as or different from each other, and are each independently hydrogen; deuterium; a substituted or unsubstituted $C_1$ to $C_{60}$ alkyl; a substituted or unsubstituted $C_6$ to $C_{60}$ aryl; or a substituted or unsubstituted $C_2$ to $C_{60}$ heteroaryl, and the definitions of $X_1$ and $X_2$ are the same as those defined in Chemical Formula 1.

According to another exemplary embodiment of the present specification, A is a direct bond; a substituted or unsubstituted phenylene; a substituted or unsubstituted biphenylene; or a substituted or unsubstituted terphenylene.

According to still another exemplary embodiment of the present specification, A is a direct bond; phenylene; biphenylene; or terphenylene.

According to an exemplary embodiment of the present application, the hetero-cyclic compound represented by Chemical Formula 1 is selected from the following compounds.

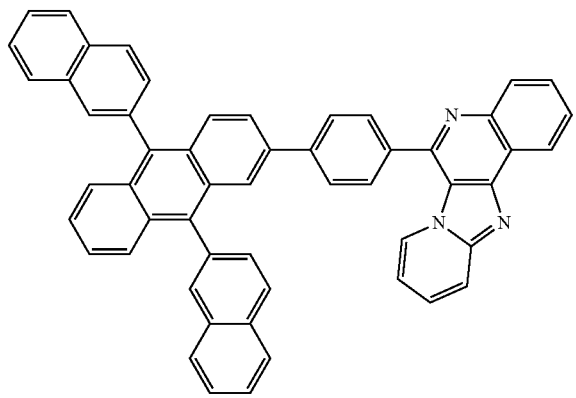
1
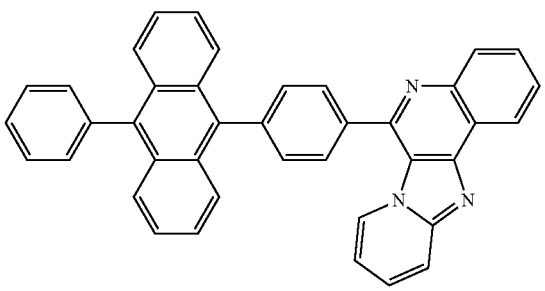
5
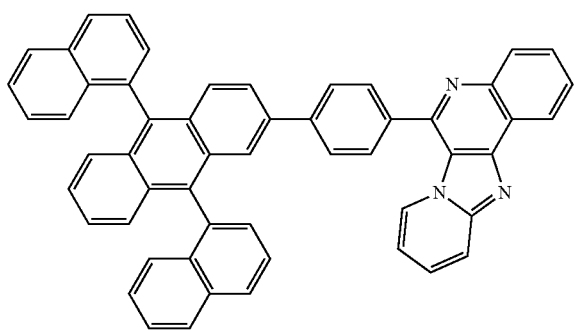
2
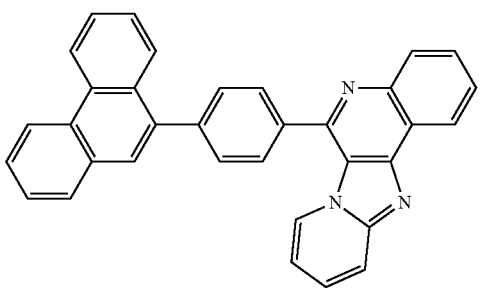
6
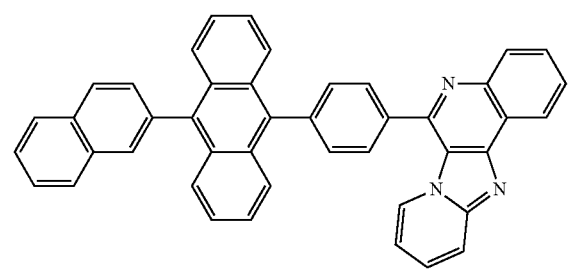
3
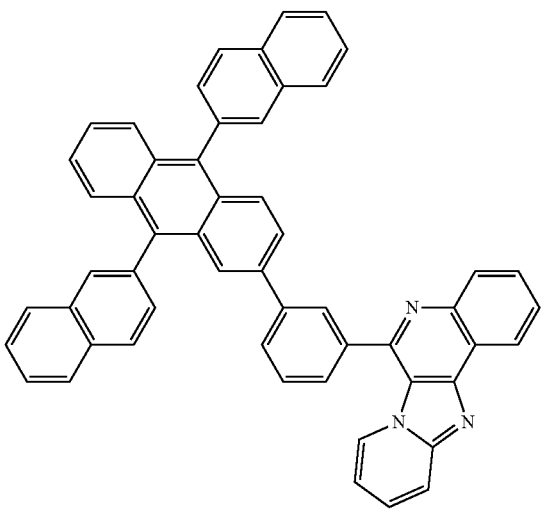
7
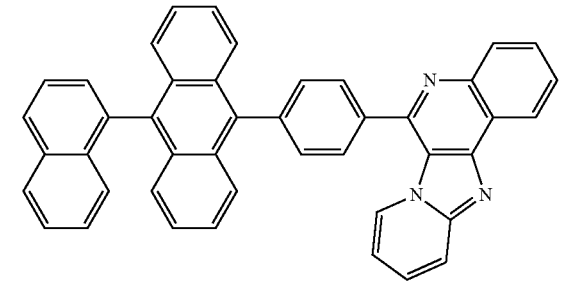
4
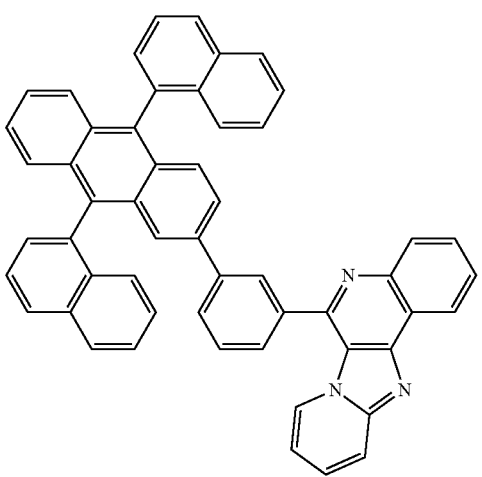
8

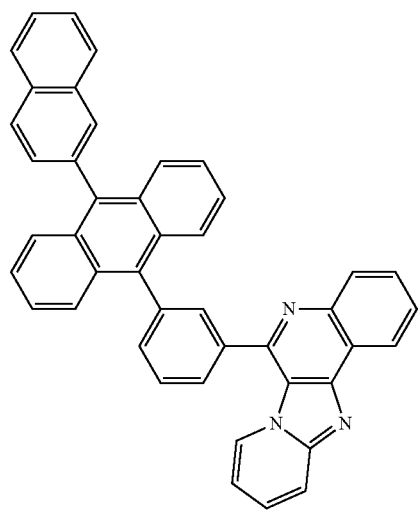
9
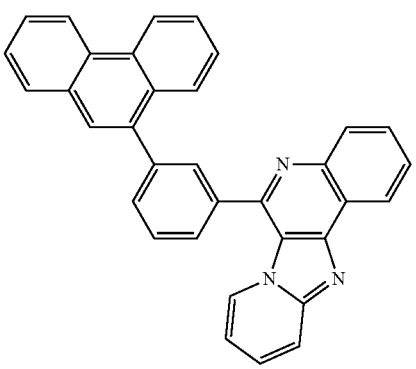
12
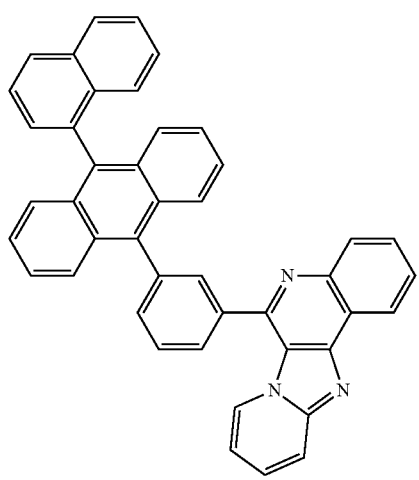
10
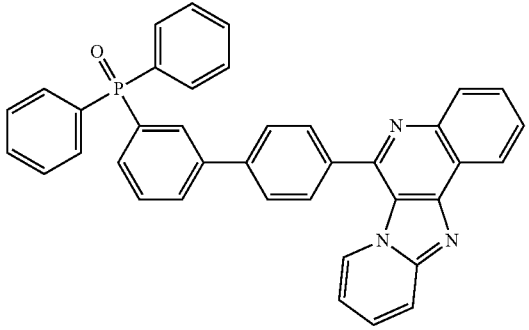
13
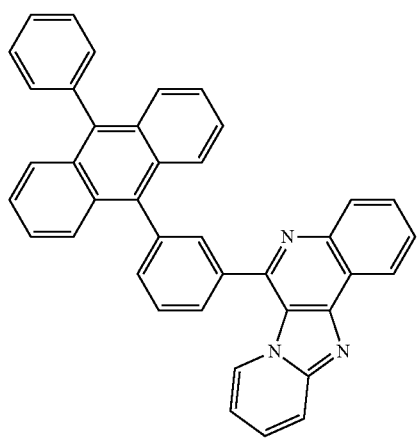
11
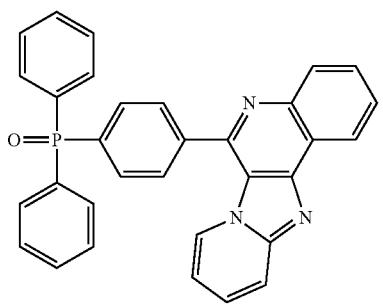
14
15

16
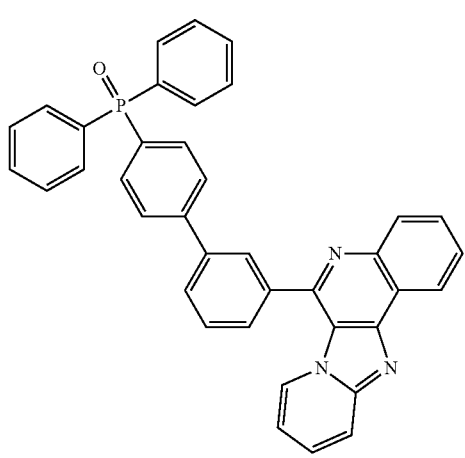
17
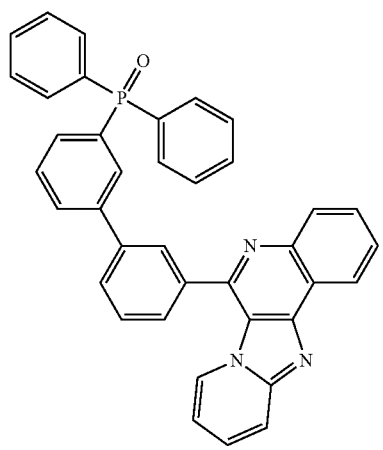
18
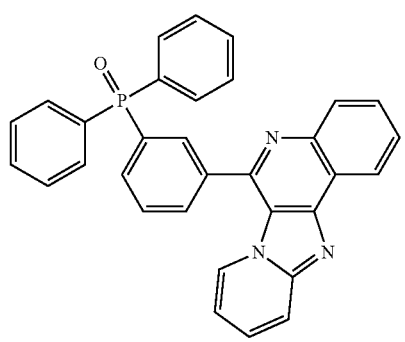
19
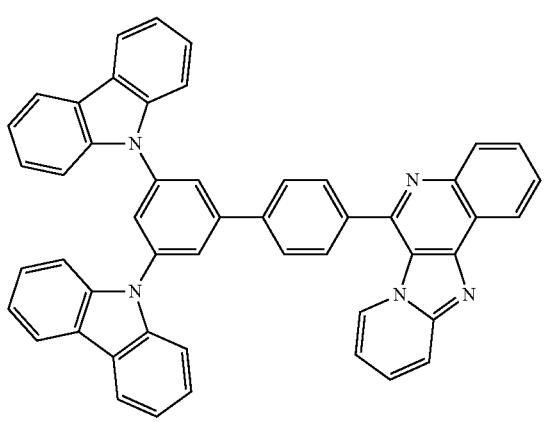
20
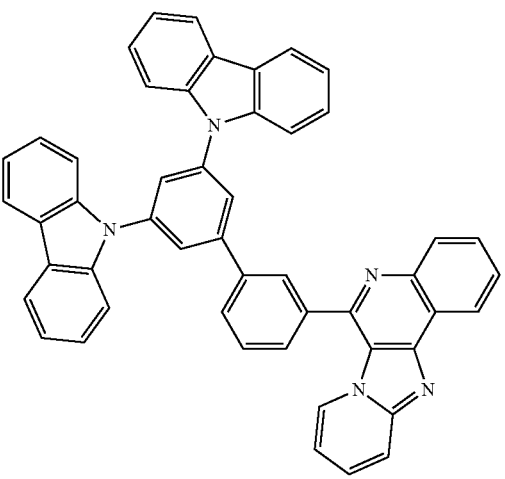
21
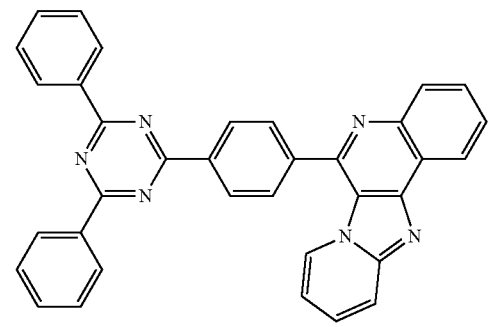
22
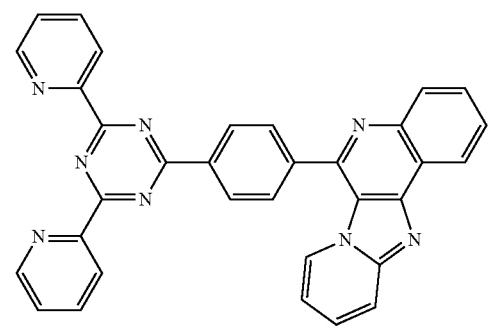
23
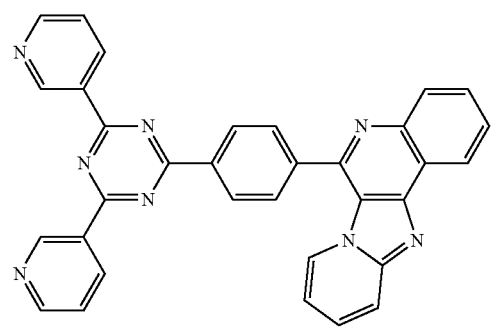

24
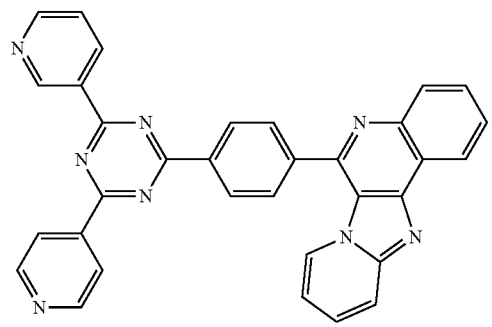
25
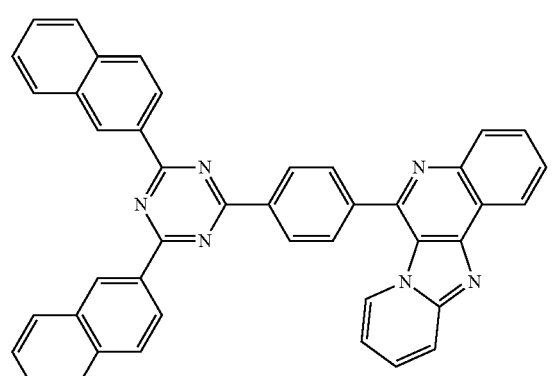
26
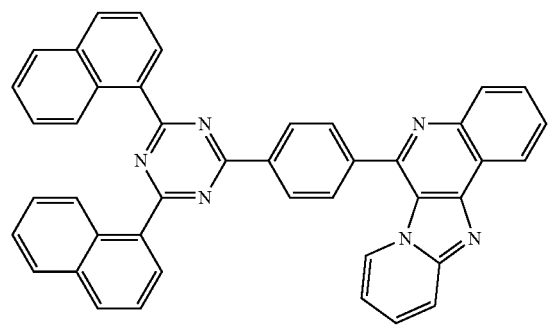
27
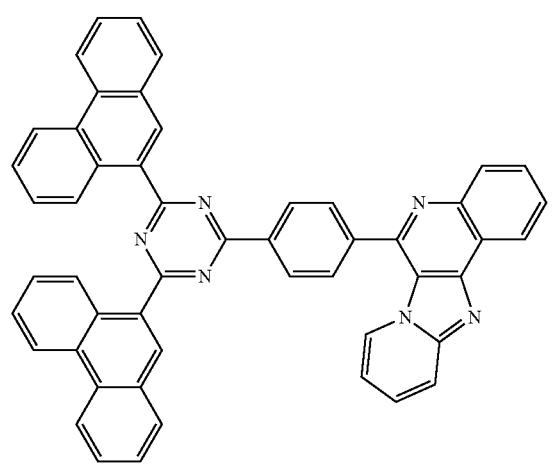
28
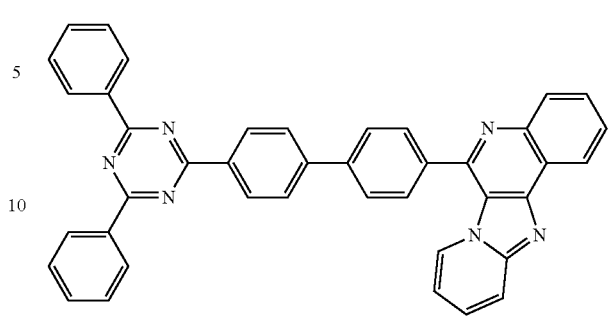
29
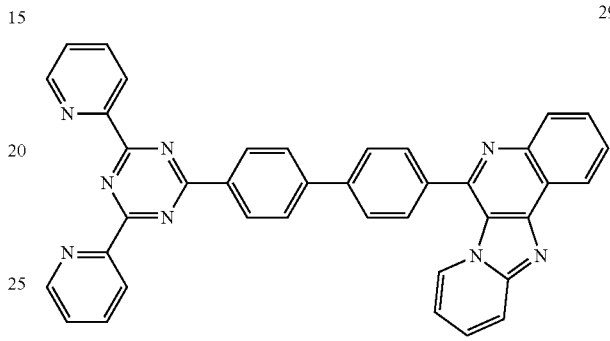
30
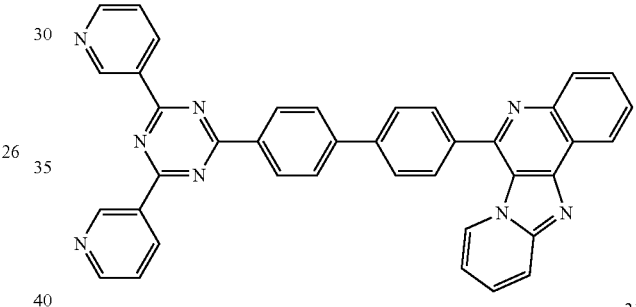
31
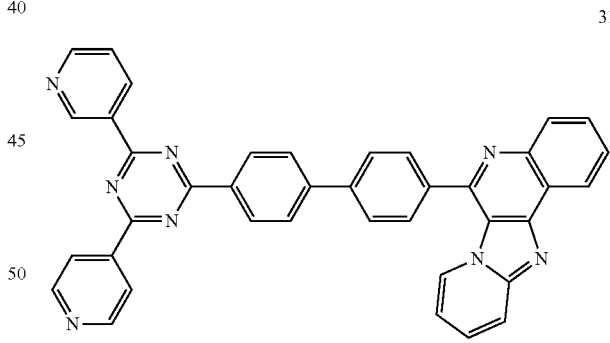
32
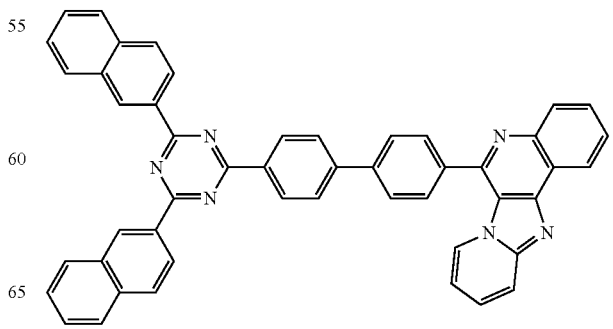

33
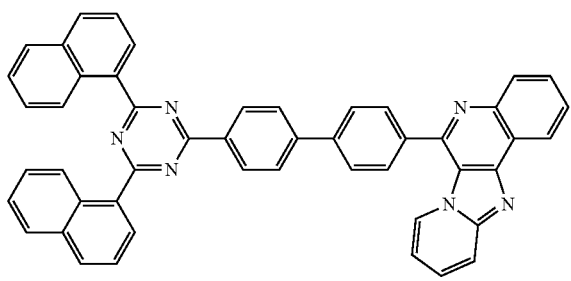
34
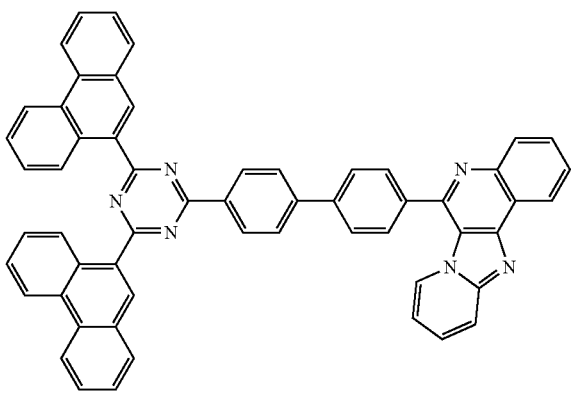
35
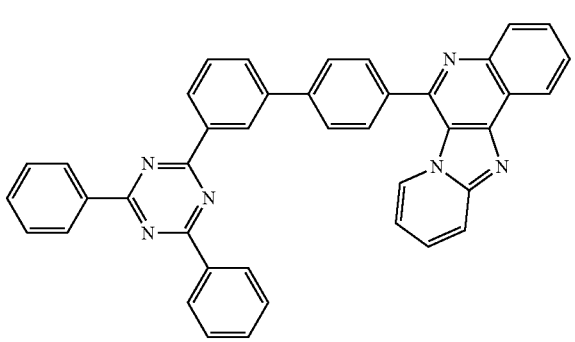
36
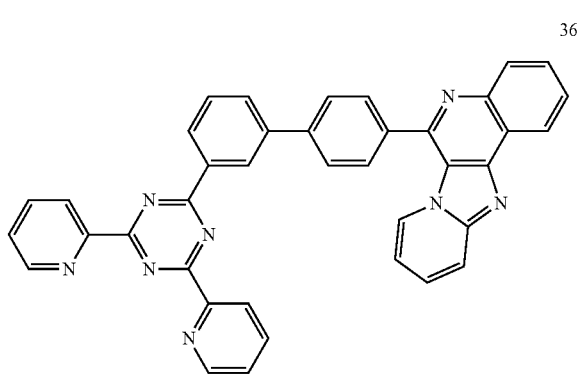
37
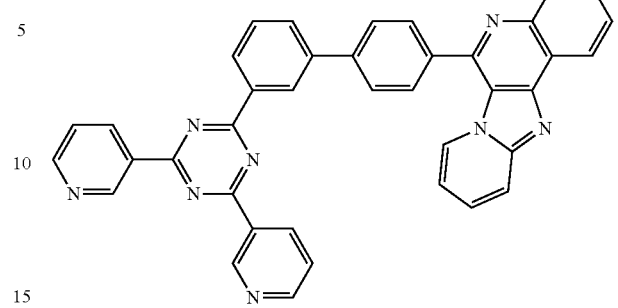
38
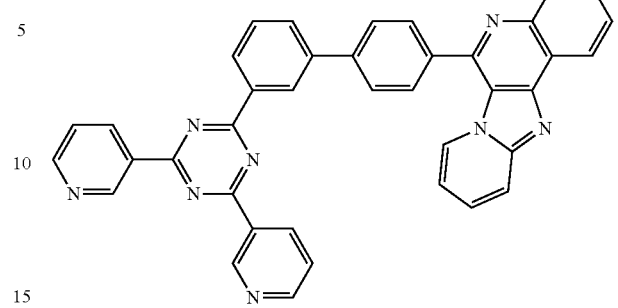
39
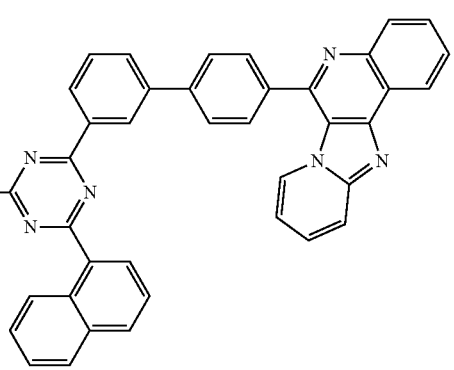
40
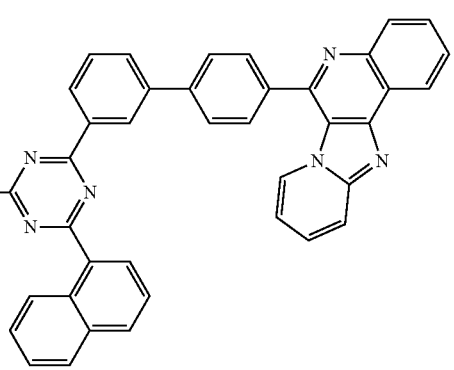

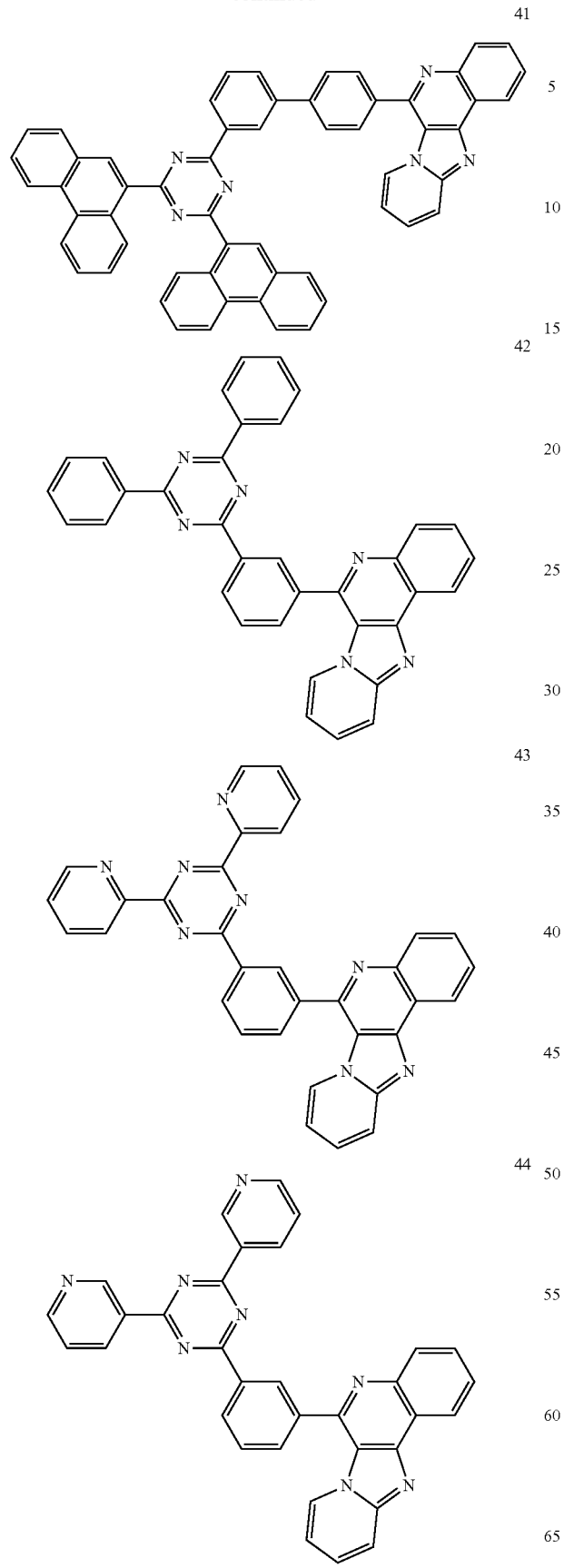
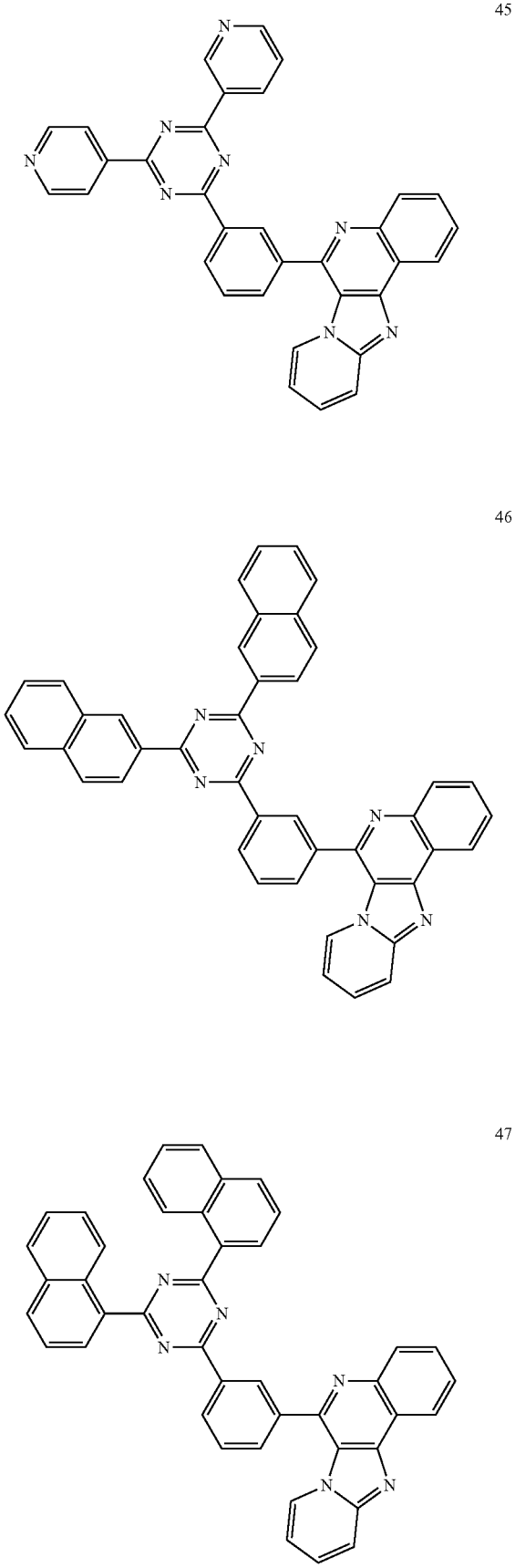

48
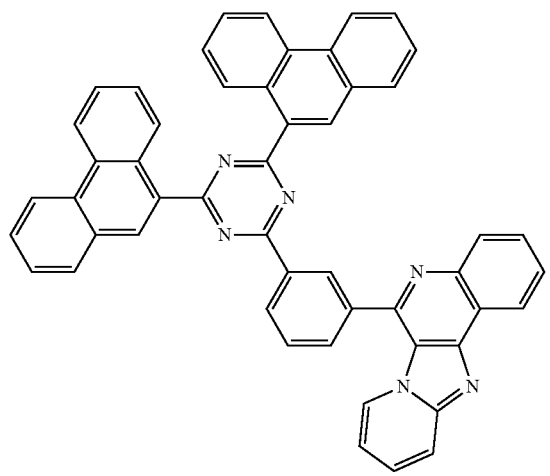
49
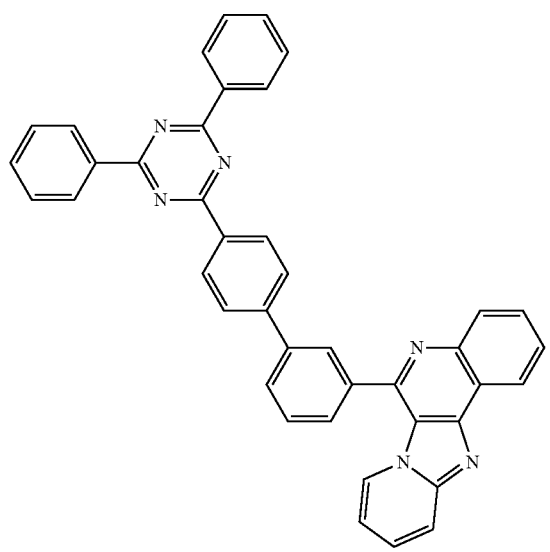
50
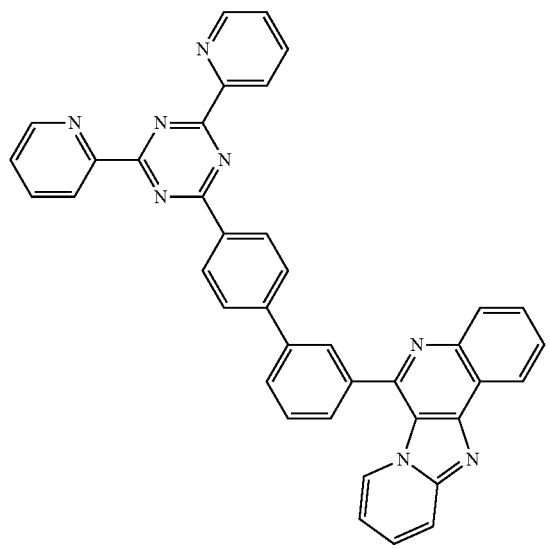
51
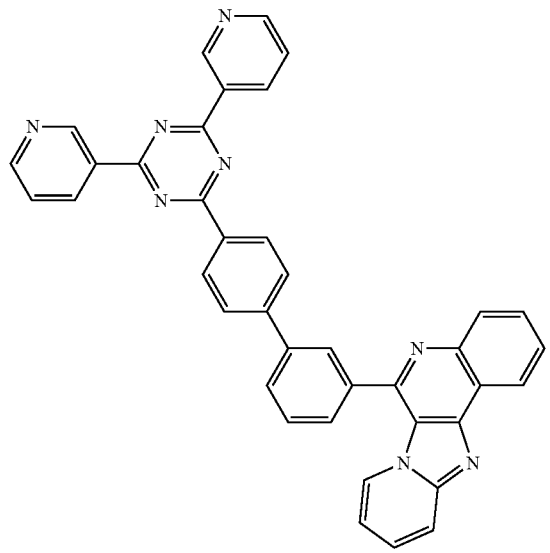
52
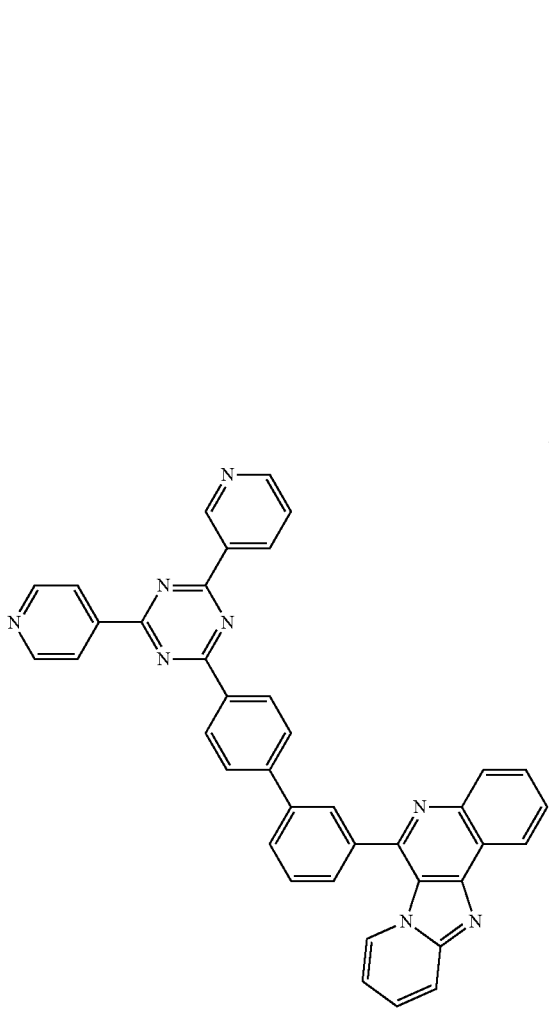

53
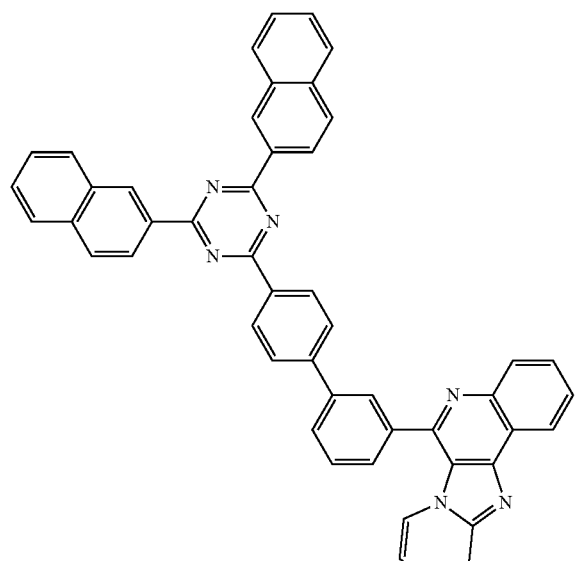
54
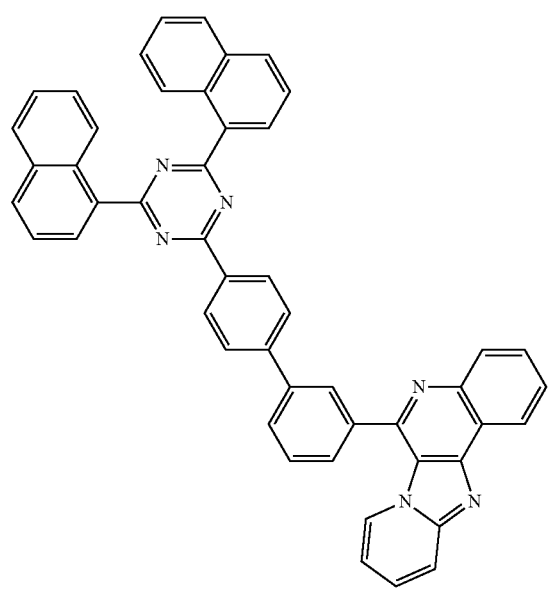
55
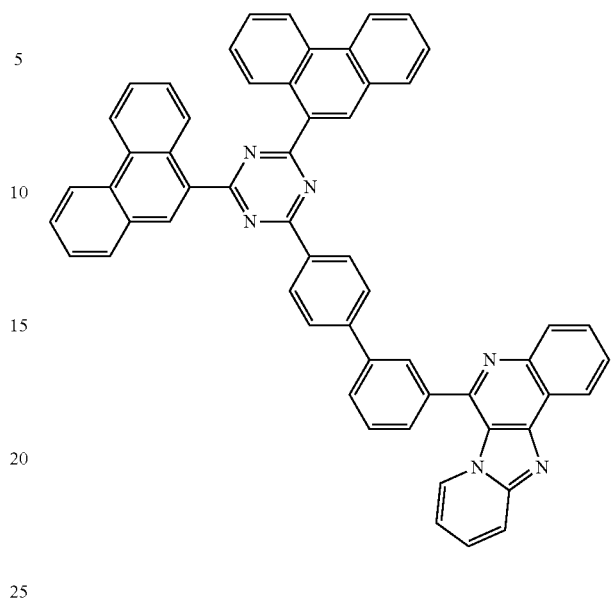
56
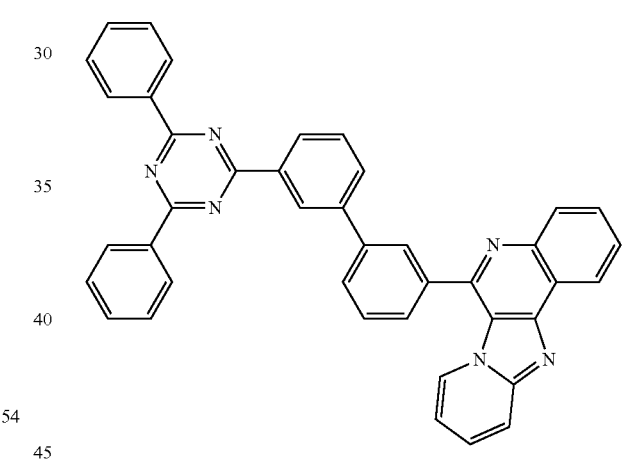
57
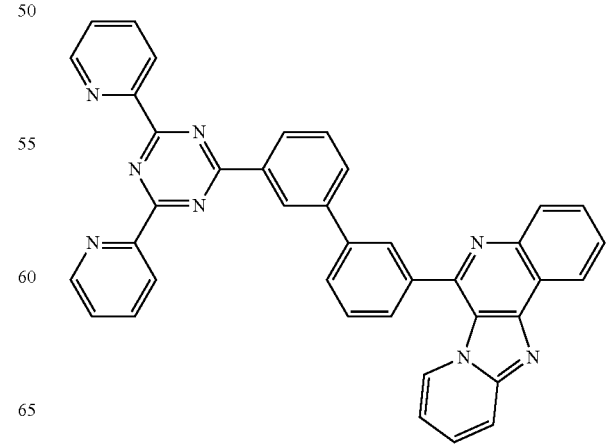

-continued
58
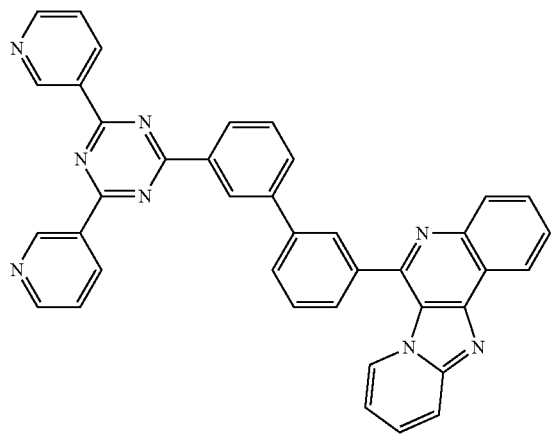
59
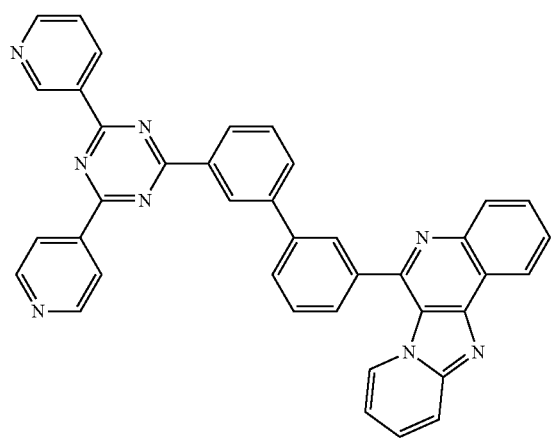
60
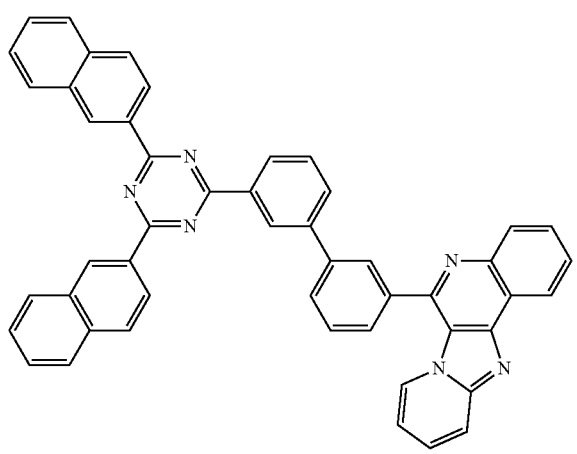
-continued
61
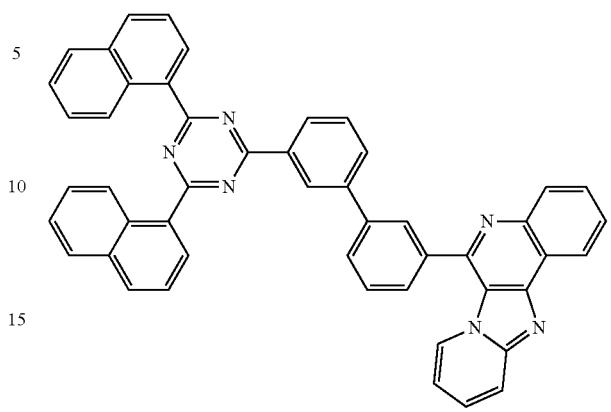
62
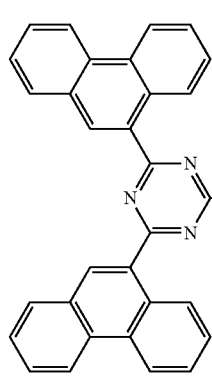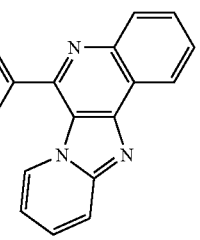
63
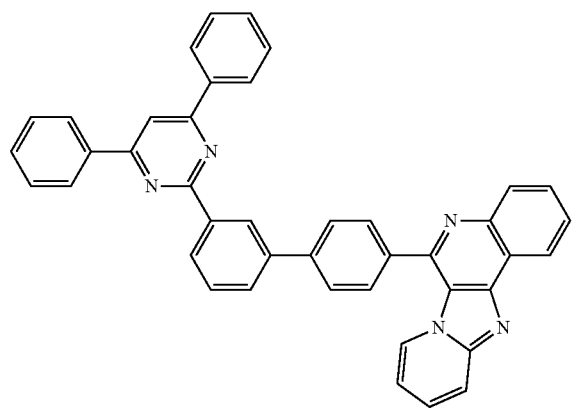

64
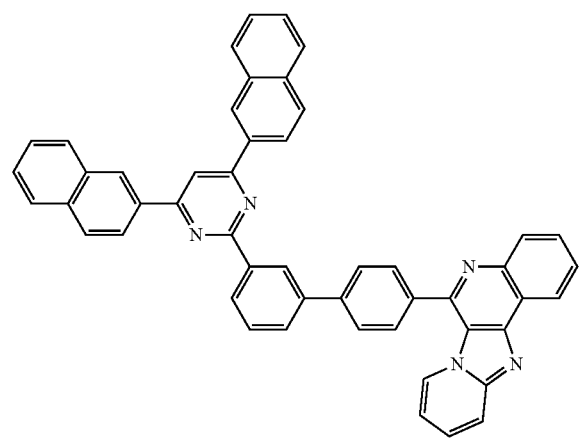
65
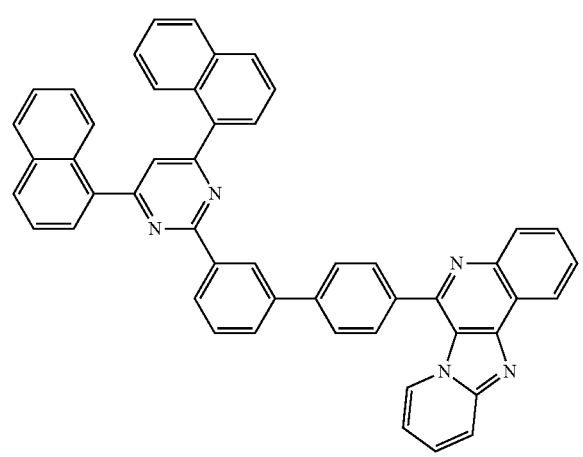
66
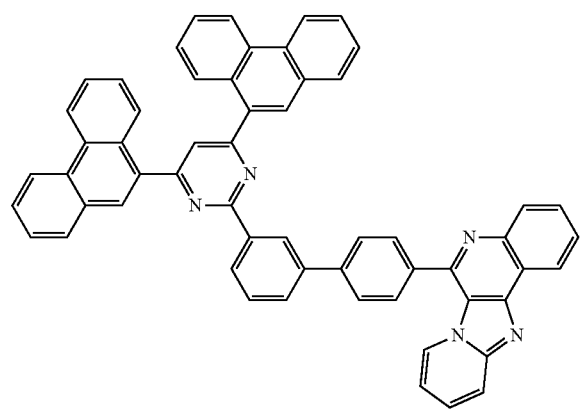
67
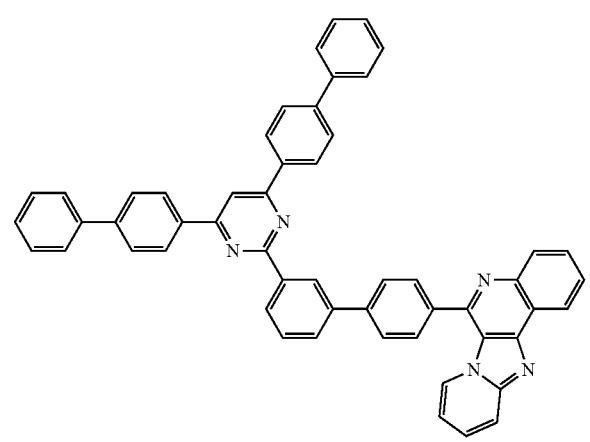
68
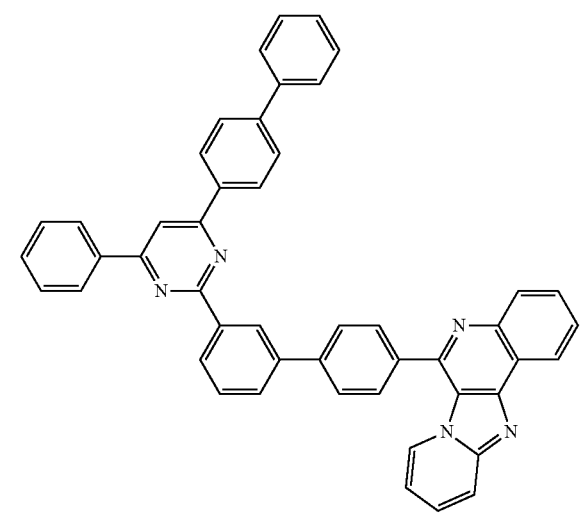
69
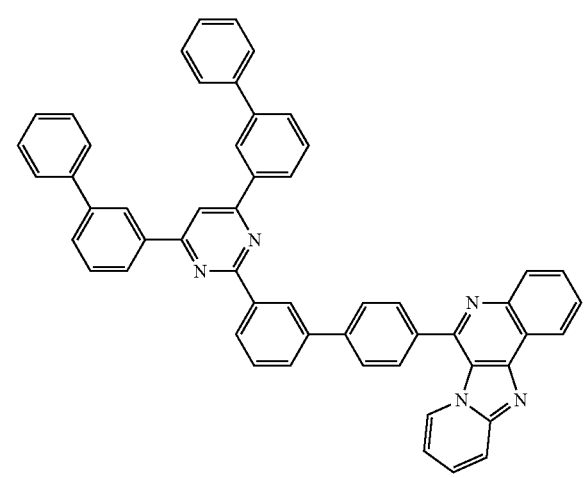

-continued

70

71

72

-continued

73

74

75

76
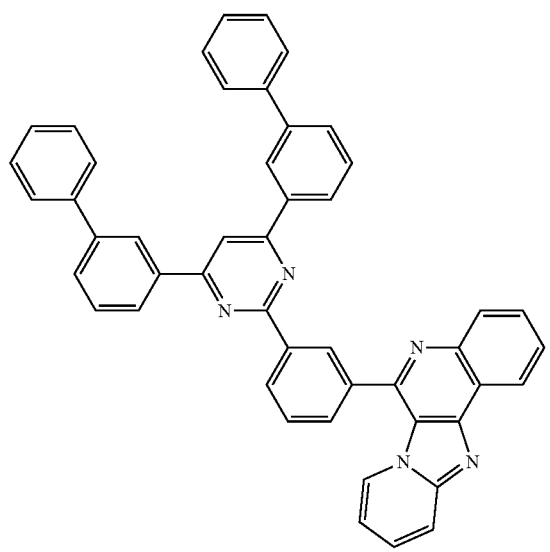
77
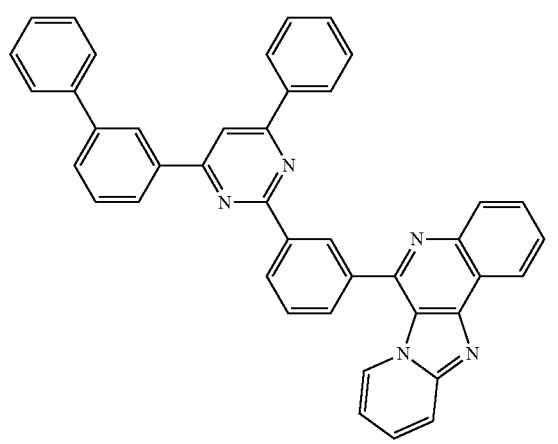
78
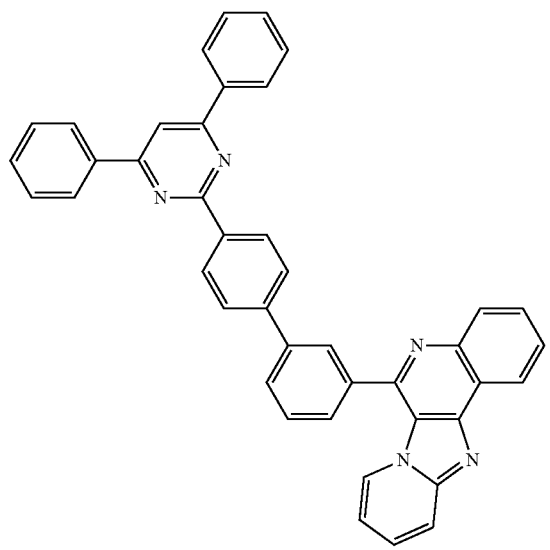
79
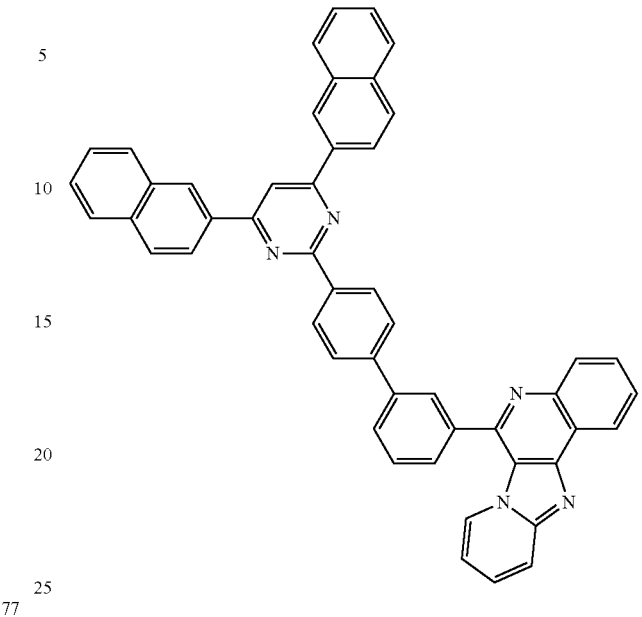
80
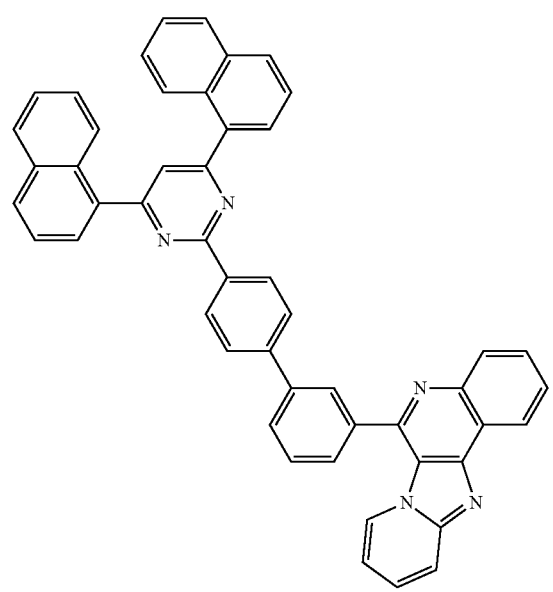

81
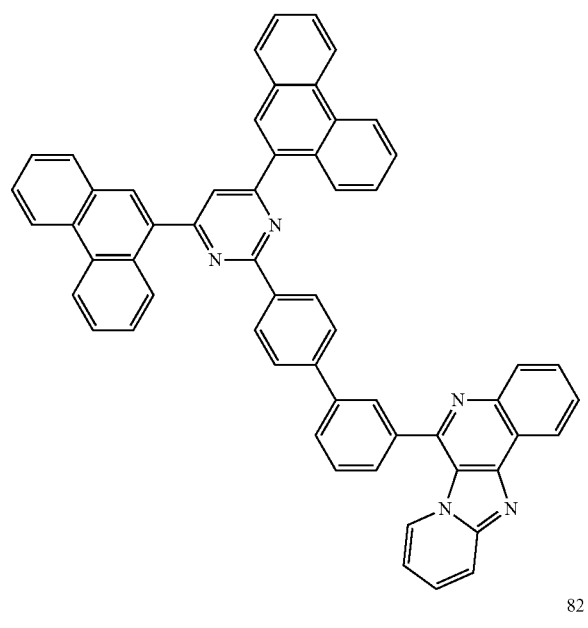
82
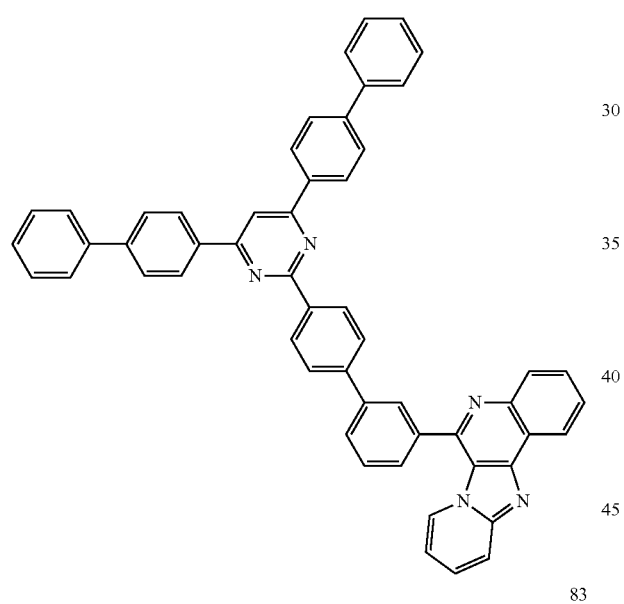
83
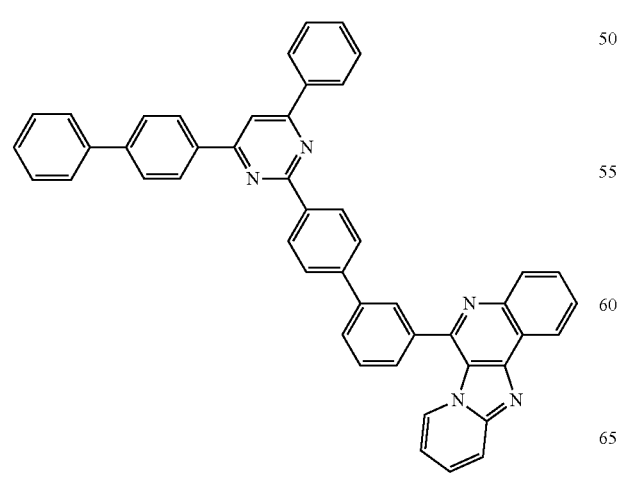
84
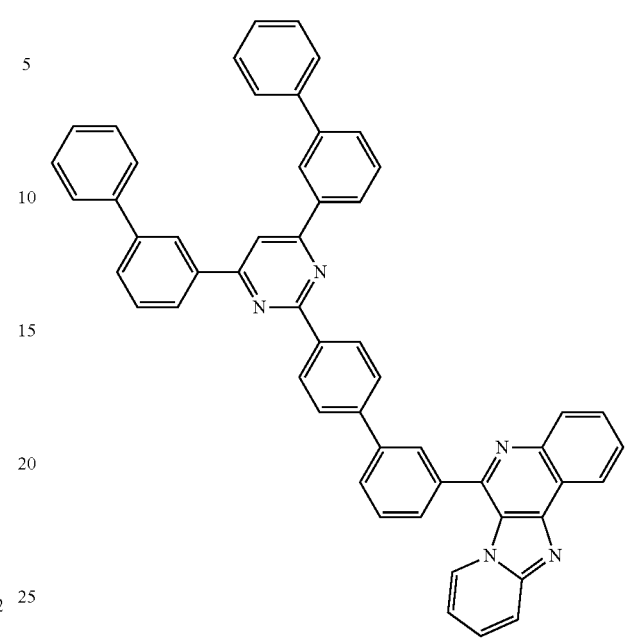
85
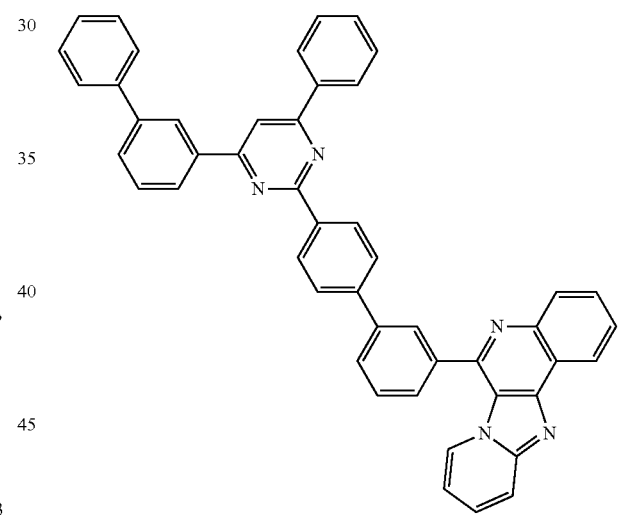
86
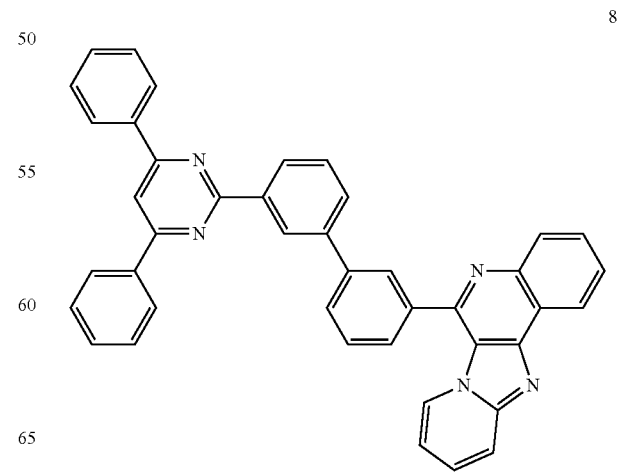

87
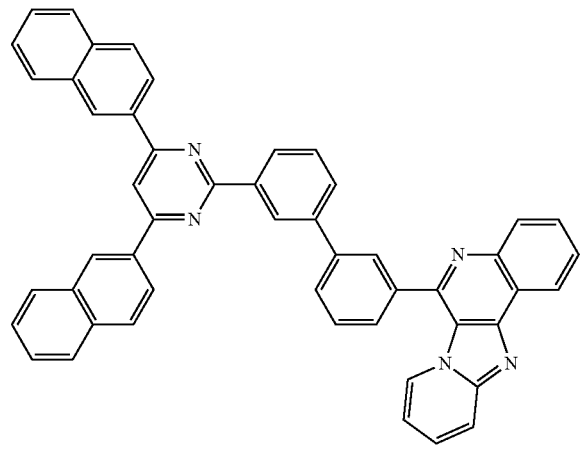
88
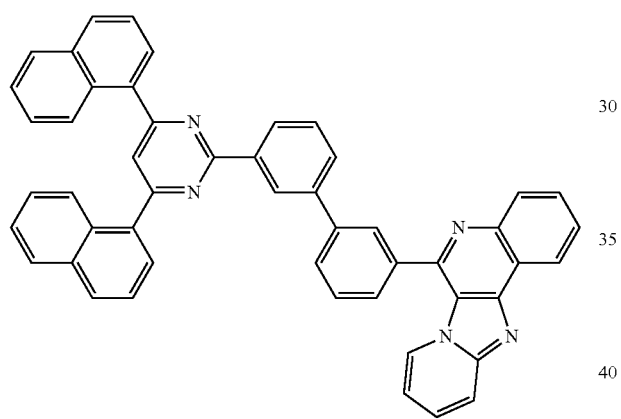
89
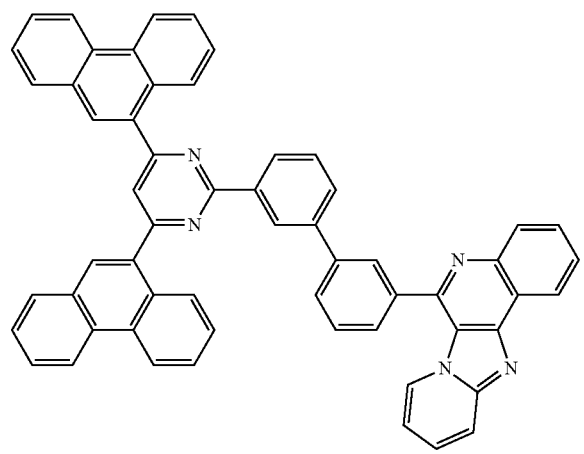
90
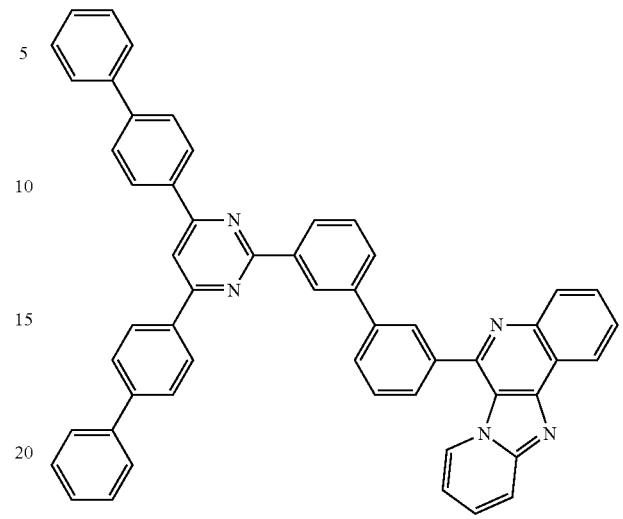
91
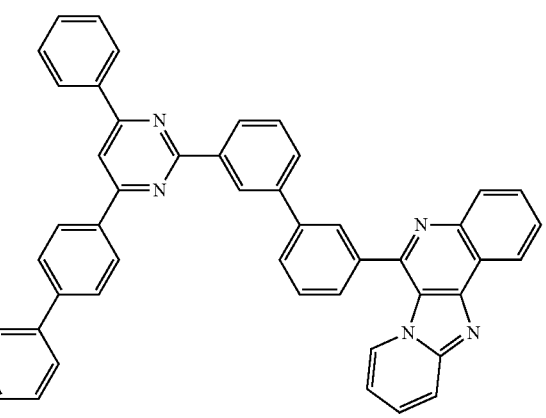
92
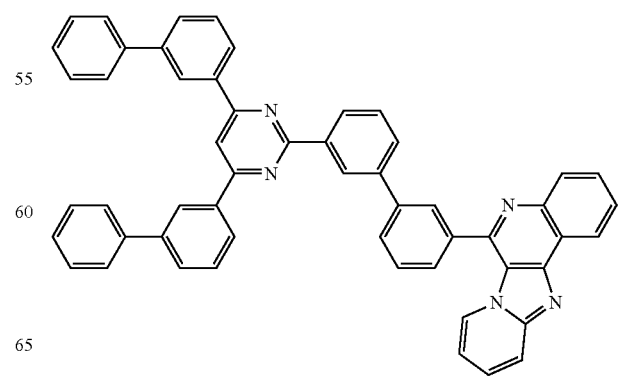

93
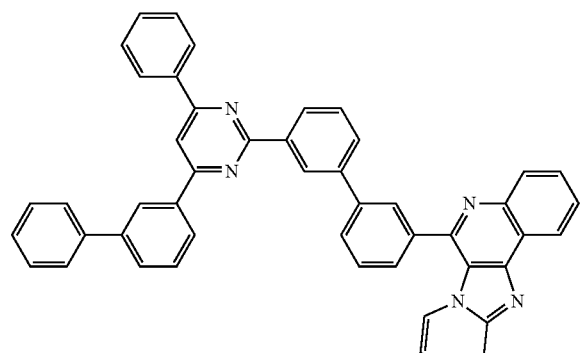
94
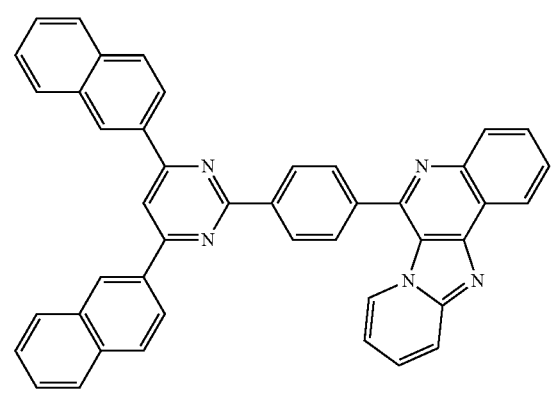
95
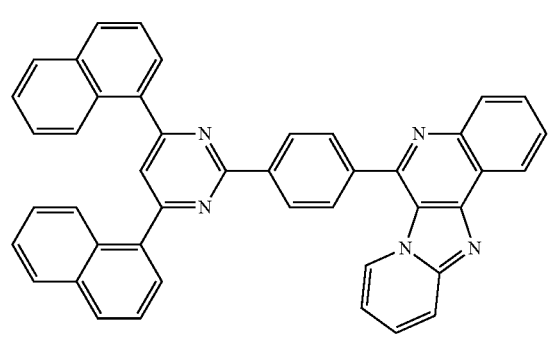
96
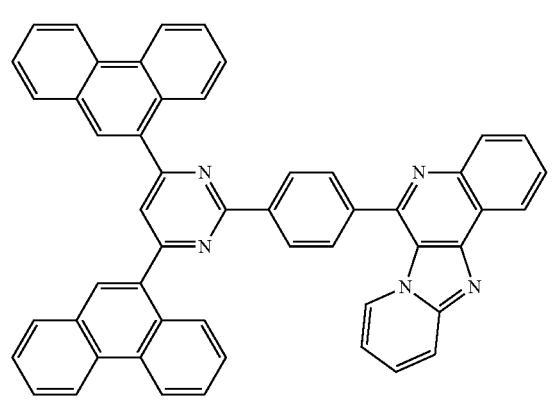
97
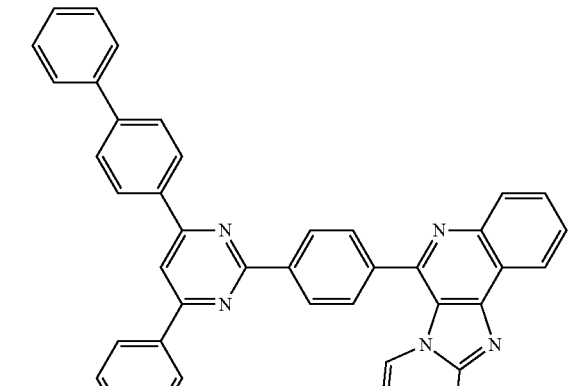
98
99
100
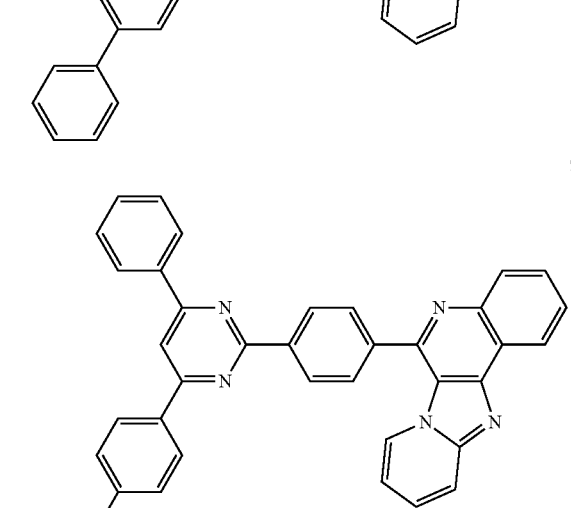

101
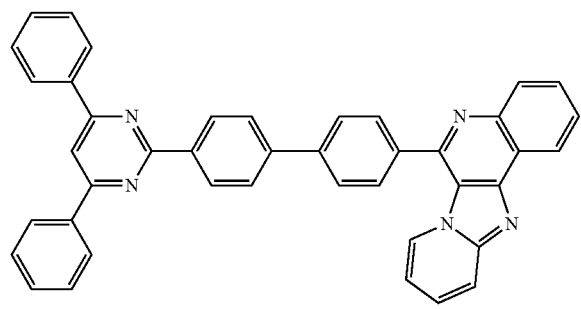
102
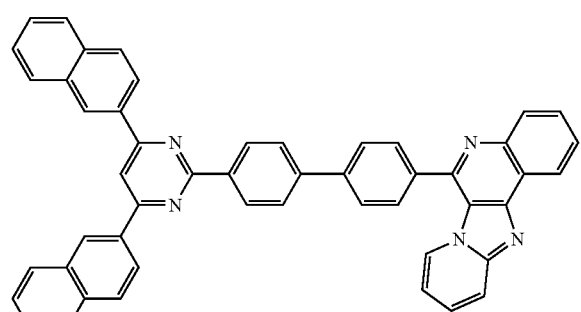
103
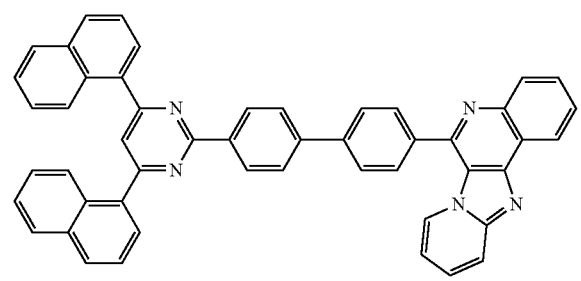
104
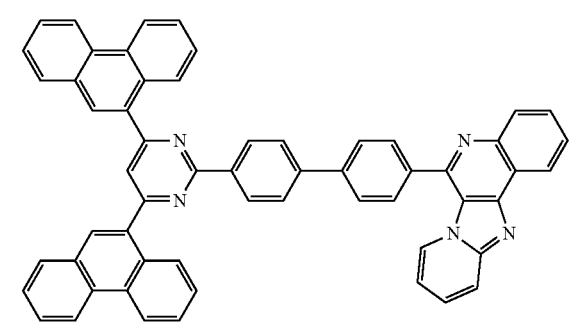
105
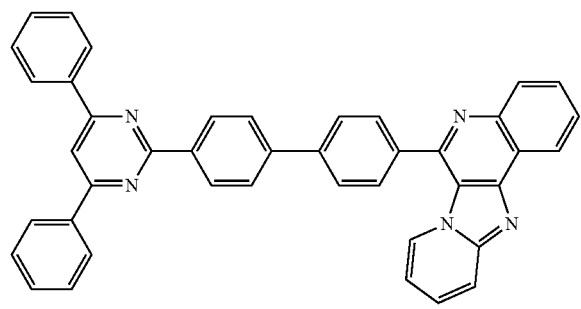
106
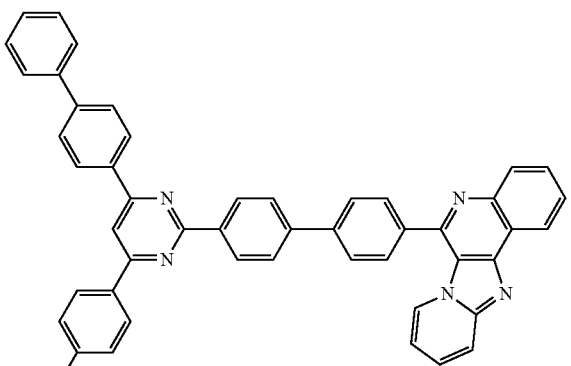
107
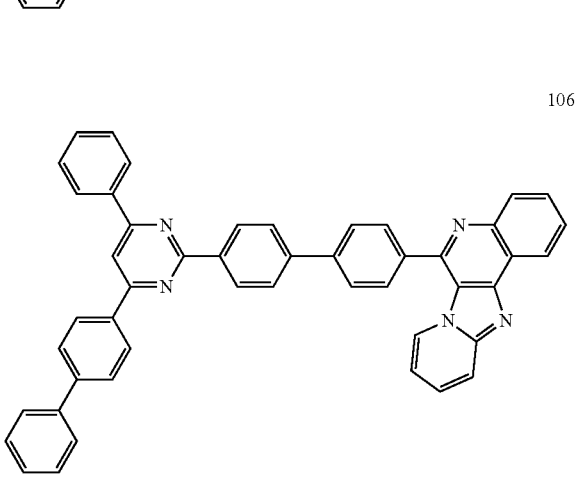
108
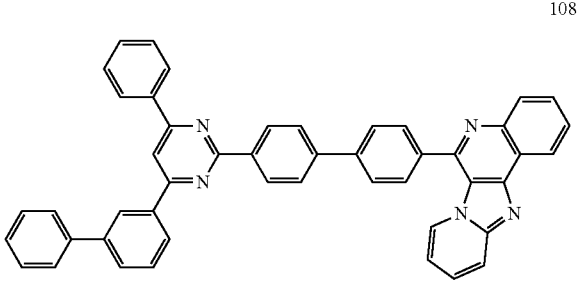

109
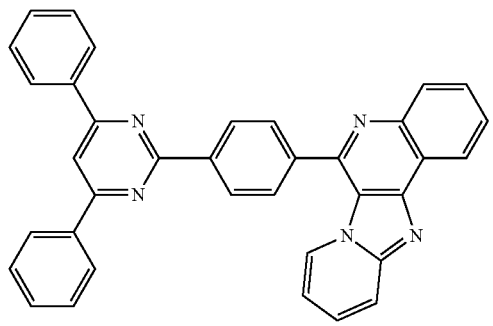
110
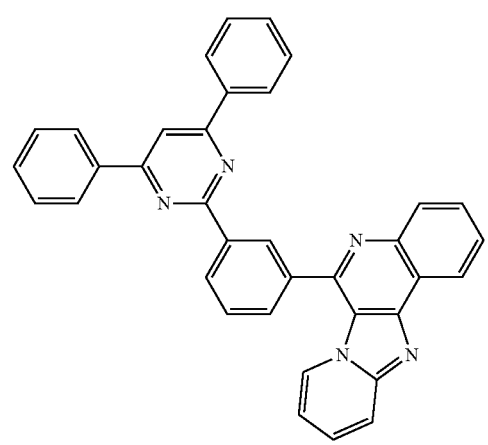
111
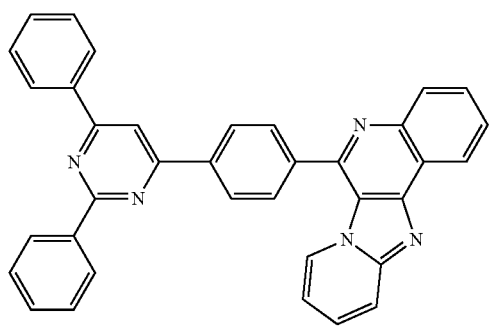
112
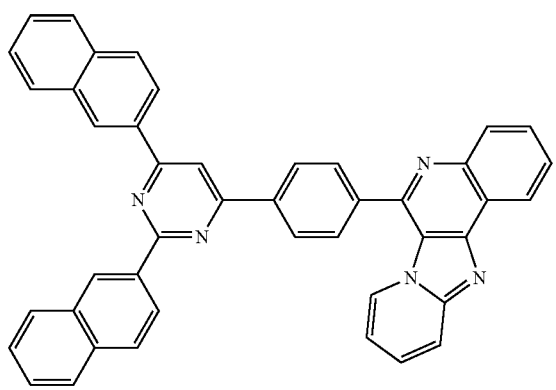
113
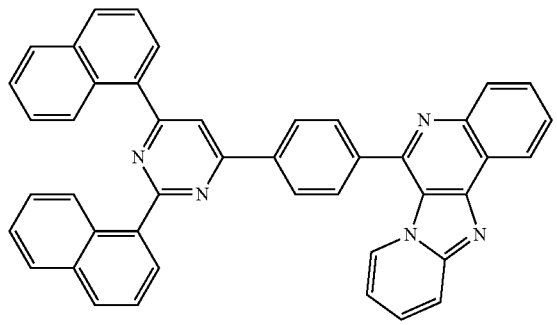
114
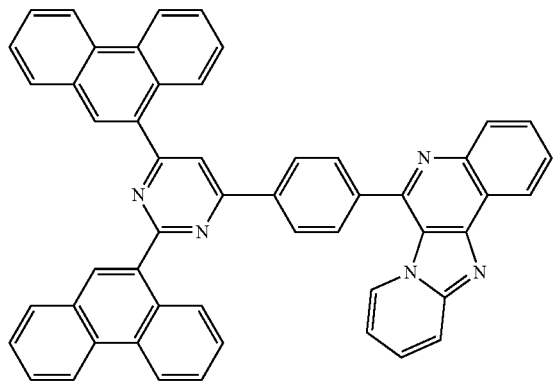
115

116 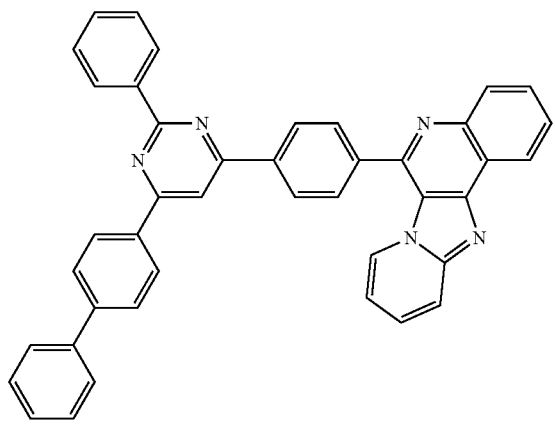
117 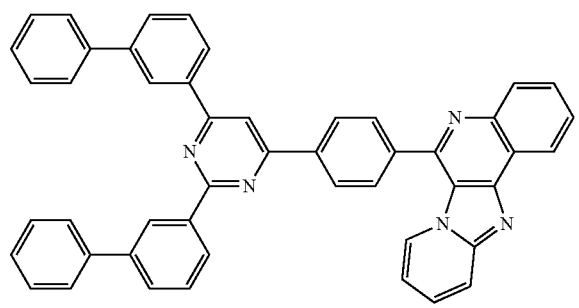
118 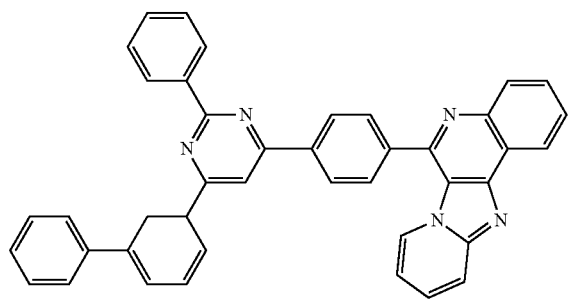
119 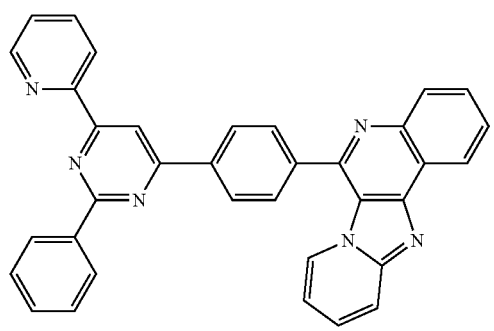
120 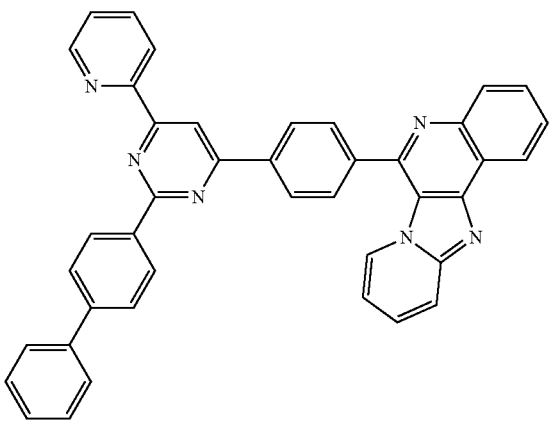
121 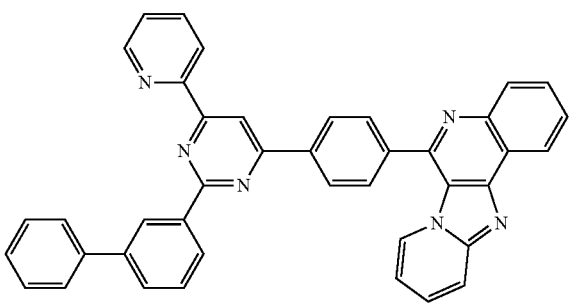
122 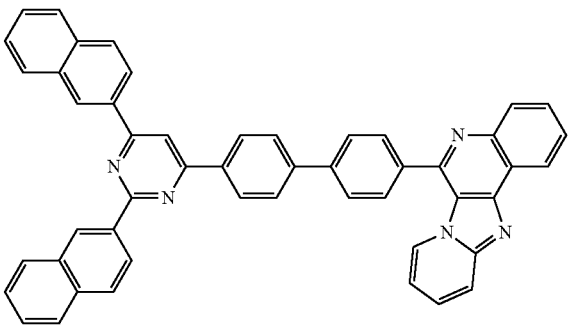
123 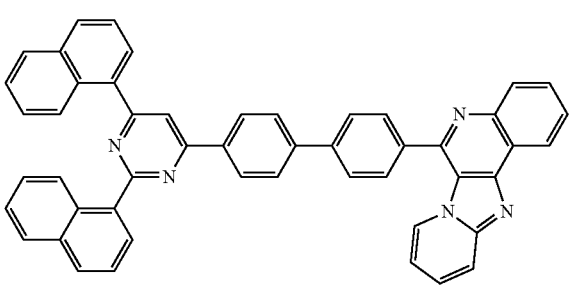

124
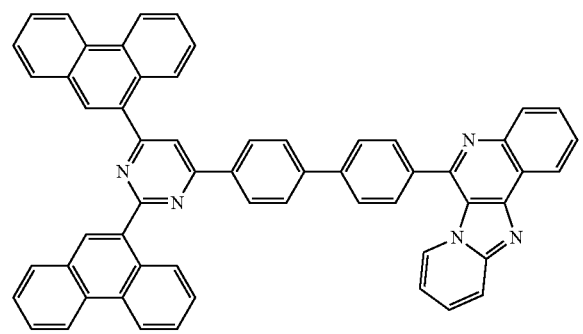
125
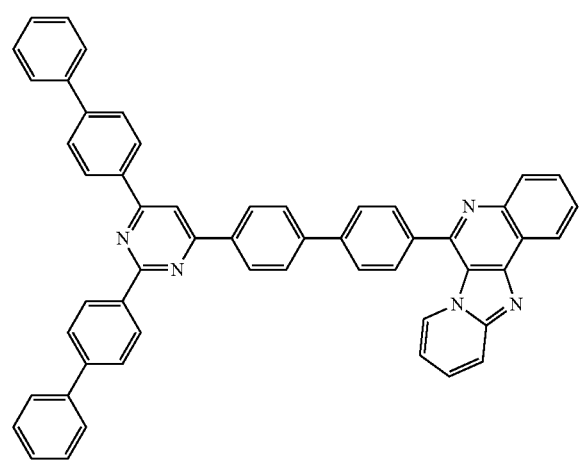
126
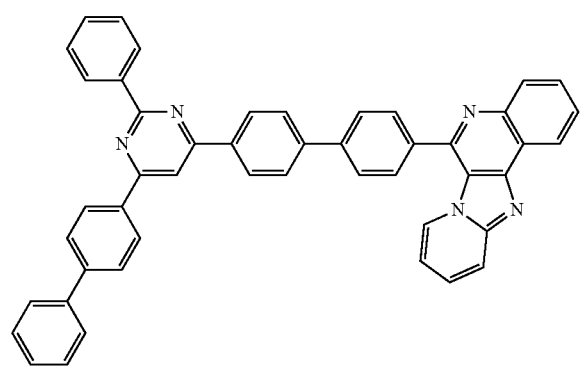
127
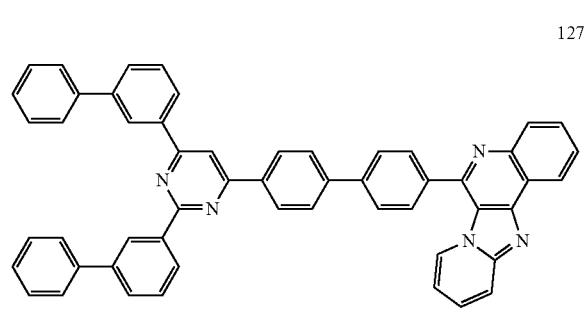
128
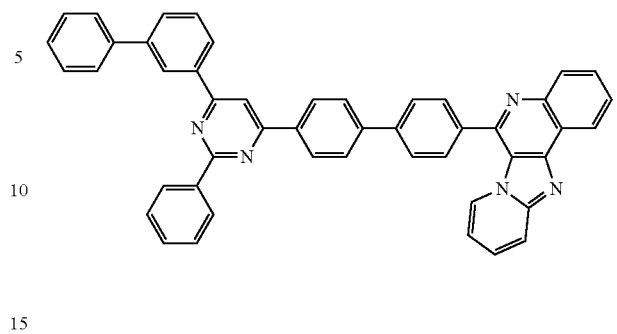
129
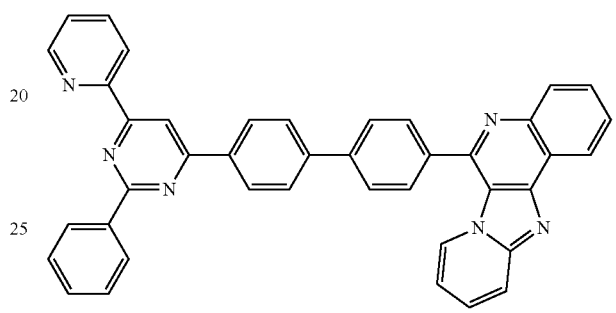
130
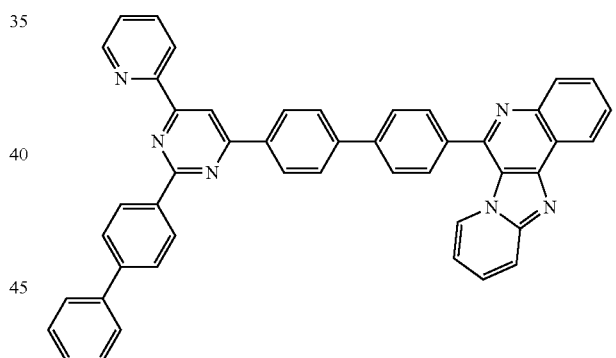
131
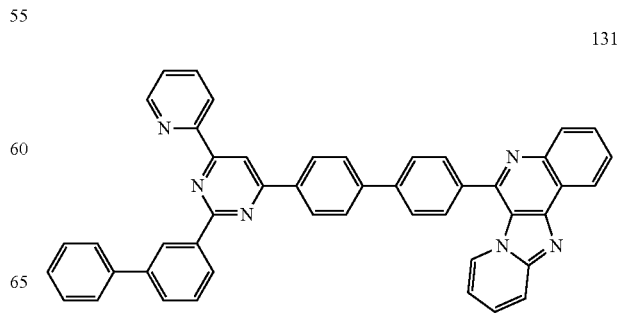

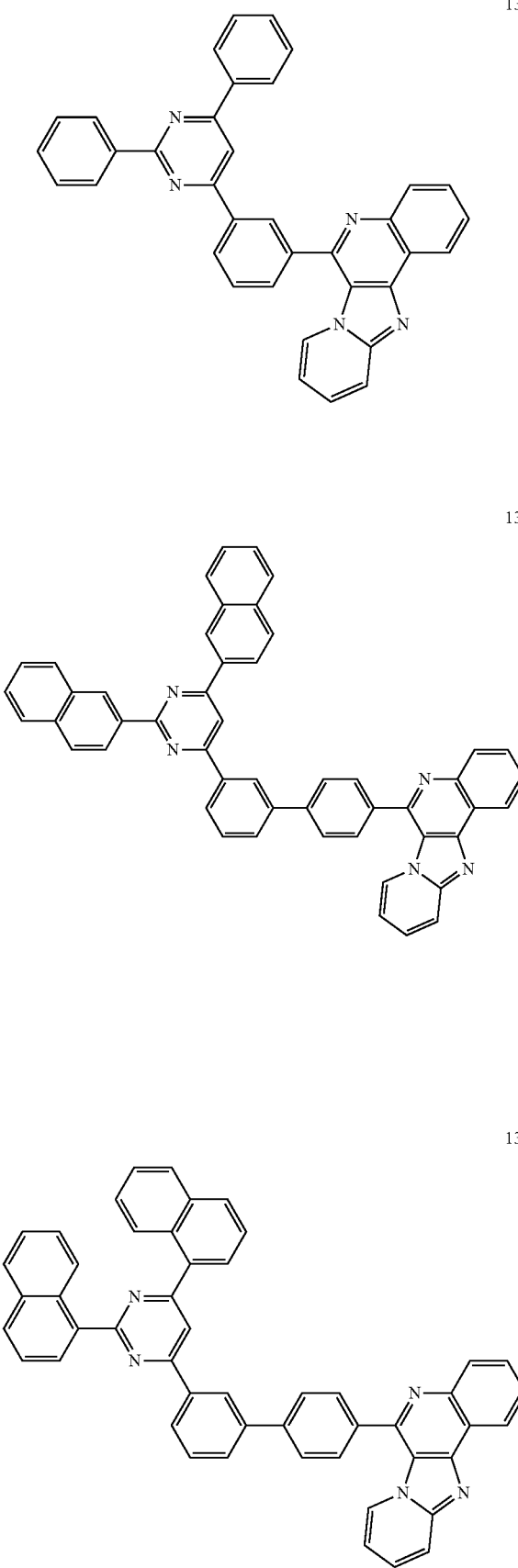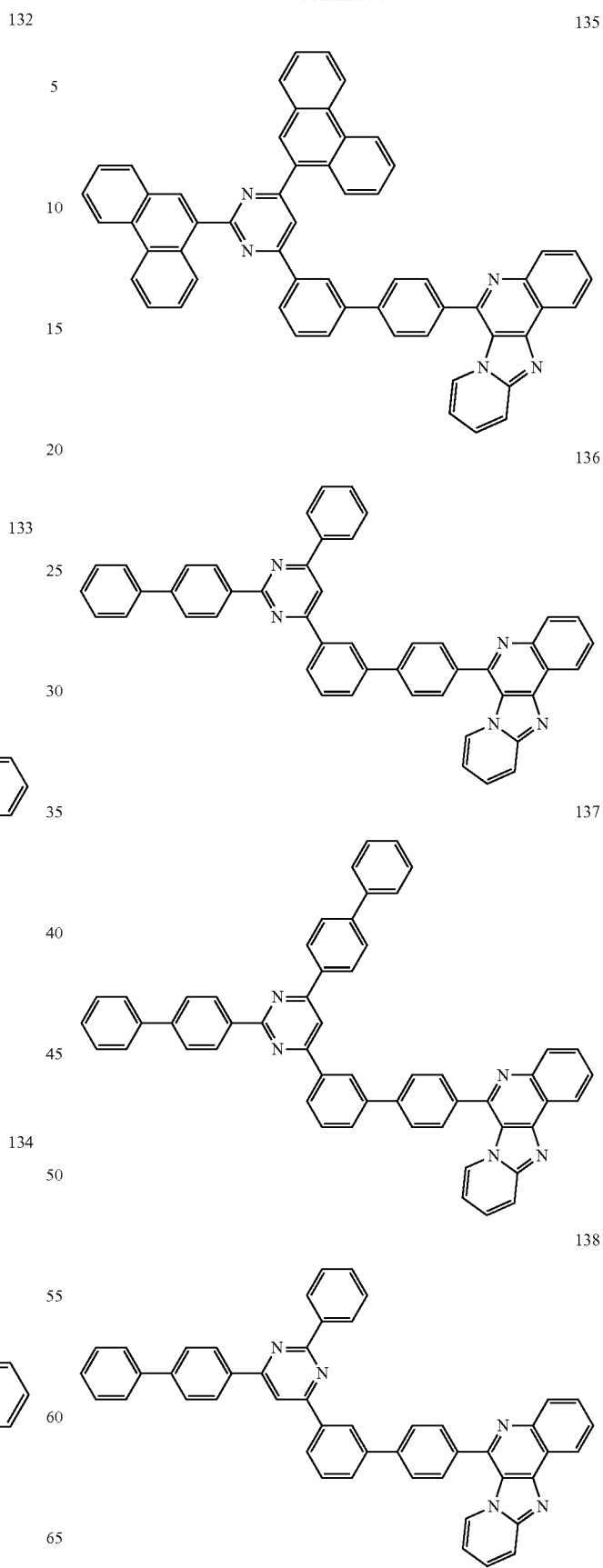

139
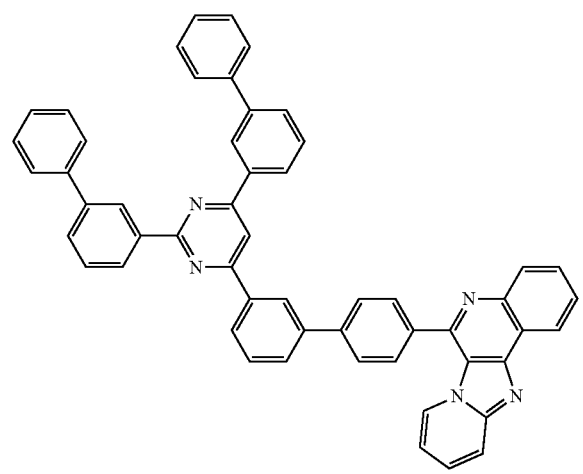
140
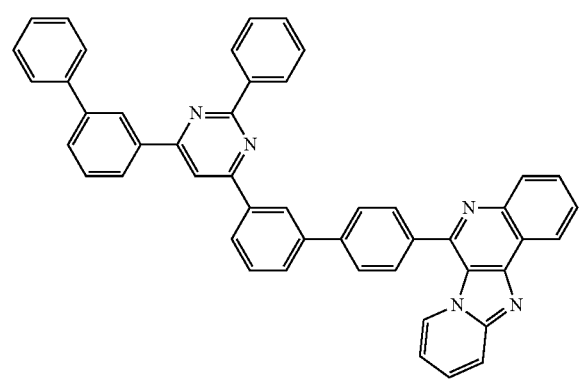
141
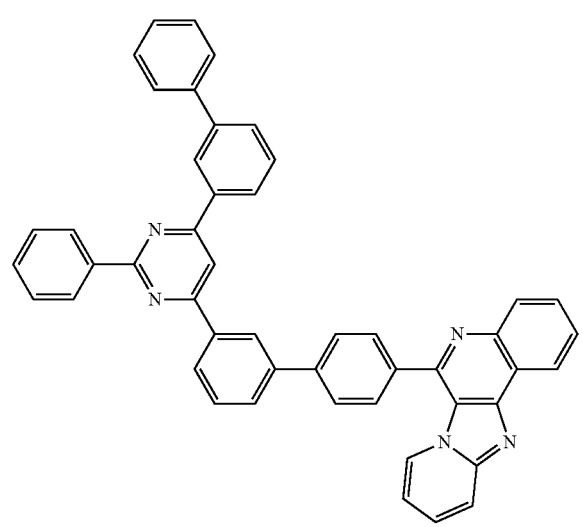
142
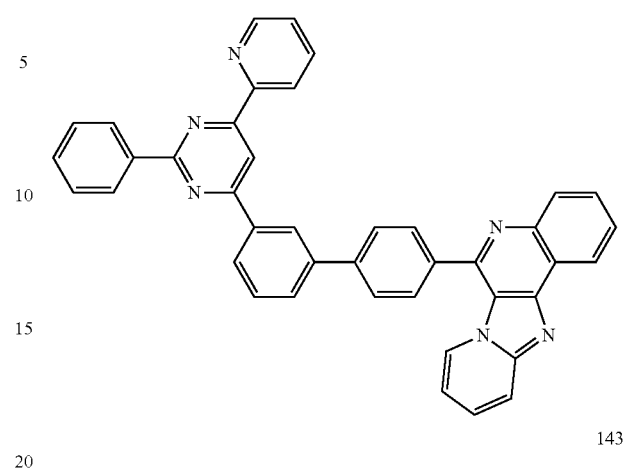
143
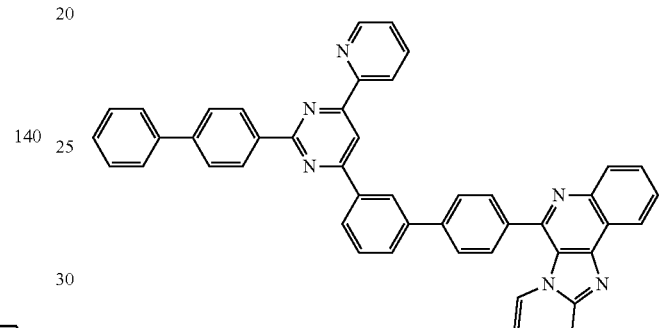
144
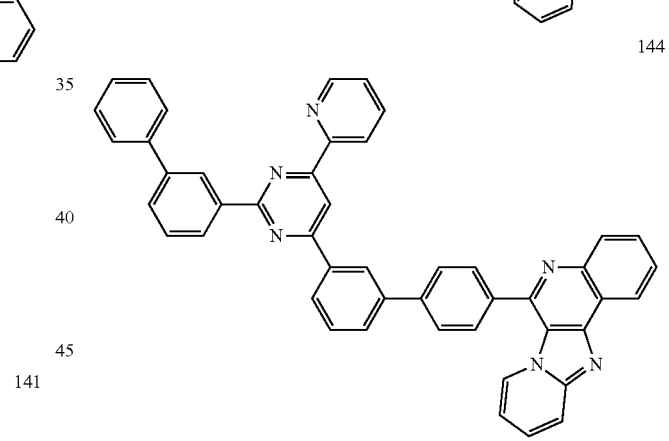
145
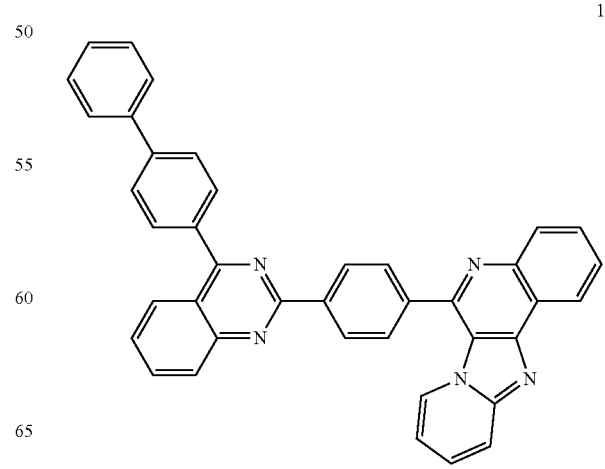

146
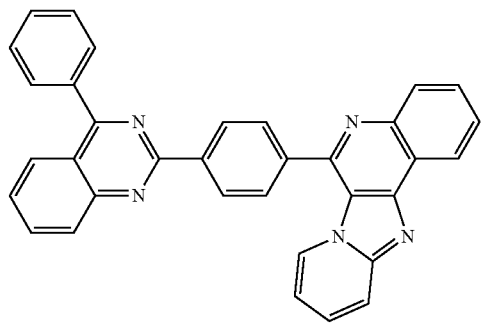
147
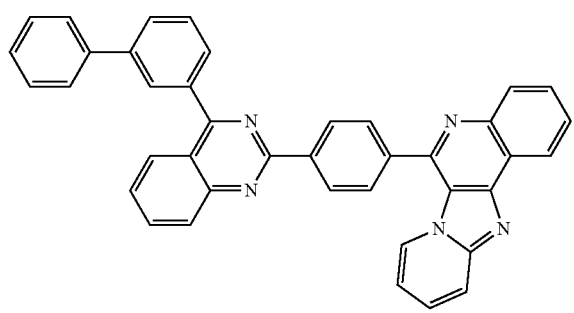
148
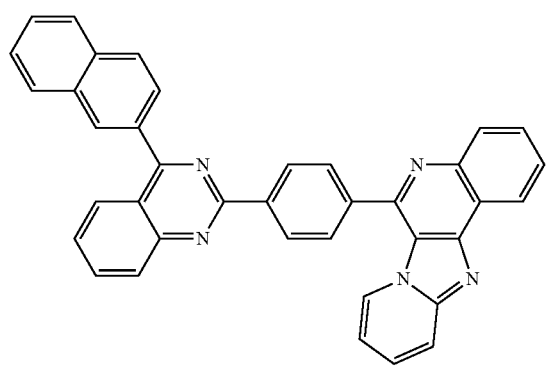
149
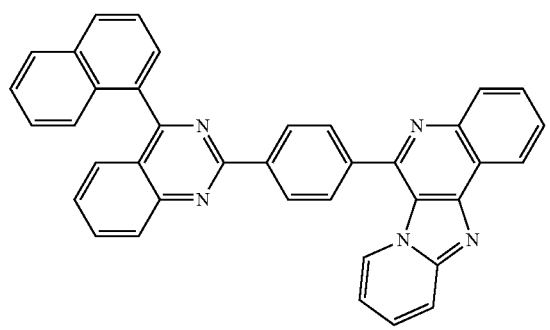
150
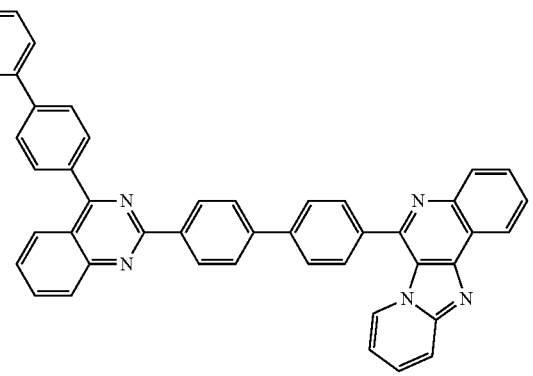
151
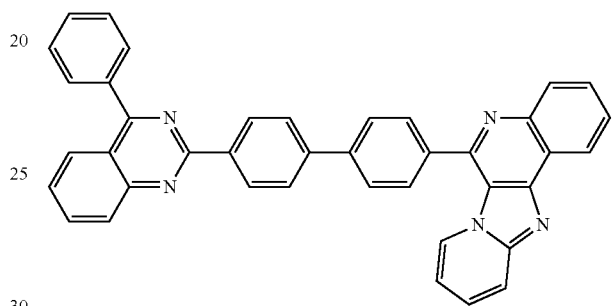
152
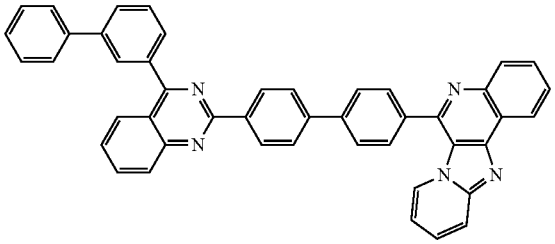
153
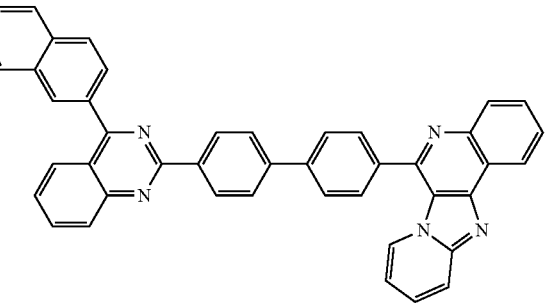
154
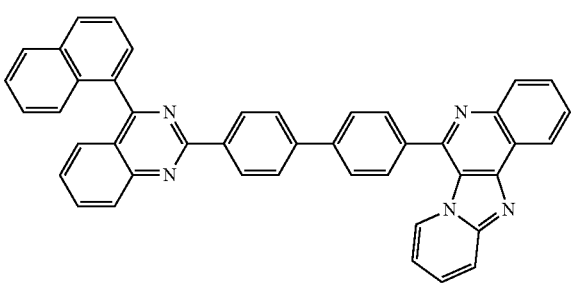

155
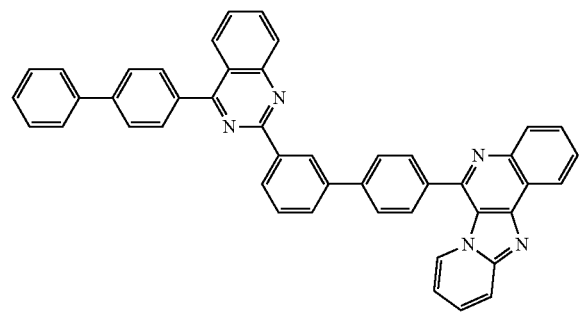
156
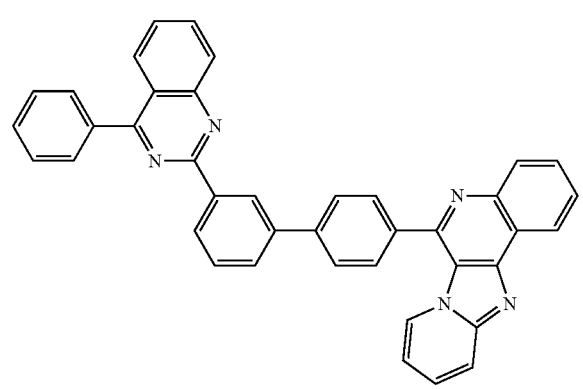
157
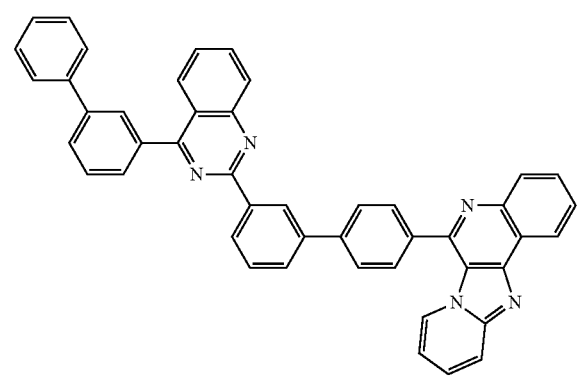
158
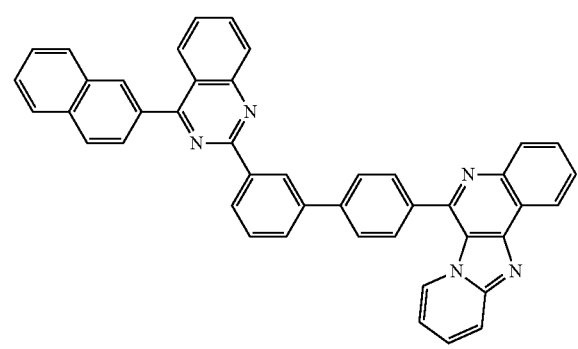
159
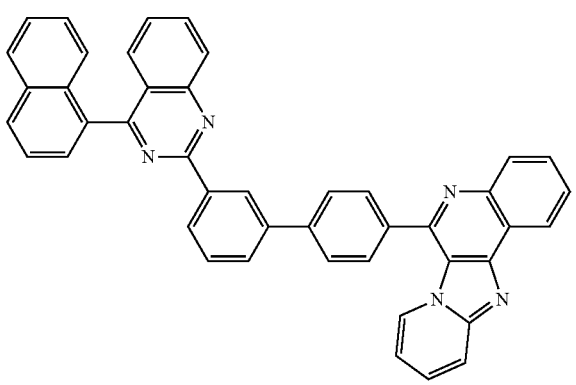
160
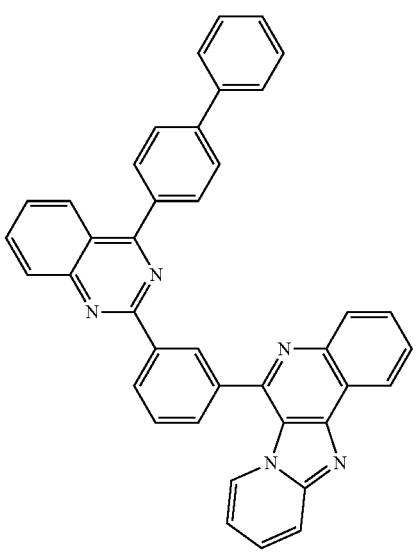
161
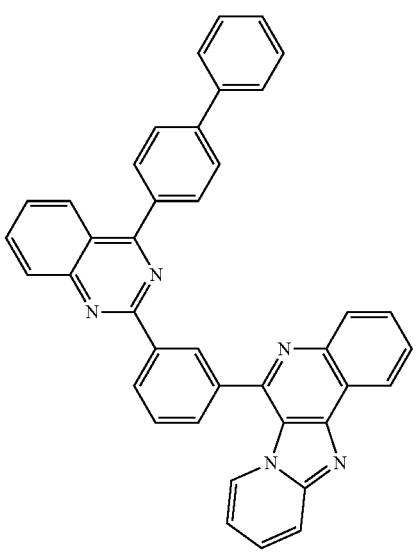

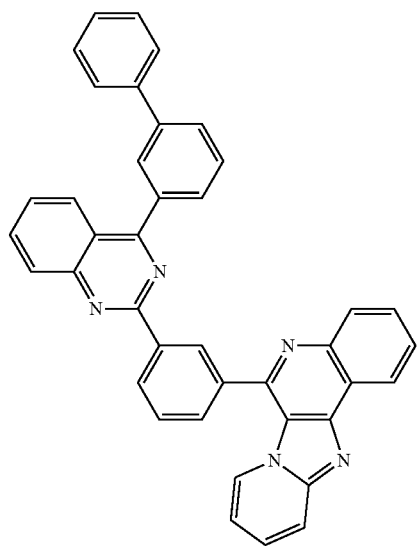
162
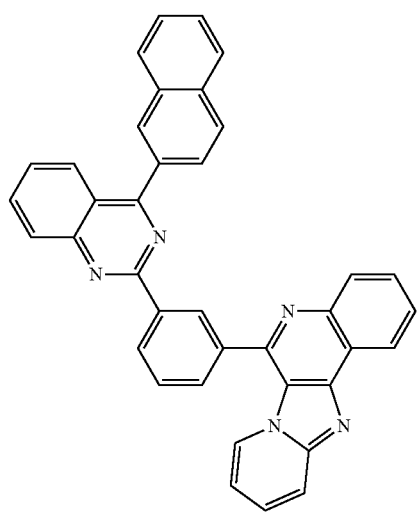
163
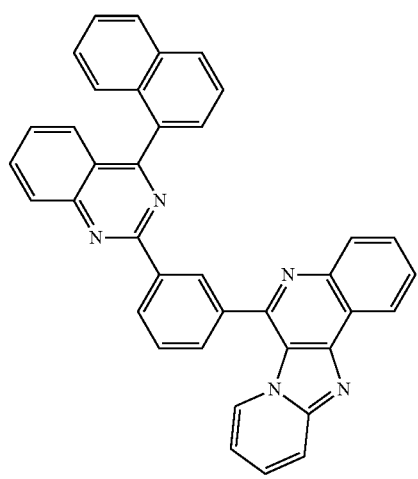
164
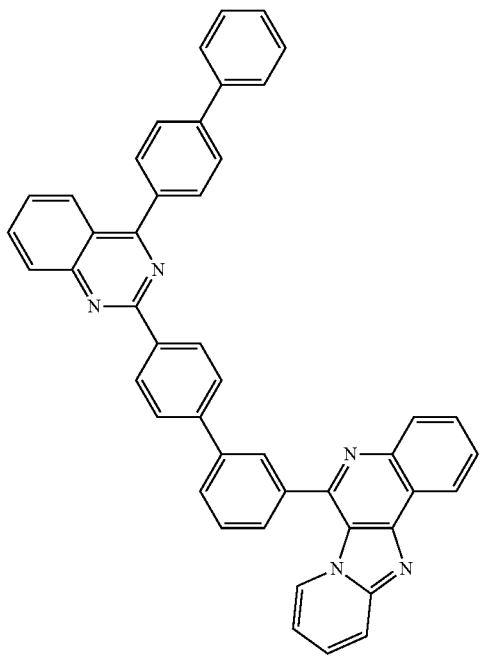
165
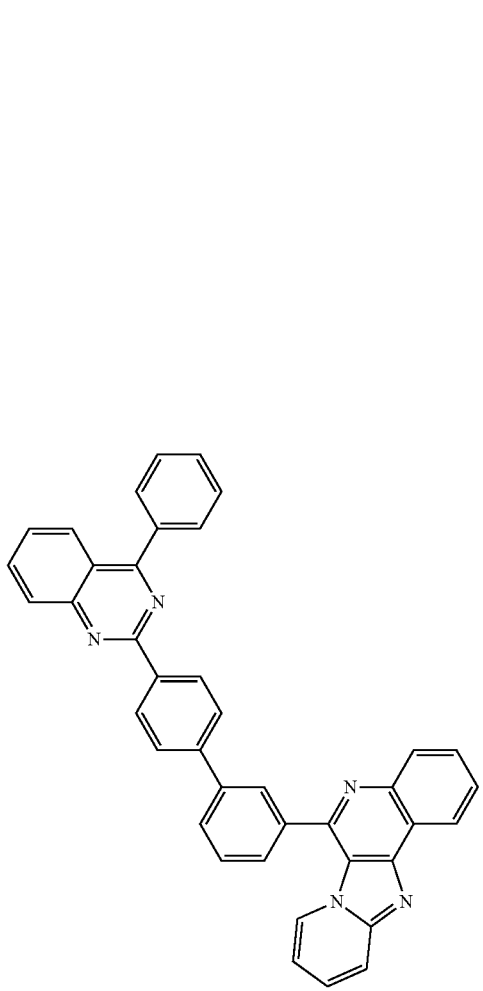
166

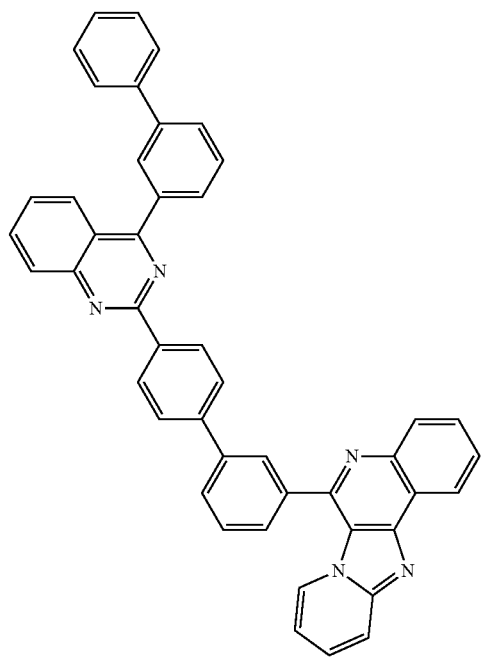
167
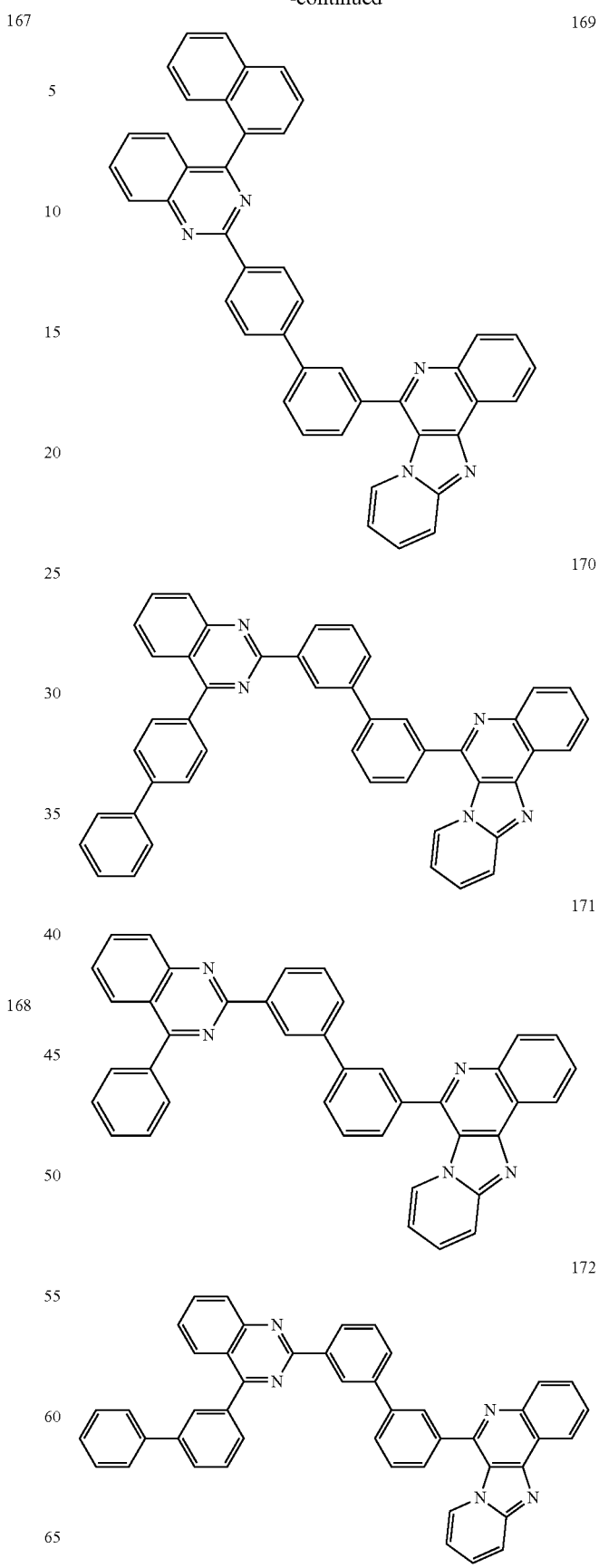

173
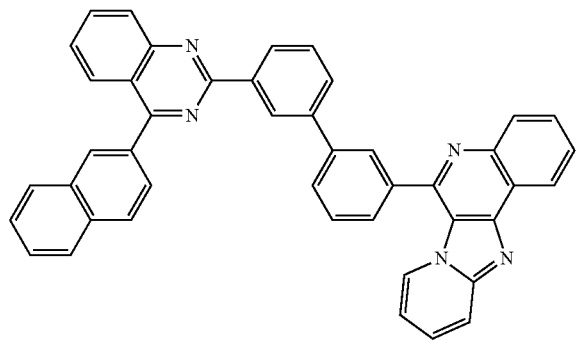
174
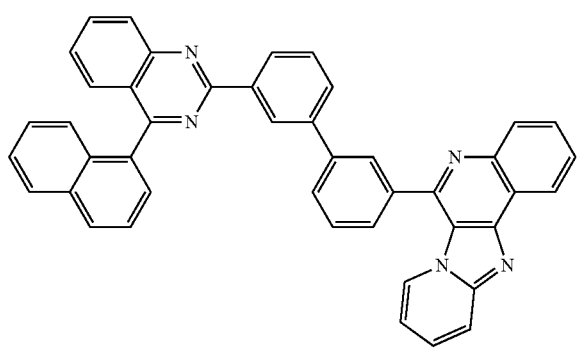
175
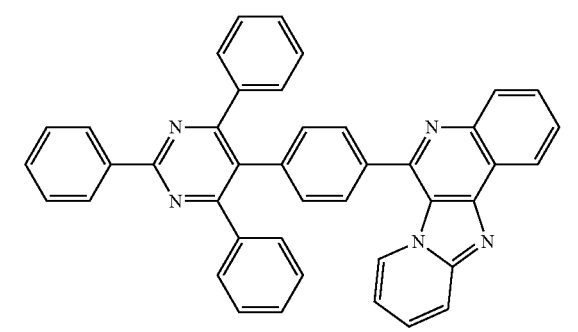
176
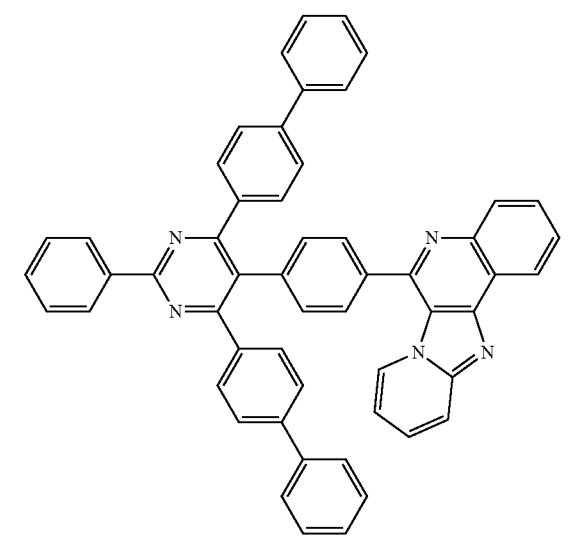
177
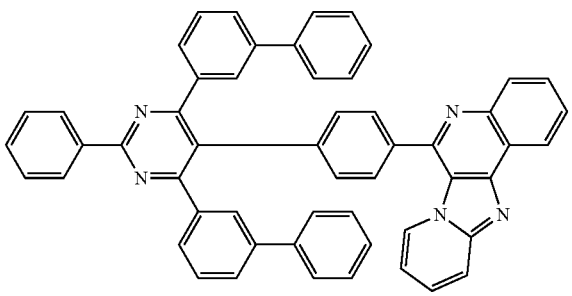
178
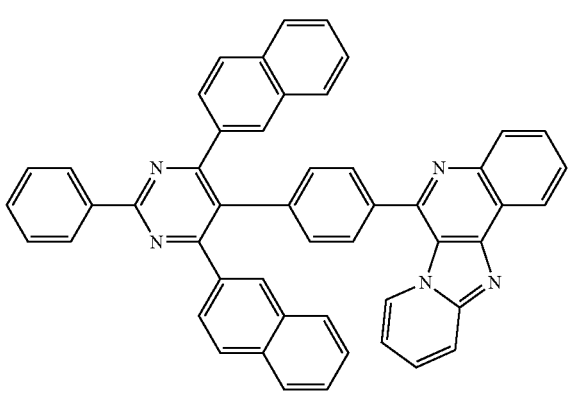
179
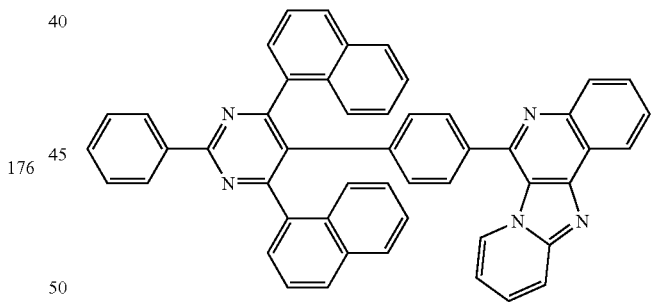
180
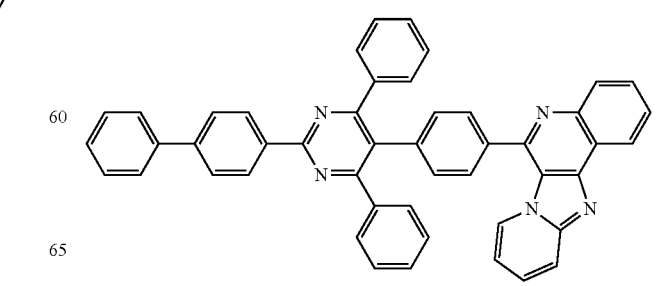

181
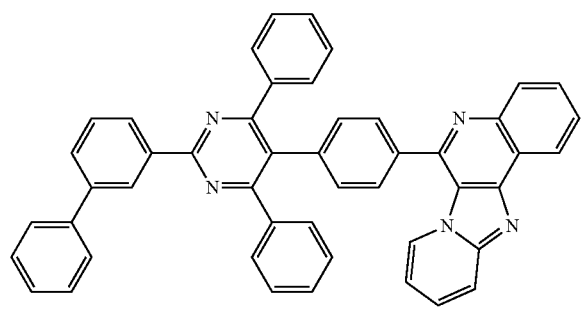
182
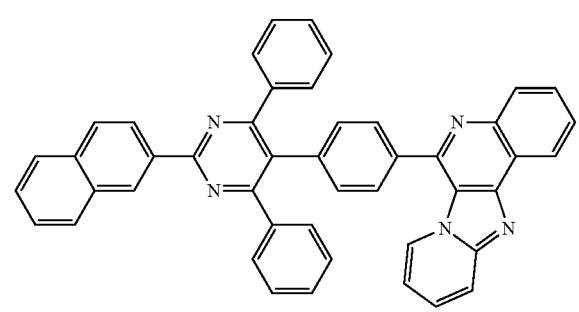
183
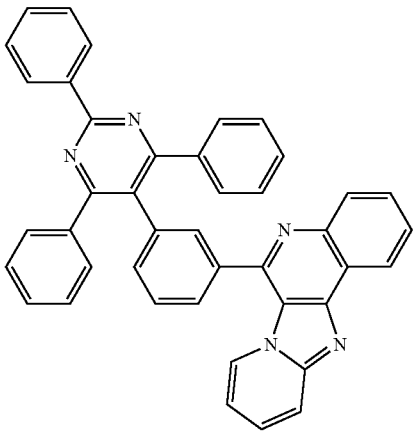
184
185
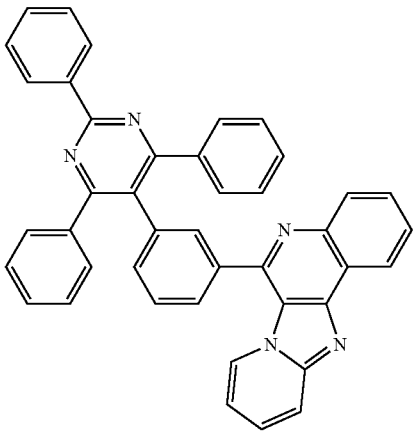
186
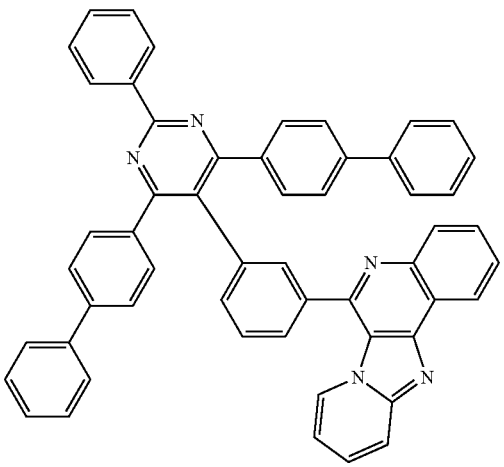
187
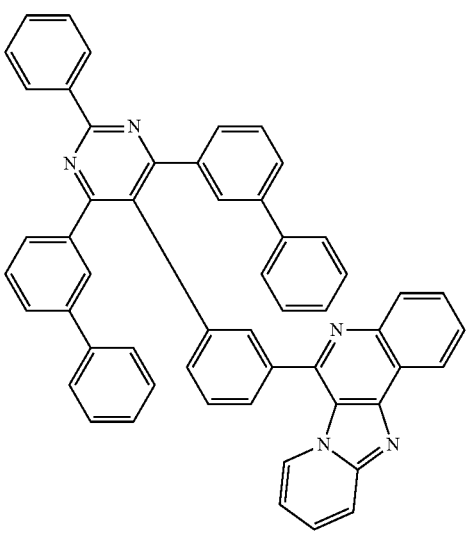

188
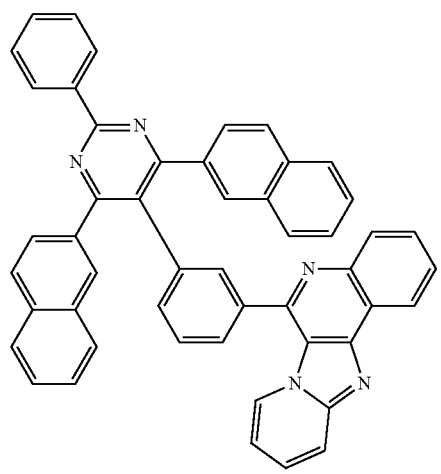
189
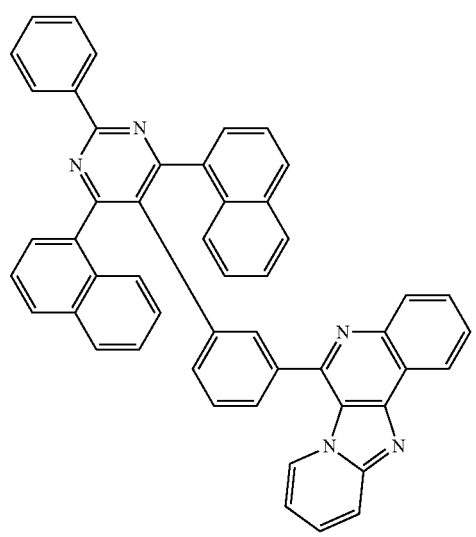
190
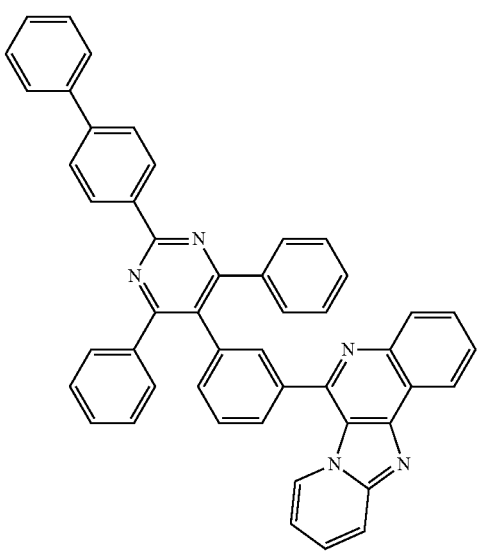
191
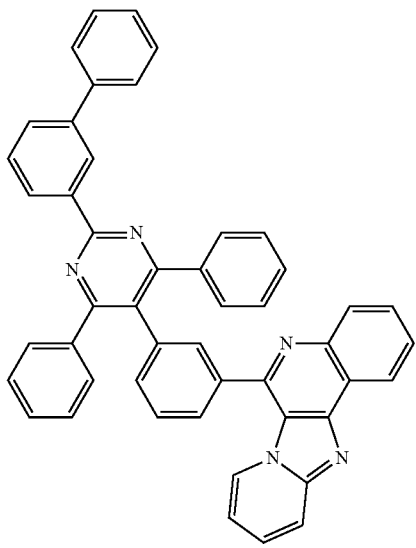
192
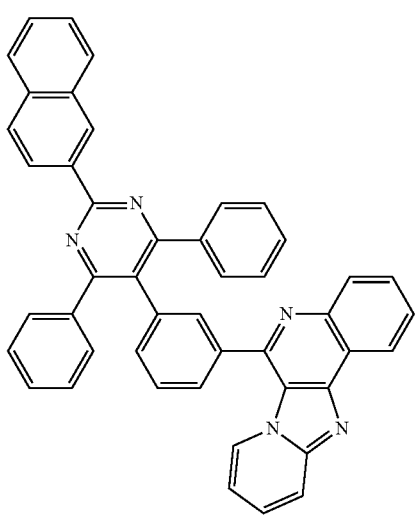
193
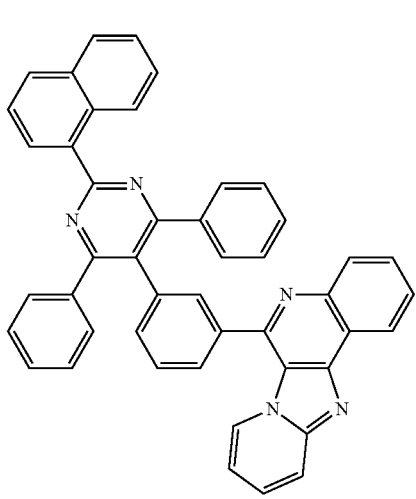

194
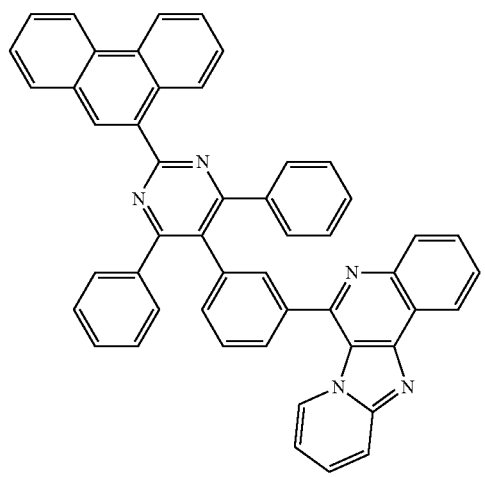
195
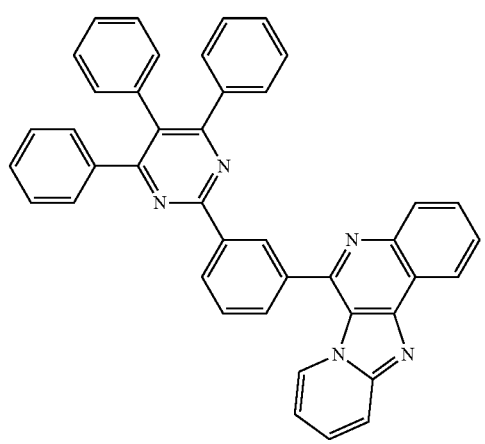
196
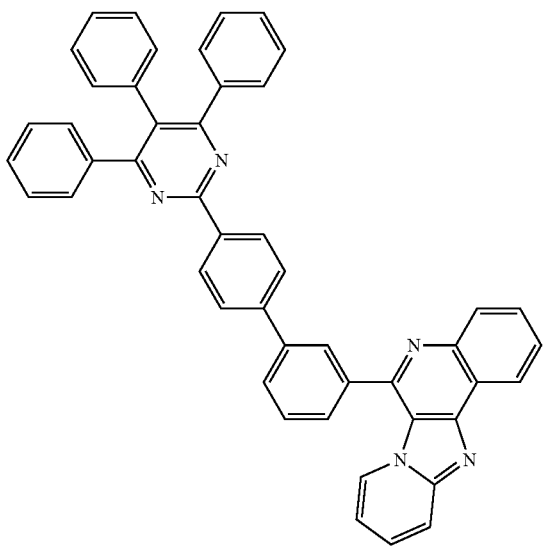
197
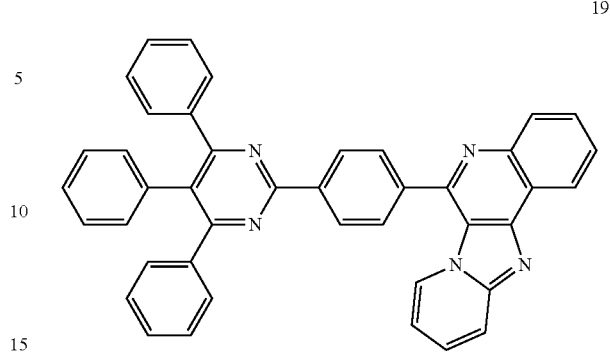
198
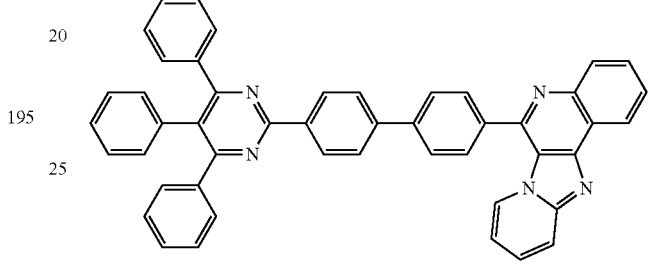
199
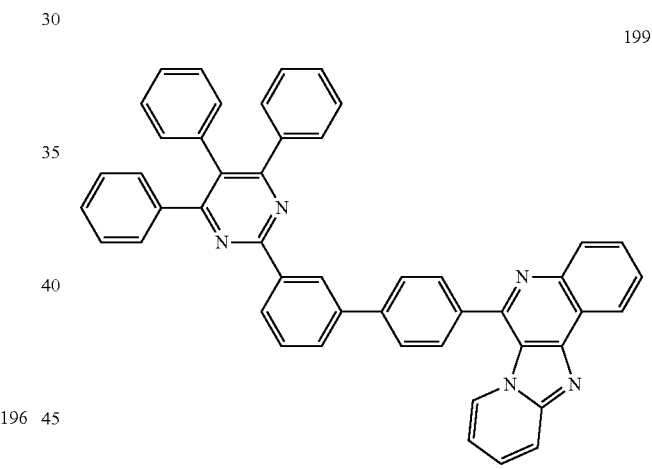
200
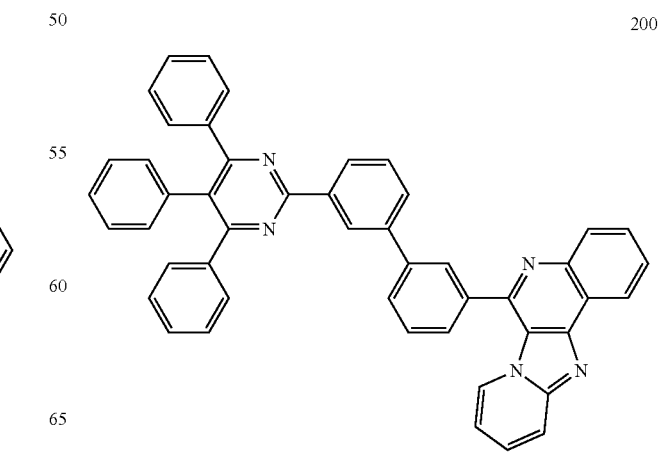

-continued
201
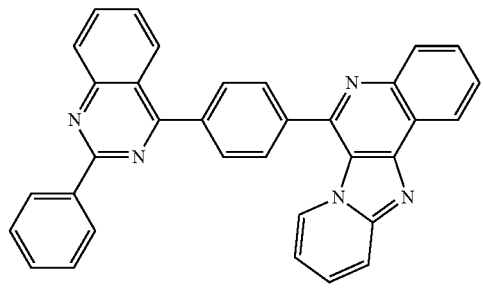
202
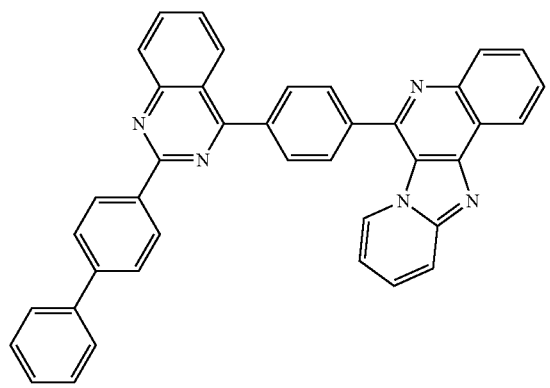
203
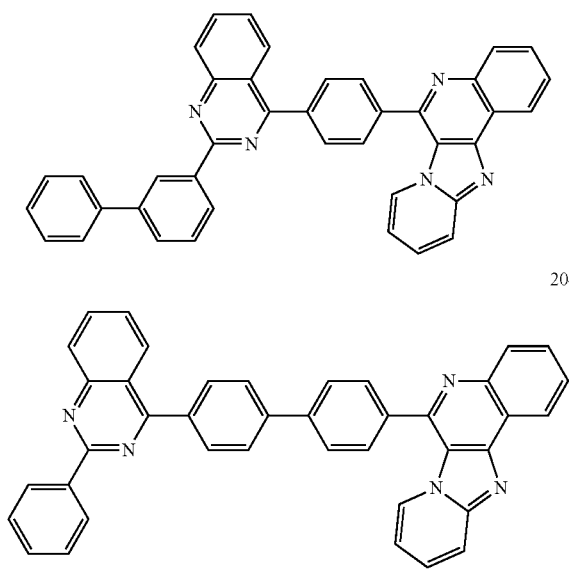
204
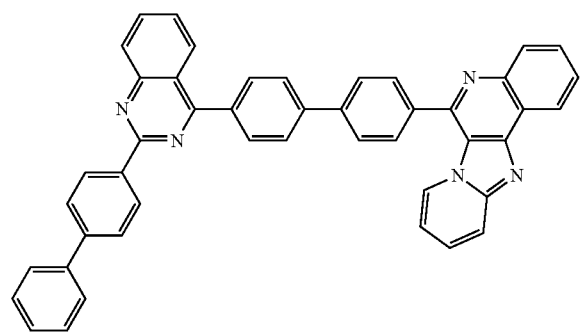
-continued
206
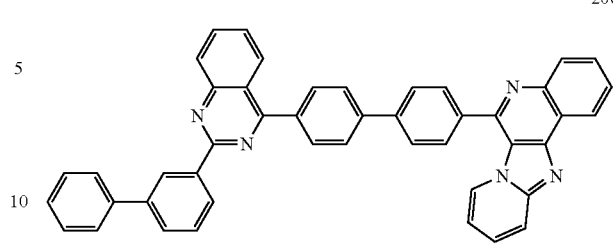
207
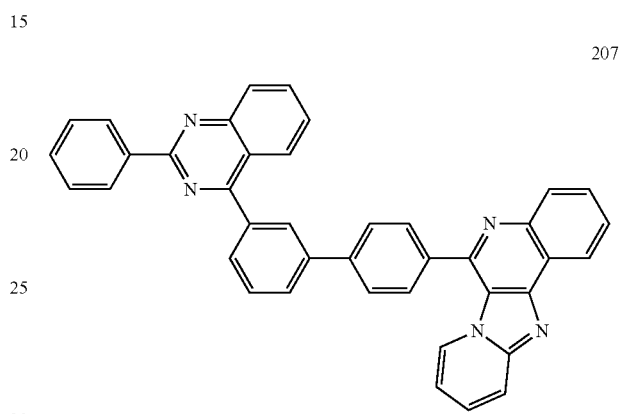
208
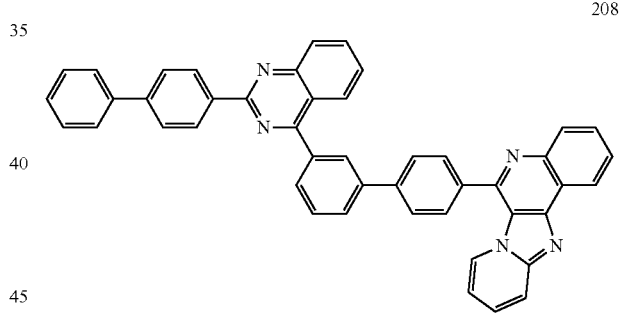
209
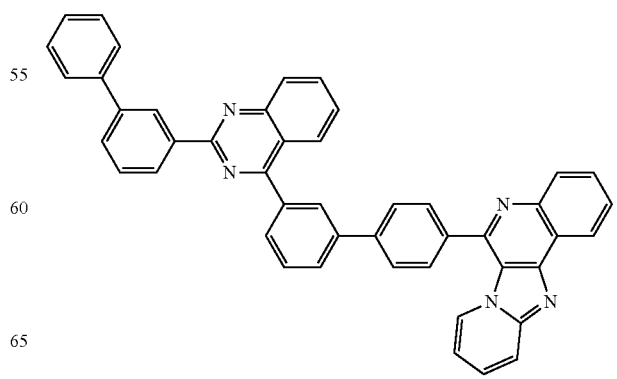

210
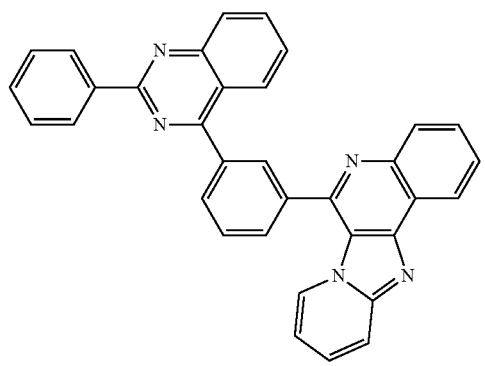
211
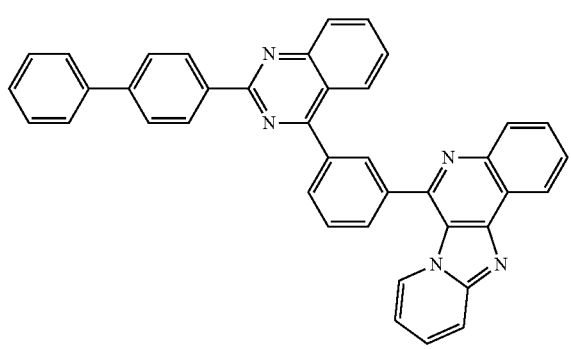
212
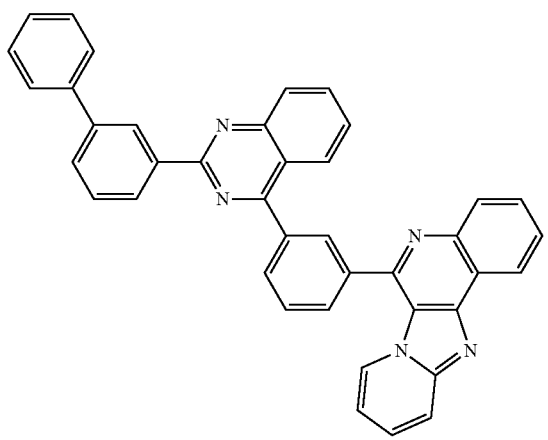
213
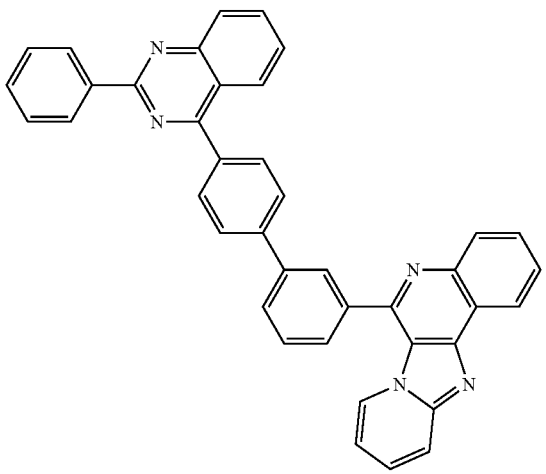
214
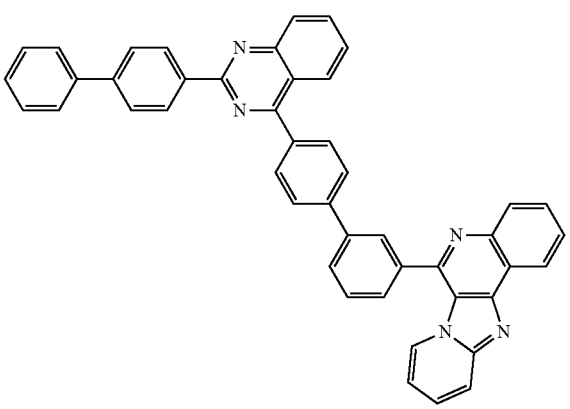
215
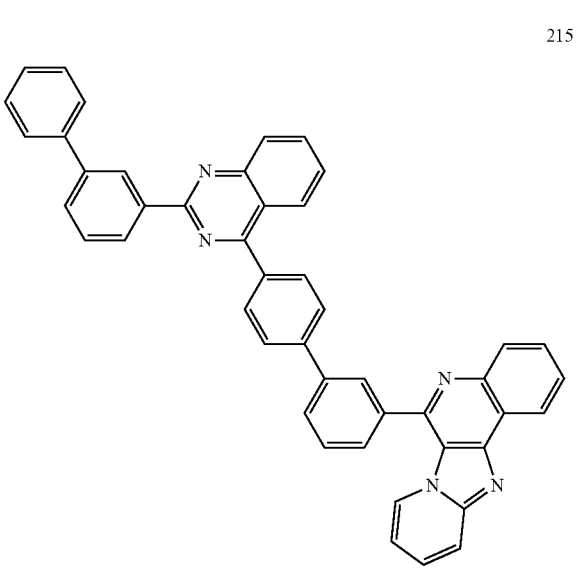

216
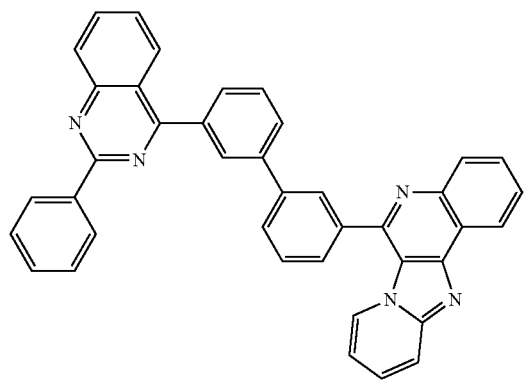
217
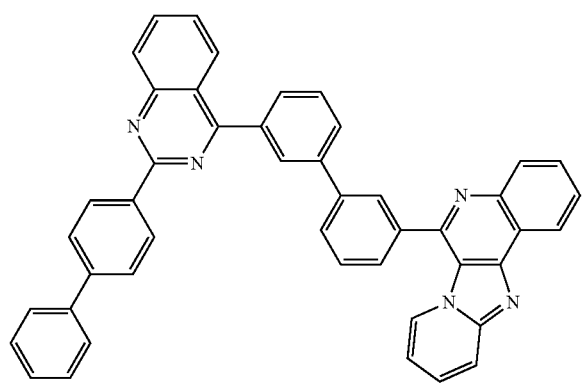
218
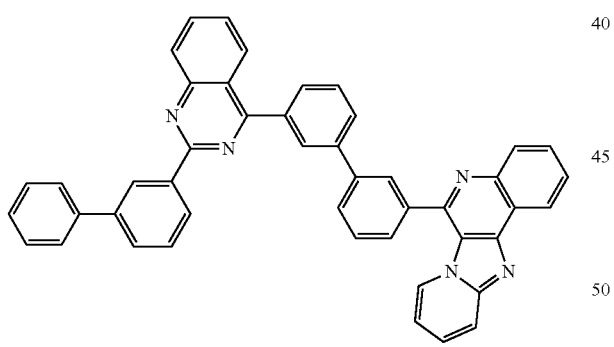
219
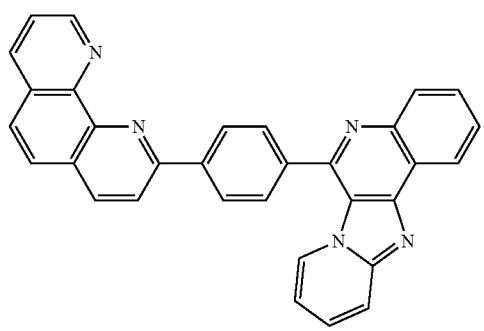
220
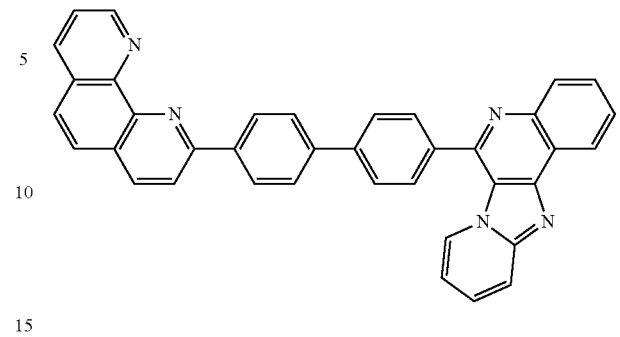
221
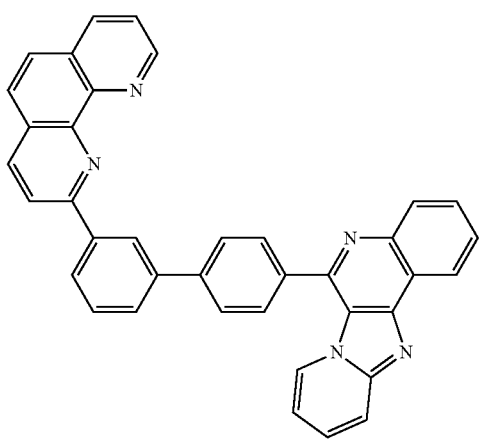
222
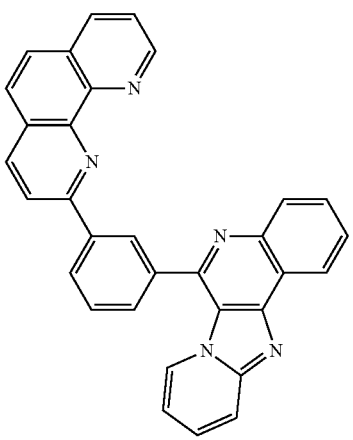

223
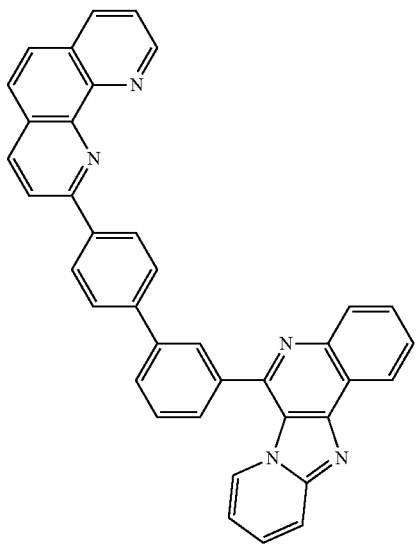
224
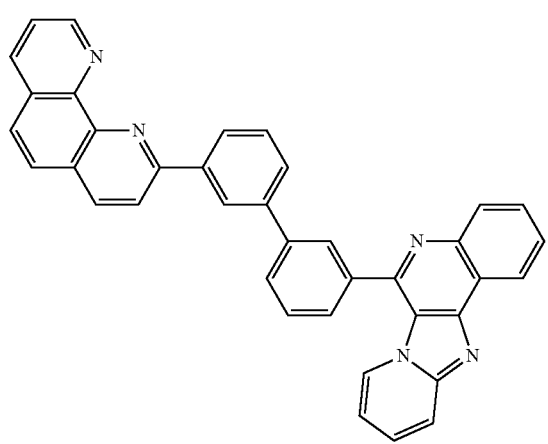
225
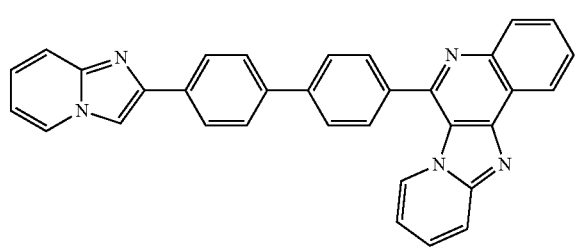
226
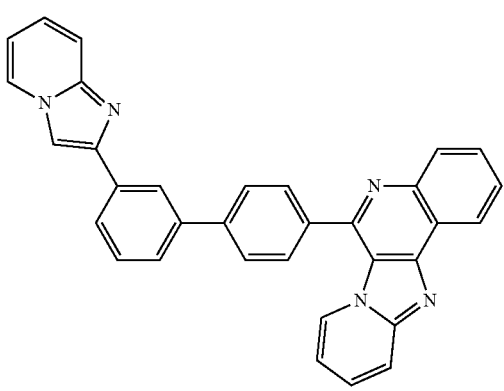
227
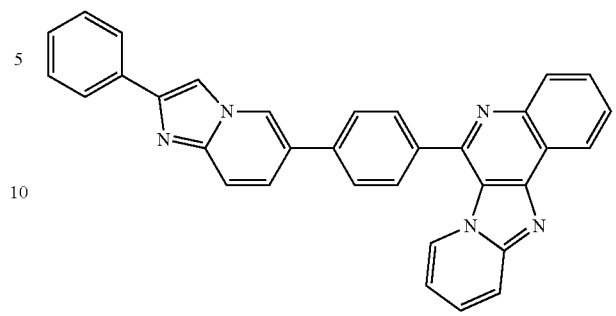
228
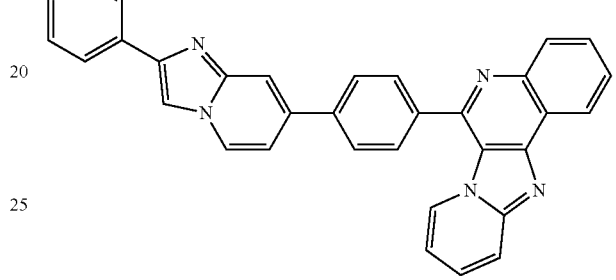
229
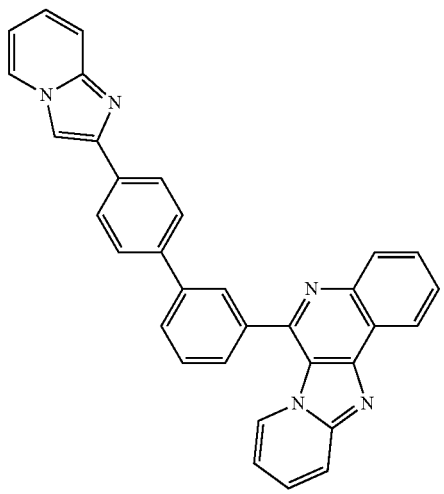
230
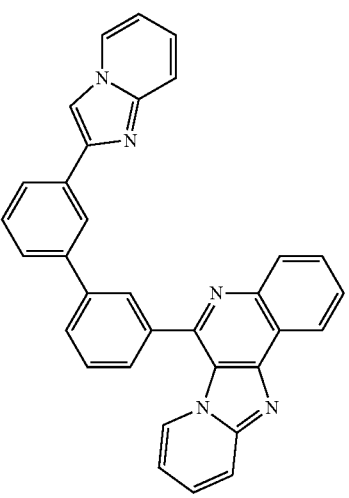

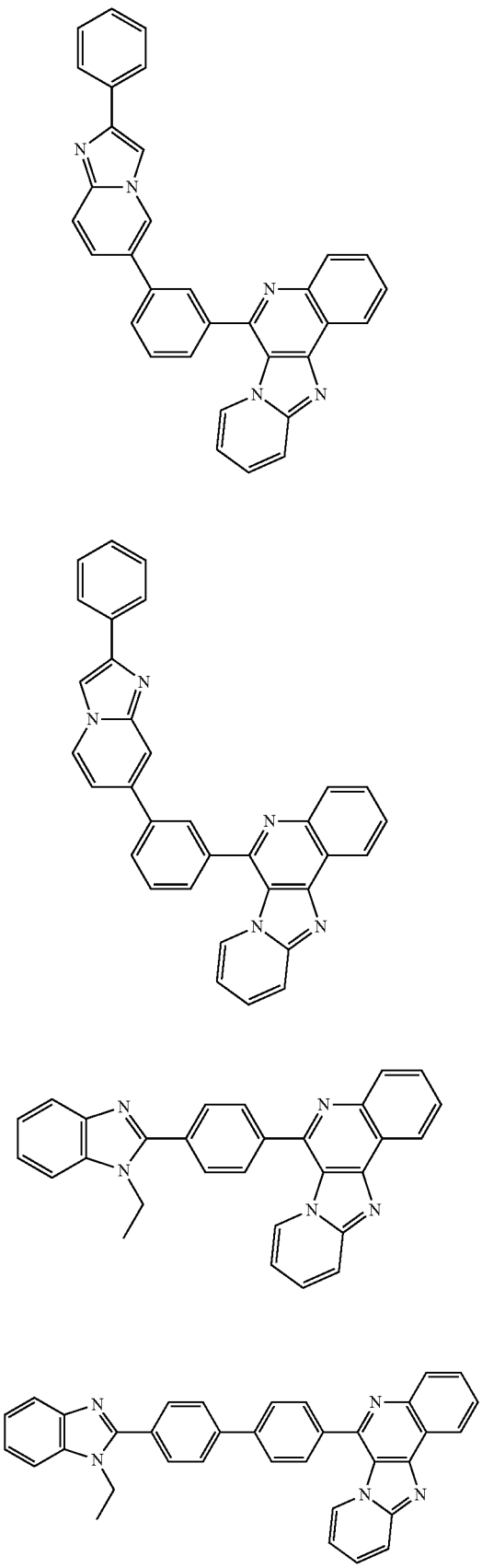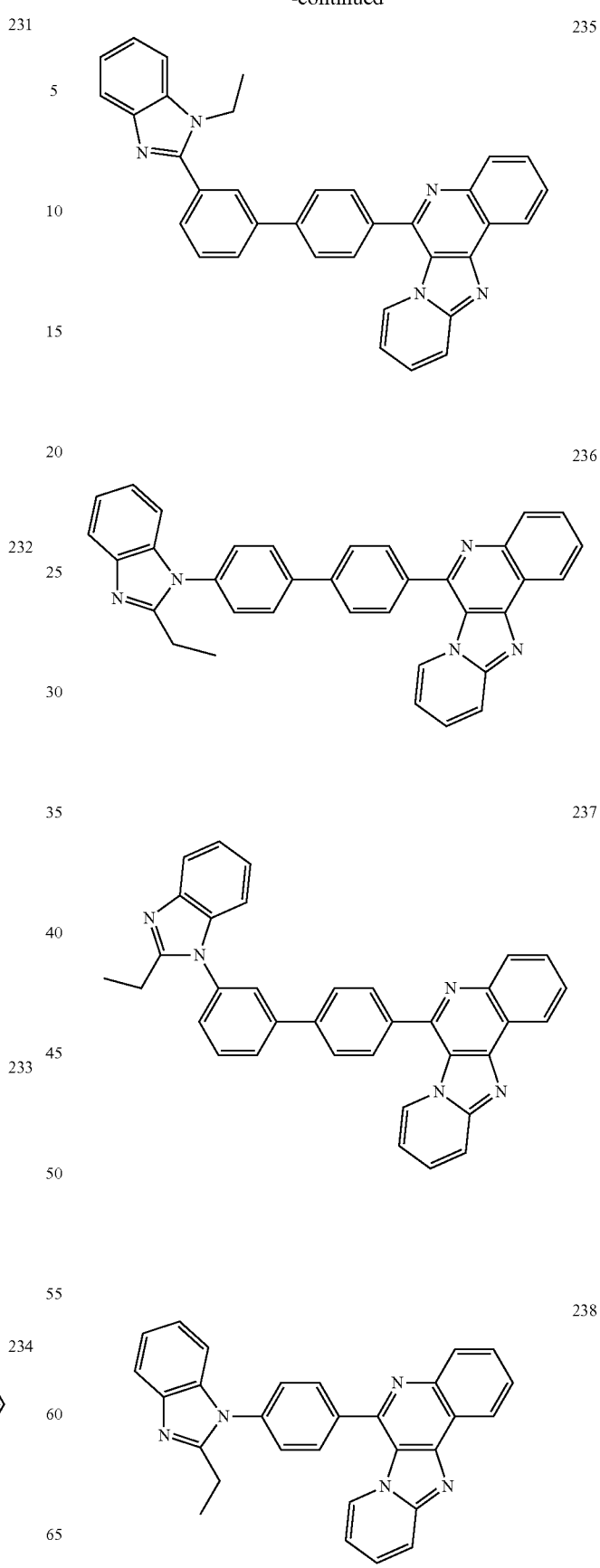

239
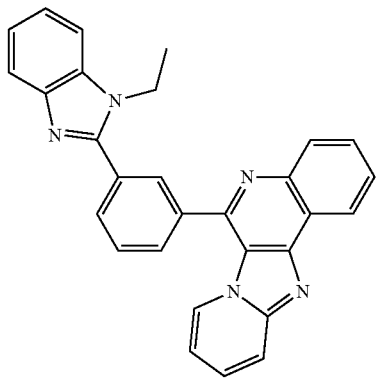
240
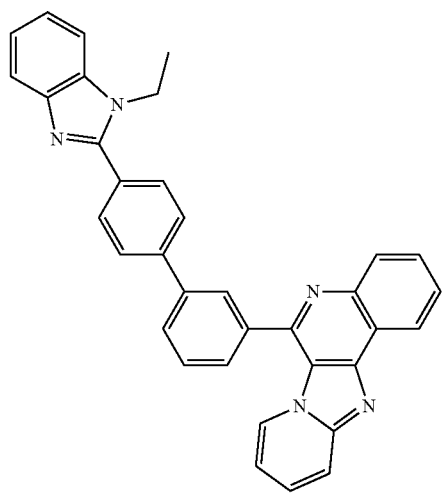
241
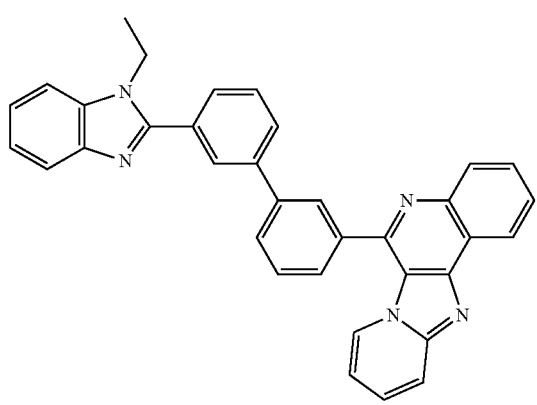
242
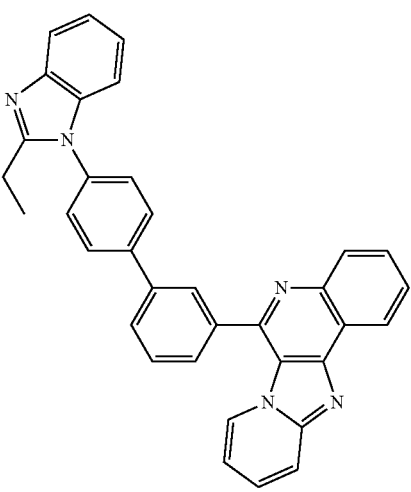
243
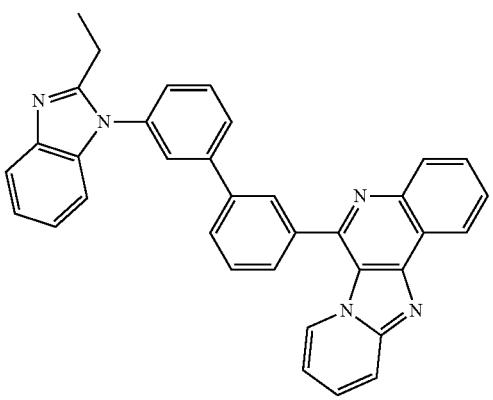
244
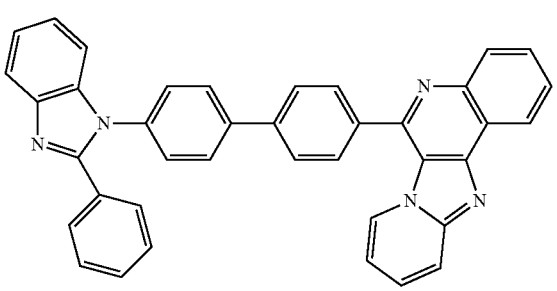
245

-continued
246
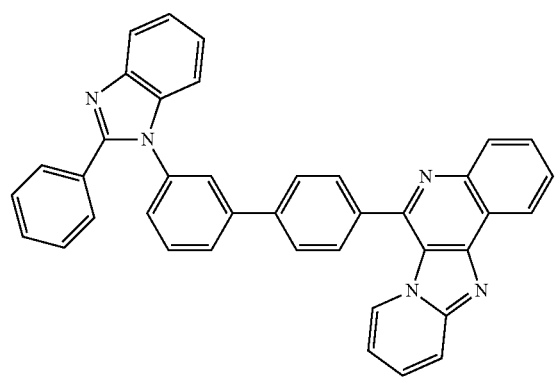
247
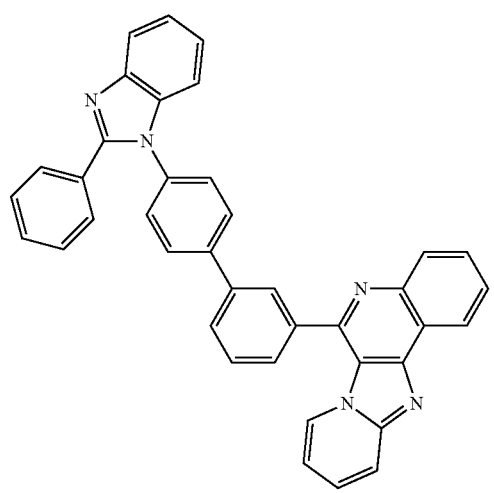
248
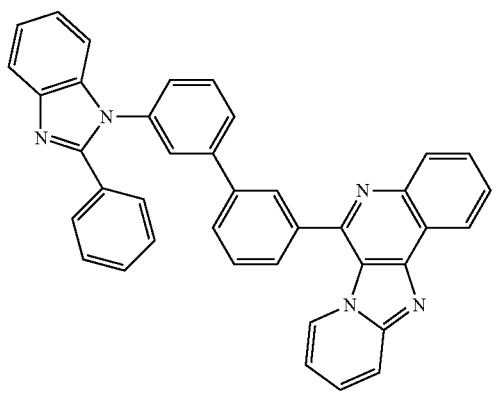
249
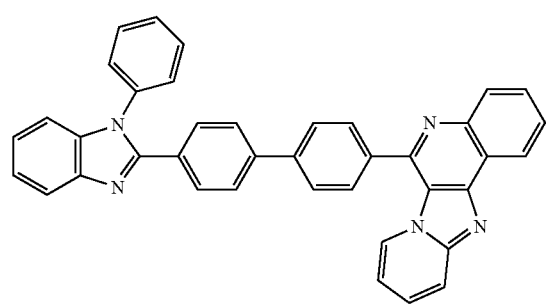
-continued
250
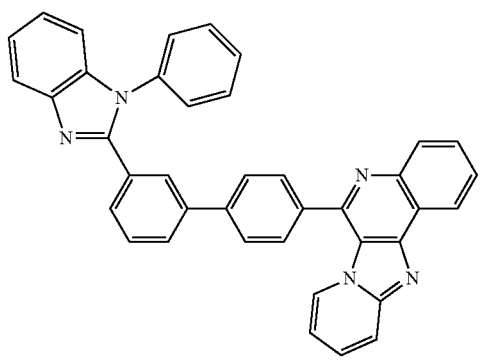
251
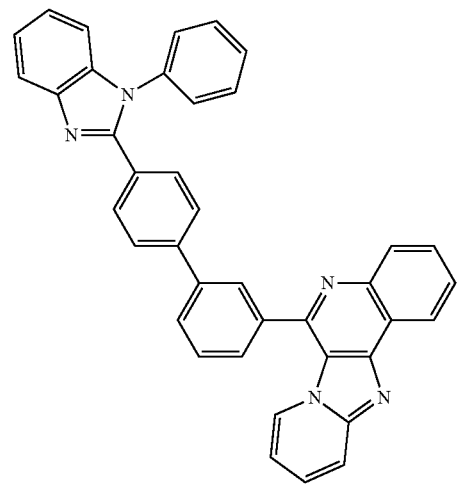
252
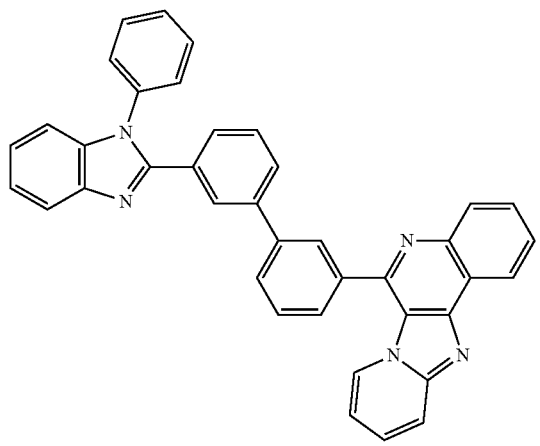
253
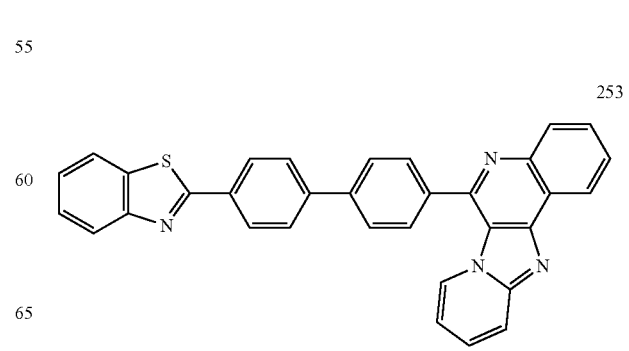

254
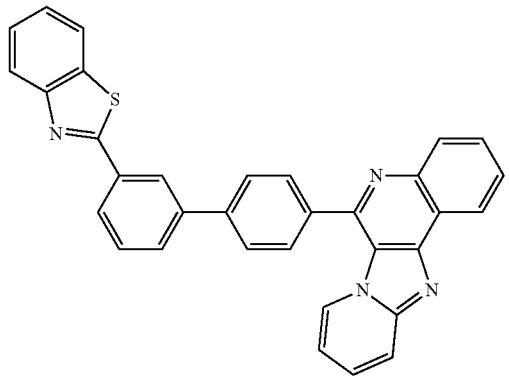
255
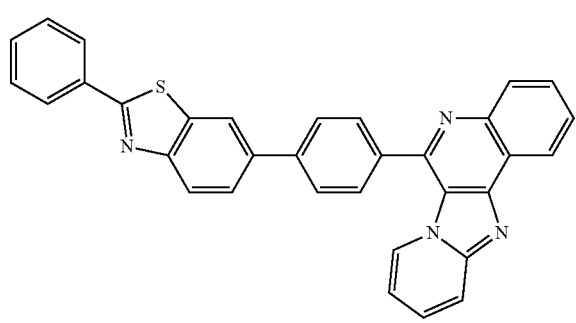
256
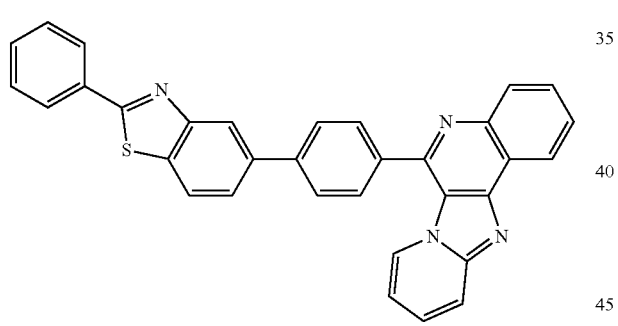
257
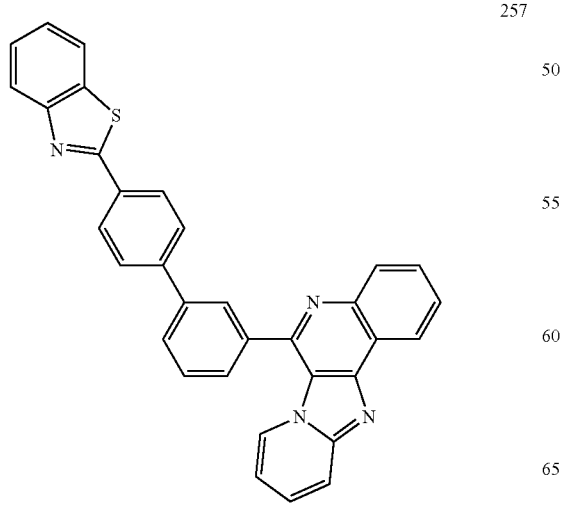
258
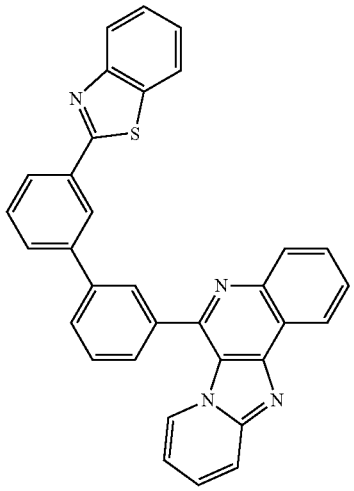
259
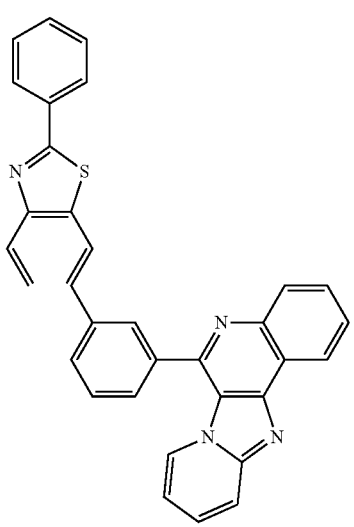
260
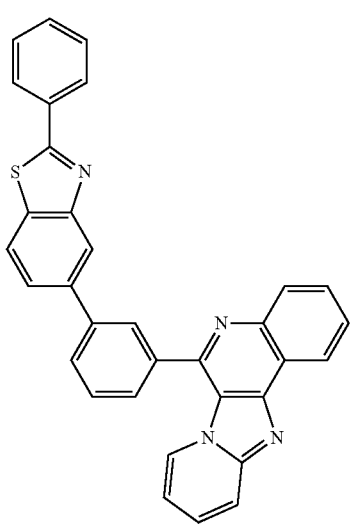

261
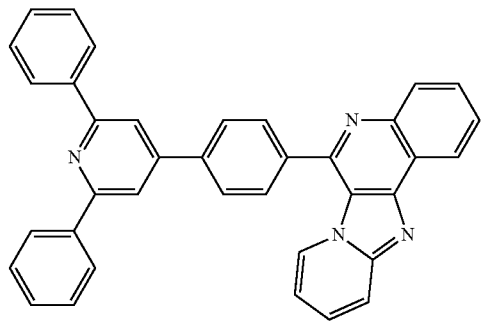
262
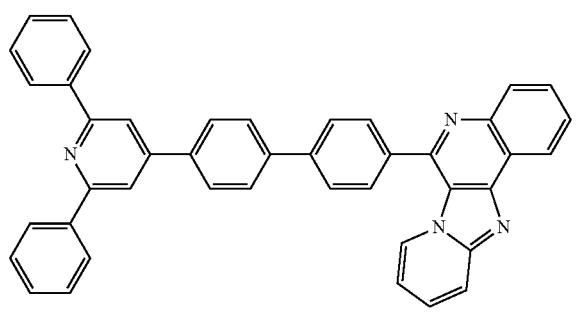
263
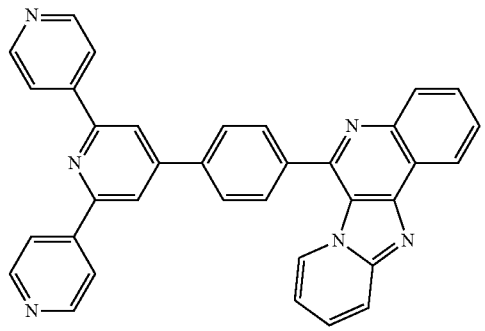
264
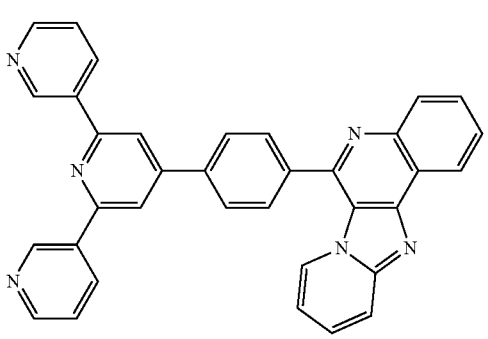
265
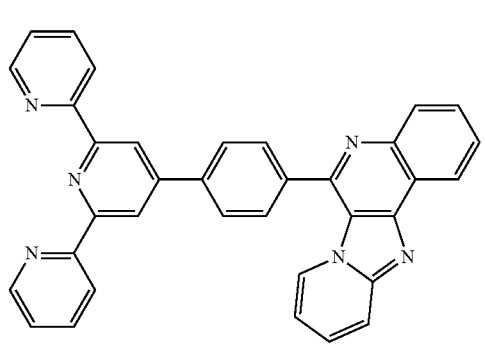
266
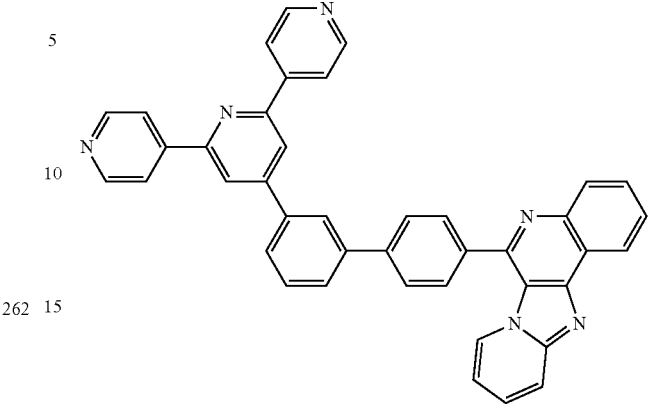
267
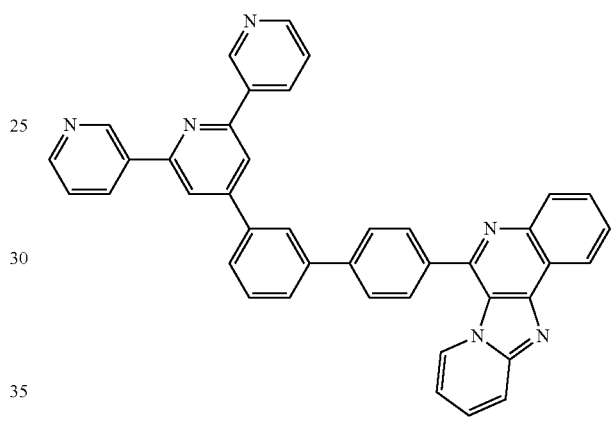
268
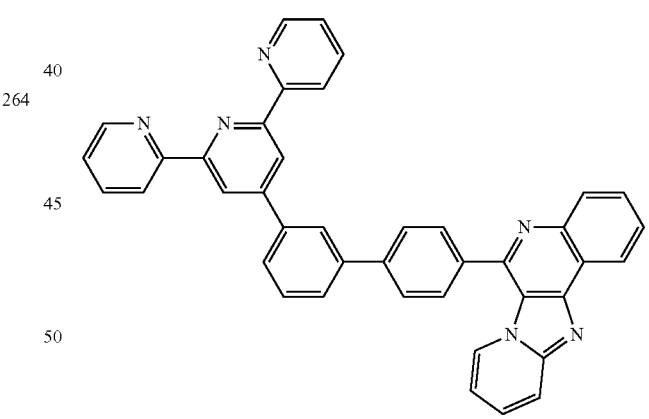
269
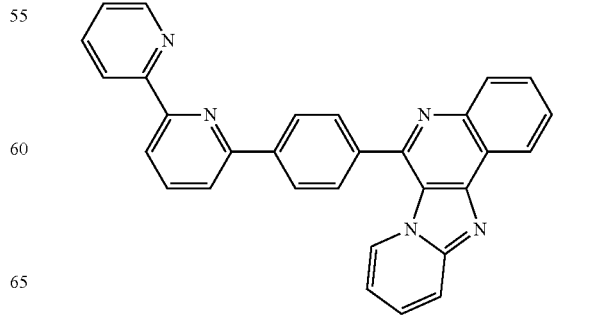

-continued
270
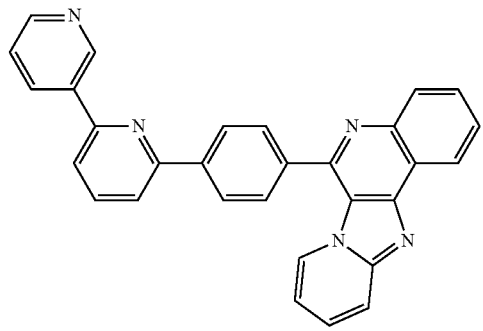
271
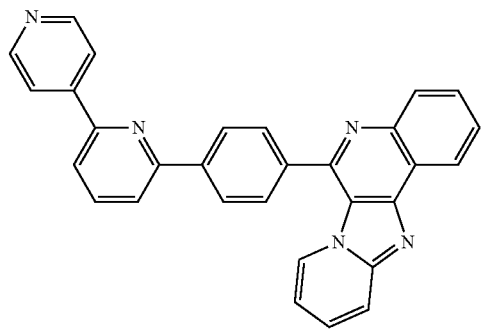
-continued
275
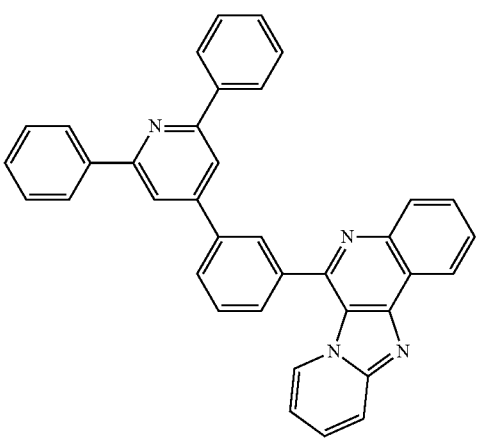
272
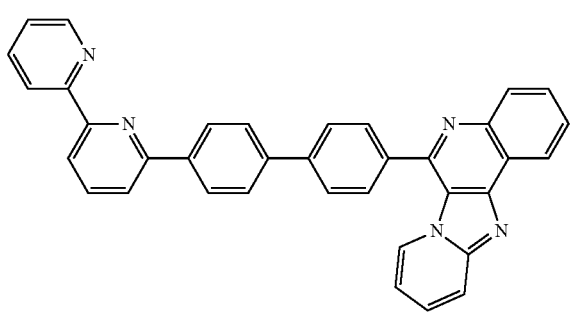
276
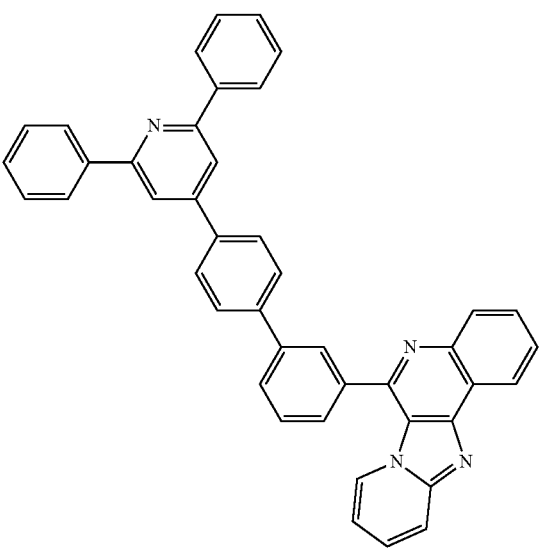
273
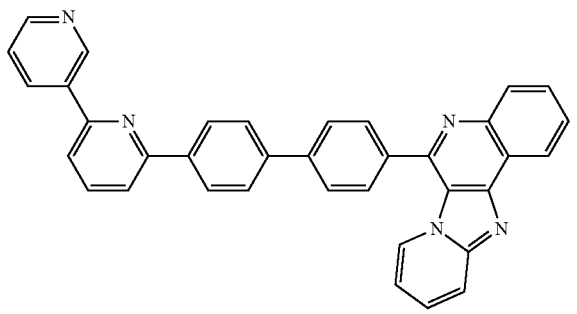
274
277
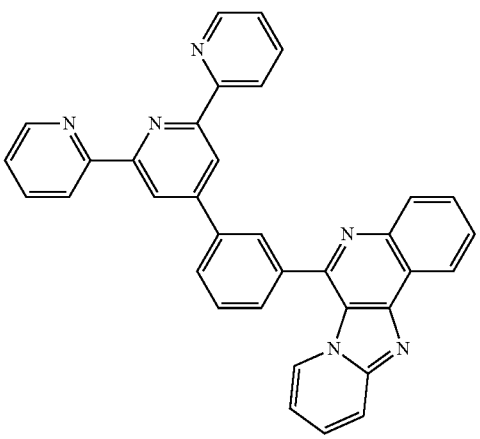

278
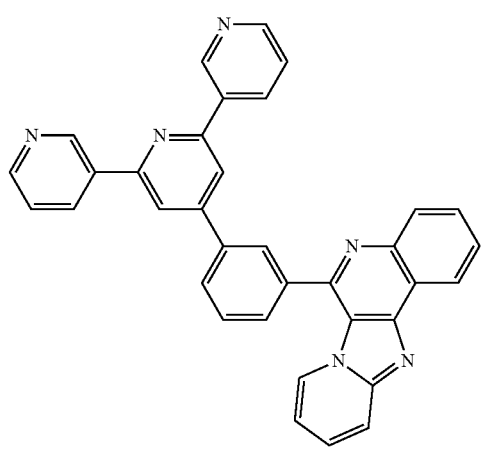
279
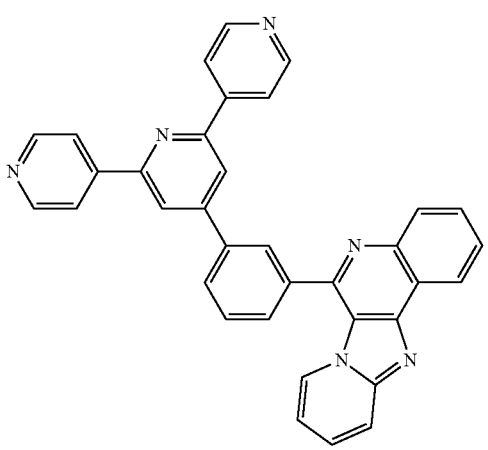
280
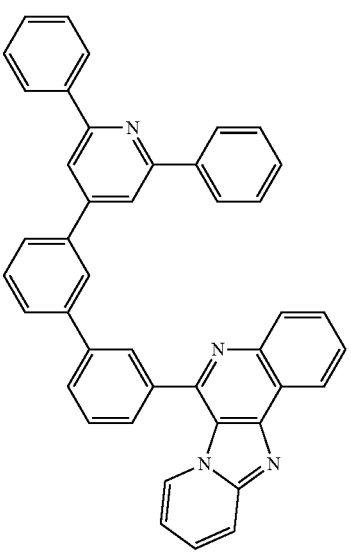
281
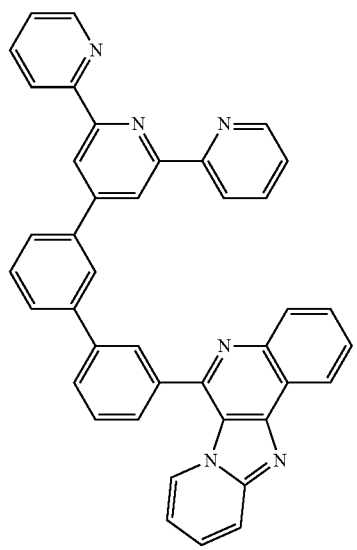
282
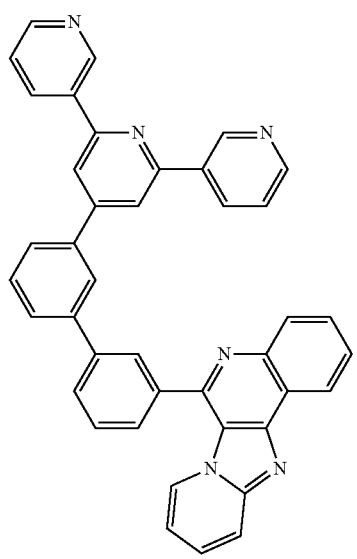
283

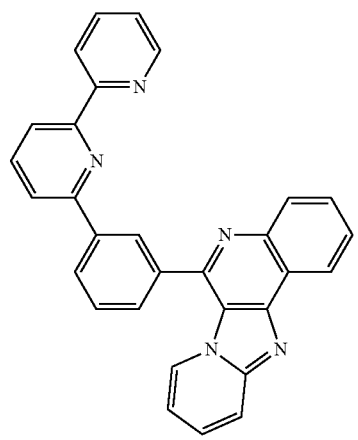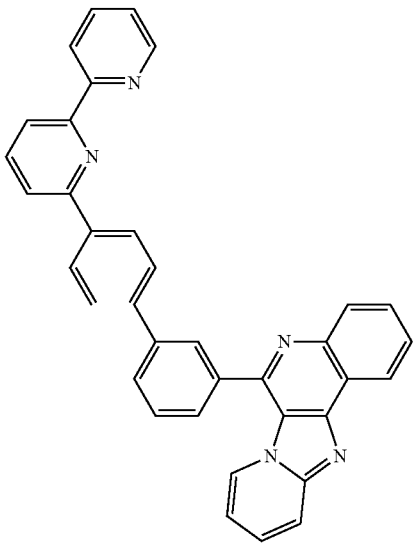

290
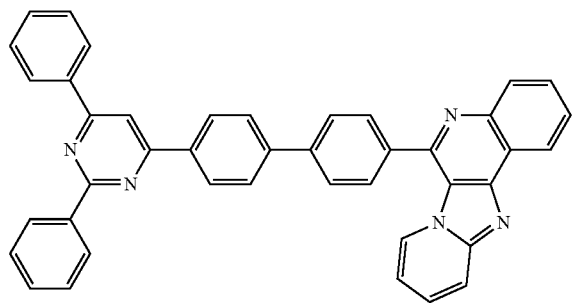
294
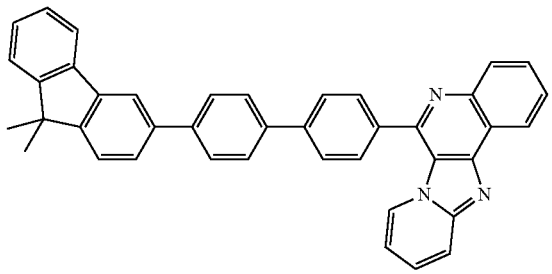
291
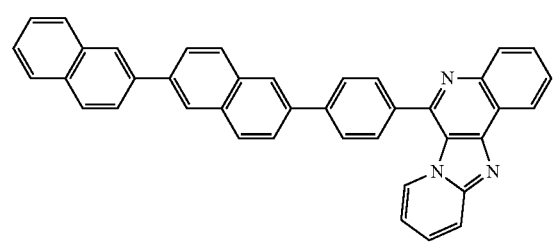
295
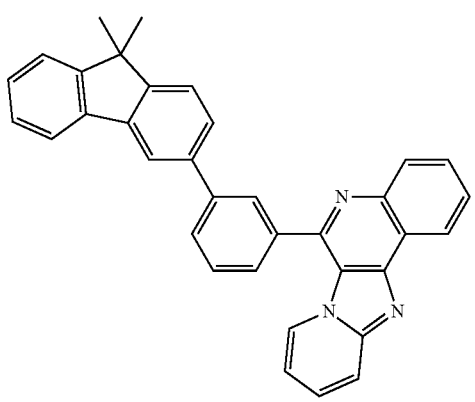
292
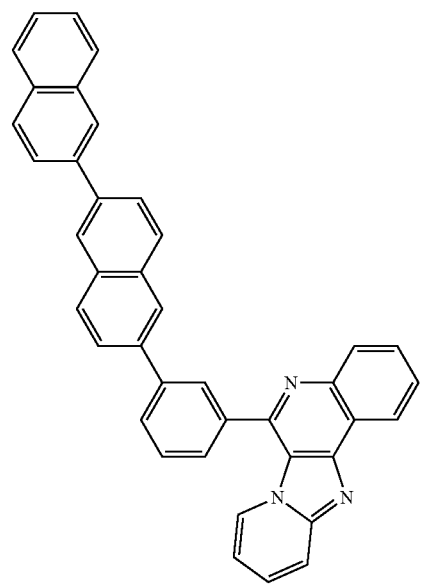
296
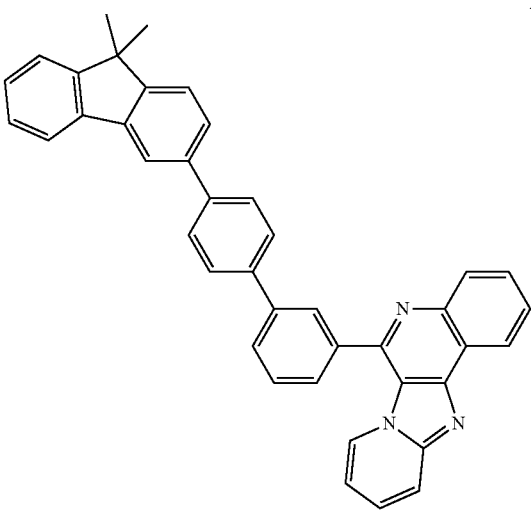
293
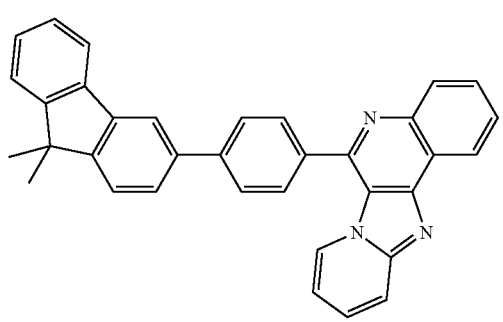
297
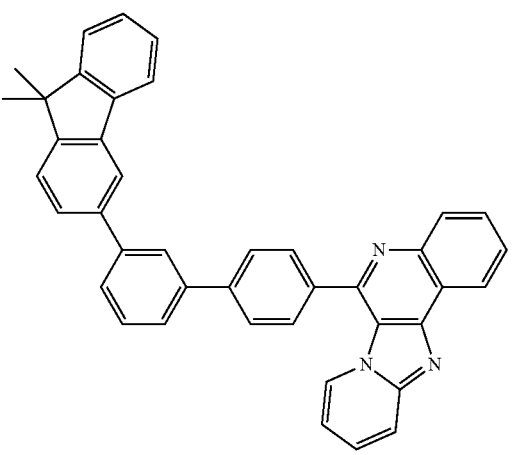

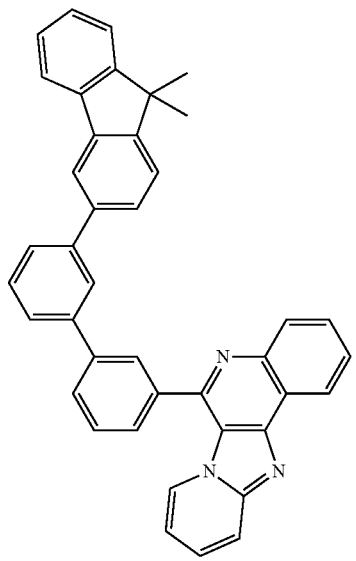
298
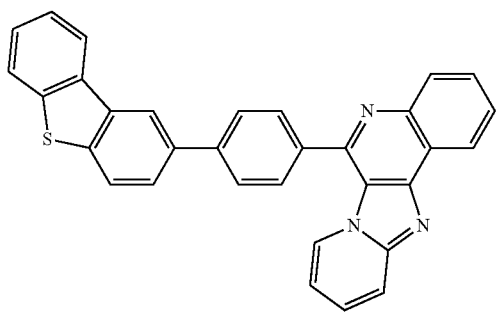
299
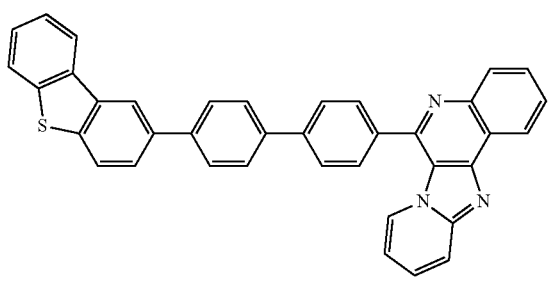
300
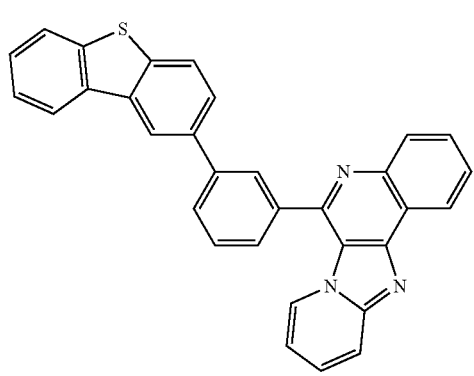
301
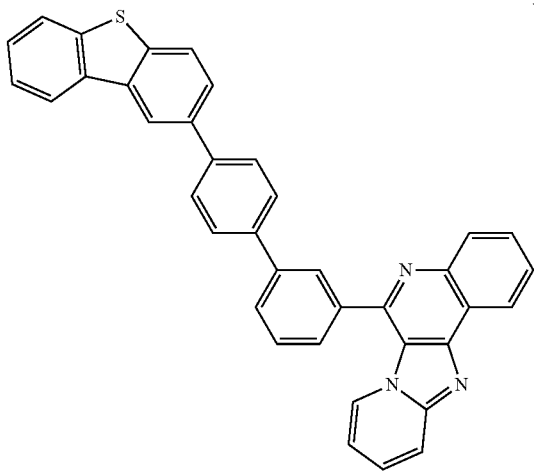
302
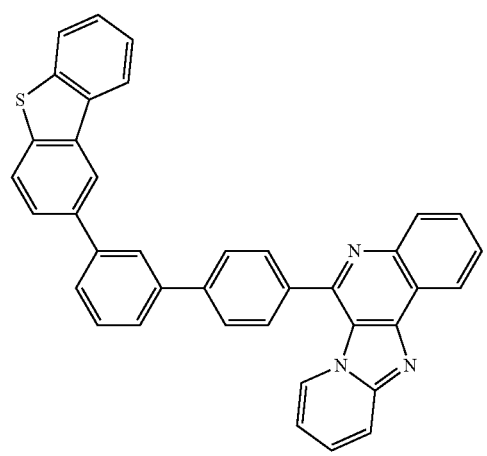
303
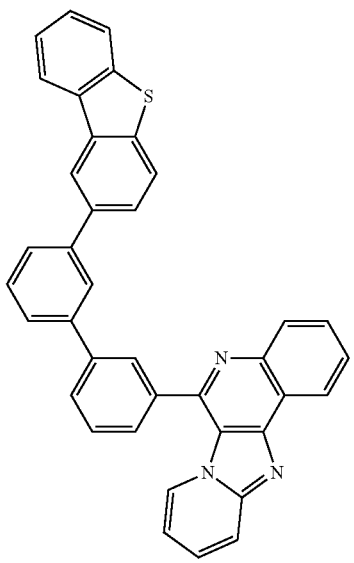
304

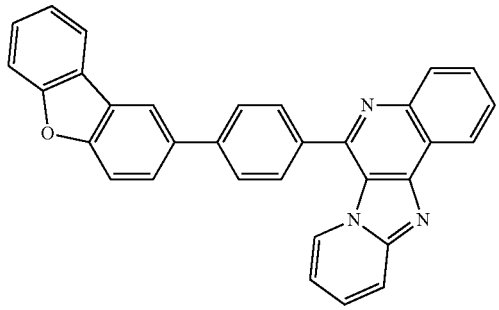
305
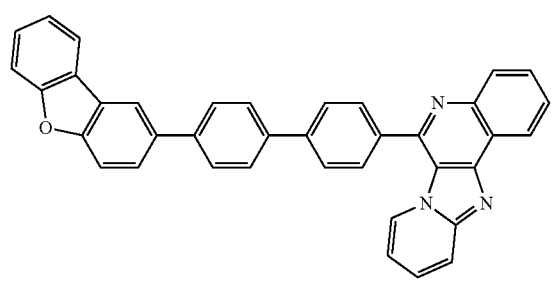
306
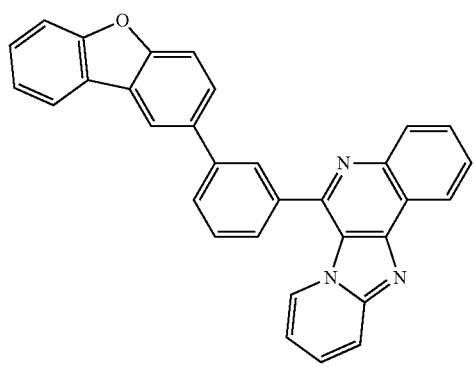
307
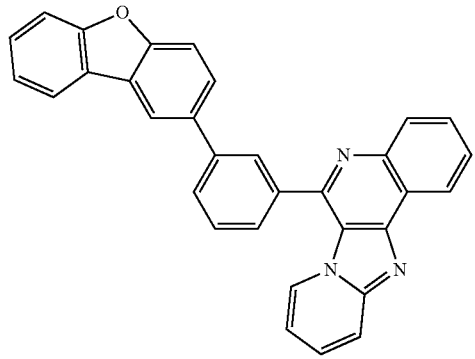
308
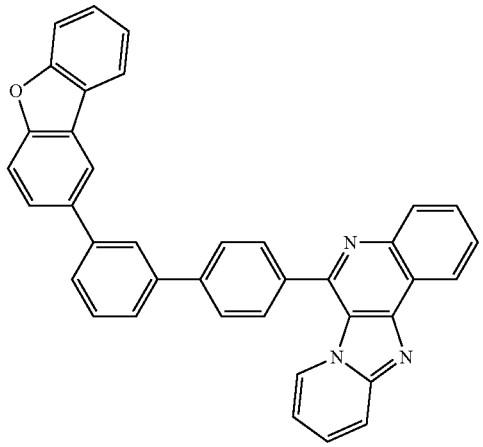
309
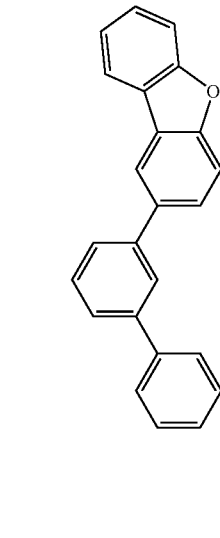
310
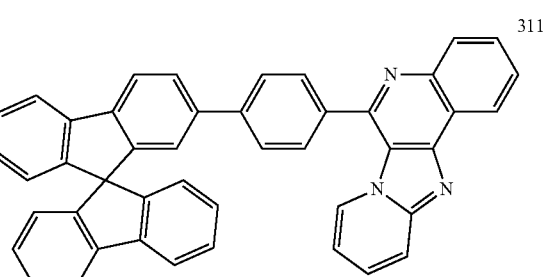
311
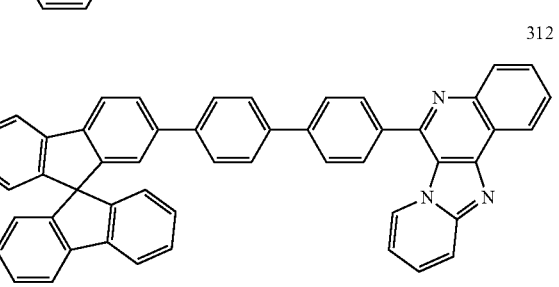
312

313
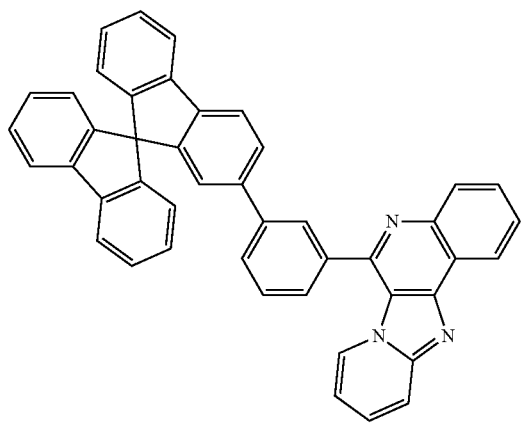
314
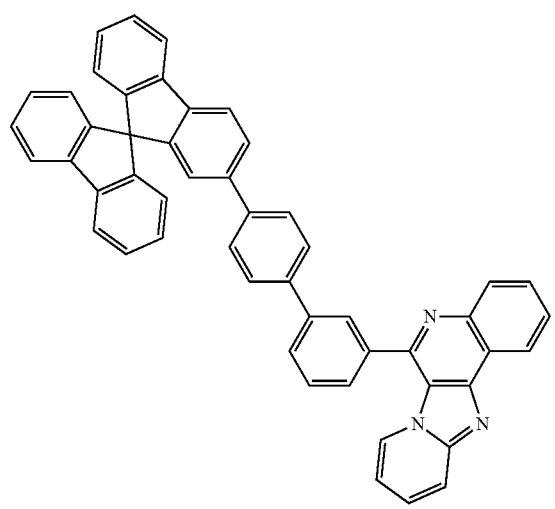
315
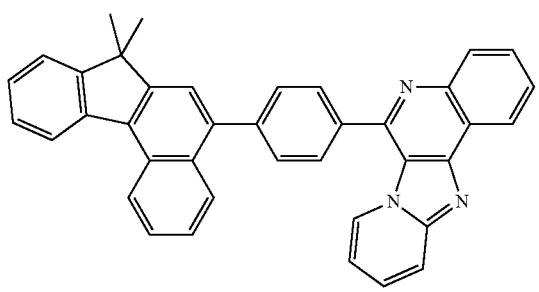
316
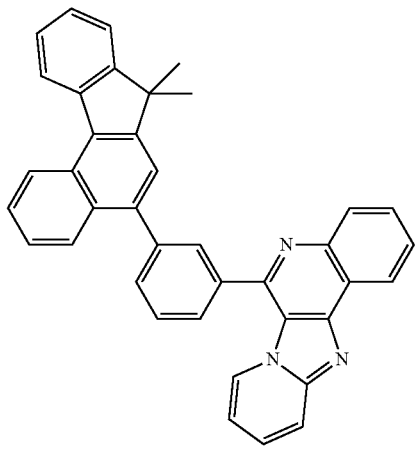
317
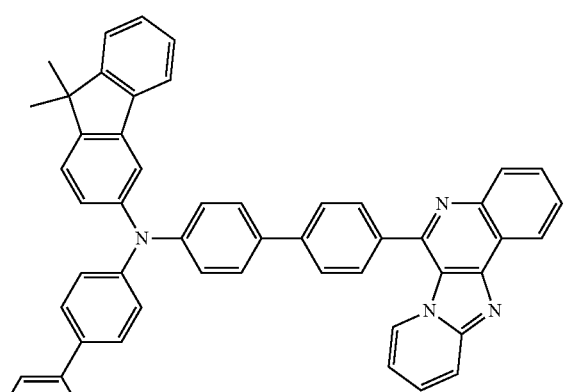
318
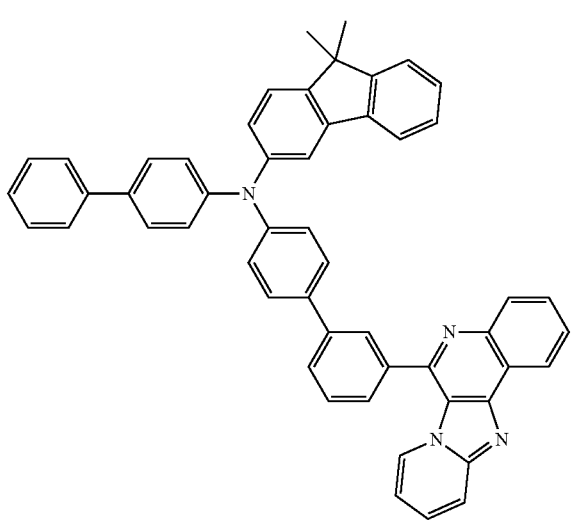

103
-continued
319
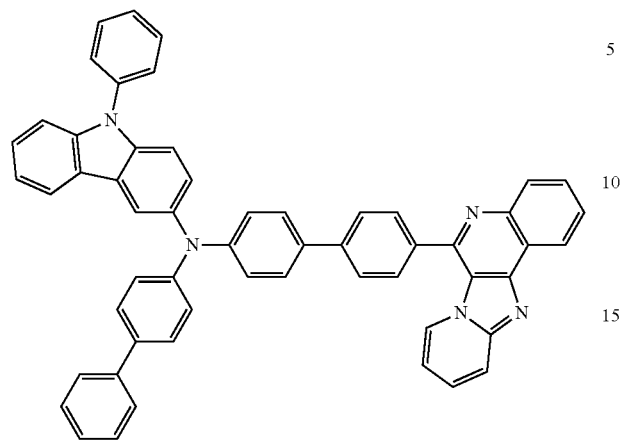
320
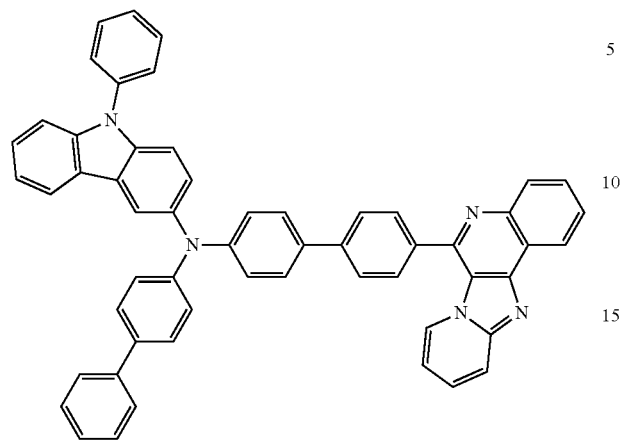
321
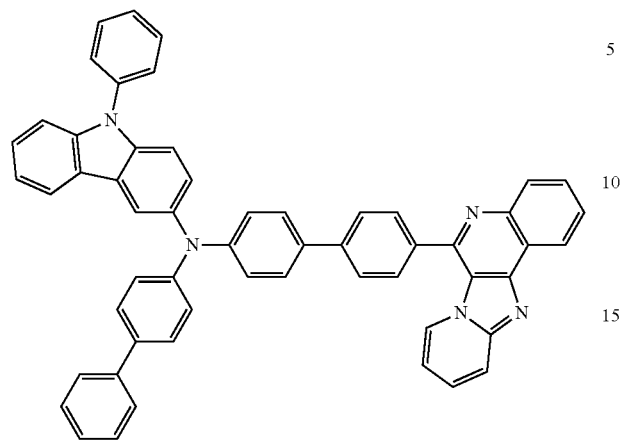
322
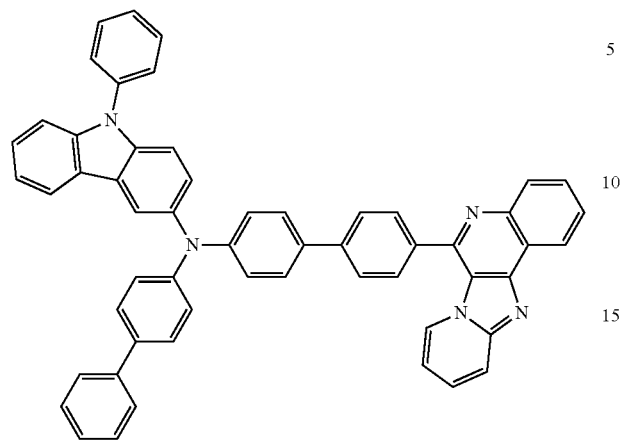
104
-continued
323
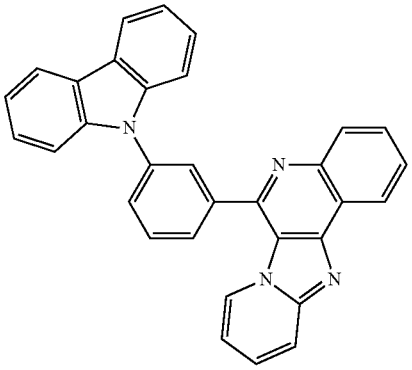
324
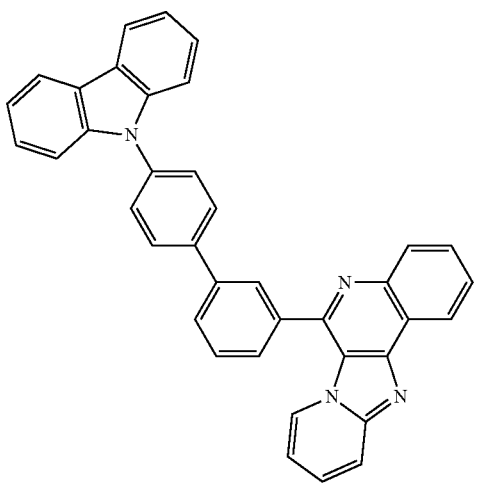
325
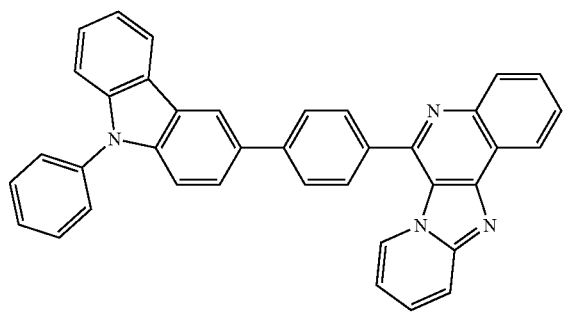
326
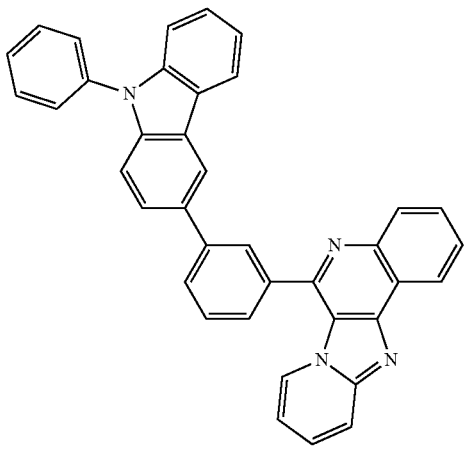

105
-continued
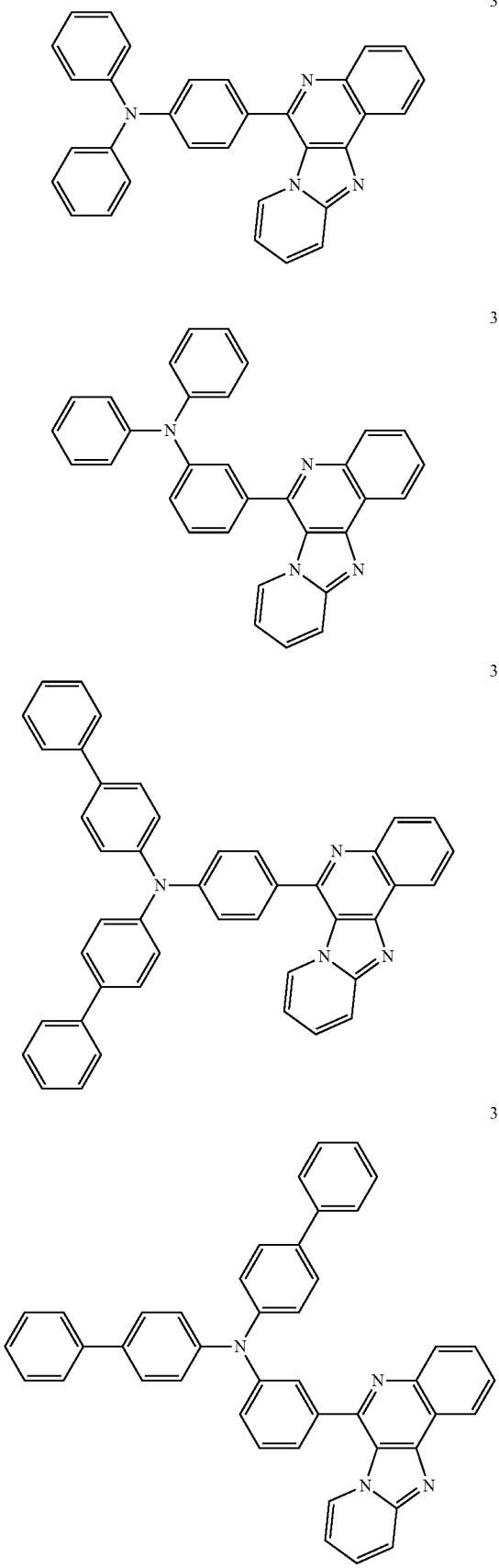
106
-continued
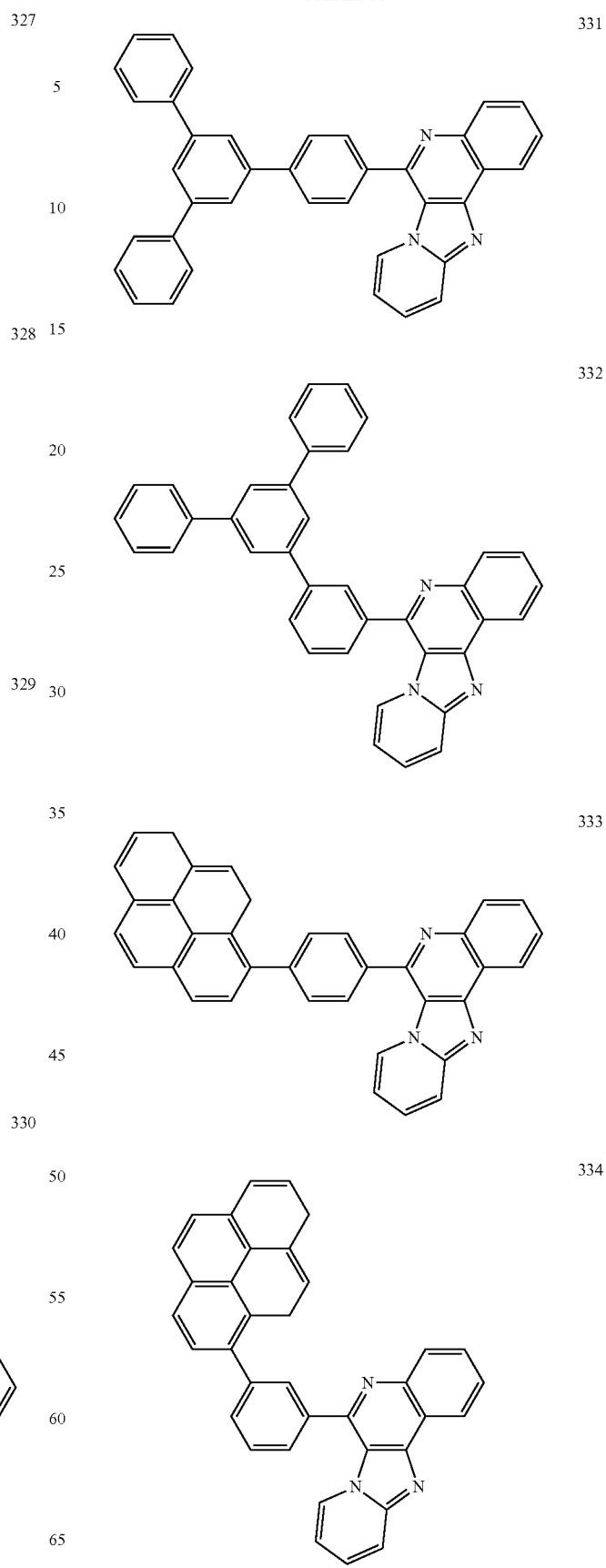

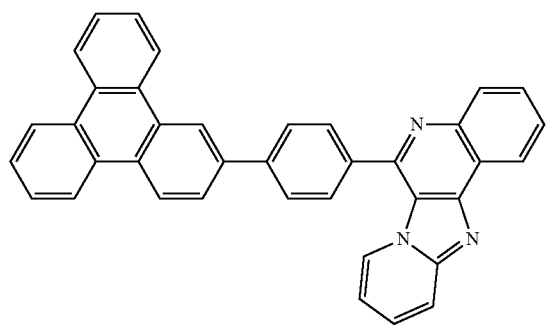
335
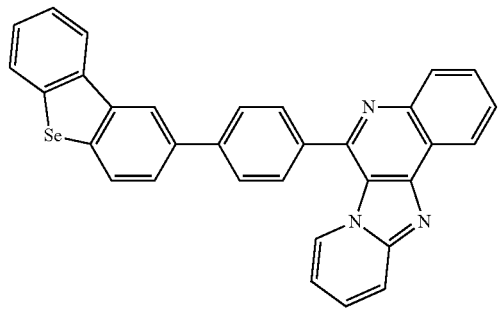
339
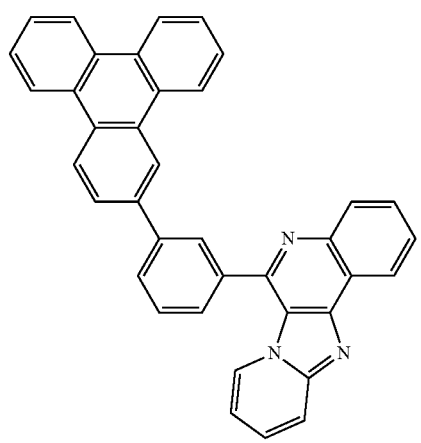
336
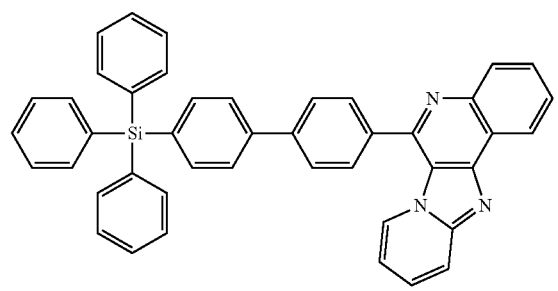
337
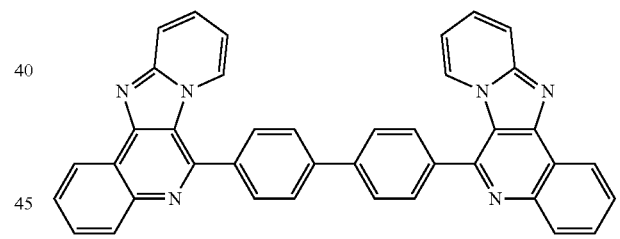
340
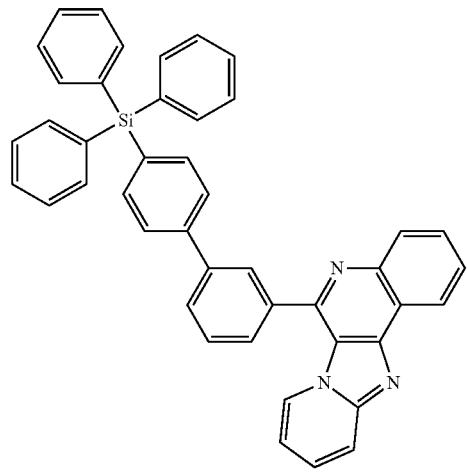
338
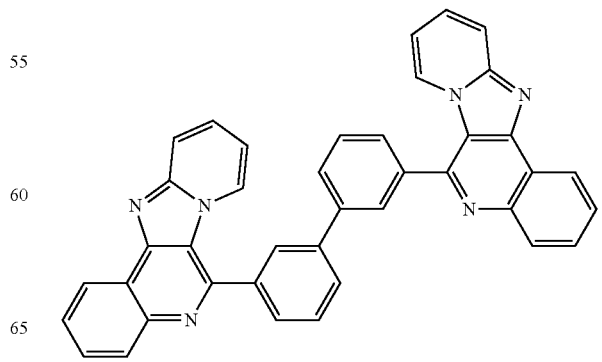
341
342

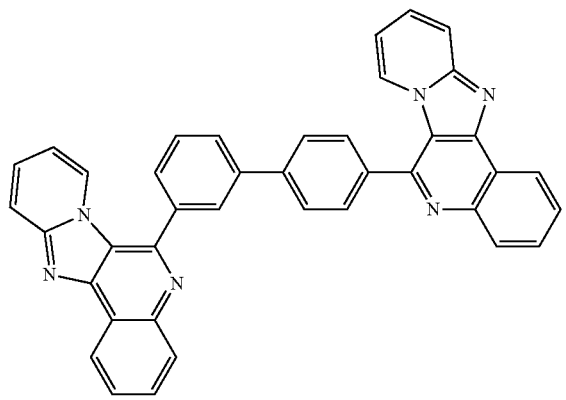
343
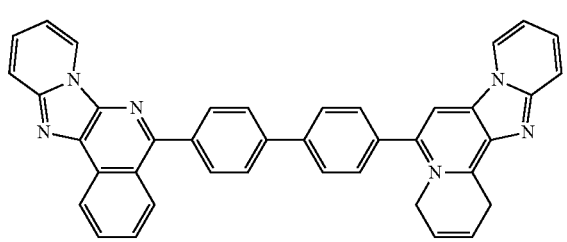
344
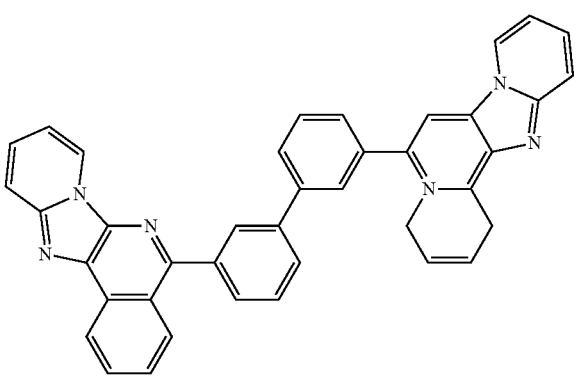
345
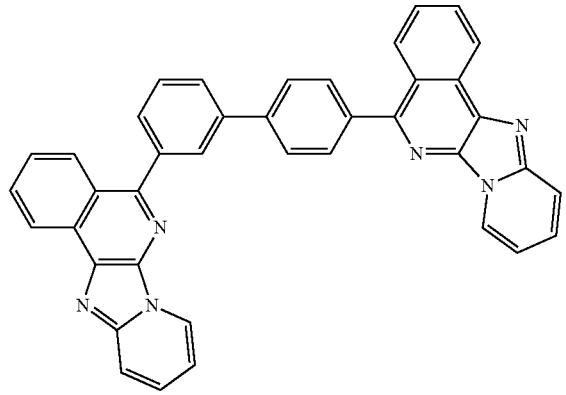
346
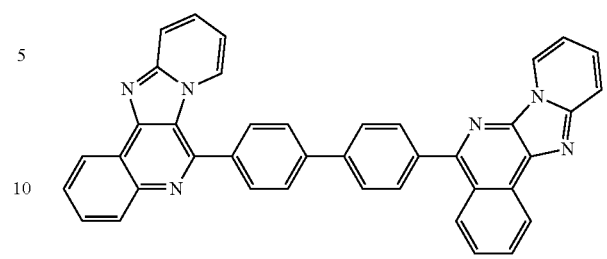
347
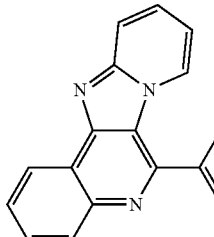
348
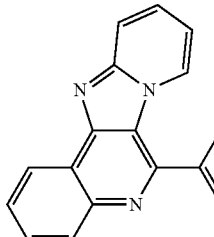
349
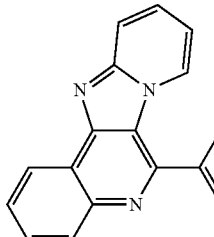
350
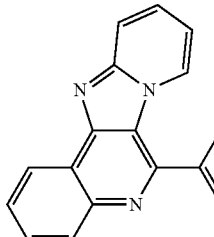
351

352
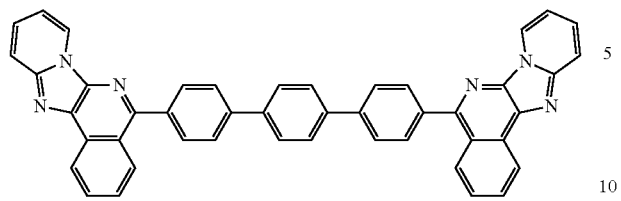
353
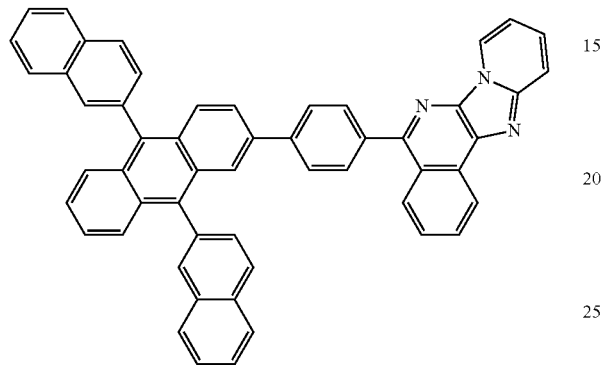
354
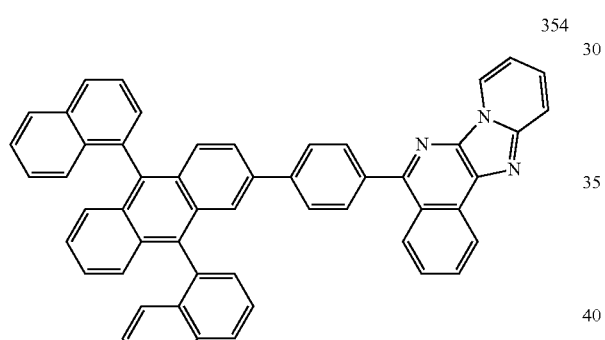
355
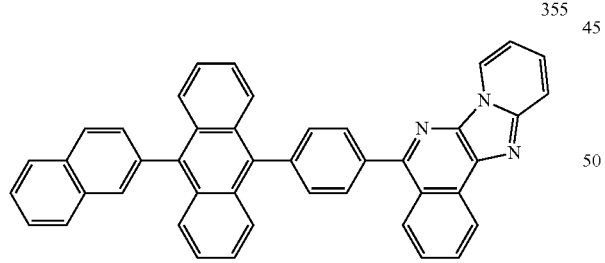
356
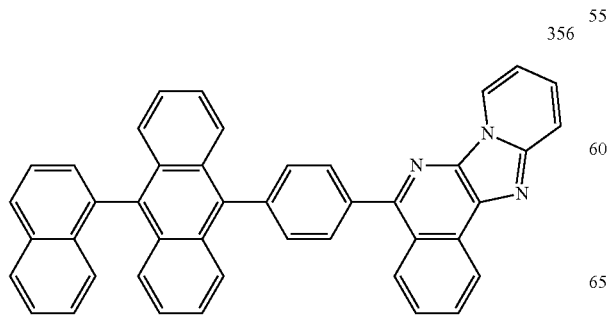
357
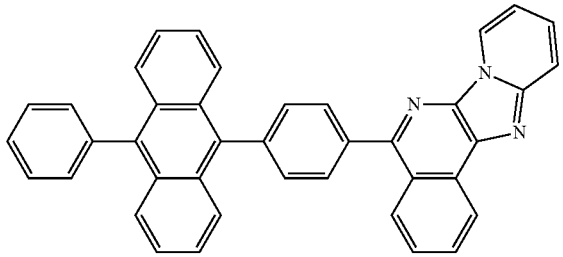
358
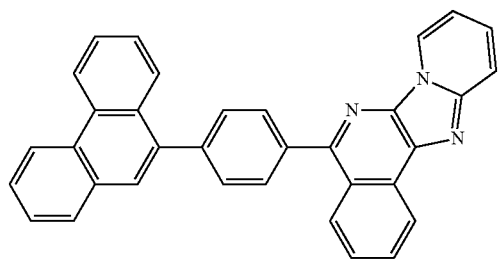
359
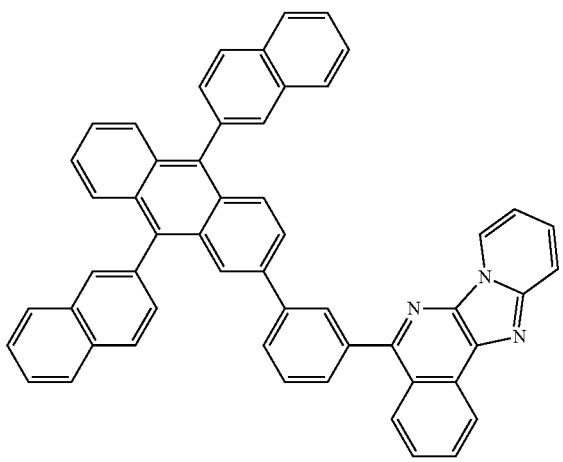
360
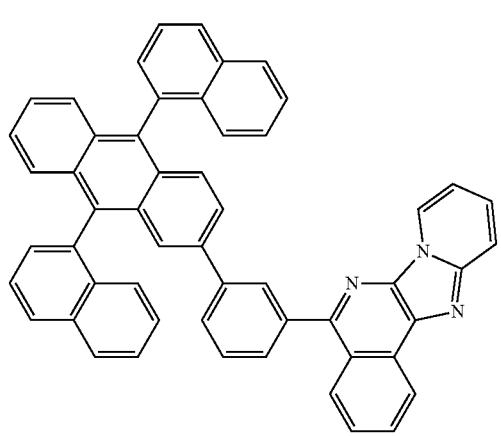

361
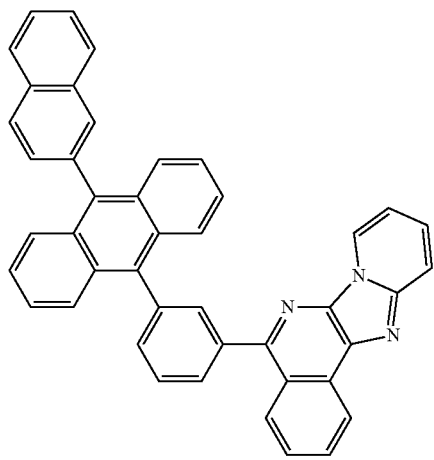
362
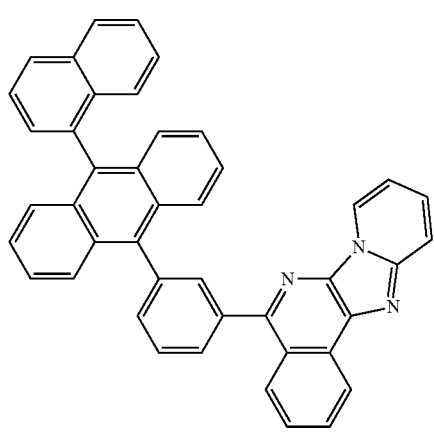
363
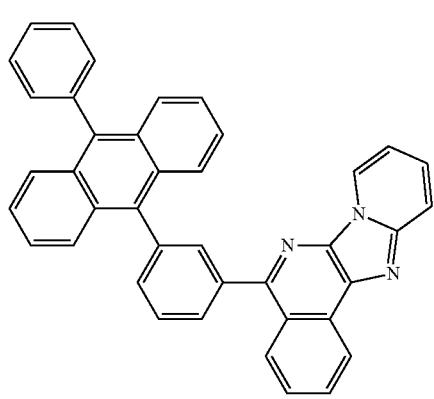
364
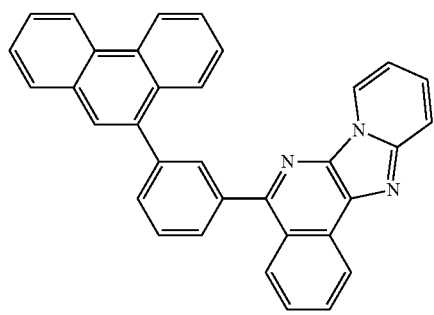
365
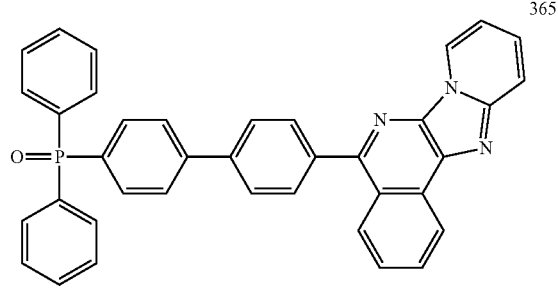
366
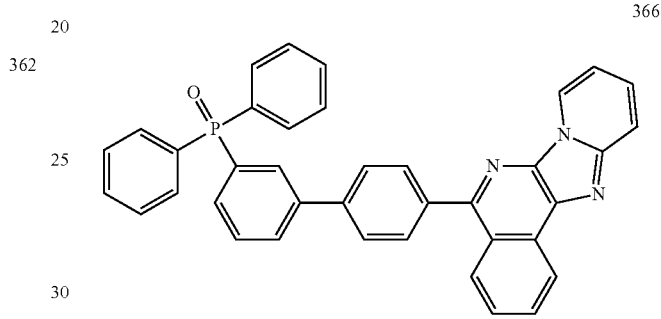
367
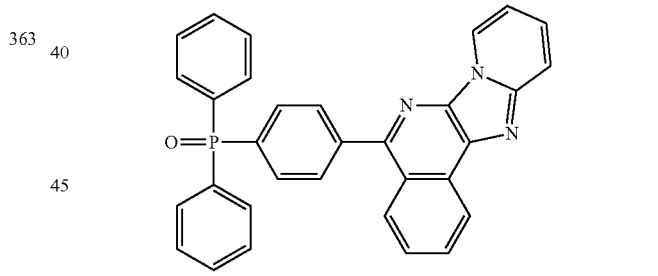
368
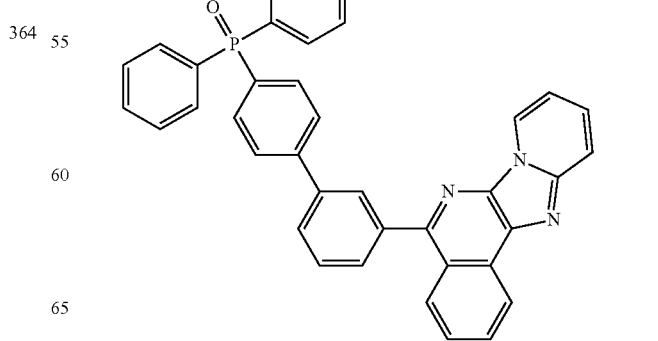

369
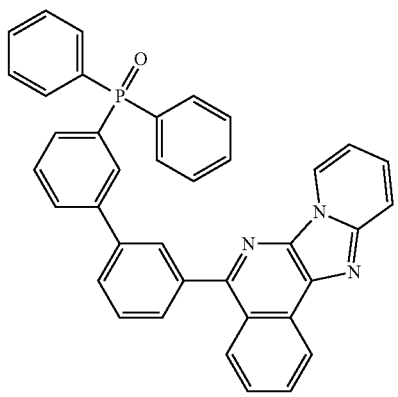
370
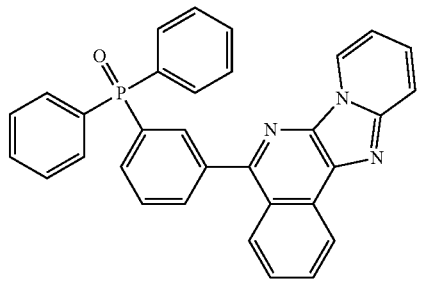
371
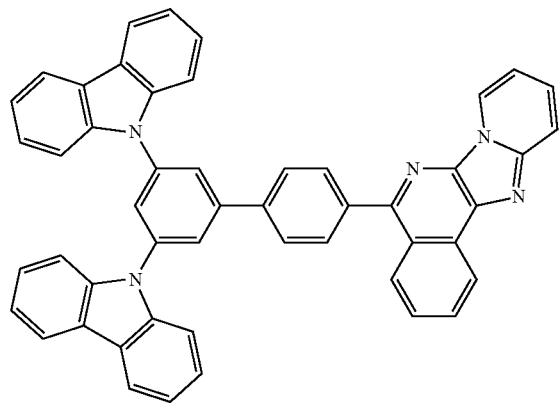
372
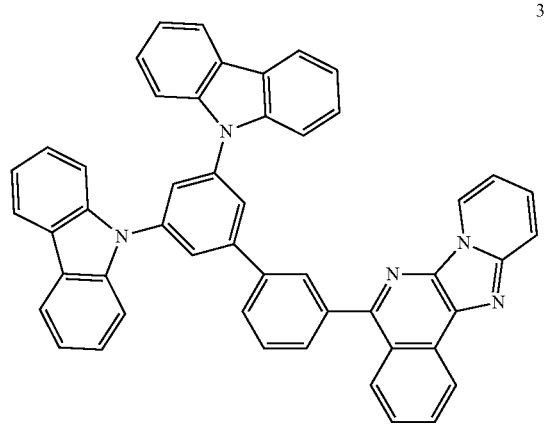
373
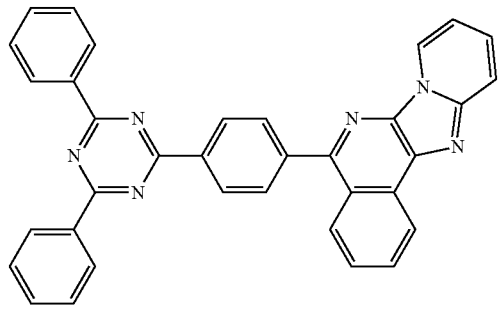
374
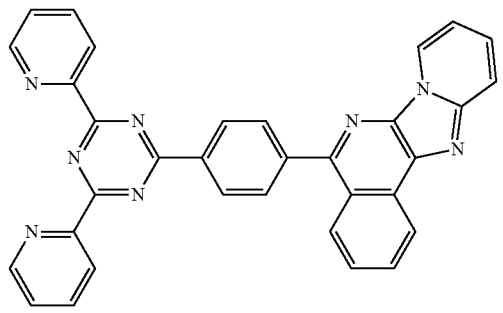
375
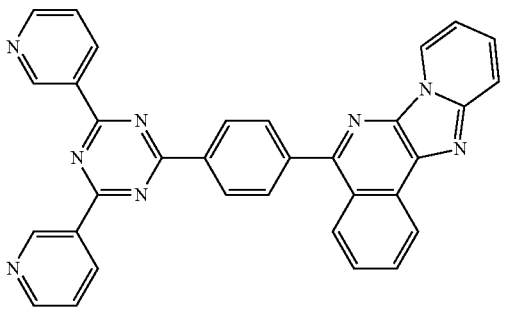
376
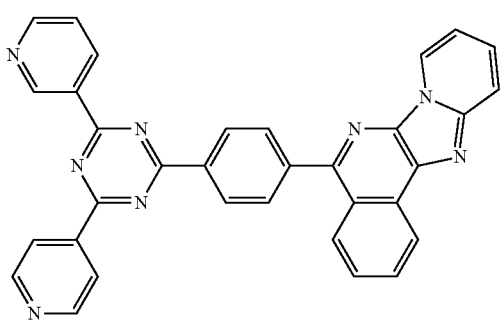

377
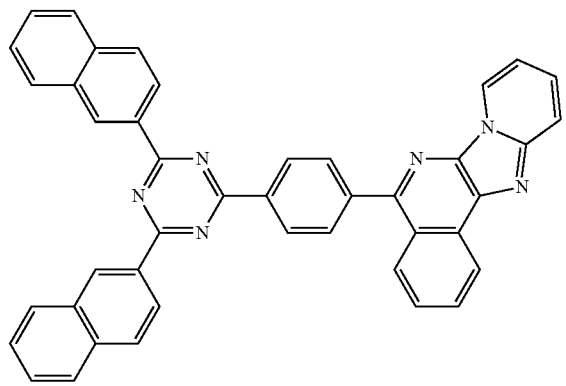
378
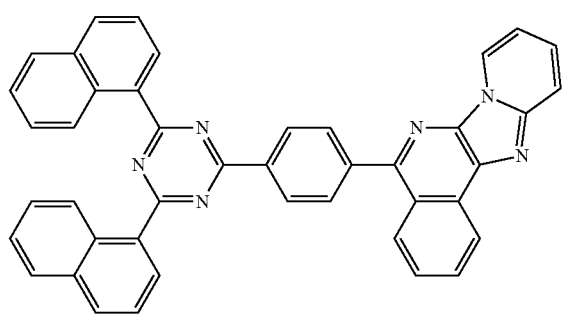
379
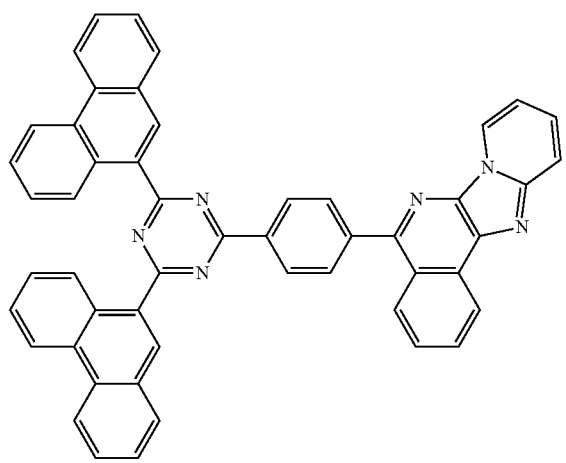
380
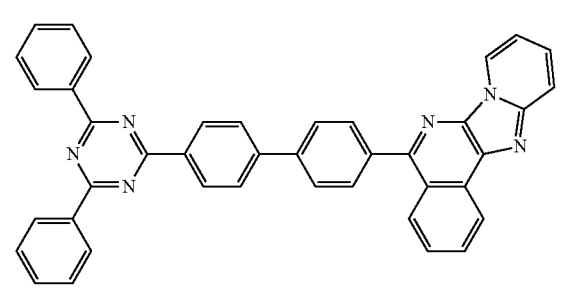
381
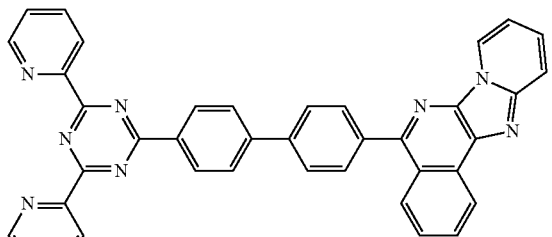
382
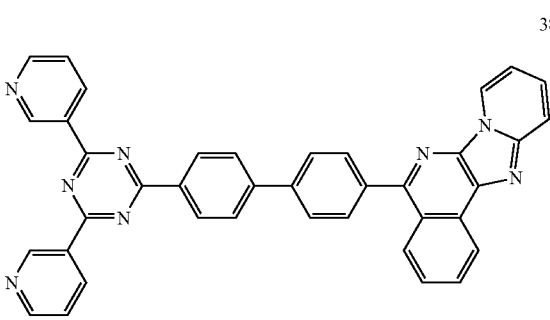
383
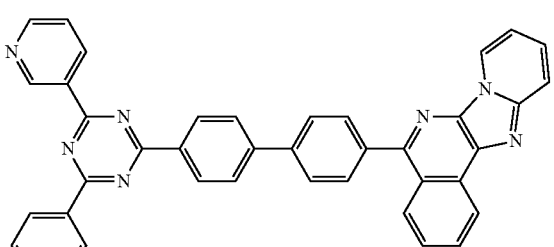
384
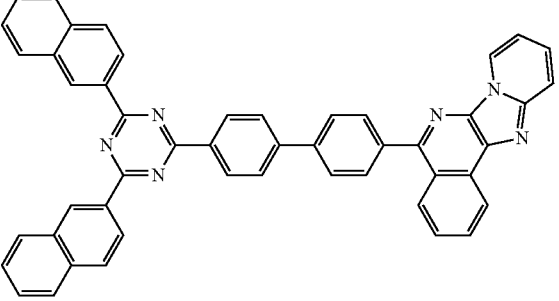
385
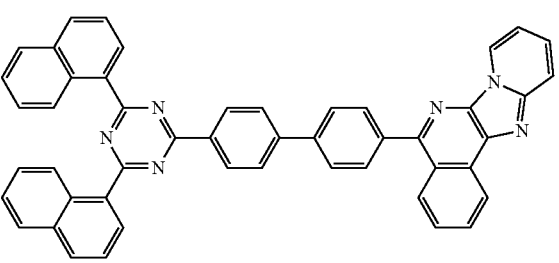

386
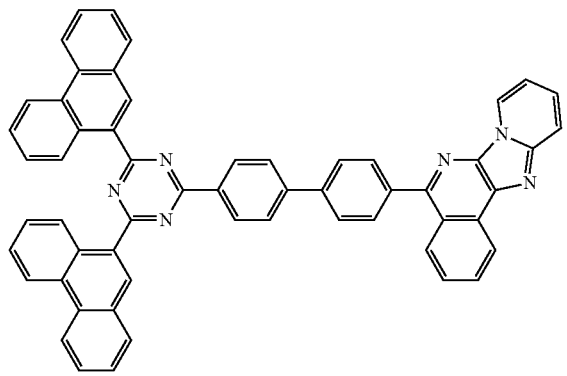
387
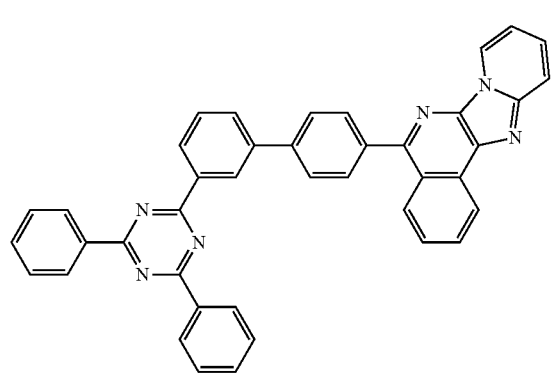
388
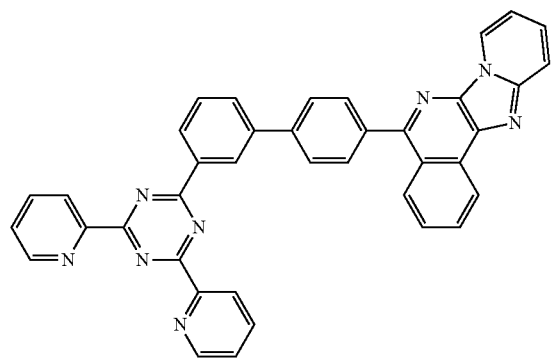
389
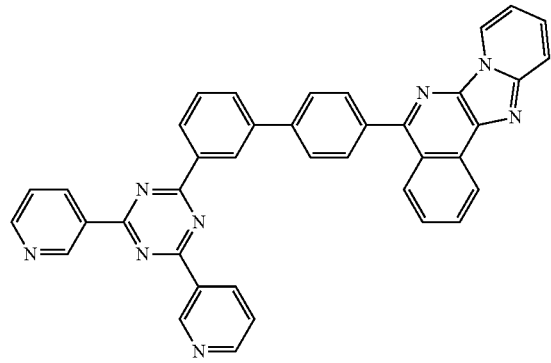
390
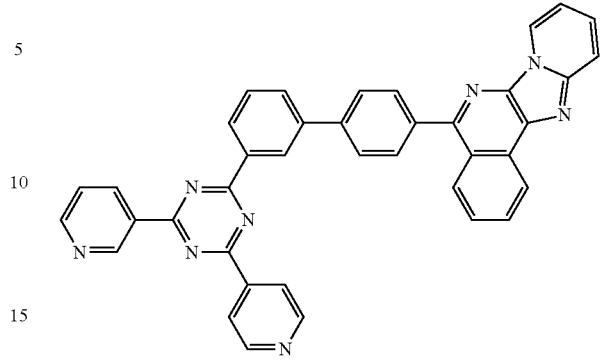
391
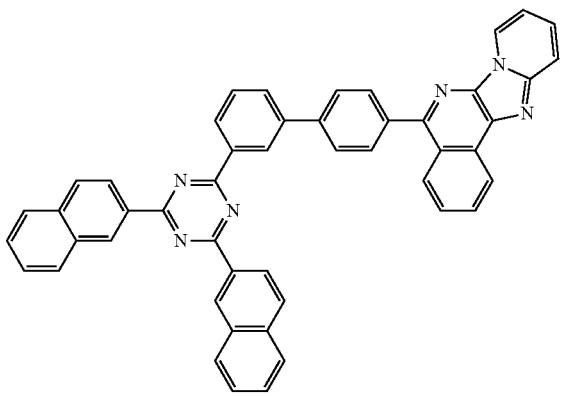
392
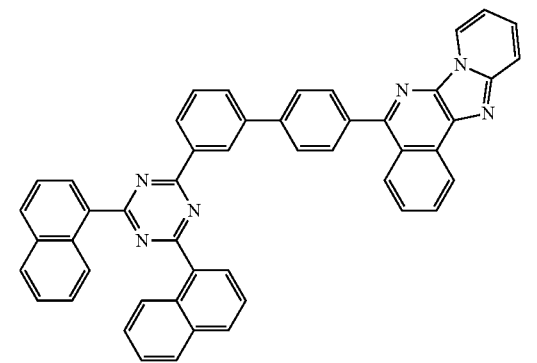
393
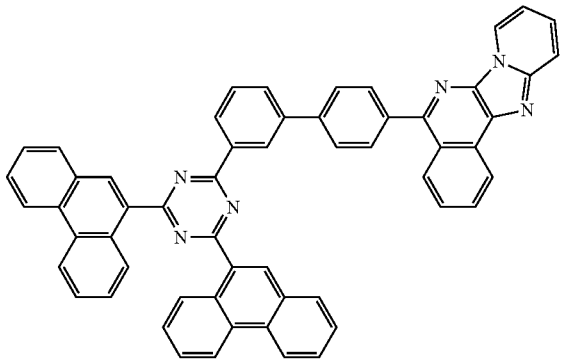

394

395

396

397
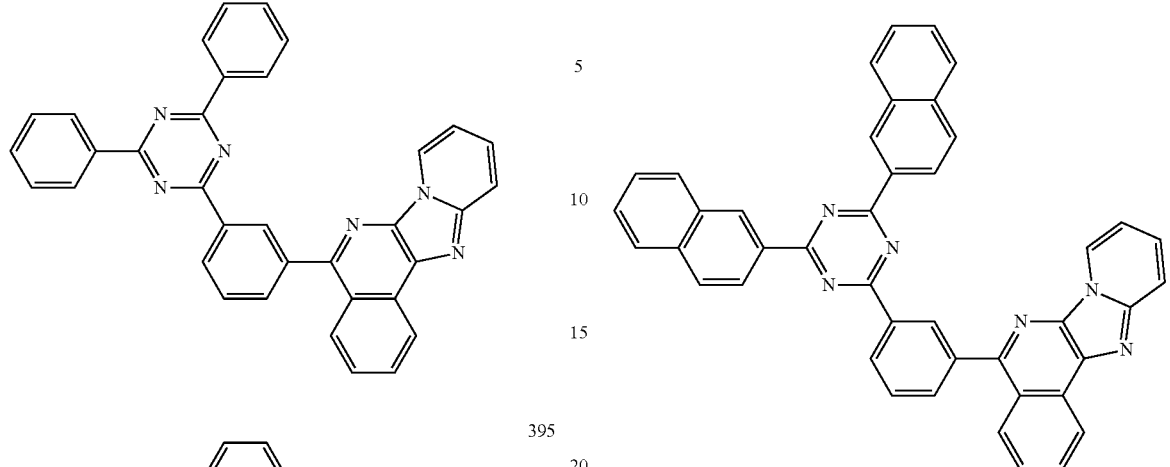
398

399
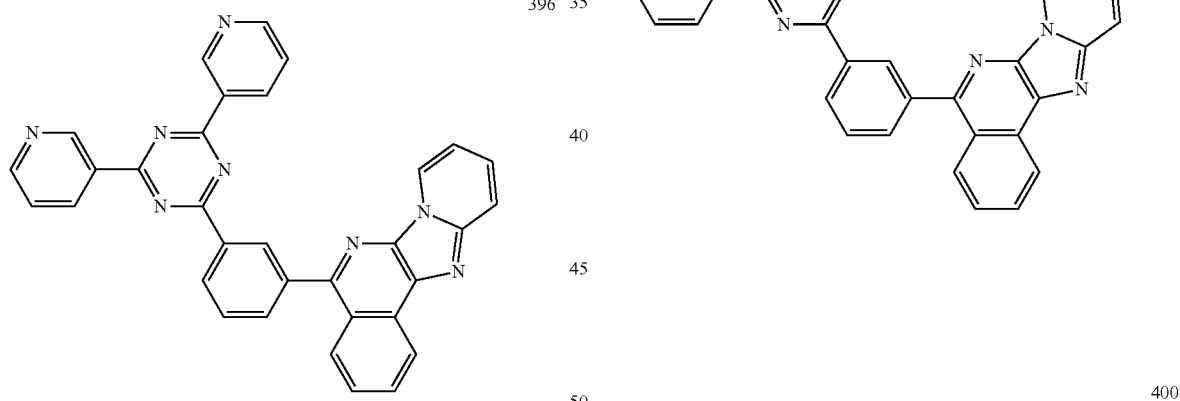
400

401
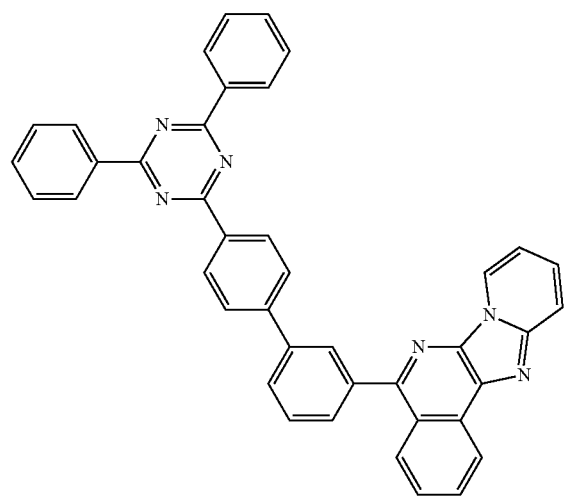
402
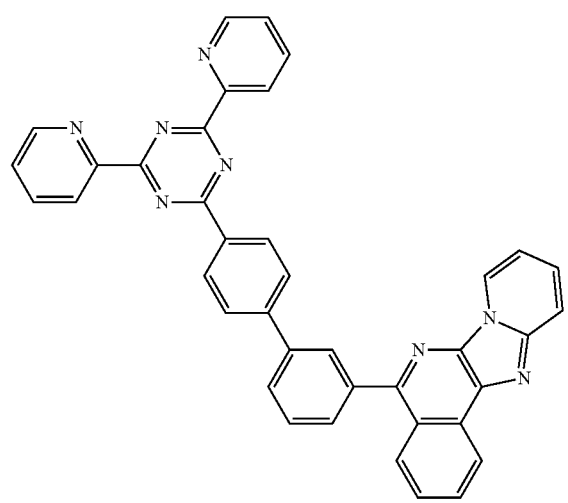
403
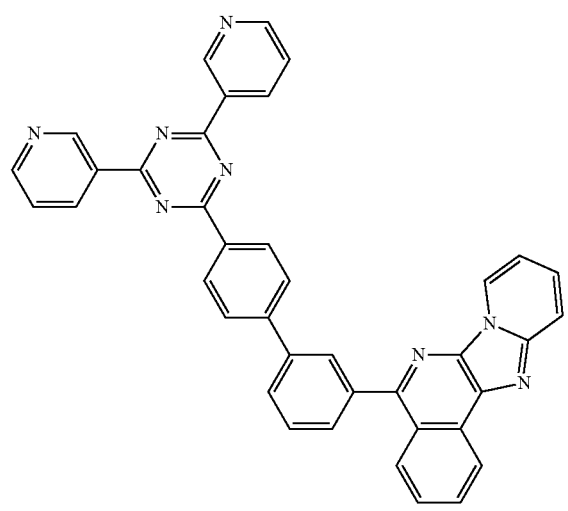
404
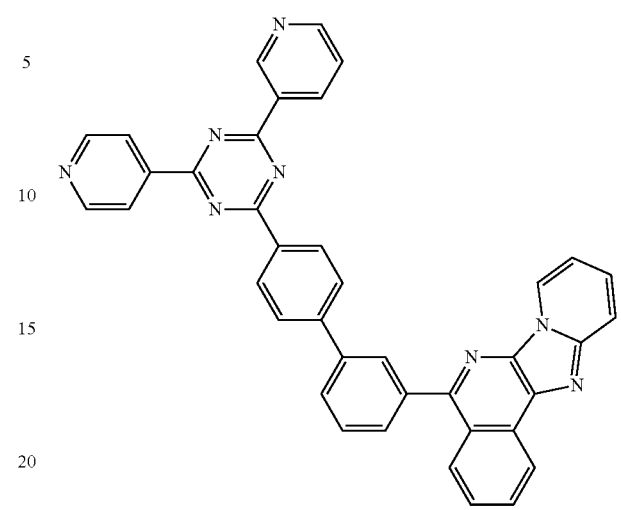
405
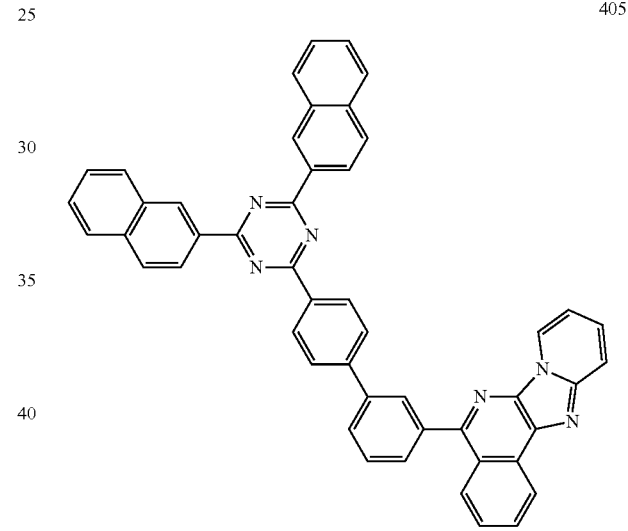
406
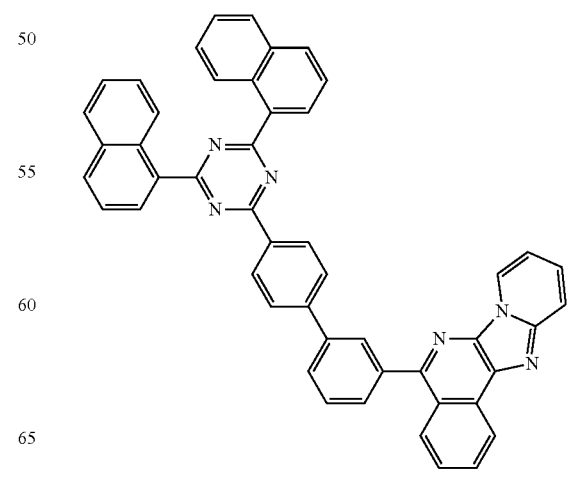

407
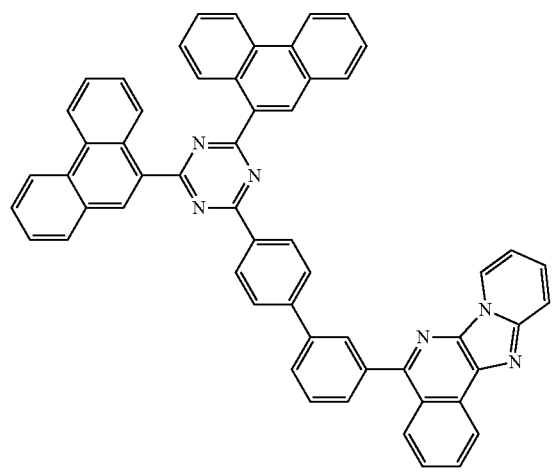
408
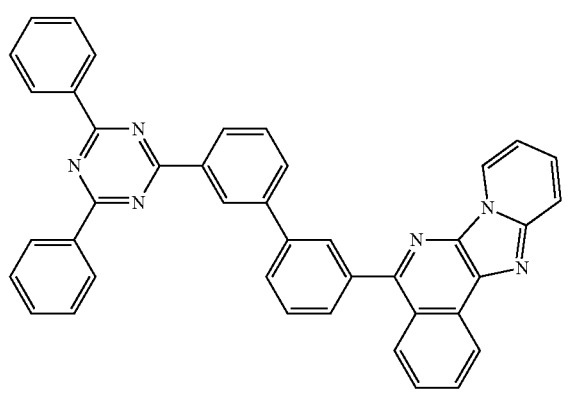
409
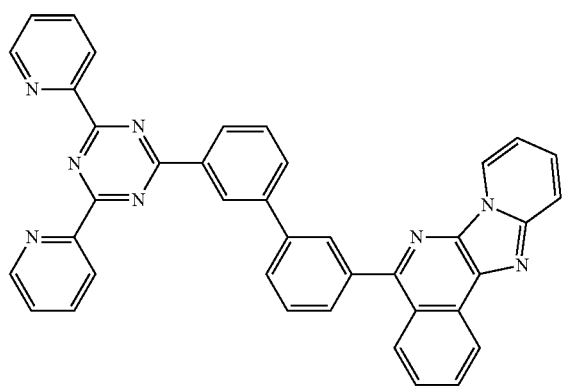
410
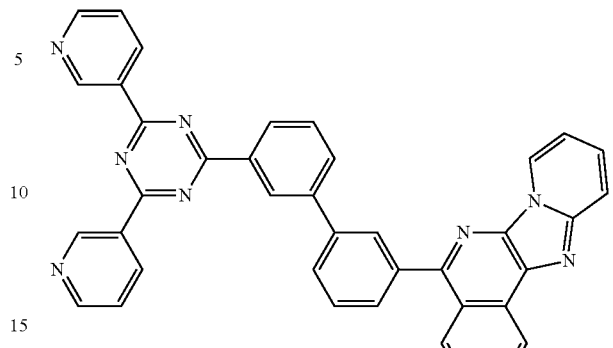
411
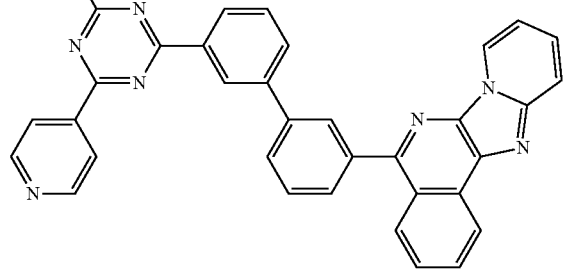
412
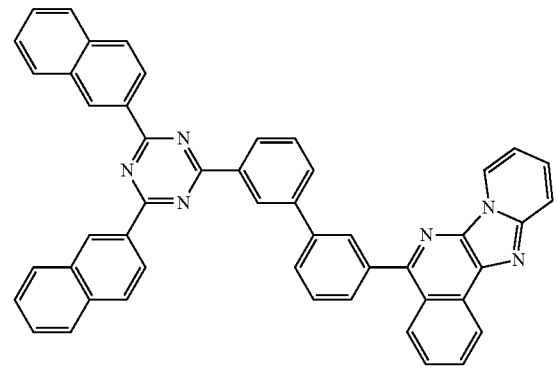
413
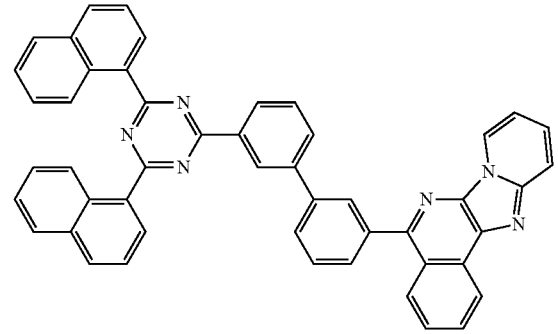

414
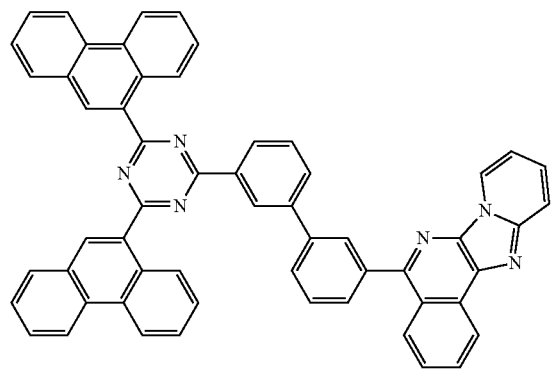
415
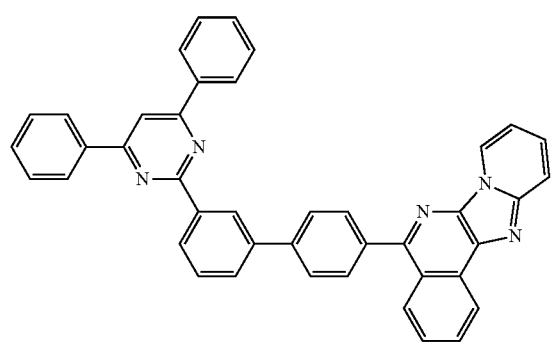
416
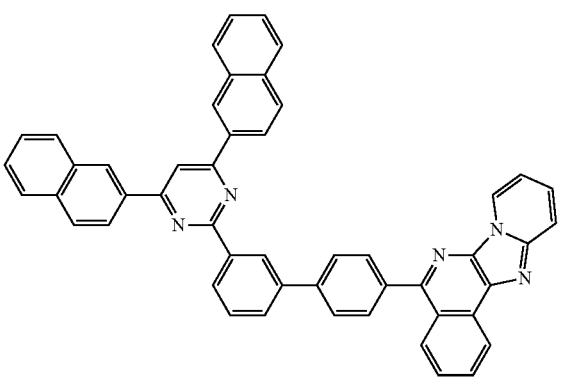
417
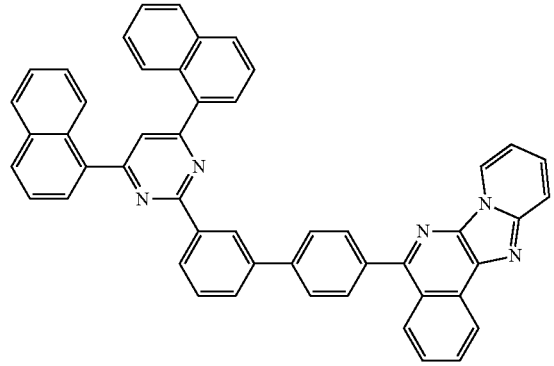
418
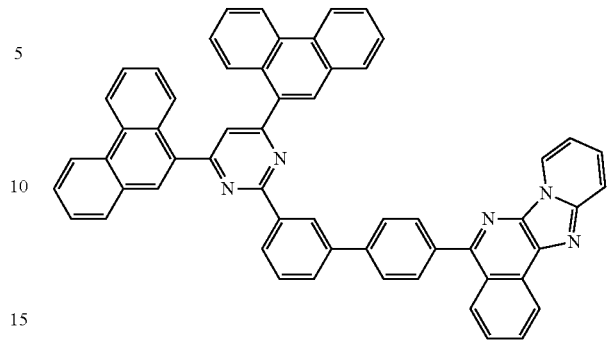
419
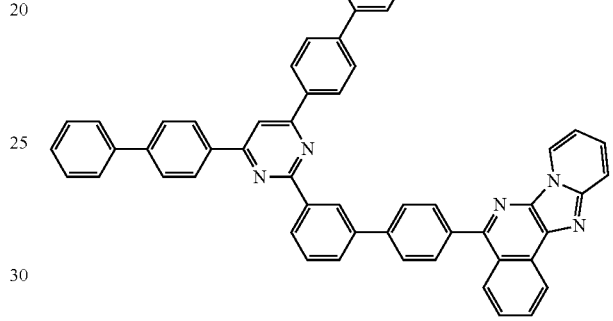
420
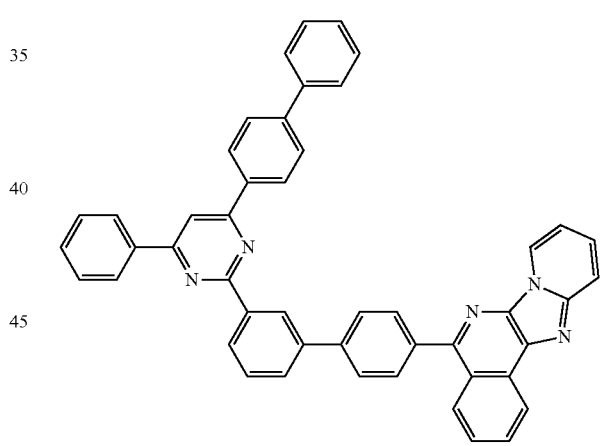
421
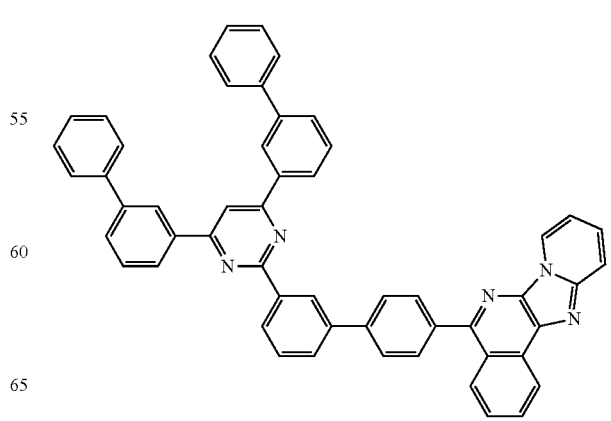

422
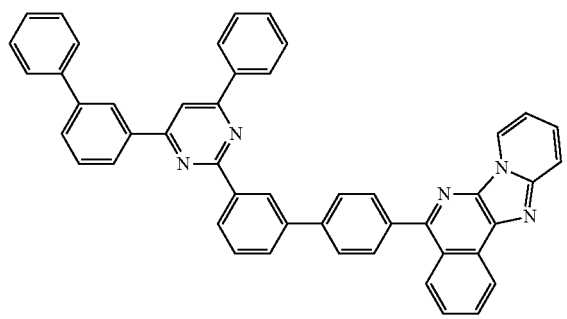
423
424
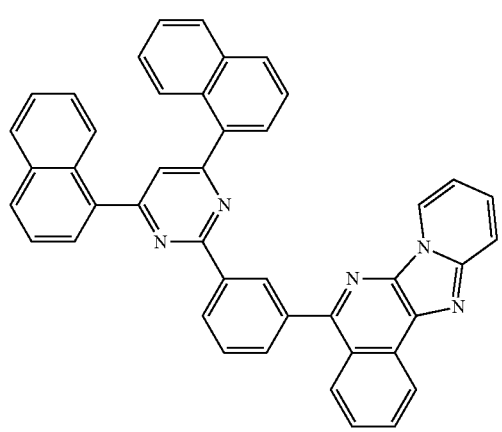
425
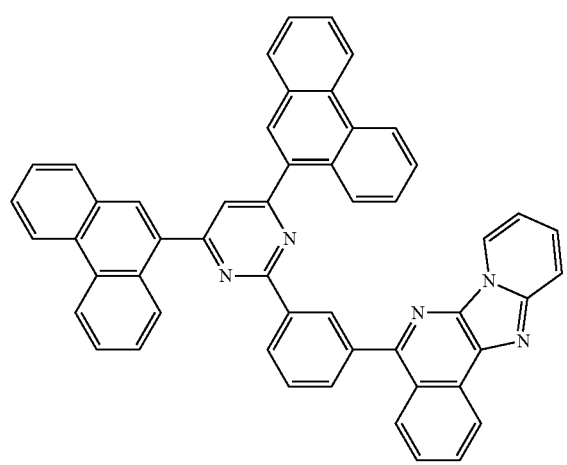
426
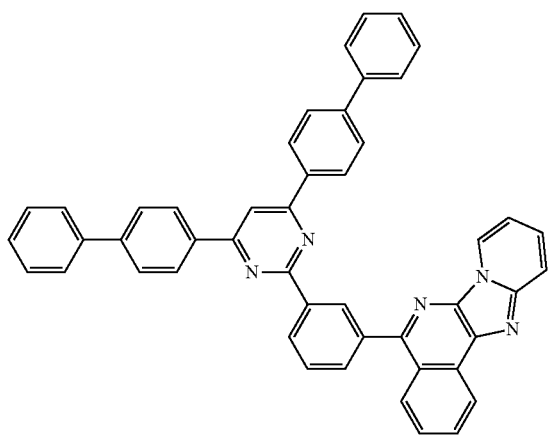
427
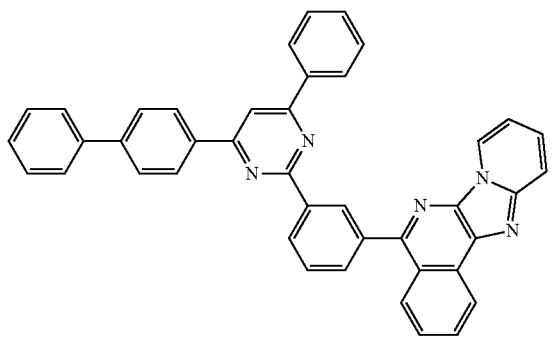

-continued
428
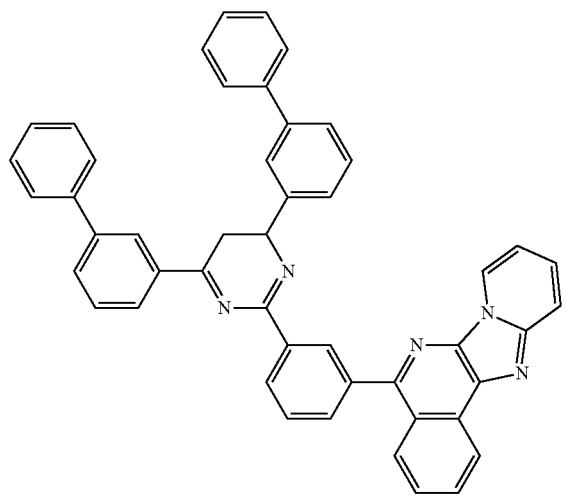
429
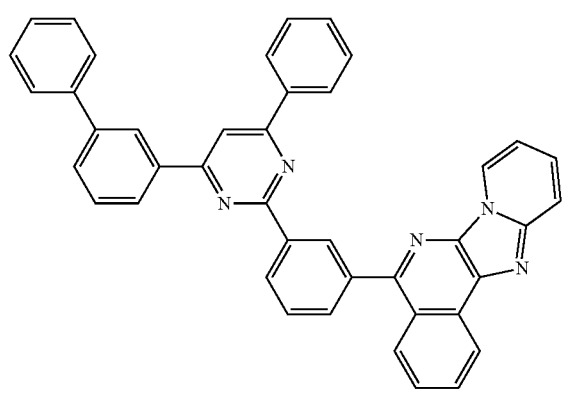
430
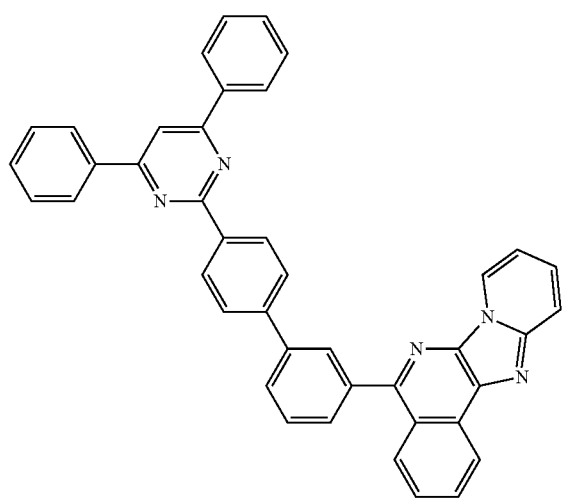
-continued
431
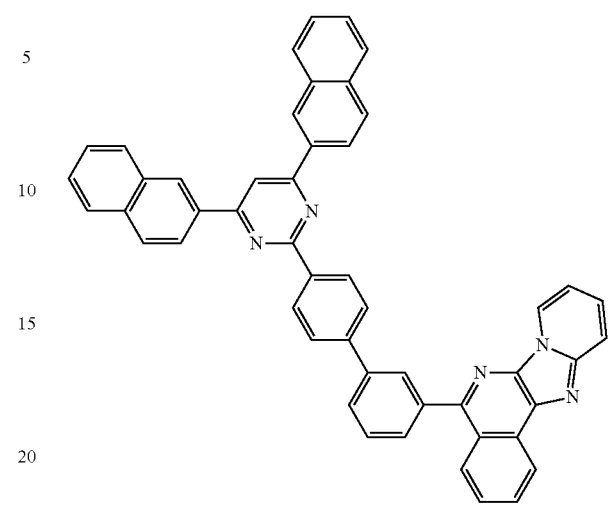
432
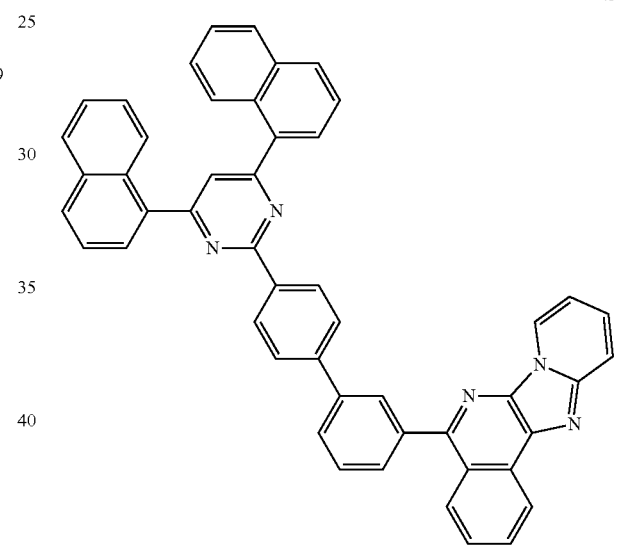
433
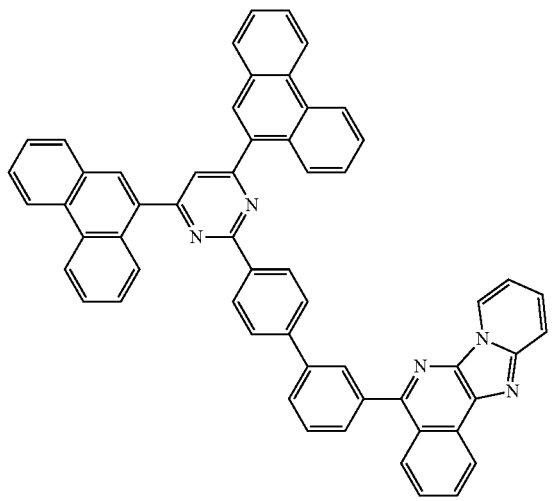

433
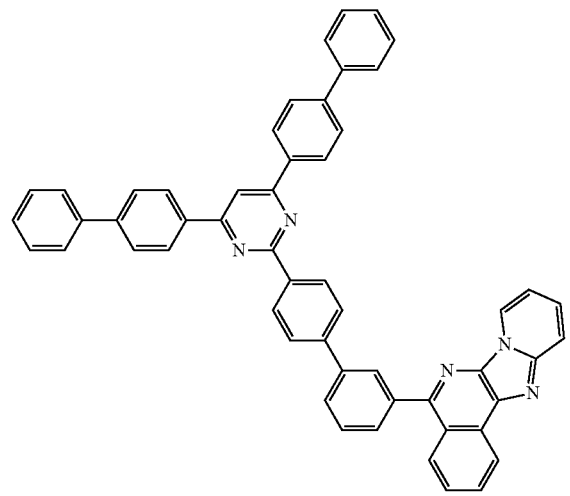
434
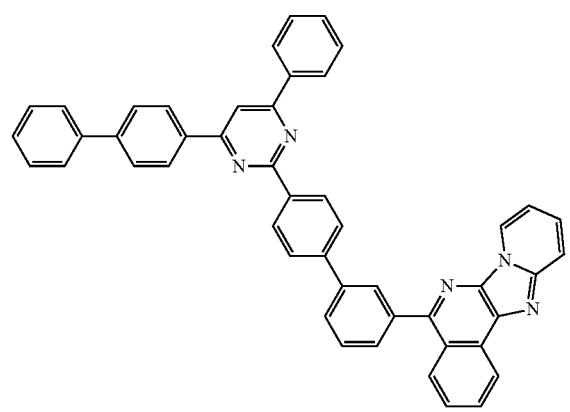
435
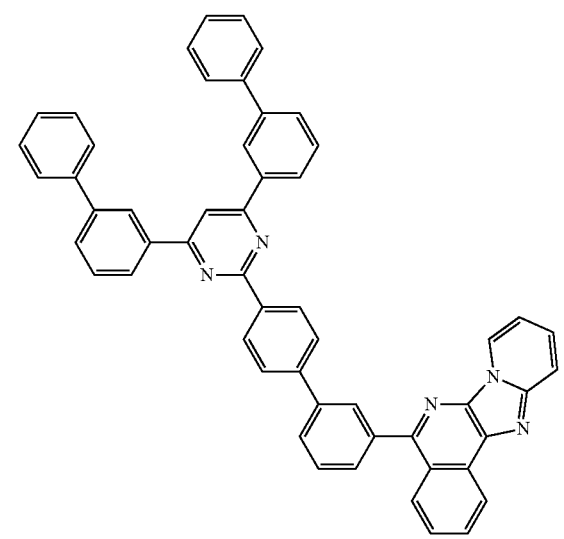
436
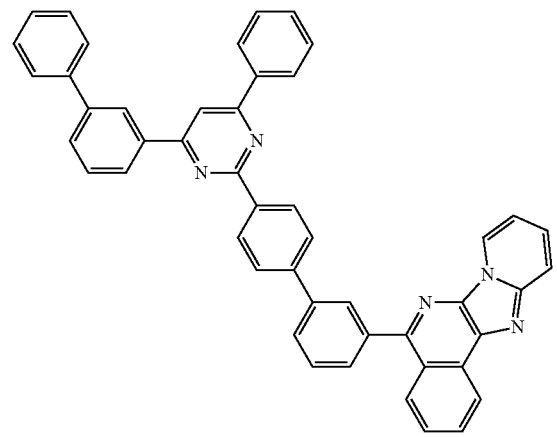
437
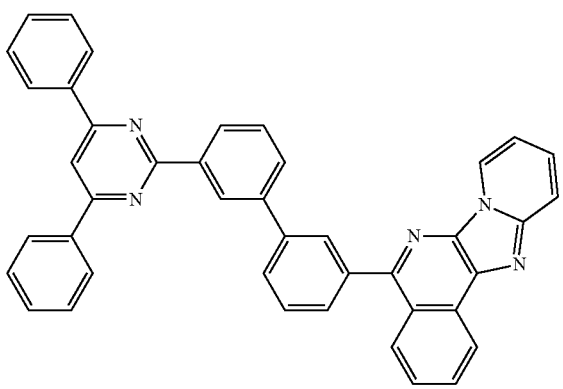
438
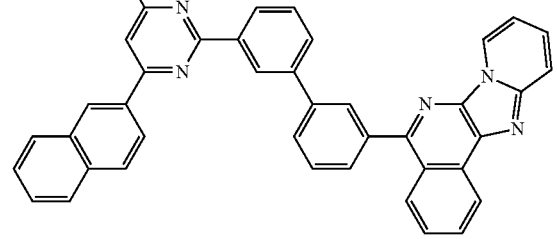
439
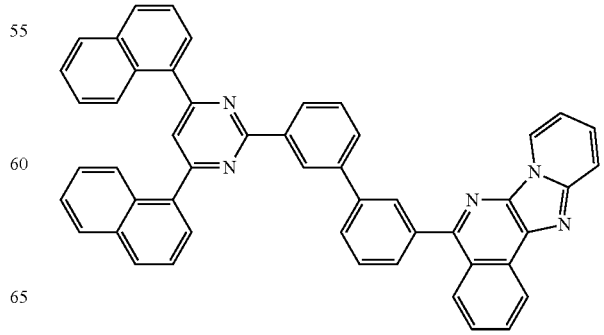
440

441
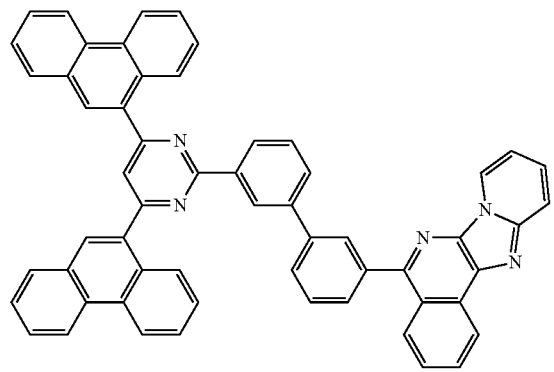
442
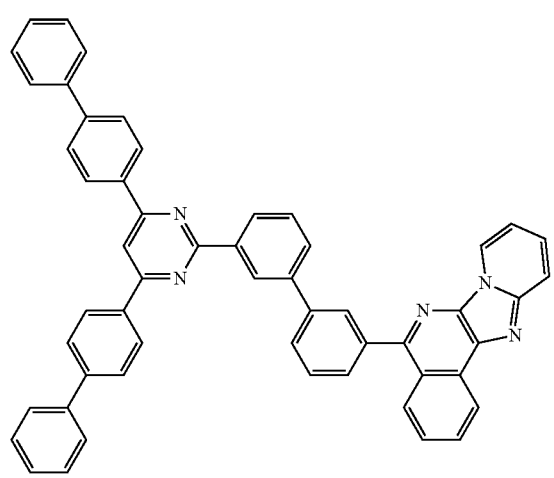
443
445
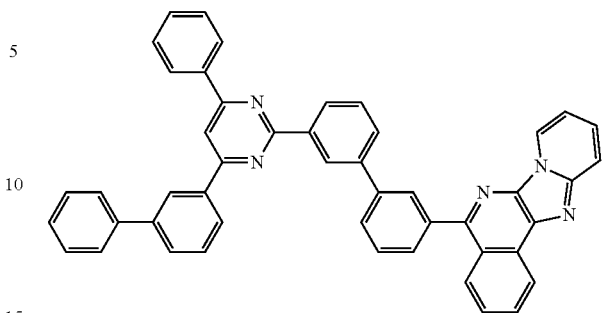
446
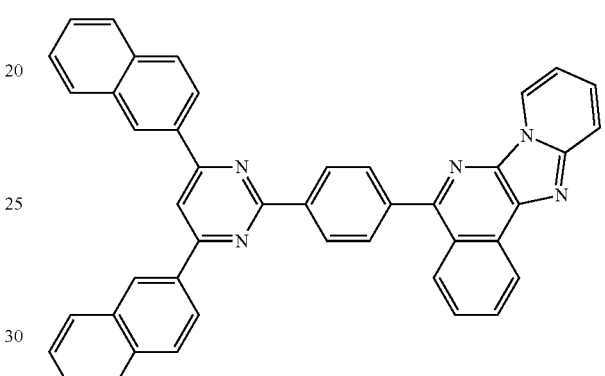
447
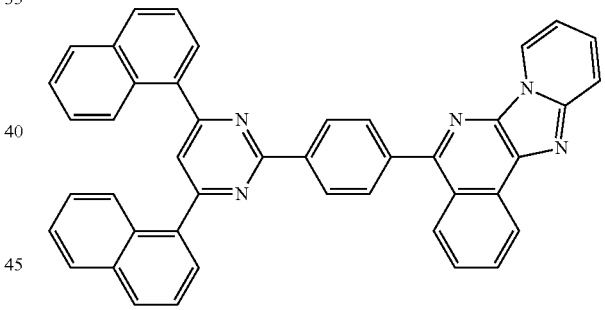
448
444
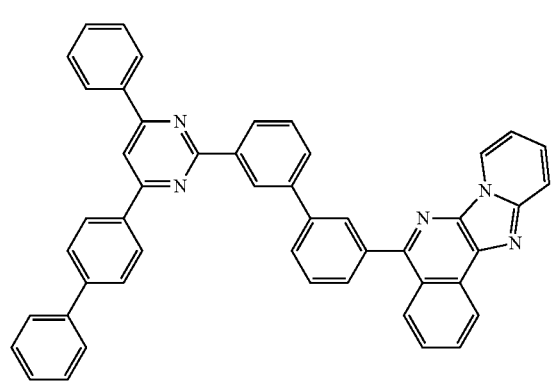
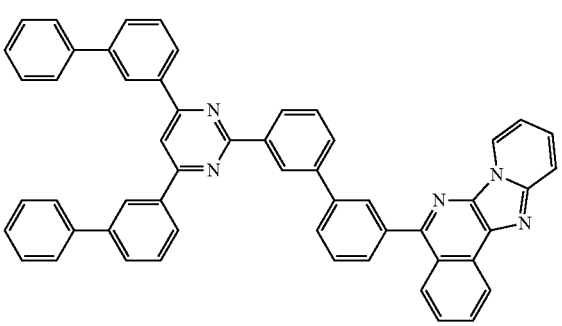
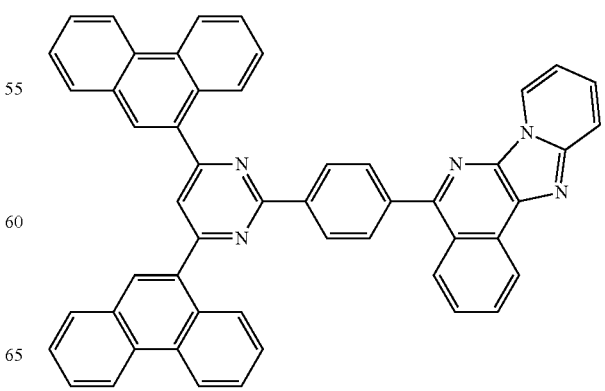

449
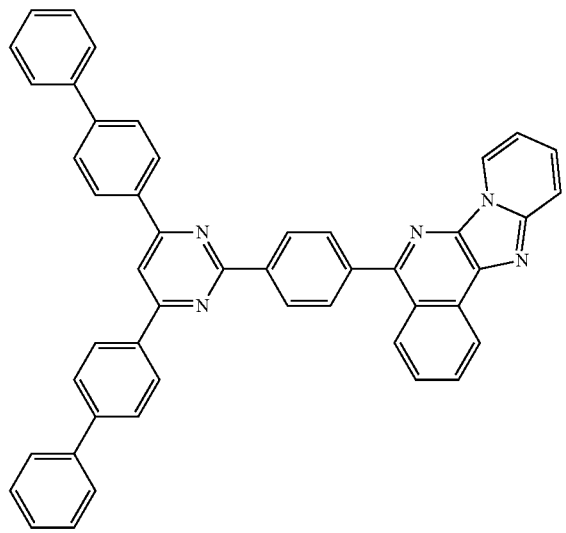
450
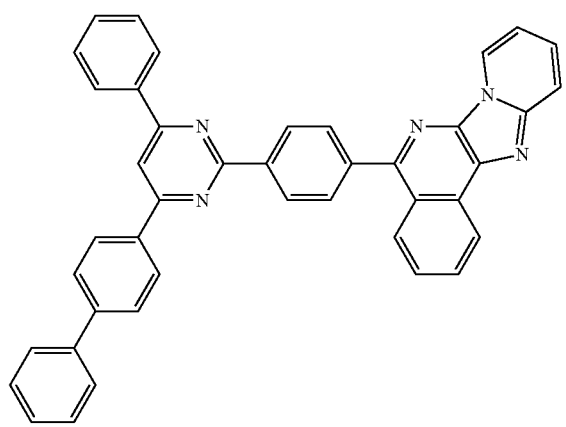
451
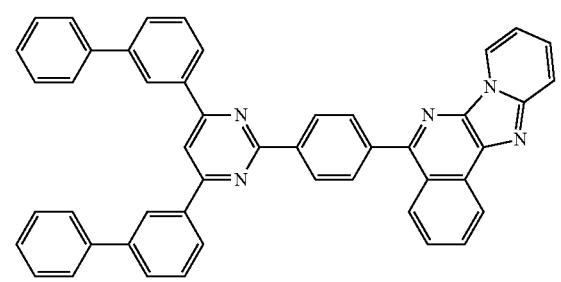
452
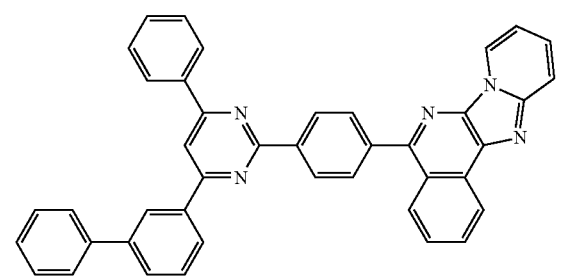
453
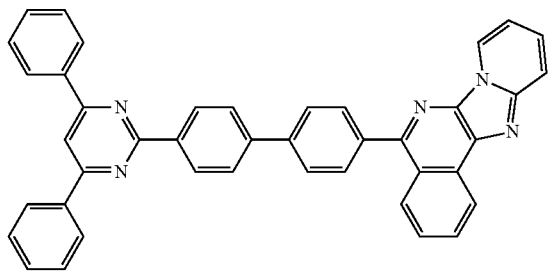
454
455
456
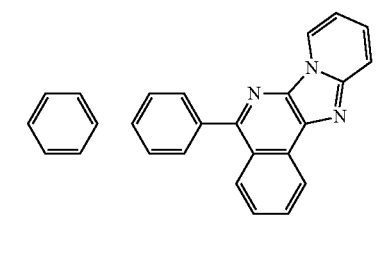

-continued
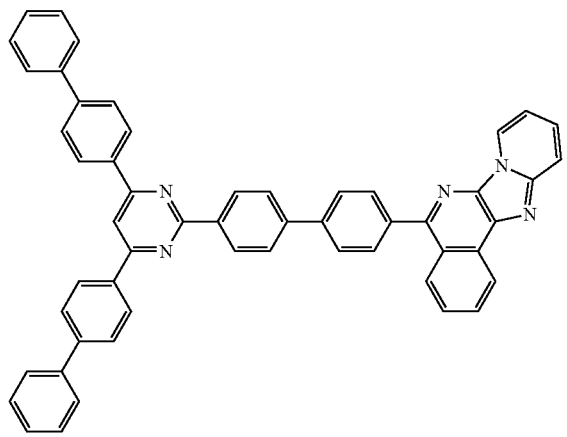
457
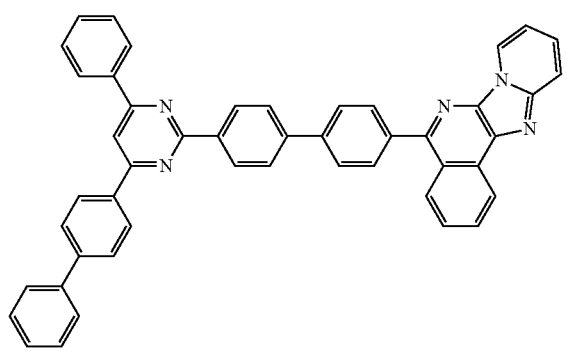
458
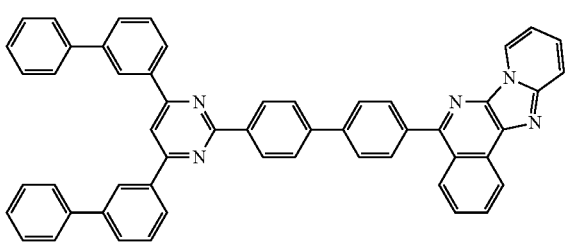
459
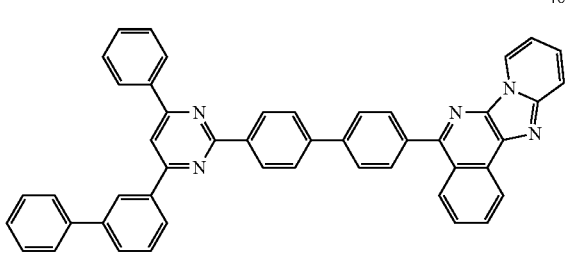
460
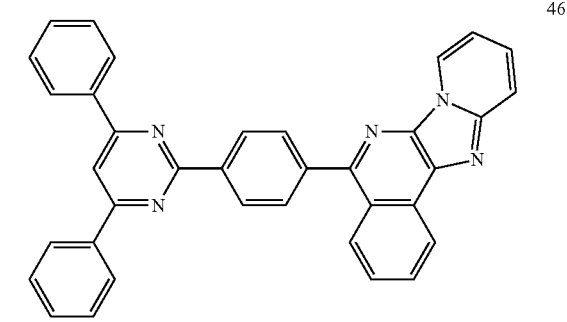
461
-continued
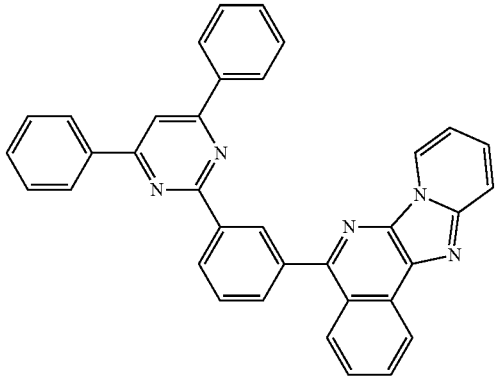
462
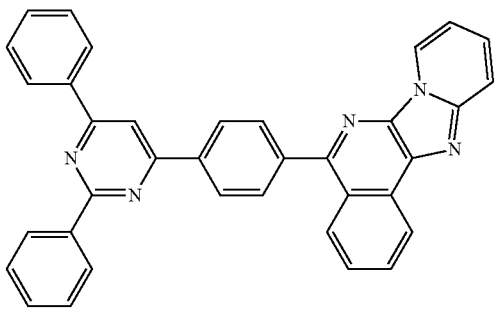
463
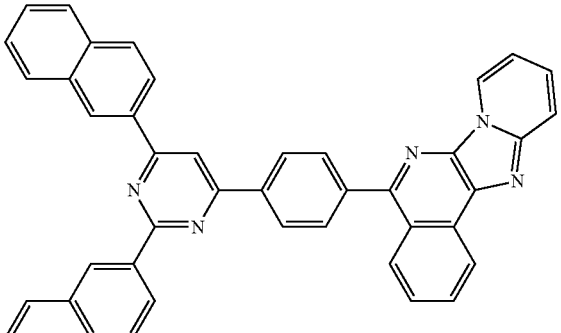
464
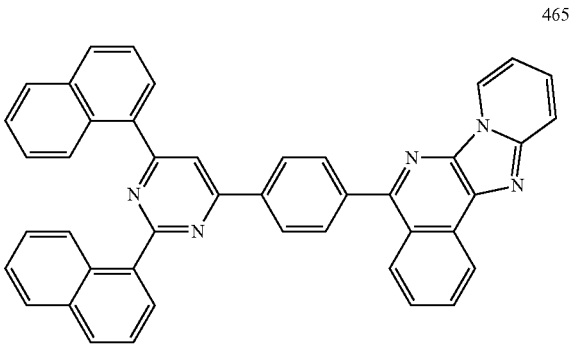
465

466
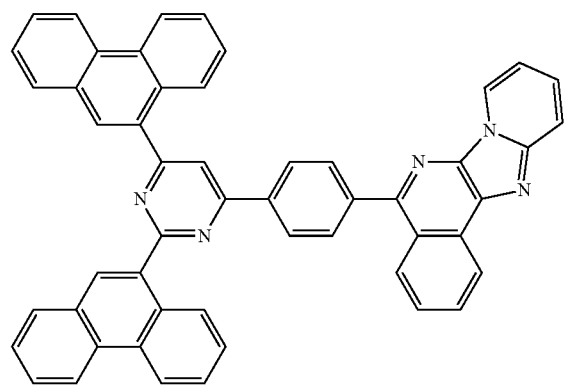
467
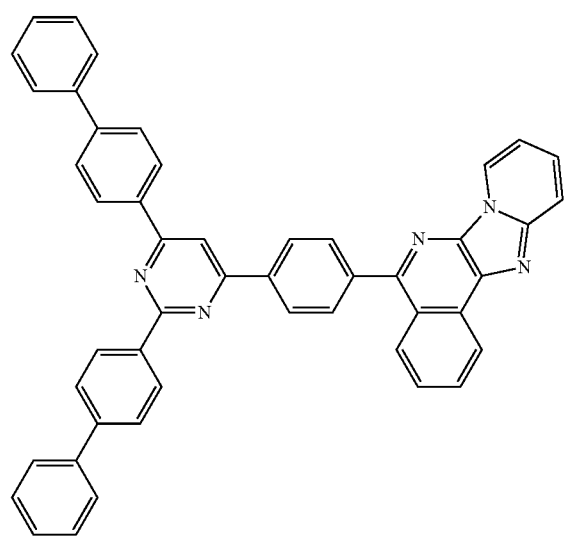
468
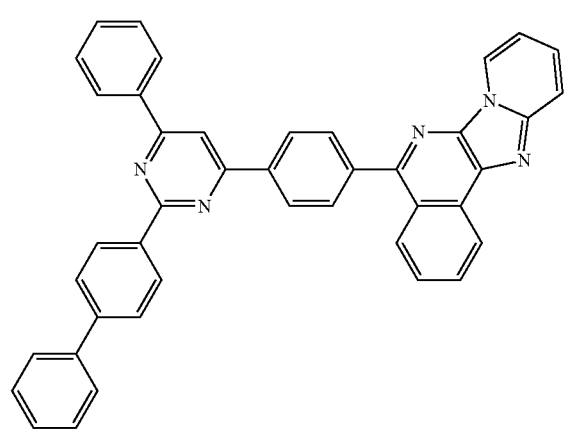
469
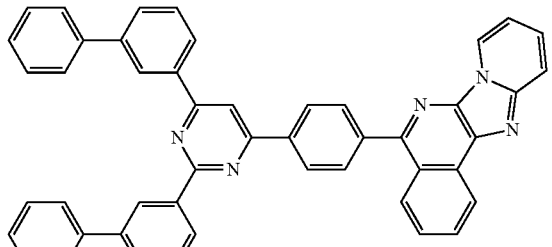
470
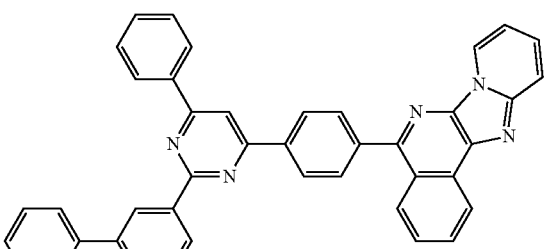
471
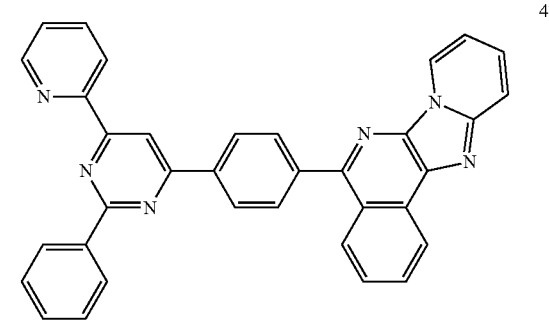
472
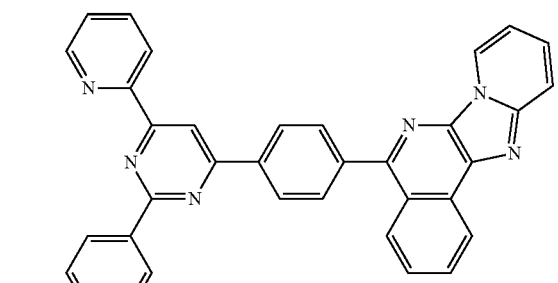
473
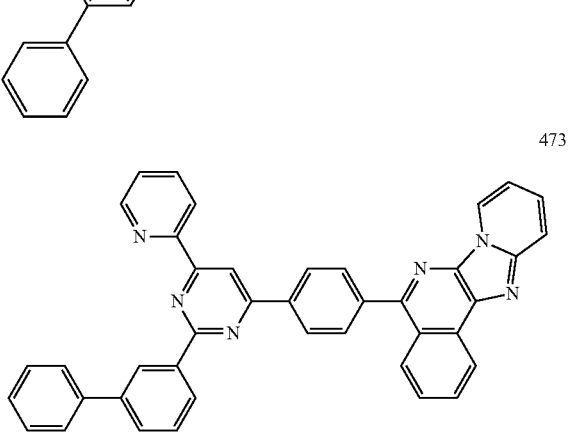

-continued
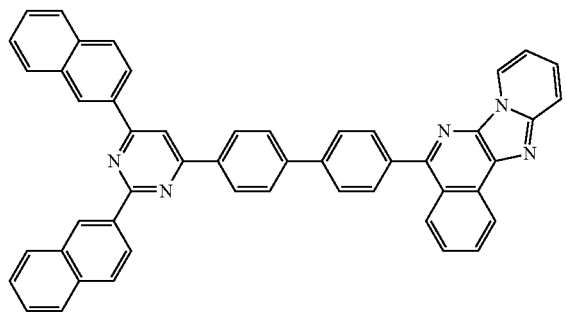
474
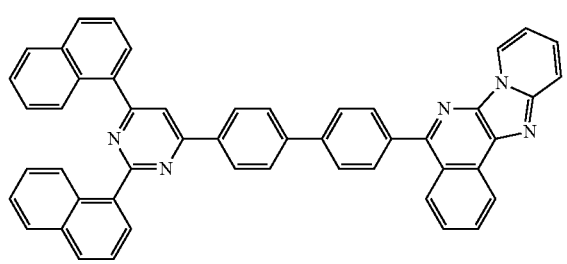
475
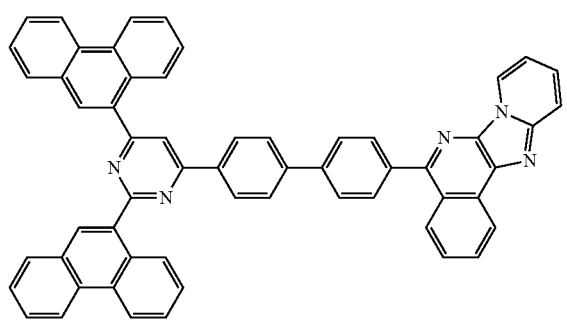
476
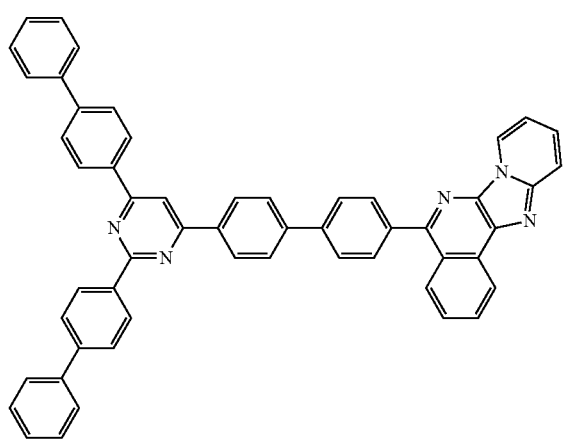
477
-continued
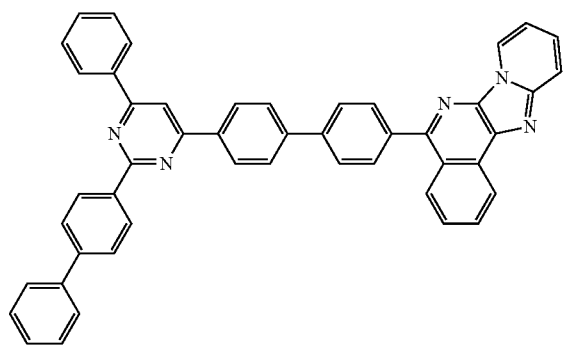
478
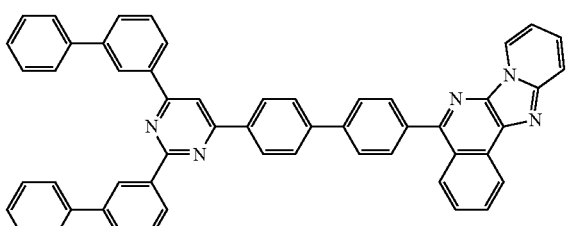
479
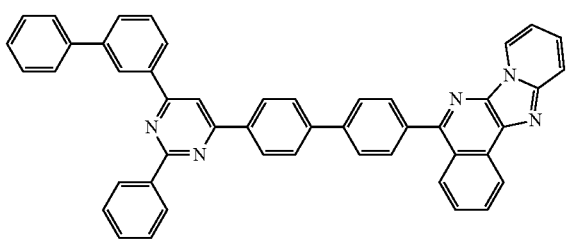
480
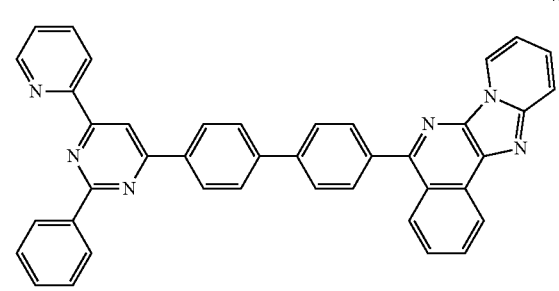
481
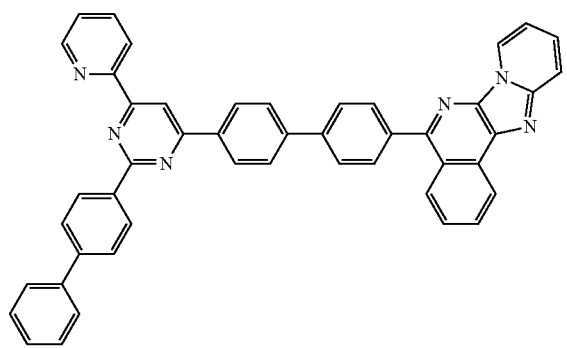
482

483
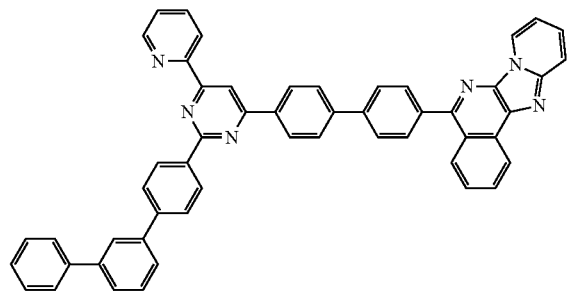
484
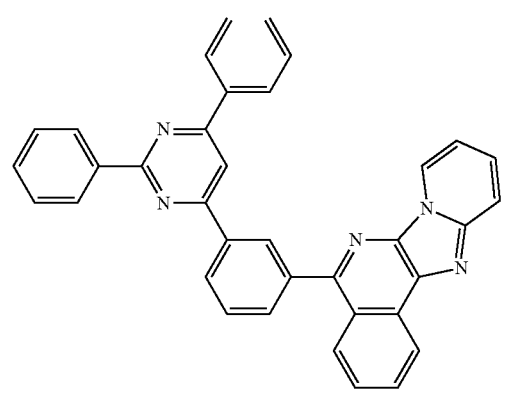
485
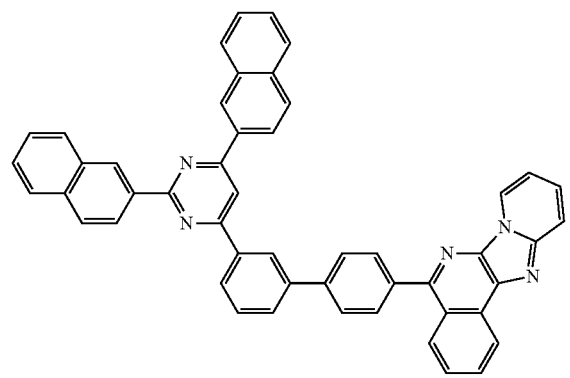
486
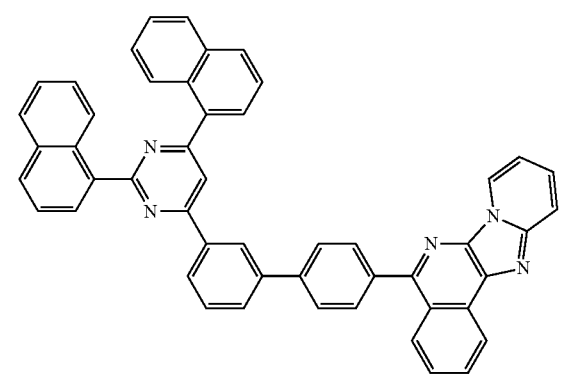
487
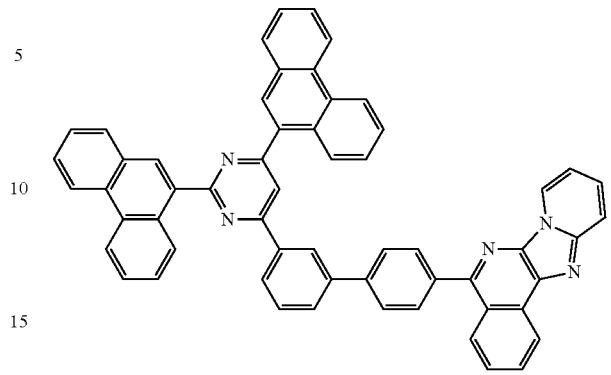
488
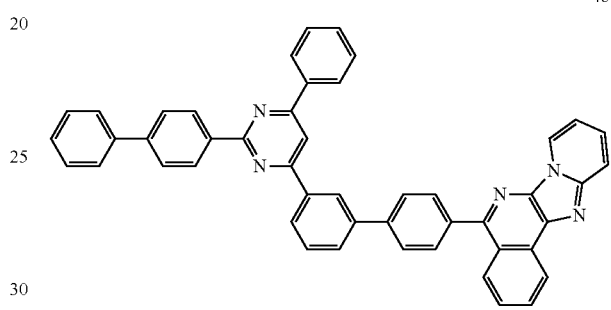
489
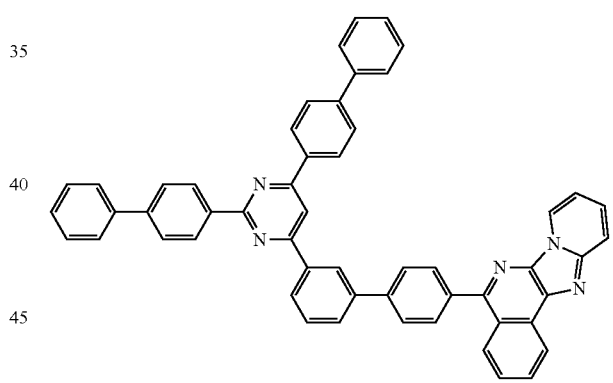
490
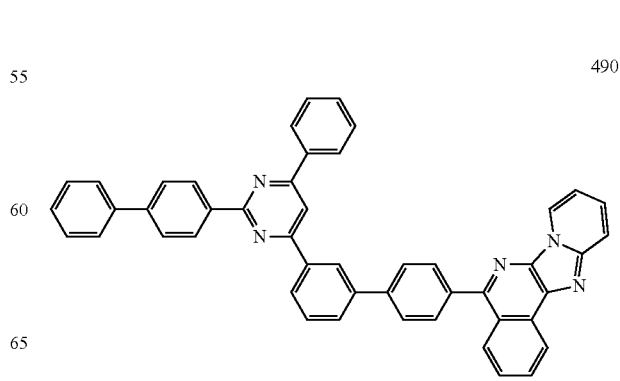

-continued
491
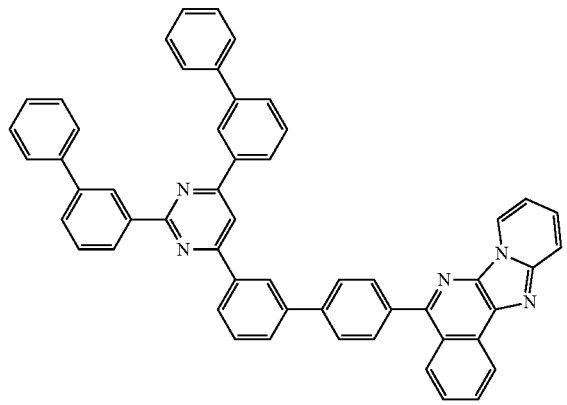
492
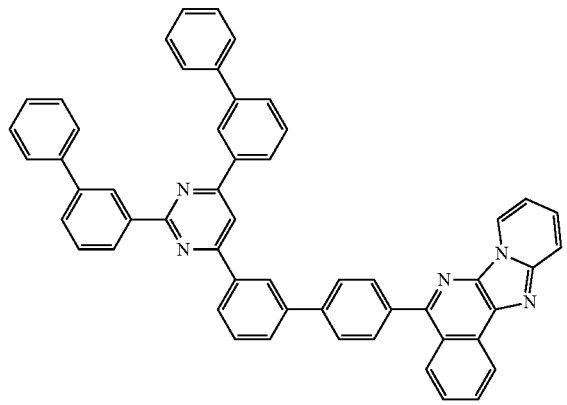
493
494
495
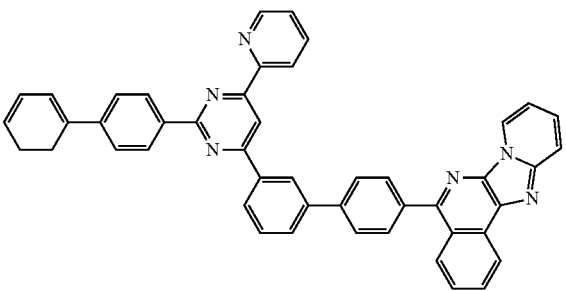
496
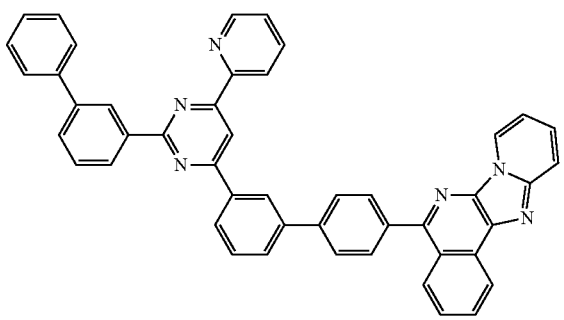
497
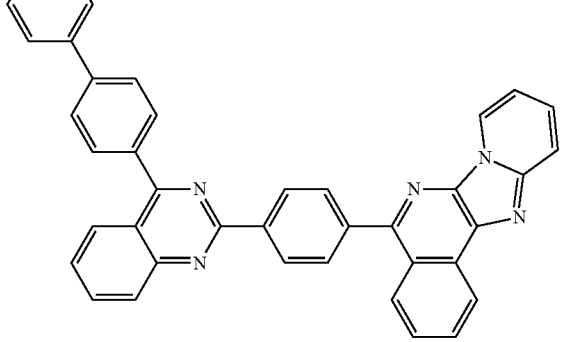
498
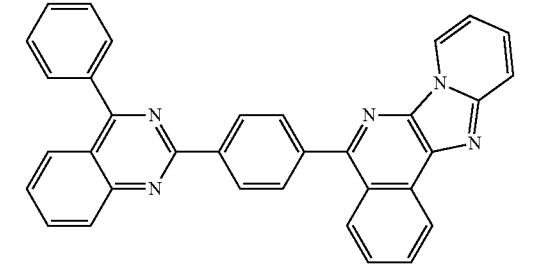
499
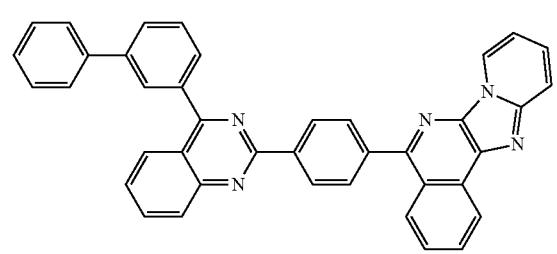

500
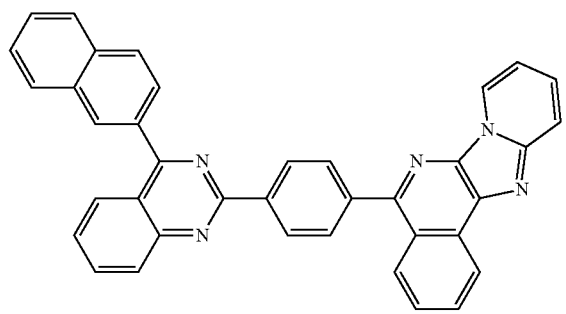
505
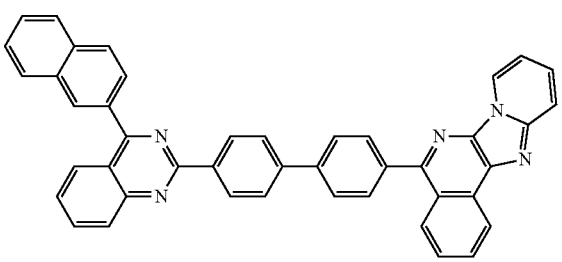
501
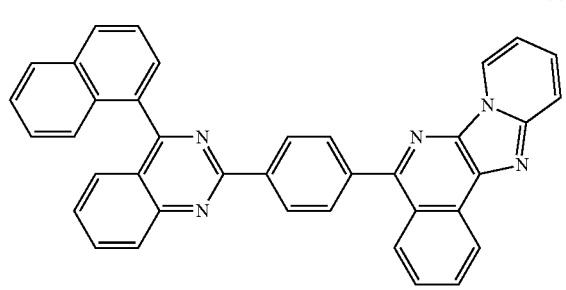
506
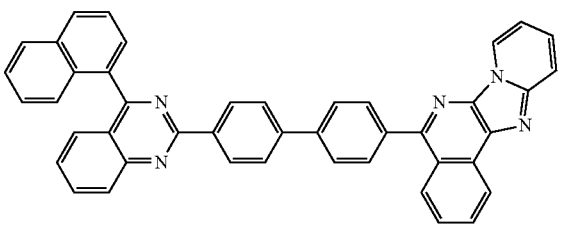
502
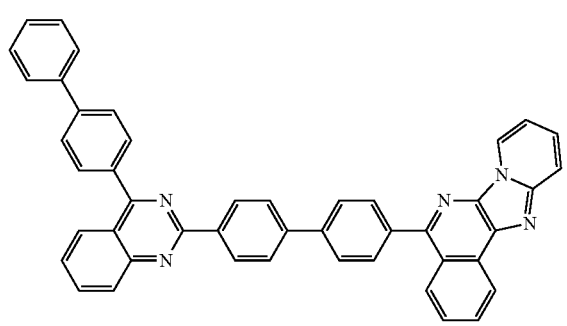
507
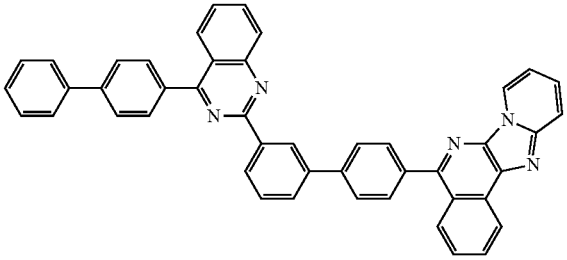
503
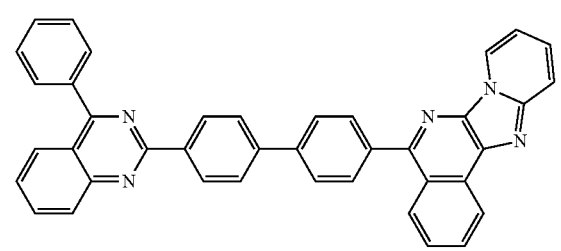
508
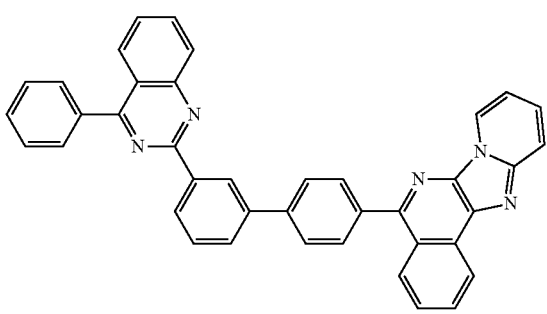
504
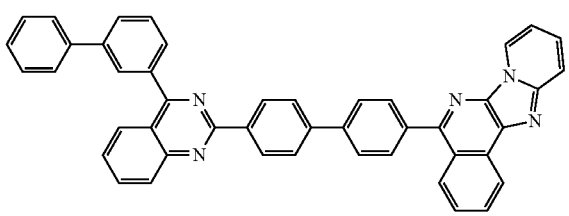
509
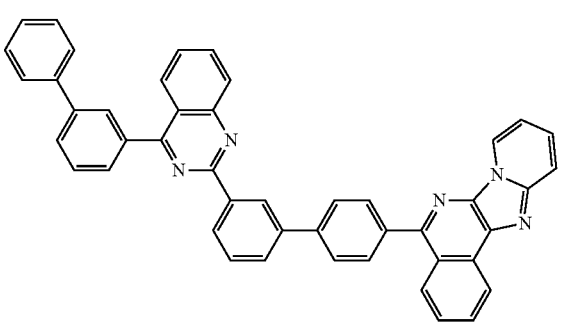

-continued
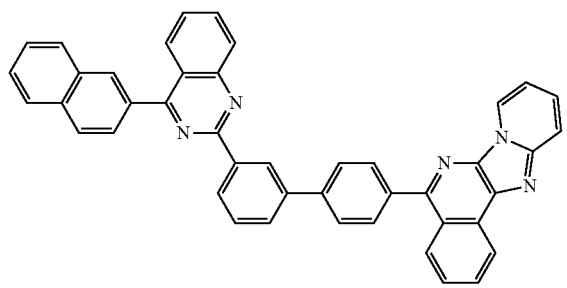
510
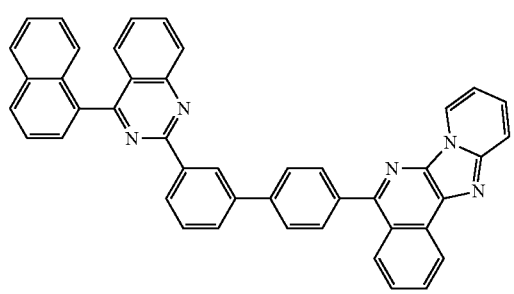
511
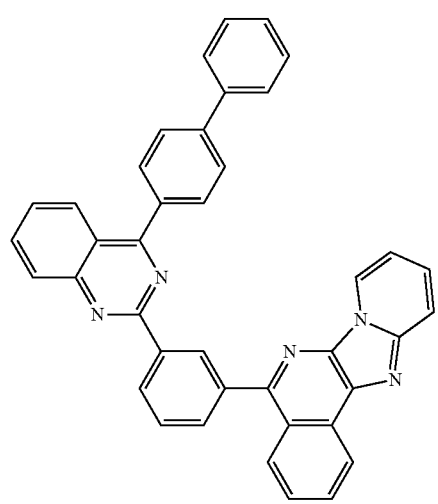
512
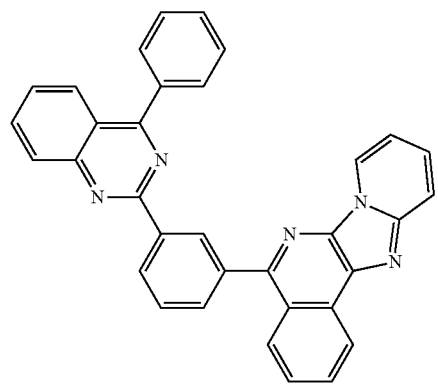
513
-continued
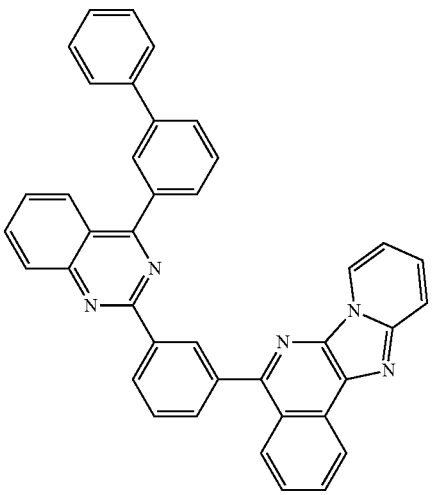
514
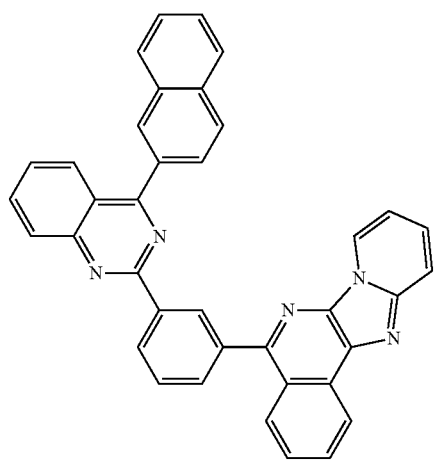
515
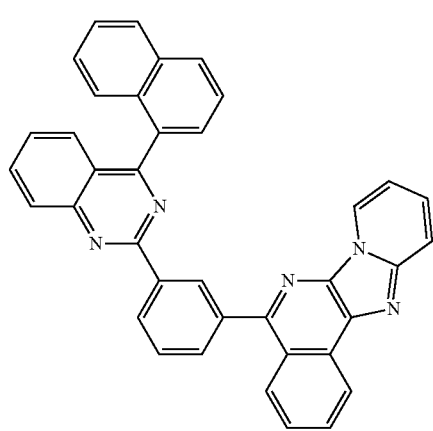
516

517
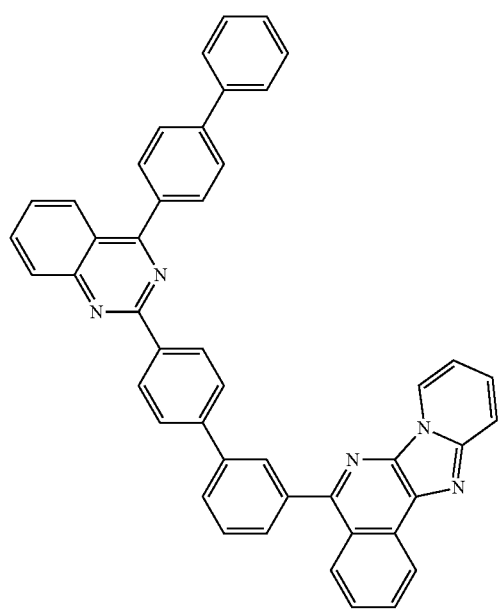
519
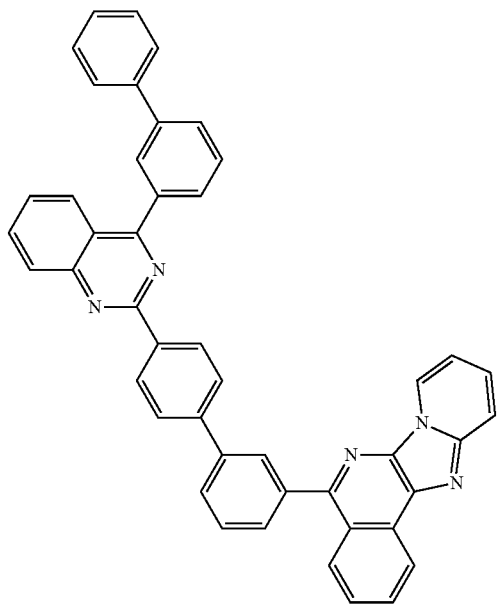
518
520

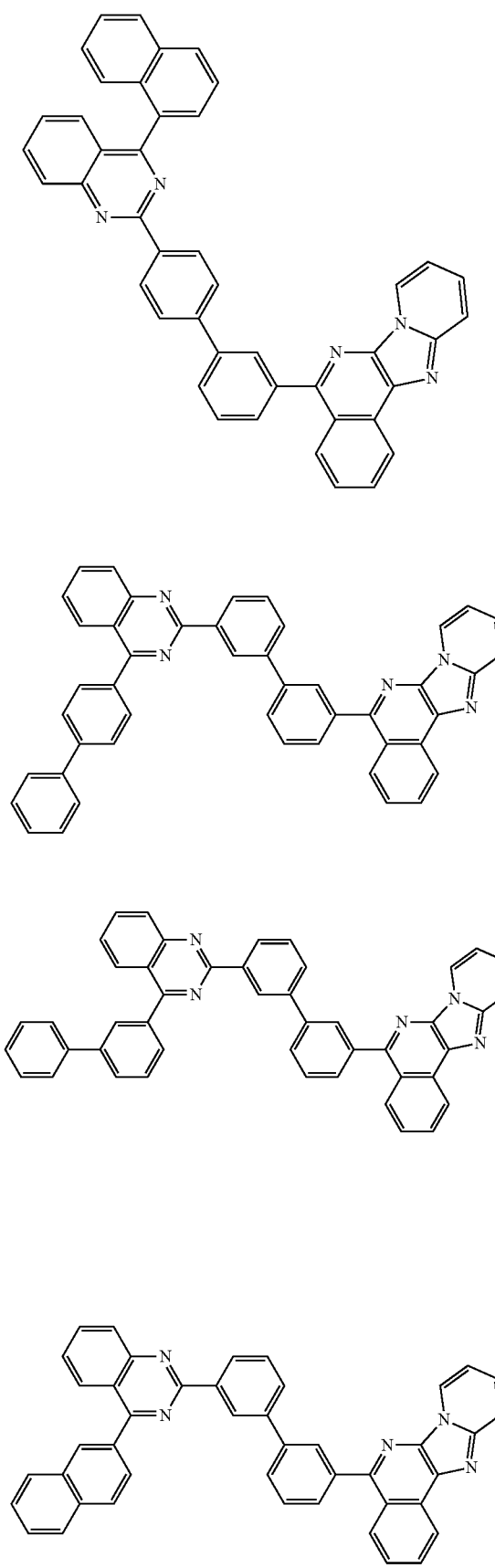
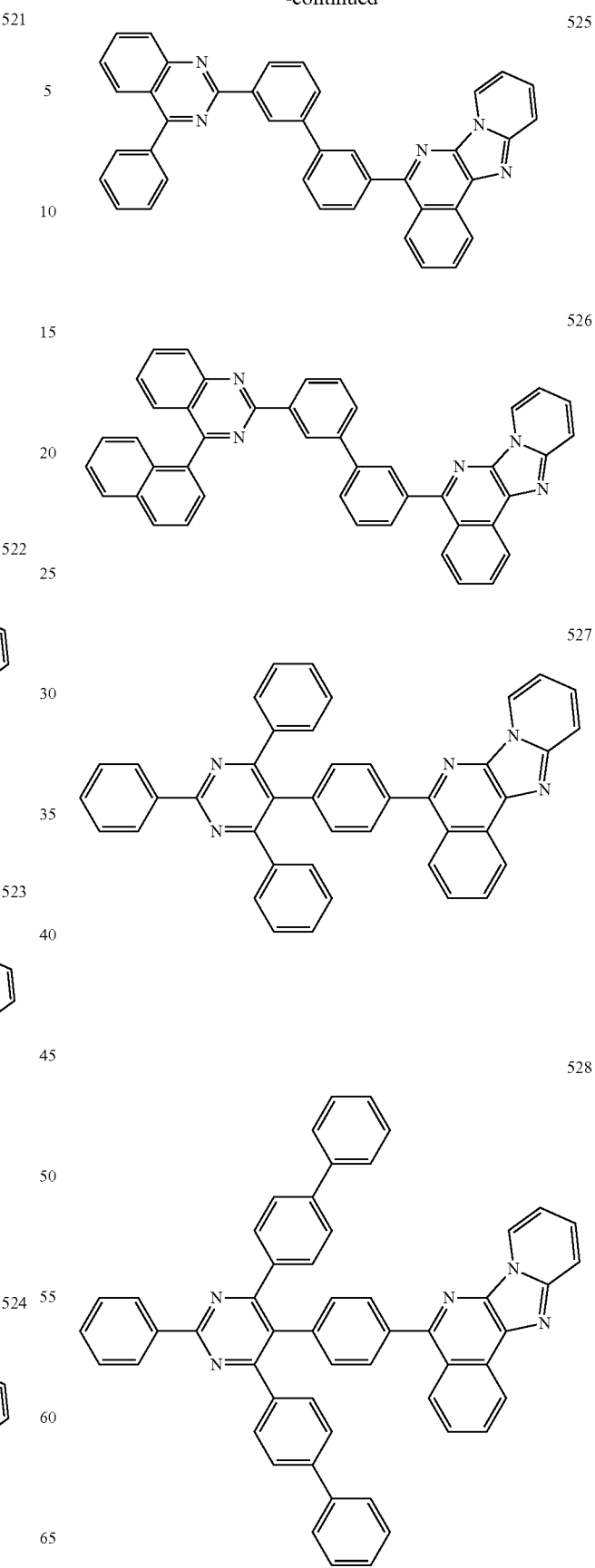

529
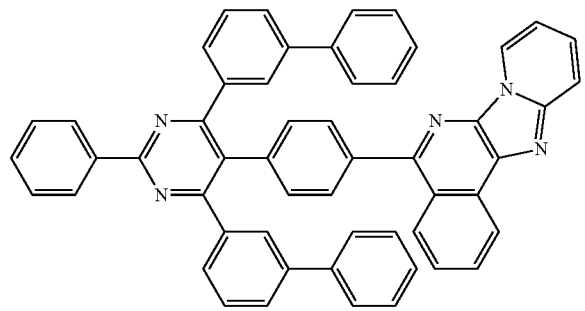
534
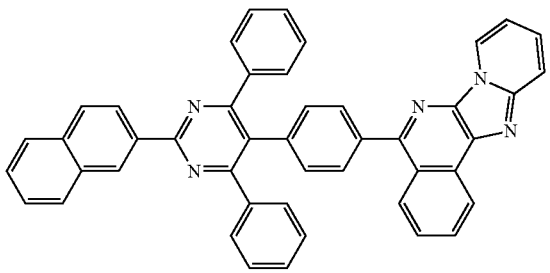
530
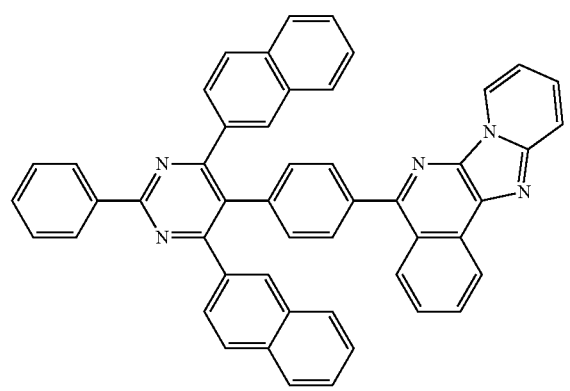
535
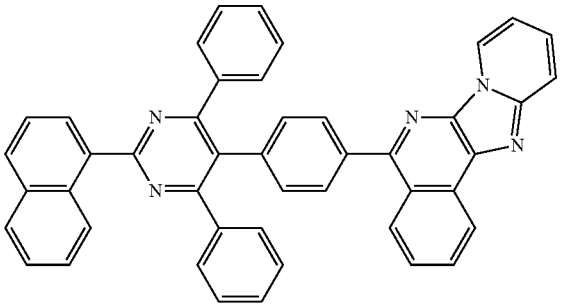
531
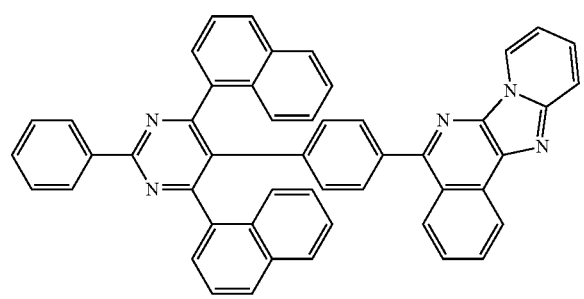
536
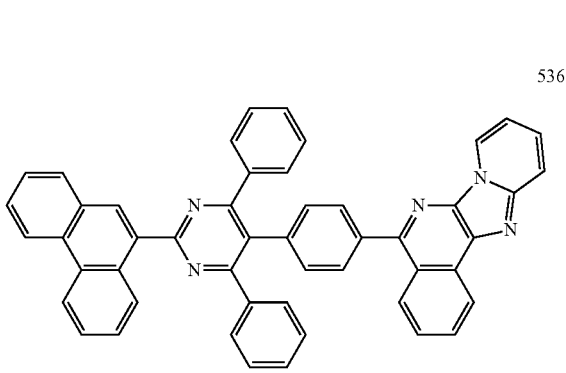
532
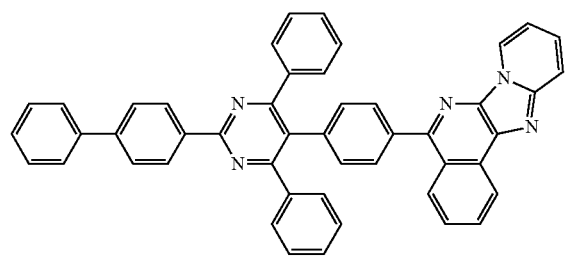
537
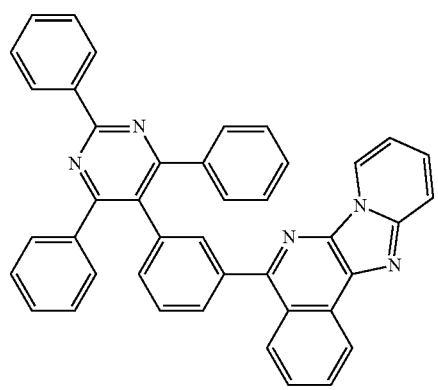
533
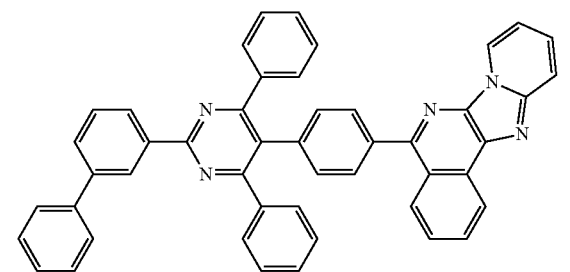

538
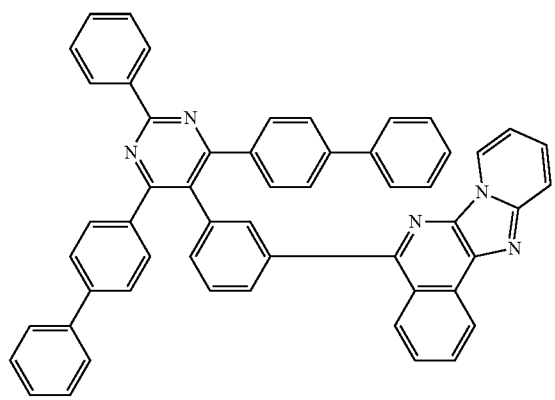
541
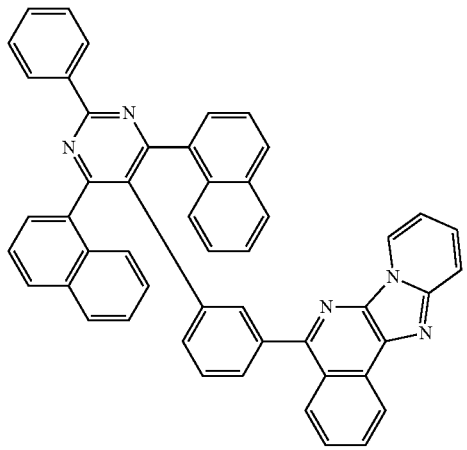
539
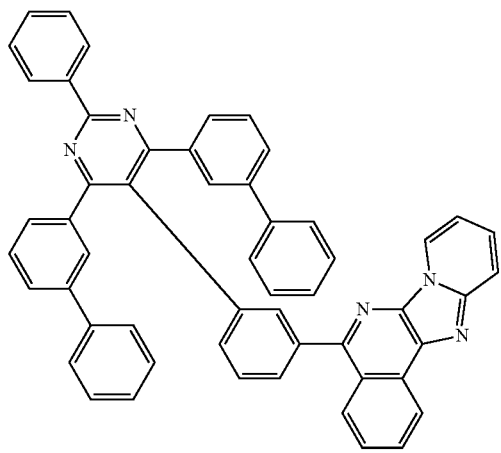
542
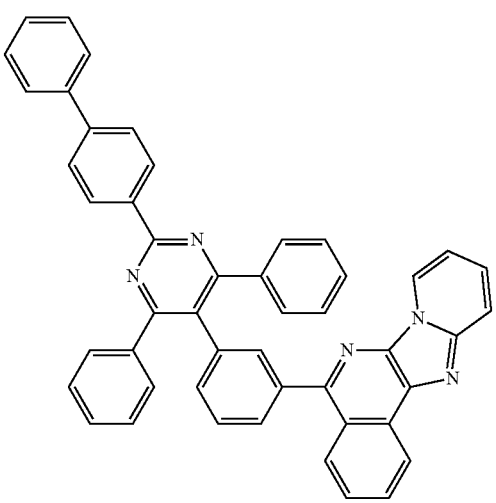
540
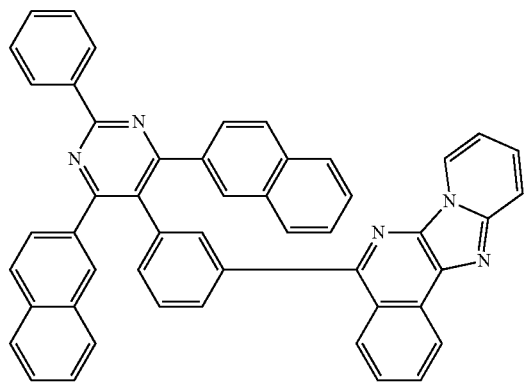
543
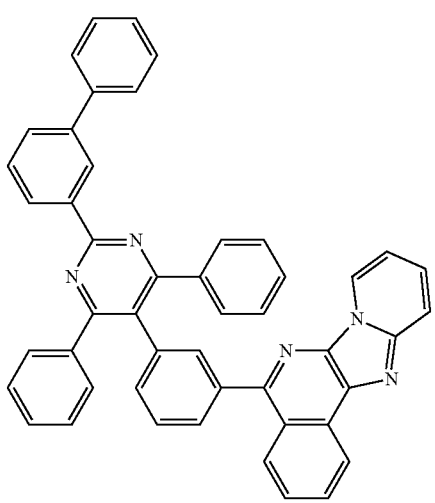

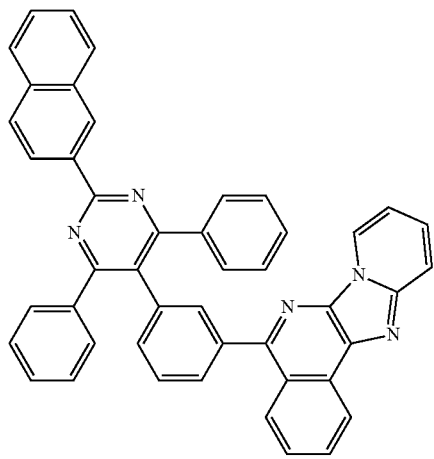
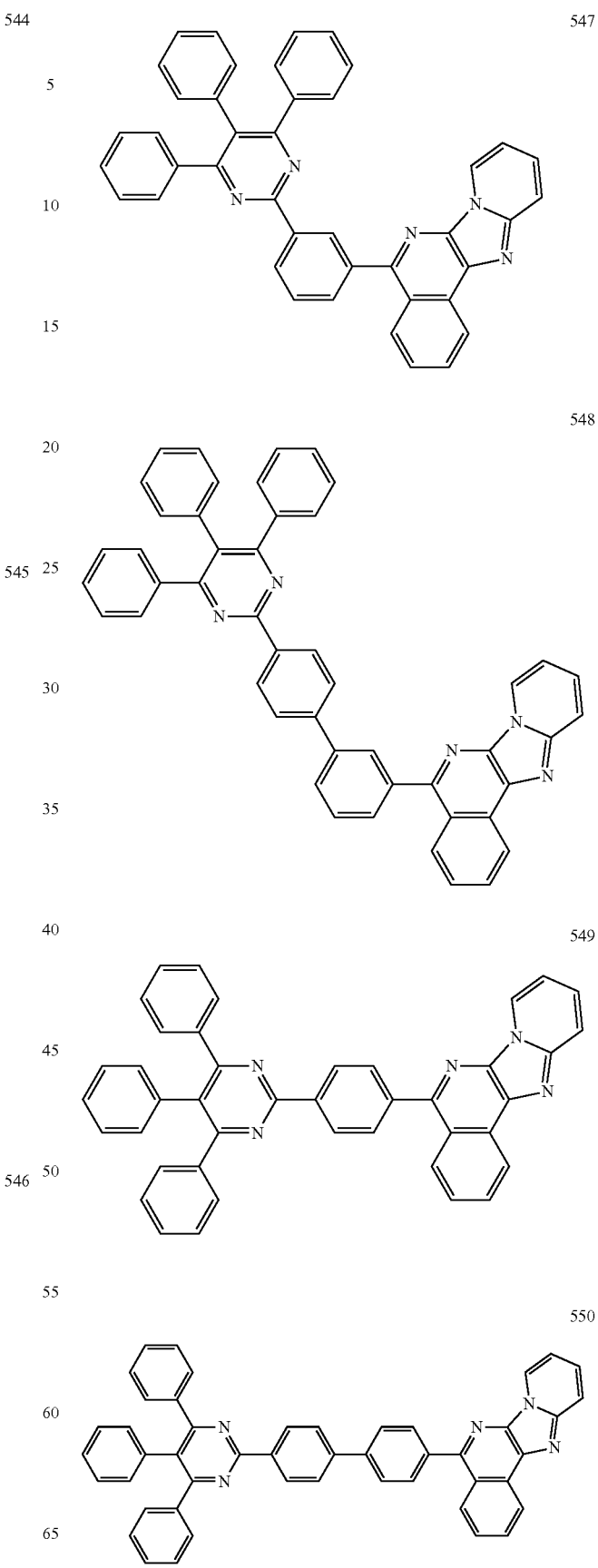

551
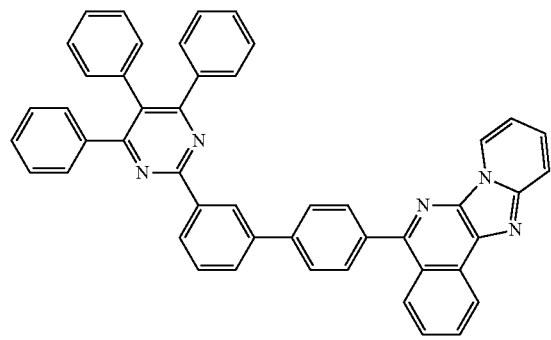
552
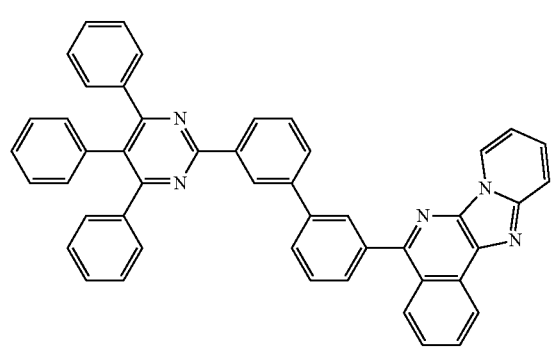
553
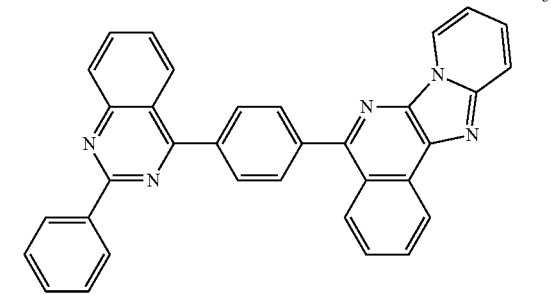
554
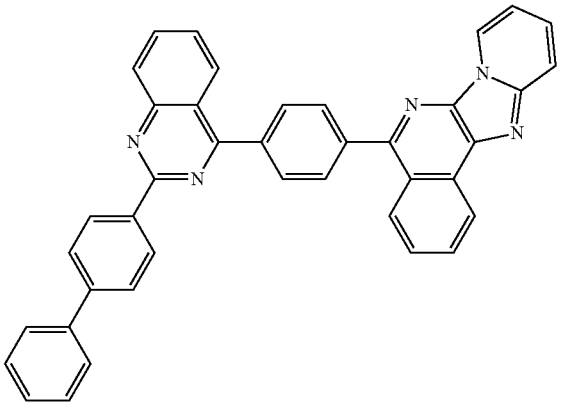
555
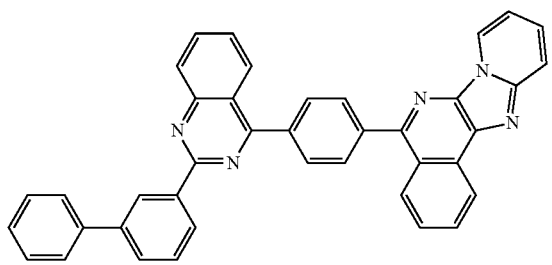
556
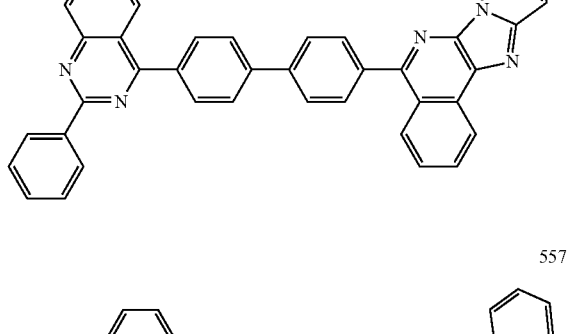
557
558
559
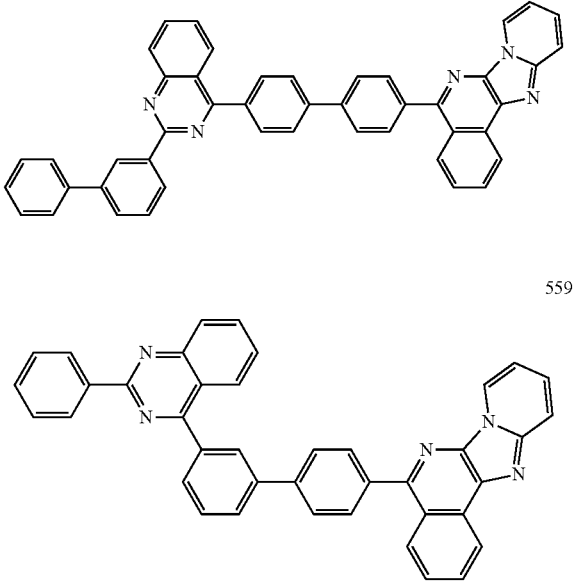

560
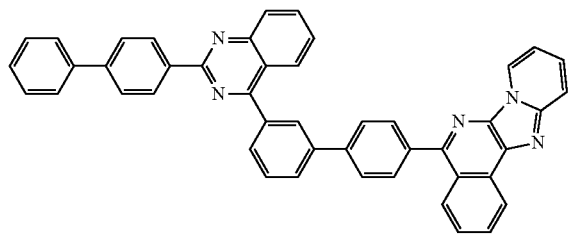
561
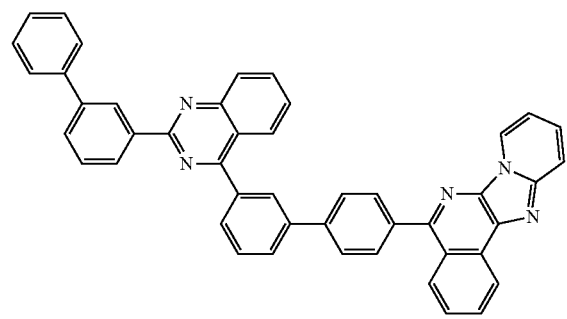
562
563
564
565
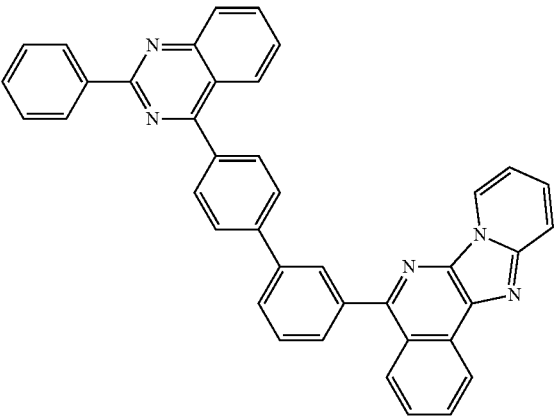
566
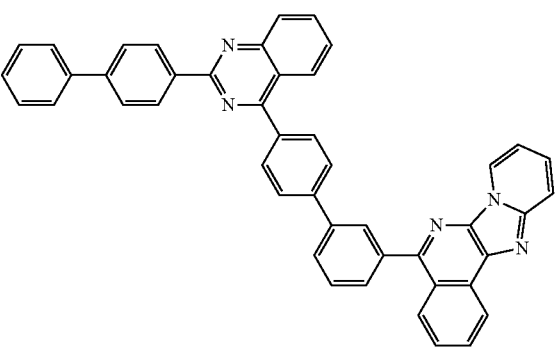
567
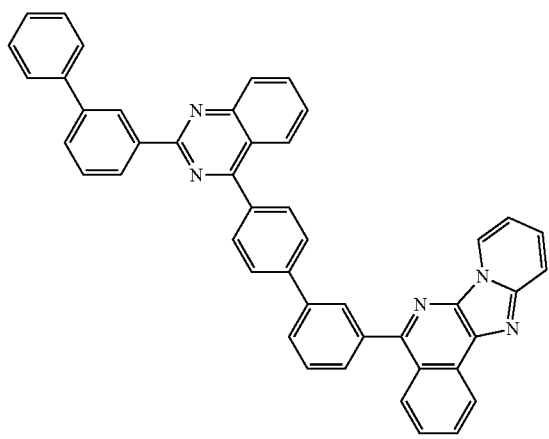
568
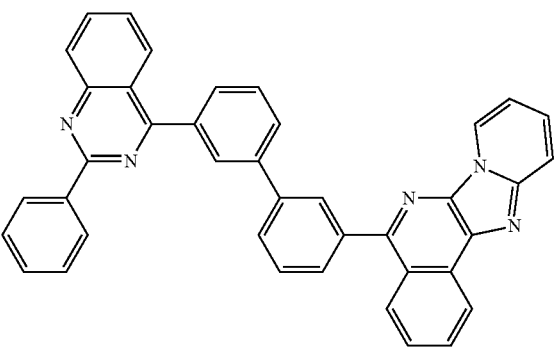

167
-continued
569
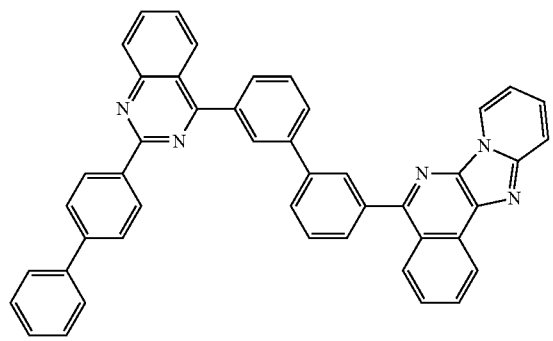
570
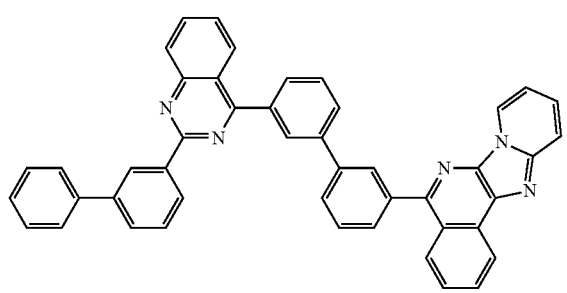
571
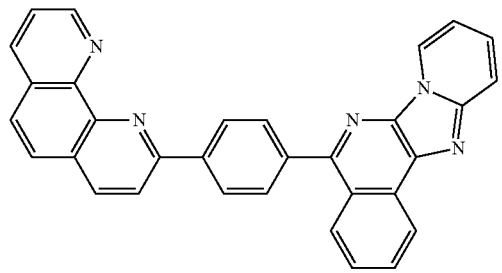
572
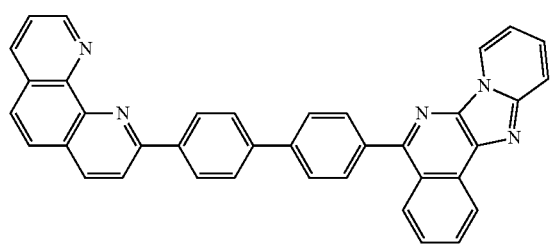
573
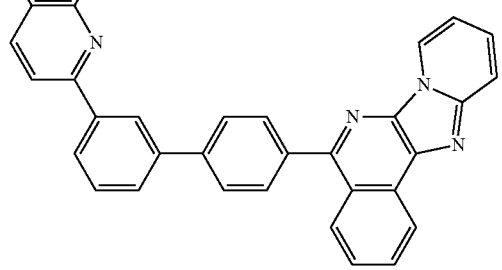
168
-continued
574
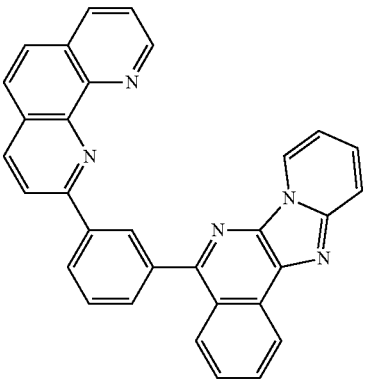
575
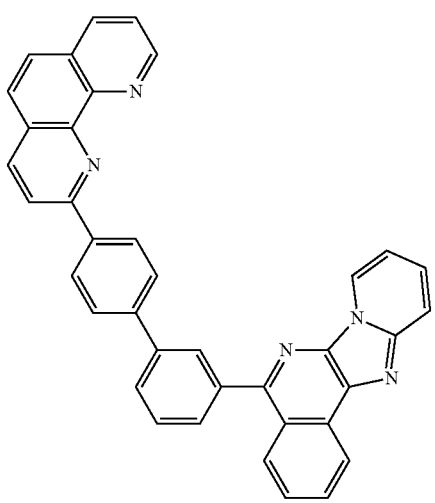
576
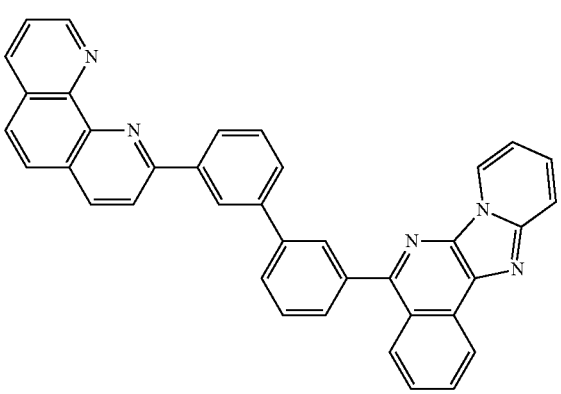
577
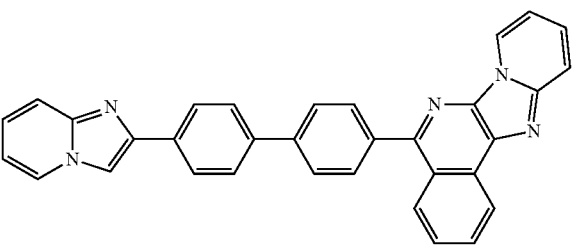

578
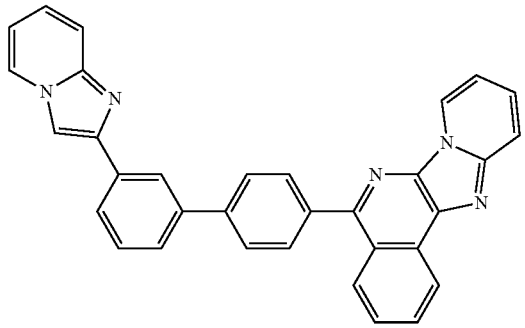
579
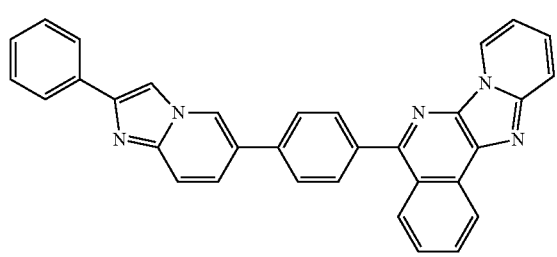
580
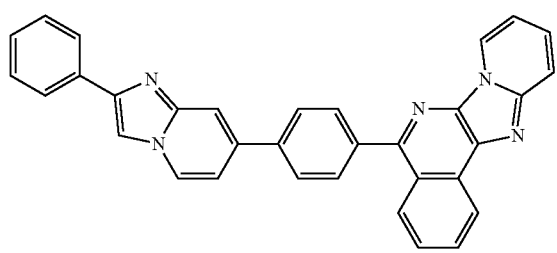
581
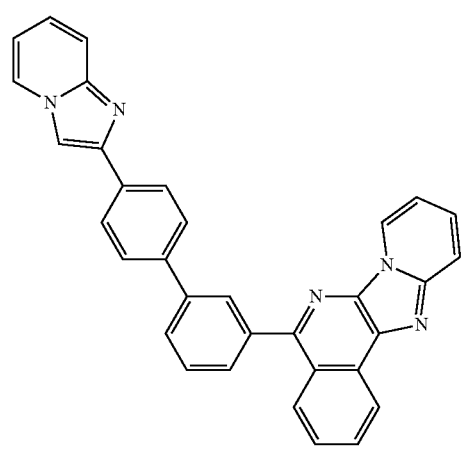
582
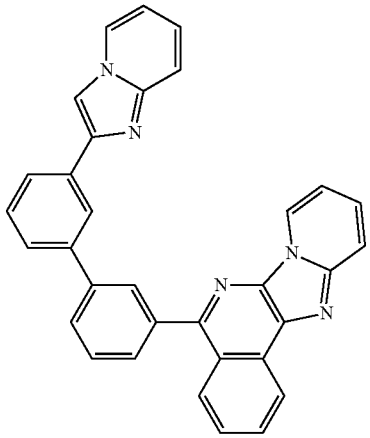
583
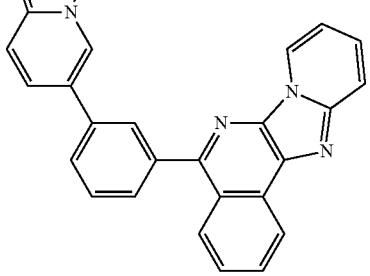
584
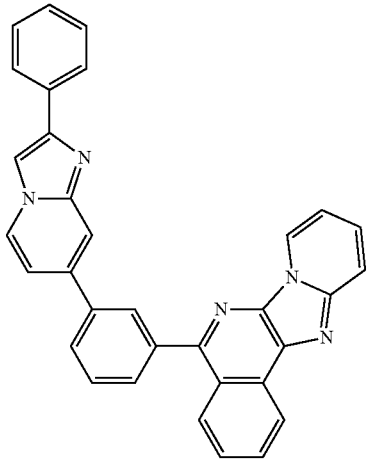
585
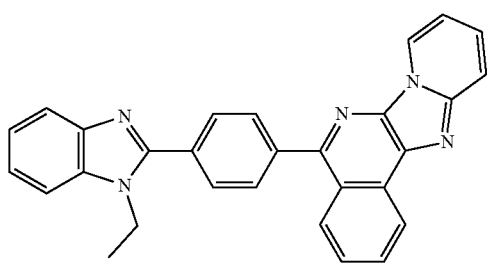

-continued
586
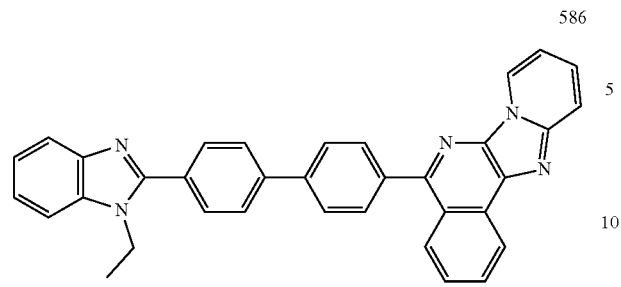
587
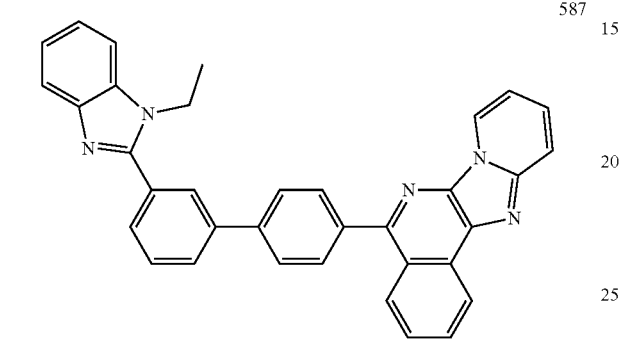
588
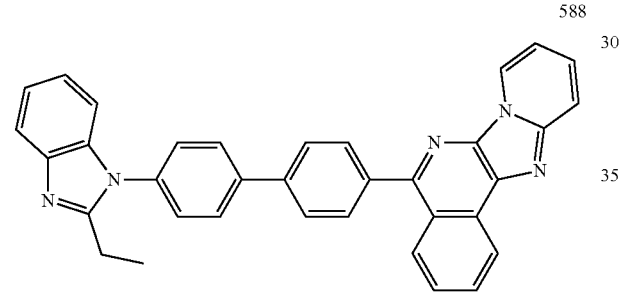
589
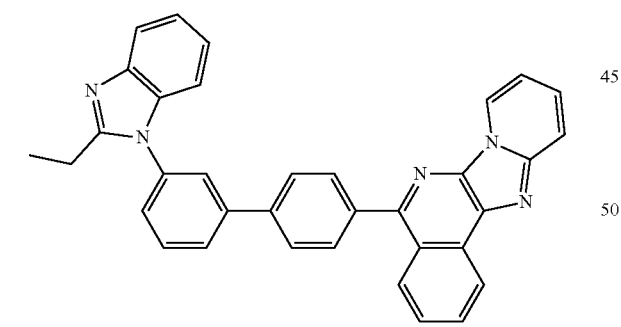
590
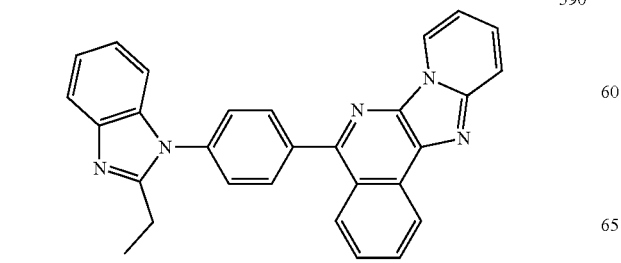
-continued
591
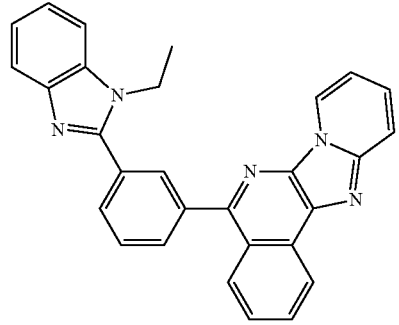
592
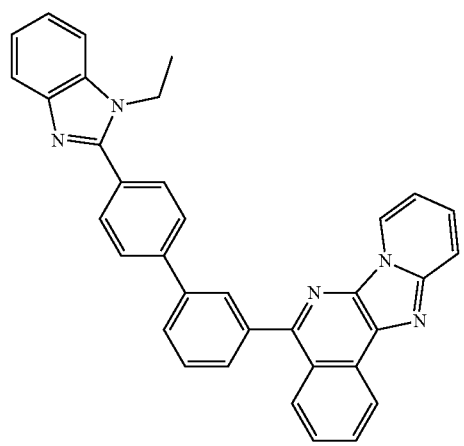
593
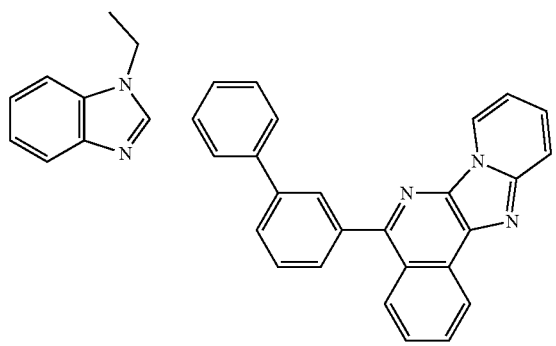
594
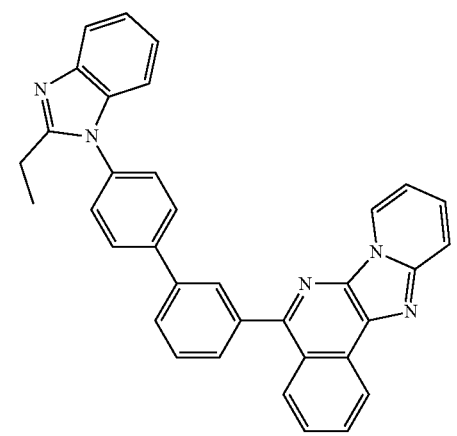

173
-continued
595
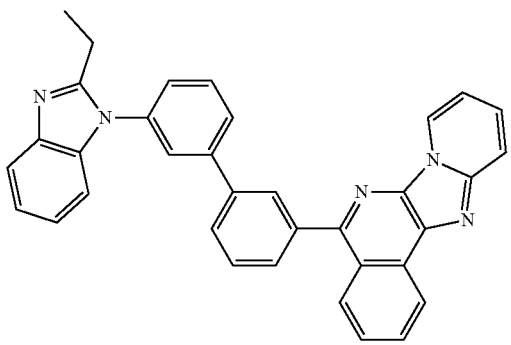
596
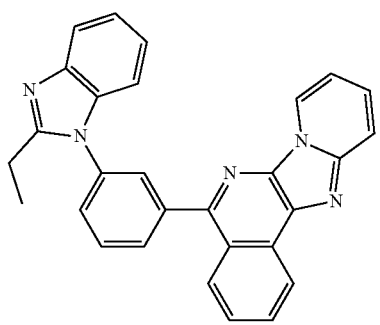
597
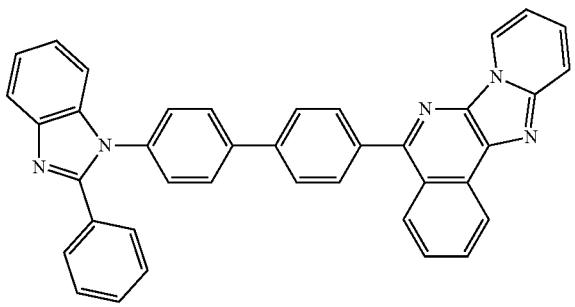
598
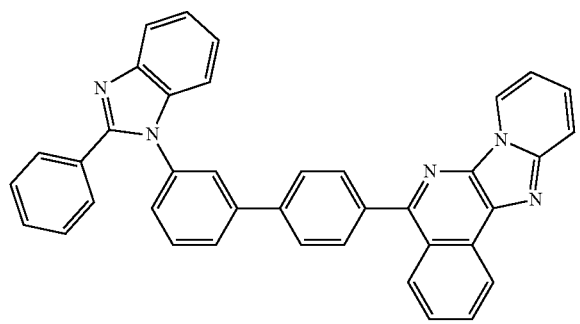
174
-continued
599
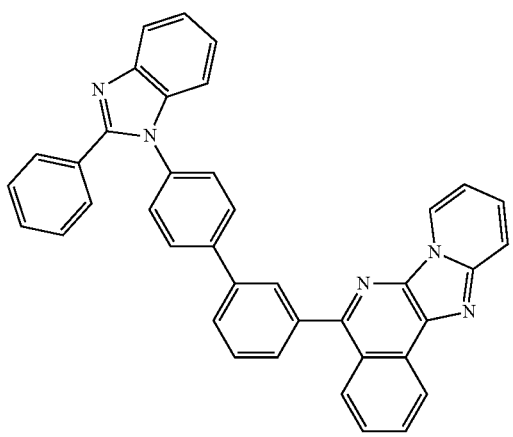
600
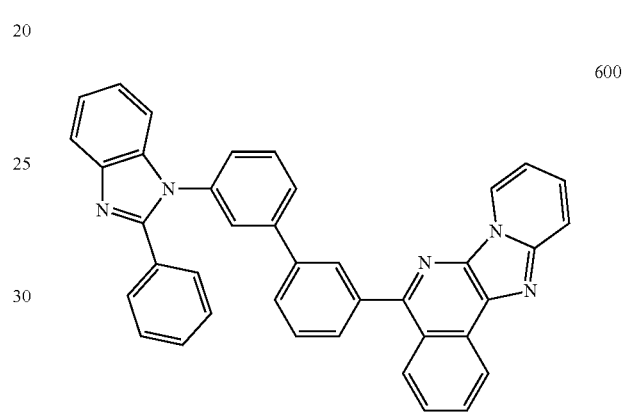
601
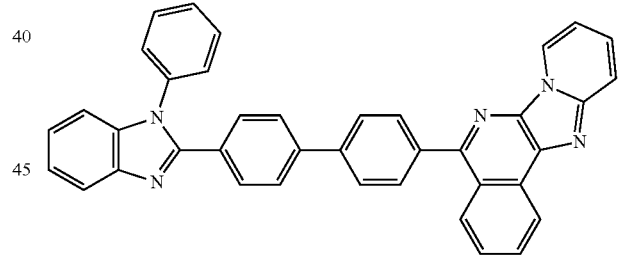
602
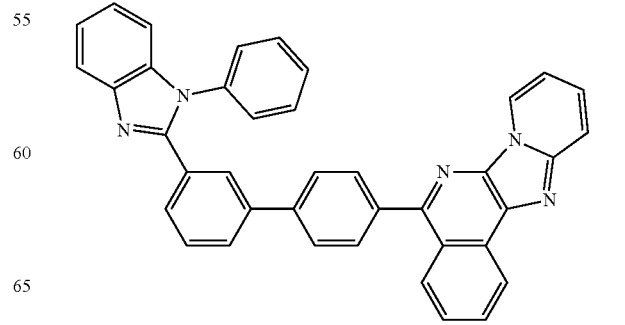

-continued
603
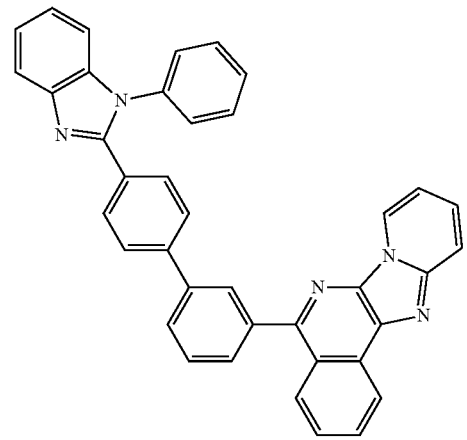
604
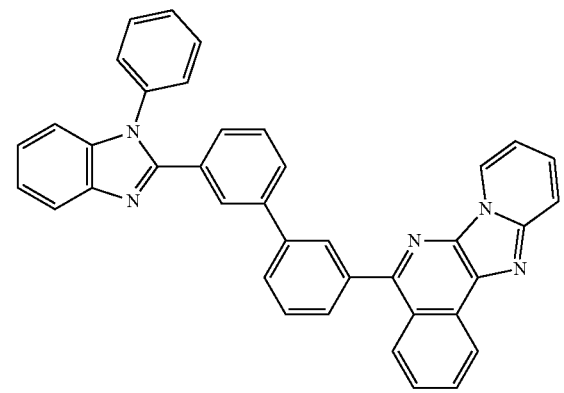
605
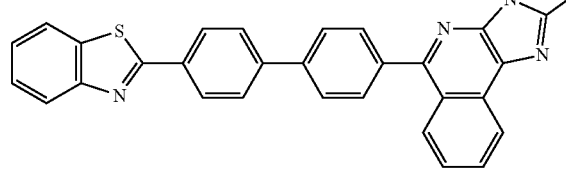
606
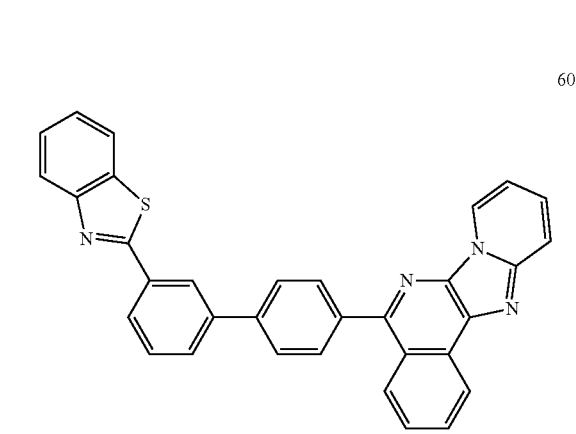
-continued
607
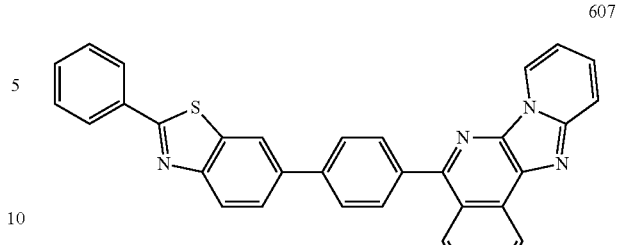
608
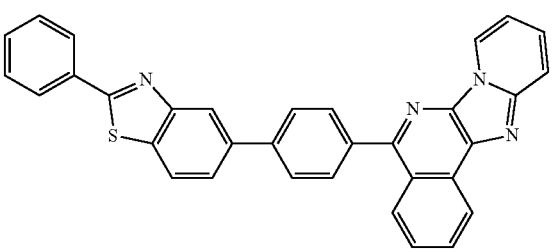
609
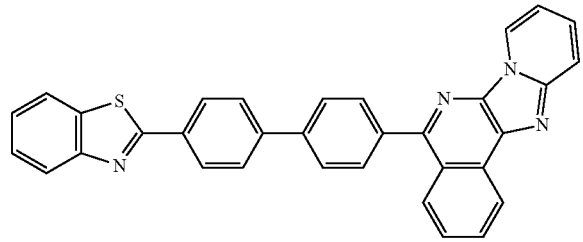
610
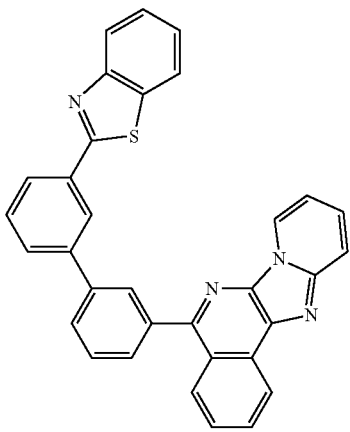

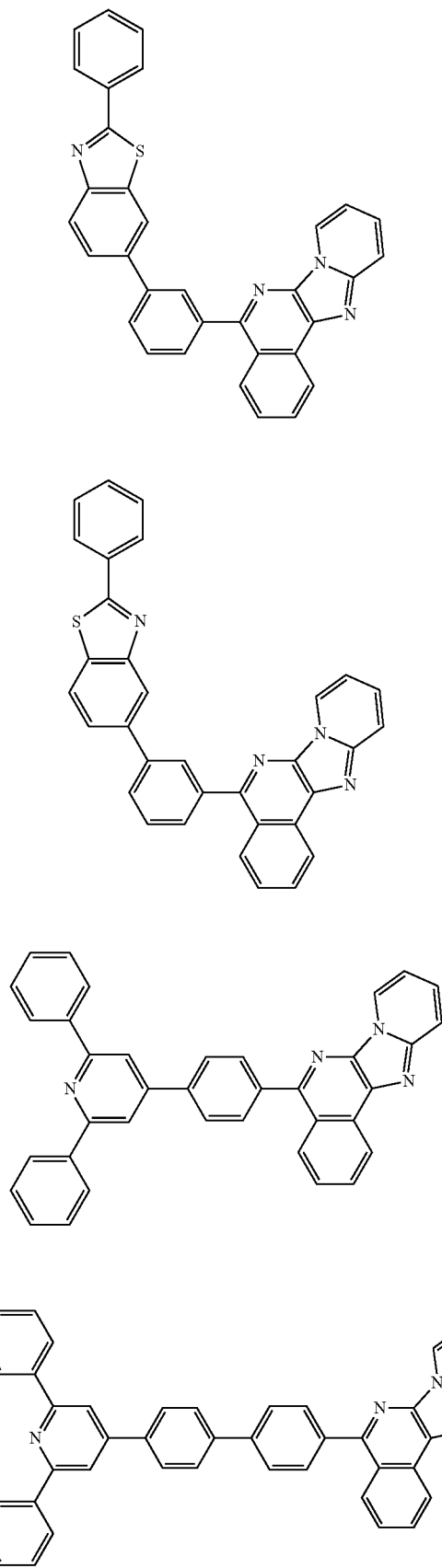

619
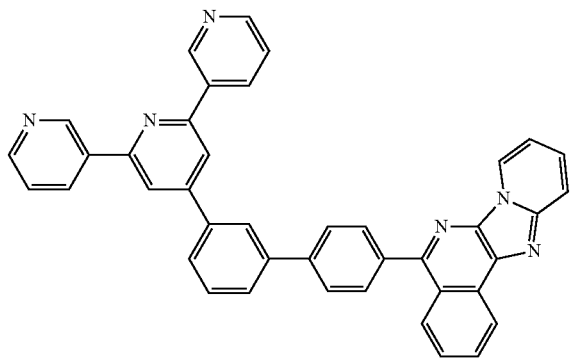
620
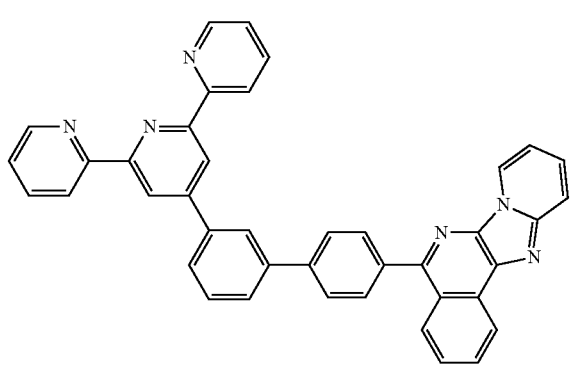
621
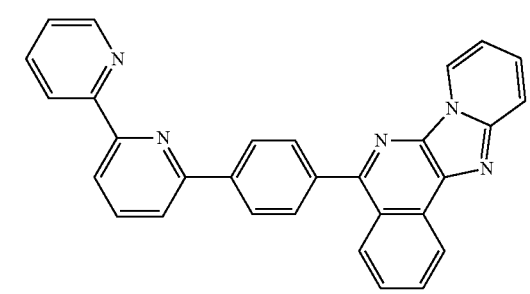
622
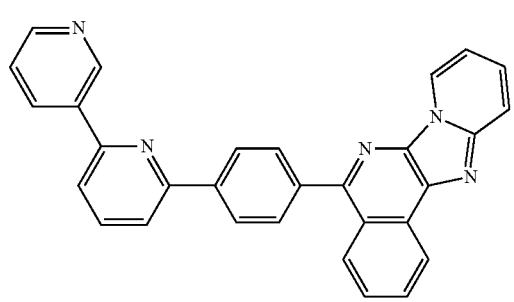
623
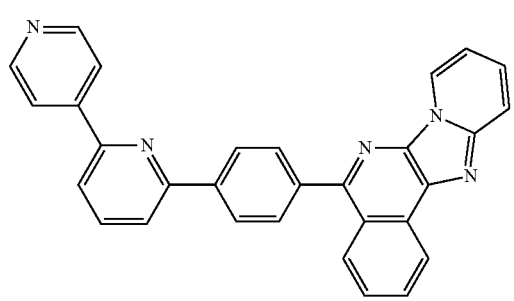
624
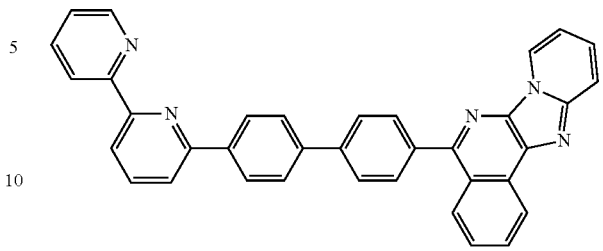
625
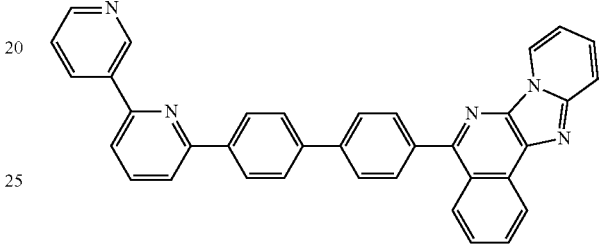
626
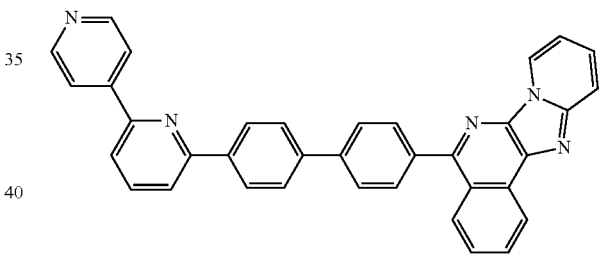
627
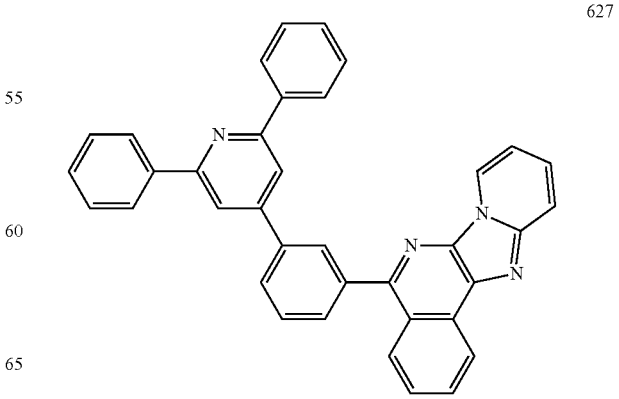

-continued
628
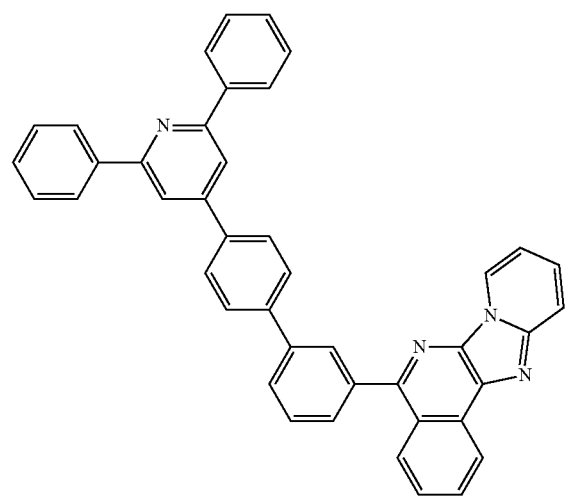
629
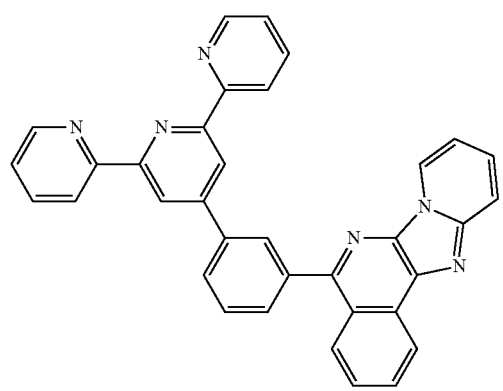
630
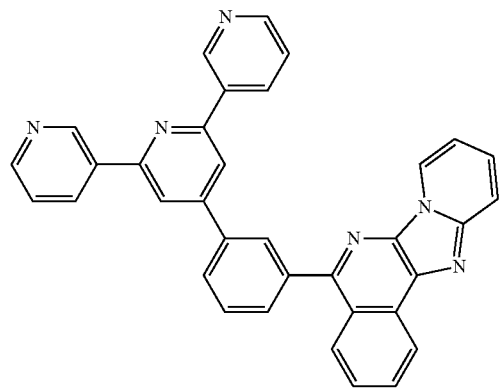
-continued
631
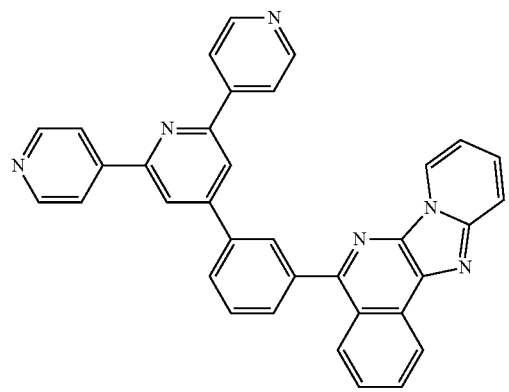
632
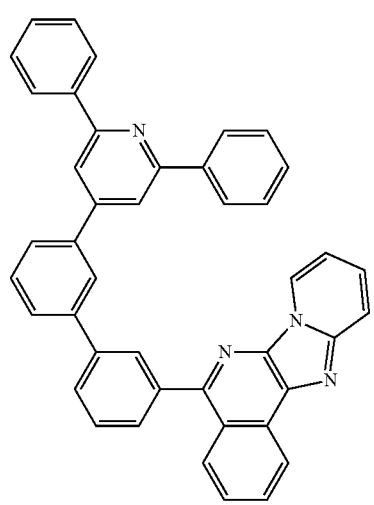
633
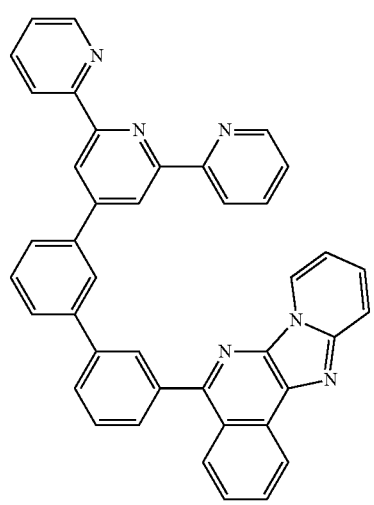

634
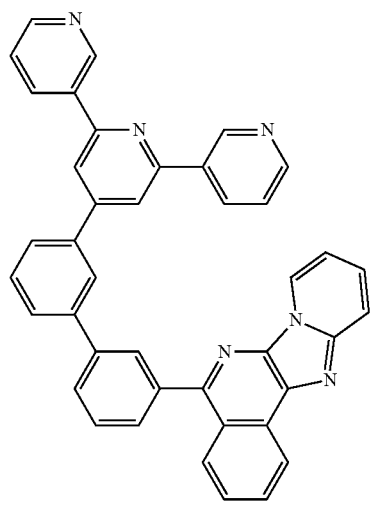
635
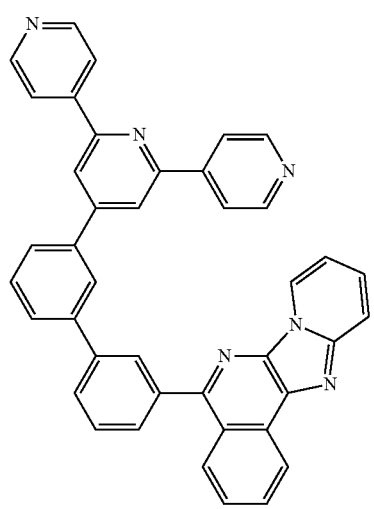
636
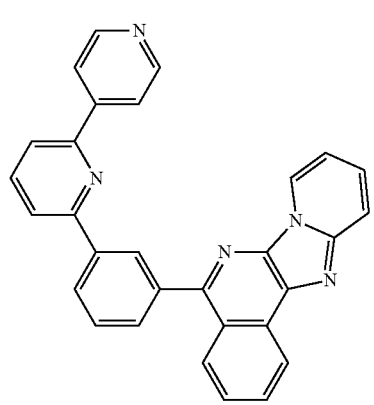
637
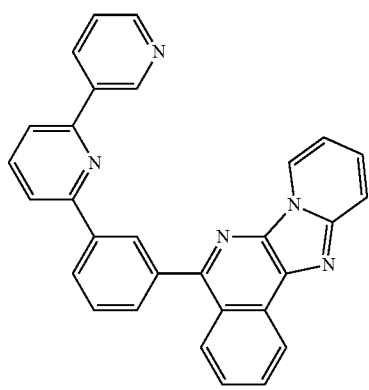
638
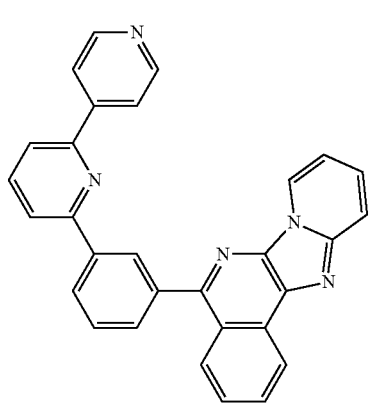
639
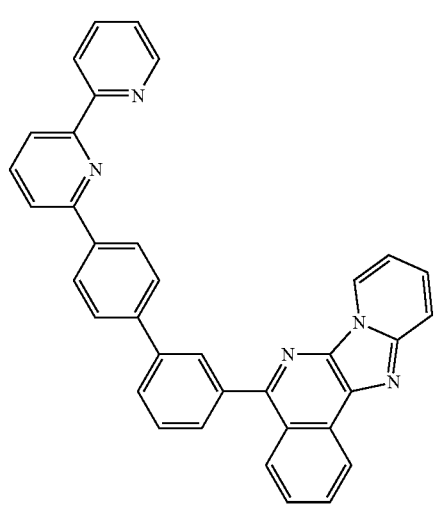

185
-continued
640
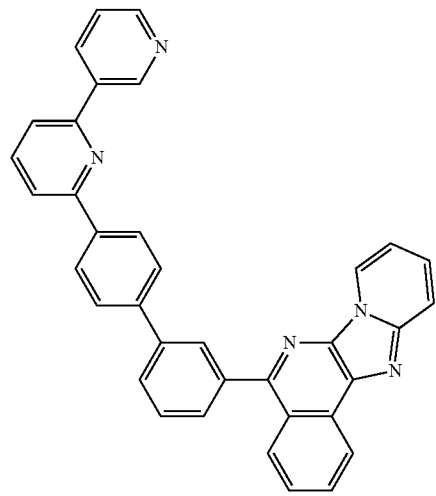
641
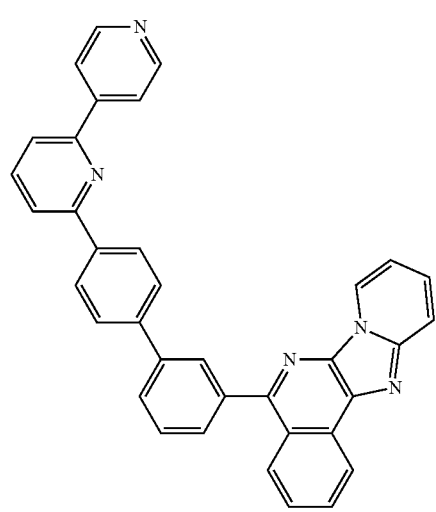
642
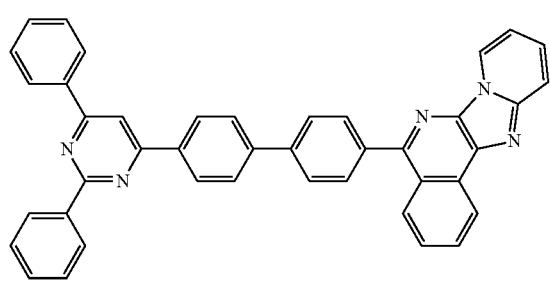
643
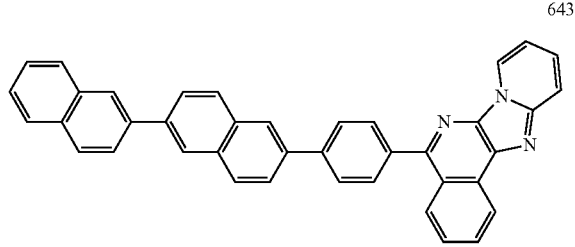
186
-continued
644
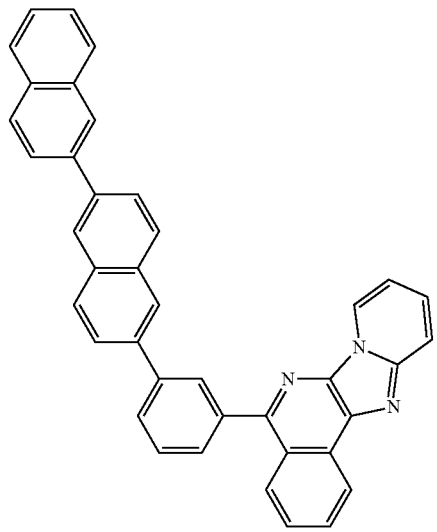
645
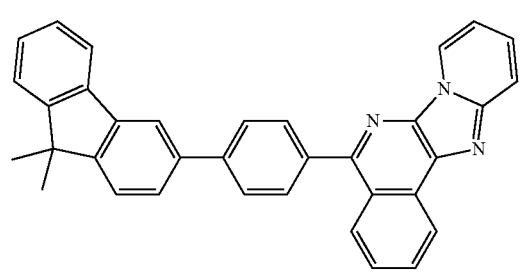
646
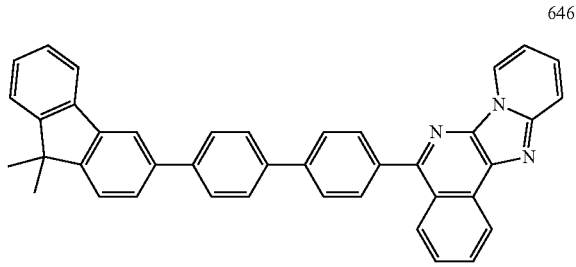
647
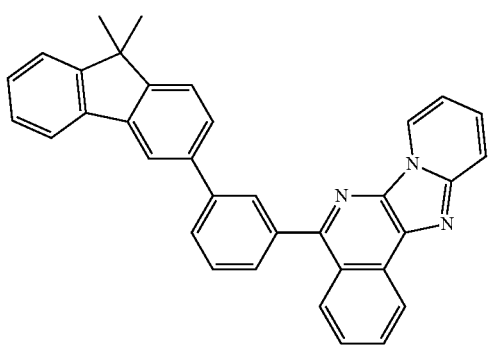

648
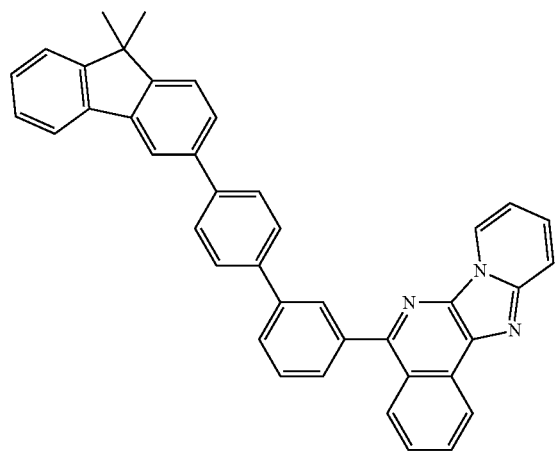
649
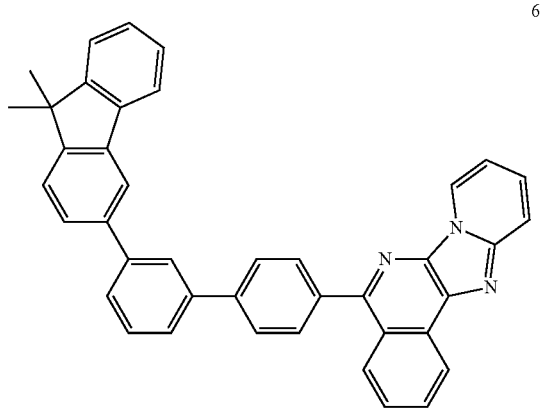
650
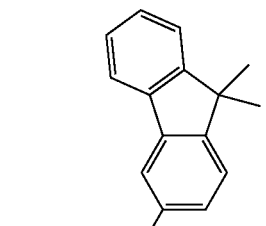
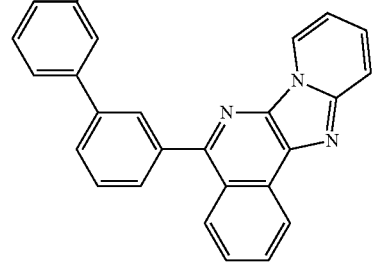
651
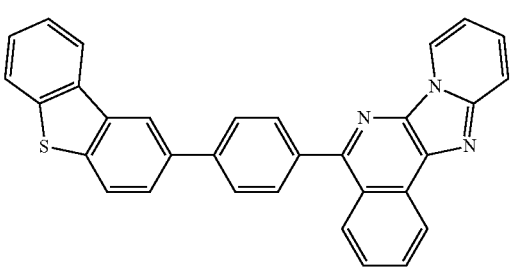
652
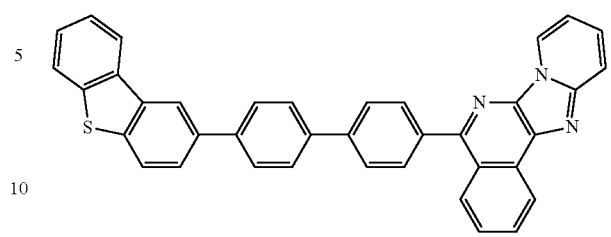
653
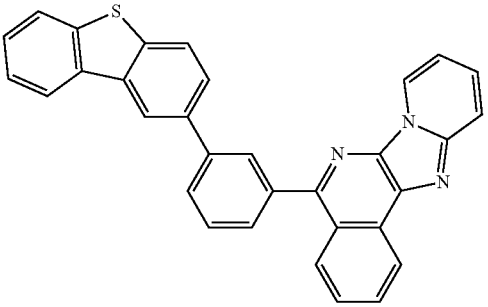
656
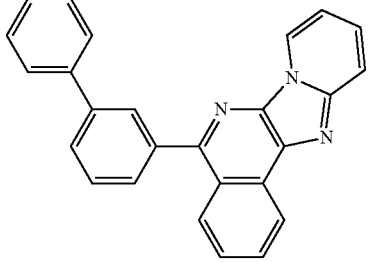
657
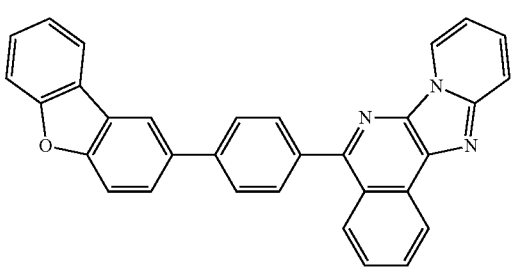
658
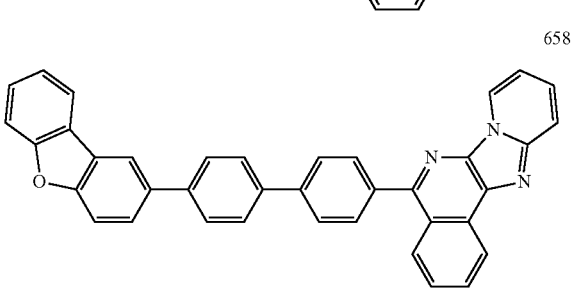

654
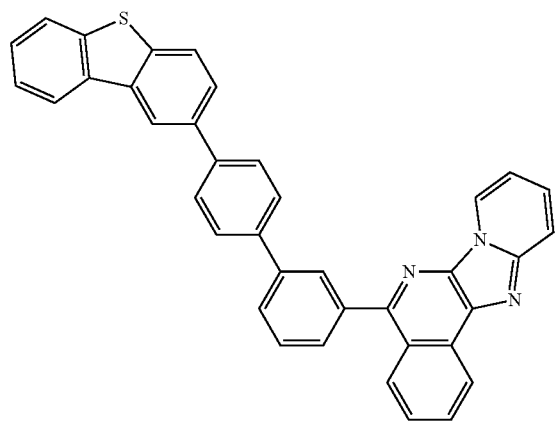
655
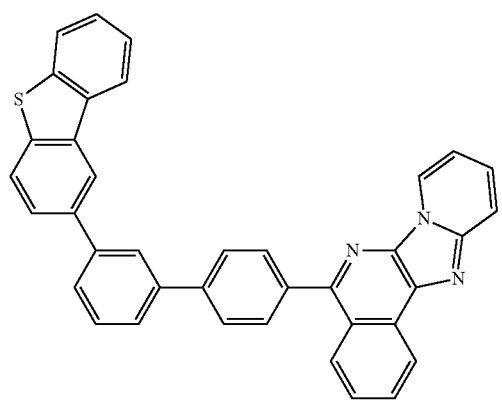
659
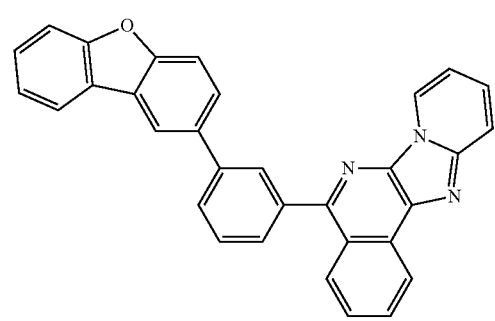
660
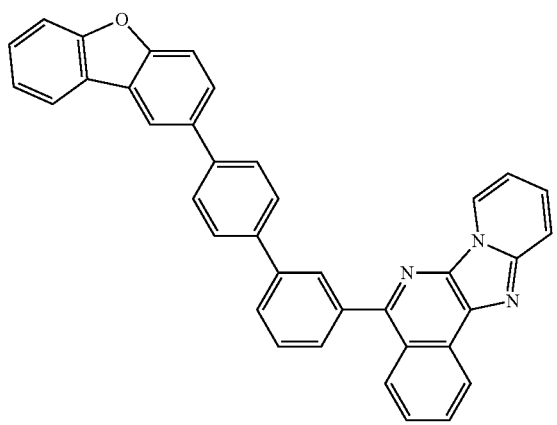
661
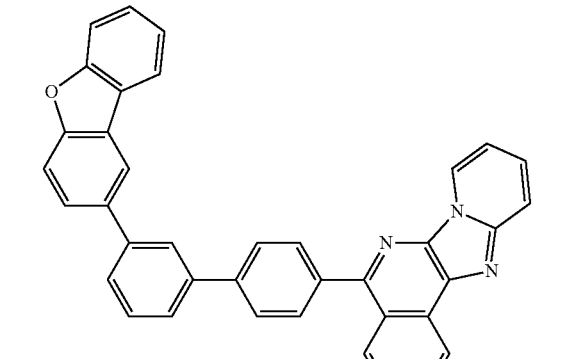
662
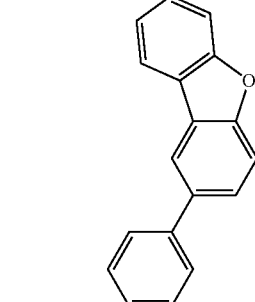
663
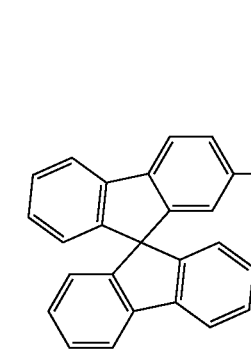
664
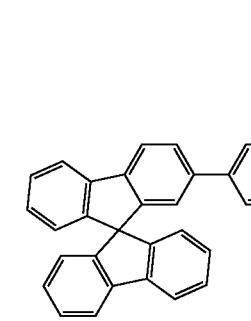

-continued
665
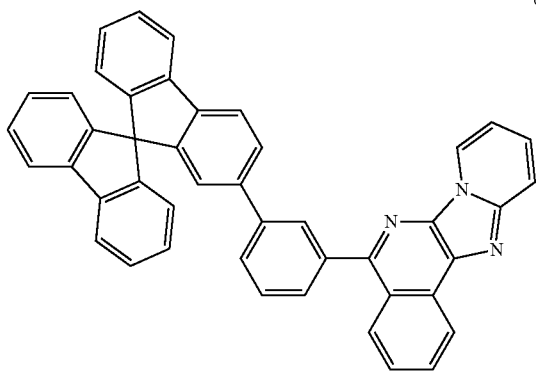
666
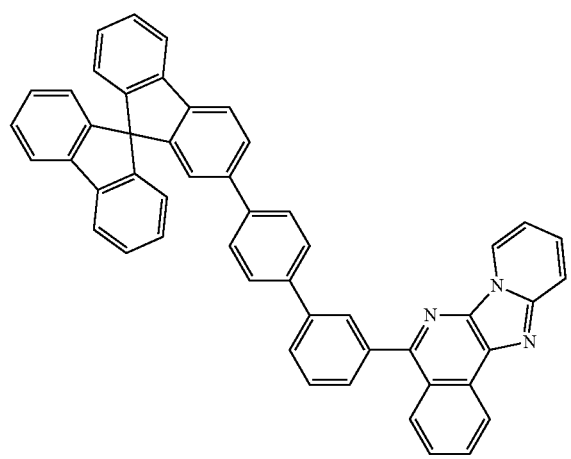
667
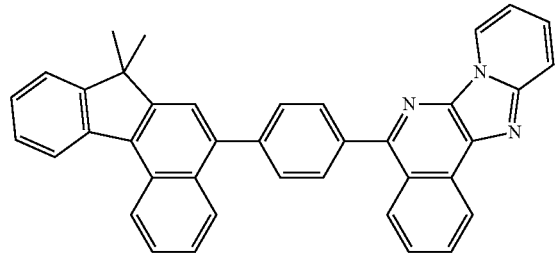
668
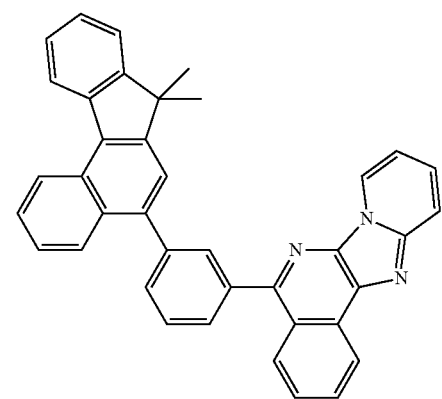
-continued
669
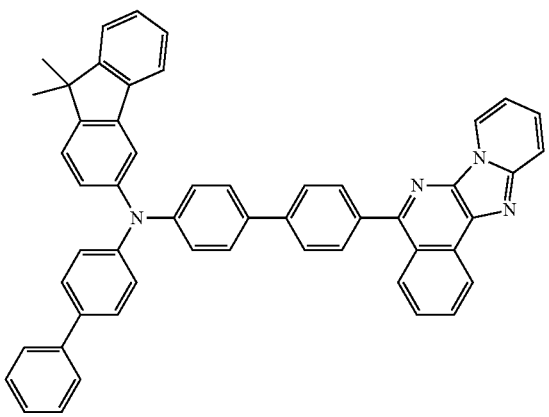
670
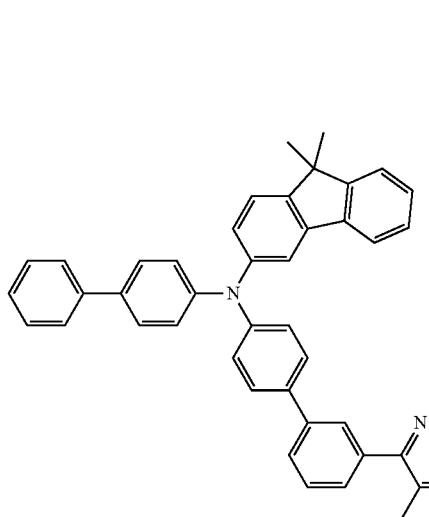
671
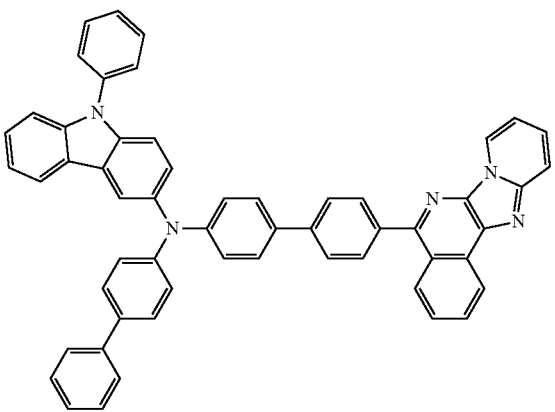

-continued
672
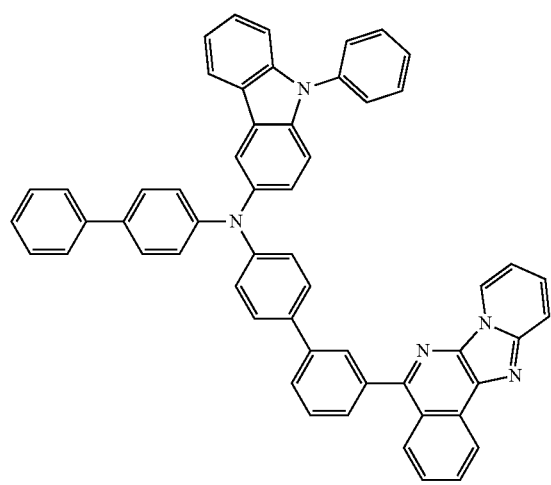
673
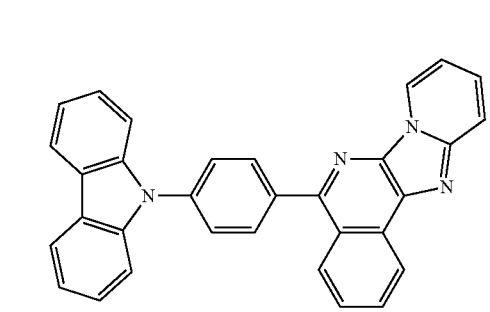
674
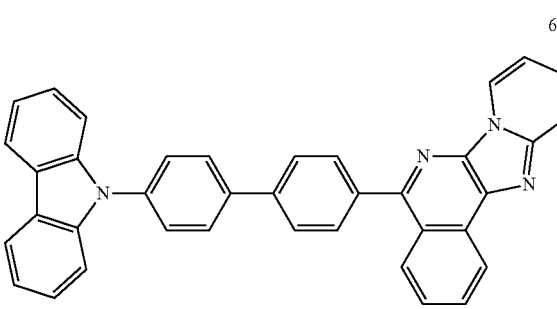
675
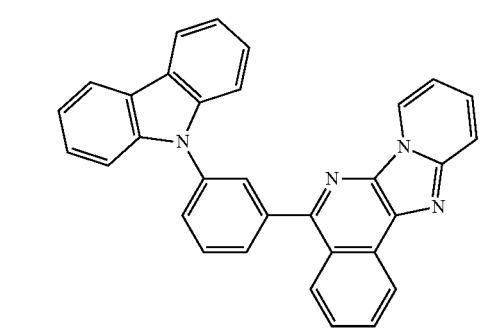
-continued
676
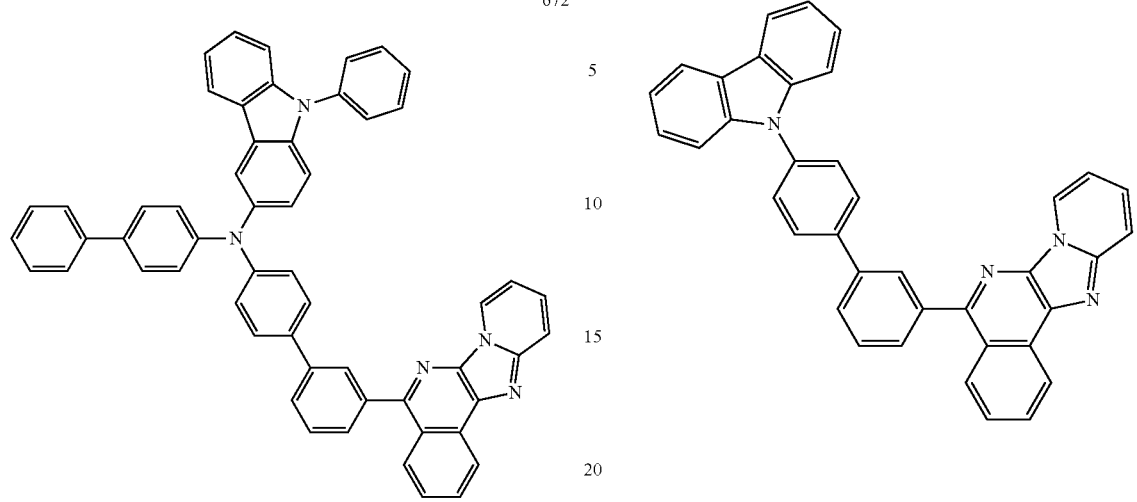
677
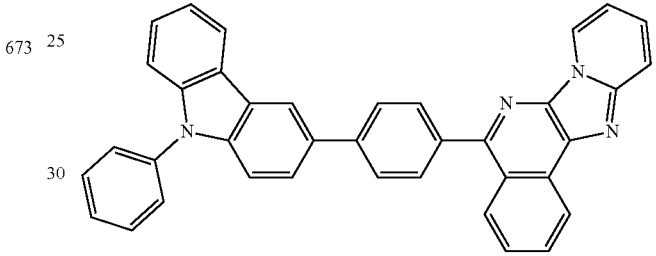
678
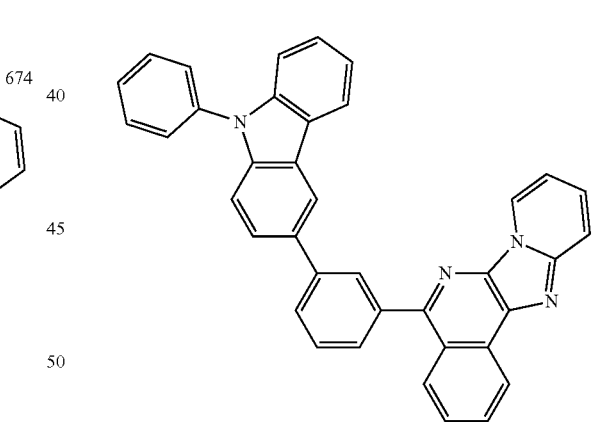
679
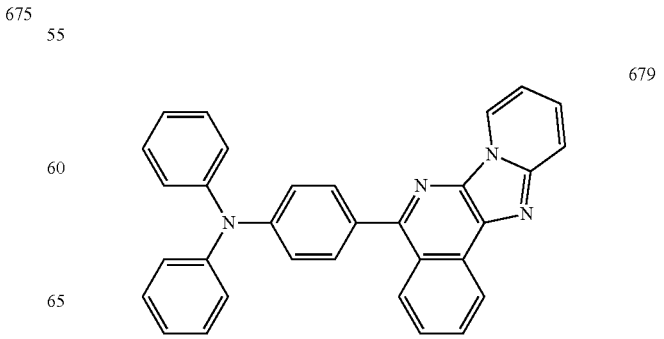

680
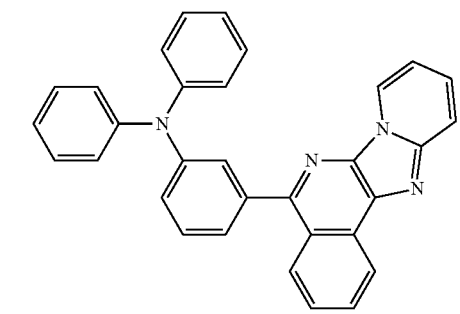
681
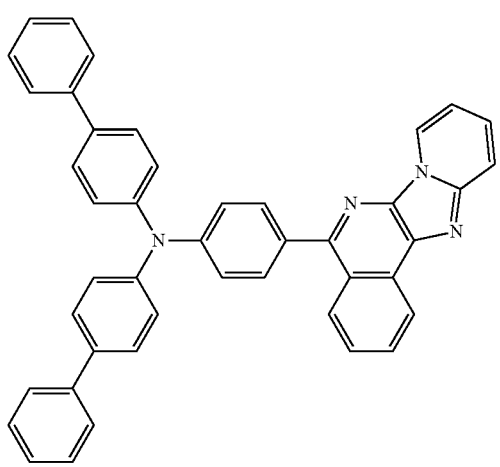
682
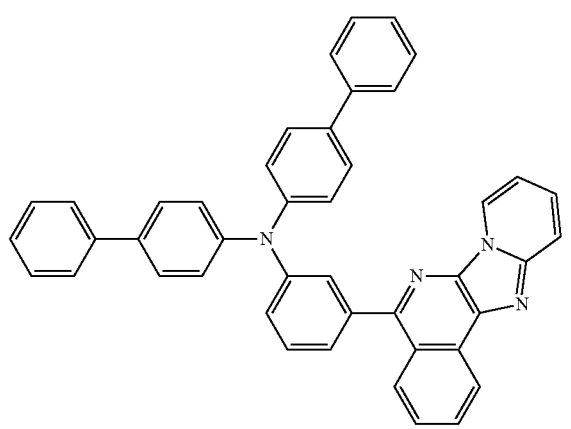
683
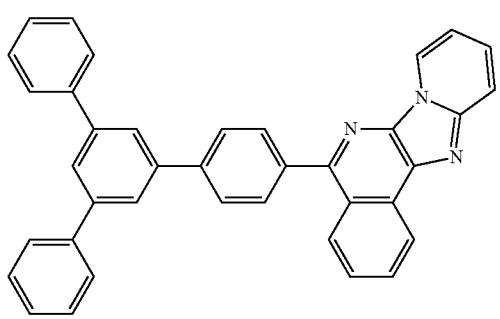
684
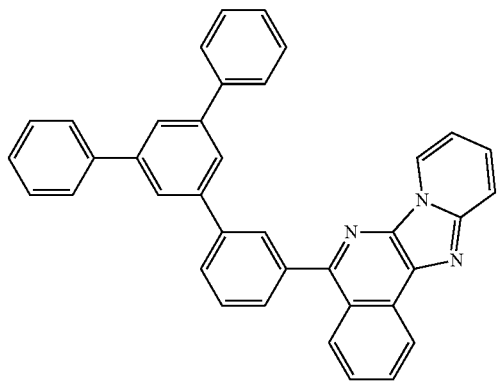
685
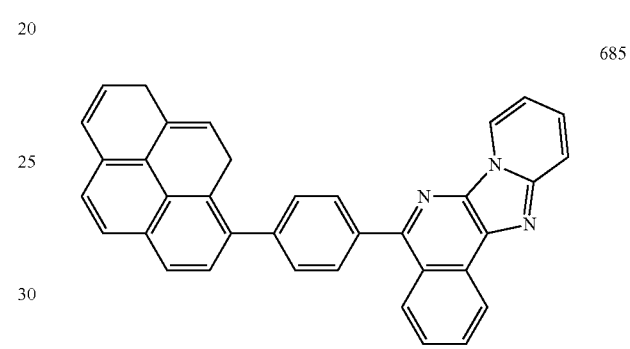
686
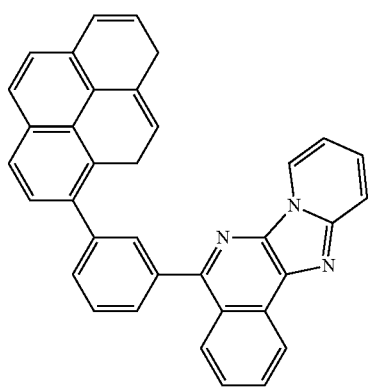
687
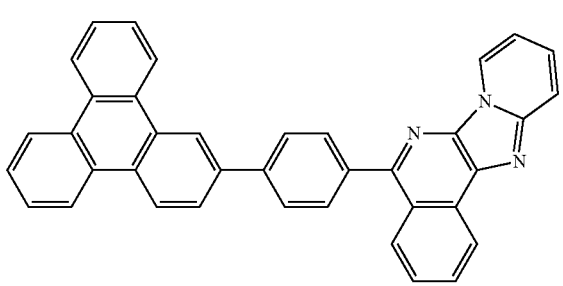

197
-continued
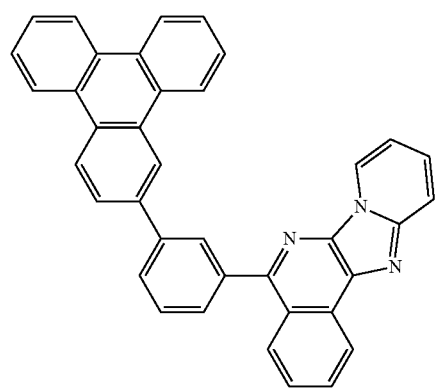
688
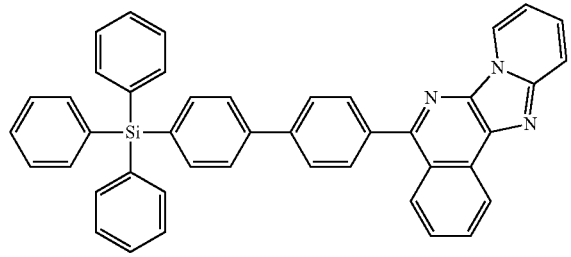
689
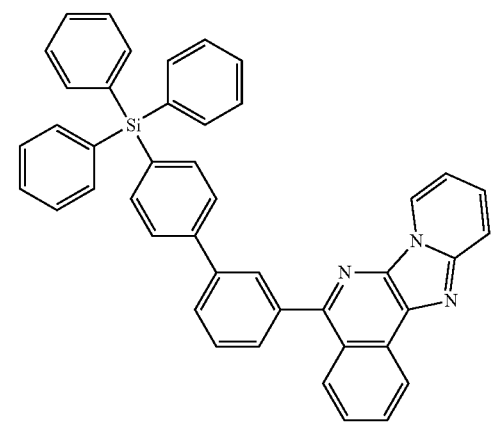
690
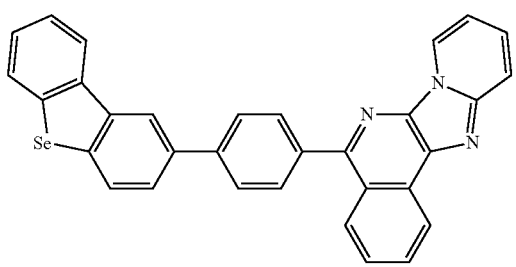
691
198
-continued
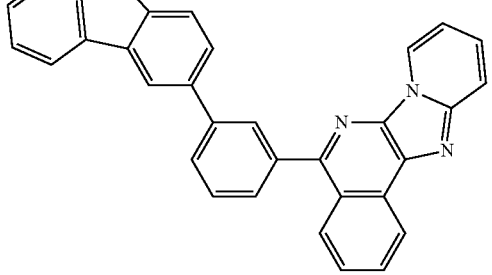
692
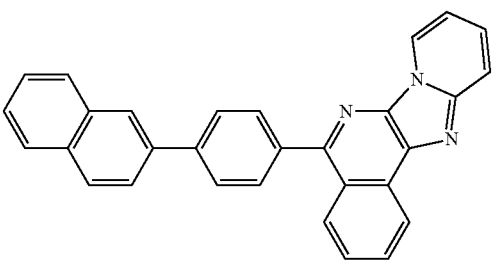
693
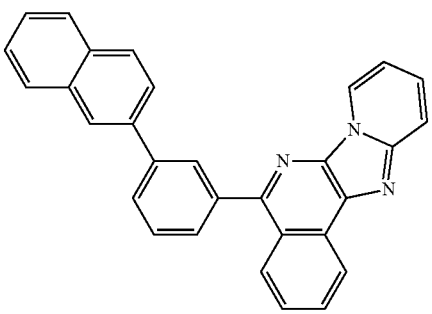
694
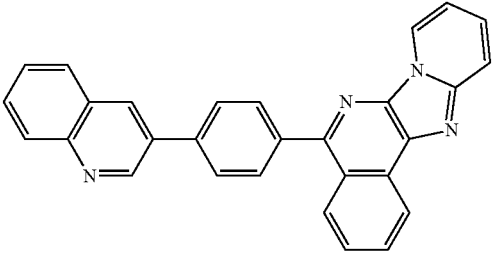
695
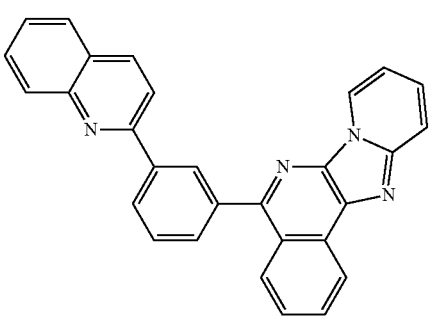
696

697
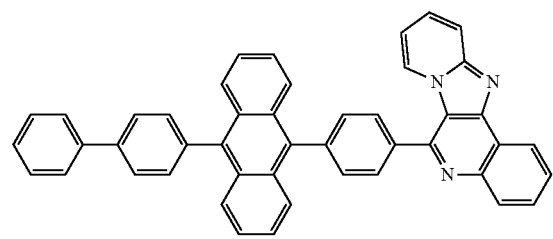
698
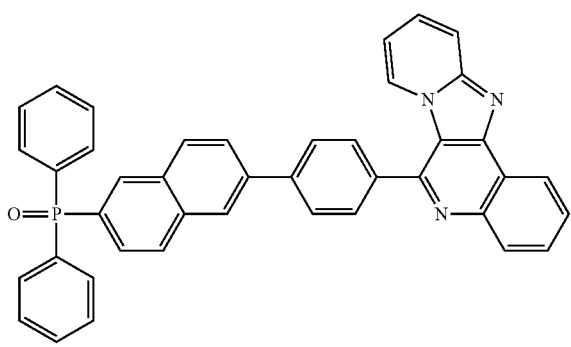
699
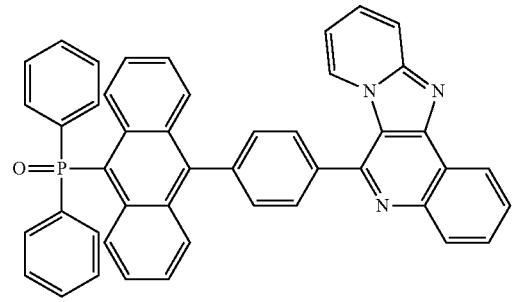
700
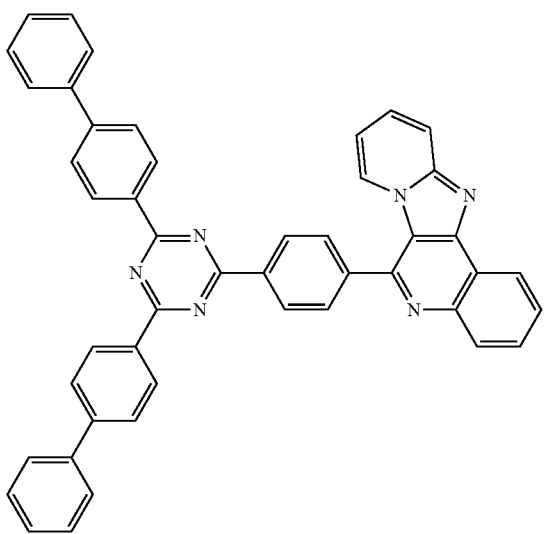
701
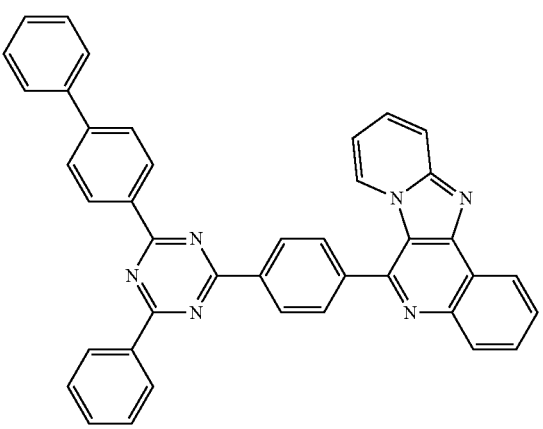
702
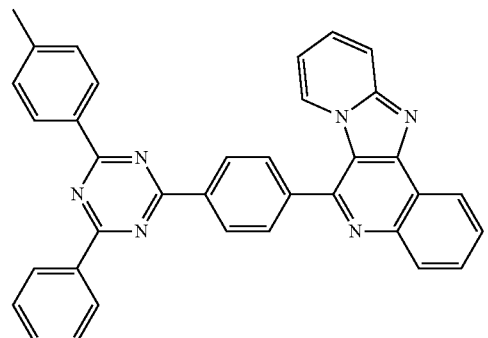
703
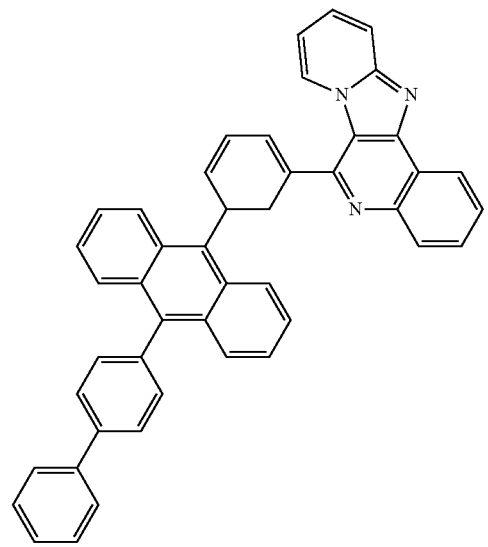

704
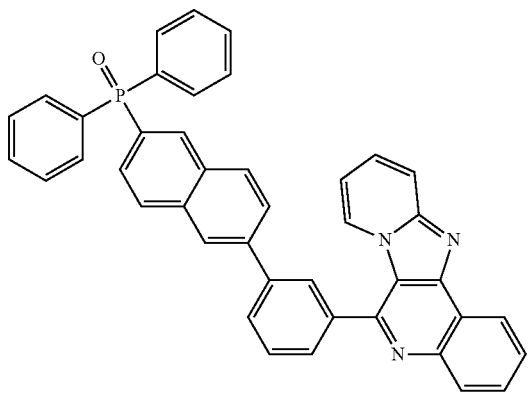
705
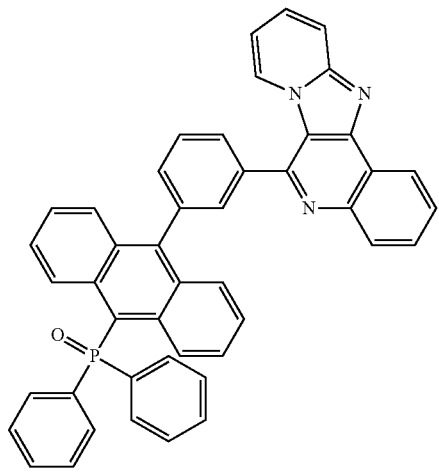
706
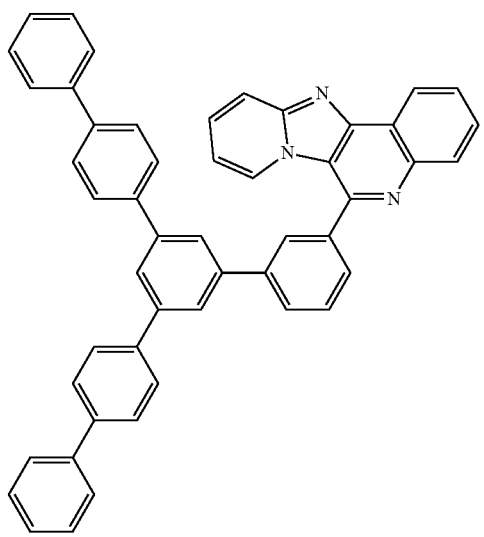
707
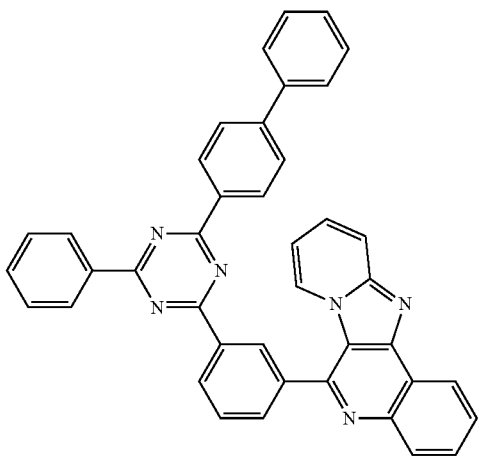
708
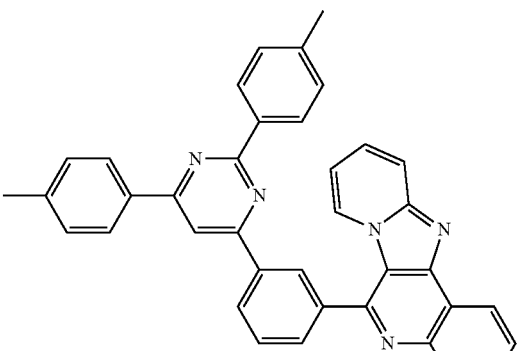
709
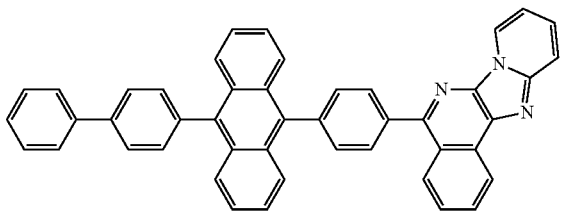
710
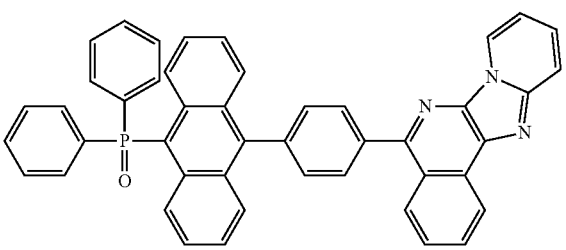

203
-continued
711
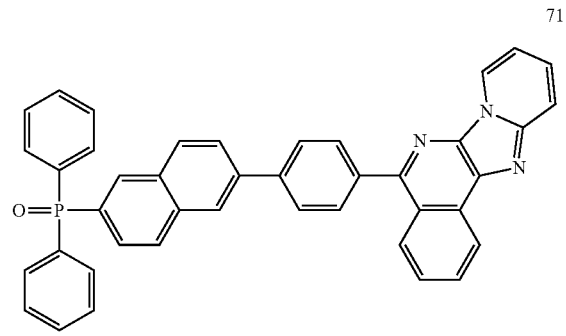
712
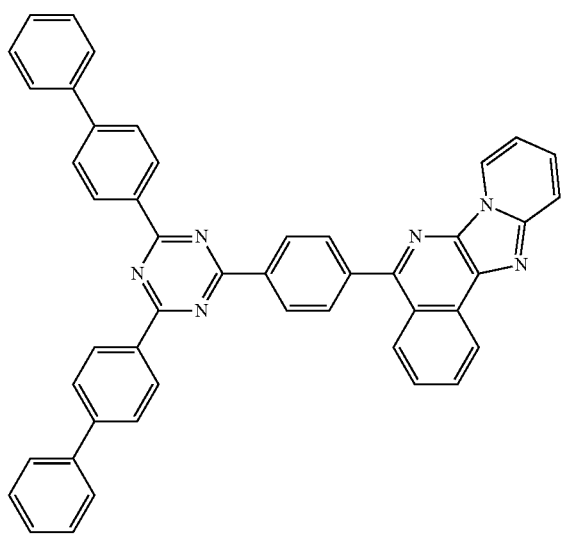
713
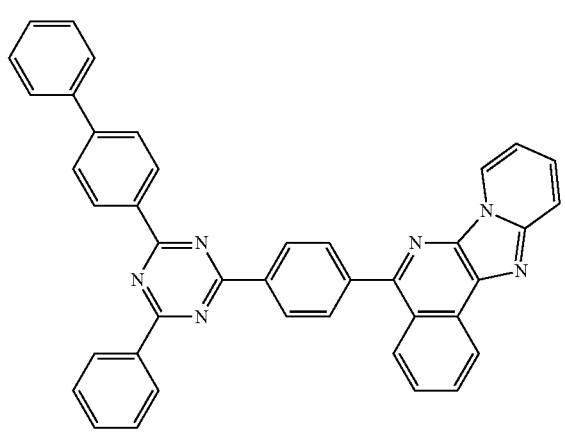
204
-continued
714
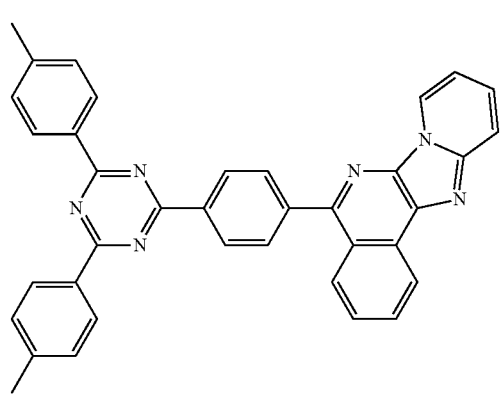
715
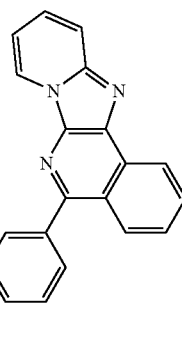
716
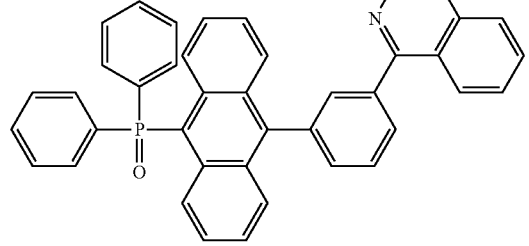
717
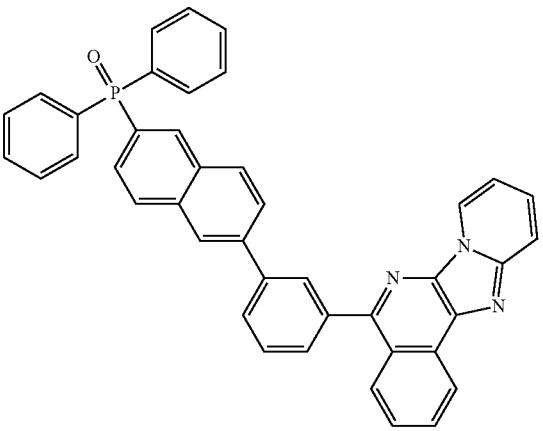

205
-continued
718
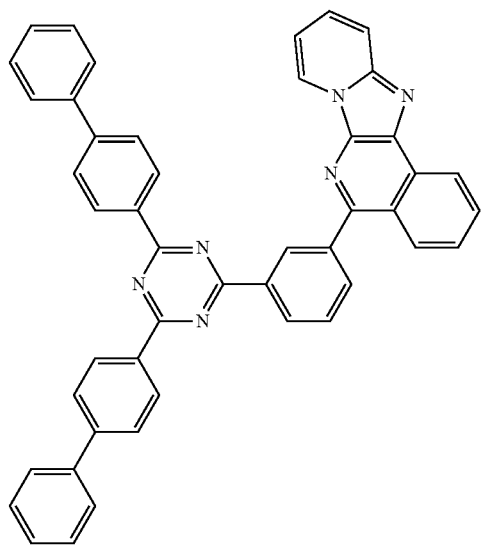
719
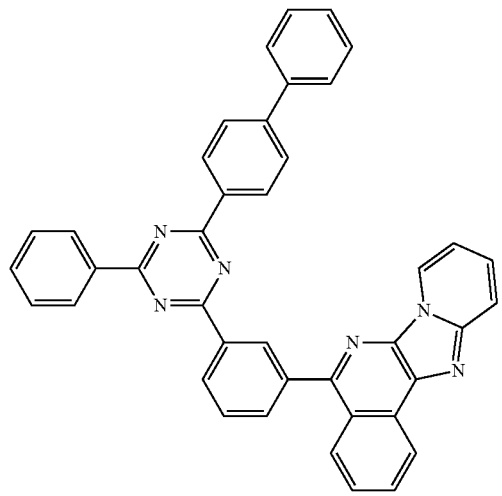
720
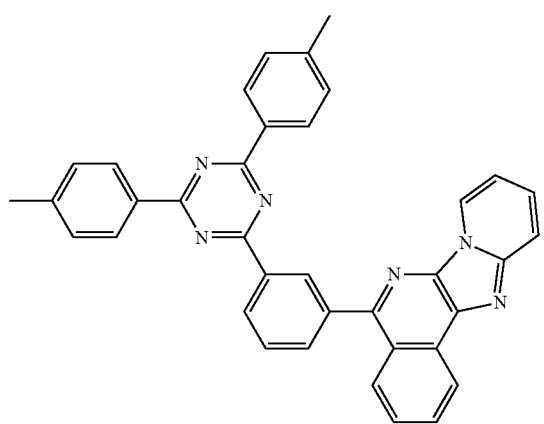
206
-continued
721
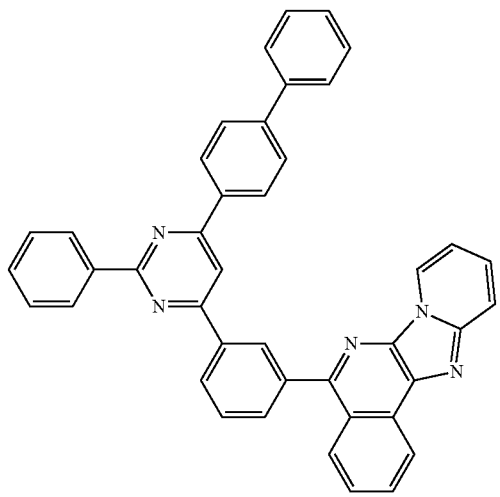
722
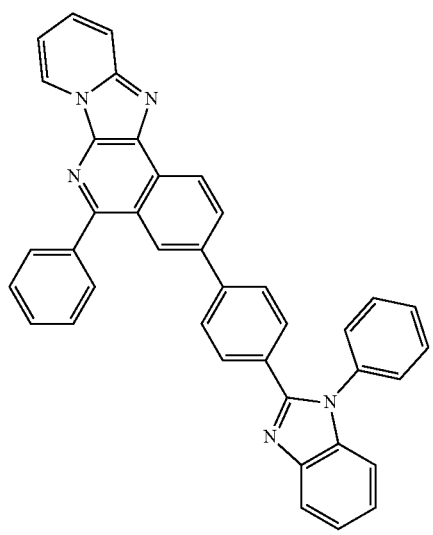
723
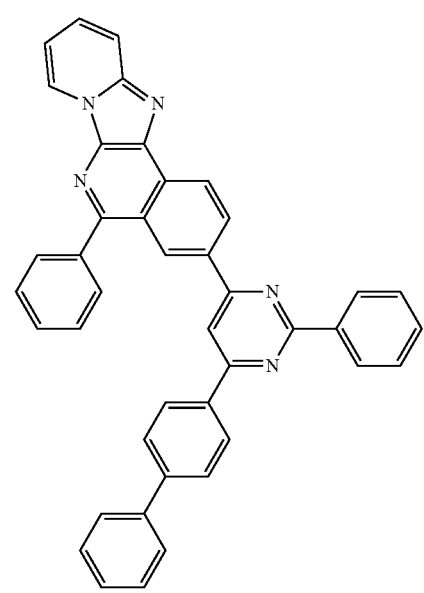

207
-continued
724
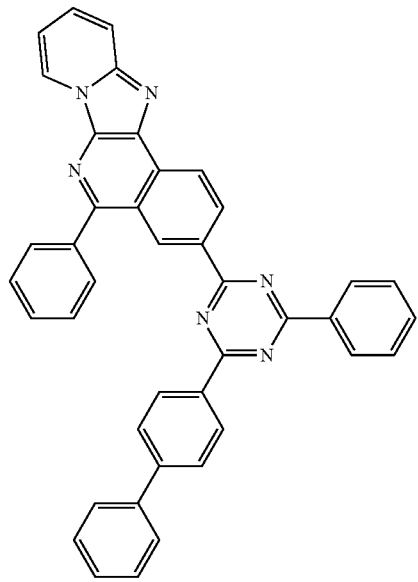
725
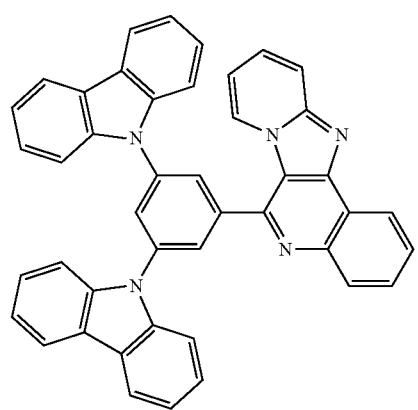
726
208
-continued
727
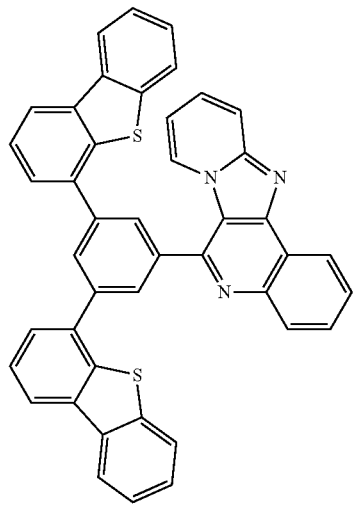
728
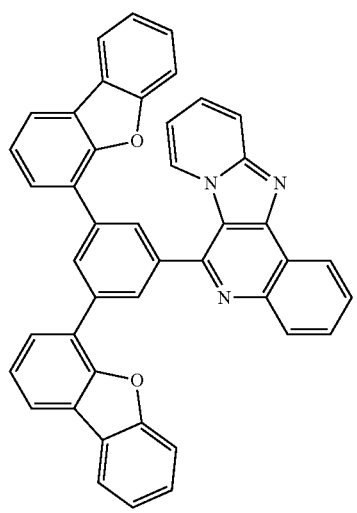
729
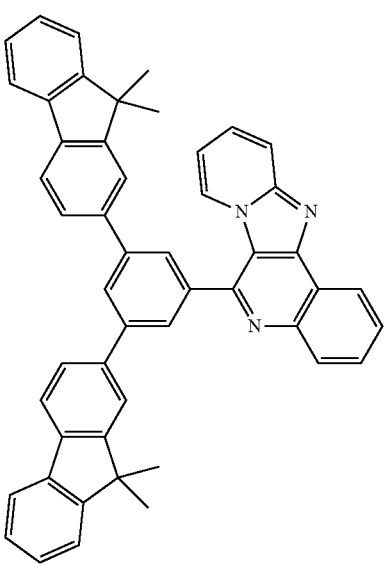

730 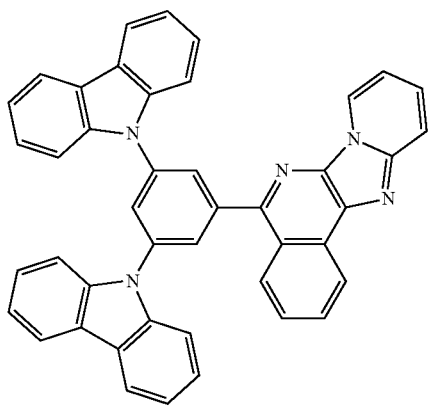

733 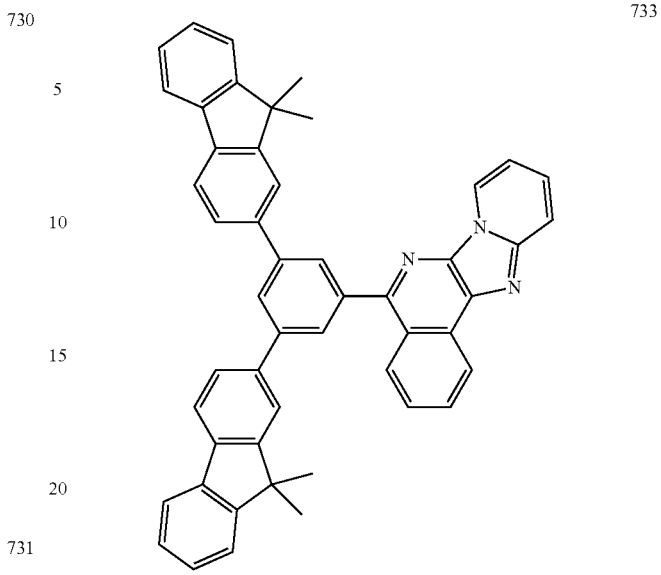

731 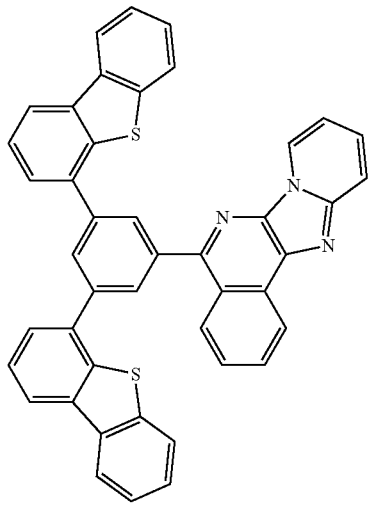

732 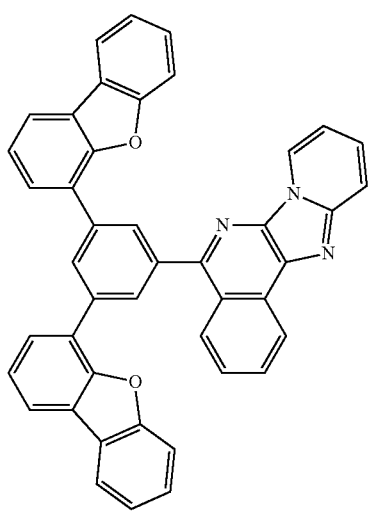

According to an exemplary embodiment of the present specification, provided is an organic light emitting device including the hetero-cyclic compound represented by Chemical Formula 1.

Specifically, the organic light emitting device according to the present specification includes a positive electrode, a negative electrode, and one or more organic material layers provided between the positive electrode and the negative electrode, in which one or more of the organic material layers include the above-described hetero-cyclic compound represented by Chemical Formula 1.

FIGS. 1 to 3 exemplify the stacking sequence of electrodes and organic material layers of an organic light emitting device according to exemplary embodiments of the present application. However, the scope of the present application is not intended to be limited by these drawings, and the structure of the organic light emitting device known in the art may also be applied to the present application.

According to FIG. 1, an organic light emitting device in which a positive electrode 200, an organic material layer 300, and a negative electrode 400 are sequentially stacked on a substrate 100 is illustrated. However, the organic light emitting device is not limited only to such a structure, and as in FIG. 2, an organic light emitting device in which a negative electrode 400, an organic material layer 300, and a positive electrode 200 are sequentially stacked on a substrate 100 may also be implemented.

FIG. 3 exemplifies a case where the organic material layer is a multilayer. The organic light emitting device according to FIG. 3 includes a hole injection layer 301, a hole transporting layer 302, a light emitting layer 303, a hole blocking layer 304, an electron transporting layer 305, and an electron injection layer 306. However, the scope of the present application is not limited by the stacking structure as described above, and if necessary, the other layers except for the light emitting layer may be omitted, and another necessary functional layer may be further added.

The organic light emitting device according to the present specification may be manufactured by the materials and methods known in the art, except that one or more layers of the organic material layers include the hetero-cyclic compound represented by Chemical Formula 1.

The hetero-cyclic compound represented by Chemical Formula 1 may alone constitute one or more layers of the organic material layers of the organic light emitting device. However, the hetero-cyclic compound represented by Chemical Formula 1 may be mixed with another material, if necessary, to constitute an organic material layer.

The hetero-cyclic compound represented by Chemical Formula 1 may be used as a material for an electron transporting layer, a hole blocking layer, and a light emitting layer, and the like in an organic light emitting device. As an example, the hetero-cyclic compound represented by Chemical Formula 1 may be used as a material for the electron transporting layer of the organic light emitting device.

Since the hetero-cyclic compound represented by Chemical Formula 1 includes two N (nitrogen) atoms which may attract electrons, the hetero-cyclic compound easily transfers electrons.

Further, the hetero-cyclic compound represented by Chemical Formula 1 has a structural form in which the compound may be stacked between molecules due to the strong planarity when an organic light emitting device is manufactured, and thus the electron mobility is high.

In the organic light emitting device according to the present specification, materials other than the hetero-cyclic compound represented by Chemical Formula 1 will be exemplified below, but these materials are illustrative only and are not intended to limit the scope of the present application, and may be replaced with materials publicly known in the art.

As a material for the positive electrode, materials having a relatively high work function may be used, and a transparent conductive oxide, a metal or a conductive polymer, and the like may be used.

As a material for the negative electrode, materials having a relatively low work function may be used, and a metal, a metal oxide, or a conductive polymer, and the like may be used.

As a hole injection material, a publicly-known hole injection material may also be used, and it is possible to use, for example, a phthalocyanine compound such as copper phthalocyanine disclosed in U.S. Pat. No. 4,356,429 or starburst-type amine derivatives described in the document [Advanced Material, 6, p. 677 (1994)], for example, tris(4-carbazoyl-9-ylphenyl)amine (TCTA), 4,4',4"-tris[phenyl(m-tolyl)amino]triphenylamine (m-MTDATA), 1,3,5-tris[4-(3-methylphenylphenylamino)phenyl]benzene (m-MTDAPB), polyaniline/dodecylbenzenesulfonic acid or poly(3,4-ethylenedioxythiophene)/poly(4-styrenesulfonate), which is a soluble conductive polymer, polyaniline/camphor sulfonic acid (or polyaniline/poly(4-styrene-sulfonate), and the like.

As the hole transporting material, a pyrazoline derivative, an arylamine-based derivative, a stilbene derivative, a triphenyldiamine derivative, and the like may be used, and a low-molecular weight or polymer material may also be used.

As the electron transporting material, it is possible to use an oxadiazole derivative, anthraquinodimethane and a derivative thereof, benzoquinone and a derivative thereof, naphthoquinone and a derivative thereof, anthraquinone and a derivative thereof, tetracyanoanthraquinodimethane and a derivative thereof, a fluorenone derivative, diphenyldicyanoethylene and a derivative thereof, a diphenoquinone derivative, a metal complex of 8-hydroxyquinoline and a derivative thereof, and the like, and a low-molecular weight material and a polymer material may also be used.

As the electron injection material, for example, LiF is typically used in the art, but the present specification is not limited thereto.

As the light emitting material, a red, green, or blue light emitting material may be used, and if necessary, two or more light emitting materials may be mixed and used. Further, as the light emitting material, a fluorescent material may also be used, but a phosphorescent material may also be used. As the light emitting material, it is also possible to use alone a material which emits light by combining holes and electrons each injected from the positive electrode and the negative electrode, but materials in which both a host material and a dopant material are involved in light emission may also be used.

Hereinafter, the present specification will be described in more detail through the Examples, but these are provided only for exemplifying the present specification, and are not for limiting the scope of the present specification.

The above-described compounds may be prepared based on the Preparation Examples to be described below. Representative examples will be described in the Preparation Examples to be described below, but if necessary, a substituent may be added or excluded, and the position of the substituent may be changed. Further, a starting material, a reactant, reaction conditions, and the like may be changed based on the technology known in the art. A person with ordinary skill in the art may change the kind or position of substituents at the other positions, if necessary, by using the technology known in the art.

The substituent may be bonded by a method known in the art, and the position of the substituent or the number of substituents may be changed according to the technology known in the art.

For example, as the hetero-cyclic compound represented by Chemical Formula 2, a core structure may be prepared as in the following Formula 1.

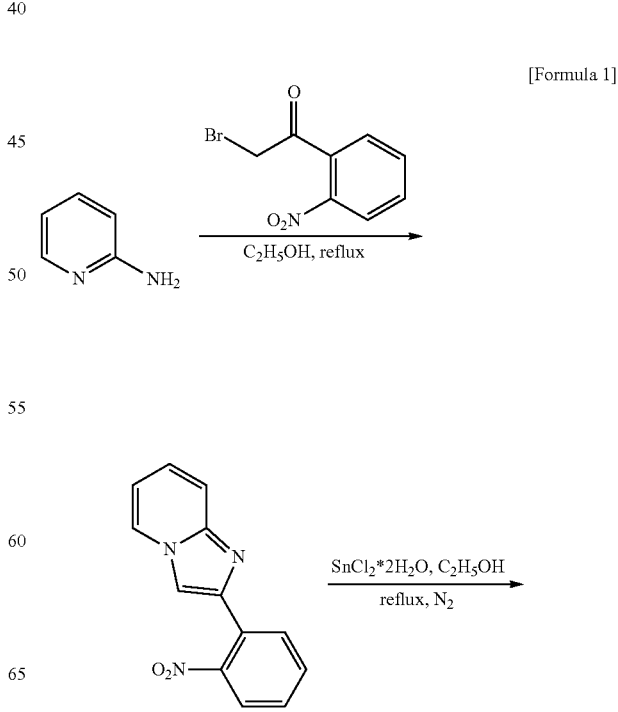

[Formula 1]

213

-continued

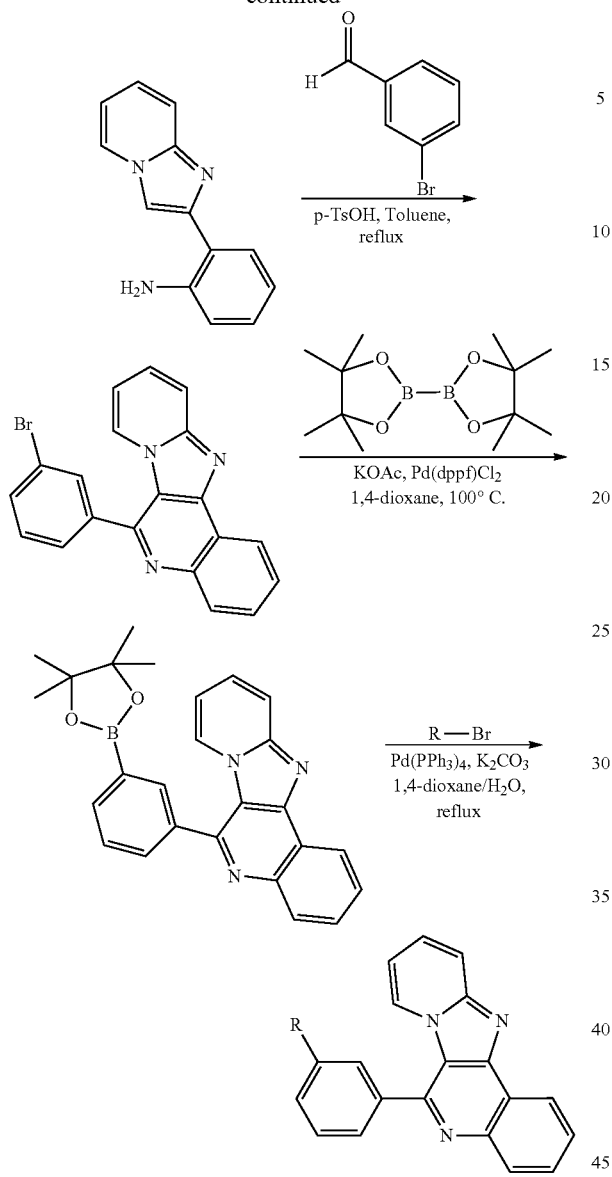

In Formula 1, R'" is the same as Z defined in Chemical Formula 1, and L is a substituted or unsubstituted phenyl. Formula 1 is an example of the reaction in which a substituent is bonded to the $R_1$ position in the core structure of Chemical Formula 2.

In addition, as the hetero-cyclic compound represented by Chemical Formula 3, a core structure may be prepared as in the following Formula 2.

[Formula 2]

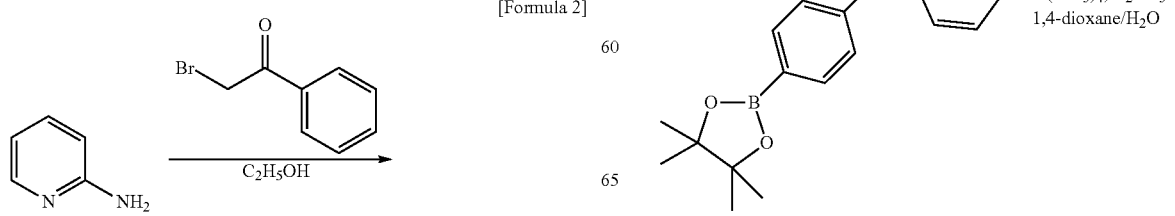

214

-continued

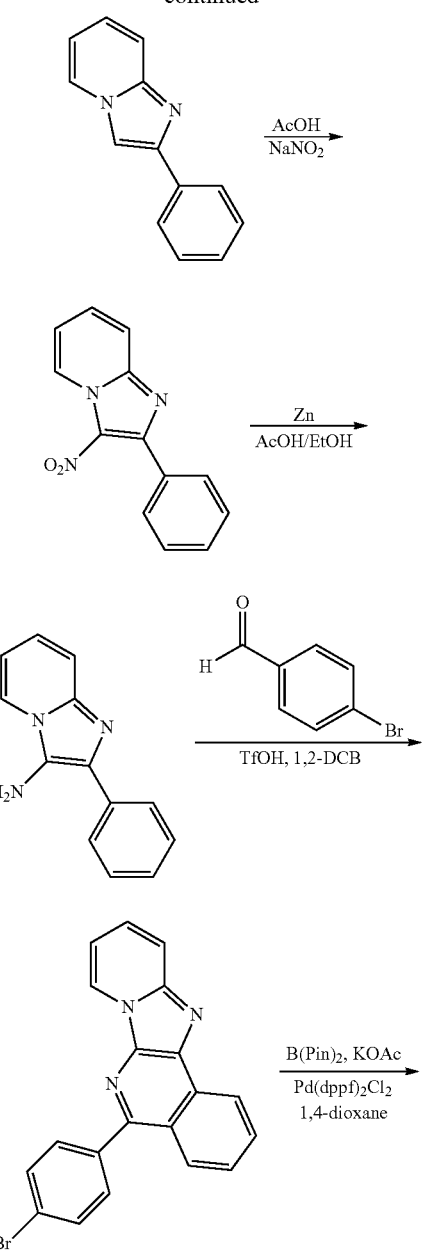

-continued

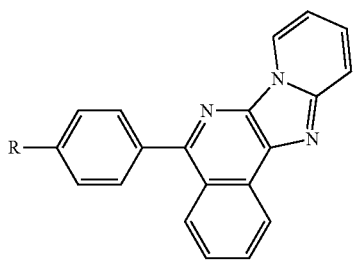

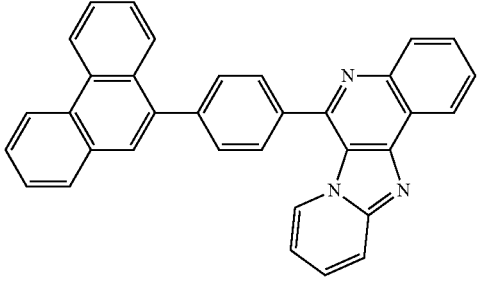
6

In Formula 2, R'" is the same as Z defined in Chemical Formula 1, and L is a substituted or unsubstituted phenyl. Formula 2 is an example of the reaction in which a substituent is bonded to the $R_1$ position in the core structure of Chemical Formula 3.

<Preparation Example 1> Preparation of Compound 6

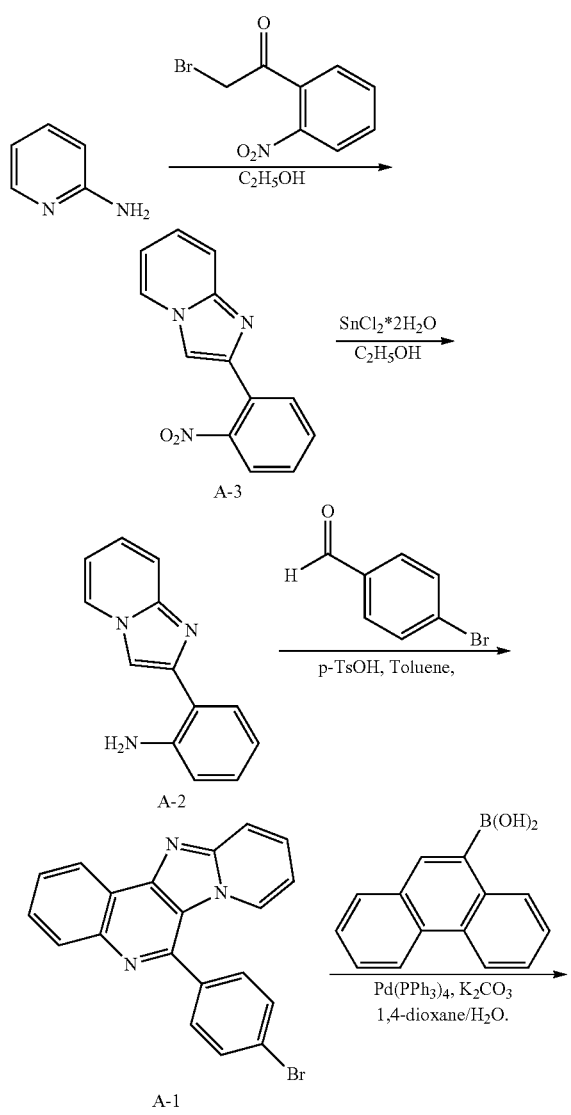

Preparation of Compound A-3

Ethanol (1,100 ml) was put into compounds 2-amino pyridine (27.0 g, 286.6 mmol, 1 eq.) and 2-bromo-2'-nitroacetophenone (70.0 g, 286.6 mmol, 1 eq.), and the resulting mixture was refluxed. After the reaction was terminated, the resulting product was cooled to normal temperature and extracted with ethyl acetate/water, the organic layer was dried over anhydrous magnesium sulfate, and then the solvent was removed by using a rotary evaporator. The resulting product was purified with column chromatography using dichloromethane and ethyl acetate to obtain 30.3 g (44%) of Target Compound A-3.

Preparation of Compound A-2

Compound A-3 (30.3 g, 126.7 mmol, 1 eq.) and tin (II) chloride dihydrate (142.9 g, 633.3 mmol, 5 eq.) were dissolved in ethanol, and the resulting solution was refluxed under injection of nitrogen. After the reaction was terminated, the solution was cooled to normal temperature, ice was added thereto, and then the pH was adjusted to approximately 8 by slowly adding sodium bicarbonate thereto. A celite bed was laid down, the filtered filtrate was extracted with ethyl acetate/water, the organic layer was dried over anhydrous magnesium sulfate, and then the solvent was removed by using a rotary evaporator. The resulting product was purified with column chromatography using dichloromethane and hexane to obtain 13.75 g (52%) of Target Compound A-2.

Preparation of Compound A-1

Compound A-2 (13.75 g, 65.71 mmol, 1 eq.), 4-bromobenzaldehyde (18.24 g, 98.57 mmol, 1.5 eq.), and p-toluenesulfonic acid (11.3 g, 65.71 mmol, 1 eq.) were dissolved in toluene, and then the resulting solution was refluxed. After the reaction was terminated, the solution was cooled to normal temperature, toluene was first removed, the resulting product was extracted with ethyl acetate/water, the organic layer was dried over anhydrous magnesium sulfate, and then the solvent was removed by using a rotary evaporator. The resulting product was purified with column chromatography using dichloromethane and methanol to obtain 9.8 g (40%) of Target Compound A-1.

Preparation of Compound 6

Compound A-1 (1.0 g, 2.67 mmol, 1 eq.), 9-phenanthracenylboronic acid (0.58 g, 2.93 mmol, 1.1 eq.), tetrakis(triphenylphosphine)palladium (0) (0.15 g, 0.13 mmol, 0.05 eq.), potassium carbonate (0.65 g, 4.72 mmol, 2 eq.), and 1,4-dioxane/water (60 ml) were mixed, and the resulting mixture was refluxed and stirred. After the reaction was terminated, the resulting product was cooled to normal temperature, a solid produced at this time was filtered, and the filtered solid was purified with column chromatography using dichloromethane and methanol to obtain 0.72 g (yield of 57%) of Target Compound 6.

<Preparation Example 2> Preparation of Compound 19

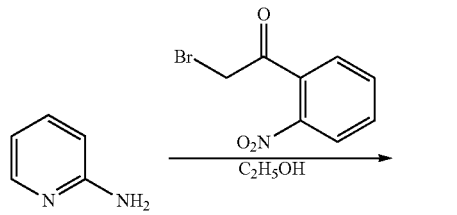

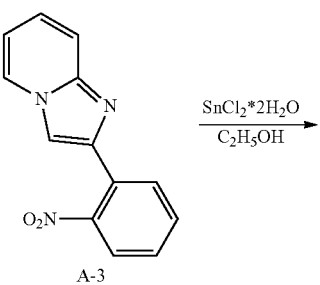

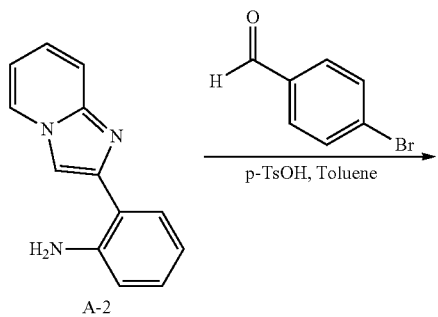

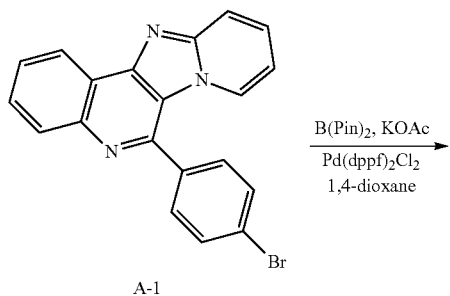

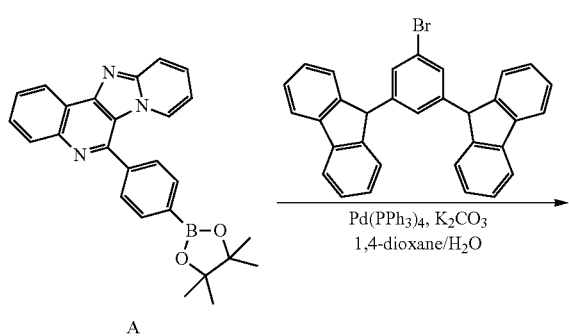

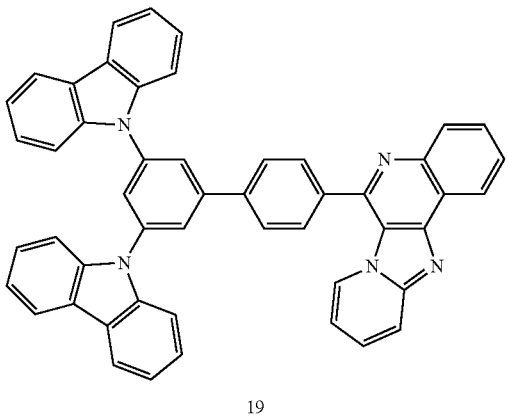

19

Preparation of Compound A

Compound A-1 (6.1 g, 16.33 mmol, 1 eq.), bis(pinacolato)diboron (6.2 g, 24.5 mmol, 1.5 eq.), [1,1'-bis(diphenylphosphino)ferrocene]dichloropalladium (II) (0.58 g, 0.82 mmol, 0.05 eq.), and potassium acetate (4.8 g, 48.99 mmol, 3 eq.) were put and dissolved in 1,4-dioxane, and then the resulting solution was stirred for 18 hours or more while being maintained at 100° C. After the reaction was terminated, the resulting product was cooled to normal temperature and extracted with ethyl acetate/water, the organic layer was dried over anhydrous magnesium sulfate, and then the solvent was removed by using a rotary evaporator. The solid produced at this time was filtered and purified with ethyl acetate to obtain 4.88 g (yield of 71%) of Target Compound A.

Preparation of Compound 19

Compound A (1.0 g, 2.37 mmol, 1 eq.), 9,9'-(5-bromo-1,3-phenylene)bis(9H-carbazole) (1.27 g, 2.61 mmol, 1.1 eq.), tetrakis(triphenylphosphine)palladium (0) (0.14 g, 0.12 mmol, 0.05 eq.), potassium carbonate (0.66 g, 4.74 mmol, 2 eq.), and 1,4-dioxane/water (60 ml) were mixed, and the resulting mixture was refluxed and stirred. After the reaction was terminated, the resulting product was cooled to normal temperature, a solid produced at this time was filtered, and the filtered solid was purified with column chromatography using dichloromethane and methanol to obtain 1.13 g (yield of 69%) of Target Compound 19.

<Preparation Example 3> Preparation of Compound 42

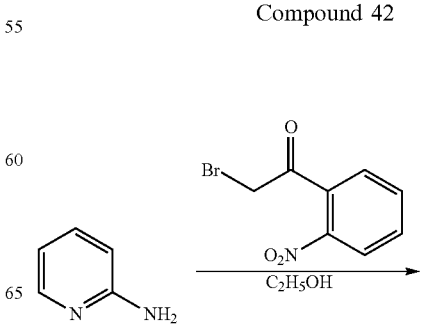

-continued

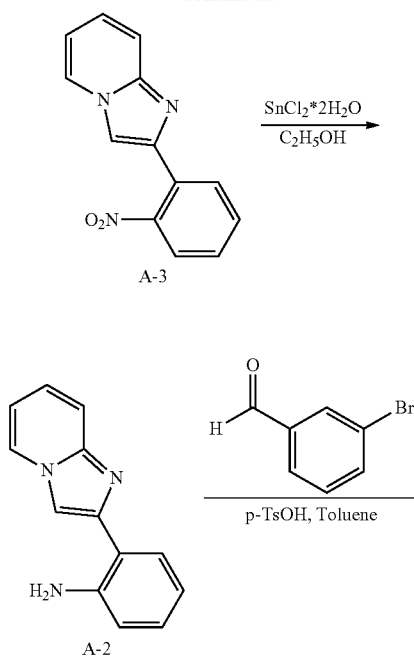

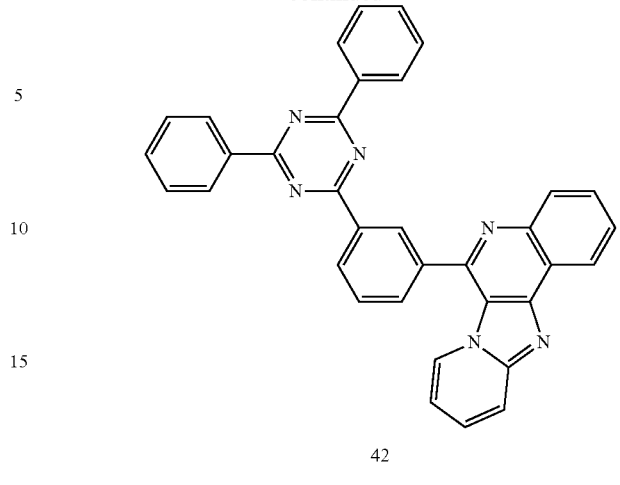

42

Preparation of Compound B-1

Compound A-2 (13.75 g, 65.71 mmol, 1 eq.), 3-bromobenzaldehyde (18.24 g, 98.57 mmol, 1.5 eq.), and p-toluenesulfonic acid (11.3 g, 65.71 mmol, 1 eq.) were dissolved in toluene, and then the resulting solution was refluxed. After the reaction was terminated, the solution was cooled to normal temperature, toluene was first removed, the resulting product was extracted with ethyl acetate/water, the organic layer was dried over anhydrous magnesium sulfate, and then the solvent was removed by using a rotary evaporator. The resulting product was purified with column chromatography using dichloromethane and methanol to obtain 9.34 g (38%) of Target Compound B-1.

Preparation of Compound B

Compound B-1 (6.1 g, 16.33 mmol, 1 eq.), bis(pinacolato)diboron (6.2 g, 24.5 mmol, 1.5 eq.), [1,1'-bis(diphenylphosphino)ferrocene]dichloropalladium (II) (0.58 g, 0.82 mmol, 0.05 eq.), and potassium acetate (4.8 g, 48.99 mmol, 3 eq.) were put and dissolved in 1,4-dioxane, and then the resulting solution was stirred for 18 hours or more while being maintained at 100° C. After the reaction was terminated, the resulting product was cooled to normal temperature and extracted with ethyl acetate/water, the organic layer was dried over anhydrous magnesium sulfate, and then the solvent was removed by using a rotary evaporator. The solid produced at this time was filtered and purified with ethyl acetate to obtain 4.4 g (yield of 64%) of Target Compound B.

Preparation of Compound 42

Compound B (1.0 g, 2.37 mmol, 1 eq.), 2-chloro-4,6-diphenyl-1,3,5-triazine (0.70 g, 2.61 mmol, 1.1 eq.), tetrakis(triphenylphosphine)palladium (0) (0.14 g, 0.12 mmol, 0.05 eq.), potassium carbonate (0.66 g, 4.74 mmol, 2 eq.), and 1,4-dioxane/water (60 ml) were mixed, and the resulting mixture was refluxed and stirred. After the reaction was terminated, the resulting product was cooled to normal temperature, a solid produced at this time was filtered, and the filtered solid was purified with column chromatography using dichloromethane and methanol to obtain 0.65 g (yield of 52%) of Target Compound 42.

<Preparation Example 4> Preparation of Compound 109

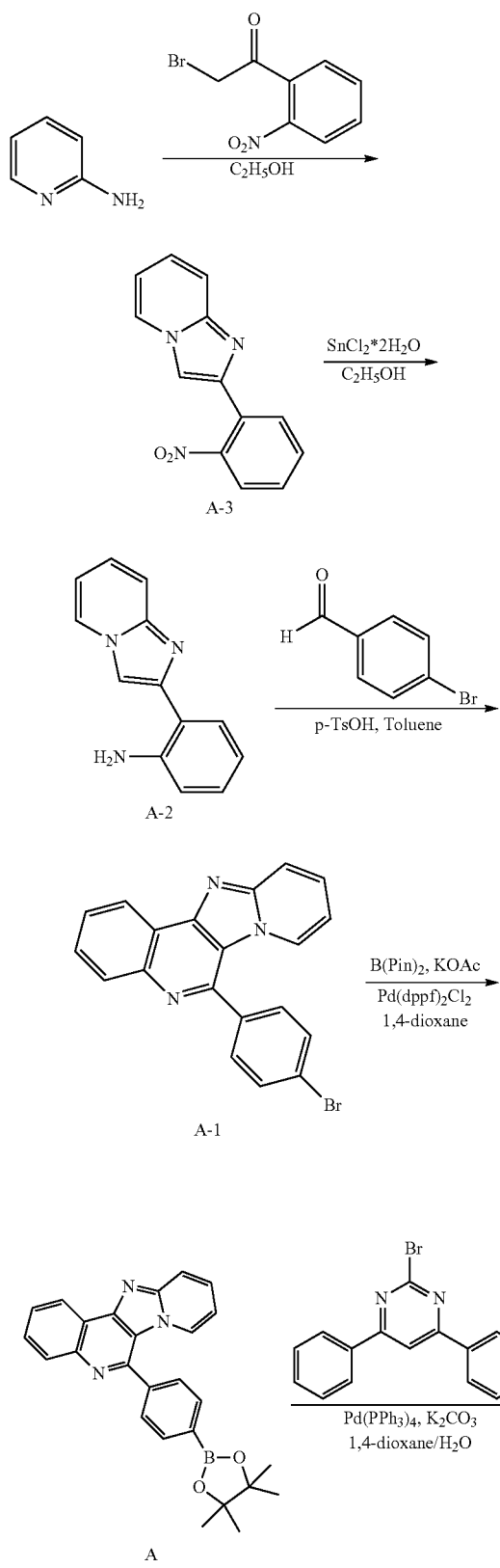

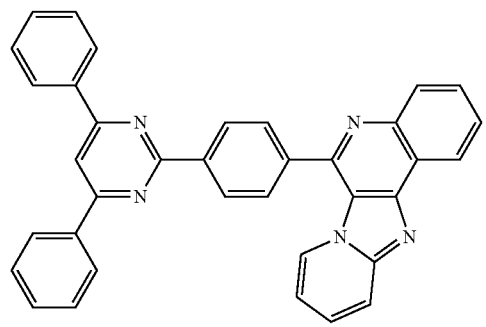

Preparation of Compound 109

Compound A (1.0 g, 2.37 mmol, 1 eq.), 2-bromo-4,6-diphenylpyridine (0.81 g, 2.61 mmol, 1.1 eq.), tetrakis(triphenylphosphine)palladium (0) (0.31 g, 0.12 mmol, 0.05 eq.), potassium carbonate (0.65 g, 4.72 mmol, 2 eq.), and 1,4-dioxane/water (60 ml) were mixed, and the resulting mixture was refluxed. After the reaction was terminated, the resulting product was cooled to normal temperature, and a solid produced at this time was filtered and washed with water. The filtered solid was purified with column chromatography using dichloromethane and methanol to obtain 0.53 g (yield of 43%) of Target Compound 109.

<Preparation Example 5> Preparation of Compound 111

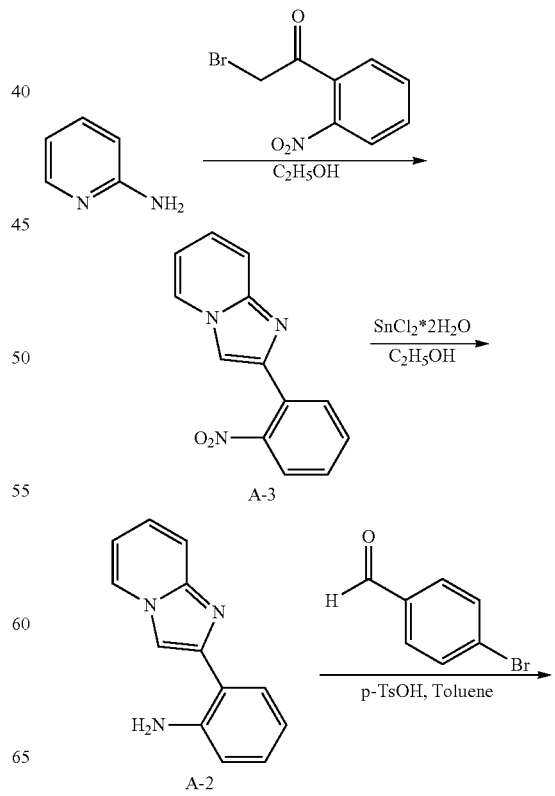

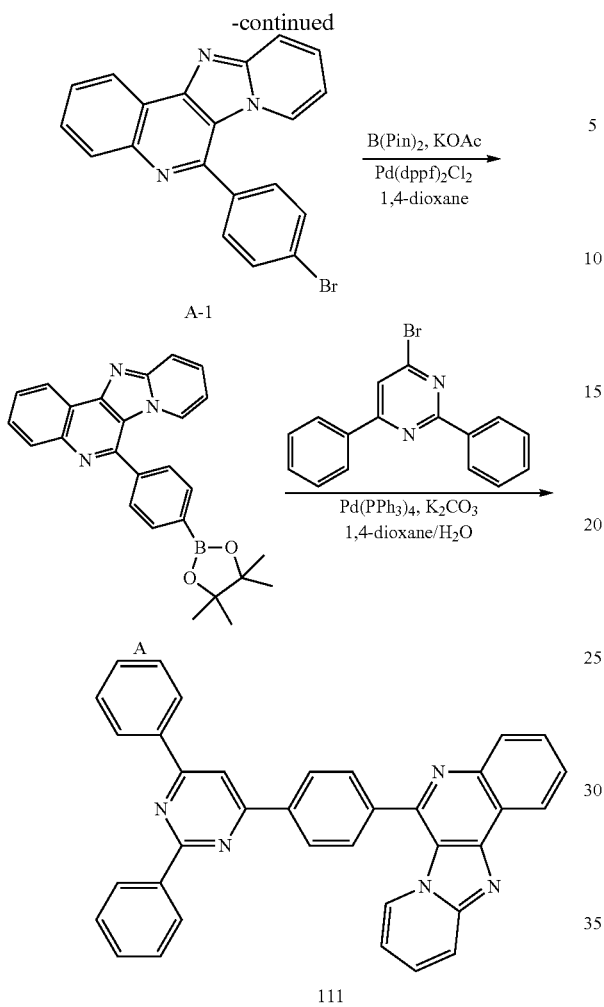
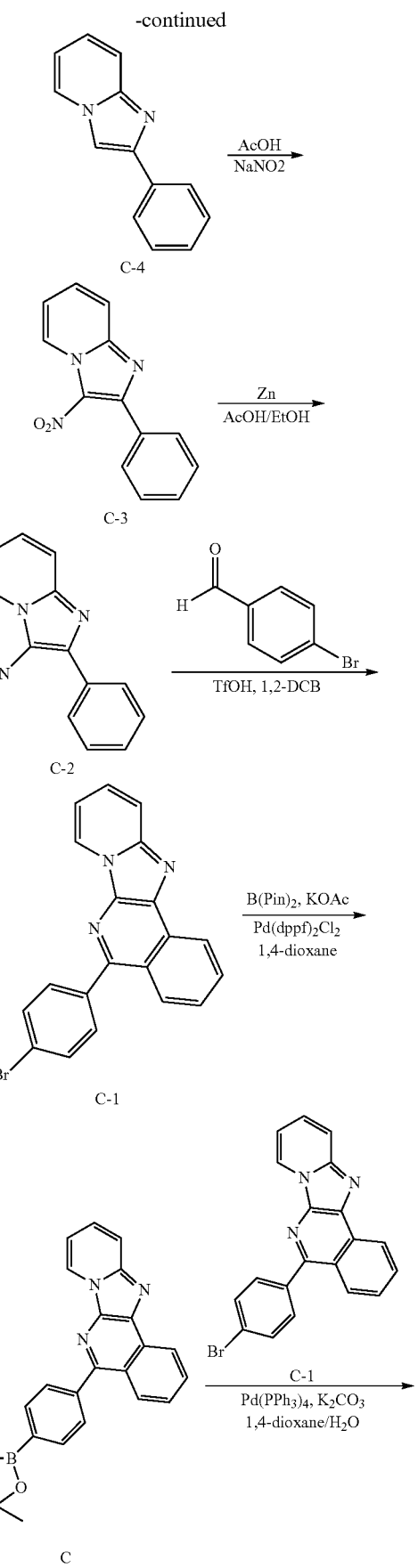

Preparation of Compound 111

Compound A (1.0 g, 2.37 mmol, 1 eq.), 4-bromo-2,6-diphenylpyrimidine (0.81 g, 2.61 mmol, 1.1 eq.), tetrakis(triphenylphosphine)palladium (0) (0.31 g, 0.12 mmol, 0.05 eq.), potassium carbonate (0.65 g, 4.72 mmol, 2 eq.), and 1,4-dioxane/water (60 ml) were mixed, and the resulting mixture was refluxed. After the reaction was terminated, the resulting product was cooled to normal temperature, and a solid produced at this time was filtered and washed with water. The filtered solid was purified with column chromatography using dichloromethane and methanol to obtain 0.53 g (yield of 43%) of Target Compound 111.

<Preparation Example 6> Preparation of Compound 344

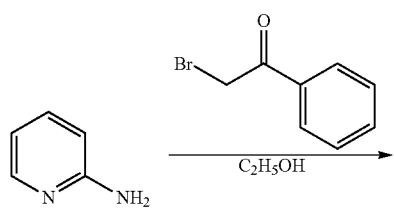

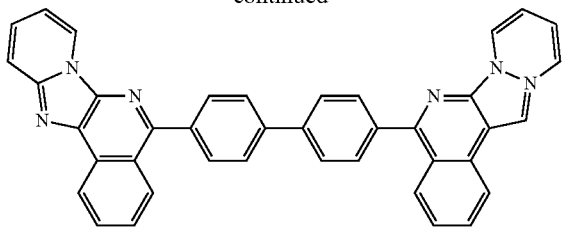

344

Preparation of Compound C-4

Ethanol (1,100 ml) was put into compounds 2-amino pyridine (27.0 g, 286.6 mmol, 1 eq.) and 2-bromoacetophenone (57 g, 286.6 mmol, 1 eq.), and the resulting mixture was refluxed. After the reaction was terminated, the resulting product was cooled to normal temperature and extracted with ethyl acetate/water, the organic layer was dried over anhydrous magnesium sulfate, and then the solvent was removed by using a rotary evaporator. The resulting product was purified with column chromatography using dichloromethane and ethyl acetate to obtain 18.37 g (yield of 33%) of Target Compound C-4.

Preparation of Compound C-3

Compound C-4 (18 g, 92.67 mmol, 1 eq.) was dissolved in acetic acid (675 ml), and then a solution of $NaNO_2$ (9.59 g, 139.0 mmol, 1.5 eq.) saturated in water was slowly added thereto at normal temperature. When the color was gradually changed to dark green, an ICE-bath was used to precipitate a solid, and then it was confirmed that the reaction has been terminated, and the solid was filtered. The filtered solid was washed with an excessive amount of water and normal hexane to obtain 22 g (yield of 70%) of Target Compound C-3.

Preparation of Compound C-2

Acetic acid and ethanol was put into a flask (550 ml) at a ratio of 1:1, and then Zn (44 g) was metered in an amount of twice the amount of Compound C-3 and added thereto. After the mixture was temporarily stirred at normal temperature, Compound C-3 (22 g, 91.96 mmol, 1 eq.) was gradually added thereto in a cooled state by using an ICE-bath, Compound C-3 was completely added thereto, and then the resulting mixture was stirred at normal temperature. When the reaction was terminated, the pH was adjusted to 13 by using a sodium hydroxide solution, the resulting product was extracted with ethyl acetate/water, the organic layer was dried over anhydrous magnesium sulfate, and then the solvent was removed by using a rotary evaporator. A solid precipitated at this time was filtered to obtain 19 g (99%) of Target Compound C-2.

Preparation of Compound C-1

Compound C-2 (10 g, 47.79 mmol, 1 eq.) and 4-bromobenzaldehyde (17.68 g, 95.58 mmol, 2 eq.) were dissolved in 1,2-dichlorobenzene (100 ml), trifluoromethanesulfonic acid (21.51 g, 143.37 mmol, 3 eq.) was slowly added thereto, and the resulting mixture was refluxed. When the reaction was terminated, the resulting product was cooled to normal temperature, and then neutralized by using $NaHCO_3$, a very excessive amount of dichloromethane was used to extract the product, and then the organic layer was removed. The remaining 1,2-dichlorobenzene was removed by distillation, a solid produced at this time was filtered and washed with ethyl acetate/normal hexane to obtain 9.48 g (53%) of Target Compound C-1.

Preparation of Compound C

Compound C-1 (5 g, 13.36 mmol, 1 eq.), bis(pinacolato) diboron (5.09 g, 20.05 mmol, 1.5 eq.), [1,1'-bis(diphenylphosphino)ferrocene]dichloropalladium (II) (0.49 g, 0.67 mmol, 0.05 eq.), and potassium acetate (3.9 g, 40.08 mmol, 3 eq.) were put and dissolved in 1,4-dioxane, and then the resulting solution was refluxed. After the reaction was terminated, the resulting product was cooled to normal temperature and extracted with dichloromethane/water, the organic layer was dried over anhydrous magnesium sulfate, and then the solvent was removed by using a rotary evaporator. The resulting product was purified with a simple silica gel filter to obtain 5.07 g (yield of 90%) of Target Compound C.

Preparation of Compound 344

Compound C (5 g, 11.87 mmol, 1 eq.), Compound C-1 (4.89 g, 13.05 mmol, 1.1 eq.), tetrakis(triphenylphosphine) palladium (0) (0.69 g, 0.59 mmol, 0.05 eq.), potassium carbonate (3.28 g, 23.74 mmol, 2 eq.), and 1,4-dioxane/water (60 ml) were mixed, and the resulting mixture was refluxed. After the reaction was terminated, the resulting product was cooled to normal temperature, and a solid produced at this time was filtered and washed with water. The filtered solid was purified by using methanol/normal hexane to obtain 4.19 g (yield of 60%) of Target Compound 344.

<Preparation Example 7> Preparation of Compound 347

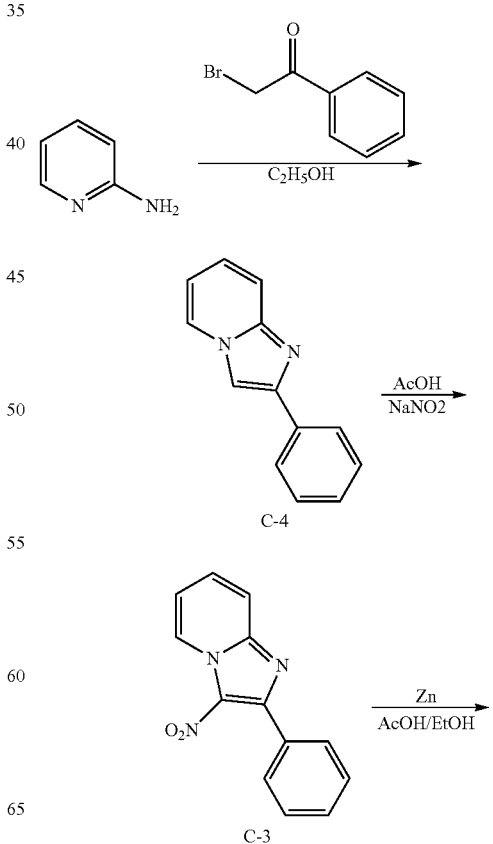

227

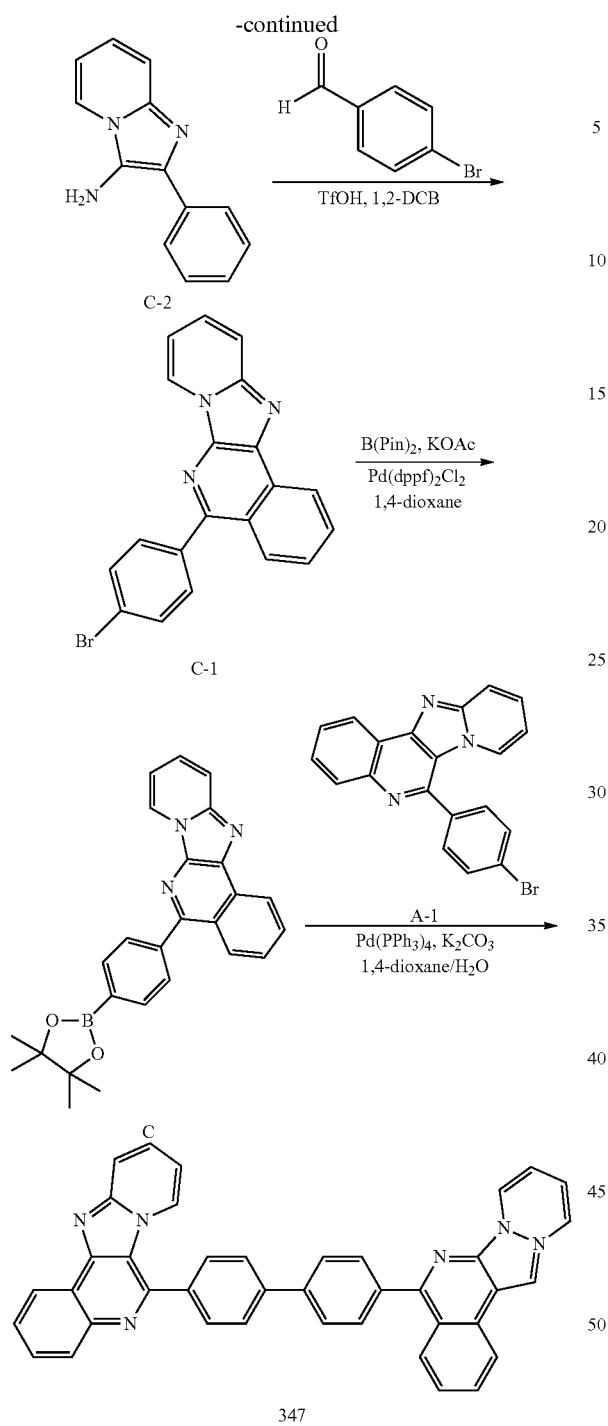

Preparation of Compound 347

Compound C (5 g, 11.87 mmol, 1 eq.), Compound A-1 (4.89 g, 13.05 mmol, 1.1 eq.), tetrakis(triphenylphosphine) palladium (0) (0.69 g, 0.59 mmol, 0.05 eq.), potassium carbonate (3.28 g, 23.74 mmol, 2 eq.), and 1,4-dioxane/water (60 ml) were mixed, and the resulting mixture was refluxed. After the reaction was terminated, the resulting product was cooled to normal temperature, and a solid produced at this time was filtered and washed with water. The filtered solid was purified by using methanol/normal hexane to obtain 4.05 g (yield of 58%) of Target Compound 347.

228

<Preparation Example 8> Preparation of Compound 367

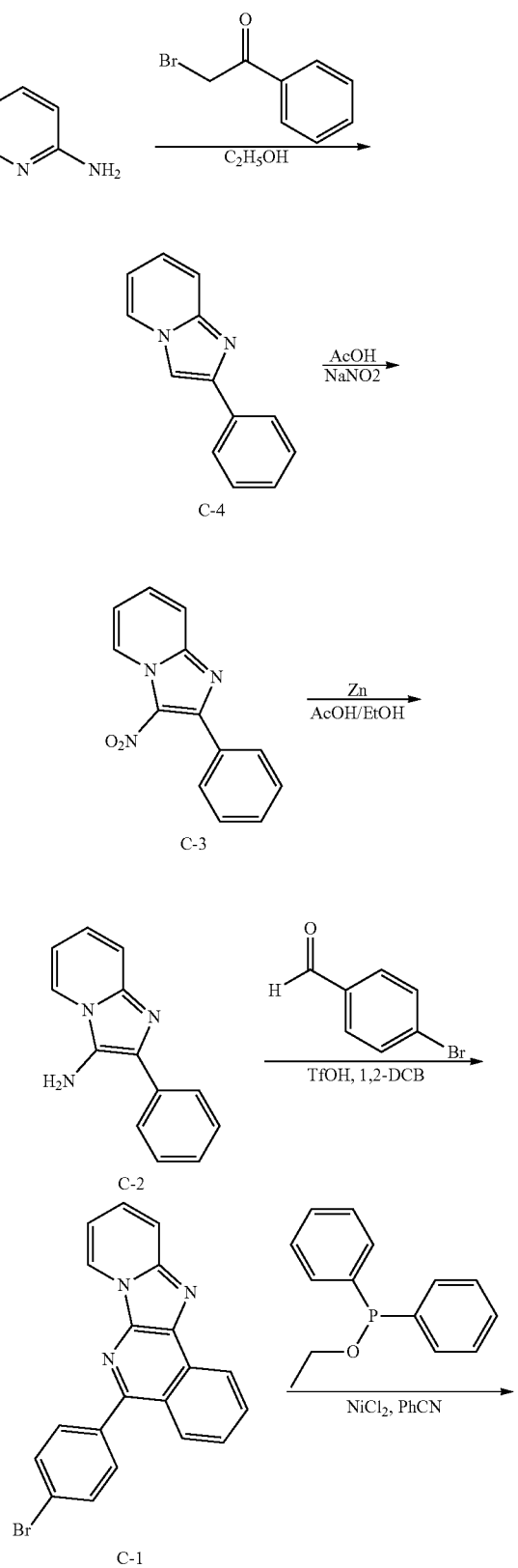

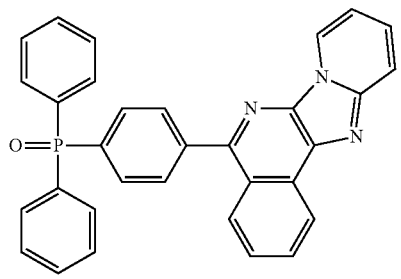

367

Preparation of Compound 367

Compound C (5 g, 11.87 mmol, 1 eq.) was dissolved in benzonitrile (75 ml), NiCl₂ (0.77 g, 5.93 mmol, 0.5 eq.) was added thereto, and then the resulting mixture was stirred at 180° C. for 1 hour. Ethoxydiphenylphosphane (13.66 g, 59.35 mmol, 5 eq.) was added thereto, and the resulting mixture was continuously stirred while being maintained at 180° C. After the reaction was terminated, the resulting product was cooled to normal temperature and extracted with ethyl acetate/water, the organic layer was dried over anhydrous magnesium sulfate, and then the solvent was removed by using a rotary evaporator.

The resulting product was purified with column chromatography using dichloromethane/ethyl acetate to obtain 5.06 g (yield of 52%) of Target Compound 367.

<Preparation Example 9> Preparation of Compound 373

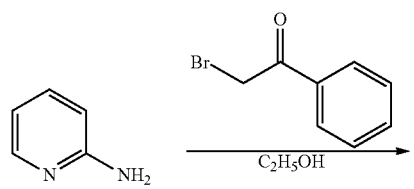

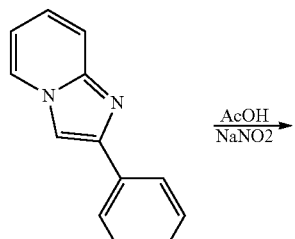

C-4

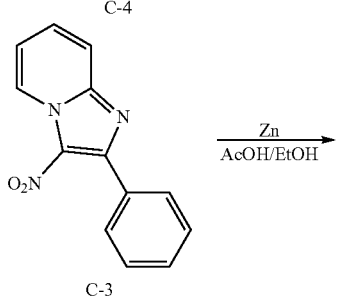

C-3

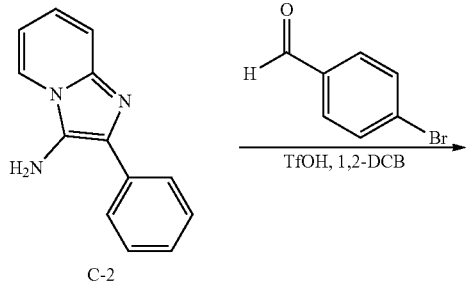

C-2

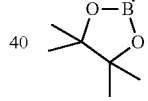

C-1

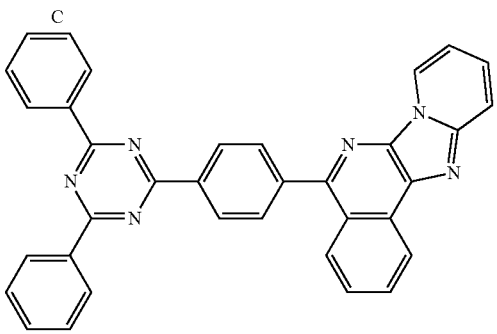

373

Preparation of Compound 373

Compound C (5 g, 11.87 mmol, 1 eq.), 2-chloro-4,6-diphenyl-1,3,5-triazine (3.5 g, 13.06 mmol, 1.1 eq.), tetrakis(triphenylphosphine)palladium (0) (0.69 g, 0.59 mmol, 0.05 eq.), potassium carbonate (3.28 g, 23.74 mmol, 2 eq.), and 1,4-dioxane/water (60 ml) were mixed, and the resulting mixture was refluxed. After the reaction was terminated, the resulting product was cooled to normal temperature, and a solid produced at this time was filtered and washed with water. The filtered solid was purified by using methanol/normal hexane to obtain 4.3 g (yield of 69%) of Target Compound 373.

<Preparation Example 10> Preparation of Compound 461

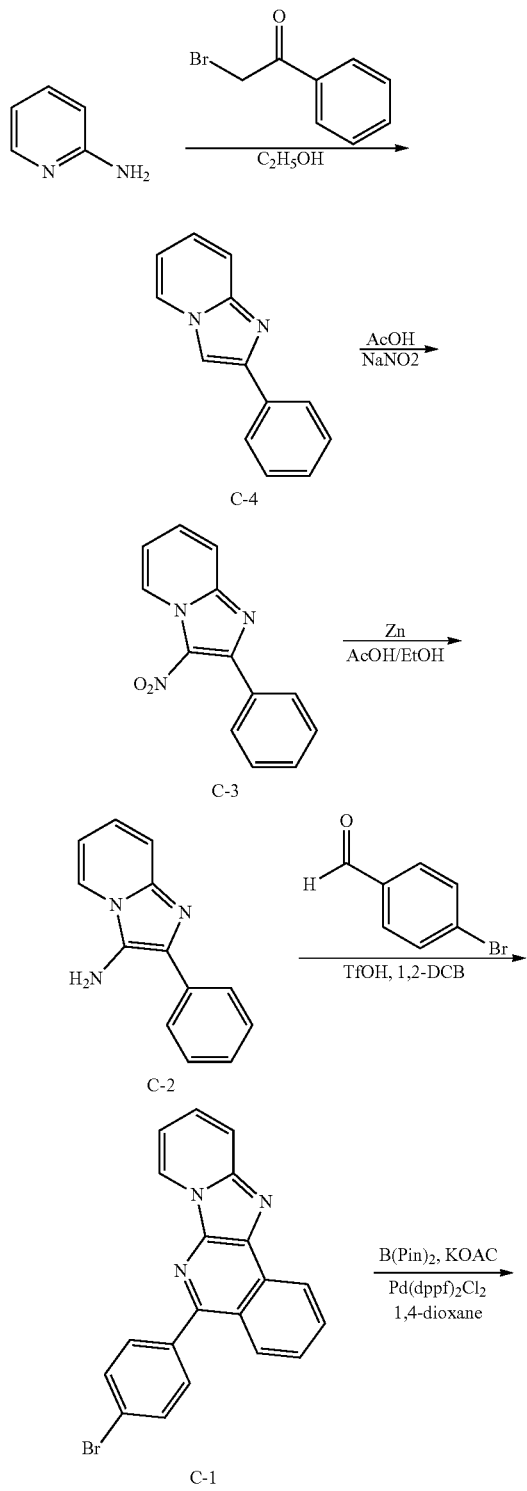

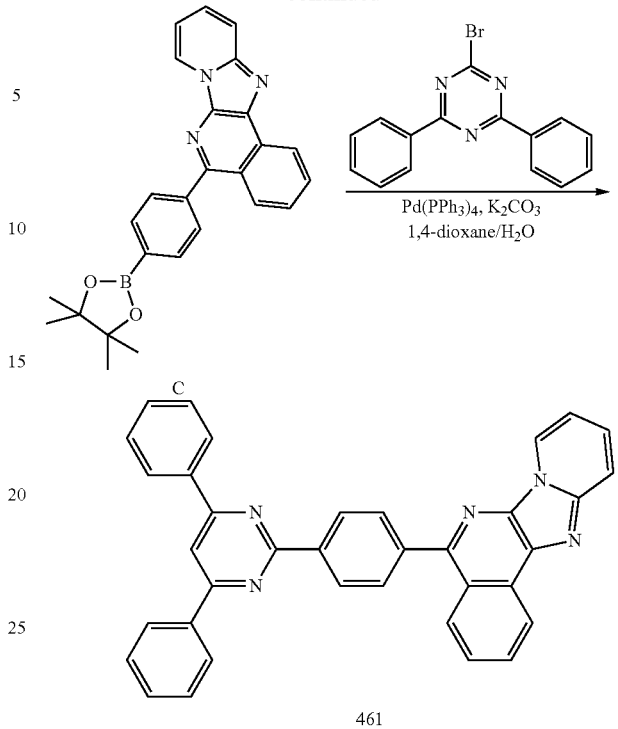

Preparation of Compound 461

Compound C (5 g, 11.87 mmol, 1 eq.), 2-bromo-4,6-diphenylpyrimidine (4.06 g, 13.06 mmol, 1.1 eq.), tetrakis(triphenylphosphine)palladium (0) (0.69 g, 0.59 mmol, 0.05 eq.), potassium carbonate (3.28 g, 23.74 mmol, 2 eq.), and 1,4-dioxane/water (60 ml) were mixed, and the resulting mixture was refluxed. After the reaction was terminated, the resulting product was cooled to normal temperature, and a solid produced at this time was filtered and washed with water. The filtered solid was purified by using methanol/normal hexane to obtain 3.93 g (yield of 63%) of Target Compound 461.

<Preparation Example 11> Preparation of Compound 463

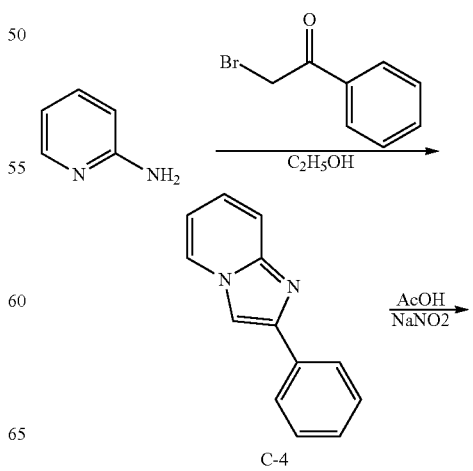

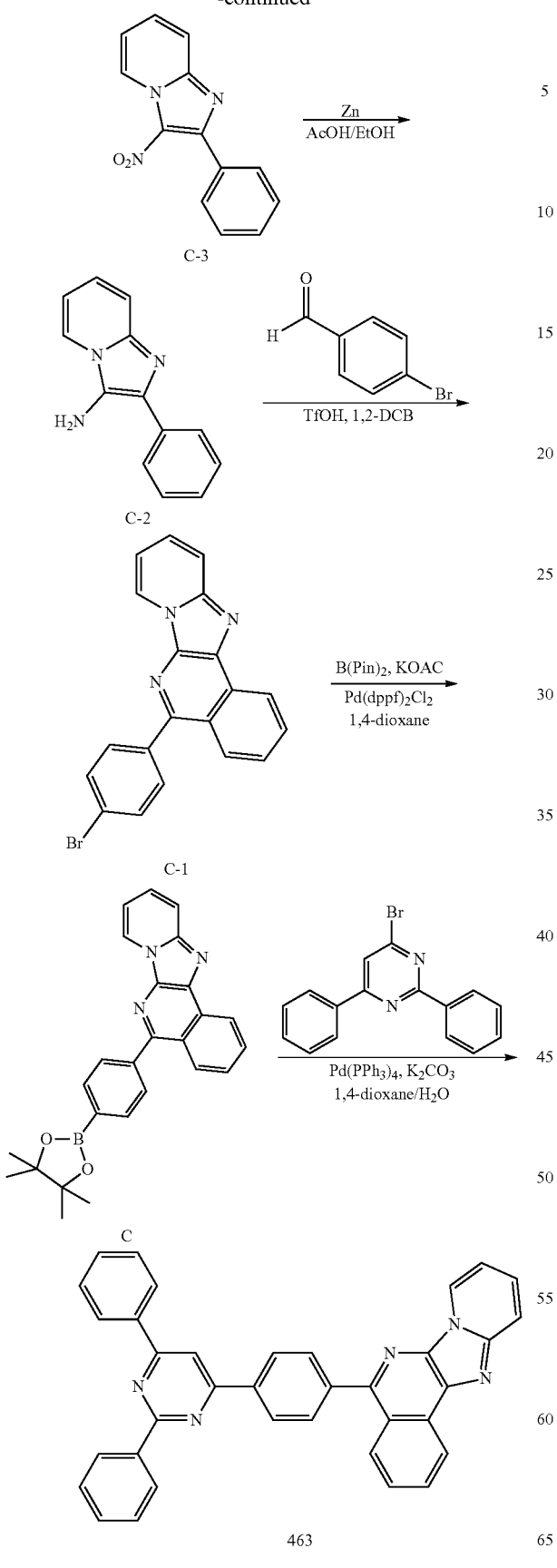

Preparation of Compound 463

Compound C (5 g, 11.87 mmol, 1 eq.), 4-bromo-2,6-diphenylpyrimidine (4.06 g, 13.06 mmol, 1.1 eq.), tetrakis(triphenylphosphine)palladium (0) (0.69 g, 0.59 mmol, 0.05 eq.), potassium carbonate (3.28 g, 23.74 mmol, 2 eq.), and 1,4-dioxane/water (60 ml) were mixed, and the resulting mixture was refluxed. After the reaction was terminated, the resulting product was cooled to normal temperature, and a solid produced at this time was filtered and washed with water. The filtered solid was purified by using methanol/normal hexane to obtain 3.8 g (yield of 61%) of Target Compound 463.

<Preparation Example 12> Preparation of Compound 468

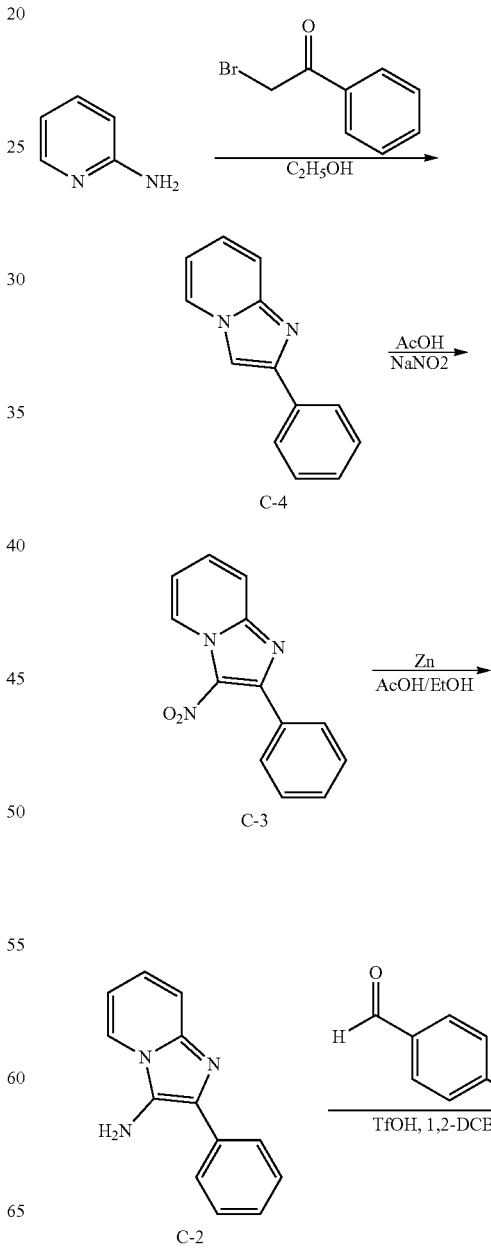

-continued

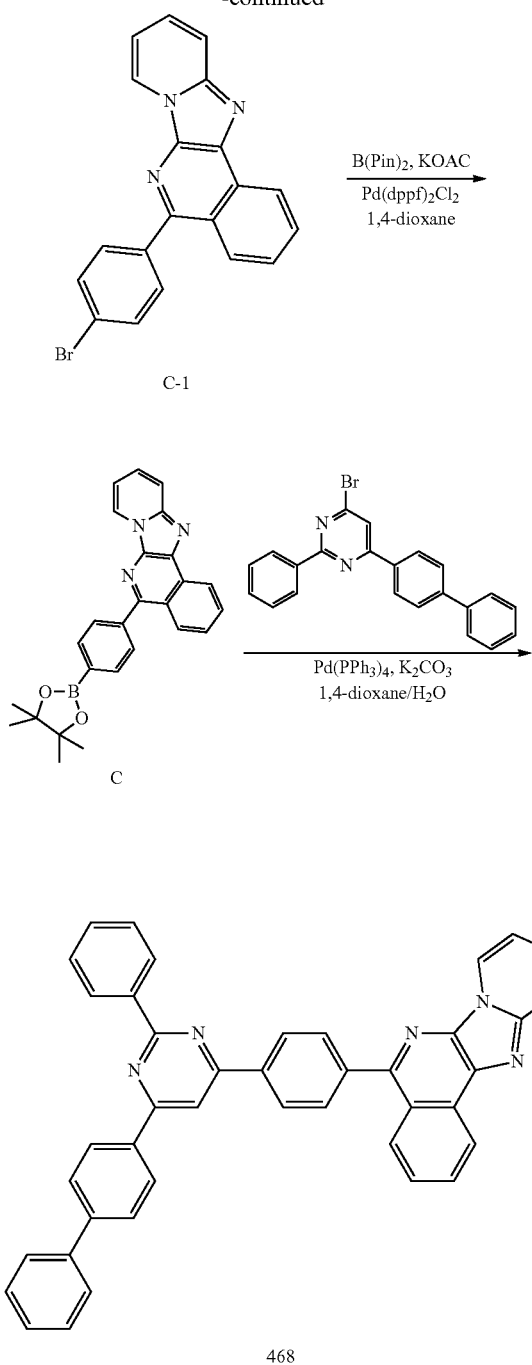

468

Preparation of Compound 468

Compound C (5 g, 11.87 mmol, 1 eq.), 4-([1,1'-biphenyl]-4-yl)-6-bromo-2-phenylpyrimidine (5.06 g, 13.06 mmol, 1.1 eq.), tetrakis(triphenylphosphine)palladium (0) (0.69 g, 0.59 mmol, 0.05 eq.), potassium carbonate (3.28 g, 23.74 mmol, 2 eq.), and 1,4-dioxane/water (60 ml) were mixed, and the resulting mixture was refluxed. After the reaction was terminated, the resulting product was cooled to normal temperature, and a solid produced at this time was filtered and washed with water. The filtered solid was purified by using methanol/normal hexane to obtain 5.07 g (yield of 71%) of Target Compound 468.

<Preparation Example 13> Preparation of Compound 478

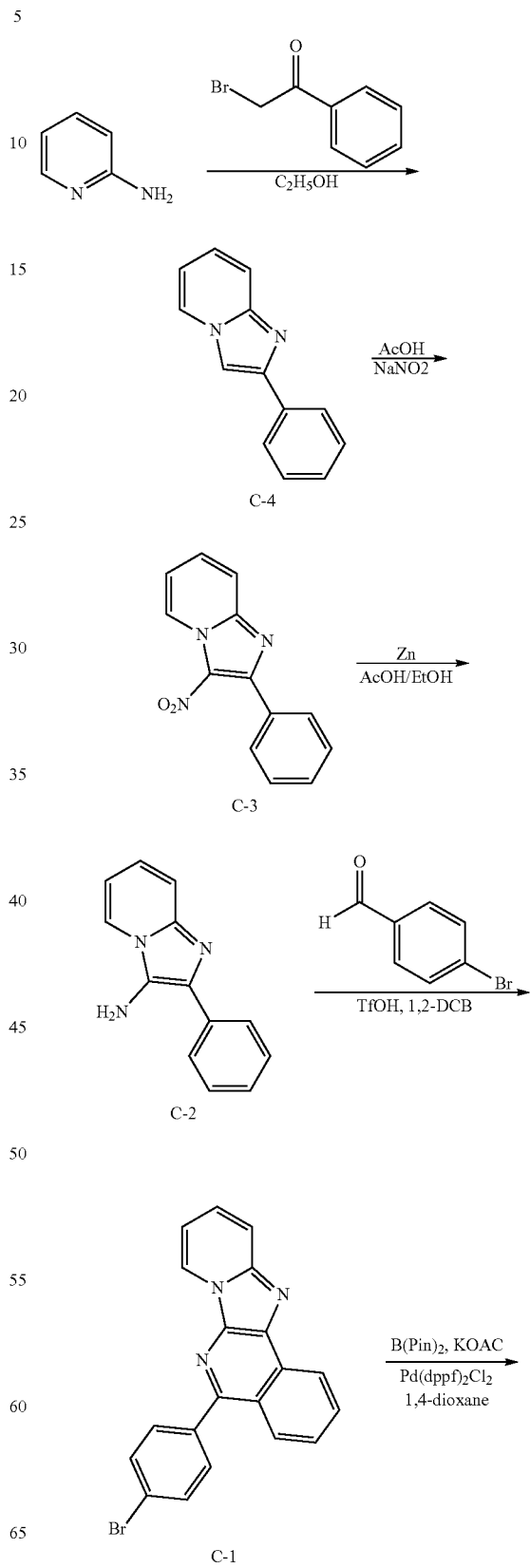

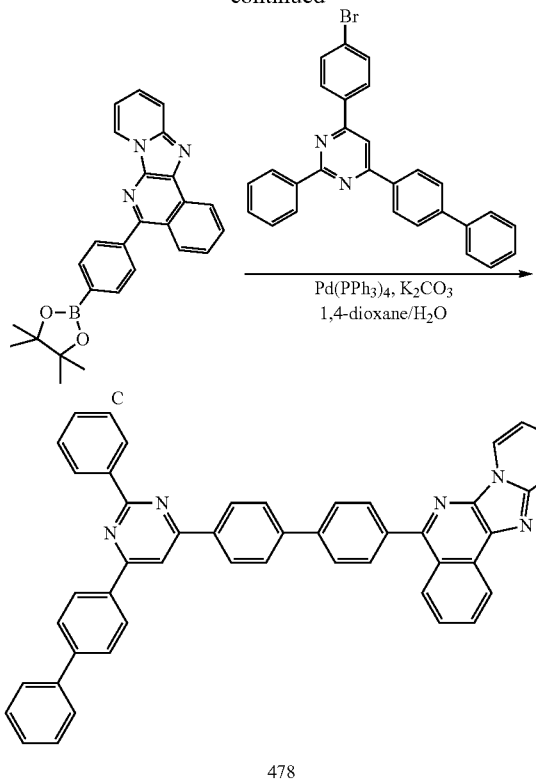
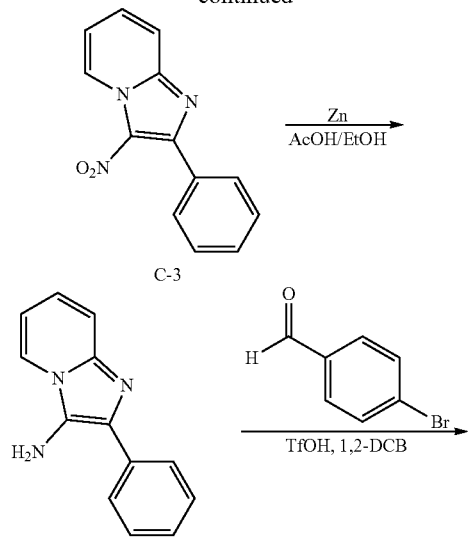
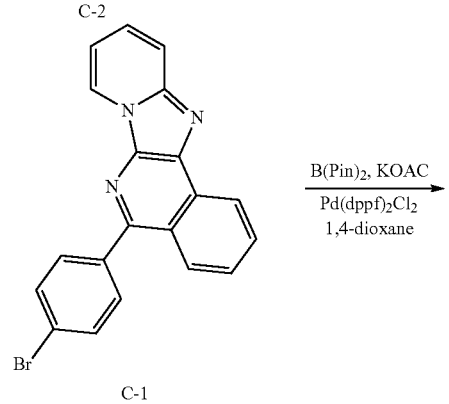
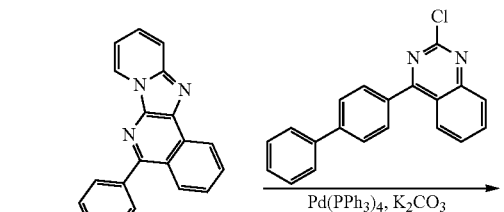

Preparation of Compound 478

Compound C (5 g, 11.87 mmol, 1 eq.), 4-([1,1'-biphenyl]-4-yl)-6-bromo-2-phenylpyrimidine (6.05 g, 13.06 mmol, 1.1 eq.), tetrakis(triphenylphosphine)palladium (0) (0.69 g, 0.59 mmol, 0.05 eq.), potassium carbonate (3.28 g, 23.74 mmol, 2 eq.), and 1,4-dioxane/water (60 ml) were mixed, and the resulting mixture was refluxed. After the reaction was terminated, the resulting product was cooled to normal temperature, and a solid produced at this time was filtered and washed with water. The filtered solid was purified by using methanol/normal hexane to obtain 6.6 g (yield of 82%) of Target Compound 478.

<Preparation Example 14> Preparation of Compound 497

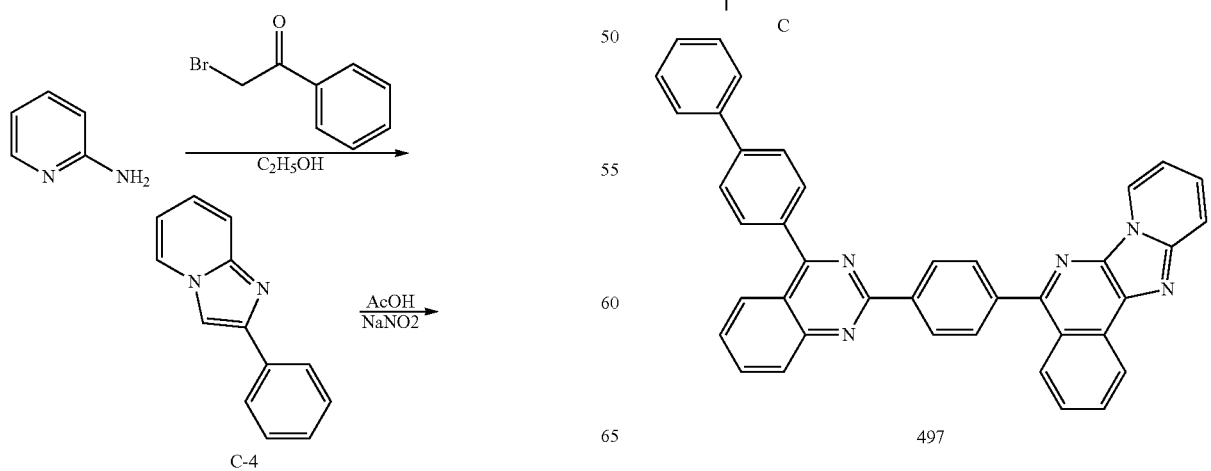

Preparation of Compound 497

Compound C (5 g, 11.87 mmol, 1 eq.), 4-([1,1'-biphenyl]-4-yl)-2-chloroquinazoline (4.14 g, 13.06 mmol, 1.1 eq.), tetrakis(triphenylphosphine)palladium (0) (0.69 g, 0.59 mmol, 0.05 eq.), potassium carbonate (3.28 g, 23.74 mmol, 2 eq.), and 1,4-dioxane/water (60 ml) were mixed, and the resulting mixture was refluxed. After the reaction was terminated, the resulting product was cooled to normal temperature, and a solid produced at this time was filtered and washed with water. The filtered solid was purified by using methanol/normal hexane to obtain 4.58 g (yield of 67%) of Target Compound 497.

<Preparation Example 15> Preparation of Compound 498

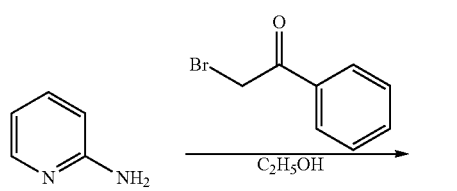

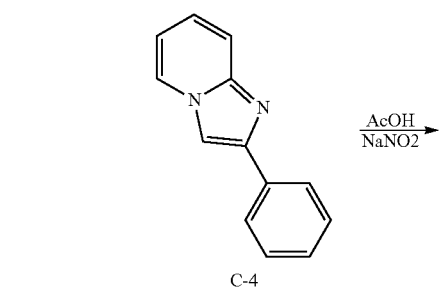

C-4

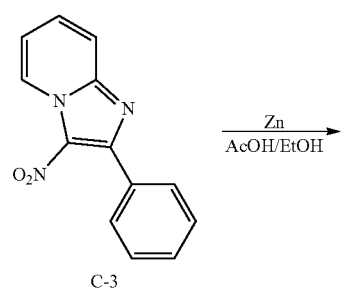

C-3

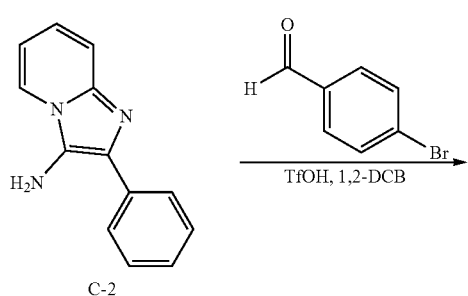

C-2

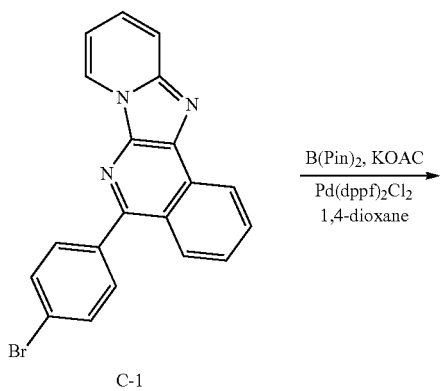

C-1

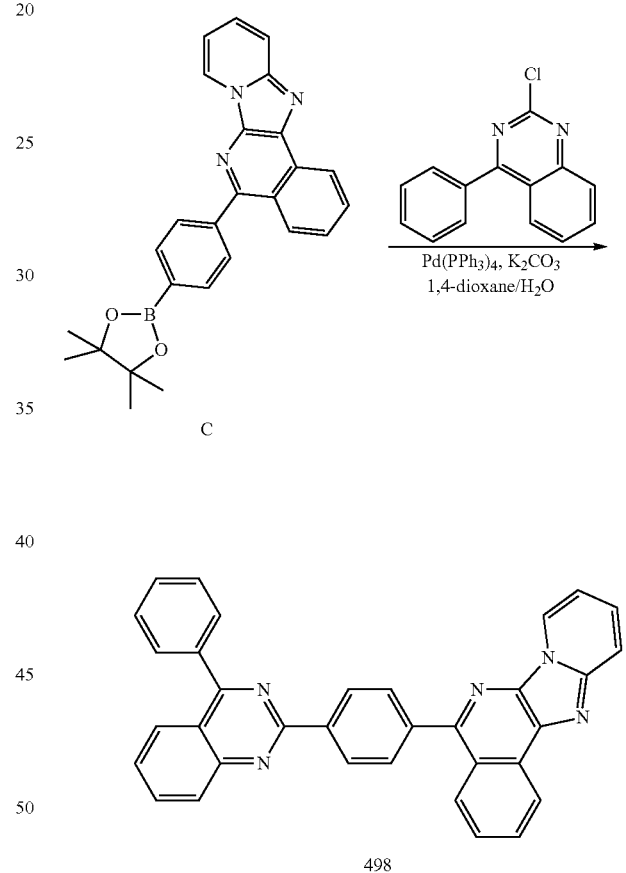

C

498

Preparation of Compound 498

Compound C (5 g, 11.87 mmol, 1 eq.), 2-chloro-4-phenylquinazoline (3.14 g, 13.06 mmol, 1.1 eq.), tetrakis(triphenylphosphine)palladium (0) (0.69 g, 0.59 mmol, 0.05 eq.), potassium carbonate (3.28 g, 23.74 mmol, 2 eq.), and 1,4-dioxane/water (60 ml) were mixed, and the resulting mixture was refluxed. After the reaction was terminated, the resulting product was cooled to normal temperature, and a solid produced at this time was filtered and washed with water. The filtered solid was purified by using methanol/normal hexane to obtain 4.62 g (yield of 78%) of Target Compound 498.

<Preparation Example 16> Preparation of Compound 537

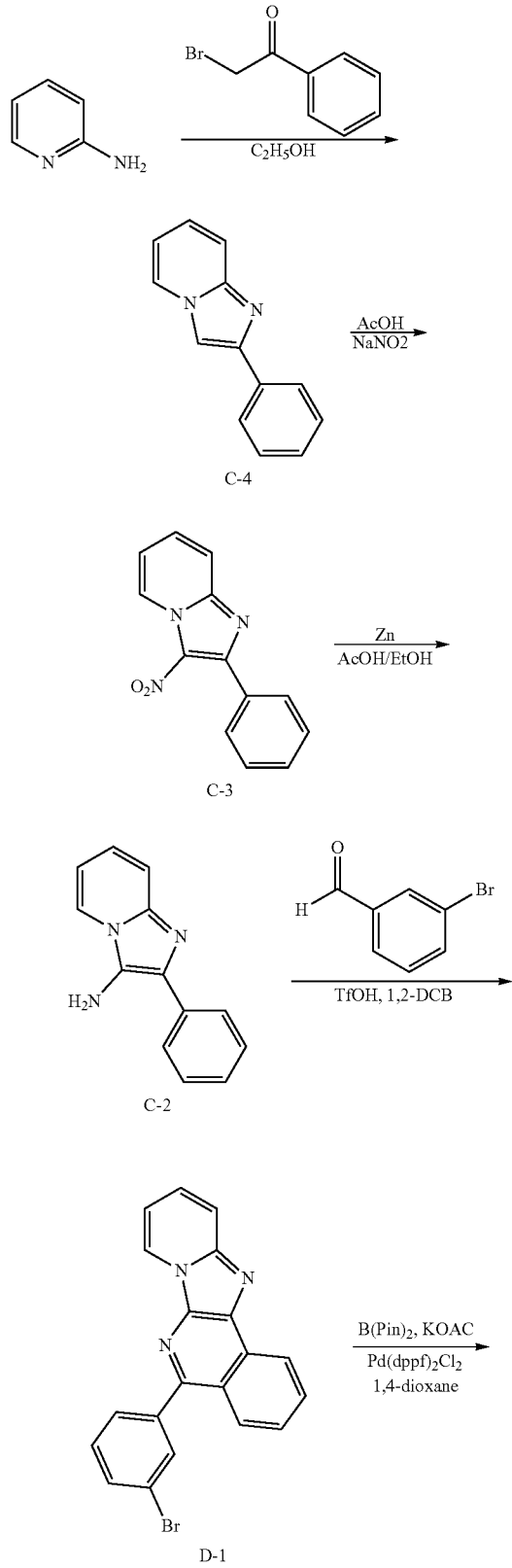

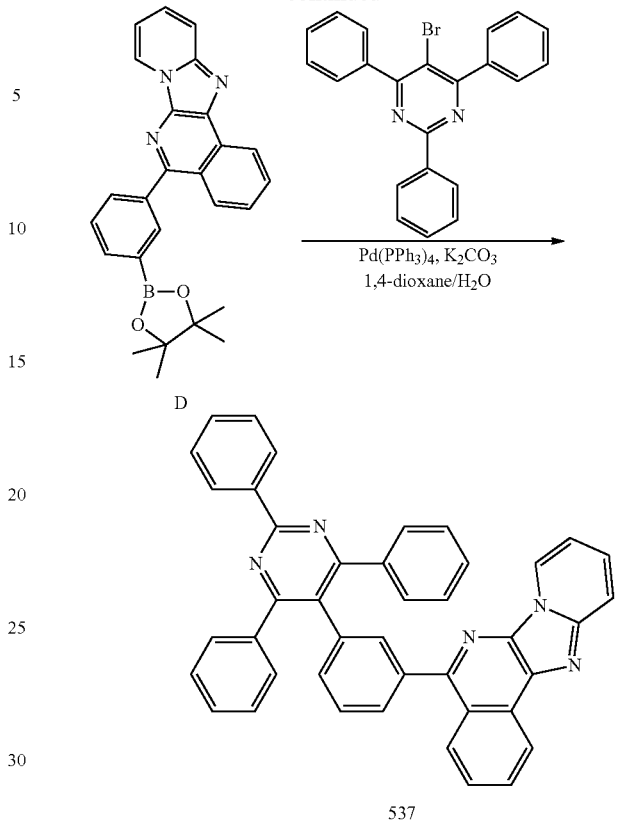

Preparation of Compound D-1

Compound C-2 (10 g, 47.79 mmol, 1 eq.) and 3-bromobenzaldehyde (17.68 g, 95.58 mmol, 2 eq.) were dissolved in 1,2-dichlorobenzene (100 ml), trifluoromethanesulfonic acid (21.51 g, 143.37 mmol, 3 eq.) was slowly added thereto, and the resulting mixture was refluxed. When the reaction was terminated, the resulting product was cooled to normal temperature, and then neutralized by using $NaHCO_3$, a very excessive amount of dichloromethane was used to extract the product, and then the organic layer was removed. The remaining 1,2-dichlorobenzene was removed by distillation, a solid produced at this time was filtered and washed with ethyl acetate/normal hexane to obtain 9.84 g (55%) of Target Compound D-1.

Preparation of Compound D

Compound D-1 (5 g, 13.36 mmol, 1 eq), bis(pinacolato)diboron (5.09 g, 20.05 mmol, 1.5 eq), [1,1'-bis(diphenylphosphino)ferrocene]dichloropalladium (II) (0.49 g, 0.67 mmol, 0.05 eq.), and potassium acetate (3.9 g, 40.08 mmol, 3 eq.) were put and dissolved in 1,4-dioxane, and then the resulting solution was refluxed. After the reaction was terminated, the resulting product was cooled to normal temperature and extracted with dichloromethane/water, the organic layer was dried over anhydrous magnesium sulfate, and then the solvent was removed by using a rotary evaporator. The resulting product was purified with a simple silica gel filter to obtain 5.2 g (yield of 92%) of Target Compound D.

Preparation of Compound 537

Compound D (5 g, 11.87 mmol, 1 eq.), 5-bromo-2,4,6-triphenylpyrimidine (5.06 g, 13.06 mmol, 1.1 eq.), tetrakis(triphenylphosphine)palladium (0) (0.69 g, 0.59 mmol, 0.05 eq.), potassium carbonate (3.28 g, 23.74 mmol, 2 eq.), and 1,4-dioxane/water (60 ml) were mixed, and the resulting mixture was refluxed. After the reaction was terminated, the resulting product was cooled to normal temperature, and a solid produced at this time was filtered and washed with water. The filtered solid was purified by using methanol/normal hexane to obtain 5.36 g (yield of 75%) of Target Compound 537.

<Preparation Example 17> Preparation of Compound 581

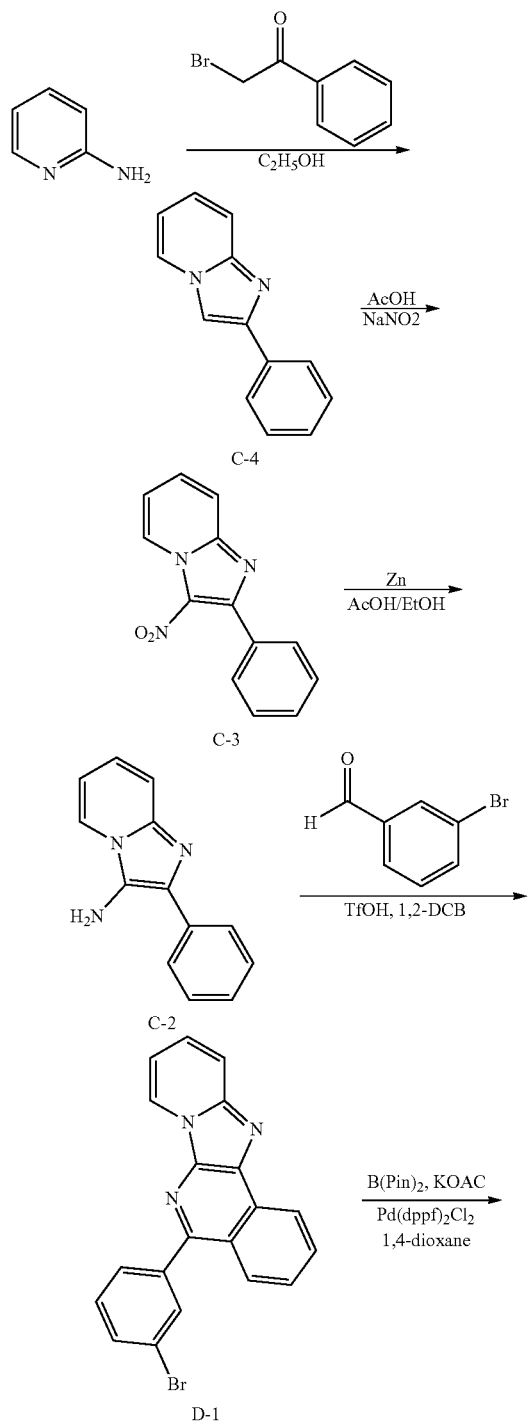

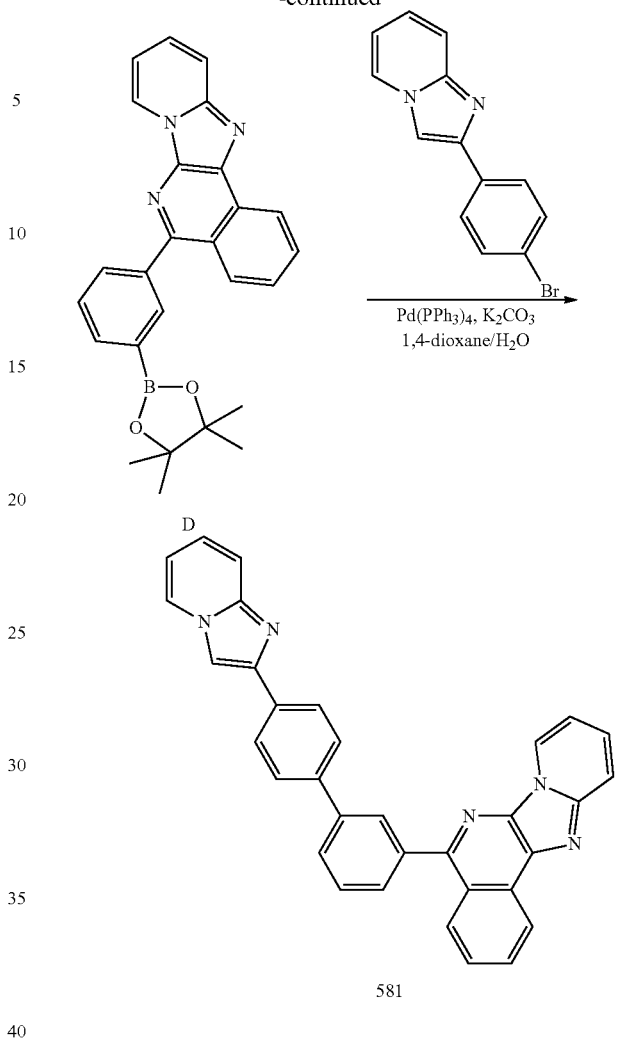

Preparation of Compound 581

Compound D (5 g, 11.87 mmol, 1 eq.), 2-(4-bromophenyl)imidazo[1,2-a]pyridine (3.57 g, 13.06 mmol, 1.1 eq.), tetrakis(triphenylphosphine)palladium (0) (0.69 g, 0.59 mmol, 0.05 eq.), potassium carbonate (3.28 g, 23.74 mmol, 2 eq.), and 1,4-dioxane/water (60 ml) were mixed, and the resulting mixture was refluxed. After the reaction was terminated, the resulting product was cooled to normal temperature, and a solid produced at this time was filtered and washed with water. The filtered solid was purified by using methanol/normal hexane to obtain 4.57 g (yield of 79%) of Target Compound 581.

<Preparation Example 18> Preparation of Compound 601

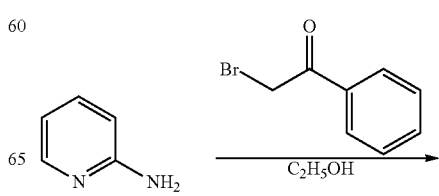

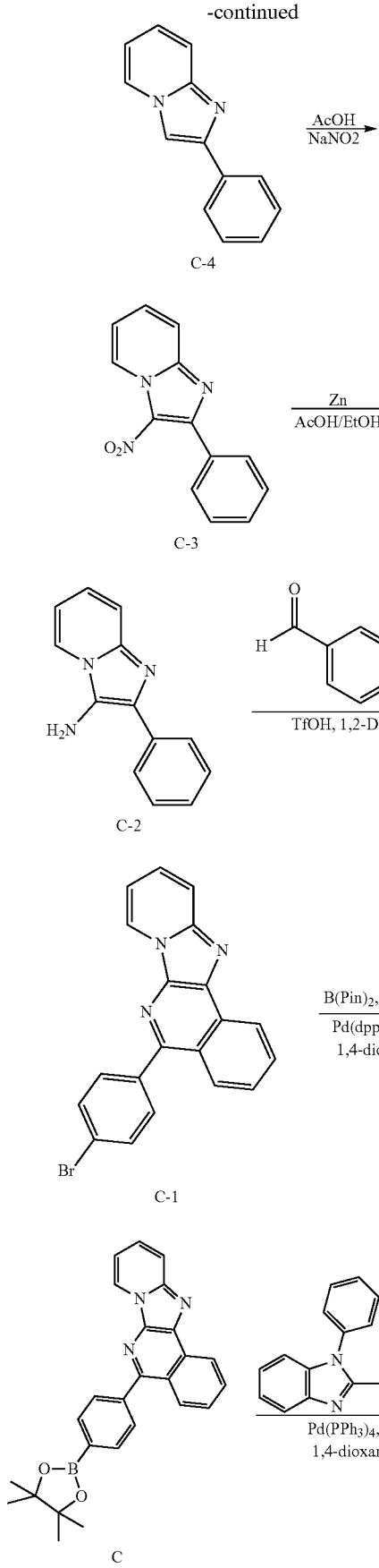

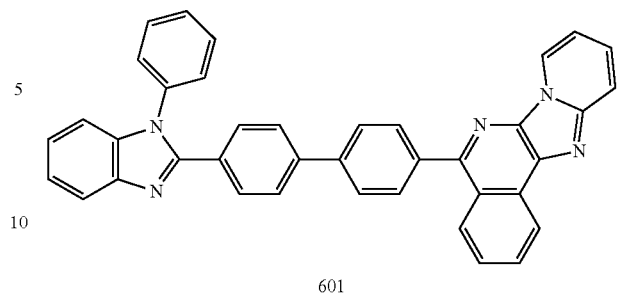

601

Preparation of Compound 601

Compound C (5 g, 11.87 mmol, 1 eq.), 2-(4-bromophenyl)-1-phenyl-1H-benzo[d]imidazole (4.56 g, 13.06 mmol, 1.1 eq.), tetrakis(triphenylphosphine)palladium (0) (0.69 g, 0.59 mmol, 0.05 eq.), potassium carbonate (3.28 g, 23.74 mmol, 2 eq.), and 1,4-dioxane/water (60 ml) were mixed, and the resulting mixture was refluxed. After the reaction was terminated, the resulting product was cooled to normal temperature, and a solid produced at this time was filtered and washed with water. The filtered solid was purified by using methanol/normal hexane to obtain 5.29 g (yield of 79%) of Target Compound 601.

<Preparation Example 19> Preparation of Compound 642

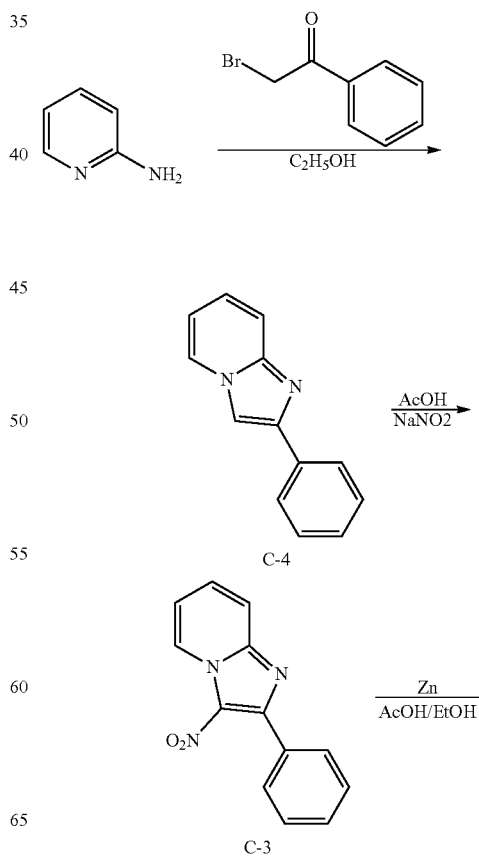

-continued

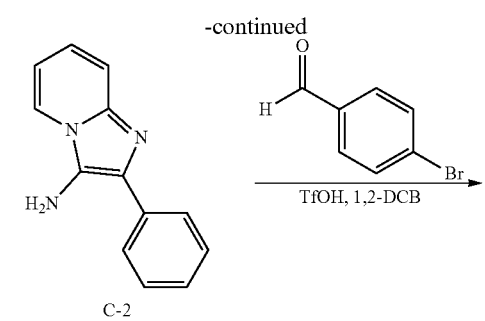

Preparation of Compound 642

Compound C (5 g, 11.87 mmol, 1 eq.), 4-(4-bromophenyl)-2,6-diphenylpyrimidine (5.06 g, 13.06 mmol, 1.1 eq.), tetrakis(triphenylphosphine)palladium (0) (0.69 g, 0.59 mmol, 0.05 eq.), potassium carbonate (3.28 g, 23.74 mmol, 2 eq.), and 1,4-dioxane/water (60 ml) were mixed, and the resulting mixture was refluxed. After the reaction was terminated, the resulting product was cooled to normal temperature, and a solid produced at this time was filtered and washed with water. The filtered solid was purified by using methanol/normal hexane to obtain 5.37 g (yield of 75%) of Target Compound 642.

<Preparation Example 20> Preparation of Compound 678

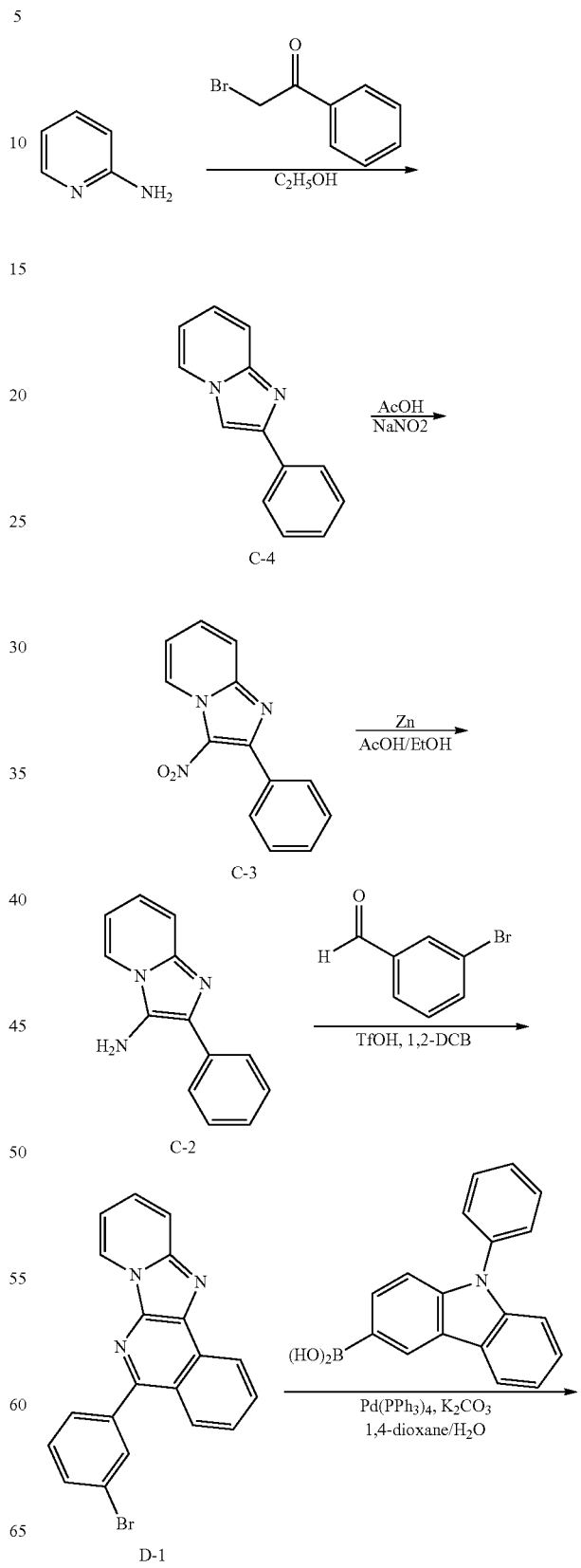

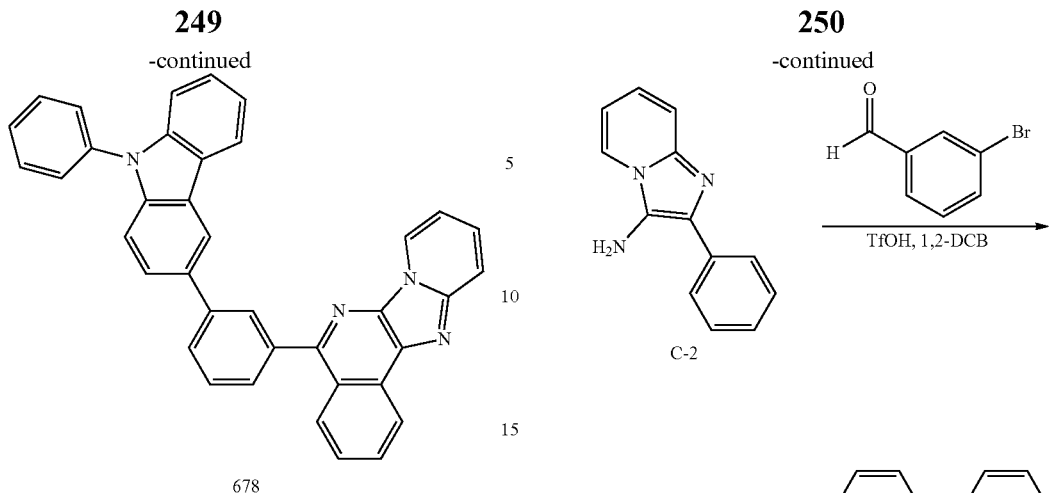

678

Preparation of Compound 678

Compound D-1 (5 g, 13.36 mmol, 1 eq.), (9-phenyl-9H-carbazol-3-yl)boronic acid (4.22 g, 14.70 mmol, 1.1 eq.), tetrakis(triphenylphosphine)palladium (0) (0.43 g, 0.37 mmol, 0.05 eq.), potassium carbonate (3.69 g, 26.72 mmol, 2 eq.), and 1,4-dioxane/water (60 ml) were mixed, and the resulting mixture was refluxed. After the reaction was terminated, the resulting product was cooled to normal temperature, and a solid produced at this time was filtered and washed with water. The filtered solid was purified by using methanol/normal hexane to obtain 5.52 g (yield of 77%) of Target Compound 678.

<Preparation Example 21> Preparation of Compound 688

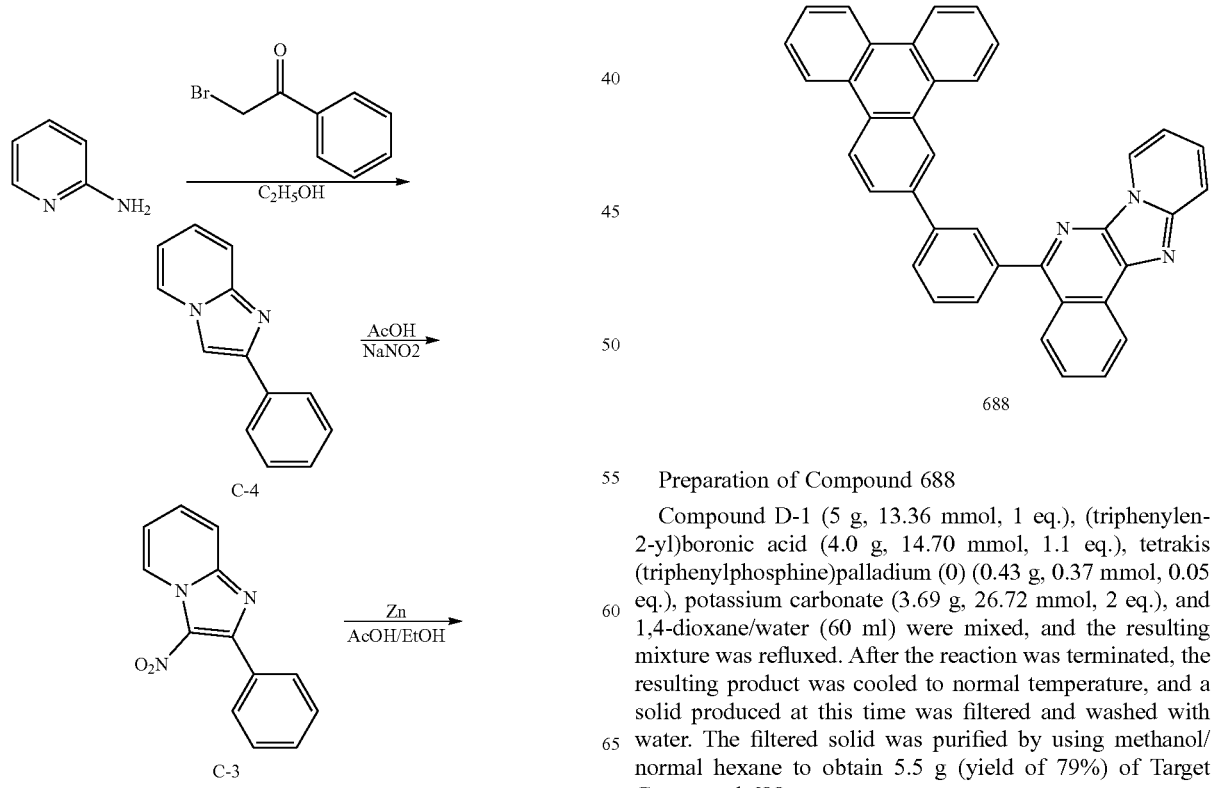

688

Preparation of Compound 688

Compound D-1 (5 g, 13.36 mmol, 1 eq.), (triphenylen-2-yl)boronic acid (4.0 g, 14.70 mmol, 1.1 eq.), tetrakis(triphenylphosphine)palladium (0) (0.43 g, 0.37 mmol, 0.05 eq.), potassium carbonate (3.69 g, 26.72 mmol, 2 eq.), and 1,4-dioxane/water (60 ml) were mixed, and the resulting mixture was refluxed. After the reaction was terminated, the resulting product was cooled to normal temperature, and a solid produced at this time was filtered and washed with water. The filtered solid was purified by using methanol/normal hexane to obtain 5.5 g (yield of 79%) of Target Compound 688.

<Preparation Example 22> Preparation of Compound 353

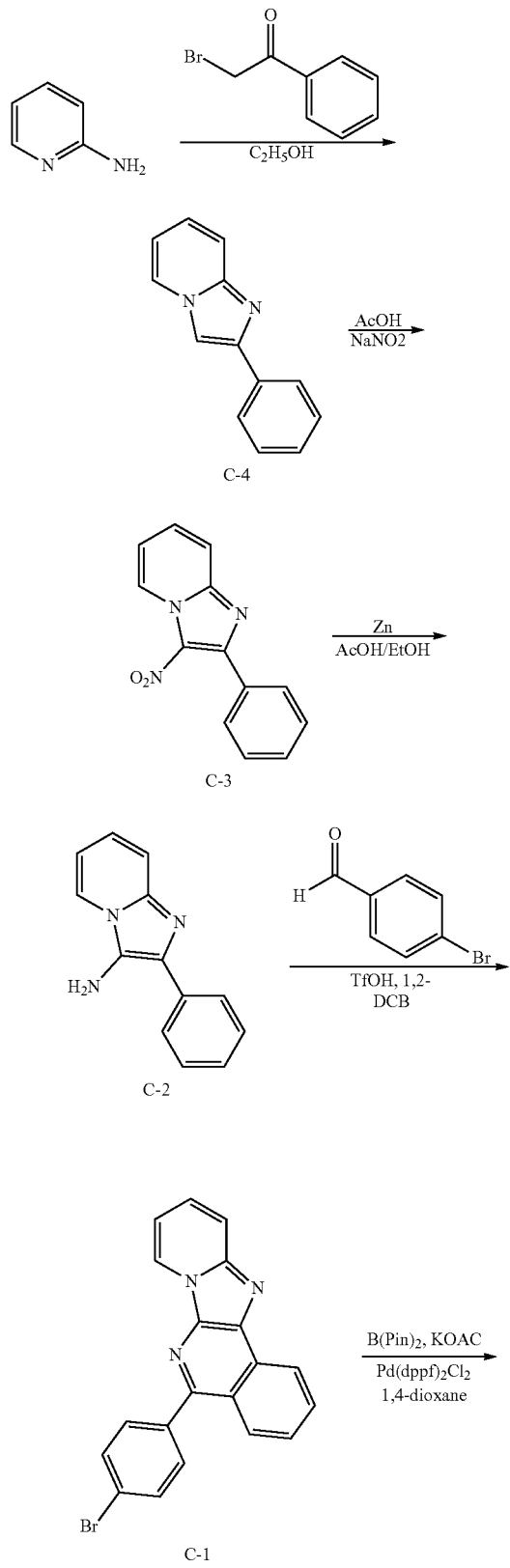

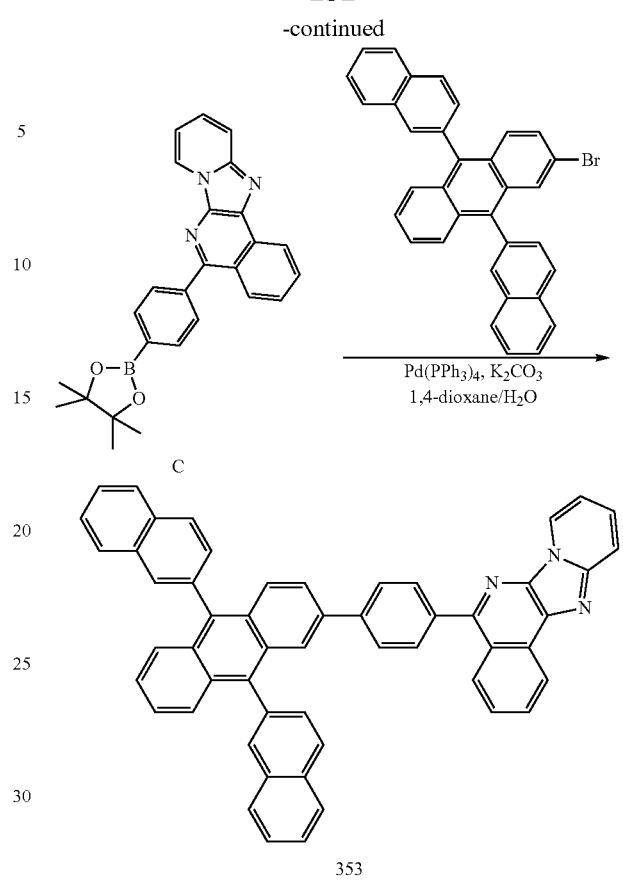

Preparation of Compound 353

A preparation was performed in the same manner as in the preparation of Compound 373, except that 2-bromo-9,10-di(naphthalen-2-yl)anthracene was used instead of the compound 2-chloro-4,6-diphenyl-1,3,5-triazine in Preparation Example 9, thereby obtaining Target Compound 353.

<Preparation Example 23> Preparation of Compound 363

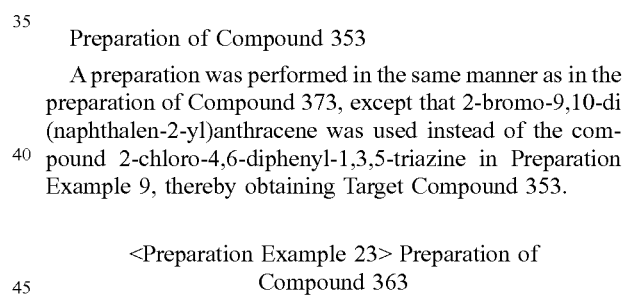

-continued
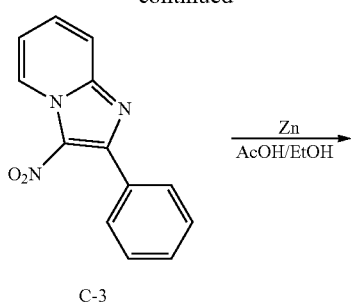
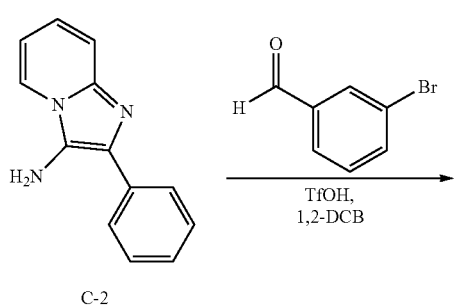
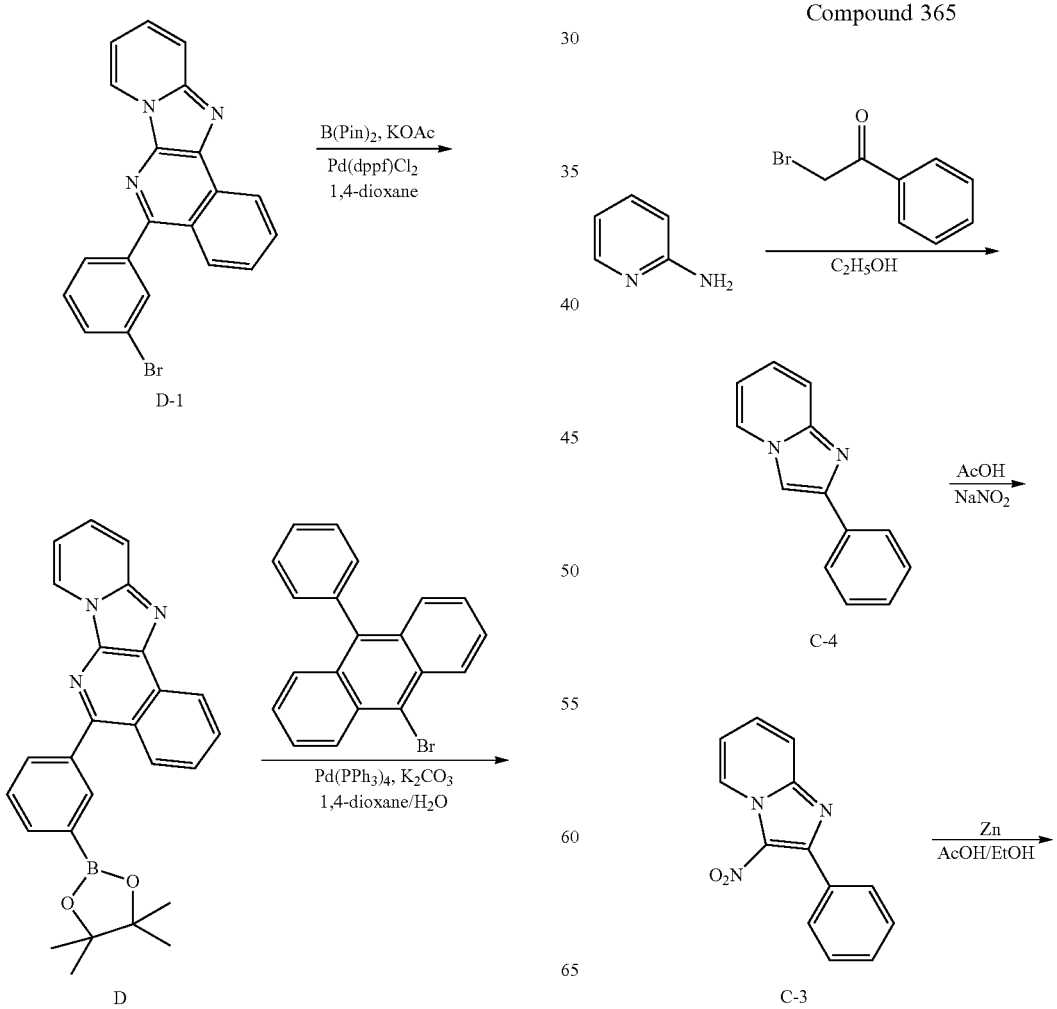
-continued
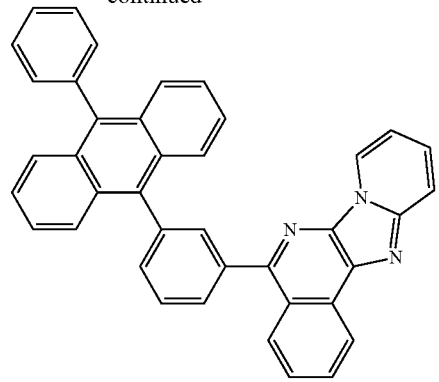
363
Preparation of Compound 363
A preparation was performed in the same manner as in the preparation of Compound 537, except that 9-bromo-10-phenylanthracene was used instead of the compound 5-bromo-2,4,6-triphenylpyrimidine in Preparation Example 16, thereby obtaining Target Compound 363.
<Preparation Example 24> Preparation of Compound 365

-continued
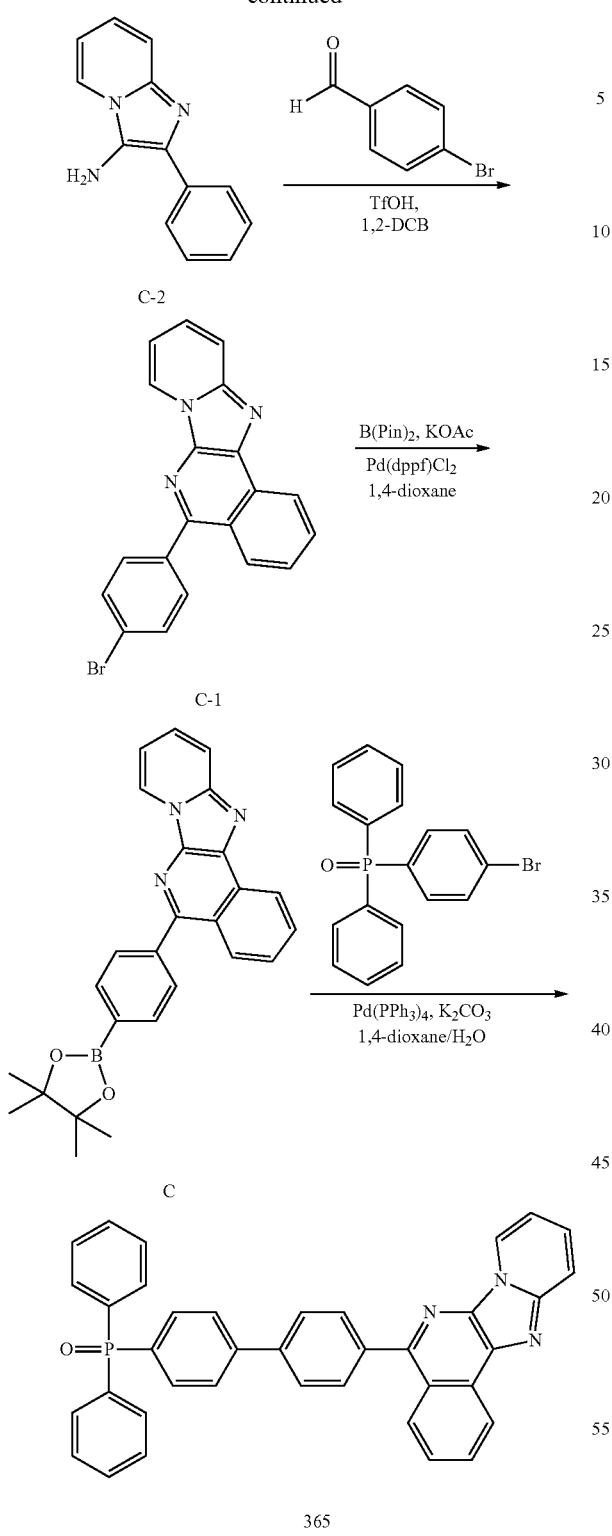
C-2
C-1
C
365
Preparation of Compound 365
A preparation was performed in the same manner as in the preparation of Compound 373, except that (4-bromophenyl)diphenylphosphine oxide was used instead of the compound 2-chloro-4,6-diphenyl-1,3,5-triazine in Preparation Example 9, thereby obtaining Target Compound 365.
<Preparation Example 25> Preparation of Compound 370
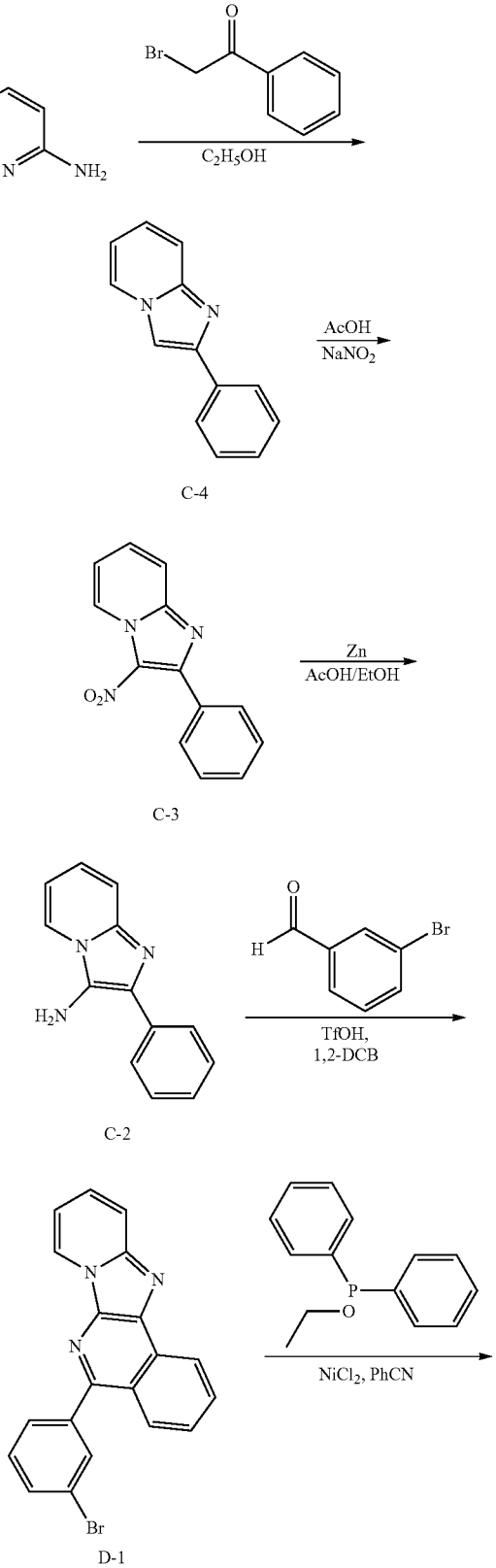
C-4
C-3
C-2
D-1

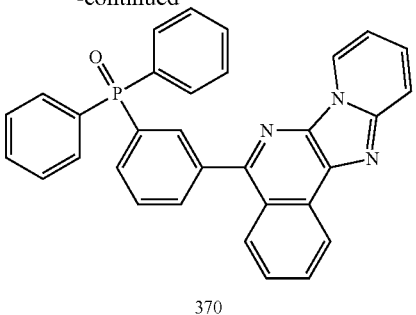

370

Preparation of Compound 370

A preparation was performed in the same manner as in the preparation of Compound 367, except that D-1 was used instead of C-1 in Preparation Example 8, thereby obtaining Target Compound 370.

<Preparation Example 26> Preparation of Compound 372

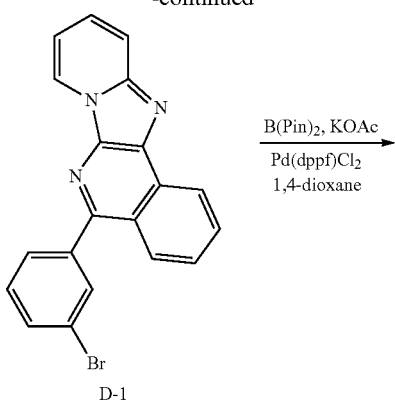

D-1

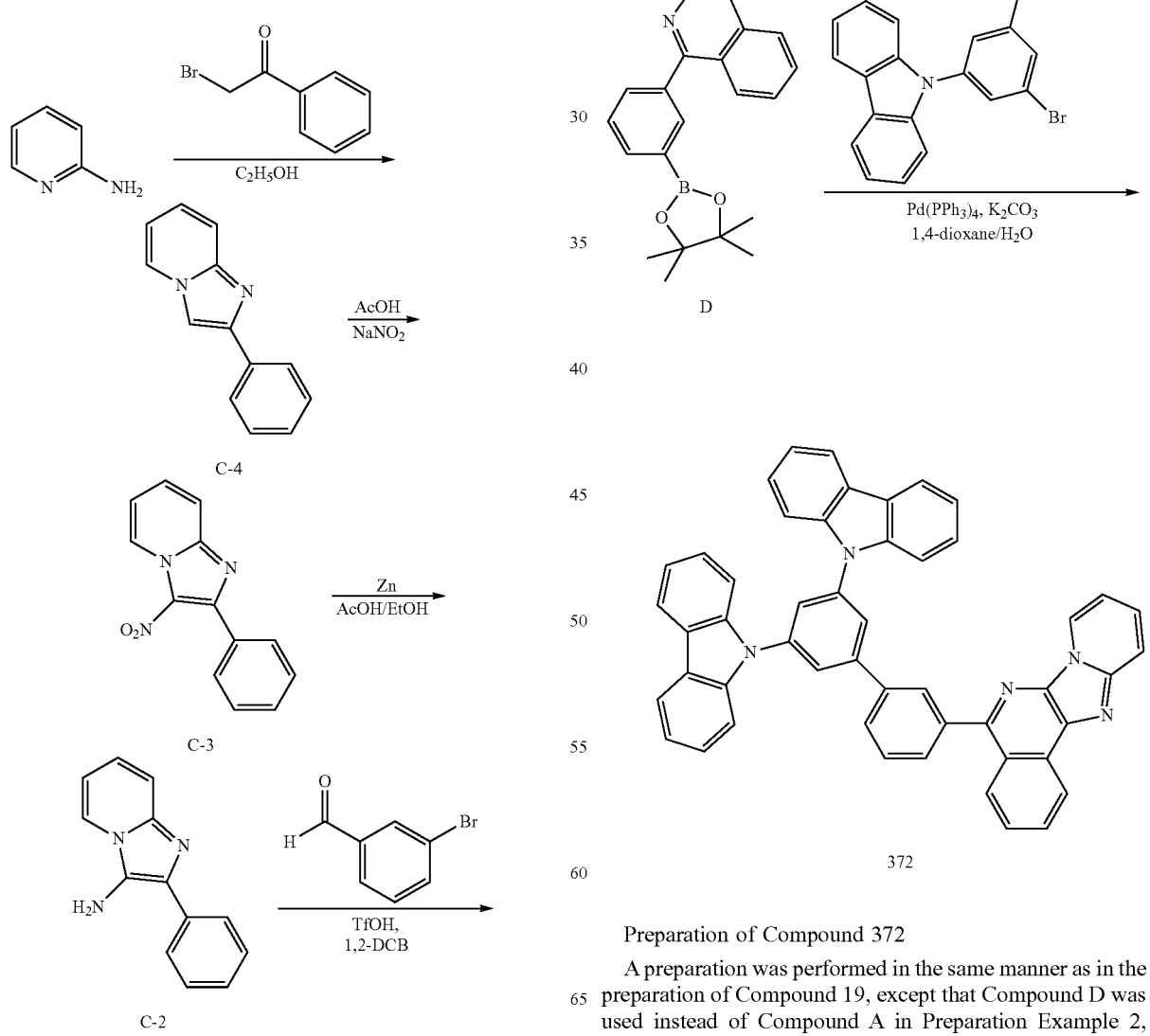

Preparation of Compound 372

A preparation was performed in the same manner as in the preparation of Compound 19, except that Compound D was used instead of Compound A in Preparation Example 2, thereby obtaining Target Compound 372.

<Preparation Example 27> Preparation of Compound 478

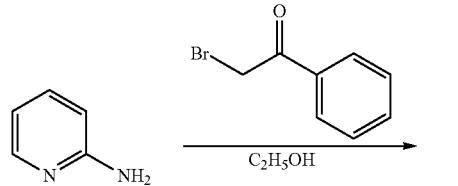

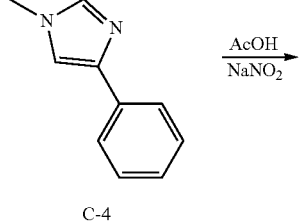

C-4

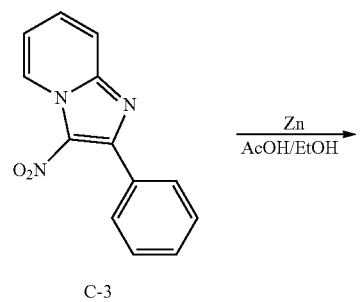

C-3

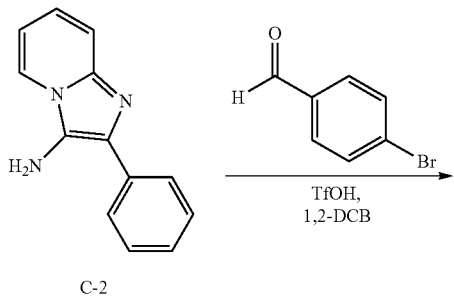

C-2

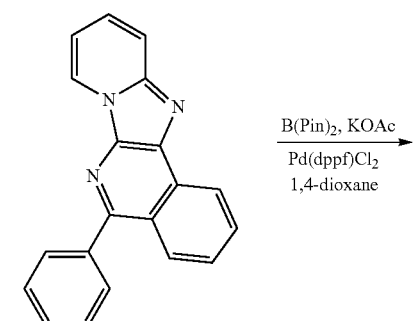

C-1

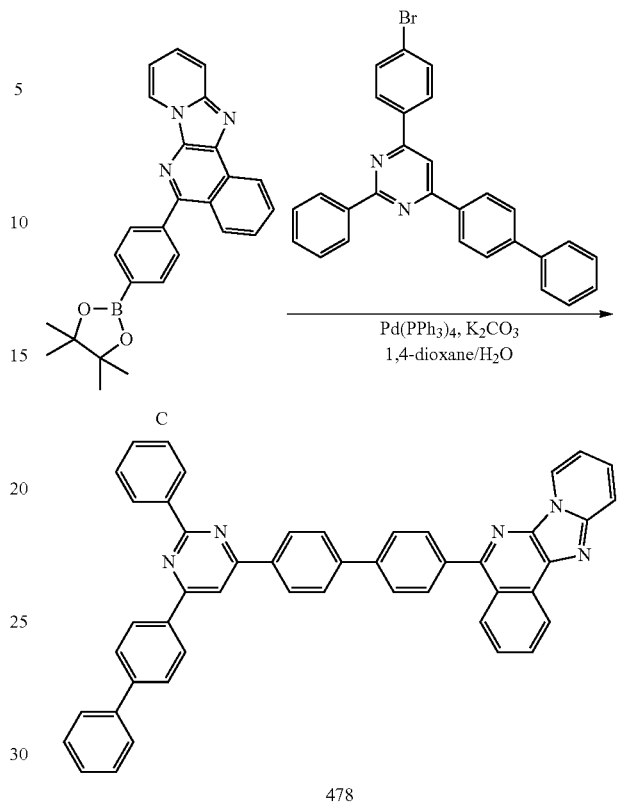

478

Preparation of Compound 478

A preparation was performed in the same manner as in the preparation of Compound 373, except that 4-([1,1'-biphenyl]-4-yl)-6-(4-bromophenyl)-2-phenylpyrimidine was used instead of the compound 2-chloro-4,6-diphenyl-1,3,5-triazine in Preparation Example 9, thereby obtaining Target Compound 478.

<Preparation Example 28> Preparation of Compound 574

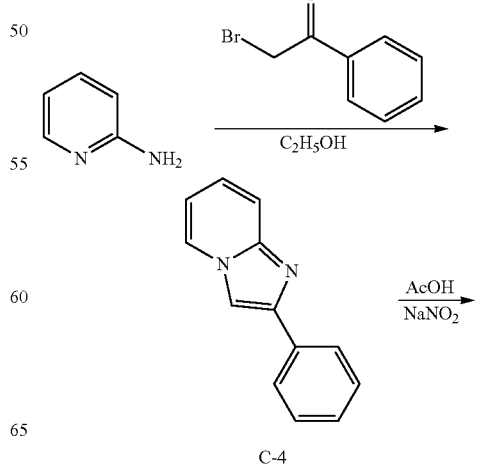

C-4

-continued
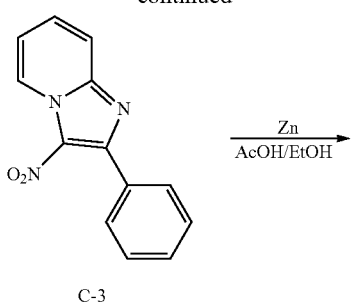
C-3
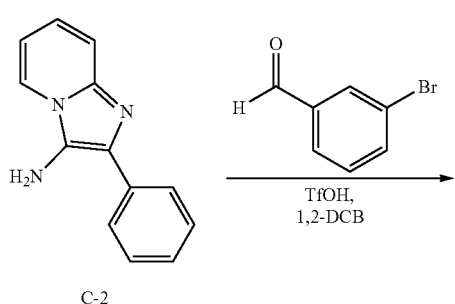
C-2
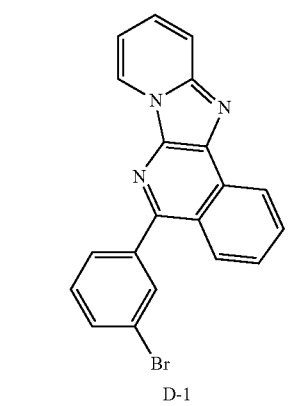
D-1
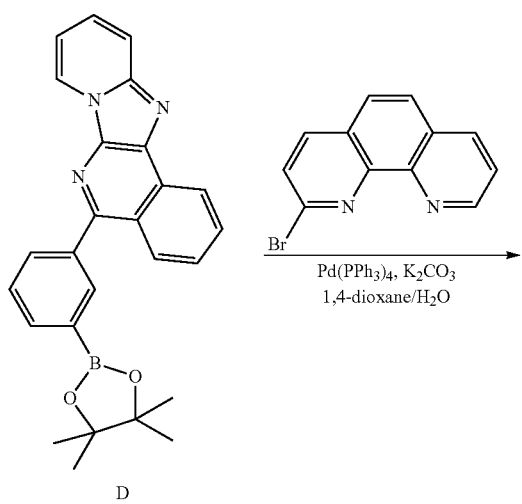
D
-continued
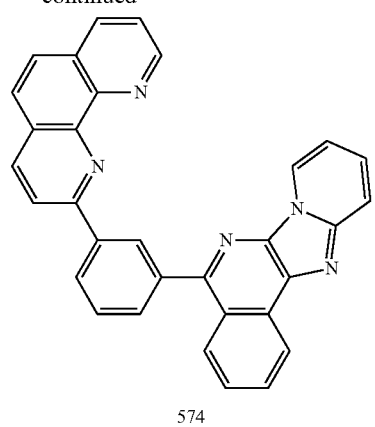
574
Preparation of Compound 574
A preparation was performed in the same manner as in the preparation of Compound 537, except that 2-bromo-1,10-phenanthroline was used instead of the compound 5-bromo-2,4,6-triphenylpyrimidine in Preparation Example 16, thereby obtaining Target Compound 574.
<Preparation Example 29> Preparation of Compound 577
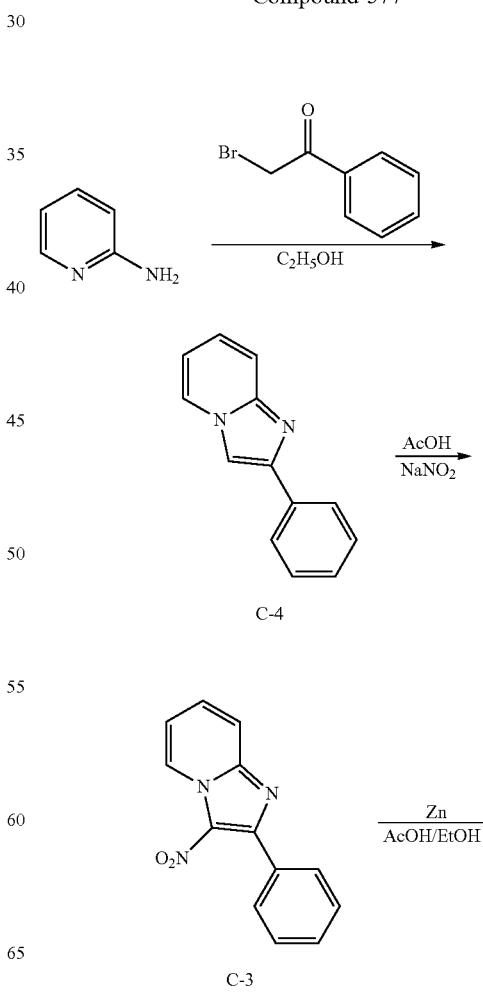
C-4
C-3

263
-continued
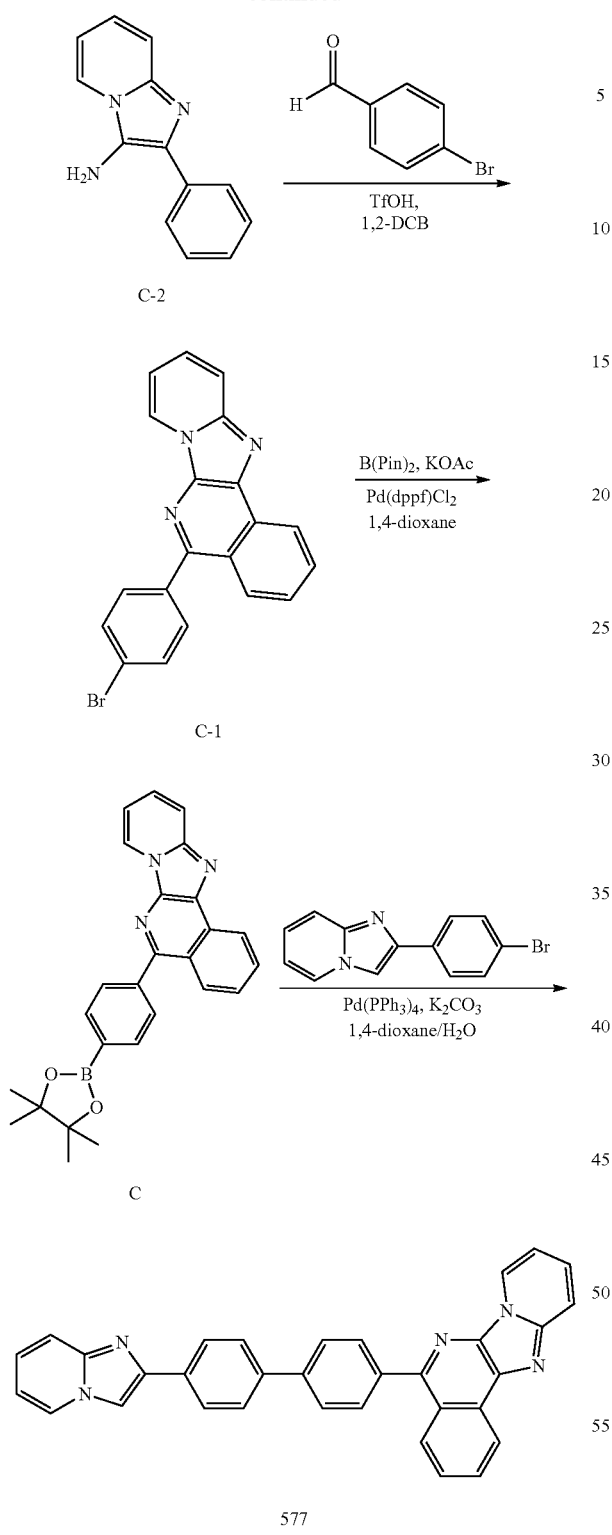
Preparation of Compound 577
A preparation was performed in the same manner as in the preparation of Compound 373, except that 2-(4-bromophenyl)imidazo[1,2-a]pyridine was used instead of the compound 2-chloro-4,6-diphenyl-1,3,5-triazine in Preparation Example 9, thereby obtaining Target Compound 577.
264
<Preparation Example 30> Preparation of Compound 711
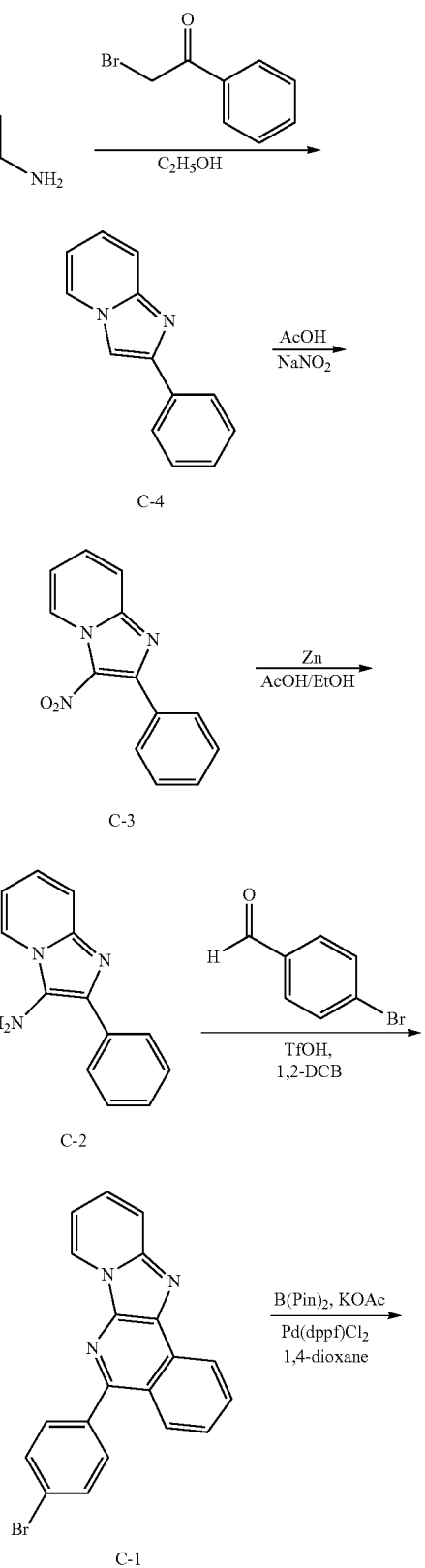

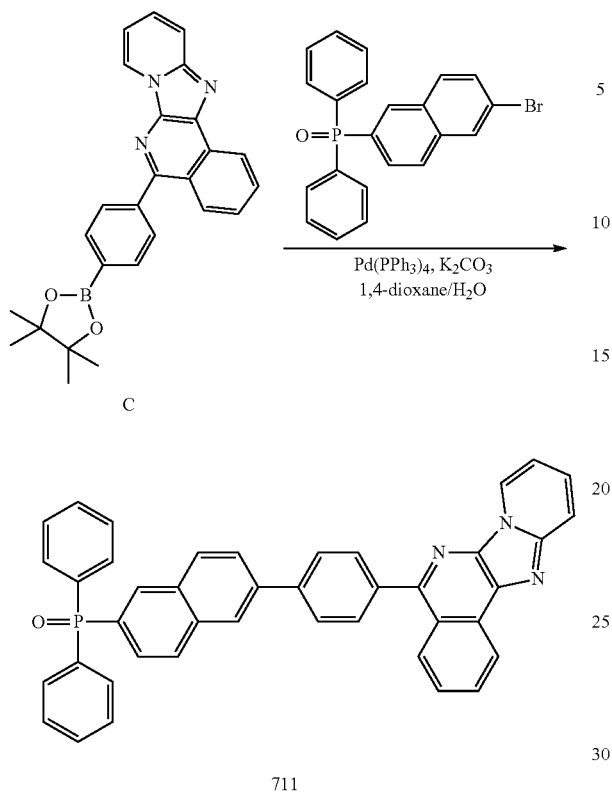
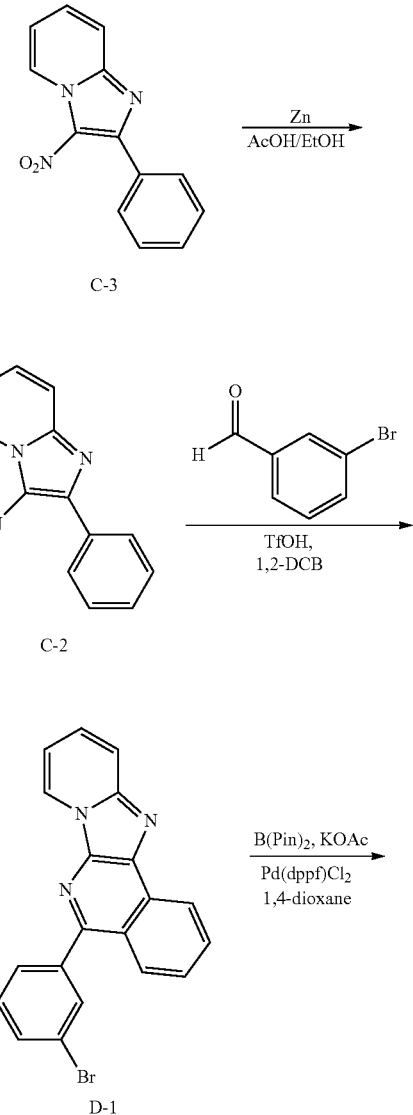
Preparation of Compound 711
A preparation was performed in the same manner as in the preparation of Compound 373, except that (6-bromonaphthalen-2-yl)diphenylphosphine oxide was used instead of the compound 2-chloro-4,6-diphenyl-1,3,5-triazine in Preparation Example 9, thereby obtaining Target Compound 711.
<Preparation Example 31> Preparation of Compound 715
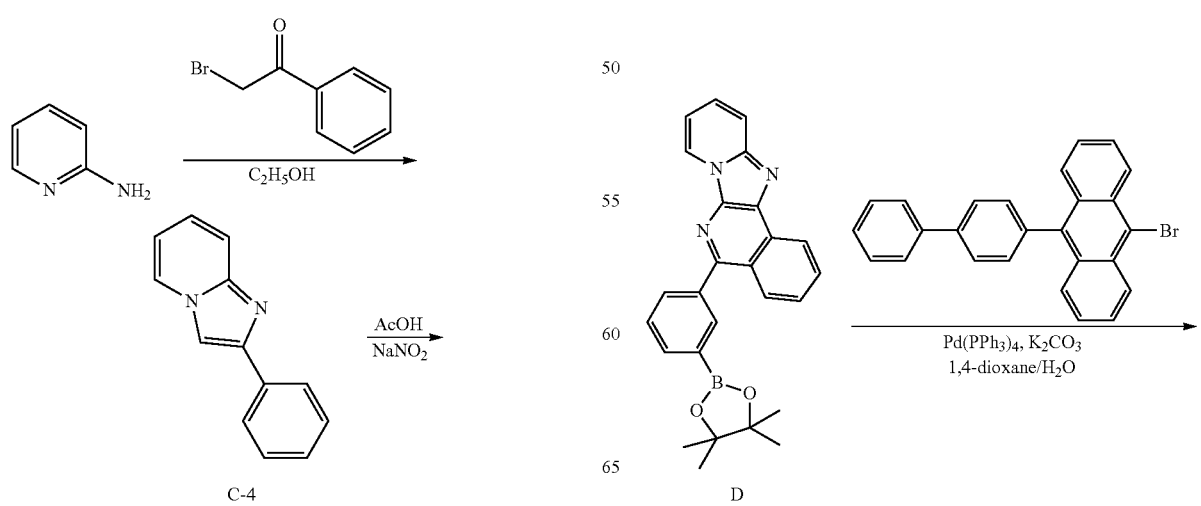

267
-continued

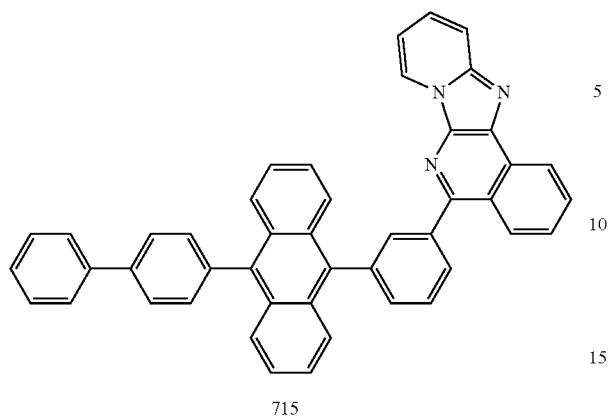
715

268
-continued

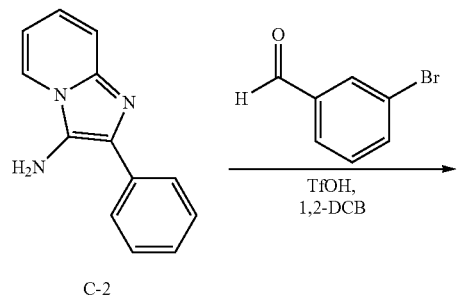
C-2

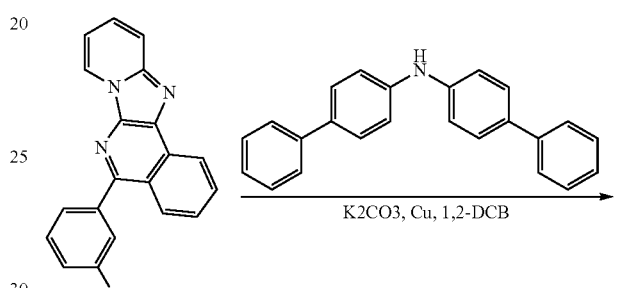
D-1

Preparation of Compound 715

A preparation was performed in the same manner as in the preparation of Compound 537, except that 9-([1,1'-biphenyl]-4-yl)-10-bromoanthracene was used instead of the compound 5-bromo-2,4,6-triphenylpyrimidine in Preparation Example 16, thereby obtaining Target Compound 715.

<Preparation Example 32> Preparation of Compound 719

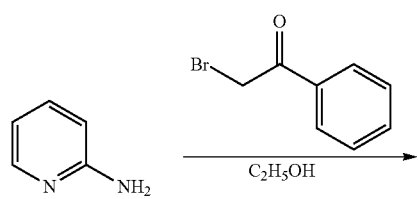

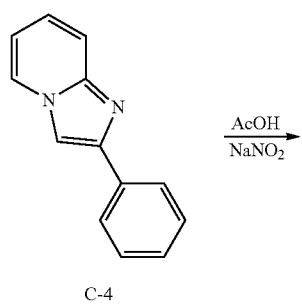
C-4

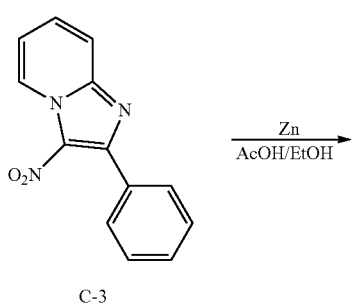
C-3

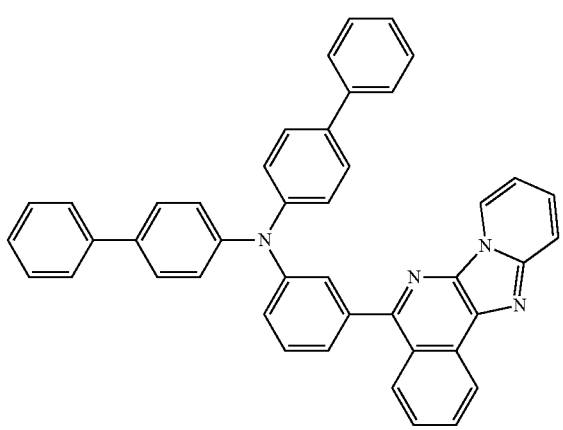
682

Preparation of Compound 719

A preparation was performed in the same manner as in the preparation of Compound 537, except that 2-([1,1'-biphenyl]-4-yl)-4-chloro-6-phenyl-1,3,5-triazine was used instead of the compound 5-bromo-2,4,6-triphenylpyrimidine in Preparation Example 16, thereby obtaining Target Compound 719.

<Preparation Example 33> Preparation of Compound 722

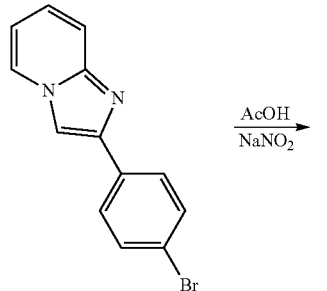

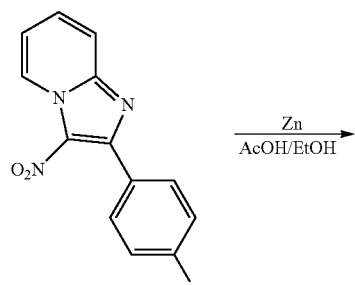

E-3

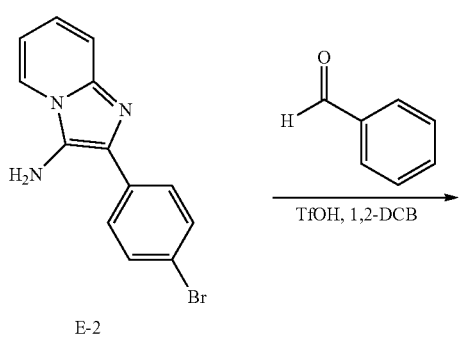

E-2

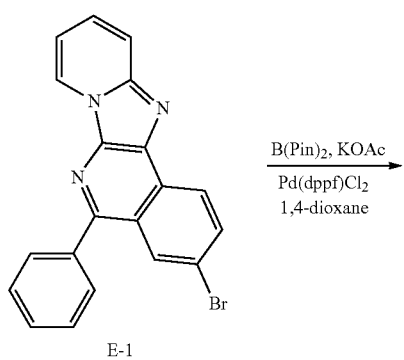

E-1

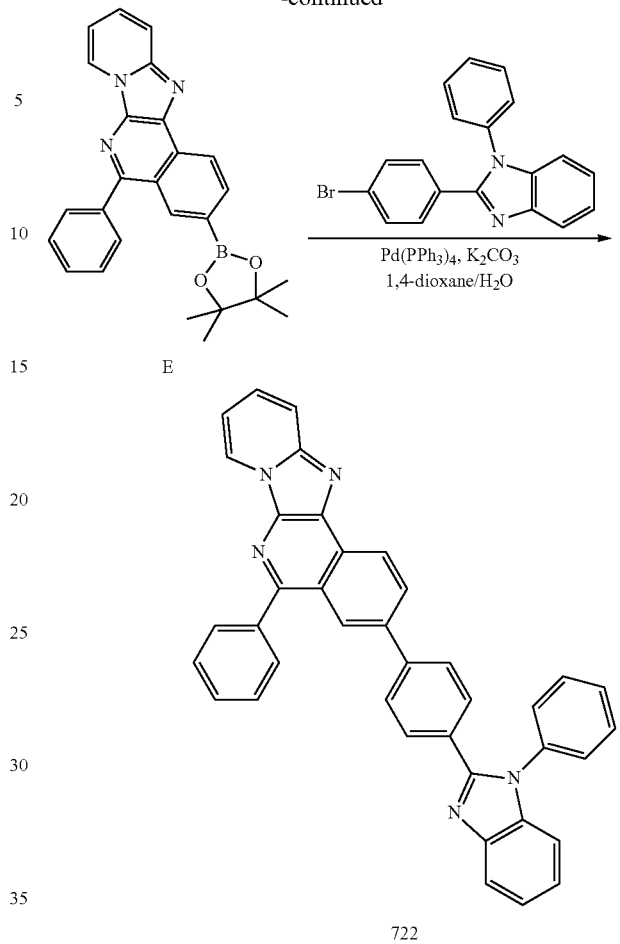

722

Preparation of Compounds E-3 and E-2

A compound 2-(4-bromophenyl)imidazo[1,2-a]pyridine (35 g, 128.14 mmol, 1 eq.) was dissolved in acetic acid (350 ml), and then a solution of $NaNO_2$ (13.26 g, 192.27 mmol, 1.5 eq.) saturated in water was slowly added thereto at normal temperature. A solid was precipitated while the color was gradually changed to bright green, it was confirmed that the reaction was terminated with TLC, and E-3 was filtered.

Zn (17.5 g) was put into a flask including acetic acid and ethanol at a ratio of 1:1 (700 ml), and the resulting mixture was stirred at normal temperature for about 10 minutes. Compound E-3 was gradually added to the above flask in a state cooled to 0° C., Compound C-3 was completely added thereto, and then the resulting mixture was stirred at normal temperature. When the reaction was terminated, the pH was adjusted to 13 by using a sodium hydroxide solution, the resulting product was extracted with ethyl acetate/water, the organic layer was dried over anhydrous magnesium sulfate, and then the solvent was removed by using a rotary evaporator. A solid precipitated at this time was filtered to obtain 28.4 g (78%) of Target Compound E-2.

Preparation of Compound E-1

Compound E-2 (28.4 g, 98.56 mmol, 1 eq.) and benzaldehyde (20.91 g, 197.12 mmol, 2 eq.) were dissolved in 1,2-dichlorobenzene (280 ml), trifluoromethanesulfonic acid (29.58 g, 197.12 mmol, 2 eq.) was slowly added thereto, and then the resulting mixture was refluxed. When the reaction was terminated, the resulting product was cooled to normal temperature, and then neutralized by using $NaHCO_3$, a very excessive amount of dichloromethane was used to extract the product, and then the organic layer was removed. The remaining 1,2-dichlorobenzene was removed by distillation, a solid produced at this time was filtered and washed with ethyl acetate/normal hexane to obtain 21 g (57%) of Target Compound E-1.

Preparation of Compound E

Compound E-1 (5 g, 13.36 mmol, 1 eq.), bis(pinacolato)diboron (5.09 g, 20.05 mmol, 1.5 eq.), [1,1'-bis(diphenylphosphino)ferrocene]dichloropalladium (II) (0.49 g, 0.67 mmol, 0.05 eq.), and potassium acetate (3.9 g, 40.08 mmol, 3 eq.) were put and dissolved in 1,4-dioxane, and then the resulting solution was refluxed. After the reaction was terminated, the resulting product was cooled to normal temperature and extracted with dichloromethane/water, the organic layer was dried over anhydrous magnesium sulfate, and then the solvent was removed by using a rotary evaporator. The resulting product was purified with a simple silica gel filter to obtain 5 g (yield of 89%) of Target Compound E.

Preparation of Compound 722

Compound E (5 g, 11.87 mmol, 1 eq.), a compound 2-(4-bromophenyl)-1-phenyl-1H-benzo[d]imidazole (4.56 g, 13.05 mmol, 1.1 eq.), tetrakis(triphenylphosphine)palladium (0) (0.69 g, 0.59 mmol, 0.05 eq.), potassium carbonate (3.28 g, 23.74 mmol, 2 eq.), and 1,4-dioxane/water (60 ml) were mixed, and the resulting mixture was refluxed. After the reaction was terminated, the resulting product was cooled to normal temperature, and a solid produced at this time was filtered and washed with water. The filtered solid was purified by using methanol/normal hexane to obtain 4 g (yield of 43%) of Target Compound 722.

<Preparation Example 34> Preparation of Compound 723

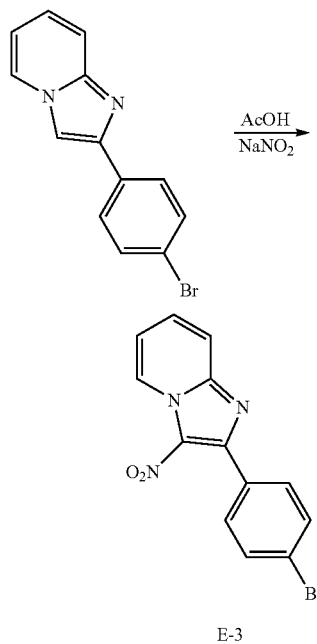

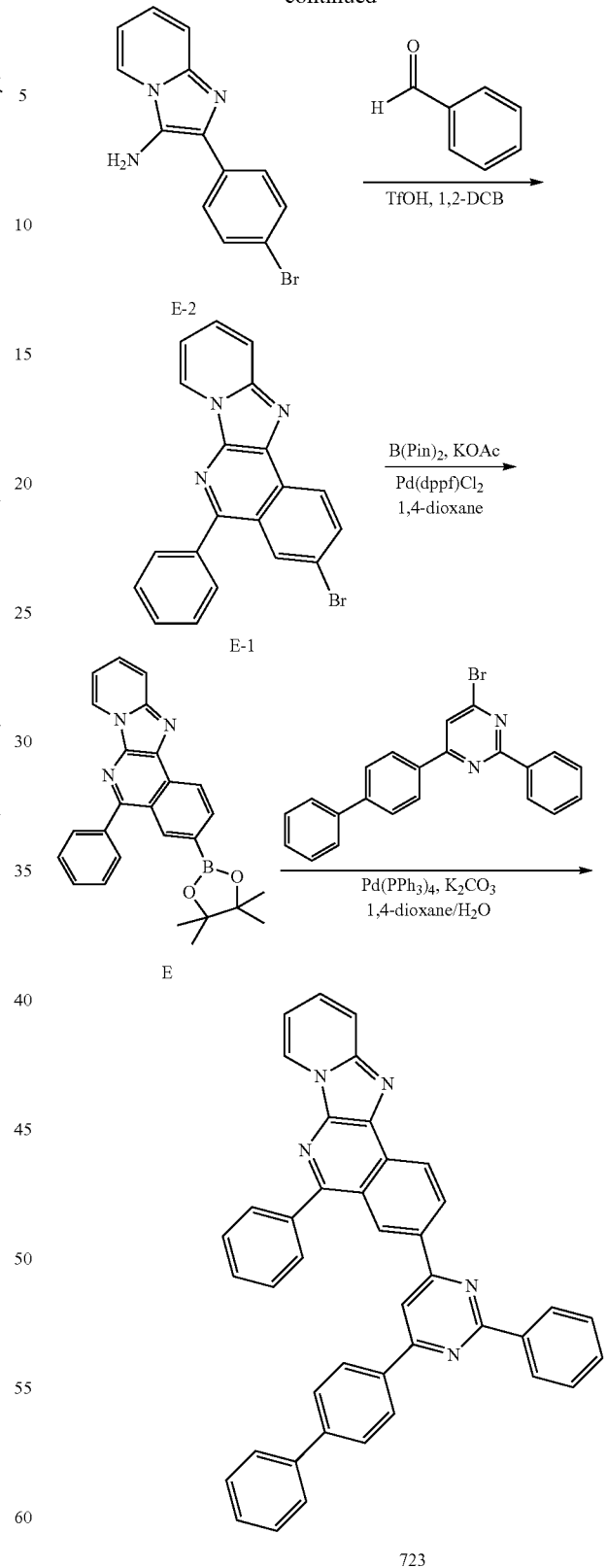

Preparation of Compound 723

A preparation was performed in the same manner as in the preparation of Compound 722, except that 4-([1,1'-biphenyl]-4-yl)-6-bromo-2-phenylpyrimidine was used instead of the compound 2-(4-bromophenyl)-1-phenyl-1H-benzo[d]imidazole in Preparation Example 33, thereby obtaining Target Compound 723.

<Preparation Example 35> Preparation of Compound 724

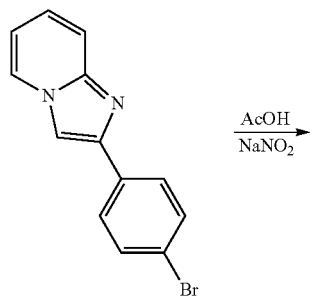

AcOH / NaNO₂ →

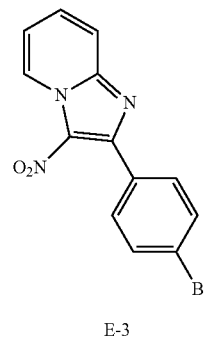

E-3

Zn / AcOH/EtOH →

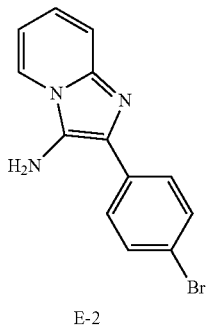

E-2

PhCHO, TfOH, 1,2-DCB →

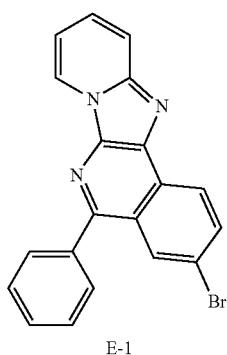

E-1

B(Pin)₂, KOAc, Pd(dppf)Cl₂, 1,4-dioxane →

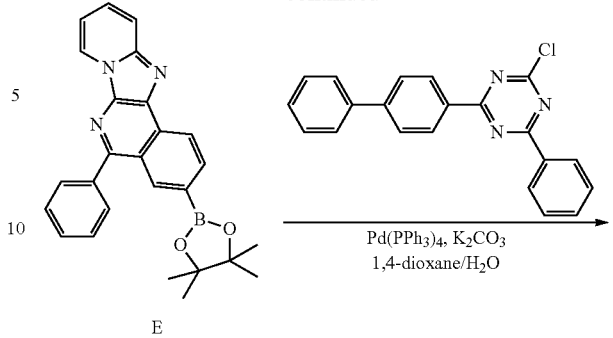

E

Pd(PPh₃)₄, K₂CO₃, 1,4-dioxane/H₂O →

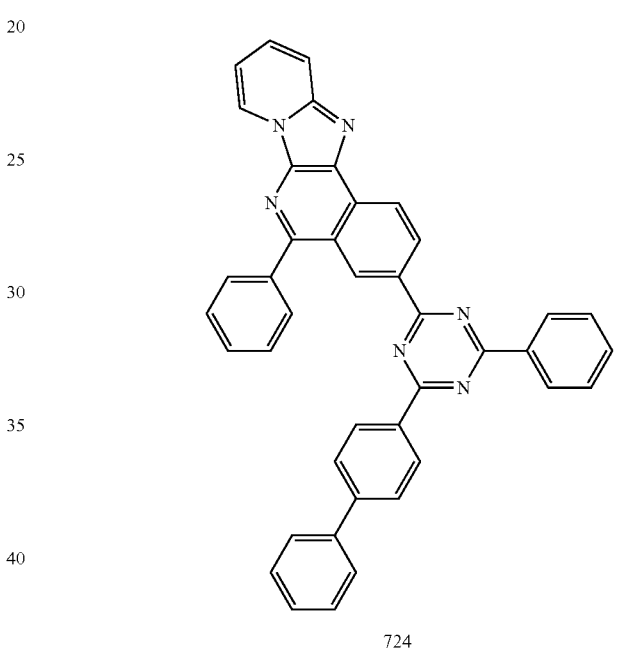

724

Preparation of Compound 724

A preparation was performed in the same manner as in the preparation of Compound 722, except that 2-([1,1'-biphenyl]-4-yl)-4-chloro-6-phenyl-1,3,5-triazine was used instead of the compound 2-(4-bromophenyl)-1-phenyl-1H-benzo[d]imidazole in Preparation Example 33, thereby obtaining Target Compound 724.

<Preparation Example 36> Preparation of Compound 727

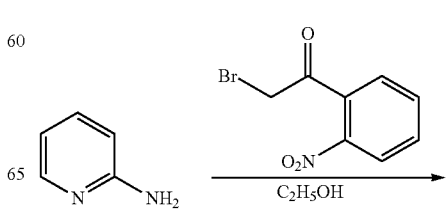

C₂H₅OH →

275
-continued

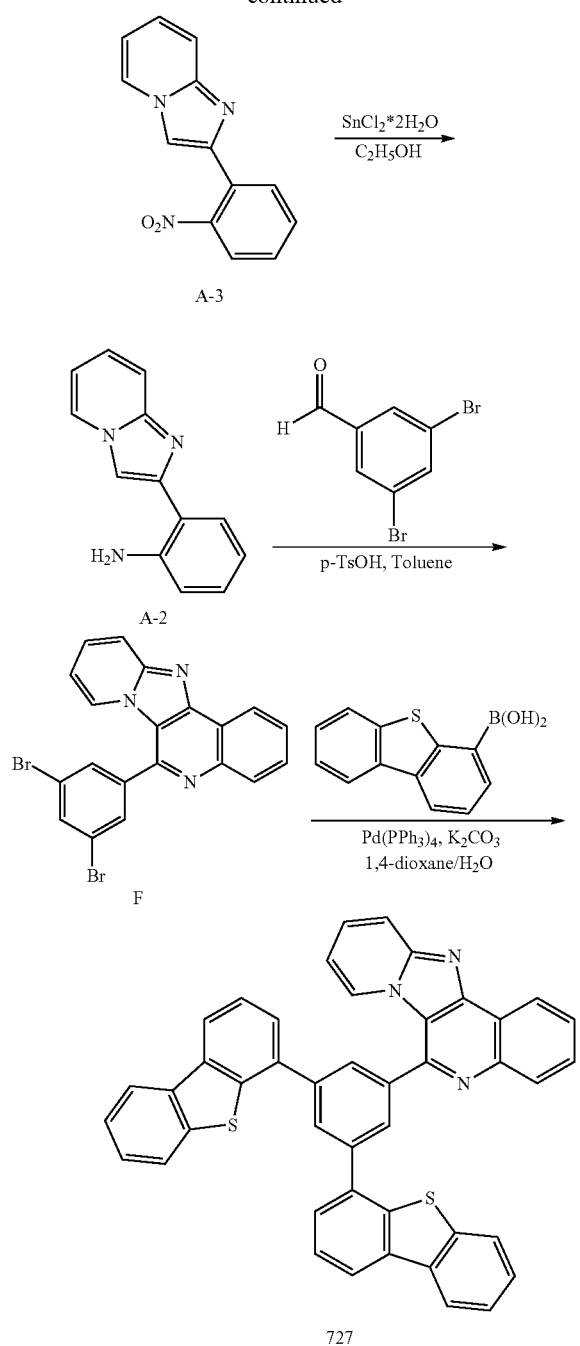

Preparation of Compound F

A preparation was performed in the same manner as in the preparation of Compound A-1, except that 3,5-dibromobenzaldehyde was used instead of the compound 4-bromobenzaldehyde in Preparation Example 1, thereby obtaining Target Compound F.

Preparation of Compound 727

A preparation was performed in the same manner as in the preparation of Compound 6, except that dibenzo[b,d]thiophen-4-ylboronic acid was used instead of the compound phenanthren-9-ylboronic acid in Preparation Example 1, thereby obtaining Target Compound 727.

276
<Preparation Example 37> Preparation of Compound 729

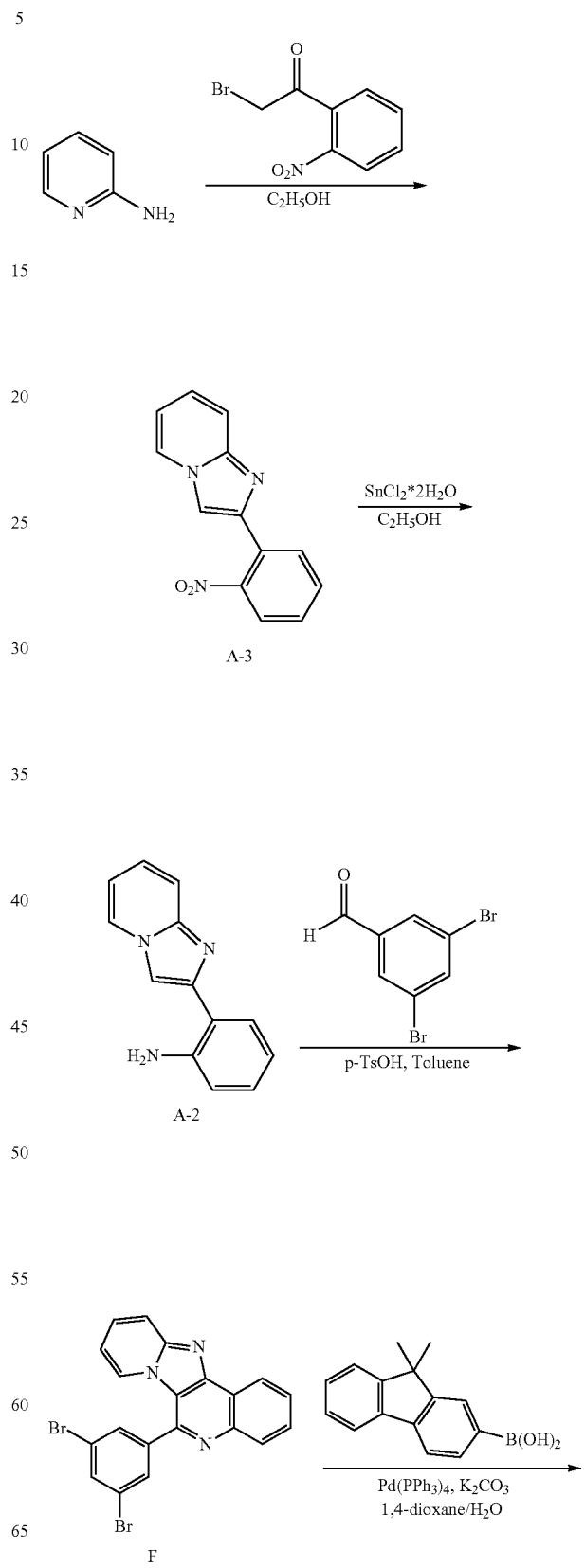

-continued

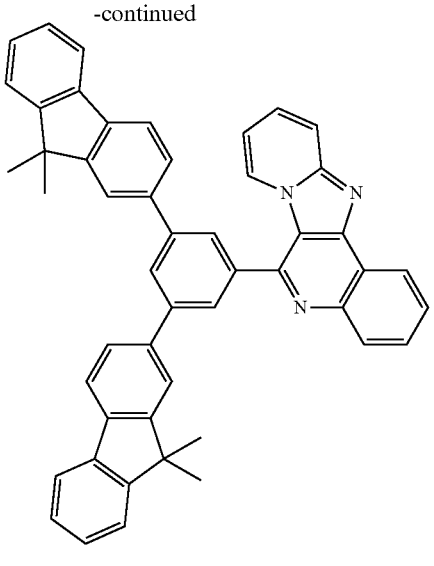

729

Preparation of Compound 729

A preparation was performed in the same manner as in the preparation of Compound 6, except that (9,9-dimethyl-9H-fluoren-2-yl)boronic acid was used instead of the compound phenanthren-9-ylboronic acid in Preparation Example 1, thereby obtaining Target Compound 729.

<Preparation Example 38> Preparation of Compound 730

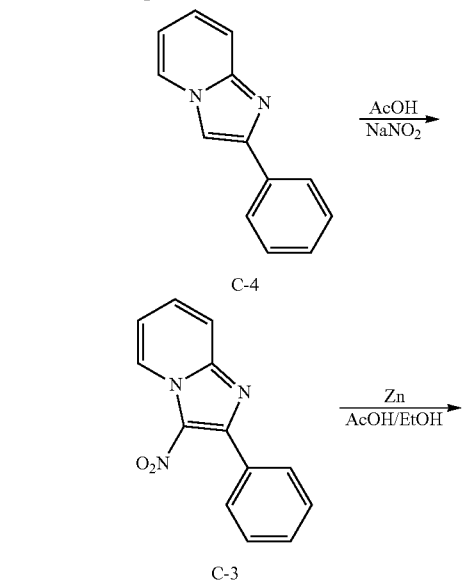

-continued

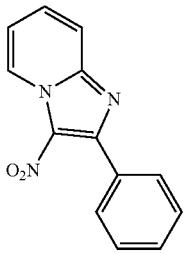

C-2

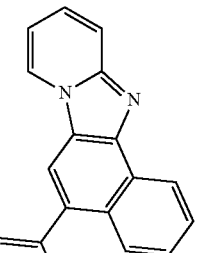

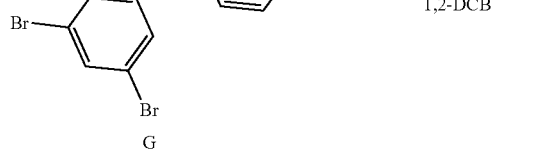

G

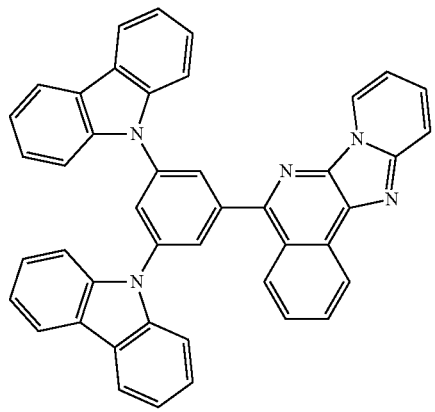

730

Preparation of Compound G

A preparation was performed in the same manner as in the preparation of Compound C-1, except that 3,5-dibromobenzaldehyde was used instead of the compound 4-bromobenzaldehyde in Preparation Example 6, thereby obtaining Target Compound G.

Preparation of Compound 730

Compound G (7 g, 15.44 mmol, 1 eq.), 9H-carbazole (5.67 g, 33.96 mmol, 2.2 eq.), Cu (3.92 g, 61.76 mmol, 4 eq.), K$_2$CO$_3$ (12.8 g, 92.64 mmol, 6 eq.), and 100 ml of 1,2-dichlorobenzene were sequentially mixed, and then the resulting mixture was refluxed and stirred. When the reaction was terminated, the resulting product was cooled to normal temperature and filtered as it is, and a filtrate obtained at this time was concentrated to obtain a solid. The resulting product was purified by using appropriate amounts of MC and normal hexane to obtain 8.7 g (90%) of Target Compound 730.

<Preparation Example 39> Preparation of Compound 732

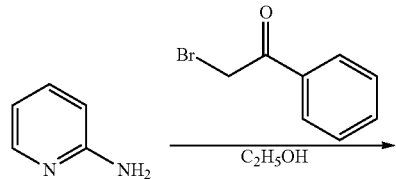

C-4

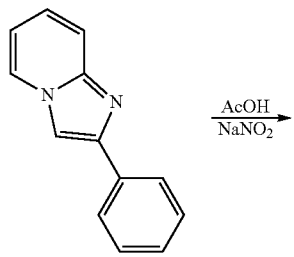

C-3

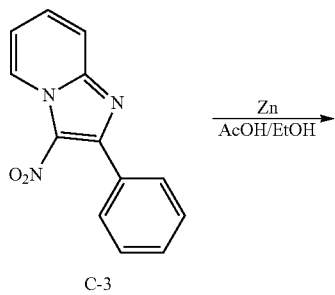

C-2

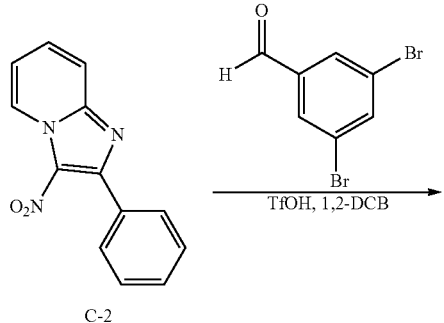

G

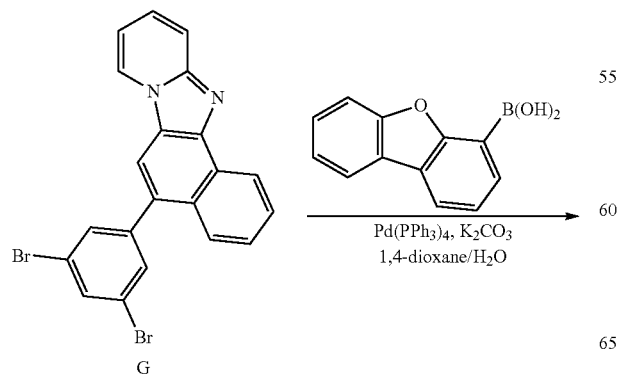

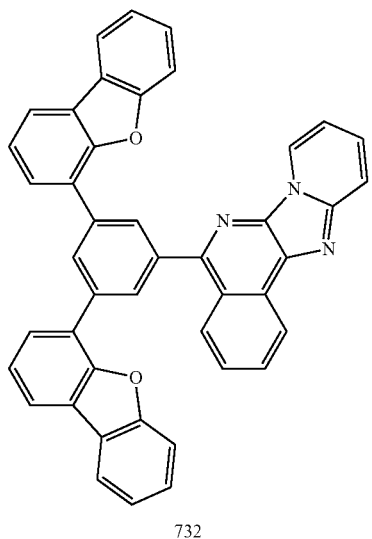 [SMILES: c1ccc2c(c1)oc1c(-c3cc(-c4nc5c(nc6ccccn65)c5ccccc45)cc(-c4cccc5c4oc4ccccc45)c3)cccc12]

732

Preparation of Compound 732

A preparation was performed in the same manner as in the preparation of Compound 6, except that dibenzo[b,d]furan-4-ylboronic acid was used instead of the compound phenanthren-9-ylboronic acid in Preparation Example 1, thereby obtaining Target Compound 732.

<Preparation Example 40> Preparation of Compound 14

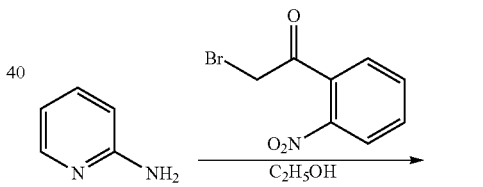

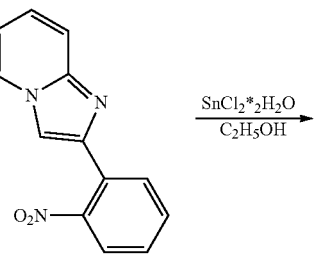

A-3

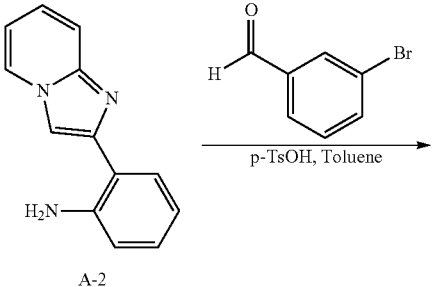

A-2

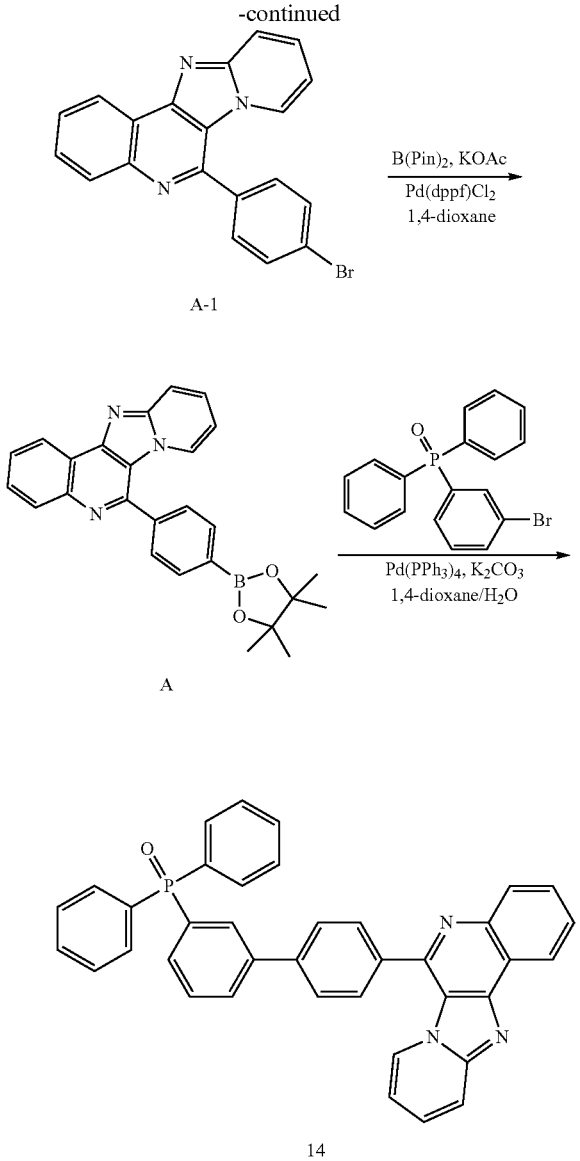

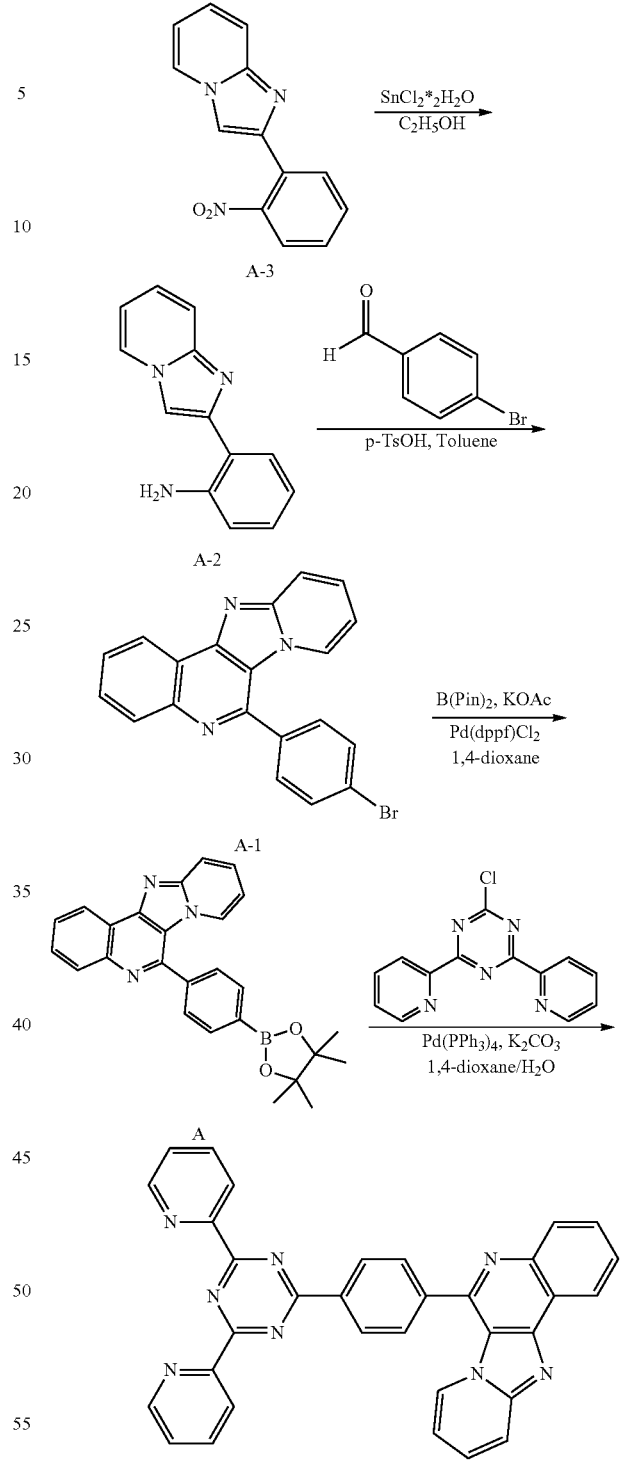

Preparation of Compound 14

A preparation was performed in the same manner as in the preparation of Compound 19, except that (3-bromophenyl)diphenylphosphine oxide was used instead of the compound 9,9'-(5-bromo-1,3-phenylene)bis(9H-carbazole) in Preparation Example 2, thereby obtaining Target Compound 14.

<Preparation Example 41> Preparation of Compound 22

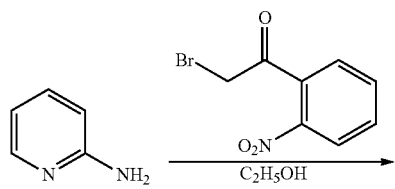

Preparation of Compound 22

A preparation was performed in the same manner as in the preparation of Compound 19, except that 2-chloro-4,6-di(pyridin-2-yl)-1,3,5-triazine was used instead of the compound 9,9'-(5-bromo-1,3-phenylene)bis(9H-carbazole) in Preparation Example 2, thereby obtaining Target Compound 22.

<Preparation Example 42> Preparation of Compound 26

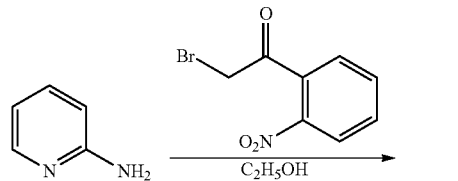

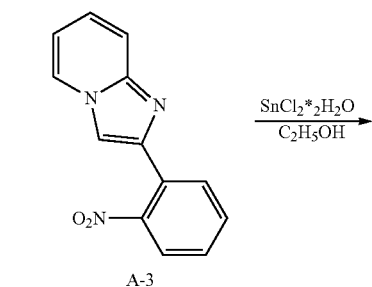

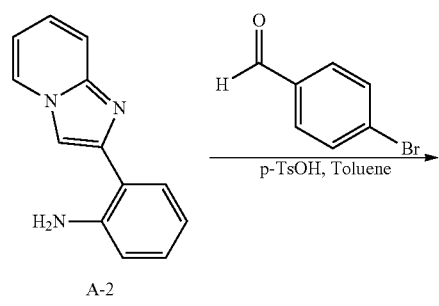

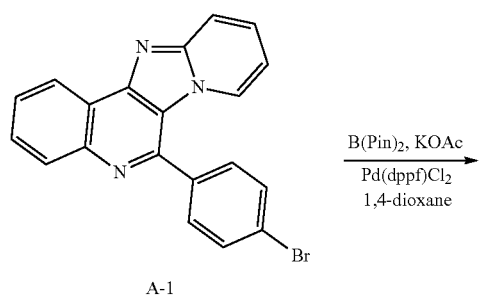

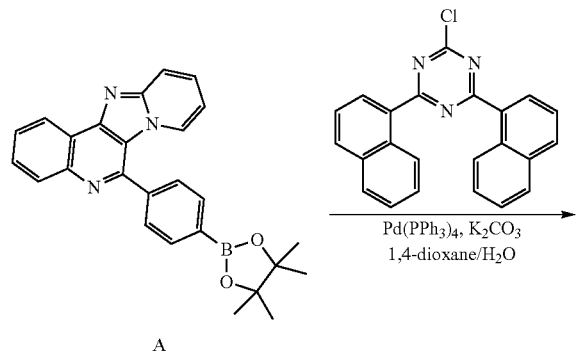

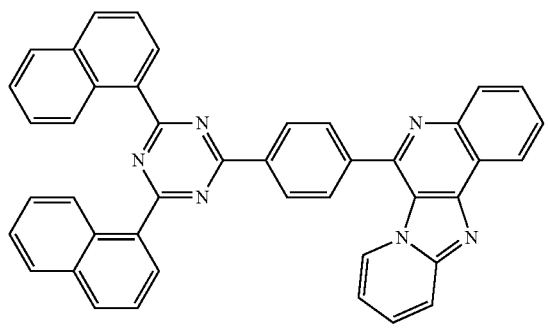

26

Preparation of Compound 26

A preparation was performed in the same manner as in the preparation of Compound 19, except that 2-bromo-4,6-di(naphthalen-1-yl)-1,3,5-triazine was used instead of the compound 9,9'-(5-bromo-1,3-phenylene)bis(9H-carbazole) in Preparation Example 2, thereby obtaining Target Compound 26.

<Preparation Example 43> Preparation of Compound 75

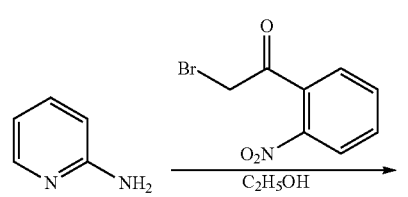

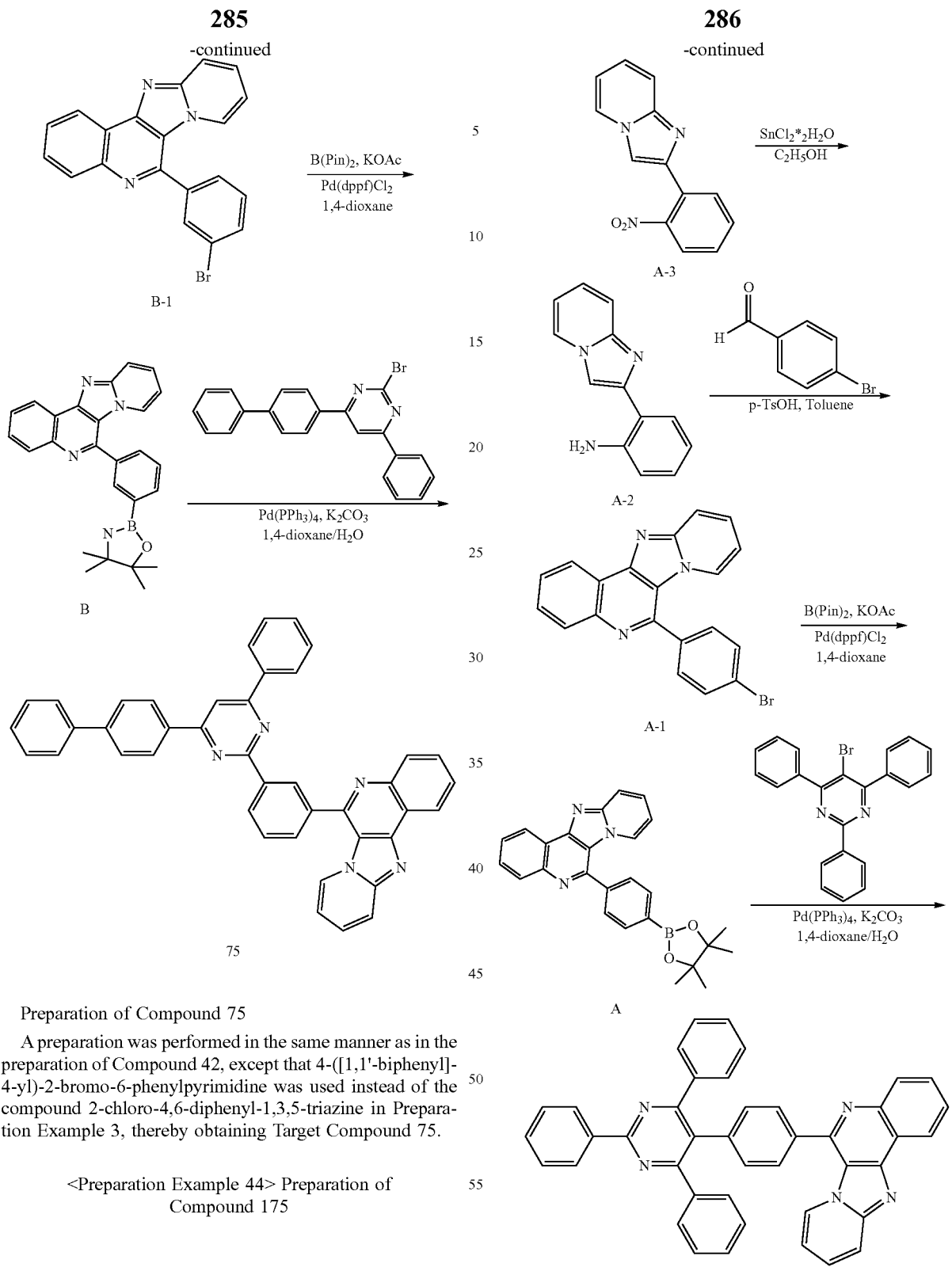

Preparation of Compound 75

A preparation was performed in the same manner as in the preparation of Compound 42, except that 4-([1,1'-biphenyl]-4-yl)-2-bromo-6-phenylpyrimidine was used instead of the compound 2-chloro-4,6-diphenyl-1,3,5-triazine in Preparation Example 3, thereby obtaining Target Compound 75.

<Preparation Example 44> Preparation of Compound 175

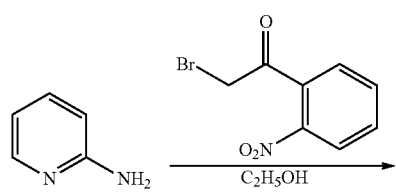

Preparation of Compound 175

A preparation was performed in the same manner as in the preparation of Compound 19, except that 5-bromo-2,4,6-triphenylpyrimidine was used instead of the compound 9,9'-(5-bromo-1,3-phenylene)bis(9H-carbazole) in Preparation Example 2, thereby obtaining Target Compound 175.

<Preparation Example 45> Preparation of Compound 202
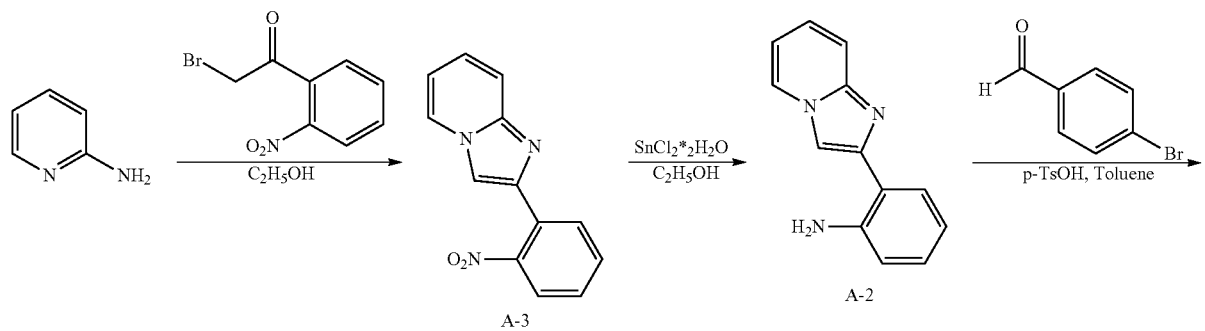
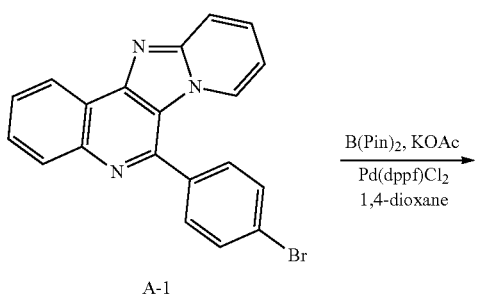
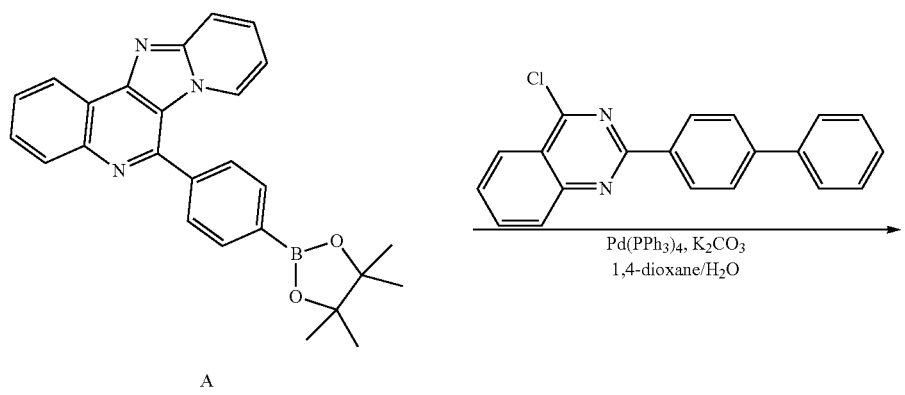
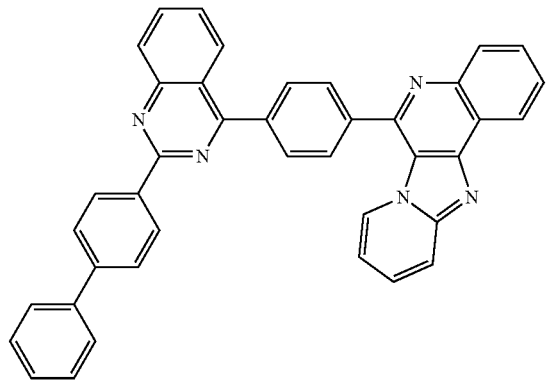

289

Preparation of Compound 202

A preparation was performed in the same manner as in the preparation of Compound 19, except that 2-([1,1'-biphenyl]-4-yl)-4-chloroquinazoline was used instead of the compound 9,9'-(5-bromo-1,3-phenylene)bis(9H-carbazole) in Preparation Example 2, thereby obtaining Target Compound 202.

<Preparation Example 46> Preparation of Compound 222

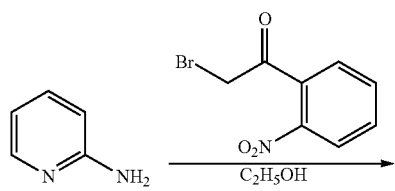

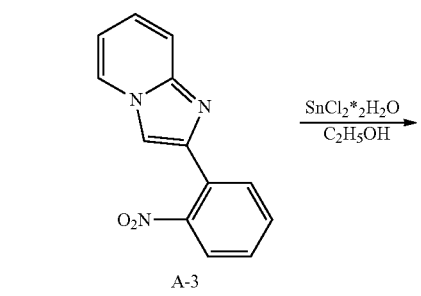

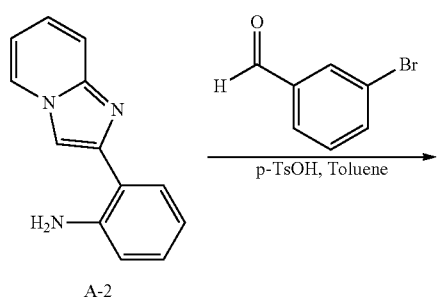

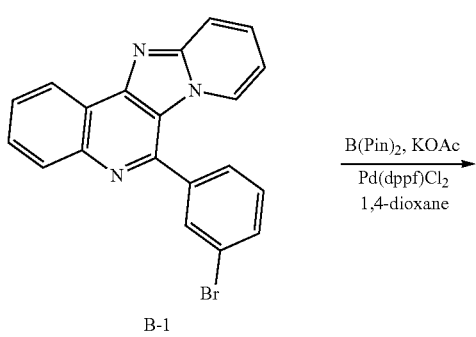

290

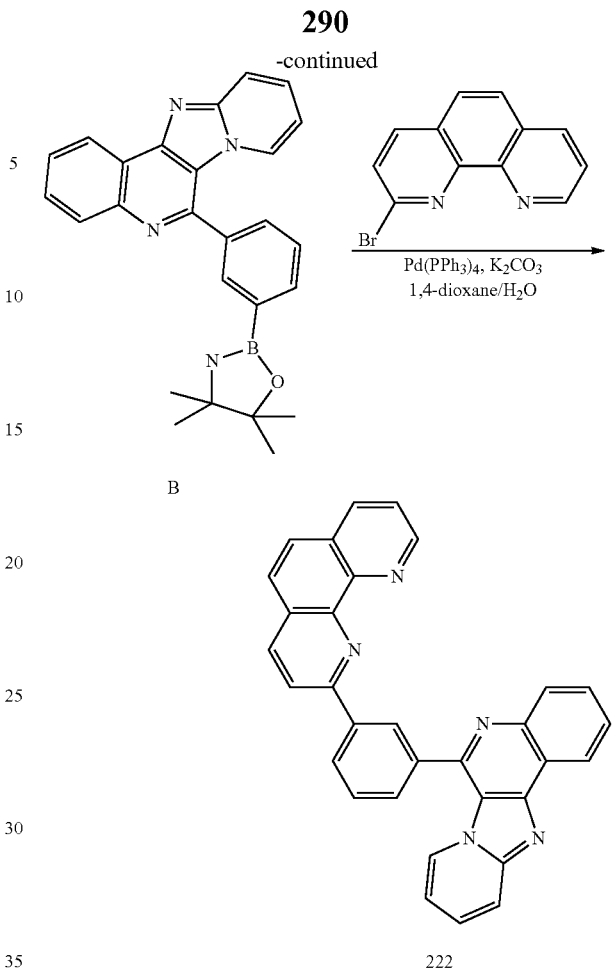

Preparation of Compound 222

A preparation was performed in the same manner as in the preparation of Compound 42, except that 2-([1,1'-biphenyl]-4-yl)-4-chloroquinazoline was used instead of the compound 2-chloro-4, 6-diphenyl-1, 3, 5-triazine in Preparation Example 3, thereby obtaining Target Compound 222.

<Preparation Example 47> Preparation of Compound 225

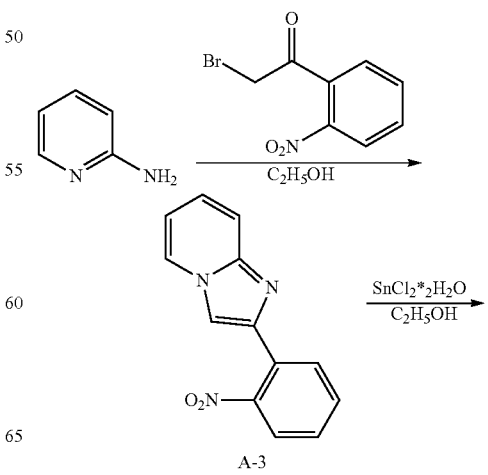

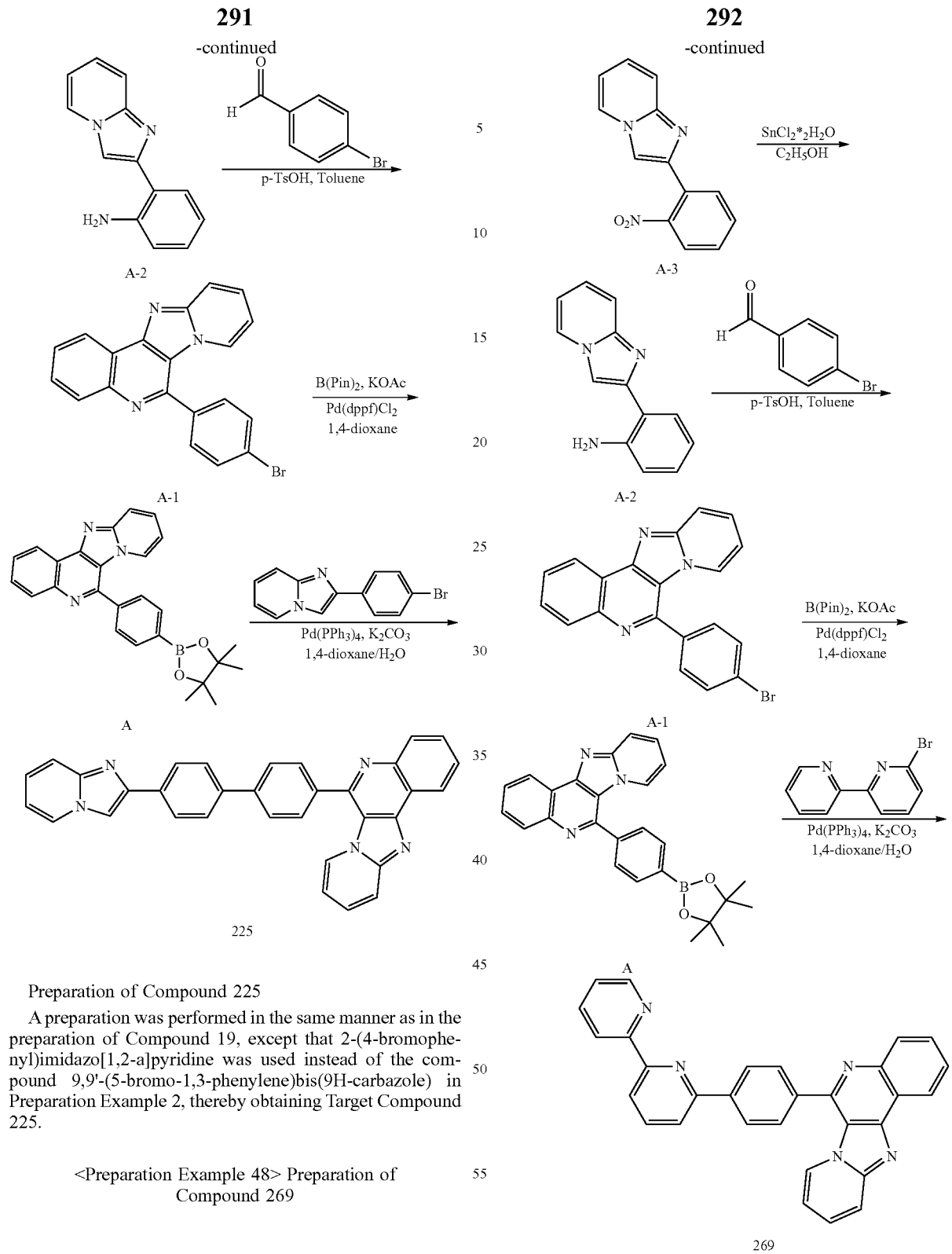

Preparation of Compound 225

A preparation was performed in the same manner as in the preparation of Compound 19, except that 2-(4-bromophenyl)imidazo[1,2-a]pyridine was used instead of the compound 9,9'-(5-bromo-1,3-phenylene)bis(9H-carbazole) in Preparation Example 2, thereby obtaining Target Compound 225.

<Preparation Example 48> Preparation of Compound 269

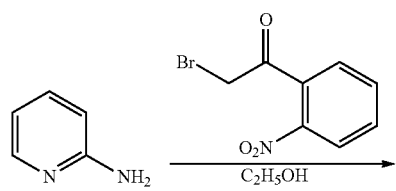

Preparation of Compound 269

A preparation was performed in the same manner as in the preparation of Compound 19, except that 6-bromo-2,2'-bipyridine was used instead of the compound 9,9'-(5-bromo-1,3-phenylene)bis(9H-carbazole) in Preparation Example 2, thereby obtaining Target Compound 269.

<Preparation Example 49> Preparation of Compound 291
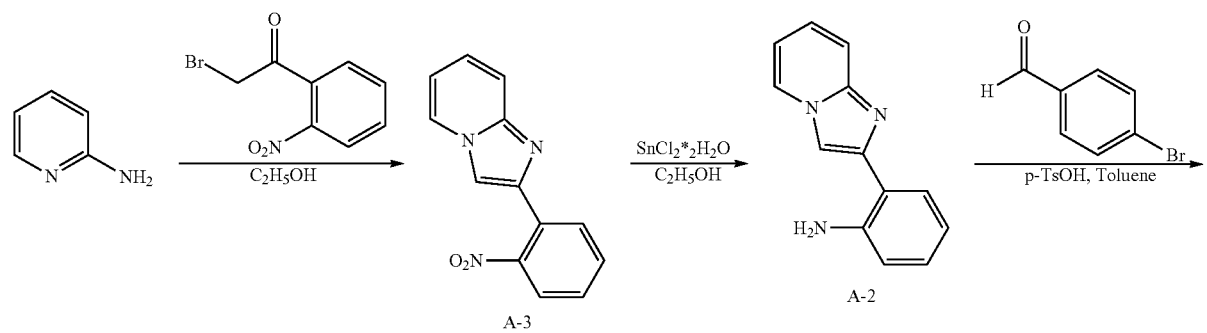
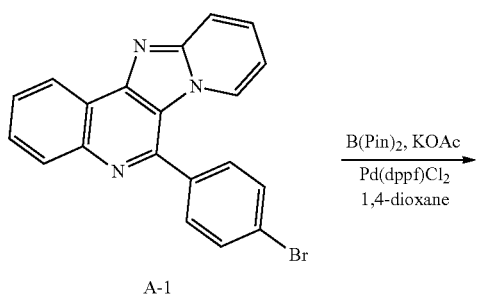
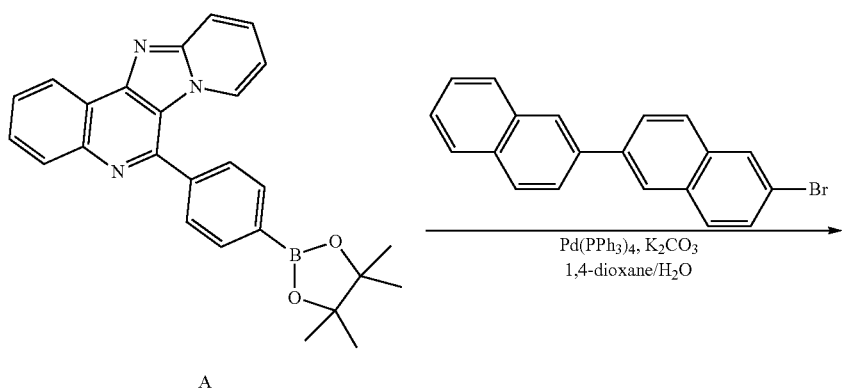
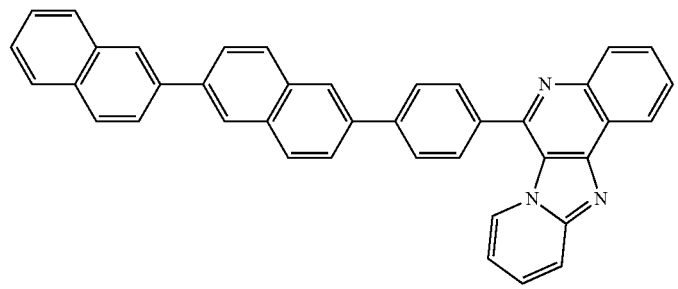
291

Preparation of Compound 291
A preparation was performed in the same manner as in the preparation of Compound 19, except that 6-bromo-2,2'-binaphthalene was used instead of the compound 9,9'-(5-bromo-1,3-phenylene)bis(9H-carbazole) in Preparation Example 2, thereby obtaining Target Compound 291.
<Preparation Example 50> Preparation of Compound 317
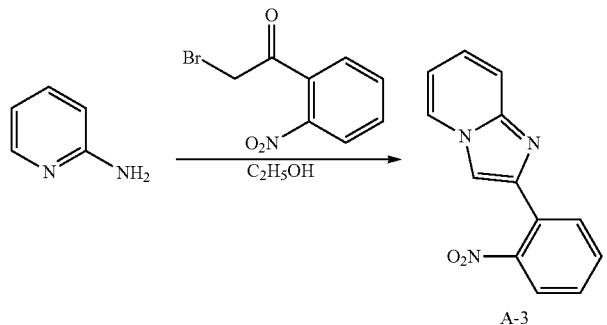
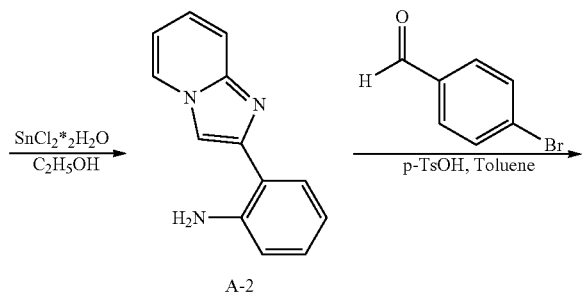
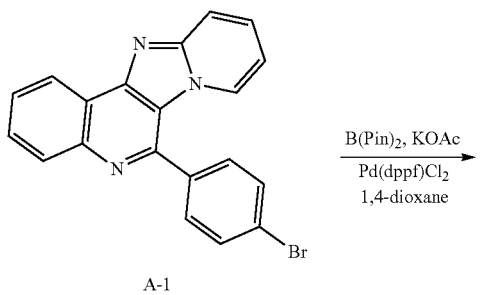
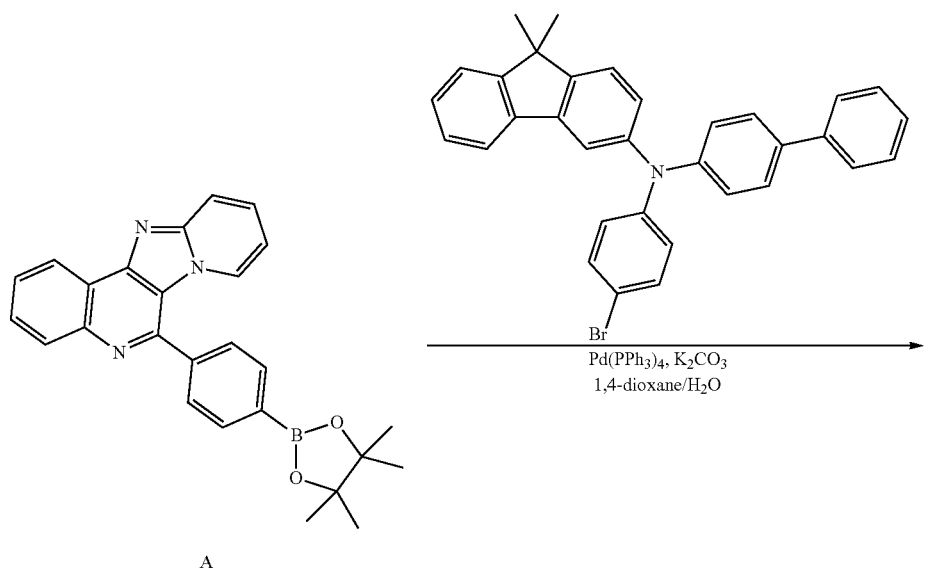

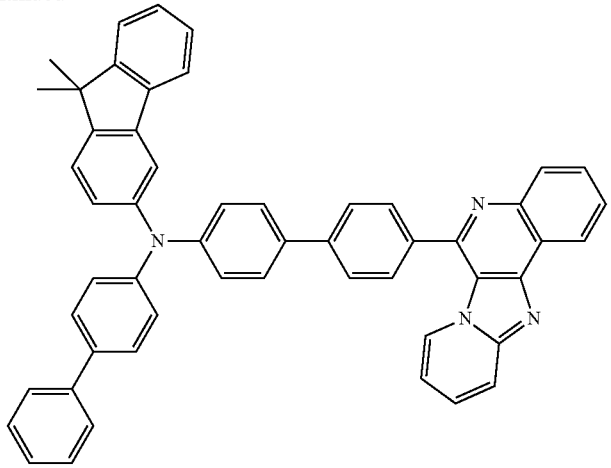

317

Preparation of Compound 317

A preparation was performed in the same manner as in the preparation of Compound 19, except that N-([1,1'-biphenyl]-4-yl)-N-(4-bromophenyl)-9,9-dimethyl-9H-fluoren-3-amine was used instead of the compound 9,9'-(5-bromo-1,3-phenylene)bis(9H-carbazole) in Preparation Example 2, thereby obtaining Target Compound 317.

<Preparation Example 51> Preparation of Compound 333

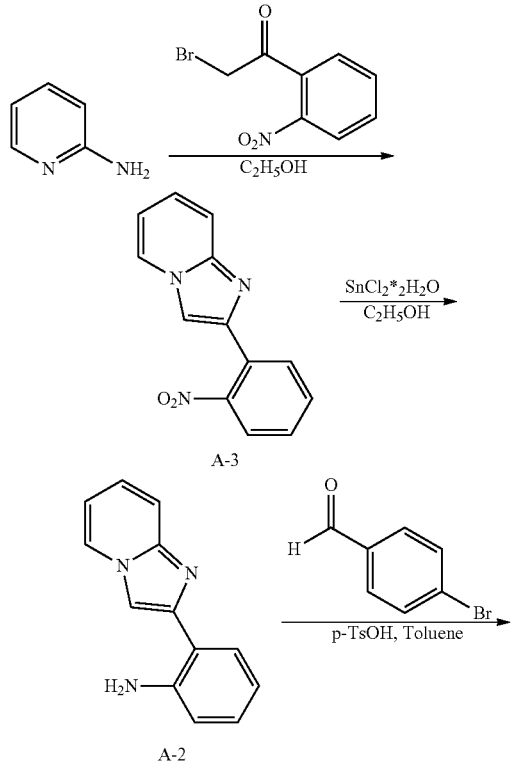

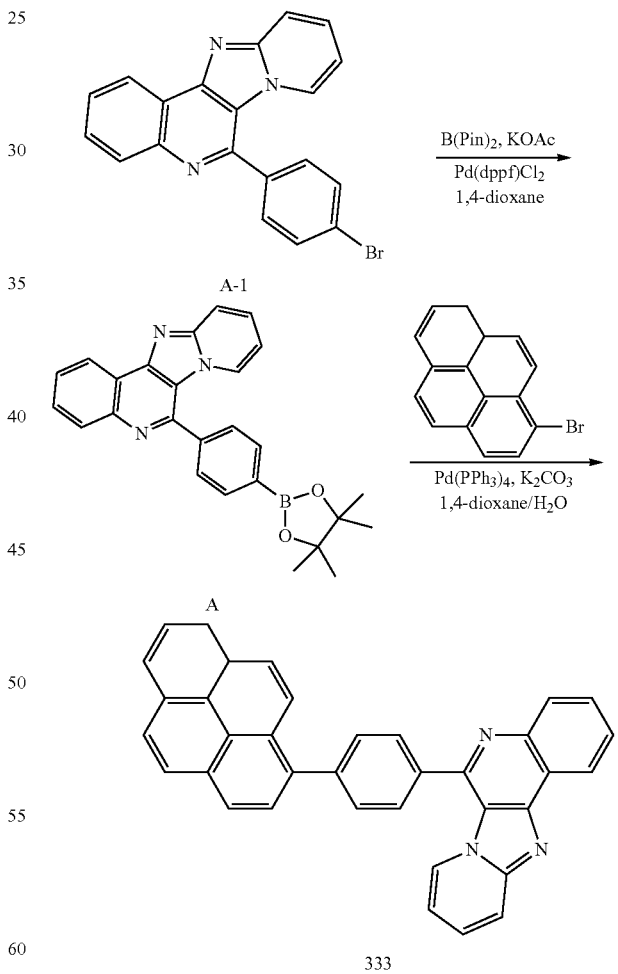

Preparation of Compound 333

A preparation was performed in the same manner as in the preparation of Compound 19, except that 8-bromo-1,9-dihydropyrene was used instead of the compound 9,9'-(5- bromo-1,3-phenylene)bis(9H-carbazole) in Preparation Example 2, thereby obtaining Target Compound 333.

<Preparation Example 52> Preparation of Compound 682

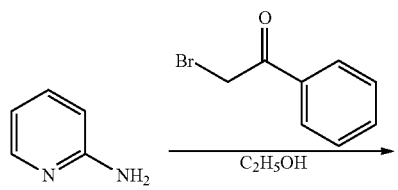

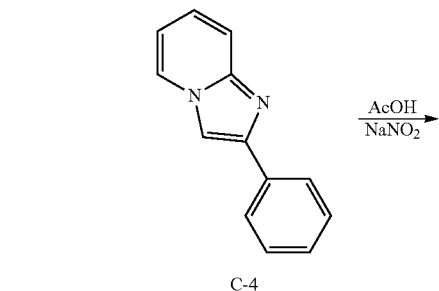

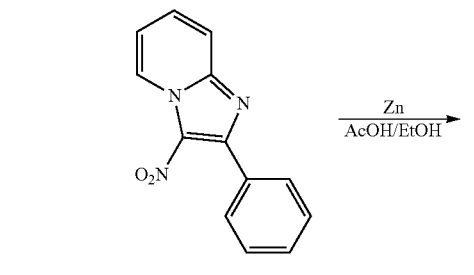

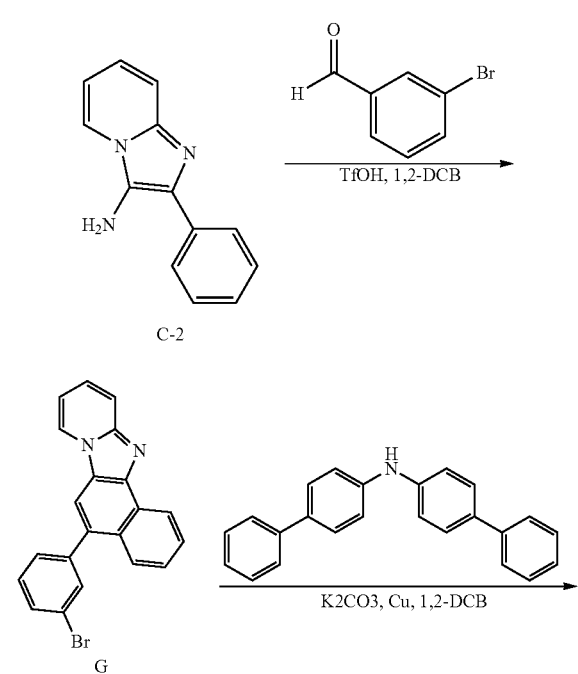

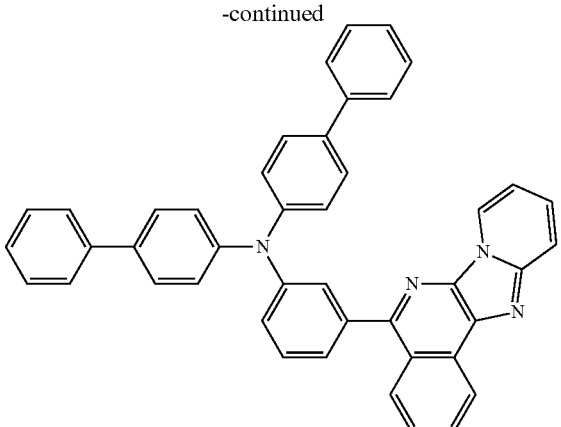

682

Preparation of Compound 682

Compound D-1 (5.8 g, 15.44 mmol, 1 eq.), di([1,1'-biphenyl]-4-yl)amine (5.45 g, 16.98 mmol, 1.2 eq.), Cu (3.92 g, 61.76 mmol, 4 eq.), $K_2CO_3$ (12.8 g, 92.64 mmol, 6 eq.), and 100 ml of 1,2-dichlorobenzene were sequentially mixed, and then the resulting mixture was refluxed and stirred. When the reaction was terminated, the resulting product was cooled to normal temperature and filtered as it is, and a filtrate obtained at this time was concentrated to obtain a solid. The resulting product was purified by using appropriate amounts of MC and normal hexane to obtain 6.2 g (73%) of Target Compound 682.

Compounds were prepared in the same manner as in the Preparation Examples, and the synthesis confirmation results thereof are shown in Tables 1 and 2. Table 1 is about the measurement values of $^1$H NMR ($CDCl_3$, 200 MHz), and Table 2 is about the measurement values of field desorption mass spectrometry (FD-MS).

TABLE 1

| Compound | $^1$H NMR($CDCl_3$, 200 Mz) |
|---|---|
| 6 | δ = 9.08(1H, d), 8.84(1H, d), 8.69(2H, d), 8.48(1H, d), 8.42(1H, d), 8.27(1H, d), 8.05(1H, s), 7.94~7.85(4H, m), 7.70~7.63(4H, m), 7.50(1H, d), 7.25(2H, t), 6.86(1H, t) |
| 19 | δ = 8.69(2H, d), 8.55(1H, d), 8.48(1H, d), 8.42(1H, d), 8.19~8.17(4H, d), 7.94~7.85(7H, m), 7.60(1H, d), 7.58~7.50(5H, m), 7.35(2H, t), 7.21~7.16(5H, m), 6.86(1H, t) |
| 42 | δ = 8.48(1H, d), 8.42~8.33(8H, m), 7.94~7.85(3H, m), 7.73(1H, t), 7.50(4 H, d), 7.21(1H, t), 6.86(1H, t) |
| 109 | δ = 8.69(2H, d), 8.48(1H, d), 8.42(1H, d), 8.23(1H, s), 7.94~7.85(7H, m), 7.55~7.49(7H, m), 7.21(1H, t), 6.86(1H, t) |
| 111 | δ = 8.69(2H, d), 8.48(1H, d), 8.42(1H, d), 8.35~8.30(4H, m), 8.23(1H, s), 7.94(3H, d), 7.87~7.85(2H, m), 7.55~7.49(7H, m), 7.21(1H, t), 6.86(1H, t) |
| 344 | δ = 8.69(4H, d), 8.48(2H, d), 7.97(2H, d), 7.88~7.85(6H, m), 7.55~7.50(6H, m), 7.21(2H, t), 6.86(2H, t) |
| 347 | δ = 8.69(4H, d), 8.48(2H, d), 8.42(1H, d), 7.97~7.85(9H, m), 7.55~7.50(4H, m), 7.21(2H, t), 6.86(2H, t) |
| 367 | δ = 8.48(1H, d), 8.36(2H, d), 7.97(3H, d), 7.88(1H, t), 7.55~7.50(9H, m), 7.21(1H, t), 6.86(1H, t) |
| 373 | δ = 8.69(2H, d), 8.48(1H, d), 8.36(4H, d), 7.97~7.96(3H, d), 7.88(1H, t), 7.55~7.50(9H, m), 7.21(1H, t), 6.86(2H, t) |

TABLE 1-continued

| Compound | ¹H NMR(CDCl₃, 200 Mz) |
|---|---|
| 461 | δ = 8.69(2H, d), 8.48(1H, d), 8.23(1H, s), 7.96~7.88(8H, m), 7.55~7.49(9H, m), 7.21(1H, t), 6.86(1H, t) |
| 463 | δ = 8.69(2H, d), 8.48(1H, d), 8.35~8.30(4H, m), 8.23(1H, s), 7.97~7.88(4H, m), 7.55~7.49(9H, m), 7.21(1H, t), 6.86(1H, t) |
| 468 | δ = 8.69(2H, d), 8.48(1H, d), 8.35~8.30(6H, m), 8.23(1H, s), 7.97~7.85(4H, m), 7.75(2H, d), 7.55~7.41(9H, m), 7.21(1H, t), 6.86(1H, t) |
| 478 | δ = 8.69(2H, d), 8.48(1H, d), 8.35~8.30(6H, m), 8.23(1H, s), 7.97~7.88(1H, t), 7.88~7.85(7H, m), 7.75(2H, d), 7.55~7.41(9H, m), 7.21(1H, t), 6.86(1H, t) |
| 497 | δ = 8.69(2H, d), 8.48(1H, d), 8.30(2H, d), 8.13(1H, d), 7.96~7.83(8H, m), 7.75(2H, d), 7.58~7.41(7H, m), 7.21(1H, t), 6.86(1H, t) |
| 498 | δ = 8.69(2H, d), 8.48(1H, d), 8.13(1H, d), 7.97~7.80(8H, m), 7.65(2H, m), 7.58~7.49(5H, m), 7.21(1H, t), 6.86(1H, t) |
| 537 | δ = 8.48(1H, d), 8.35~8.33(3H, m), 7.97(1H, t), 7.88(1H, t), 7.80(4H, d), 7.73(1H, t), 7.65(4H, t), 7.55~7.49(9H, m), 7.21(1H, t), 6.86(1H, t) |
| 581 | δ = 8.48(2H, d), 8.33~8.26(5H, m), 7.97(1H, d), 7.88~7.85(3H, m), 7.73(1H, t), 7.61~7.54(5H, m), 7.21(1H, t), 6.86(1H, t) |
| 601 | δ = 8.69(2H, d), 8.56(1H, d), 8.48(1H, d), 7.97~7.81(7H, m), 7.62~7.48(7H, m), 7.38(2H, d), 7.25~7.21(4H, m), 6.86(1H, t) |
| 642 | δ = 8.69(2H, d), 8.48(1H, d), 8.35~8.30(4H, m), 8.23(1H, s), 7.97~7.85(8H, m), 7.55~7.49(9H, m), 7.21(1H, t), 6.86(1H, t) |
| 678 | δ = 8.55(1H, d), 8.48(1H, d), 8.33(2H, d), 7.99~7.88(5H, m), 7.77~7.73(2H, t), 7.62~7.50(9H, m), 7.35(1H, t) 7.21(1H, m), 6.86(1H, t) |
| 688 | δ = 9.60(1H, d), 9.27(1H, s), 8.48(1H, d), 8.37~8.30(5H, m), 7.97(1H, d), 7.88(1H, d), 7.73~7.50(11H, m), 7.21(1H, t), 6.86(1H, t) |
| 14 | δ = 8.69(2H, d), 8.48(1H, d), 8.42(1H, d), 8.13(1H, s), 7.94~7.74(12H, m), 7.51(6H, m), 7.21(1H, t), 6.86(1H, t) |
| 22 | δ = 8.69(2H, d), 8.59(2H, d), 8.48(1H, d), 8.42(1H, d), 8.24(2H, d), 7.96~7.85(7H, m), 7.50(1H, d), 7.40(2H, t), 7.21(1H, t), 6.86(1H, t) |
| 26 | δ = 8.97(2H, d), 8.69(2H, d), 8.48(1H, d), 8.42(1H, d), 8.25(1H, d), 8.15~7.85(11H, m), 7.59~7.50(5H, m), 7.21(1H, t), 6.86(1H, t) |
| 75 | δ = 8.48(1H, d), 8.42~8.30(6H, m), 8.23(1H, s), 7.94(3H, d), 7.87~7.75(7H, m), 7.55~7.41(7H, m), 7.21(1H, t), 6.86(1H, t) |
| 175 | δ = 8.69(2H, d), 8.48(2H, d), 8.42~8.35(3H, m), 7.94~7.80(7H, m), 7.65(4H, t), 7.50~7.49(6H, m), 7.21~7.20(3H, m), 6.86(1H, t) |
| 202 | δ = 8.69(2H, d), 8.48(1H, d), 8.42(1H, d), 8.30(2H, d), 8.13(1H, d), 7.96~7.83(7H, m), 7.75(2H, d), 7.58(1H, t), 7.50~7.41(4H, m), 7.25(2H, d), 7.21(1H, t), 6.86(1H, t) |
| 222 | δ = 8.80(1H, d), 8.72~8.71(2H, d), 8.48~8.42(3H, m), 8.33(2H, d), 8.20(1H, d), 7.94~7.85(4H, m), 7.73(1H, t), 7.56(1H, t), 7.50(1H, d), 7.29(1H, d), 7.21(1H, t), 6.86(1H, t) |
| 225 | δ = 8.69(2H, d), 8.48(2H, d), 8.42(1H, t), 8.30~8.26(3H, m), 7.94~7.85(7H, m), 7.54~7.50(2H, m), 7.21(2H, d), 6.86(1H, t) |
| 269 | δ = 9.18(1H, d), 8.78(1H, d), 8.69(4H, s), 8.55(1H, d), 8.48(1H, d), 8.42(1H, t), 7.94~7.85(3H, m), 7.74(1H, d), 7.50(1H, d), 7.37(1H, t), 7.23~7.21(2H, t), 6.88~6.86(2H, t) |
| 291 | δ = 8.69(2H, d), 8.48(1H, d), 8.42(1H, t), 8.09~7.85(10H, m), 7.63~7.50(6H, m), 7.40~7.38(3H, t), 7.21(1H, t), 6.86(1H, t) |
| 317 | δ = 8.68(2H, d), 8.48(1H, d), 8.42(1H, d), 7.94~7.85(6H, m), 7.75(2H, d), 7.62(1H, d), 7.55~7.38(13H, m), 7.37(4H, t), 7.21(1H, t), 7.06(1H, d), 6.86(1H, t), 1.69(6H, s) |
| 333 | δ = 8.69(2H, d), 8.52(1H, d), 8.48(1H, d), 8.42(1H, d), 8.30(1H, d), 8.15(2H, d), 8.08~8.04(4H, m), 7.94~7.85(4H, m), 7.70(1H, d), 7.50(1H, d), 7.25~7.21(3H, m), 6.86(1H, t) |
| 353 | δ = 8.99(1H, s), 8.69(2H, d), 8.48(1H, d), 8.42(1H, d), 8.20(2H, m), 8.09~7.85(10H, m), 7.63~7.38(14H, m), 7.21(1H, t), 6.86(1H, t) |
| 363 | δ = 8.48(1H, d), 8.33(1H, t), 8.21(4H, m), 7.97(1H, t), 7.88(1H, t), 7.73(1H, t), 7.61~7.50(8H, m), 7.41~7.37(5H, m), 7.21(1H, t), 6.86(1H, t) |
| 365 | δ = 8.69(2H, d), 8.48(1H, d), 7.97(3H, s), 7.88~7.77(9H, m), 7.55~7.51(9H, m), 7.21(1H, t), 6.86(1H, t) |
| 370 | δ = 8.48(1H, d), 8.28(1H, d), 7.99~7.97(2H, m), 7.88(1H, t), 7.55~7.44(10H, m), 7.25~7.21(2H, t), 7.15(4H, m), 6.86(1H, t) |
| 372 | δ = 8.55(1H, d), 8.48(1H, d), 8.33(2H, s), 8.19~8.17(4H, m), 7.97~7.88(4H, m), 7.73(1H, t), 7.60~7.50(9H, m), 7.35(2H, t), 7.21~7.16(5H, m), 6.86(1H, t) |
| 574 | δ = 8.80(1H, d), 8.72~8.71(2H, d), 8.48~8.45(2H, t), 8.33(2H, d), 8.20(1H, d), 7.97~7.88(3H, m), 7.73(1H, t), 7.56~7.50(4H, m), 7.29(1H, d), 7.21(1H, t), 6.86(1H, t) |
| 577 | δ = 8.69(2H, d), 8.48(2H, d), 8.30~8.26(3H, t), 7.97(1H, d), 7.88~7.85(5H, m), 7.55~7.50(4H, m), 7.21(2H, d), 6.86(1H, t) |
| 682 | δ = 8.48(1H, d), 7.97(1H, t), 7.89~7.88(2H, t), 7.75(4H, d), 7.66(1H, s), 7.55~7.50(12H, m), 7.49~7.37(6H, m), 7.21~7.18(2H, m), 6.86(1H, t) |
| 711 | δ = 8.69(2H, d), 8.48(1H, d), 8.43(1H, s), 8.16(1H, d), 8.03~7.97(3H, m), 7.88~7.77(7H, m), 7.55~7.50(10H, m), 7.38(1H, t), 7.21(1H, t), 6.86(1H, t) |
| 715 | δ = 8.48(1H, d), 8.33(2H, t), 8.21(4H, m), 7.97(1H, t), 7.88(1H, t), 7.75~7.73(3H, m), 7.61~7.37(11H, m), 7.25(4H, s), 7.21(1H, t), 6.86(1H, t) |
| 719 | δ = 8.48(1H, d), 8.38~8.33(5H, m), 7.96(2H, d), 7.97~7.88(2H, t), 7.75~7.73(3H, m), 7.55~7.41(9H, m), 7.25~7.21(3H, m), 6.86(1H, t) |
| 722 | δ = 8.56(1H, d), 8.48(1H, d), 8.19(1H, d), 8.13(1H, d), 8.05(1H, s), 7.96(2H, d), 7.81(1H, d), 7.65~7.48(9H, m), 7.38(2H, d), 7.28~7.21(4H, m), 6.86(1H, t) |
| 723 | δ = 8.48(1H, d), 8.35(2H, d), 8.30(2H, d), 8.23(1H, s), 8.19(3H, m), 8.07(1H, d), 7.90(1H, d), 7.85(2H, d), 7.75(2H, d), 7.65(2H, t), 7.50~7.41(8H, m), 7.21(1H, t), 6.86(1H, t) |
| 724 | δ = 8.48(1H, d), 8.36(2H, t), 8.19(3H, m), 8.07(1H, d), 7.96(2H, d), 7.90(1H, d), 7.75(2H, d), 7.65(2H, t), 7.50~7.41(8H, m), 7.25(2H, d), 7.21(1H, d), 6.86(1H, t) |
| 727 | δ = 8.55(2H, d), 8.48~8.42(6H, m), 8.32(2H, d), 8.04(1H, s), 7.94~7.85(5H, m), 7.70(2H, t), 7.56~7.49(5H, m), 7.93(1H, t), 6.86(1H, t) |
| 729 | δ = 8.48(1H, d), 8.43~8.42(3H, m), 8.09(2H, d), 8.04(1H, s), 7.94~7.85(8H, m), 7.78(2H, d), 7.55(2H, d), 7.50(1H, d), 7.38(2H, t), 7.28~7.21(3H, m), 6.86(1H, t) |
| 730 | δ = 8.56(2H, d), 8.55~8.48(3H, d), 8.19(2H, d), 7.97~7.88(4H, m), 7.60(1H, s), 7.58~7.50(7H, m), 7.35(2H, t), 7.21~7.16(5H, m), 6.86(1H, t) |
| 732 | δ = 8.48(1H, d), 8.43(2H, s), 8.08(2H, d), 8.02~7.97(6H, d), 7.88(1H, t), 7.55~7.50(7H, m), 7.39(2H, t), 7.31(2H, t), 7.21(1H, t), 6.86(1H, t) |

TABLE 2

| Compound | FD-MS | Compound | FD-MS |
|---|---|---|---|
| 1 | m/z = 723.27(C54H33N3 = 723.88) | 2 | m/z = 723.27(C54H33N3 = 723.88) |

TABLE 2-continued

| Compound | FD-MS | Compound | FD-MS |
|---|---|---|---|
| 3 | m/z = 597.22(C44H27N3 = 597.72) | 4 | m/z = 597.22(C44H27N3 = 597.72) |
| 5 | m/z = 547.20(C40H25N3 = 547.66) | 6 | m/z = 471.17(C34H21N3 = 471.56) |
| 7 | m/z = 723.27(C54H33N3 = 723.88) | 8 | m/z = 723.27(C54H33N3 = 723.88) |
| 9 | m/z = 597.22(C44H27N3 = 597.72) | 10 | m/z = 597.22(C44H27N3 = 597.72) |
| 11 | m/z = 547.20(C40H25N3 = 547.66) | 12 | m/z = 471.17(C34H21N3 = 471.56) |
| 13 | m/z = 571.18(C38H26N3OP = 571.62) | 14 | m/z = 571.18(C38H26N3OP = 571.62) |
| 15 | m/z = 495.15(C32H22N3OP = 495.52) | 16 | m/z = 571.18(C38H26N3OP = 571.62) |
| 17 | m/z = 571.18(C38H26N3OP = 571.62) | 18 | m/z = 495.15(C32H22N3OP = 495.52) |
| 19 | m/z = 701.26(C50H31N5 = 701.83) | 20 | m/z = 701.26(C50H31N5 = 701.83) |
| 21 | m/z = 526.19(C35H22N6 = 526.60) | 22 | m/z = 528.18(C33H20N8 = 528.58) |
| 23 | m/z = 528.18(C33H20N8 = 528.58) | 24 | m/z = 528.18(C33H20N8 = 528.58) |
| 25 | m/z = 626.22(C43H26N6 = 626.72) | 26 | m/z = 626.22(C43H26N6 = 626.72) |
| 27 | m/z = 726.25(C51H30N6 = 726.84) | 28 | m/z = 602.22(C41H26N6 = 602.70) |
| 29 | m/z = 604.21(C39H24N8 = 604.68) | 30 | m/z = 604.21(C39H24N8 = 604.68) |
| 31 | m/z = 604.21(C39H24N8 = 604.68) | 32 | m/z = 702.25(C49H30N6 = 702.82) |
| 33 | m/z = 702.25(C49H30N6 = 702.82) | 34 | m/z = 802.28(C57H34N6 = 802.94) |
| 35 | m/z = 602.22(C41H26N6 = 602.70) | 36 | m/z = 604.21(C39H24N8 = 604.68) |
| 37 | m/z = 604.21(C39H24N8 = 604.68) | 38 | m/z = 604.21(C39H24N8 = 604.68) |
| 39 | m/z = 702.25(C49H30N6 = 702.82) | 40 | m/z = 702.25(C49H30N6 = 702.82) |
| 41 | m/z = 802.28(C57H34N6 = 802.94) | 42 | m/z = 526.19(C35H22N6 = 526.60) |
| 43 | m/z = 528.18(C33H20N8 = 528.58) | 44 | m/z = 528.18(C33H20N8 = 528.58) |
| 45 | m/z = 528.18(C33H20N8 = 528.58) | 46 | m/z = 626.22(C43H26N6 = 626.72) |
| 47 | m/z = 626.22(C43H26N6 = 626.72) | 48 | m/z = 726.25(C51H30N6 = 726.84) |
| 49 | m/z = 602.22(C41H26N6 = 602.70) | 50 | m/z = 604.21(C39H24N8 = 604.68) |
| 51 | m/z = 604.21(C39H24N8 = 604.68) | 52 | m/z = 604.21(C39H24N8 = 604.68) |
| 53 | m/z = 702.25(C49H30N6 = 702.82) | 54 | m/z = 702.25(C49H30N6 = 702.82) |
| 55 | m/z = 802.28(C57H34N6 = 802.94) | 56 | m/z = 602.22(C41H26N6 = 602.70) |
| 57 | m/z = 604.21(C39H24N8 = 604.68) | 58 | m/z = 604.21(C39H24N8 = 604.68) |
| 59 | m/z = 604.21(C39H24N8 = 604.68) | 60 | m/z = 702.25(C49H30N6 = 702.82) |
| 61 | m/z = 702.25(C49H30N6 = 702.82) | 62 | m/z = 802.28(C57H34N6 = 802.94) |
| 63 | m/z = 601.23(C42H27N5 = 601.71) | 64 | m/z = 701.26(C50H31N5 = 701.83) |
| 65 | m/z = 701.26(C50H31N5 = 701.83) | 66 | m/z = 801.29(C58H35N5 = 801.95) |
| 67 | m/z = 753.29(C54H35N5 = 753.91) | 68 | m/z = 677.26(C48H31N5 = 677.81) |
| 69 | m/z = 753.29(C54H35N5 = 753.91) | 70 | m/z = 677.26(C48H31N5 = 677.81) |
| 71 | m/z = 625.23(C44H27N5 = 625.73) | 72 | m/z = 625.23(C44H27N5 = 625.73) |
| 73 | m/z = 725.26(C52H31N5 = 725.86) | 74 | m/z = 677.26(C48H31N5 = 677.81) |
| 75 | m/z = 601.23(C42H27N5 = 601.71) | 76 | m/z = 677.26(C48H31N5 = 677.81) |
| 77 | m/z = 601.23(C42H27N5 = 601.71) | 78 | m/z = 601.23(C42H27N5 = 601.71) |
| 79 | m/z = 701.26(C50H31N5 = 701.83) | 80 | m/z = 701.26(C50H31N5 = 701.83) |

TABLE 2-continued

| Compound | FD-MS | Compound | FD-MS |
|---|---|---|---|
| 81 | m/z = 801.29(C58H35N5 = 801.95) | 82 | m/z = 753.29(C54H35N5 = 753.91) |
| 83 | m/z = 677.26(C48H31N5 = 677.81) | 84 | m/z = 753.29(C54H35N5 = 753.91) |
| 85 | m/z = 677.26(C48H31N5 = 677.81) | 86 | m/z = 601.23(C42H27N5 = 601.71) |
| 87 | m/z = 701.26(C50H31N5 = 701.83) | 88 | m/z = 701.26(C50H31N5 = 701.83) |
| 89 | m/z = 801.29(C58H35N5 = 801.95) | 90 | m/z = 753.29(C54H35N5 = 753.91) |
| 91 | m/z = 677.26(C48H31N5 = 677.81) | 92 | m/z = 753.29(C54H35N5 = 753.91) |
| 93 | m/z = 677.26(C48H31N5 = 677.81) | 94 | m/z = 625.23(C44H27N5 = 625.73) |
| 95 | m/z = 625.23(C44H27N5 = 625.73) | 96 | m/z = 725.26(C52H31N5 = 725.86) |
| 97 | m/z = 677.26(C48H31N5 = 677.81) | 98 | m/z = 601.23(C42H27N5 = 601.71) |
| 99 | m/z = 677.26(C48H31N5 = 677.81) | 100 | m/z = 601.23(C42H27N5 = 601.71) |
| 101 | m/z = 601.23(C42H27N5 = 601.71) | 102 | m/z = 701.26(C50H31N5 = 701.83) |
| 103 | m/z = 701.26(C50H31N5 = 701.83) | 104 | m/z = 801.29(C58H35N5 = 801.95) |
| 105 | m/z = 753.29(C54H35N5 = 753.91) | 106 | m/z = 677.26(C48H31N5 = 677.81) |
| 107 | m/z = 753.29(C54H35N5 = 753.91) | 108 | m/z = 677.26(C48H31N5 = 677.81) |
| 109 | m/z = 525.20(C36H23N5 = 525.62) | 110 | m/z = 525.20(C36H23N5 = 525.62) |
| 111 | m/z = 525.20(C36H23N5 = 525.62) | 112 | m/z = 625.23(C44H27N5 = 625.73) |
| 113 | m/z = 625.23(C44H27N5 = 625.73) | 114 | m/z = 725.26(C52H31N5 = 725.86) |
| 115 | m/z = 677.26(C48H31N5 = 677.81) | 116 | m/z = 601.23(C42H27N5 = 601.71) |
| 117 | m/z = 677.26(C48H31N5 = 677.81) | 118 | m/z = 601.23(C42H27N5 = 601.71) |
| 119 | m/z = 526.19(C35H22N6 = 526.60) | 120 | m/z = 602.22(C41H26N6 = 602.70) |
| 121 | m/z = 602.22(C41H26N6 = 602.70) | 122 | m/z = 701.26(C50H31N5 = 701.83) |
| 123 | m/z = 701.26(C50H31N5 = 701.83) | 124 | m/z = 801.29(C58H35N5 = 801.95) |
| 125 | m/z = 753.29(C54H35N5 = 753.91) | 126 | m/z = 677.26(C48H31N5 = 677.81) |
| 127 | m/z = 753.29(C54H35N5 = 753.91) | 128 | m/z = 677.26(C48H31N5 = 677.81) |
| 129 | m/z = 602.22(C41H26N6 = 602.70) | 130 | m/z = 678.25(C47H30N6 = 677.80) |
| 131 | m/z = 678.25(C47H30N6 = 677.80) | 132 | m/z = 525.20(C36H23N5 = 525.62) |
| 133 | m/z = 701.26(C50H31N5 = 701.83) | 134 | m/z = 701.26(C50H31N5 = 701.83) |
| 135 | m/z = 801.29(C58H35N5 = 801.95) | 136 | m/z = 677.26(C48H31N5 = 677.81) |
| 137 | m/z = 753.29(C54H35N5 = 753.91) | 138 | m/z = 677.26(C48H31N5 = 677.81) |
| 139 | m/z = 753.29(C54H35N5 = 753.91) | 140 | m/z = 677.26(C48H31N5 = 677.81) |
| 141 | m/z = 677.26(C48H31N5 = 677.81) | 142 | m/z = 602.22(C41H26N6 = 602.70) |
| 143 | m/z = 678.25(C47H30N6 = 678.80) | 144 | m/z = 678.25(C47H30N6 = 678.80) |
| 145 | m/z = 575.21(C40H25N5 = 575.67) | 146 | m/z = 499.18(C34H21N5 = 499.58) |
| 147 | m/z = 575.21(C40H25N5 = 575.67) | 148 | m/z = 549.20(C38H23N5 = 549.64) |
| 149 | m/z = 549.20(C38H23N5 = 549.64) | 150 | m/z = 651.24(C46H29N5 = 651.77) |
| 151 | m/z = 575.21(C40H25N5 = 575.67) | 152 | m/z = 651.24(C46H29N5 = 651.77) |
| 153 | m/z = 625.23(C44H27N5 = 625.73) | 154 | m/z = 625.23(C44H27N5 = 625.73) |
| 155 | m/z = 651.24(C46H29N5 = 651.77) | 156 | m/z = 575.21(C40H25N5 = 575.67) |
| 157 | m/z = 651.24(C46H29N5 = 651.77) | 158 | m/z = 625.23(C44H27N5 = 625.73) |

TABLE 2-continued

| Compound | FD-MS | Compound | FD-MS |
|---|---|---|---|
| 159 | m/z = 625.23(C44H27N5 = 625.73) | 160 | m/z = 575.21(C40H25N5 = 575.67) |
| 161 | m/z = 499.18(C34H21N5 = 499.58) | 162 | m/z = 575.21(C40H25N5 = 575.67) |
| 163 | m/z = 549.20(C38H23N5 = 549.64) | 164 | m/z = 549.20(C38H23N5 = 549.64) |
| 165 | m/z = 651.24(C46H29N5 = 651.77) | 166 | m/z = 575.21(C40H25N5 = 575.67) |
| 167 | m/z = 651.24(C46H29N5 = 651.77) | 168 | m/z = 625.23(C44H27N5 = 625.73) |
| 169 | m/z = 625.23(C44H27N5 = 625.73) | 170 | m/z = 651.24(C46H29N5 = 651.77) |
| 171 | m/z = 575.21(C40H25N5 = 575.67) | 172 | m/z = 651.24(C46H29N5 = 651.77) |
| 173 | m/z = 625.23(C44H27N5 = 625.73) | 174 | m/z = 625.23(C44H27N5 = 625.73) |
| 175 | m/z = 601.23(C42H27N5 = 601.71) | 176 | m/z = 753.29(C54H35N5 = 753.91) |
| 177 | m/z = 753.29(C54H35N5 = 753.91) | 178 | m/z = 701.26(C50H31N5 = 701.83) |
| 179 | m/z = 701.26(C50H31N5 = 701.83) | 180 | m/z = 677.26(C48H31N5 = 677.81) |
| 181 | m/z = 677.26(C48H31N5 = 677.81) | 182 | m/z = 651.24(C46H29N5 = 651.77) |
| 183 | m/z = 651.24(C46H29N5 = 651.77) | 184 | m/z = 701.26(C50H31N5 = 701.83) |
| 185 | m/z = 601.23(C42H27N5 = 601.71) | 186 | m/z = 753.29(C54H35N5 = 753.91) |
| 187 | m/z = 753.29(C54H35N5 = 753.91) | 188 | m/z = 701.26(C50H31N5 = 701.83) |
| 189 | m/z = 701.26(C50H31N5 = 701.83) | 190 | m/z = 677.26(C48H31N5 = 677.81) |
| 191 | m/z = 677.26(C48H31N5 = 677.81) | 192 | m/z = 651.24(C46H29N5 = 651.77) |
| 193 | m/z = 651.24(C46H29N5 = 651.77) | 194 | m/z = 701.26(C50H31N5 = 701.83) |
| 195 | m/z = 601.23(C42H27N5 = 601.71) | 196 | m/z = 677.26(C48H31N5 = 677.81) |
| 197 | m/z = 601.23(C42H27N5 = 601.71) | 198 | m/z = 677.26(C48H31N5 = 677.81) |
| 199 | m/z = 677.26(C48H31N5 = 677.81) | 200 | m/z = 677.26(C48H31N5 = 677.81) |
| 201 | m/z = 499.18(C34H21N5 = 499.58) | 202 | m/z = 575.21(C40H25N5 = 575.67) |
| 203 | m/z = 575.21(C40H25N5 = 575.67) | 204 | m/z = 575.21(C40H25N5 = 575.67) |
| 205 | m/z = 651.24(C46H29N5 = 651.77) | 206 | m/z = 651.24(C46H29N5 = 651.77) |
| 207 | m/z = 575.21(C40H25N5 = 575.67) | 208 | m/z = 651.24(C46H29N5 = 651.77) |
| 209 | m/z = 651.24(C46H29N5 = 651.77) | 210 | m/z = 499.18(C34H21N5 = 499.58) |
| 211 | m/z = 575.21(C40H25N5 = 575.67) | 212 | m/z = 575.21(C40H25N5 = 575.67) |
| 213 | m/z = 575.21(C40H25N5 = 575.67) | 214 | m/z = 651.24(C46H29N5 = 651.77) |
| 215 | m/z = 651.24(C46H29N5 = 651.77) | 216 | m/z = 575.21(C40H25N5 = 575.67) |
| 217 | m/z = 651.24(C46H29N5 = 651.77) | 218 | m/z = 651.24(C46H29N5 = 651.77) |
| 219 | m/z = 473.16(C32H19N5 = 473.54) | 220 | m/z = 549.20(C38H23N5 = 549.64) |
| 221 | m/z = 549.20(C38H23N5 = 549.64) | 222 | m/z = 473.16(C32H19N5 = 473.54) |
| 223 | m/z = 549.20(C38H23N5 = 549.64) | 224 | m/z = 549.20(C38H23N5 = 549.64) |
| 225 | m/z = 487.18(C33H21N5 = 487.57) | 226 | m/z = 487.18(C33H21N5 = 487.57) |
| 227 | m/z = 487.18(C33H21N5 = 487.57) | 228 | m/z = 487.18(C33H21N5 = 487.57) |
| 229 | m/z = 487.18(C33H21N5 = 487.57) | 230 | m/z = 487.18(C33H21N5 = 487.57) |
| 231 | m/z = 487.18(C33H21N5 = 487.57) | 232 | m/z = 487.18(C33H21N5 = 487.57) |
| 233 | m/z = 439.18(C29H21N5 = 439.52) | 234 | m/z = 515.21(C35H25N5 = 515.62) |
| 235 | m/z = 515.21(C35H25N5 = 515.62) | 236 | m/z = 515.21(C35H25N5 = 515.62) |

TABLE 2-continued

| Compound | FD-MS | Compound | FD-MS |
|---|---|---|---|
| 237 | m/z = 515.21(C35H25N5 = 515.62) | 238 | m/z = 439.18(C29H21N5 = 439.52) |
| 239 | m/z = 439.18(C29H21N5 = 439.52) | 240 | m/z = 515.21(C35H25N5 = 515.62) |
| 241 | m/z = 515.21(C35H25N5 = 515.62) | 242 | m/z = 515.21(C35H25N5 = 515.62) |
| 243 | m/z = 515.21(C35H25N5 = 515.62) | 244 | m/z = 439.18(C29H21N5 = 439.52) |
| 245 | m/z = 563.21(C39H25N5 = 563.66) | 246 | m/z = 563.21(C39H25N5 = 563.66) |
| 247 | m/z = 563.21(C39H25N5 = 563.66) | 248 | m/z = 563.21(C39H25N5 = 563.66) |
| 249 | m/z = 563.21(C39H25N5 = 563.66) | 250 | m/z = 563.21(C39H25N5 = 563.66) |
| 251 | m/z = 563.21(C39H25N5 = 563.66) | 252 | m/z = 563.21(C39H25N5 = 563.66) |
| 253 | m/z = 504.14(C33H20N4S = 504.61) | 254 | m/z = 504.14(C33H20N4S = 504.61) |
| 255 | m/z = 504.14(C33H20N4S = 504.61) | 256 | m/z = 504.14(C33H20N4S = 504.61) |
| 257 | m/z = 504.14(C33H20N4S = 504.61) | 258 | m/z = 504.14(C33H20N4S = 504.61) |
| 259 | m/z = 504.14(C33H20N4S = 504.61) | 260 | m/z = 504.14(C33H20N4S = 504.61) |
| 261 | m/z = 524.20(C37H24N4 = 524.63) | 262 | m/z = 600.23(C43H28N4 = 600.73) |
| 263 | m/z = 526.19(C35H22N6 = 526.60) | 264 | m/z = 526.19(C35H22N6 = 526.60) |
| 265 | m/z = 526.19(C35H22N6 = 526.60) | 266 | m/z = 602.22(C41H26N6 = 602.70) |
| 267 | m/z = 602.22(C41H26N6 = 602.70) | 268 | m/z = 602.22(C41H26N6 = 602.70) |
| 269 | m/z = 449.16(C30H19N5 = 449.52) | 270 | m/z = 449.16(C30H19N5 = 449.52) |
| 271 | m/z = 449.16(C30H19N5 = 449.52) | 272 | m/z = 525.20(C36H23N5 = 525.62) |
| 273 | m/z = 525.20(C36H23N5 = 525.62) | 274 | m/z = 525.20(C36H23N5 = 525.62) |
| 275 | m/z = 524.20(C37H24N4 = 524.63) | 276 | m/z = 600.23(C43H28N4 = 600.73) |
| 277 | m/z = 526.19(C35H22N6 = 526.60) | 278 | m/z = 526.19(C35H22N6 = 526.60) |
| 279 | m/z = 526.19(C35H22N6 = 526.60) | 280 | m/z = 600.23(C43H28N4 = 600.73) |
| 281 | m/z = 602.22(C41H26N6 = 602.70) | 282 | m/z = 602.22(C41H26N6 = 602.70) |
| 283 | m/z = 602.22(C41H26N6 = 602.70) | 284 | m/z = 449.16(C30H19N5 = 449.52) |
| 285 | m/z = 449.16(C30H19N5 = 449.52) | 286 | m/z = 449.16(C30H19N5 = 449.52) |
| 287 | m/z = 525.20(C36H23N5 = 525.62) | 288 | m/z = 525.20(C36H23N5 = 525.62) |
| 289 | m/z = 525.20(C36H23N5 = 525.62) | 290 | m/z = 601.23(C42H27N5 = 601.71) |
| 291 | m/z = 547.20(C40H25N3 = 547.66) | 292 | m/z = 547.20(C40H25N3 = 547.66) |
| 293 | m/z = 487.20(C35H25N3 = 487.61) | 294 | m/z = 563.24(C41H29N3 = 563.70) |
| 295 | m/z = 487.20(C35H25N3 = 487.61) | 296 | m/z = 563.24(C41H29N3 = 563.70) |
| 297 | m/z = 563.24(C41H29N3 = 563.70) | 298 | m/z = 563.24(C41H29N3 = 563.70) |
| 299 | m/z = 477.13(C32H19N3S = 477.58) | 300 | m/z = 553.16(C38H23N3S = 553.68) |
| 301 | m/z = 477.13(C32H19N3S = 477.58) | 302 | m/z = 553.16(C38H23N3S = 553.68) |
| 303 | m/z = 553.16(C38H23N3S = 553.68) | 304 | m/z = 553.16(C38H23N3S = 553.68) |
| 305 | m/z = 461.15(C32H19N3O = 461.52) | 306 | m/z = 537.18(C38H23N3O = 537.62) |
| 307 | m/z = 461.15(C32H19N3O = 461.52) | 308 | m/z = 537.18(C38H23N3O = 537.62) |
| 309 | m/z = 537.18(C38H23N3O = 537.62) | 310 | m/z = 537.18(C38H23N3O = 537.62) |
| 311 | m/z = 609.22(C45H27N3 = 609.73) | 312 | m/z = 685.25(C51H31N3 = 685.83) |
| 313 | m/z = 609.22(C45H27N3 = 609.73) | 314 | m/z = 685.25(C51H31N3 = 685.83) |

TABLE 2-continued

| Compound | FD-MS | Compound | FD-MS |
|---|---|---|---|
| 315 | m/z = 537.22(C39H27N3 = 537.67) | 316 | m/z = 537.22(C39H27N3 = 537.67) |
| 317 | m/z = 730.31(C53H38N4 = 730.91) | 318 | m/z = 730.31(C53H38N4 = 730.91) |
| 319 | m/z = 779.30(C56H37N5 = 779.95) | 320 | m/z = 779.30(C56H37N5 = 779.95) |
| 321 | m/z = 460.17(C32H20N4 = 460.54) | 322 | m/z = 536.20(C38H24N4 = 536.64) |
| 323 | m/z = 460.17(C32H20N4 = 460.54) | 324 | m/z = 536.20(C38H24N4 = 536.64) |
| 325 | m/z = 536.20(C38H24N4 = 536.64) | 326 | m/z = 536.20(C38H24N4 = 536.64) |
| 327 | m/z = 462.18(C32H22N4 = 462.56) | 328 | m/z = 462.18(C32H22N4 = 462.56) |
| 329 | m/z = 614.25(C44H30N4 = 614.75) | 330 | m/z = 614.25(C44H30N4 = 614.75) |
| 331 | m/z = 523.20(C38H25N3 = 523.64) | 332 | m/z = 523.20(C38H25N3 = 523.64) |
| 333 | m/z = 497.19(C36H23N3 = 497.60) | 334 | m/z = 497.19(C36H23N3 = 497.60) |
| 335 | m/z = 521.19(C38H23N3 = 521.62) | 336 | m/z = 521.19(C38H23N3 = 521.62) |
| 337 | m/z = 629.23(C44H31N3Si = 629.84) | 338 | m/z = 629.23(C44H31N3Si = 629.84) |
| 339 | m/z = 525.07(C32H19N3Se = 524.49) | 340 | m/z = 525.07(C32H19N3Se = 524.49) |
| 341 | m/z = 588.21(C40H24N6 = 588.67) | 342 | m/z = 588.21(C40H24N6 = 588.67) |
| 343 | m/z = 588.21(C40H24N6 = 588.67) | 344 | m/z = 588.21(C40H24N6 = 588.67) |
| 345 | m/z = 588.21(C40H24N6 = 588.67) | 346 | m/z = 588.21(C40H24N6 = 588.67) |
| 347 | m/z = 588.21(C40H24N6 = 588.67) | 348 | m/z = 588.21(C40H24N6 = 588.67) |
| 349 | m/z = 588.21(C40H24N6 = 588.67) | 350 | m/z = 588.21(C40H24N6 = 588.67) |
| 351 | m/z = 664.24(C46H286N = 664.77) | 352 | m/z = 664.24(C46H286N = 664.77) |
| 353 | m/z = 723.27(C54H33N3 = 723.88) | 354 | m/z = 723.27(C54H33N3 = 723.88) |
| 355 | m/z = 597.22(C44H27N3 = 597.72) | 356 | m/z = 597.22(C44H27N3 = 597.72) |
| 357 | m/z = 547.20(C40H25N3 = 547.66) | 358 | m/z = 471.17(C34H21N3 = 471.56) |
| 359 | m/z = 723.27(C54H33N3 = 723.88) | 360 | m/z = 723.27(C54H33N3 = 723.88) |
| 361 | m/z = 597.22(C44H27N3 = 597.72) | 362 | m/z = 597.22(C44H27N3 = 597.72) |
| 363 | m/z = 547.20(C40H25N3 = 547.66) | 364 | m/z = 471.17(C34H21N3 = 471.56) |
| 365 | m/z = 571.18(C38H26N3OP = 571.62) | 366 | m/z = 571.18(C38H26N3OP = 571.62) |
| 367 | m/z = 495.15(C32H22N3OP = 495.52) | 368 | m/z = 571.18(C38H26N3OP = 571.62) |
| 369 | m/z = 571.18(C38H26N3OP = 571.62) | 370 | m/z = 495.15(C32H22N3OP = 495.52) |
| 371 | m/z = 701.26(C50H31N5 = 701.83) | 372 | m/z = 701.26(C50H31N5 = 701.83) |
| 373 | m/z = 526.19(C35H22N6 = 526.60) | 374 | m/z = 528.18(C33H20N8 = 528.58) |
| 375 | m/z = 528.18(C33H20N8 = 528.58) | 376 | m/z = 528.18(C33H20N8 = 528.58) |
| 377 | m/z = 626.22(C43H26N6 = 626.72) | 378 | m/z = 626.22(C43H26N6 = 626.72) |
| 379 | m/z = 726.25(C51H30N6 = 726.84) | 380 | m/z = 602.22(C41H26N6 = 602.70) |
| 381 | m/z = 604.21(C39H24N8 = 604.68) | 382 | m/z = 604.21(C39H24N8 = 604.68) |
| 383 | m/z = 604.21(C39H24N8 = 604.68) | 384 | m/z = 702.25(C49H30N6 = 702.82) |
| 385 | m/z = 702.25(C49H30N6 = 702.82) | 386 | m/z = 802.28(C57H34N6 = 802.94) |
| 387 | m/z = 602.22(C41H26N6 = 602.70) | 388 | m/z = 604.21(C39H24N8 = 604.68) |
| 389 | m/z = 604.21(C39H24N8 = 604.68) | 390 | m/z = 604.21(C39H24N8 = 604.68) |
| 391 | m/z = 702.25(C49H30N6 = 702.82) | 392 | m/z = 702.25(C49H30N6 = 702.82) |

TABLE 2-continued

| Compound | FD-MS | Compound | FD-MS |
|---|---|---|---|
| 393 | m/z = 802.28(C57H34N6 = 802.94) | 394 | m/z = 526.19(C35H22N6 = 526.60) |
| 395 | m/z = 528.18(C33H20N8 = 528.58) | 396 | m/z = 528.18(C33H20N8 = 528.58) |
| 397 | m/z = 528.18(C33H20N8 = 528.58) | 398 | m/z = 626.22(C43H26N6 = 626.72) |
| 399 | m/z = 626.22(C43H26N6 = 626.72) | 400 | m/z = 726.25(C51H30N6 = 726.84) |
| 401 | m/z = 602.22(C41H26N6 = 602.70) | 402 | m/z = 604.21(C39H24N8 = 604.68) |
| 403 | m/z = 604.21(C39H24N8 = 604.68) | 404 | m/z = 604.21(C39H24N8 = 604.68) |
| 405 | m/z = 702.25(C49H30N6 = 702.82) | 406 | m/z = 702.25(C49H30N6 = 702.82) |
| 407 | m/z = 802.28(C57H34N6 = 802.94) | 408 | m/z = 602.22(C41H26N6 = 602.70) |
| 409 | m/z = 604.21(C39H24N8 = 604.68) | 410 | m/z = 604.21(C39H24N8 = 604.68) |
| 411 | m/z = 604.21(C39H24N8 = 604.68) | 412 | m/z = 702.25(C49H30N6 = 702.82) |
| 413 | m/z = 702.25(C49H30N6 = 702.82) | 414 | m/z = 802.28(C57H34N6 = 802.94) |
| 415 | m/z = 601.23(C42H27N5 = 601.71) | 416 | m/z = 701.26(C50H31N5 = 701.83) |
| 417 | m/z = 701.26(C50H31N5 = 701.83) | 418 | m/z = 801.29(C58H35N5 = 801.95) |
| 419 | m/z = 753.29(C54H35N5 = 753.91) | 420 | m/z = 677.26(C48H31N5 = 677.81) |
| 421 | m/z = 753.29(C54H35N5 = 753.91) | 422 | m/z = 677.26(C48H31N5 = 677.81) |
| 423 | m/z = 625.23(C44H27N5 = 625.73) | 424 | m/z = 625.23(C44H27N5 = 625.73) |
| 425 | m/z = 725.26(C52H31N5 = 725.86) | 426 | m/z = 677.26(C48H31N5 = 677.81) |
| 427 | m/z = 601.23(C42H27N5 = 601.71) | 428 | m/z = 677.26(C48H31N5 = 677.81) |
| 429 | m/z = 601.23(C42H27N5 = 601.71) | 430 | m/z = 601.23(C42H27N5 = 601.71) |
| 431 | m/z = 701.26(C50H31N5 = 701.83) | 432 | m/z = 701.26(C50H31N5 = 701.83 |
| 433 | m/z = 801.29(C58H35N5 = 801.95) | 434 | m/z = 753.29(C54H35N5 = 753.91) |
| 435 | m/z = 677.26(C48H31N5 = 677.81) | 436 | m/z = 753.29(C54H35N5 = 753.91) |
| 437 | m/z = 677.26(C48H31N5 = 677.81) | 438 | m/z = 601.23(C42H27N5 = 601.71) |
| 439 | m/z = 701.26(C50H31N5 = 701.83) | 440 | m/z = 701.26(C50H31N5 = 701.83) |
| 441 | m/z = 801.29(C58H35N5 = 801.95) | 442 | m/z = 753.29(C54H35N5 = 753.91) |
| 443 | m/z = 677.26(C48H31N5 = 677.81) | 444 | m/z = 753.29(C54H35N5 = 753.91) |
| 445 | m/z = 677.26(C48H31N5 = 677.81) | 446 | m/z = 625.23(C44H27N5 = 625.73) |
| 447 | m/z = 625.23(C44H27N5 = 625.73) | 448 | m/z = 725.26(C52H31N5 = 725.86) |
| 449 | m/z = 677.26(C48H31N5 = 677.81) | 450 | m/z = 601.23(C42H27N5 = 601.71) |
| 451 | m/z = 677.26(C48H31N5 = 677.81) | 452 | m/z = 601.23(C42H27N5 = 601.71) |
| 453 | m/z = 601.23(C42H27N5 = 601.71) | 454 | m/z = 701.26(C50H31N5 = 701.83) |
| 455 | m/z = 701.26(C50H31N5 = 701.83) | 456 | m/z = 801.29(C58H35N5 = 801.95) |
| 457 | m/z = 753.29(C54H35N5 = 753.91) | 458 | m/z = 677.26(C48H31N5 = 677.81) |
| 459 | m/z = 753.29(C54H35N5 = 753.91) | 460 | m/z = 677.26(C48H31N5 = 677.81) |
| 461 | m/z = 525.20(C36H23N5 = 525.62) | 462 | m/z = 525.20(C36H23N5 = 525.62) |
| 463 | m/z = 525.20(C36H23N5 = 525.62) | 464 | m/z = 625.23(C44H27N5 = 625.73) |
| 465 | m/z = 625.23(C44H27N5 = 625.73) | 466 | m/z = 725.26(C52H31N5 = 725.86) |
| 467 | m/z = 677.26(C48H31N5 = 677.81) | 468 | m/z = 601.23(C42H27N5 = 601.71) |
| 469 | m/z = 677.26(C48H31N5 = 677.81) | 470 | m/z = 601.23(C42H27N5 = 601.71) |

TABLE 2-continued

| Compound | FD-MS | Compound | FD-MS |
|---|---|---|---|
| 471 | m/z = 526.19(C35H22N6 = 526.60) | 472 | m/z = 602.22(C41H26N6 = 602.70) |
| 473 | m/z = 602.22(C41H26N6 = 602.70) | 474 | m/z = 701.26(C50H31N5 = 701.83) |
| 475 | m/z = 701.26(C50H31N5 = 701.83) | 476 | m/z = 801.29(C58H35N5 = 801.95) |
| 477 | m/z = 753.29(C54H35N5 = 753.91) | 478 | m/z = 677.26(C48H31N5 = 677.81) |
| 479 | m/z = 753.29(C54H35N5 = 753.91) | 480 | m/z = 677.26(C48H31N5 = 677.81) |
| 481 | m/z = 602.22(C41H26N6 = 602.70) | 482 | m/z = 678.25(C47H30N6 = 677.80) |
| 483 | m/z = 678.25(C47H30N6 = 677.80) | 484 | m/z = 525.20(C36H23N5 = 525.62) |
| 485 | m/z = 701.26(C50H31N5 = 701.83) | 486 | m/z = 701.26(C50H31N5 = 701.83) |
| 487 | m/z = 801.29(C58H35N5 = 801.95) | 488 | m/z = 677.26(C48H31N5 = 677.81) |
| 489 | m/z = 753.29(C54H35N5 = 753.91) | 490 | m/z = 677.26(C48H31N5 = 677.81) |
| 491 | m/z = 753.29(C54H35N5 = 753.91) | 492 | m/z = 677.26(C48H31N5 = 677.81) |
| 493 | m/z = 677.26(C48H31N5 = 677.81) | 494 | m/z = 602.22(C41H26N6 = 602.70) |
| 495 | m/z = 678.25(C47H30N6 = 678.80) | 496 | m/z = 678.25(C47H30N6 = 678.80) |
| 497 | m/z = 575.21(C40H25N5 = 575.67) | 498 | m/z = 499.18(C34H21N5 = 499.58) |
| 499 | m/z = 575.21(C40H25N5 = 575.67) | 500 | m/z = 549.20(C38H23N5 = 549.64) |
| 501 | m/z = 549.20(C38H23N5 = 549.64) | 502 | m/z = 651.24(C46H29N5 = 651.77) |
| 503 | m/z = 575.21(C40H25N5 = 575.67) | 504 | m/z = 651.24(C46H29N5 = 651.77) |
| 505 | m/z = 625.23(C44H27N5 = 625.73) | 506 | m/z = 625.23(C44H27N5 = 625.73) |
| 507 | m/z = 651.24(C46H29N5 = 651.77) | 508 | m/z = 575.21(C40H25N5 = 575.67) |
| 509 | m/z = 651.24(C46H29N5 = 651.77) | 510 | m/z = 625.23(C44H27N5 = 625.73) |
| 511 | m/z = 625.23(C44H27N5 = 625.73) | 512 | m/z = 575.21(C40H25N5 = 575.67) |
| 513 | m/z = 499.18(C34H21N5 = 499.58) | 514 | m/z = 575.21(C40H25N5 = 575.67) |
| 515 | m/z = 549.20(C38H23N5 = 549.64) | 516 | m/z = 549.20(C38H23N5 = 549.64) |
| 517 | m/z = 651.24(C46H29N5 = 651.77) | 518 | m/z = 575.21(C40H25N5 = 575.67) |
| 519 | m/z = 651.24(C46H29N5 = 651.77) | 520 | m/z = 625.23(C44H27N5 = 625.73) |
| 521 | m/z = 625.23(C44H27N5 = 625.73) | 522 | m/z = 651.24(C46H29N5 = 651.77) |
| 523 | m/z = 575.21(C40H25N5 = 575.67) | 524 | m/z = 651.24(C46H29N5 = 651.77) |
| 525 | m/z = 625.23(C44H27N5 = 625.73) | 526 | m/z = 625.23(C44H27N5 = 625.73) |
| 527 | m/z = 601.23(C42H27N5 = 601.71) | 528 | m/z = 753.29(C54H35N5 = 753.91) |
| 529 | m/z = 753.29(C54H35N5 = 753.91) | 530 | m/z = 701.26(C50H31N5 = 701.83) |
| 531 | m/z = 701.26(C50H31N5 = 701.83) | 532 | m/z = 677.26(C48H31N5 = 677.81) |
| 533 | m/z = 677.26(C48H31N5 = 677.81) | 534 | m/z = 651.24(C46H29N5 = 651.77) |
| 535 | m/z = 651.24(C46H29N5 = 651.77) | 536 | m/z = 701.26(C50H31N5 = 701.83) |
| 537 | m/z = 601.23(C42H27N5 = 601.71) | 538 | m/z = 753.29(C54H35N5 = 753.91) |
| 539 | m/z = 753.29(C54H35N5 = 753.91) | 540 | m/z = 701.26(C50H31N5 = 701.83) |
| 541 | m/z = 701.26(C50H31N5 = 701.83) | 542 | m/z = 677.26(C48H31N5 = 677.81) |
| 543 | m/z = 677.26(C48H31N5 = 677.81) | 544 | m/z = 651.24(C46H29N5 = 651.77) |
| 545 | m/z = 651.24(C46H29N5 = 651.77) | 546 | m/z = 701.26(C50H31N5 = 701.83) |
| 547 | m/z = 601.23(C42H27N5 = 601.71) | 548 | m/z = 677.26(C48H31N5 = 677.81) |

TABLE 2-continued

| Compound | FD-MS | Compound | FD-MS |
|---|---|---|---|
| 549 | m/z = 601.23(C42H27N5 = 601.71) | 550 | m/z = 677.26(C48H31N5 = 677.81) |
| 551 | m/z = 677.26(C48H31N5 = 677.81) | 552 | m/z = 677.26(C48H31N5 = 677.81) |
| 553 | m/z = 499.18(C34H21N5 = 499.58) | 554 | m/z = 575.21(C40H25N5 = 575.67) |
| 555 | m/z = 575.21(C40H25N5 = 575.67) | 556 | m/z = 575.21(C40H25N5 = 575.67) |
| 557 | m/z = 651.24(C46H29N5 = 651.77) | 558 | m/z = 651.24(C46H29N5 = 651.77) |
| 559 | m/z = 575.21(C40H25N5 = 575.67) | 560 | m/z = 651.24(C46H29N5 = 651.77) |
| 561 | m/z = 651.24(C46H29N5 = 651.77) | 562 | m/z = 499.18(C34H21N5 = 499.58) |
| 563 | m/z = 575.21(C40H25N5 = 575.67) | 564 | m/z = 575.21(C40H25N5 = 575.67) |
| 565 | m/z = 575.21(C40H25N5 = 575.67) | 566 | m/z = 651.24(C46H29N5 = 651.77) |
| 567 | m/z = 651.24(C46H29N5 = 651.77) | 568 | m/z = 575.21(C40H25N5 = 575.67) |
| 569 | m/z = 651.24(C46H29N5 = 651.77) | 570 | m/z = 651.24(C46H29N5 = 651.77) |
| 571 | m/z = 473.16(C32H19N5 = 473.54) | 572 | m/z = 549.20(C38H23N5 = 549.64) |
| 573 | m/z = 549.20(C38H23N5 = 549.64) | 574 | m/z = 473.16(C32H19N5 = 473.54) |
| 575 | m/z = 549.20(C38H23N5 = 549.64) | 576 | m/z = 549.20(C38H23N5 = 549.64) |
| 577 | m/z = 487.18(C33H21N5 = 487.57) | 578 | m/z = 487.18(C33H21N5 = 487.57) |
| 579 | m/z = 487.18(C33H21N5 = 487.57) | 580 | m/z = 487.18(C33H21N5 = 487.57) |
| 581 | m/z = 487.18(C33H21N5 = 487.57) | 582 | m/z = 487.18(C33H21N5 = 487.57) |
| 583 | m/z = 487.18(C33H21N5 = 487.57) | 584 | m/z = 487.18(C33H21N5 = 487.57) |
| 585 | m/z = 439.18(C29H21N5 = 439.52) | 586 | m/z = 515.21(C35H25N5 = 515.62) |
| 587 | m/z = 515.21(C35H25N5 = 515.62) | 588 | m/z = 515.21(C35H25N5 = 515.62) |
| 589 | m/z = 515.21(C35H25N5 = 515.62) | 590 | m/z = 439.18(C29H21N5 = 439.52) |
| 591 | m/z = 439.18(C29H21N5 = 439.52) | 592 | m/z = 515.21(C35H25N5 = 515.62) |
| 593 | m/z = 515.21(C35H25N5 = 515.62) | 594 | m/z = 515.21(C35H25N5 = 515.62) |
| 595 | m/z = 515.21(C35H25N5 = 515.62) | 596 | m/z = 439.18(C29H21N5 = 439.52) |
| 597 | m/z = 563.21(C39H25N5 = 563.66) | 598 | m/z = 563.21(C39H25N5 = 563.66) |
| 599 | m/z = 563.21(C39H25N5 = 563.66) | 600 | m/z = 563.21(C39H25N5 = 563.66) |
| 601 | m/z = 563.21(C39H25N5 = 563.66) | 602 | m/z = 563.21(C39H25N5 = 563.66) |
| 603 | m/z = 563.21(C39H25N5 = 563.66) | 604 | m/z = 563.21(C39H25N5 = 563.66) |
| 605 | m/z = 504.14(C33H20N4S = 504.61) | 606 | m/z = 504.14(C33H20N4S = 504.61) |
| 607 | m/z = 504.14(C33H20N4S = 504.61) | 608 | m/z = 504.14(C33H20N4S = 504.61) |
| 609 | m/z = 504.14(C33H20N4S = 504.61) | 610 | m/z = 504.14(C33H20N4S = 504.61) |
| 611 | m/z = 504.14(C33H20N4S = 504.61) | 612 | m/z = 504.14(C33H20N4S = 504.61) |
| 613 | m/z = 524.20(C37H24N4 = 524.63) | 614 | m/z = 600.23(C43H28N4 = 600.73) |
| 615 | m/z = 526.19(C35H22N6 = 526.60) | 616 | m/z = 526.19(C35H22N6 = 526.60) |
| 617 | m/z = 526.19(C35H22N6 = 526.60) | 618 | m/z = 602.22(C41H26N6 = 602.70) |
| 619 | m/z = 602.22(C41H26N6 = 602.70) | 620 | m/z = 602.22(C41H26N6 = 602.70) |
| 621 | m/z = 449.16(C30H19N5 = 449.52) | 622 | m/z = 449.16(C30H19N5 = 449.52) |
| 623 | m/z = 449.16(C30H19N5 = 449.52) | 624 | m/z = 525.20(C36H23N5 = 525.62) |
| 625 | m/z = 525.20(C36H23N5 = 525.62) | 626 | m/z = 525.20(C36H23N5 = 525.62) |

TABLE 2-continued

| Compound | FD-MS | Compound | FD-MS |
|---|---|---|---|
| 627 | m/z = 524.20(C37H24N4 = 524.63) | 628 | m/z = 600.23(C43H28N4 = 600.73) |
| 629 | m/z = 526.19(C35H22N6 = 526.60) | 630 | m/z = 526.19(C35H22N6 = 526.60) |
| 631 | m/z = 526.19(C35H22N6 = 526.60) | 632 | m/z = 600.23(C43H28N4 = 600.73) |
| 633 | m/z = 602.22(C41H26N6 = 602.70) | 634 | m/z = 602.22(C41H26N6 = 602.70) |
| 635 | m/z = 602.22(C41H26N6 = 602.70) | 636 | m/z = 449.16(C30H19N5 = 449.52) |
| 637 | m/z = 449.16(C30H19N5 = 449.52) | 638 | m/z = 449.16(C30H19N5 = 449.52) |
| 639 | m/z = 525.20(C36H23N5 = 525.62) | 640 | m/z = 525.20(C36H23N5 = 525.62) |
| 641 | m/z = 525.20(C36H23N5 = 525.62) | 642 | m/z = 601.23(C42H27N5 = 601.71) |
| 643 | m/z = 547.20(C40H25N3 = 547.66) | 644 | m/z = 547.20(C40H25N3 = 547.66) |
| 645 | m/z = 487.20(C35H25N3 = 487.61) | 646 | m/z = 563.24(C41H29N3 = 563.70) |
| 647 | m/z = 487.20(C35H25N3 = 487.61) | 648 | m/z = 563.24(C41H29N3 = 563.70) |
| 649 | m/z = 563.24(C41H29N3 = 563.70) | 650 | m/z = 563.24(C41H29N3 = 563.70) |
| 651 | m/z = 477.13(C32H19N3S = 477.58) | 652 | m/z = 553.16(C38H23N3S = 553.68) |
| 653 | m/z = 477.13(C32H19N3S = 477.58) | 654 | m/z = 553.16(C38H23N3S = 553.68) |
| 655 | m/z = 553.16(C38H23N3S = 553.68) | 656 | m/z = 553.16(C38H23N3S = 553.68) |
| 657 | m/z = 461.15(C32H19N3O = 461.52) | 658 | m/z = 537.18(C38H23N3O = 537.62) |
| 659 | m/z = 461.15(C32H19N3O = 461.52) | 660 | m/z = 537.18(C38H23N3O = 537.62) |
| 661 | m/z = 537.18(C38H23N3O = 537.62) | 662 | m/z = 537.18(C38H23N3O = 537.62) |
| 663 | m/z = 609.22(C45H27N3 = 609.73) | 664 | m/z = 685.25(C51H31N3 = 685.83) |
| 665 | m/z = 609.22(C45H27N3 = 609.73) | 666 | m/z = 685.25(C51H31N3 = 685.83) |
| 667 | m/z = 537.22(C39H27N3 = 537.67) | 668 | m/z = 537.22(C39H27N3 = 537.67) |
| 669 | m/z = 730.31(C53H38N4 = 730.91) | 670 | m/z = 730.31(C53H38N4 = 730.91) |
| 671 | m/z = 779.30(C56H37N5 = 779.95) | 672 | m/z = 779.30(C56H37N5 = 779.95) |
| 673 | m/z = 460.17(C32H20N4 = 460.54) | 674 | m/z = 536.20(C38H24N4 = 536.64) |
| 675 | m/z = 460.17(C32H20N4 = 460.54) | 676 | m/z = 536.20(C38H24N4 = 536.64) |
| 677 | m/z = 536.20(C38H24N4 = 536.64) | 678 | m/z = 536.20(C38H24N4 = 536.64) |
| 679 | m/z = 462.18(C32H22N4 = 462.56) | 680 | m/z = 462.18(C32H22N4 = 462.56) |
| 681 | m/z = 614.25(C44H30N4 = 614.75) | 682 | m/z = 614.25(C44H30N4 = 614.75) |
| 683 | m/z = 523.20(C38H25N3 = 523.64) | 684 | m/z = 523.20(C38H25N3 = 523.64) |
| 685 | m/z = 497.19(C36H23N3 = 497.60) | 686 | m/z = 497.19(C36H23N3 = 497.60) |
| 687 | m/z = 521.19(C38H23N3 = 521.62) | 688 | m/z = 521.19(C38H23N3 = 521.62) |
| 689 | m/z = 629.23(C44H31N3Si = 629.84) | 690 | m/z = 629.23(C44H31N3Si = 629.84) |
| 691 | m/z = 525.07(C32H19N3Se = 524.49) | 692 | m/z = 525.07(C32H19N3Se = 524.49) |
| 693 | m/z = 421.16(C30H19N3 = 421.50) | 694 | m/z = 421.16(C30H19N3 = 421.50) |
| 695 | m/z = 422.15(C29H18N4 = 422.49) | 696 | m/z = 422.15(C29H18N4 = 422.49) |
| 697 | m/z = 623.24(C46H29N3 = 623.76) | 698 | m/z = 621.20(C42H28N3OP = 621.68) |
| 699 | m/z = 671.21(C46H30N3OP = 671.74) | 700 | m/z = 678.25(C47H30N6 = 678.80) |
| 701 | m/z = 602.22(C41H26N6 = 602.70) | 702 | m/z = 554.22(C37H26N6 = 554.66) |
| 703 | m/z = 623.24(C46H29N3 = 623.76) | 704 | m/z = 621.20(C42H28N3OP = 621.68) |

TABLE 2-continued

| Compound | FD-MS | Compound | FD-MS |
|---|---|---|---|
| 705 | m/z = 671.21(C46H30N3OP = 671.74) | 706 | m/z = 678.25(C47H30N6 = 678.80) |
| 707 | m/z = 602.22(C41H26N6 = 602.70) | 708 | m/z = 554.22(C37H26N6 = 554.66) |
| 709 | m/z = 623.24(C46H29N3 = 623.76) | 710 | m/z = 621.20(C42H28N3OP = 621.68) |
| 711 | m/z = 671.21(C46H30N3OP = 671.74) | 712 | m/z = 678.25(C47H30N6 = 678.80) |
| 713 | m/z = 602.22(C41H26N6 = 602.70) | 714 | m/z = 554.22(C37H26N6 = 554.66) |
| 715 | m/z = 623.24(C46H29N3 = 623.76) | 716 | m/z = 621.20(C42H28N3OP = 621.68) |
| 717 | m/z = 671.21(C46H30N3OP = 671.74) | 718 | m/z = 678.25(C47H30N6 = 678.80) |
| 719 | m/z = 602.22(C41H26N6 = 602.70) | 720 | m/z = 554.22(C37H26N6 = 554.66) |
| 721 | m/z = 601.23(C42H27N5 = 601.71) | 722 | m/z = 563.21(C39H25N5 = 563.66) |
| 723 | m/z = 601.23(C42H27N5 = 601.71) | 724 | m/z = 602.22(C41H26N6 = 602.70) |
| 725 | m/z = 473.16(C32H19N5 = 473.54) | 726 | m/z = 625.23(C44H27N5 = 625.73) |
| 727 | m/z = 659.15(C44H25N3S2 = 659.82) | 728 | m/z = 627.19(C44H25N3S2 = 627.70) |
| 729 | m/z = 679.30(C50H37N3 = 679.87) | 730 | m/z = 625.23(C44H27N5 = 625.73) |
| 731 | m/z = 659.15(C44H25N3S2 = 659.82) | 732 | m/z = 627.19(C44H25N3S2 = 627.70) |
| 733 | m/z = 679.30(C50H37N3 = 679.87) | | |

Meanwhile, FIGS. 4 to 30 are graphs showing the light emission absorption spectra obtained by measuring photoluminescence (PL) or low temperature photoluminescence (LTPL) in a specific UV wavelength region. PL was measured at normal temperature by using a model name LS55 spectrometer manufactured by Perkin Elmer Inc., and LTPL was measuring by using a model name F7000 spectrometer manufactured by HITACHI, Ltd., and an analysis was made under the low temperature condition of −196° C. (77 K) by using liquid nitrogen.

FIG. 4 illustrates a measurement graph of PL of Compound 6 at a wavelength of 254 nm.

FIG. 5 illustrates a measurement graph of PL of Compound 19 at a wavelength of 240 nm.

FIG. 6 illustrates a measurement graph of PL of Compound 109 at a wavelength of 349 nm.

FIG. 7 illustrates a measurement graph of PL of Compound 111 at a wavelength of 255 nm.

FIG. 8 illustrates a measurement graph of PL of Compound 373 at a wavelength of 272 nm.

FIG. 9 illustrates a measurement graph of PL of Compound 478 at a wavelength of 257 nm.

FIG. 10 illustrates a measurement graph of PL of Compound 601 at a wavelength of 255 nm.

FIG. 11 illustrates a measurement graph of PL of Compound 642 at a wavelength of 257 nm.

FIG. 12 illustrates a measurement graph of LTPL of Compound 6 at a wavelength of 279 nm.

FIG. 13 illustrates a measurement graph of LTPL of Compound 19 at a wavelength of 338 nm.

FIG. 14 illustrates a measurement graph of LTPL of Compound 109 at a wavelength of 349 nm.

FIG. 15 illustrates a measurement graph of LTPL of Compound 111 at a wavelength of 323 nm.

FIG. 16 illustrates a measurement graph of LTPL of Compound 373 at a wavelength of 385 nm.

FIG. 17 illustrates a measurement graph of LTPL of Compound 478 at a wavelength of 374 nm.

FIG. 18 illustrates a measurement graph of LTPL of Compound 601 at a wavelength of 375 nm.

FIG. 19 illustrates a measurement graph of LTPL of Compound 642 at a wavelength of 376 nm.

FIG. 20 illustrates a measurement graph of PL of Compound 353 at a wavelength of 275 nm.

FIG. 21 illustrates a measurement graph of PL of Compound 365 at a wavelength of 257 nm.

FIG. 22 illustrates a measurement graph of PL of Compound 367 at a wavelength of 253 nm.

FIG. 23 illustrates a measurement graph of PL of Compound 370 at a wavelength of 252 nm.

FIG. 24 illustrates a measurement graph of PL of Compound 372 at a wavelength of 241 nm.

FIG. 25 illustrates a measurement graph of PL of Compound 574 at a wavelength of 279 nm.

FIG. 26 illustrates a measurement graph of PL of Compound 577 at a wavelength of 254 nm.

FIG. 27 illustrates a measurement graph of PL of Compound 711 at a wavelength of 256 nm.

FIG. 28 illustrates a measurement graph of PL of Compound 719 at a wavelength of 260 nm.

FIG. 29 illustrates a measurement graph of PL of Compound 722 at a wavelength of 320 nm.

FIG. 30 illustrates a measurement graph of PL of Compound 724 at a wavelength of 314 nm.

In the graphs of FIGS. 4 to 30, the y-coordinate refers to intensity, and the x-coordinate refers to wavelength (unit: nm).

Manufacture of Organic Light Emitting Device

Comparative Example 1

Trichloroethylene, acetone, ethanol, and distilled water were sequentially used to ultrasonically wash a transparent electrode ITO thin film obtained from glass for an organic light emitting device (manufactured by Samsung-Corning Co., Ltd.) for each of 5 minutes, and then the ITO thin film was placed in isopropanol, stored, and then used.

Next, an ITO substrate was disposed in a substrate folder of a vacuum deposition equipment, and the following 4,4', 4"-tris(N,N-(2-naphthyl)-phenylamino)triphenyl amine (2-TNATA) was placed in a cell in the vacuum deposition equipment.

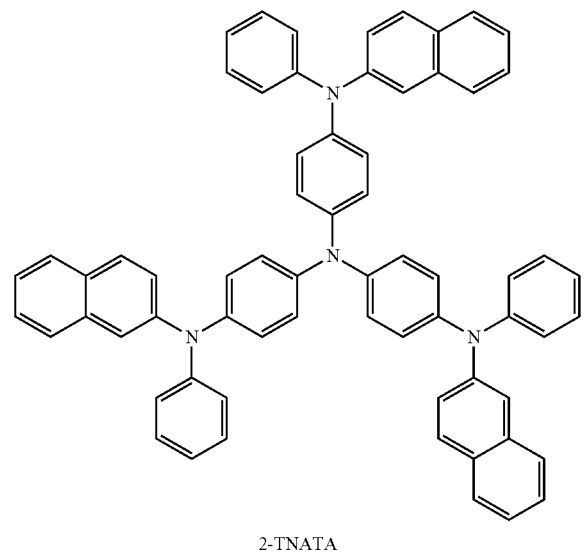 [SMILES: c1ccc(N(c2ccc(N(c3ccc(N(c4ccccc4)c4ccc5ccccc5c4)cc3)c3ccc(N(c4ccccc4)c4ccc5ccccc5c4)cc3)cc2)c2ccc3ccccc3c2)cc1]

2-TNATA

Subsequently, air in the chamber was evacuated until the degree of vacuum in the chamber reached $10^{-6}$ torr, and then a hole injection layer having a thickness of 600 Å was deposited on the ITO substrate by applying current to the cell to evaporate 2-TNATA. A hole transporting layer having a thickness of 300 Å was deposited on the hole injection layer by placing the following N,N'-bis(α-naphthyl)-N,N'-diphenyl-4,4'-diamine (NPB) in another cell in the vacuum deposition equipment and applying current to the cell to evaporate NPB.

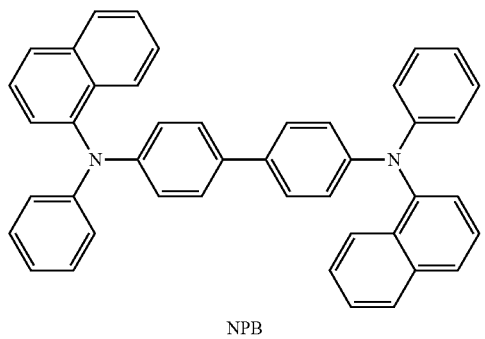 [SMILES: c1ccc(N(c2ccc(-c3ccc(N(c4ccccc4)c4cccc5ccccc45)cc3)cc2)c2cccc3ccccc23)cc1 ; "NPB"]

NPB

The hole injection layer and the hole transporting layer were formed as described above, and then a blue light emitting material having the following structure was deposited as a light emitting layer thereon. Specifically, the blue light emitting host material H1 was vacuum deposited to have a thickness of 200 Å on one cell in the vacuum deposition equipment, and the blue light emitting dopant material D1 was vacuum deposited thereon in an amount of 5% with respect to the host material.

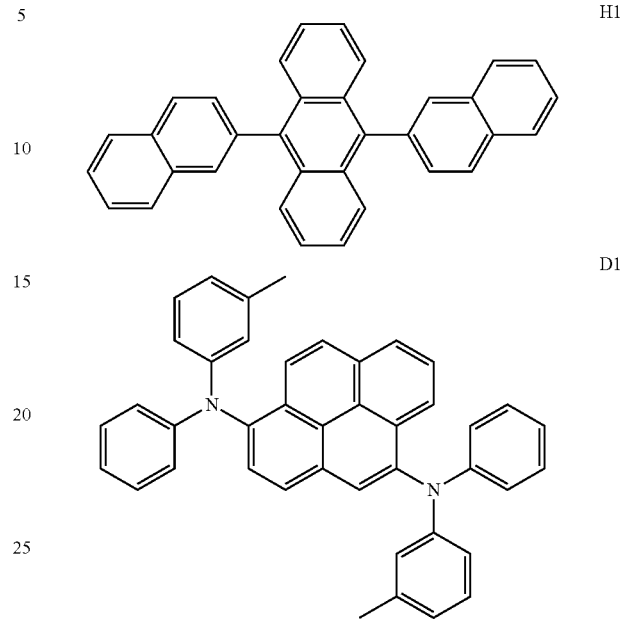

Subsequently, a compound having the following structural formula E1 as an electron transporting layer was deposited to have a thickness of 300 Å.

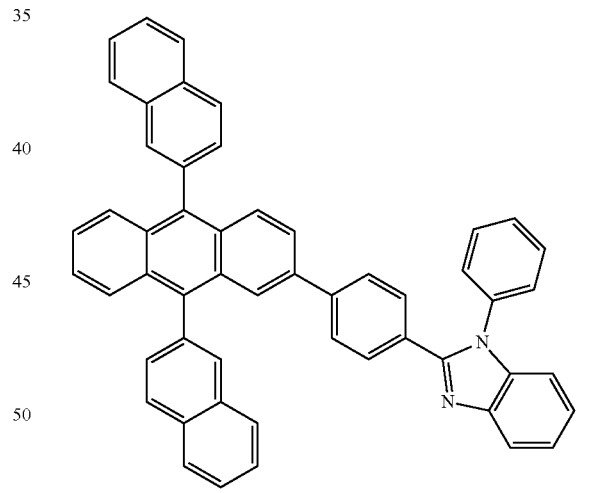

An organic light emitting device was manufactured by depositing lithium fluoride (LiF) as an electron injection layer to have a thickness of 10 Å and allowing the Al negative electrode to have a thickness of 1000 Å.

Meanwhile, all the organic compounds required for manufacturing an organic light emitting device were subjected to vacuum sublimed purification under $10^{-6}$ to $10^{-8}$ torr for each material, and used for the manufacture of the organic light emitting device.

Example 1

An organic light emitting device was manufactured in the same manner as in Comparative Example 1, except that the compounds synthesized in the Preparation Examples were used instead of E1 used when the electron transporting layer was formed in Comparative Example 1.

<Experimental Example> Evaluation of Organic Light Emitting Device

For each of the organic light emitting devices manufactured in Comparative Example 1 and Example 1, the driving voltage, the efficiency, the color coordinate, and the service life were measured at a light emitting brightness of 700 cd/m² and evaluated, and the results are shown in the following Table 3. In this case, the service life was measured by using M6000PMX manufactured by Mac Science Co., Ltd.

TABLE 3

| Experimental Example | Electron transporting layer | Driving voltage (V) | Efficiency (cd/A) | Color coordinate (x, y) | Service life ($T_{50}$) |
|---|---|---|---|---|---|
| Comparative Example 1 | E1 | 4.7 | 4.5 | (0.15, 0.18) | 330 |
| Example 1 | Compound 6 | 4.5 | 4.6 | (0.15, 0.18) | 400 |
| | Compound 19 | 4.5 | 4.8 | (0.15, 0.15) | 420 |
| | Compound 42 | 4.3 | 5 | (0.15, 0.15) | 450 |
| | Compound 109 | 4.5 | 4.6 | (0.15, 0.18) | 400 |
| | Compound 14 | 4.5 | 4.6 | (0.15, 0.18) | 400 |
| | Compound 22 | 4.5 | 4.8 | (0.15, 0.18) | 420 |
| | Compound 26 | 4.3 | 5 | (0.15, 0.15) | 450 |
| | Compound 75 | 4.5 | 4.6 | (0.15, 0.18) | 400 |
| | Compound 105 | 4.3 | 5 | (0.15, 0.15) | 450 |
| | Compound 130 | 4.5 | 4.6 | (0.15, 0.18) | 400 |
| | Compound 153 | 4.3 | 5 | (0.15, 0.15) | 450 |
| | Compound 161 | 4.5 | 4.8 | (0.15, 0.18) | 420 |
| | Compound 175 | 4.3 | 5 | (0.15, 0.15) | 450 |
| | Compound 197 | 4.3 | 5 | (0.15, 0.15) | 450 |
| | Compound 202 | 4.5 | 4.6 | (0.15, 0.18) | 400 |
| | Compound 222 | 4.5 | 4.8 | (0.15, 0.18) | 420 |
| | Compound 225 | 4.3 | 5 | (0.15, 0.15) | 450 |
| | Compound 234 | 4.5 | 4.6 | (0.15, 0.18) | 400 |
| | Compound 247 | 4.3 | 5 | (0.15, 0.15) | 450 |
| | Compound 253 | 4.5 | 4.6 | (0.15, 0.18) | 400 |
| | Compound 265 | 4.3 | 5 | (0.15, 0.15) | 450 |
| | Compound 269 | 4.5 | 4.6 | (0.15, 0.18) | 400 |
| | Compound 291 | 4.5 | 4.8 | (0.15, 0.18) | 420 |
| | Compound 293 | 4.3 | 5 | (0.15, 0.15) | 450 |
| | Compound 299 | 4.5 | 4.6 | (0.15, 0.18) | 400 |
| | Compound 307 | 4.3 | 5 | (0.15, 0.15) | 450 |
| | Compound 313 | 4.5 | 4.6 | (0.15, 0.18) | 400 |
| | Compound 317 | 4.3 | 5 | (0.15, 0.15) | 450 |
| | Compound 322 | 4.5 | 4.8 | (0.15, 0.18) | 420 |
| | Compound 330 | 4.3 | 5 | (0.15, 0.15) | 450 |
| | Compound 332 | 4.3 | 5 | (0.15, 0.15) | 450 |
| | Compound 333 | 4.5 | 4.6 | (0.15, 0.18) | 400 |
| | Compound 335 | 4.3 | 5 | (0.15, 0.15) | 450 |
| | Compound 338 | 4.5 | 4.8 | (0.15, 0.18) | 420 |
| | Compound 340 | 4.3 | 5 | (0.15, 0.15) | 450 |
| | Compound 111 | 4.5 | 4.8 | (0.15, 0.18) | 420 |
| | Compound 344 | 4.3 | 5 | (0.15, 0.15) | 450 |
| | Compound 347 | 4.5 | 4.6 | (0.15, 0.18) | 400 |
| | Compound 353 | 4.3 | 5 | (0.15, 0.15) | 450 |
| | Compound 355 | 4.5 | 4.8 | (0.15, 0.18) | 420 |
| | Compound 357 | 4.3 | 5 | (0.15, 0.15) | 450 |
| | Compound 359 | 4.5 | 4.6 | (0.15, 0.18) | 400 |
| | Compound 360 | 4.5 | 4.8 | (0.15, 0.18) | 420 |
| | Compound 361 | 4.3 | 5 | (0.15, 0.15) | 450 |
| | Compound 363 | 4.5 | 4.6 | (0.15, 0.18) | 400 |
| | Compound 364 | 4.3 | 5 | (0.15, 0.15) | 450 |
| | Compound 365 | 4.5 | 4.6 | (0.15, 0.18) | 400 |
| | Compound 367 | 4.3 | 5 | (0.15, 0.15) | 450 |
| | Compound 368 | 4.5 | 4.8 | (0.15, 0.18) | 420 |
| | Compound 370 | 4.3 | 5 | (0.15, 0.15) | 450 |
| | Compound 371 | 4.3 | 5 | (0.15, 0.15) | 450 |
| | Compound 372 | 4.5 | 4.6 | (0.15, 0.18) | 400 |
| | Compound 373 | 4.3 | 5 | (0.15, 0.15) | 450 |
| | Compound 376 | 4.5 | 4.8 | (0.15, 0.18) | 420 |
| | Compound 377 | 4.3 | 5 | (0.15, 0.15) | 450 |
| | Compound 379 | 4.5 | 4.6 | (0.15, 0.18) | 400 |
| | Compound 380 | 4.3 | 5 | (0.15, 0.15) | 450 |
| | Compound 387 | 4.5 | 4.8 | (0.15, 0.18) | 420 |
| | Compound 394 | 4.3 | 5 | (0.15, 0.15) | 450 |
| | Compound 398 | 4.3 | 5 | (0.15, 0.15) | 450 |
| | Compound 401 | 4.5 | 4.6 | (0.15, 0.18) | 400 |
| | Compound 405 | 4.3 | 5 | (0.15, 0.15) | 450 |
| | Compound 415 | 4.5 | 4.8 | (0.15, 0.18) | 420 |
| | Compound 419 | 4.3 | 5 | (0.15, 0.15) | 450 |
| | Compound 426 | 4.3 | 5 | (0.15, 0.15) | 450 |

TABLE 3-continued

| Experimental Example | Electron transporting layer | Driving voltage (V) | Efficiency (cd/A) | Color coordinate (x, y) | Service life ($T_{50}$) |
|---|---|---|---|---|---|
| | Compound 427 | 4.5 | 4.6 | (0.15, 0.18) | 400 |
| | Compound 429 | 4.3 | 5 | (0.15, 0.15) | 450 |
| | Compound 430 | 4.5 | 4.8 | (0.15, 0.18) | 420 |
| | Compound 435 | 4.3 | 5 | (0.15, 0.15) | 450 |
| | Compound 436 | 4.3 | 5 | (0.15, 0.15) | 450 |
| | Compound 438 | 4.5 | 4.6 | (0.15, 0.18) | 400 |
| | Compound 443 | 4.3 | 5 | (0.15, 0.15) | 450 |
| | Compound 449 | 4.5 | 4.8 | (0.15, 0.18) | 420 |
| | Compound 450 | 4.3 | 5 | (0.15, 0.15) | 450 |
| | Compound 453 | 4.5 | 4.6 | (0.15, 0.18) | 400 |
| | Compound 457 | 4.3 | 5 | (0.15, 0.15) | 450 |
| | Compound 458 | 4.5 | 4.6 | (0.15, 0.18) | 400 |
| | Compound 461 | 4.3 | 5 | (0.15, 0.15) | 450 |
| | Compound 461 | 4.5 | 4.8 | (0.15, 0.18) | 420 |
| | Compound 462 | 4.3 | 5 | (0.15, 0.15) | 450 |
| | Compound 463 | 4.3 | 5 | (0.15, 0.15) | 450 |
| | Compound 463 | 4.5 | 4.6 | (0.15, 0.18) | 400 |
| | Compound 467 | 4.3 | 5 | (0.15, 0.15) | 450 |
| | Compound 468 | 4.5 | 4.8 | (0.15, 0.18) | 420 |
| | Compound 468 | 4.3 | 5 | (0.15, 0.15) | 450 |
| | Compound 471 | 4.5 | 4.6 | (0.15, 0.18) | 400 |
| | Compound 472 | 4.3 | 5 | (0.15, 0.15) | 450 |
| | Compound 473 | 4.5 | 4.6 | (0.15, 0.18) | 400 |
| | Compound 477 | 4.3 | 5 | (0.15, 0.15) | 450 |
| | Compound 478 | 4.5 | 4.8 | (0.15, 0.18) | 420 |
| | Compound 478 | 4.3 | 5 | (0.15, 0.15) | 450 |
| | Compound 484 | 4.5 | 4.6 | (0.15, 0.18) | 400 |
| | Compound 485 | 4.3 | 5 | (0.15, 0.15) | 450 |
| | Compound 486 | 4.5 | 4.6 | (0.15, 0.18) | 400 |
| | Compound 490 | 4.3 | 5 | (0.15, 0.15) | 450 |
| | Compound 492 | 4.5 | 4.8 | (0.15, 0.18) | 420 |
| | Compound 495 | 4.3 | 5 | (0.15, 0.15) | 450 |
| | Compound 497 | 4.3 | 5 | (0.15, 0.15) | 450 |
| | Compound 498 | 4.5 | 4.6 | (0.15, 0.18) | 400 |
| | Compound 500 | 4.5 | 4.6 | (0.15, 0.18) | 400 |
| | Compound 502 | 4.3 | 5 | (0.15, 0.15) | 450 |
| | Compound 503 | 4.5 | 4.8 | (0.15, 0.18) | 420 |
| | Compound 506 | 4.3 | 5 | (0.15, 0.15) | 450 |
| | Compound 507 | 4.5 | 4.6 | (0.15, 0.18) | 400 |
| | Compound 512 | 4.3 | 5 | (0.15, 0.15) | 450 |
| | Compound 517 | 4.5 | 4.6 | (0.15, 0.18) | 400 |
| | Compound 522 | 4.3 | 5 | (0.15, 0.15) | 450 |
| | Compound 523 | 4.5 | 4.8 | (0.15, 0.18) | 420 |
| | Compound 527 | 4.3 | 5 | (0.15, 0.15) | 450 |
| | Compound 530 | 4.5 | 4.6 | (0.15, 0.18) | 400 |
| | Compound 532 | 4.5 | 4.8 | (0.15, 0.18) | 420 |
| | Compound 537 | 4.3 | 5 | (0.15, 0.15) | 450 |
| | Compound 540 | 4.5 | 4.6 | (0.15, 0.18) | 400 |
| | Compound 545 | 4.3 | 5 | (0.15, 0.15) | 450 |
| | Compound 547 | 4.5 | 4.8 | (0.15, 0.18) | 420 |
| | Compound 554 | 4.3 | 5 | (0.15, 0.15) | 450 |
| | Compound 559 | 4.5 | 4.6 | (0.15, 0.18) | 400 |
| | Compound 560 | 4.5 | 4.8 | (0.15, 0.18) | 420 |
| | Compound 562 | 4.3 | 5 | (0.15, 0.15) | 450 |
| | Compound 565 | 4.5 | 4.6 | (0.15, 0.18) | 400 |
| | Compound 568 | 4.3 | 5 | (0.15, 0.15) | 450 |
| | Compound 571 | 4.5 | 4.8 | (0.15, 0.18) | 420 |
| | Compound 572 | 4.3 | 5 | (0.15, 0.15) | 450 |
| | Compound 574 | 4.5 | 4.6 | (0.15, 0.18) | 400 |
| | Compound 575 | 4.5 | 4.8 | (0.15, 0.18) | 420 |
| | Compound 576 | 4.3 | 5 | (0.15, 0.15) | 450 |
| | Compound 577 | 4.3 | 5 | (0.15, 0.15) | 450 |
| | Compound 581 | 4.5 | 4.6 | (0.15, 0.18) | 400 |
| | Compound 584 | 4.5 | 4.8 | (0.15, 0.18) | 420 |
| | Compound 587 | 4.3 | 5 | (0.15, 0.15) | 450 |
| | Compound 595 | 4.5 | 4.6 | (0.15, 0.18) | 400 |
| | Compound 597 | 4.5 | 4.6 | (0.15, 0.18) | 400 |
| | Compound 600 | 4.3 | 5 | (0.15, 0.15) | 450 |
| | Compound 601 | 4.5 | 4.8 | (0.15, 0.18) | 420 |
| | Compound 603 | 4.3 | 5 | (0.15, 0.15) | 450 |
| | Compound 605 | 4.5 | 4.6 | (0.15, 0.18) | 400 |
| | Compound 607 | 4.5 | 4.8 | (0.15, 0.18) | 420 |
| | Compound 609 | 4.3 | 5 | (0.15, 0.15) | 450 |
| | Compound 610 | 4.3 | 5 | (0.15, 0.15) | 450 |
| | Compound 613 | 4.5 | 4.6 | (0.15, 0.18) | 400 |
| | Compound 615 | 4.3 | 5 | (0.15, 0.15) | 450 |

TABLE 3-continued

| Experimental Example | Electron transporting layer | Driving voltage (V) | Efficiency (cd/A) | Color coordinate (x, y) | Service life ($T_{50}$) |
|---|---|---|---|---|---|
| | Compound 621 | 4.5 | 4.8 | (0.15, 0.18) | 420 |
| | Compound 624 | 4.3 | 5 | (0.15, 0.15) | 450 |
| | Compound 627 | 4.5 | 4.6 | (0.15, 0.18) | 400 |
| | Compound 632 | 4.5 | 4.6 | (0.15, 0.18) | 400 |
| | Compound 636 | 4.3 | 5 | (0.15, 0.15) | 450 |
| | Compound 639 | 4.5 | 4.8 | (0.15, 0.18) | 420 |
| | Compound 642 | 4.3 | 5 | (0.15, 0.15) | 450 |
| | Compound 644 | 4.5 | 4.6 | (0.15, 0.18) | 400 |
| | Compound 645 | 4.5 | 4.8 | (0.15, 0.18) | 420 |
| | Compound 650 | 4.3 | 5 | (0.15, 0.15) | 450 |
| | Compound 651 | 4.3 | 5 | (0.15, 0.15) | 450 |
| | Compound 656 | 4.5 | 4.6 | (0.15, 0.18) | 400 |
| | Compound 657 | 4.3 | 5 | (0.15, 0.15) | 450 |
| | Compound 662 | 4.5 | 4.8 | (0.15, 0.18) | 420 |
| | Compound 663 | 4.3 | 5 | (0.15, 0.15) | 450 |
| | Compound 665 | 4.5 | 4.6 | (0.15, 0.18) | 400 |
| | Compound 669 | 4.5 | 4.8 | (0.15, 0.18) | 420 |
| | Compound 672 | 4.3 | 5 | (0.15, 0.15) | 450 |
| | Compound 675 | 4.3 | 5 | (0.15, 0.15) | 450 |
| | Compound 676 | 4.5 | 4.6 | (0.15, 0.18) | 400 |
| | Compound 678 | 4.3 | 5 | (0.15, 0.15) | 450 |
| | Compound 679 | 4.5 | 4.8 | (0.15, 0.18) | 420 |
| | Compound 682 | 4.3 | 5 | (0.15, 0.15) | 450 |
| | Compound 684 | 4.3 | 5 | (0.15, 0.15) | 450 |
| | Compound 685 | 4.5 | 4.6 | (0.15, 0.18) | 400 |
| | Compound 687 | 4.3 | 5 | (0.15, 0.15) | 450 |
| | Compound 688 | 4.5 | 4.9 | (0.15, 0.15) | 390 |
| | Compound 690 | 4.5 | 4.6 | (0.15, 0.18) | 400 |
| | Compound 692 | 4.5 | 4.6 | (0.15, 0.18) | 400 |
| | Compound 693 | 4.5 | 4.6 | (0.15, 0.18) | 400 |
| | Compound 695 | 4.5 | 4.6 | (0.15, 0.18) | 400 |
| | Compound 709 | 4.5 | 4.8 | (0.15, 0.15) | 420 |
| | Compound 711 | 4.3 | 5 | (0.15, 0.15) | 450 |
| | Compound 712 | 4.5 | 4.6 | (0.15, 0.18) | 400 |
| | Compound 713 | 4.5 | 4.6 | (0.15, 0.18) | 400 |
| | Compound 714 | 4.5 | 4.8 | (0.15, 0.15) | 420 |
| | Compound 715 | 4.3 | 5 | (0.15, 0.15) | 450 |
| | Compound 718 | 4.5 | 4.6 | (0.15, 0.18) | 400 |
| | Compound 719 | 4.5 | 4.6 | (0.15, 0.18) | 400 |
| | Compound 722 | 4.5 | 4.8 | (0.15, 0.15) | 420 |
| | Compound 723 | 4.3 | 5 | (0.15, 0.15) | 450 |
| | Compound 724 | 4.3 | 5 | (0.15, 0.15) | 450 |
| | Compound 725 | 4.5 | 4.6 | (0.15, 0.18) | 400 |
| | Compound 726 | 4.5 | 4.8 | (0.15, 0.18) | 420 |
| | Compound 727 | 4.3 | 5 | (0.15, 0.15) | 450 |
| | Compound 728 | 4.3 | 5 | (0.15, 0.15) | 450 |
| | Compound 729 | 4.5 | 4.6 | (0.15, 0.18) | 400 |
| | Compound 730 | 4.5 | 4.8 | (0.15, 0.18) | 420 |
| | Compound 731 | 4.3 | 5 | (0.15, 0.15) | 450 |
| | Compound 732 | 4.3 | 5 | (0.15, 0.15) | 450 |
| | Compound 424 | 4.3 | 5 | (0.15, 0.15) | 450 |
| | Compound 556 | 4.5 | 4.8 | (0.15, 0.18) | 420 |

As can be seen from the result of Table 3, an organic electroluminescence device using the compound of the present specification as an electron transporting layer material of an organic light emitting device has a low driving voltage, an improved light emitting efficiency, and a significantly improved service life as compared to Comparative Example 1.

The invention claimed is:

1. A hetero-cyclic compound represented by the following Chemical Formula 4 or 5:

[Chemical Formula 4]

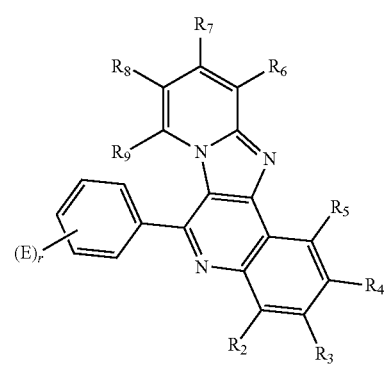

-continued

[Chemical Formula 5]

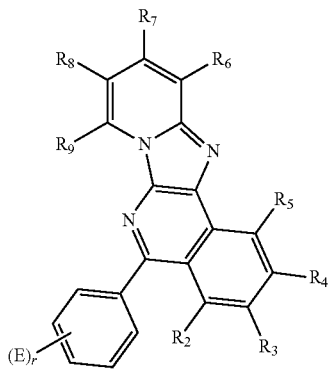

[Chemical Formula 6]

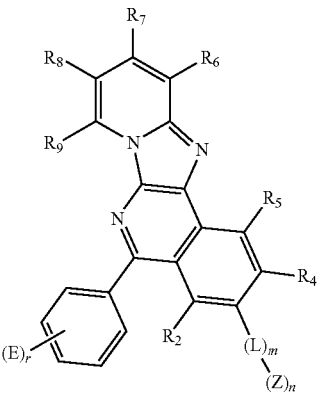

in Chemical Formula 4 and 5, $R_2$ to $R_9$ are the same as or different from each other, and are each independently selected from the group consisting of hydrogen; deuterium; halogen; —$SiR_{10}R_{11}R_{12}$; —$P(=O)R_{13}R_{14}$; a substituted or unsubstituted $C_6$ to $C_{60}$ aryl; a substituted or unsubstituted $C_2$ to $C_{60}$ heteroaryl; and an amine which is unsubstituted or substituted with one or more substituents selected from a substituted or unsubstituted $C_1$ to $C_{60}$ alkyl, a substituted or unsubstituted $C_6$ to $C_{60}$ aryl, and a substituted or unsubstituted $C_2$ to $C_{60}$ heteroaryl, $R_{10}$ to $R_{14}$ are the same as or different from each other, and are each independently hydrogen; deuterium; a substituted or unsubstituted $C_1$ to $C_{60}$ alkyl; a substituted or unsubstituted $C_6$ to $C_{60}$ aryl; or a substituted or unsubstituted $C_2$ to $C_{60}$ heteroaryl, and E is selected from the group consisting of hydrogen; deuterium; —$SiR_{20}R_{21}R_{22}$; —$P(=O)R_{23}R_{24}$; a substituted phenyl group; a substituted or unsubstituted $C_{10}$ to $C_{60}$ polycyclic aryl; a substituted or unsubstituted $C_2$ to $C_{60}$ heteroaryl; and an amine which is unsubstituted or substituted with a substituted or unsubstituted $C_6$ to $C_{60}$ aryl, or a substituted or unsubstituted $C_2$ to $C_{60}$ heteroaryl, wherein when E is substituted, a substituent is selected from the group consisting of $C_1$ to $C_{60}$ alkyl group; $C_6$ to $C_{60}$ aryl group unsubstituted or substituted with $C_1$ to $C_{60}$ alkyl group; $C_2$ to $C_{60}$ heteroaryl group unsubstituted or substituted with a substituent selected from the group consisting of $C_1$ to $C_{60}$ alkyl group, $C_2$ to $C_{60}$ hetereoaryl group, and $C_6$ to $C_{60}$ aryl group unsubstituted or substituted with $C_1$ to $C_{60}$ alkyl group; amine group; —$SiR_{20}R_{21}R_{22}$; and —$P(=O)R_{23}R_{24}$, wherein when E is hydrogen, $R_3$ is selected from the group consisting of a substituted or unsubstituted $C_6$ to $C_{60}$ aryl, and a substituted or unsubstituted $C_2$ to $C_{60}$ heteroaryl, r is an integer of 1 to 5, when r is 2 or more, E's are the same as or different from each other, $R_{20}$ to $R_{24}$ are the same as or different from each other, and are each independently hydrogen; deuterium; a substituted or unsubstituted $C_1$ to $C_{60}$ alkyl; a substituted or unsubstituted $C_6$ to $C_{60}$ aryl; or a substituted or unsubstituted $C_2$ to $C_{60}$ heteroaryl.

2. The hetero-cyclic compound of claim 1, wherein Chemical Formula 5 is represented by any one of the following Chemical Formula 6:

in Chemical Formula 6,

E is selected from the group consisting of hydrogen; deuterium; halogen; —$SiR_{20}R_{21}R_{22}$; —$P(=O)R_{23}R_{24}$; a substituted or unsubstituted $C_1$ to $C_{60}$ alkyl; a substituted phenyl group; a substituted or unsubstituted $C_{10}$ to $C_{60}$ polycyclic aryl; a substituted or unsubstituted $C_2$ to $C_{60}$ heteroaryl; and an amine which is unsubstituted or substituted with a substituted or unsubstituted $C_6$ to $C_{60}$ aryl, or a substituted or unsubstituted $C_2$ to $C_{60}$ heteroaryl, wherein when E is substituted, a substituent is selected from the group consisting of $C_1$ to $C_{60}$ alkyl group; $C_6$ to $C_{60}$ aryl group unsubstituted or substituted with $C_1$ to $C_{60}$ alkyl group; $C_2$ to $C_{60}$ heteroaryl group unsubstituted or substituted with a substituent selected from the group consisting of $C_1$ to $C_{60}$ alkyl group, $C_2$ to $C_{60}$ heteroaryl group, and $C_6$ to $C_{60}$ aryl group unsubstituted or substituted with $C_1$ to $C_{60}$ alkyl group; amine group; —$SiR_{20}R_{21}R_{22}$; and —$P(=O)R_{23}R_{24}$, r is an integer of 1 to 5, when r is 2 or more, E's are the same as or different from each other, $R_{20}$ to $R_{24}$ are the same as or different from each other, and are each independently hydrogen; deuterium; a substituted or unsubstituted $C_1$ to $C_{60}$ alkyl; a substituted or unsubstituted $C_6$ to $C_{60}$ aryl; or a substituted or unsubstituted $C_2$ to $C_{60}$ heteroaryl, L is selected from the group consisting of a direct bond; a substituted or unsubstituted $C_6$ to $C_{60}$ arylene; and a substituted or unsubstituted $C_2$ to $C_{60}$ heteroarylene, m is an integer of 1 to 3, n is an integer of 1 to 3, Z is selected from the group consisting of hydrogen; deuterium; —$P(=O)R_{15}R_{16}$; —$SiR_{17}R_{18}R_{19}$; a substituted or unsubstituted $C_1$ to $C_{60}$ alkyl; a substituted or unsubstituted $C_6$ to $C_{60}$ aryl; a substituted or unsubstituted $C_2$ to $C_{60}$ heteroaryl; and an amine which is unsubstituted or substituted with one or more substituents selected from a substituted or unsubstituted $C_1$ to $C_{60}$ alkyl, a substituted or unsubstituted $C_6$ to $C_{60}$ aryl, and a substituted or unsubstituted $C_2$ to $C_{60}$ heteroaryl, wherein when E is hydrogen, Z is selected from the group consisting of a substituted or unsubstituted $C_6$ to $C_{60}$ aryl, and a substituted or unsubstituted $C_2$ to $C_{60}$ heteroaryl, when m is 2 or more, L's are the same as or different from each other, when n is 2 or more, Z's are the same as or different from each other, R$_{15}$ to R$_{19}$ are the same as or different from each other, and are each independently hydrogen; deuterium; a substituted or unsubstituted C$_1$ to C$_{60}$ alkyl; a substituted or unsubstituted C$_6$ to C$_{60}$ aryl; or a substituted or unsubstituted C$_2$ to C$_{60}$ heteroaryl, and the definitions of R$_2$ and R$_4$ to R$_9$ are the same as those defined in Chemical Formula 5.

3. The hetero-cyclic compound of claim 1, wherein the hetero-cyclic compound represented by Chemical Formula 4 or 5 is selected from the following compounds:

1

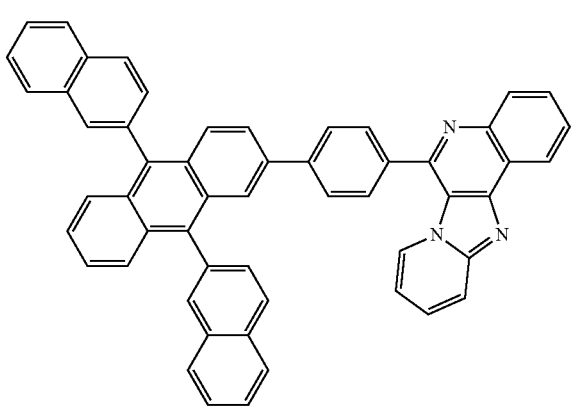

2

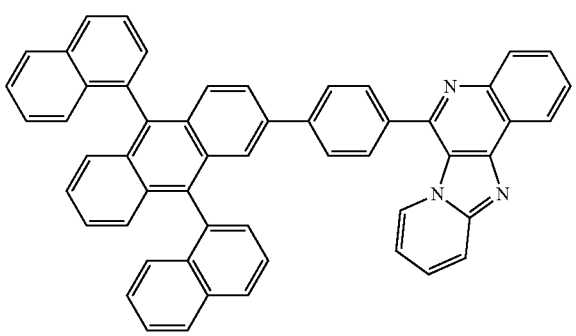

3

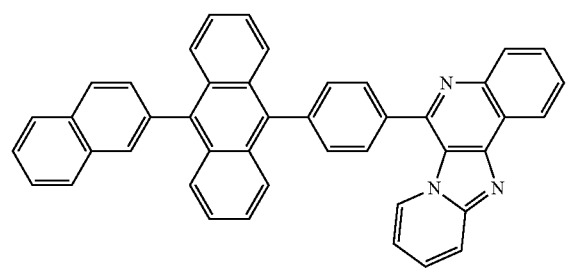

-continued

4

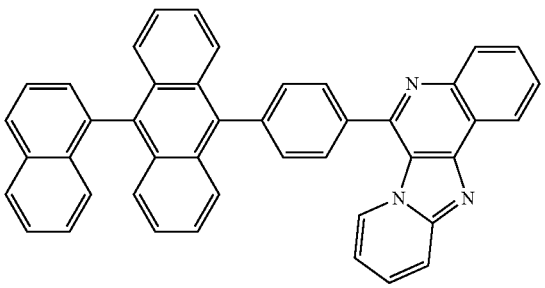

5

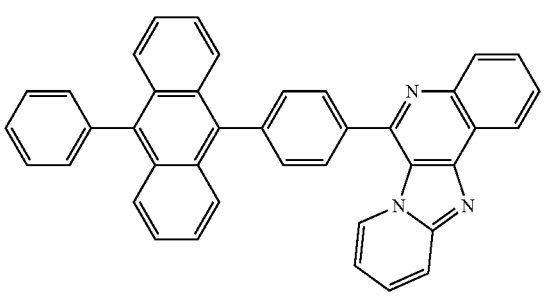

6

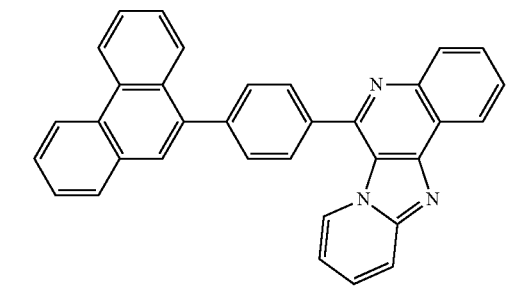

7

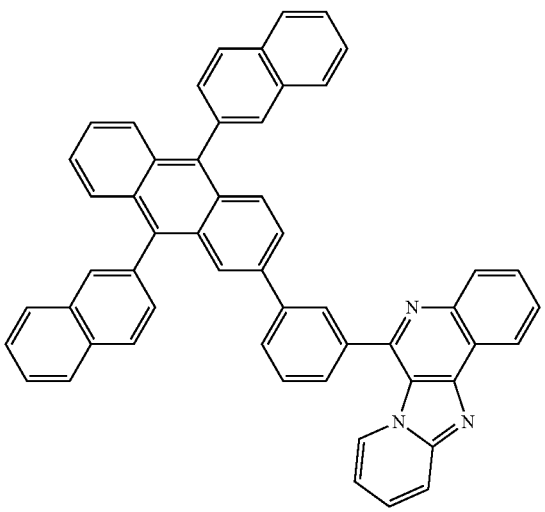

8
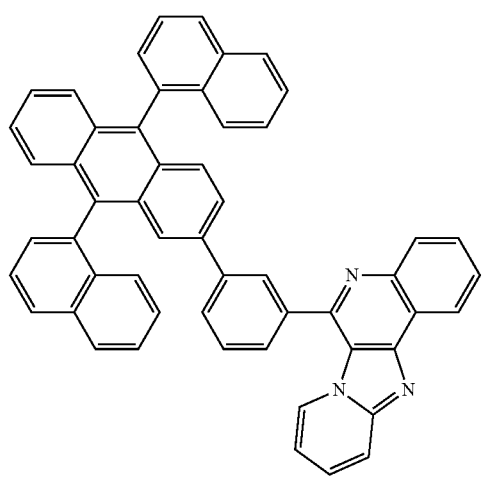
9
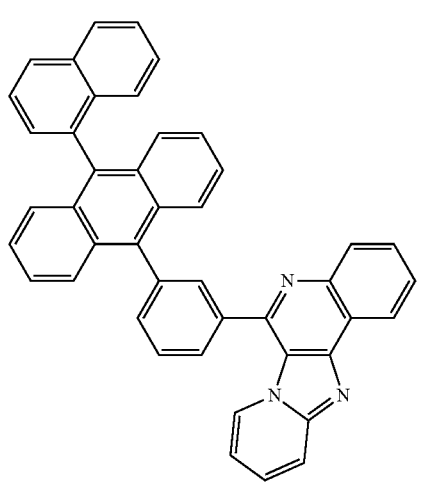
10
11
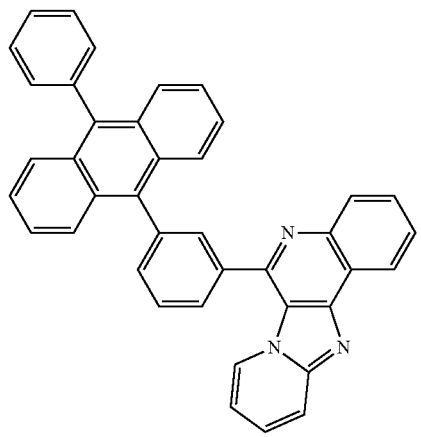
12
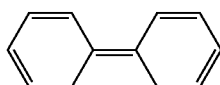
13
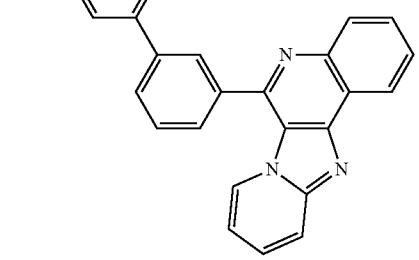
14
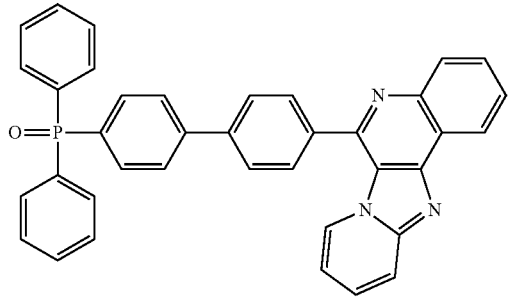
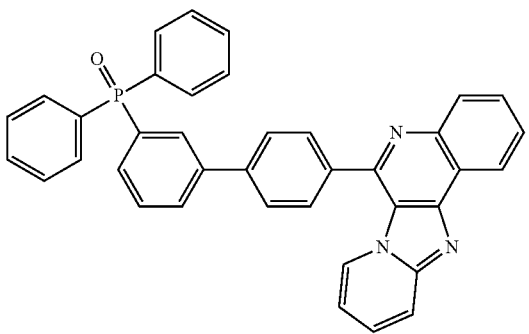

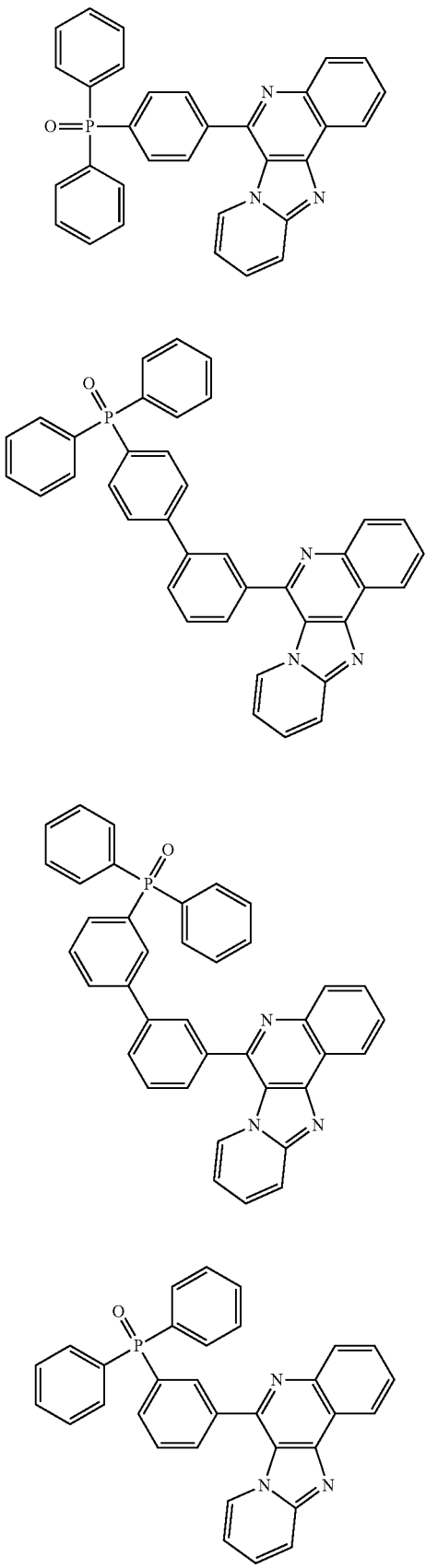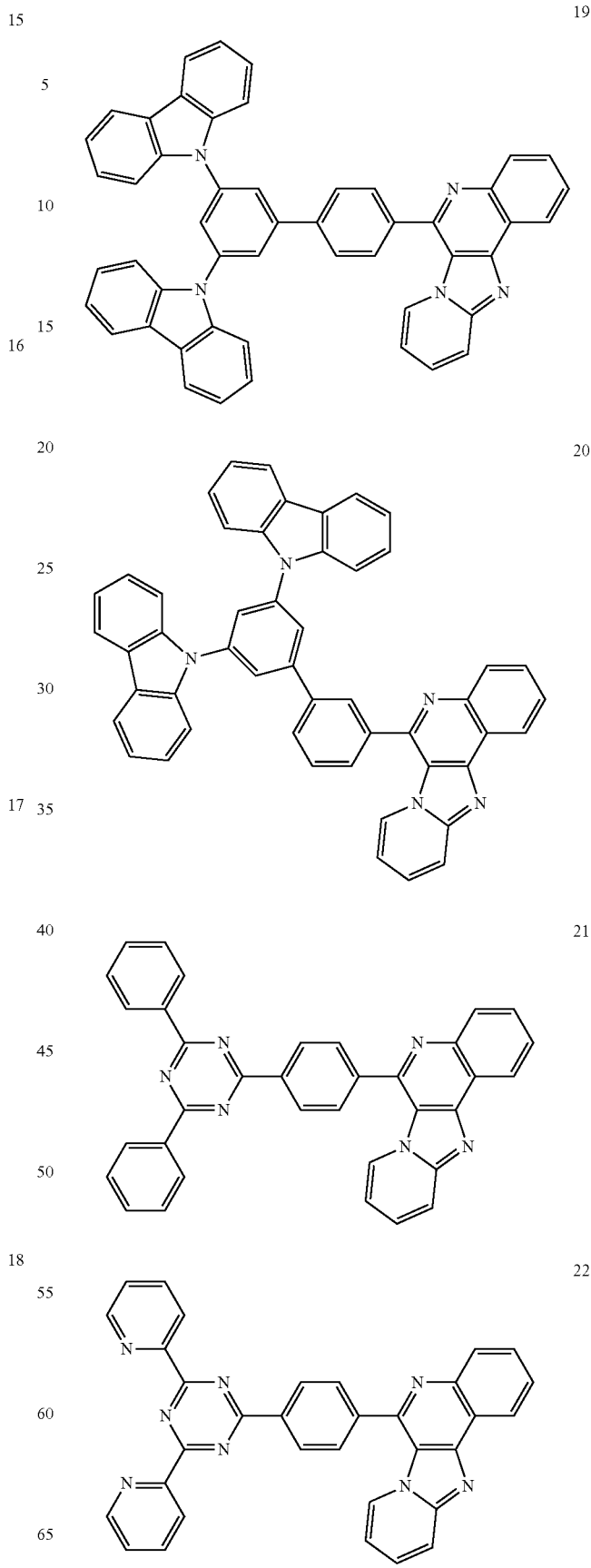

23
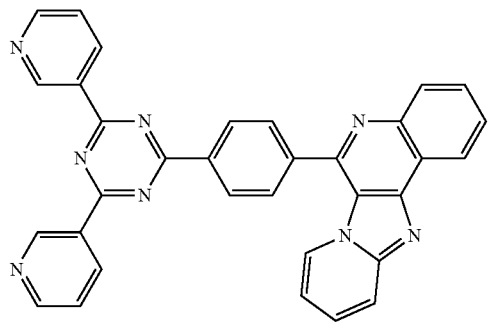
24
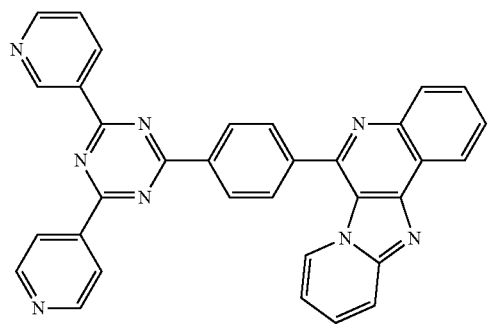
25
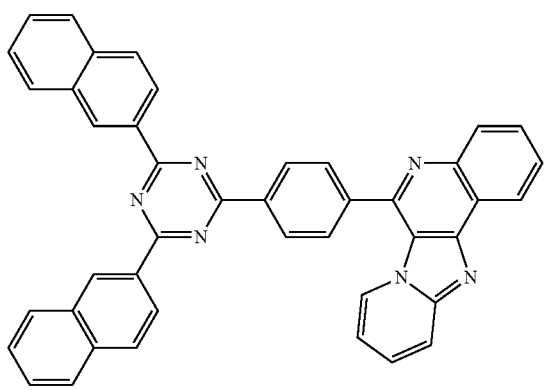
26
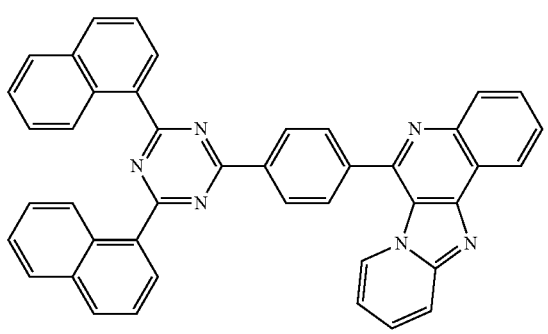
27
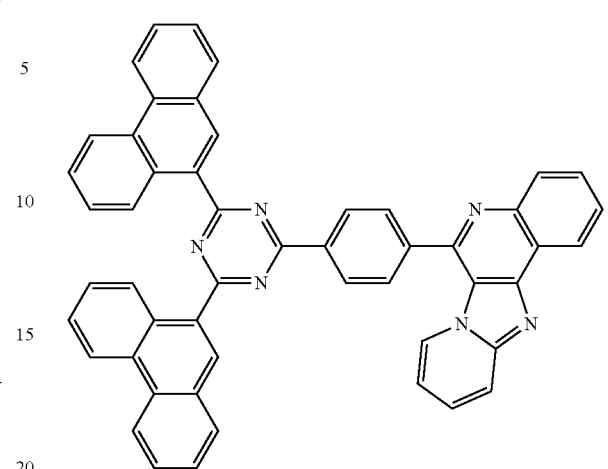
28
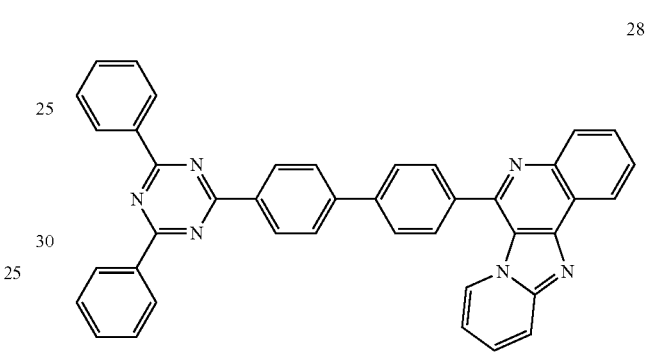
29
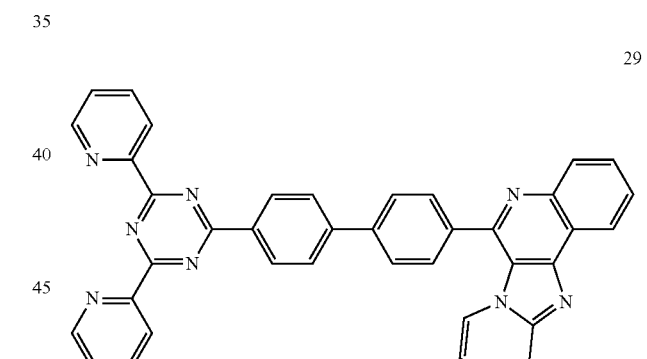
30
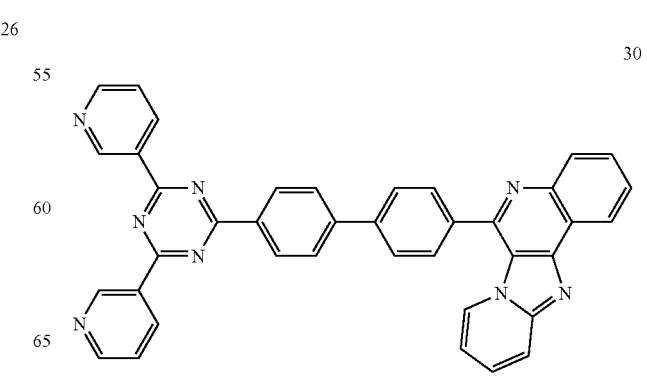

31
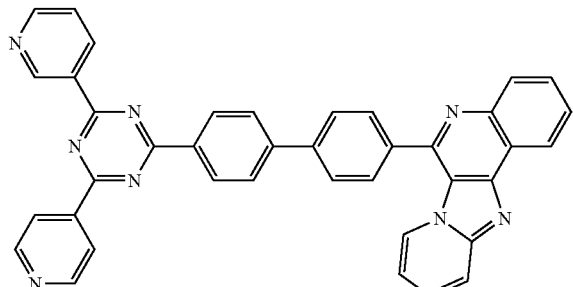
32
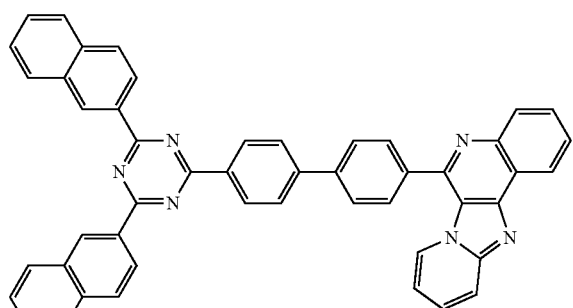
33
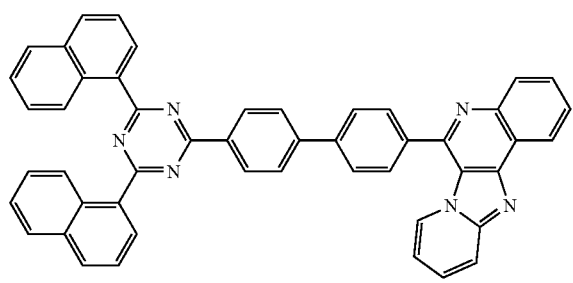
34
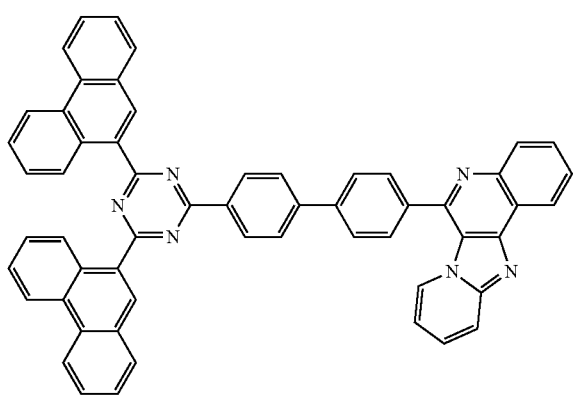
35
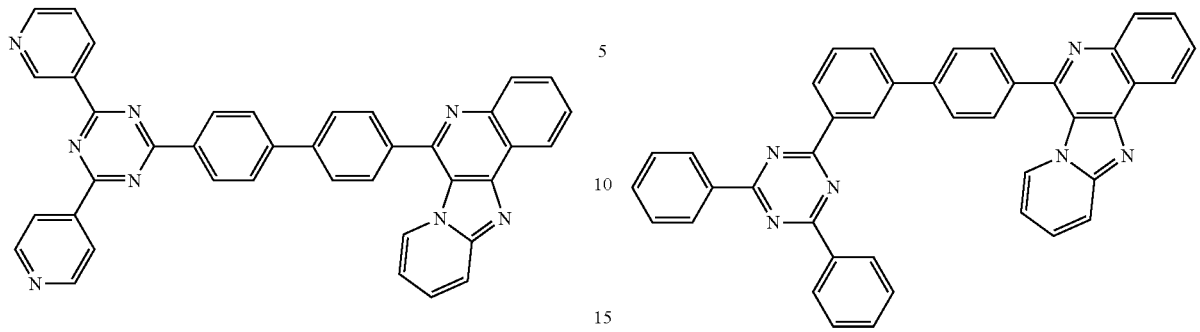

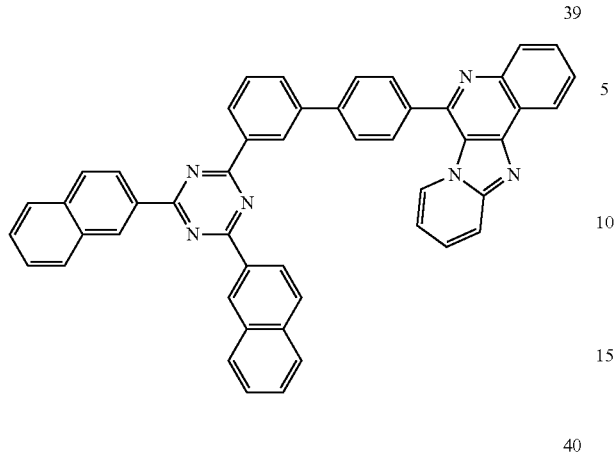
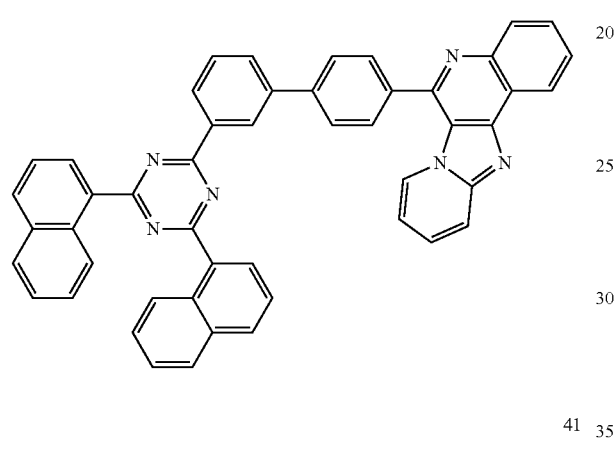
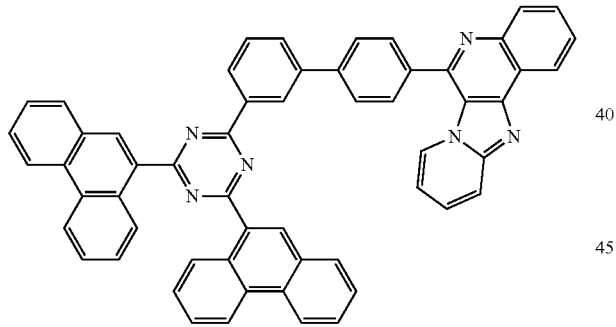
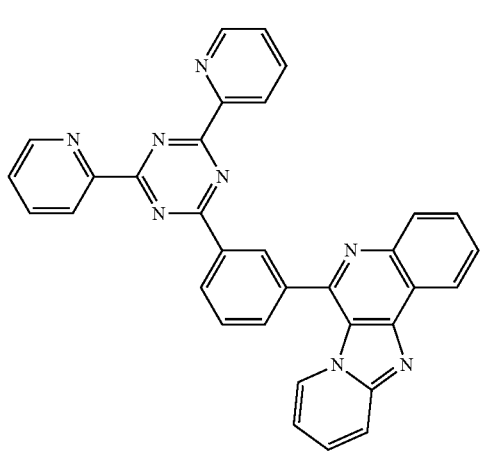
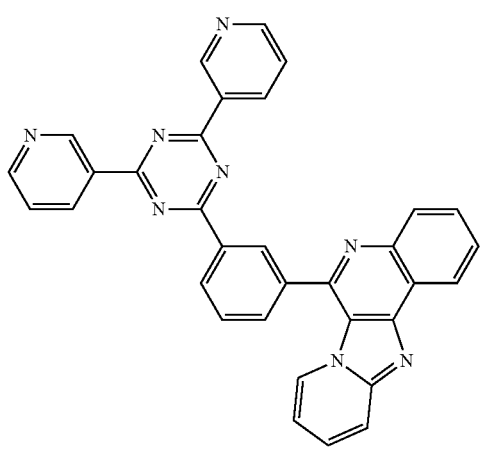
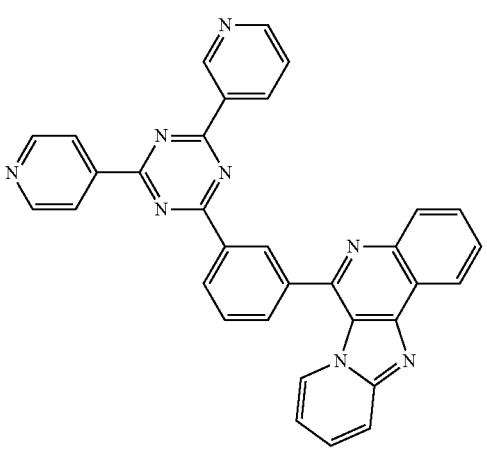

46
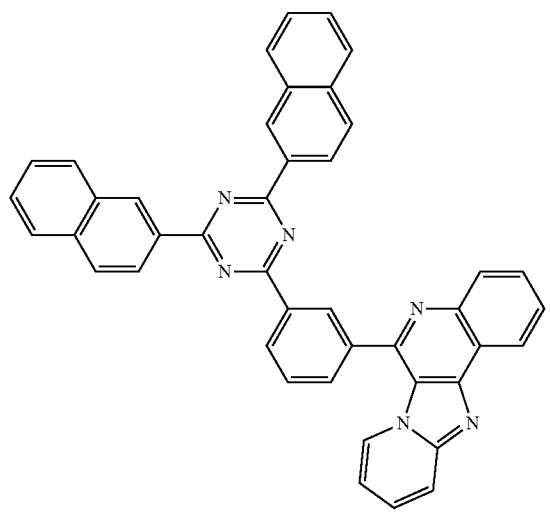
47
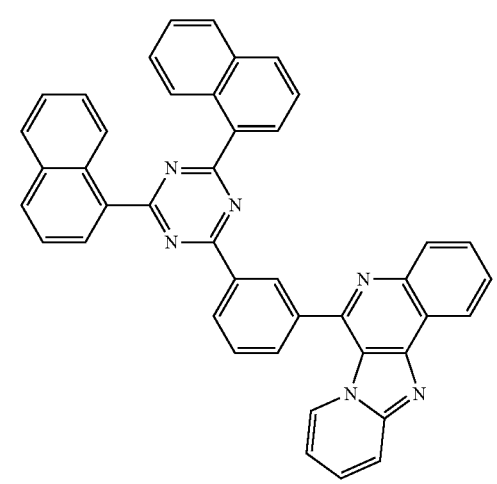
48
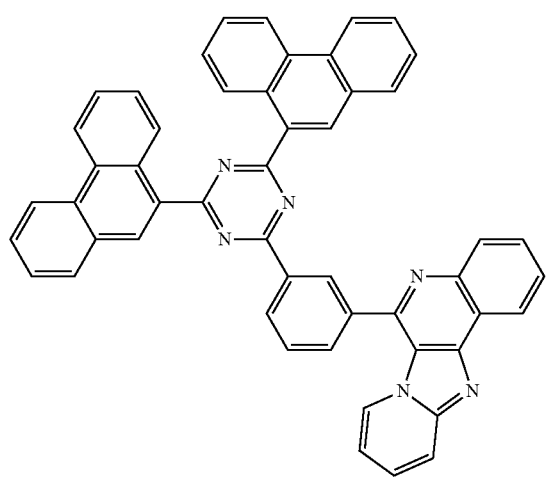
49
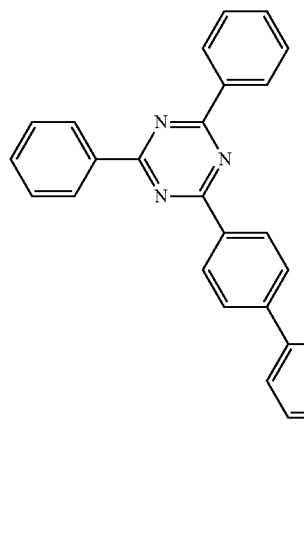
50
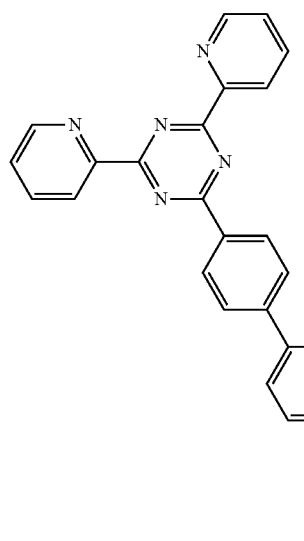

51
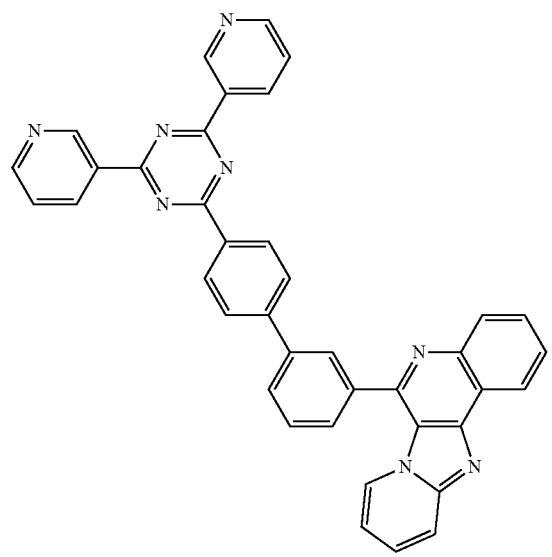
52
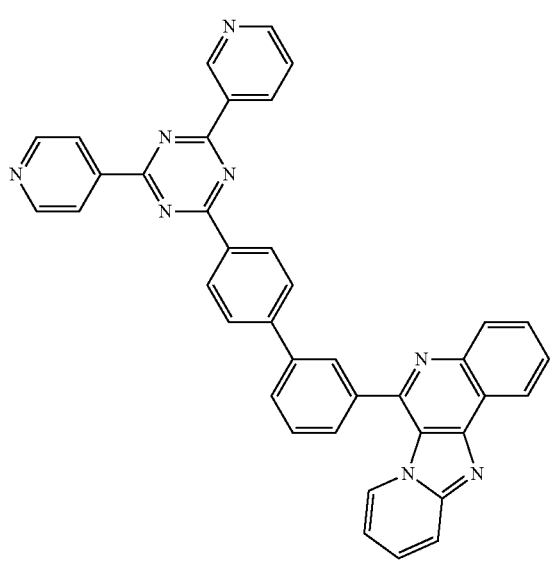
53
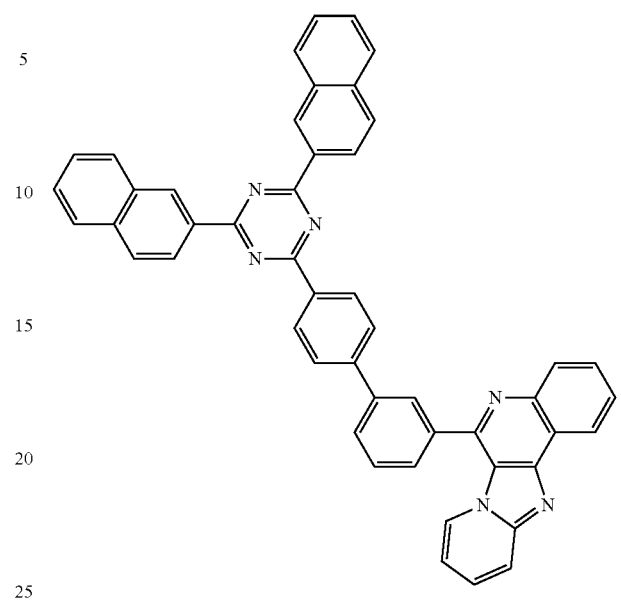
54
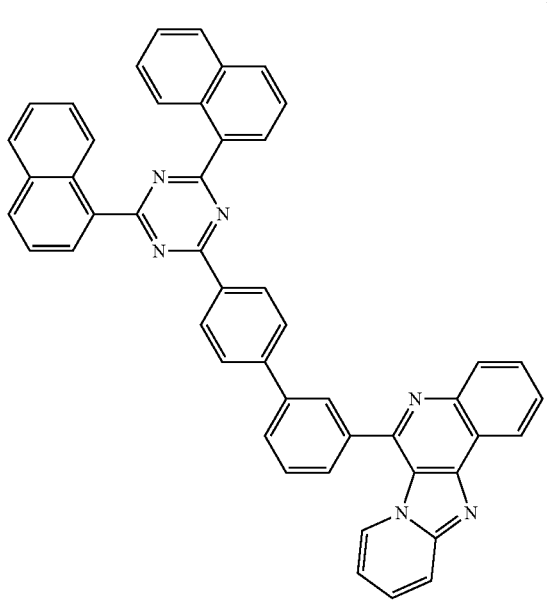

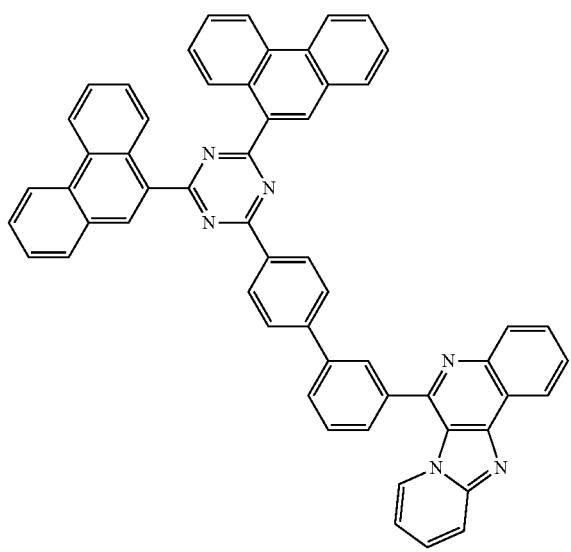
55
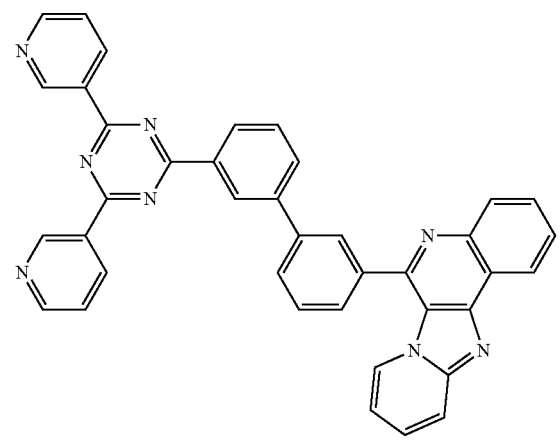
58
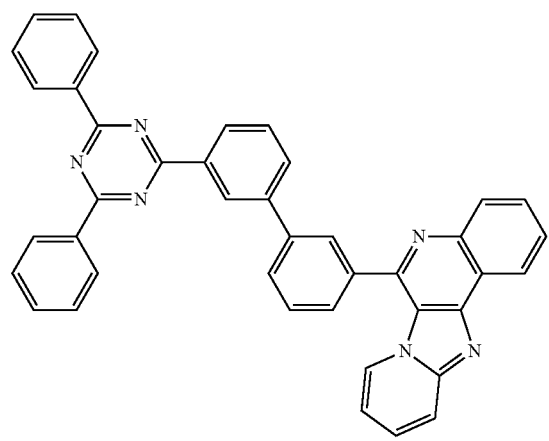
56
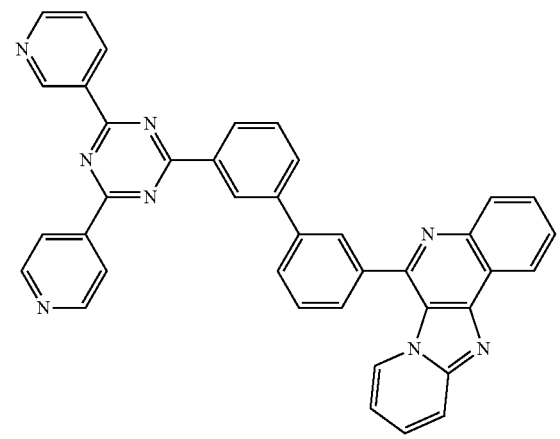
59
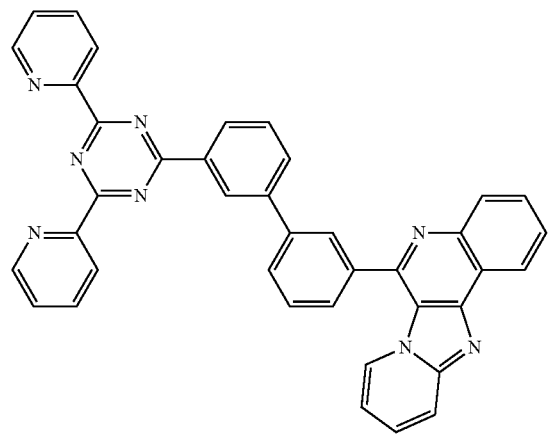
57
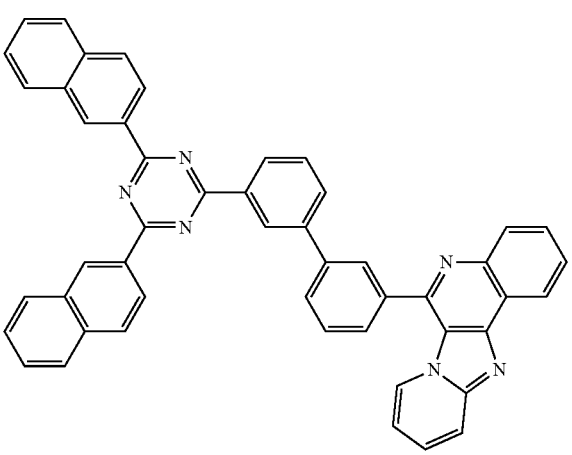
60

61
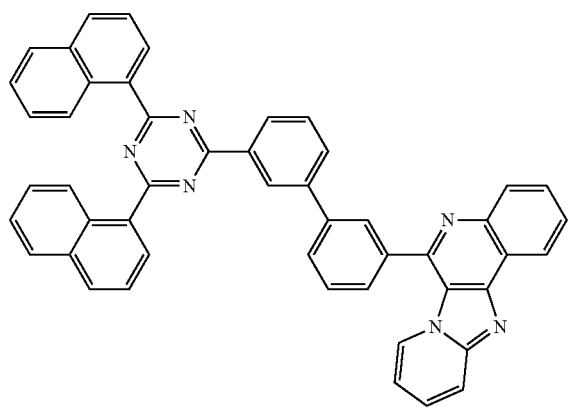
64
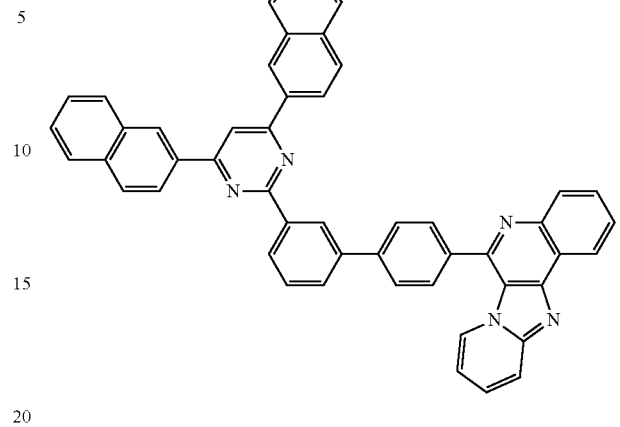
62
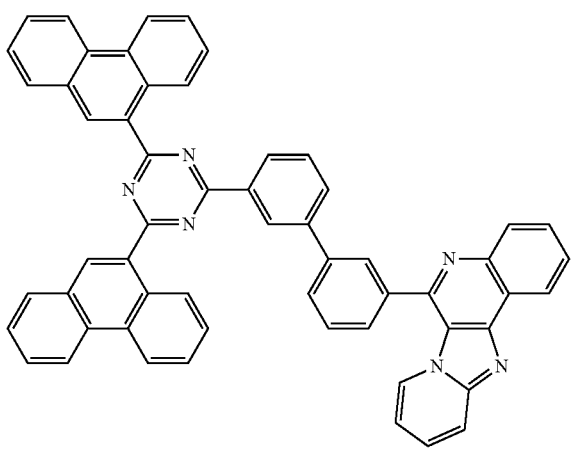
65
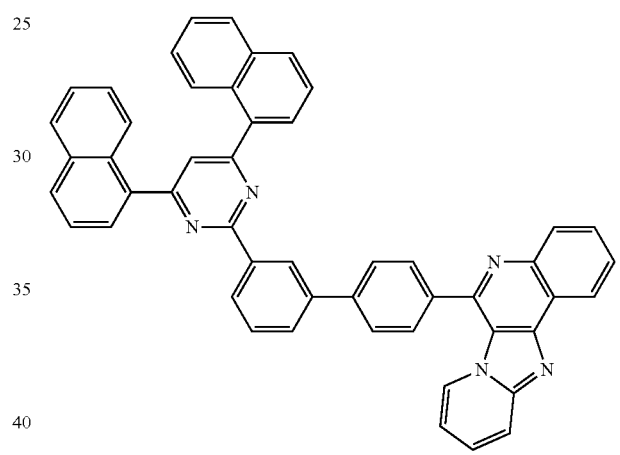
63
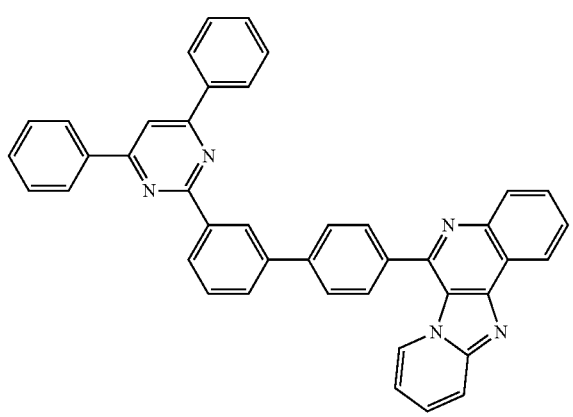
66
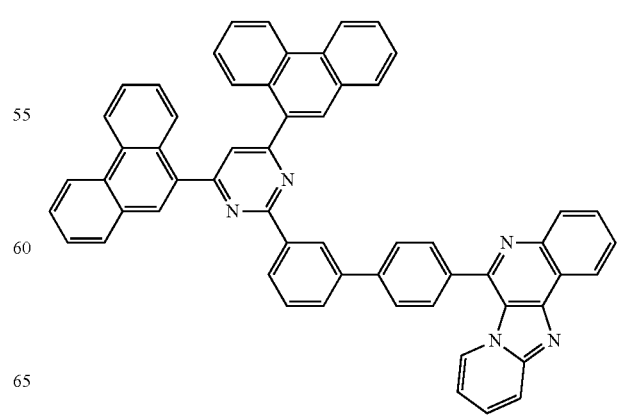

67
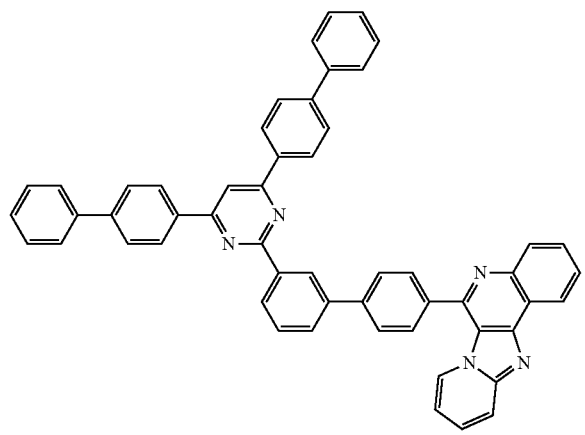
68
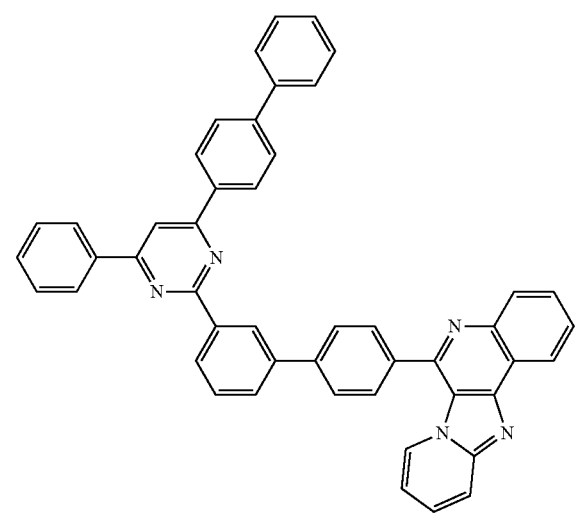
69
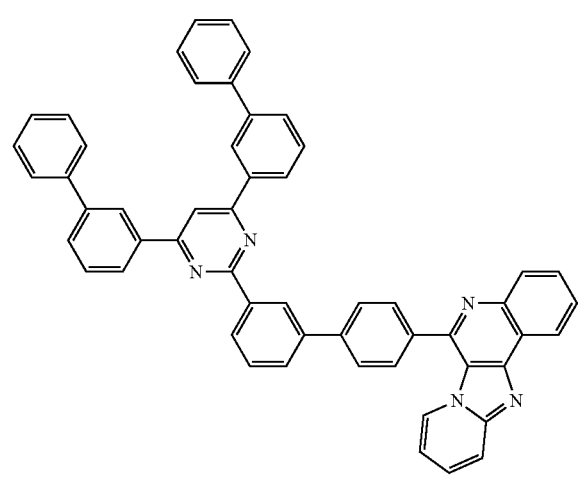
70
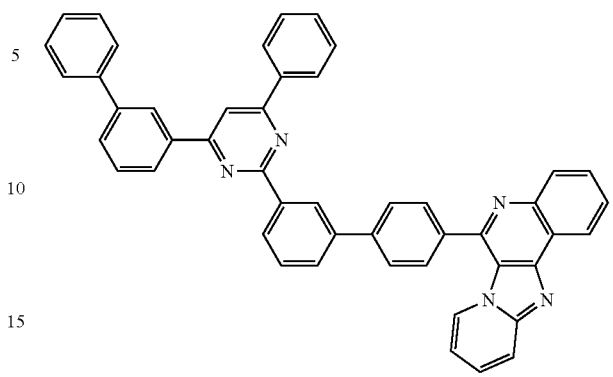
71
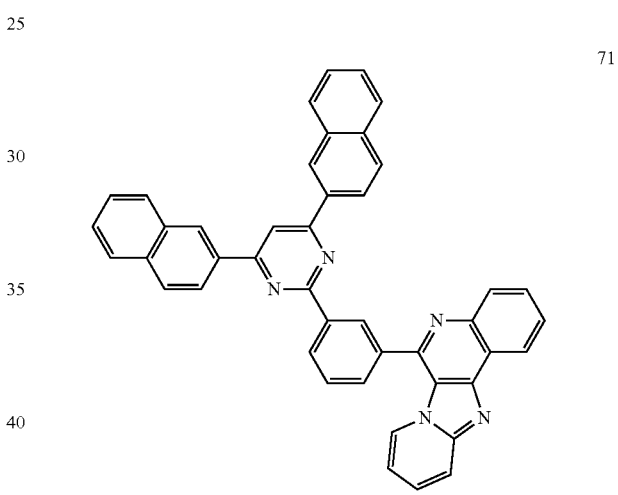
72
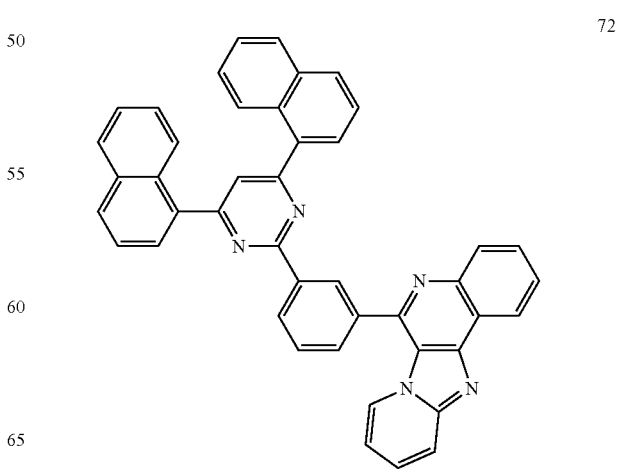

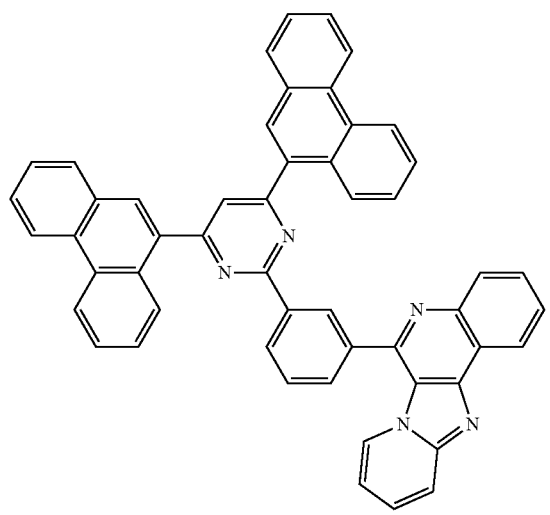
73
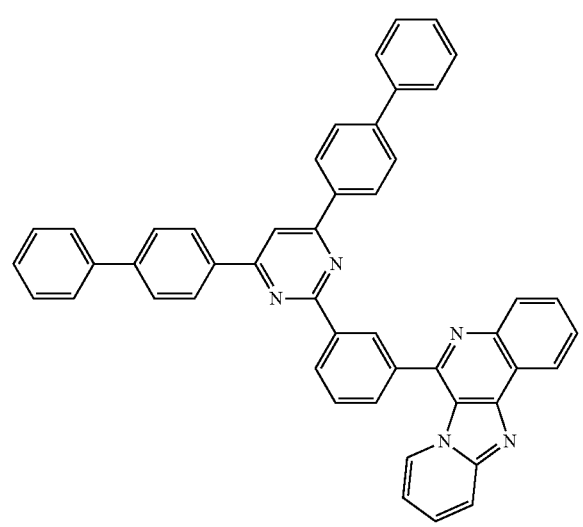
74
75
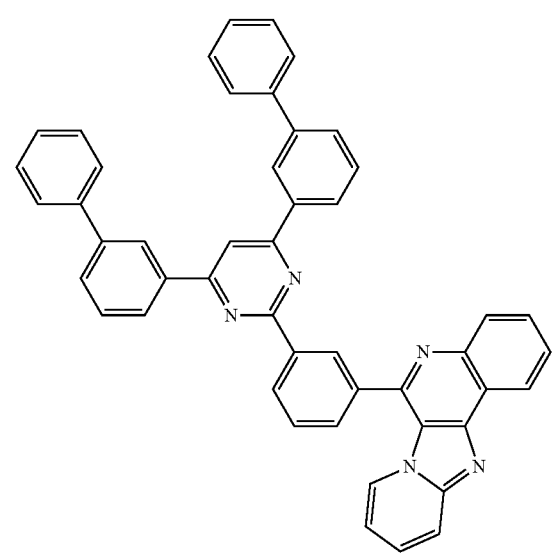
76
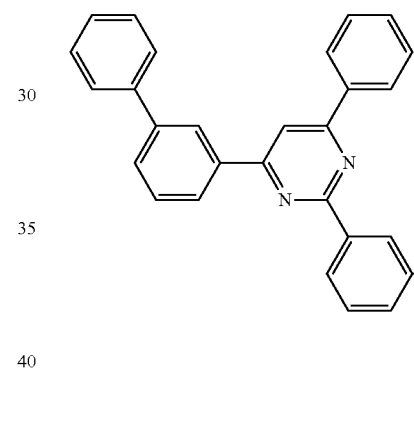
77
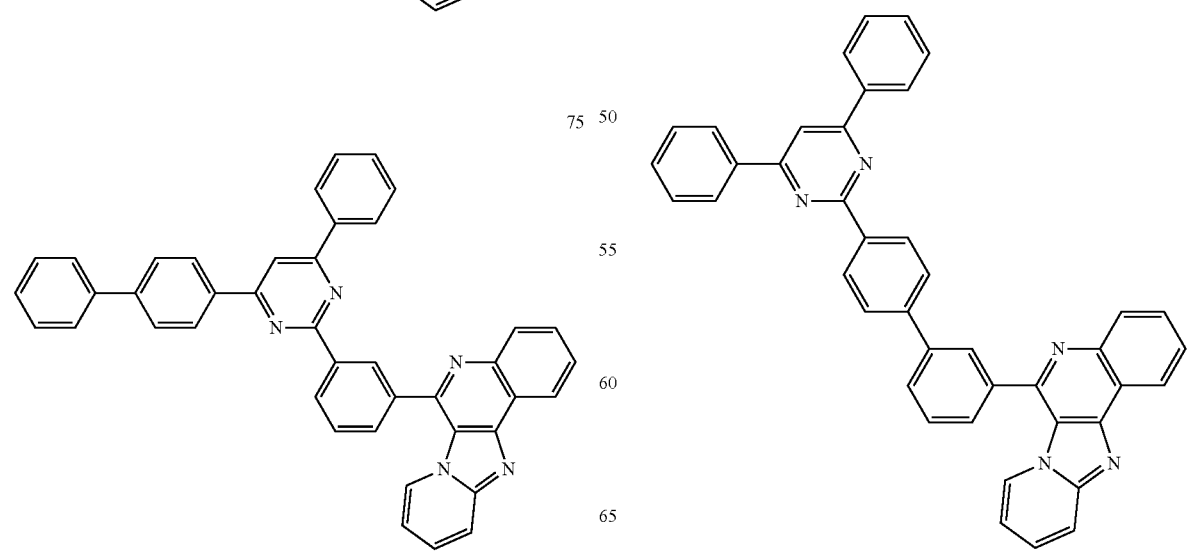
78

79
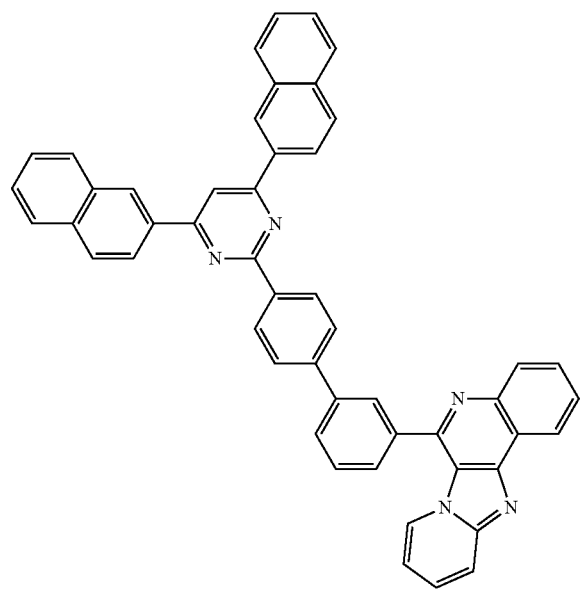
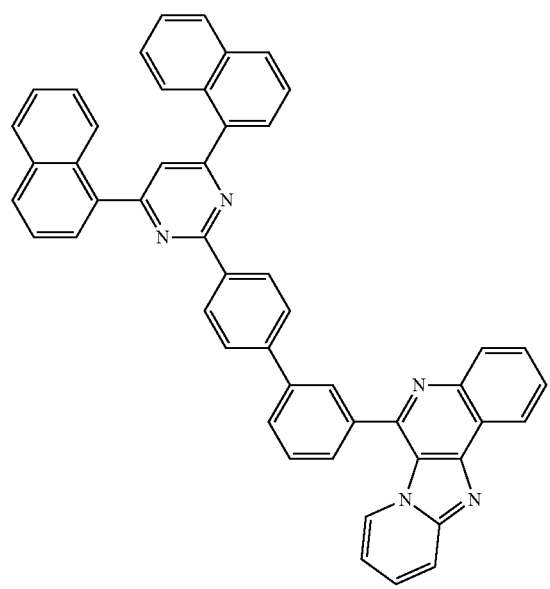
81
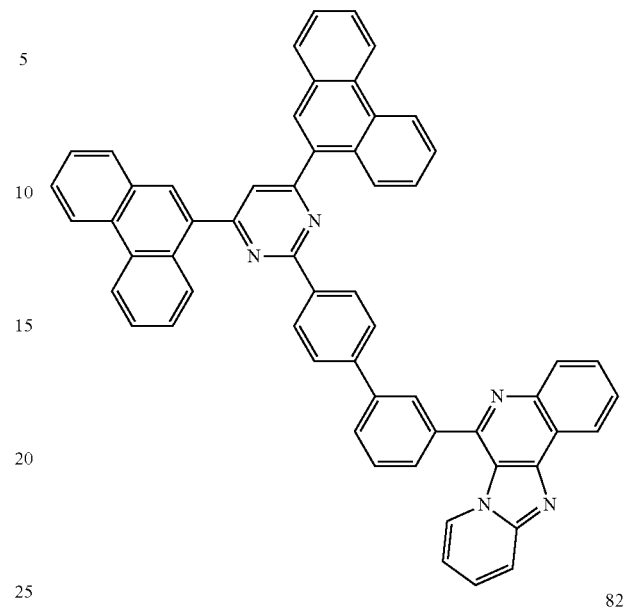
82
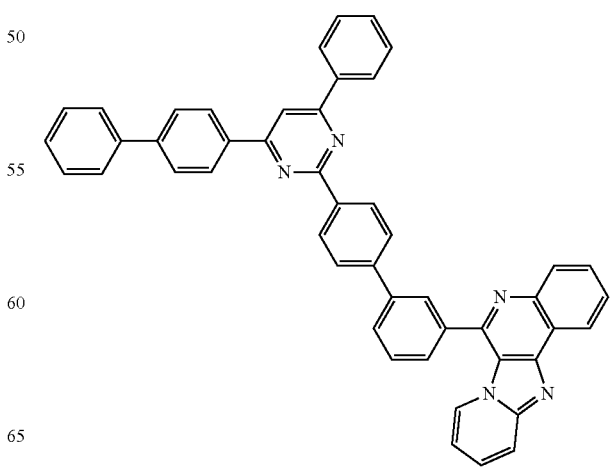
83

84
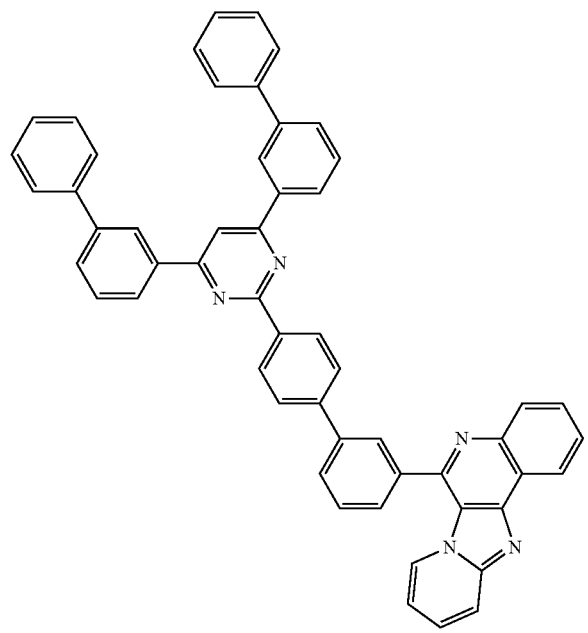
85
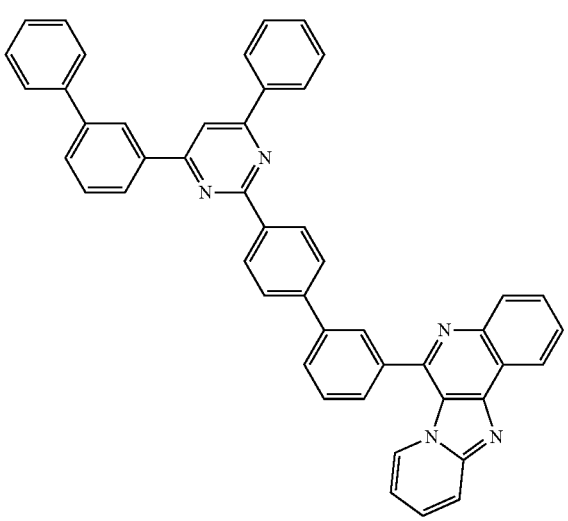
86
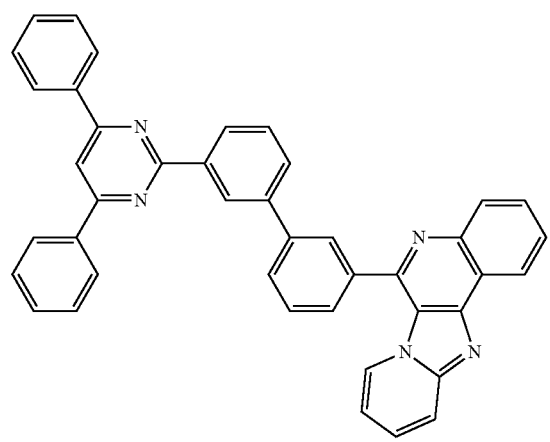
87
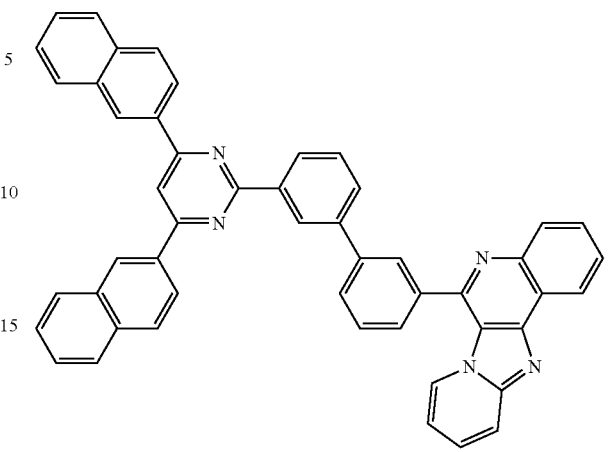
88
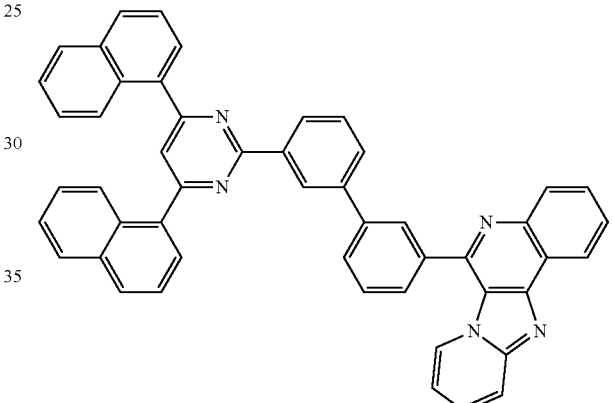
89
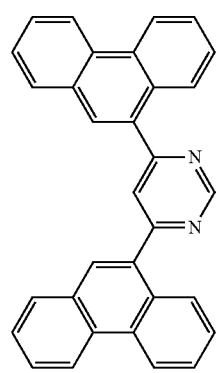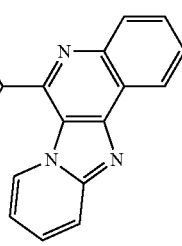

90
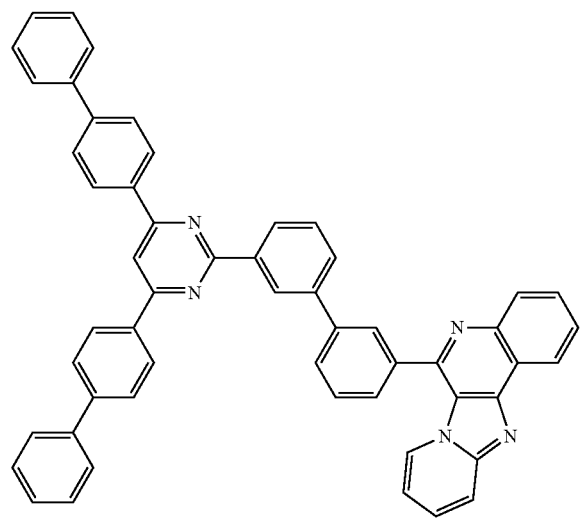
91
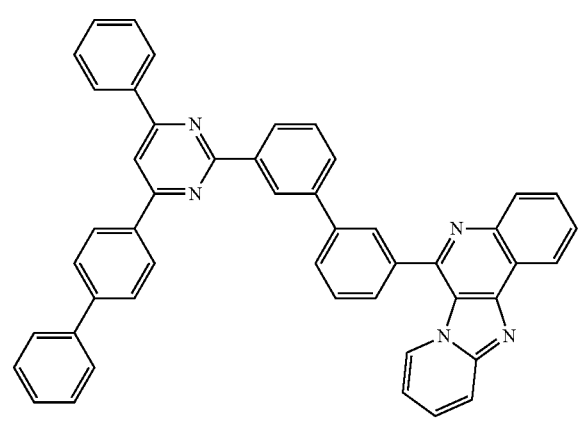
92
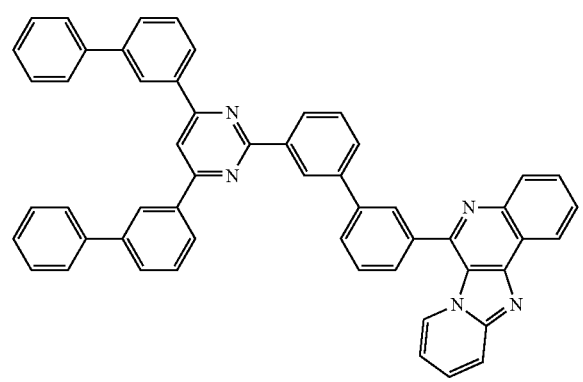
93
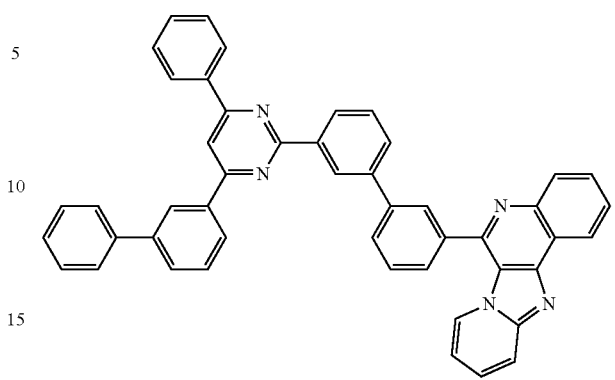
94
95
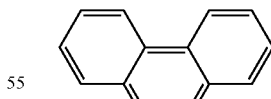
96
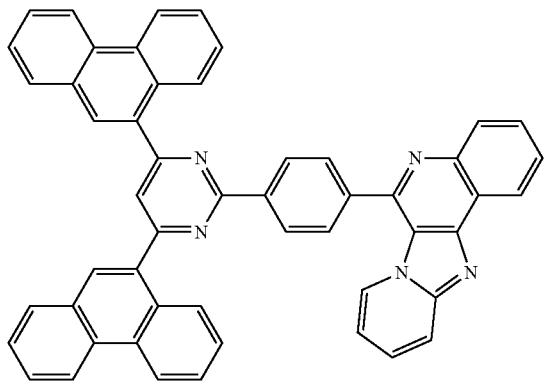

97
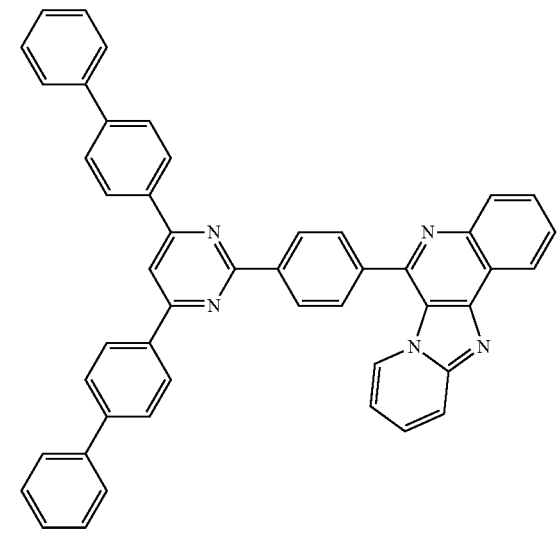
98
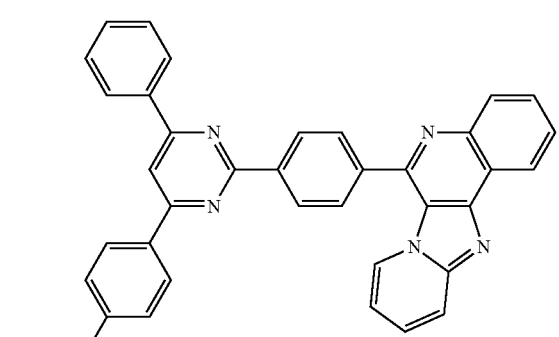
99
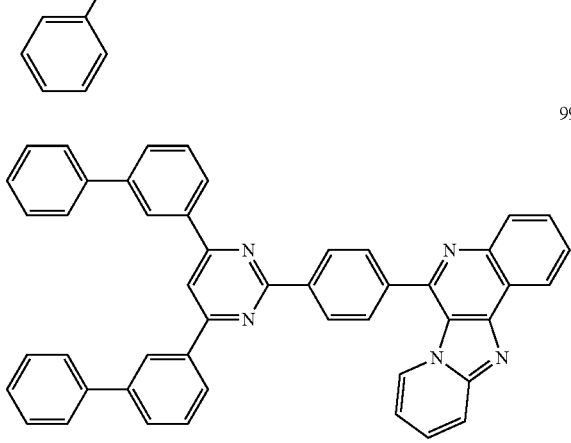
100
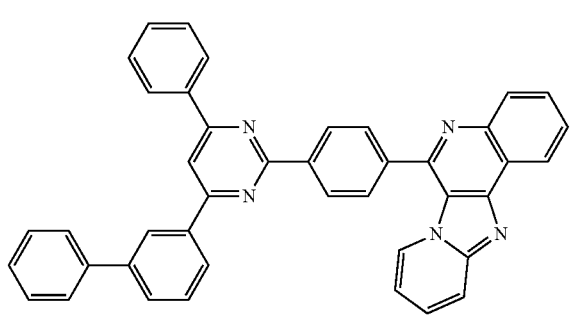
101
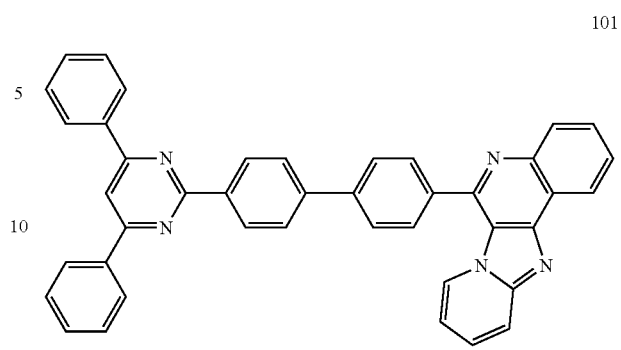
102
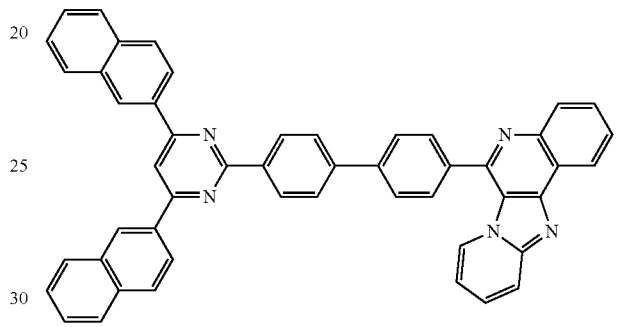
103
104

105
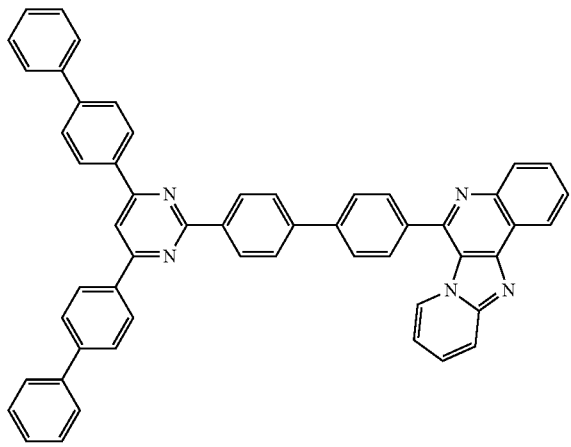
106
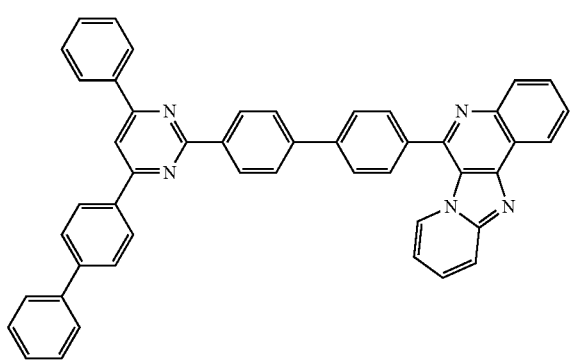
107
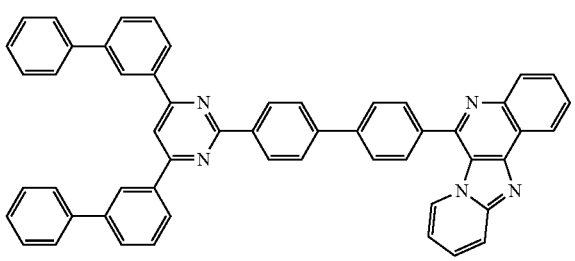
108
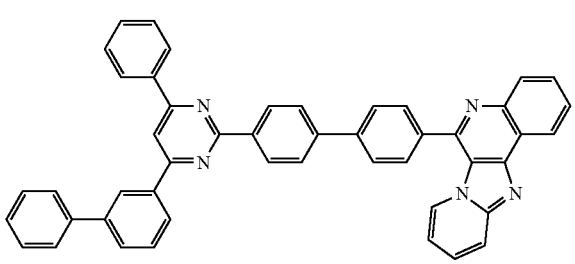
109
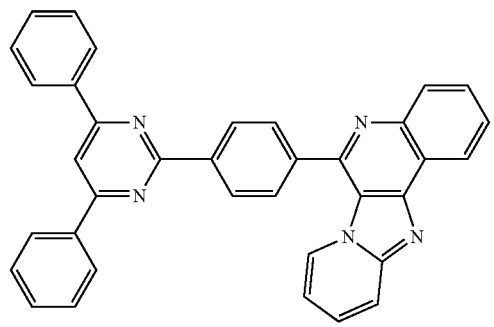
110
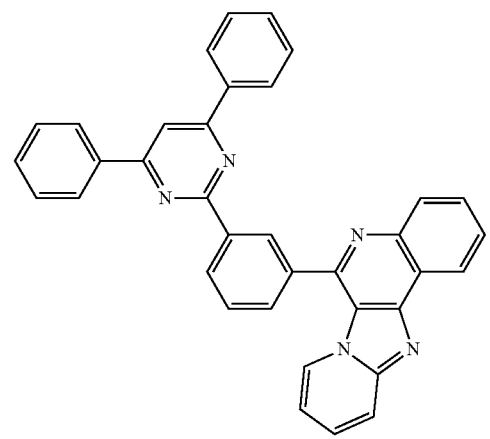
111
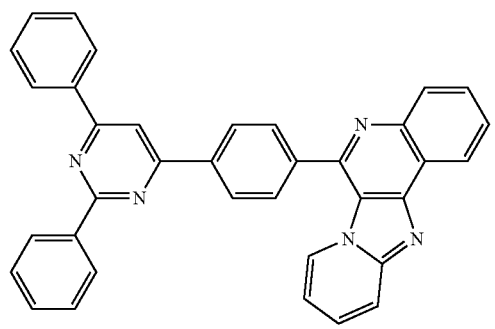
112
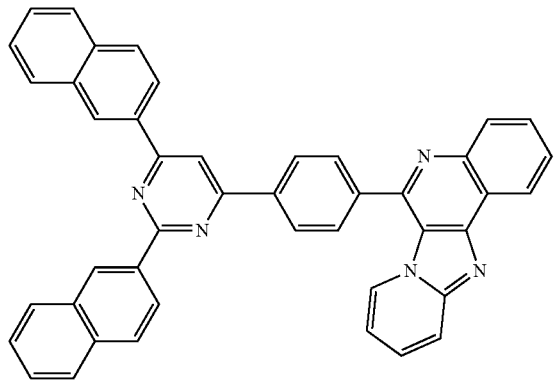

113
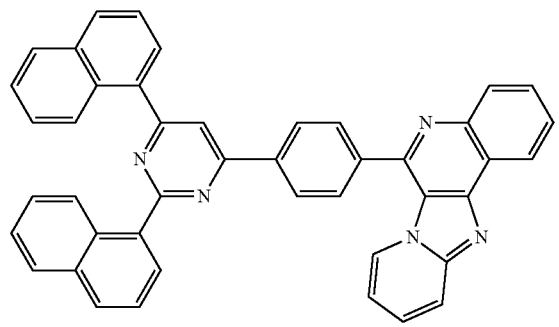
114
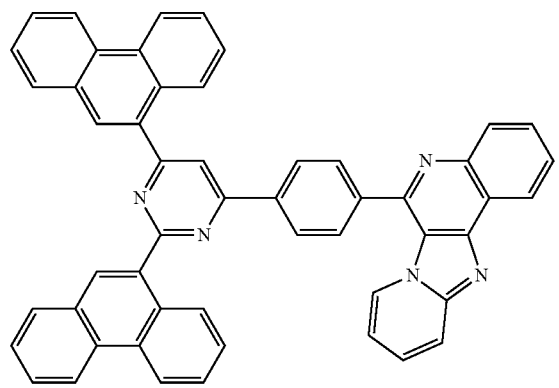
115
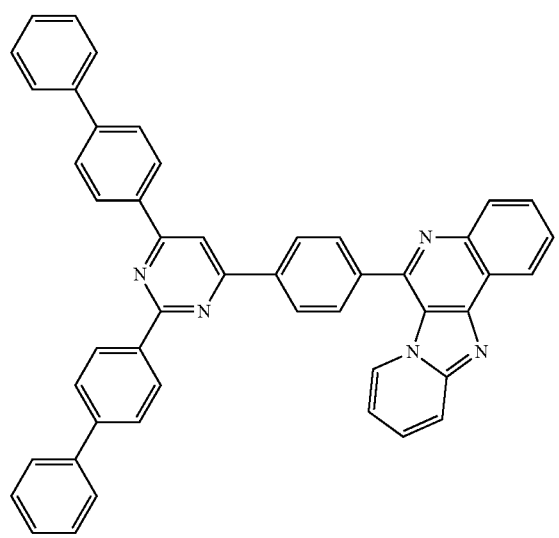
116
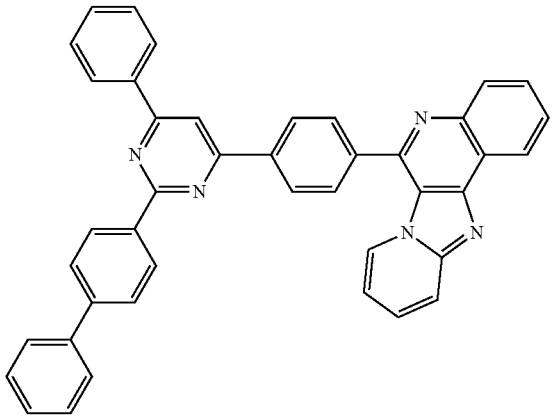
117
118
119
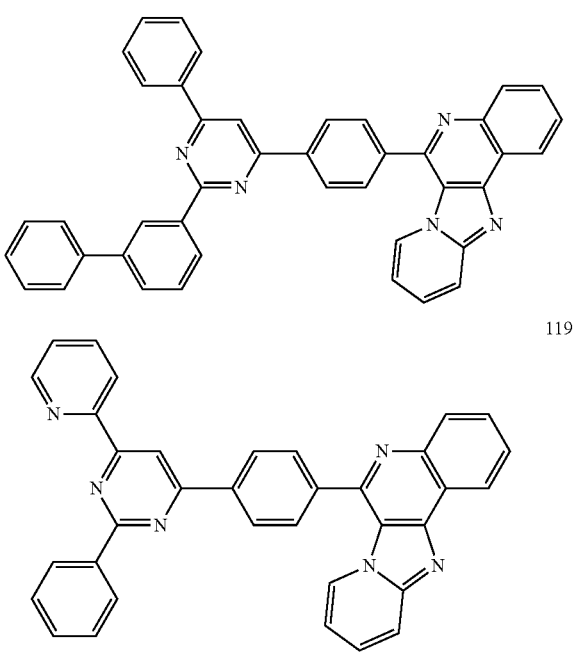

120
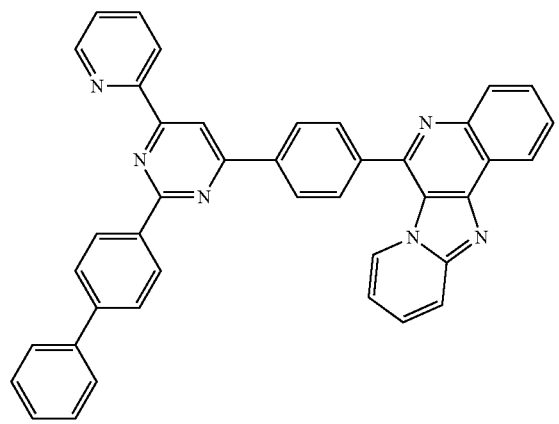
121
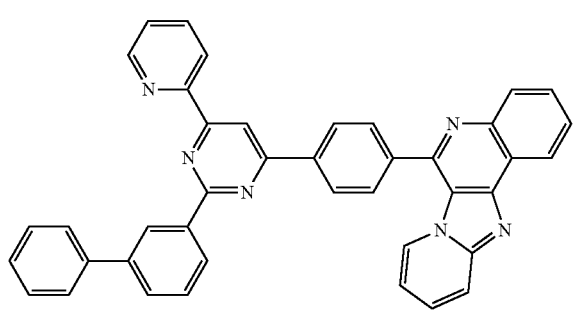
122
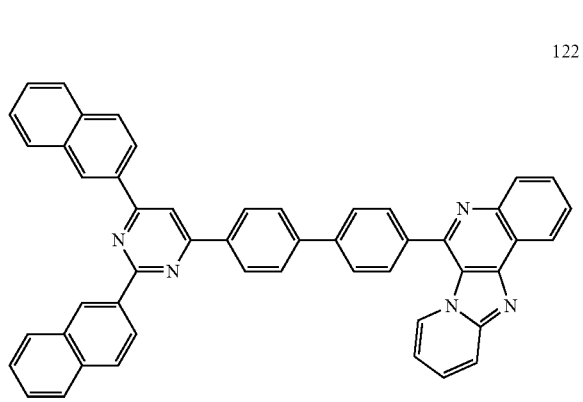
123
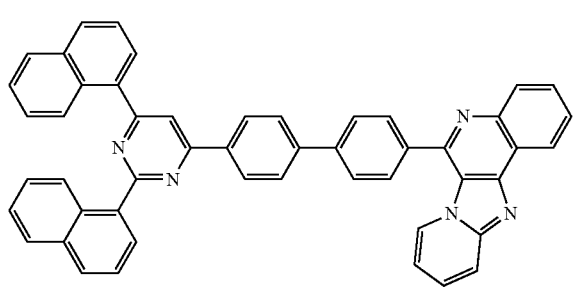
124
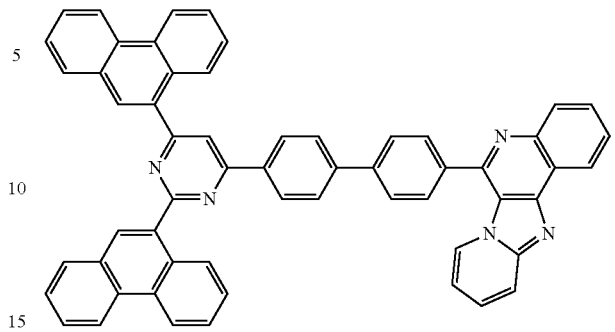
125
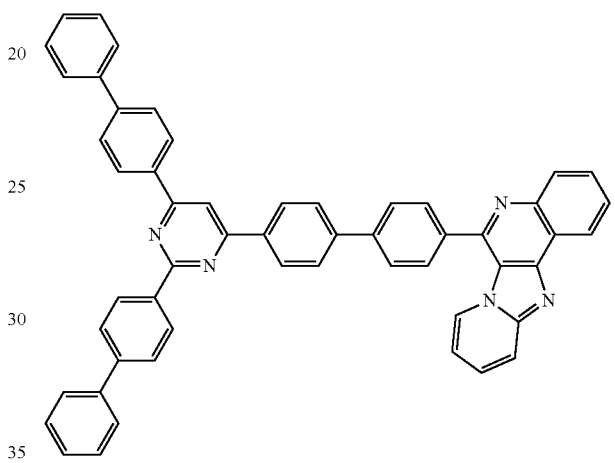
126
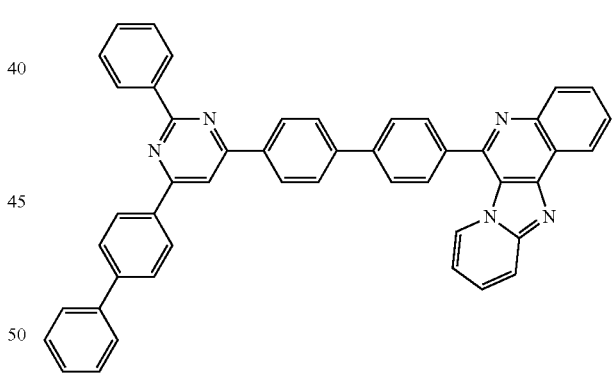
127
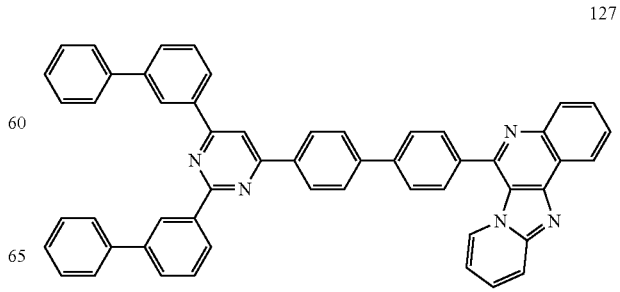

128
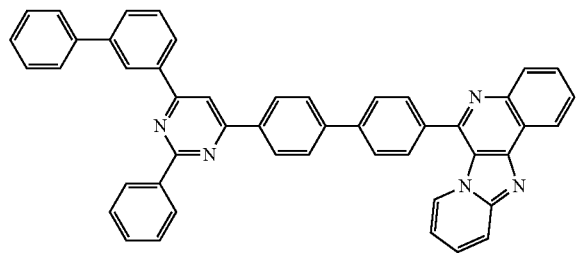
129
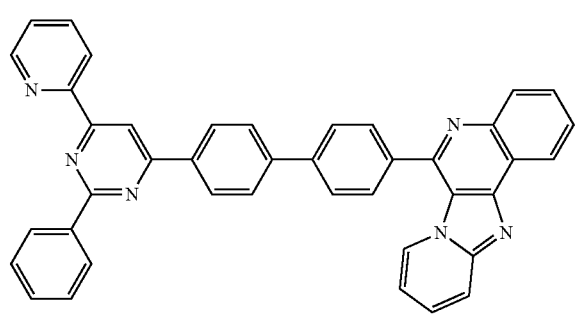
130
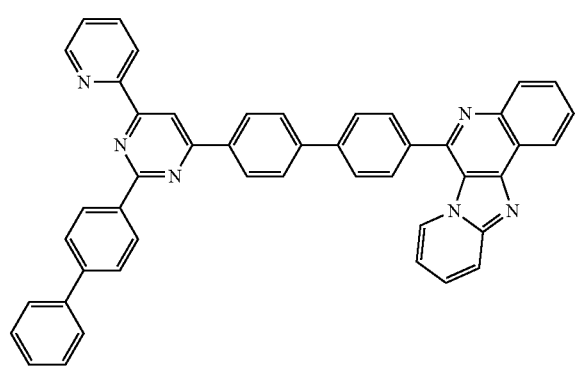
131
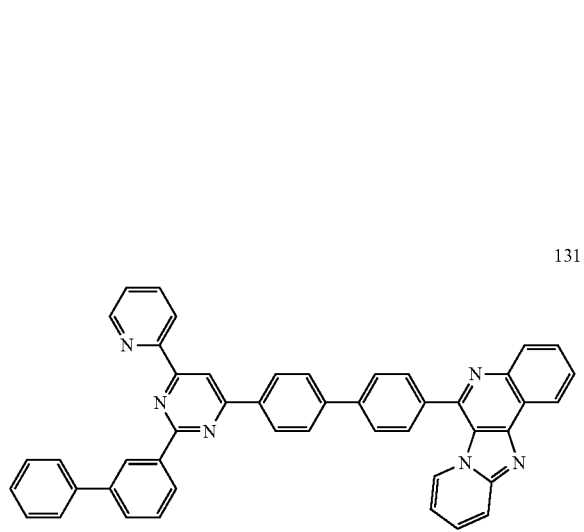
132
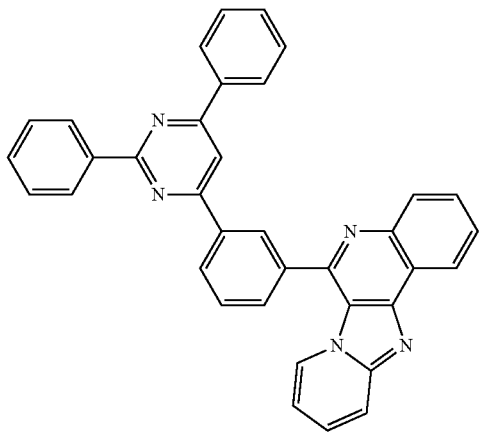
133
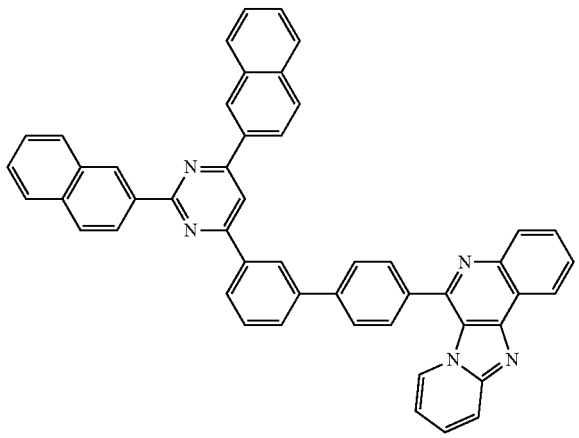
134
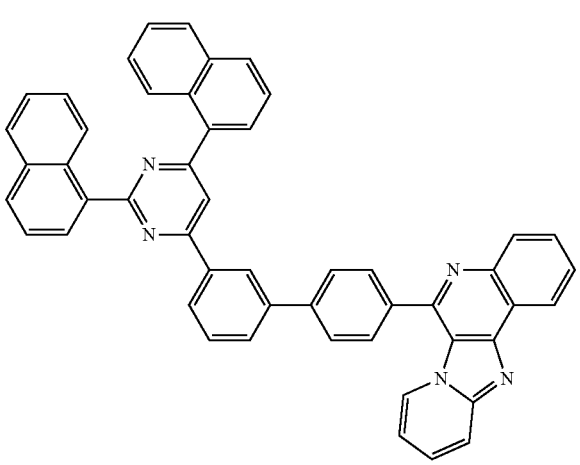

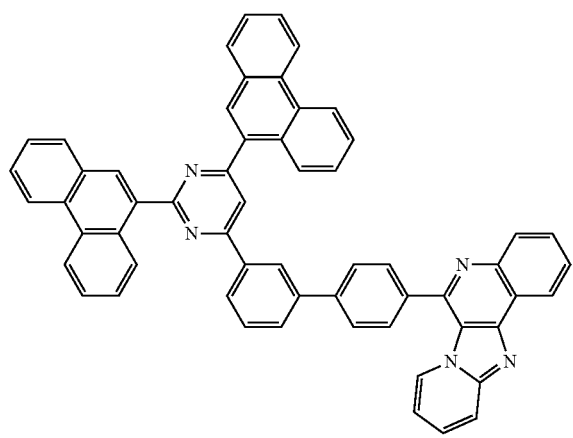
135
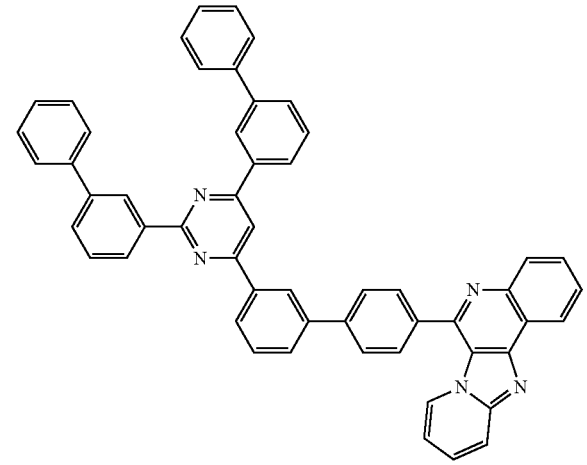
139
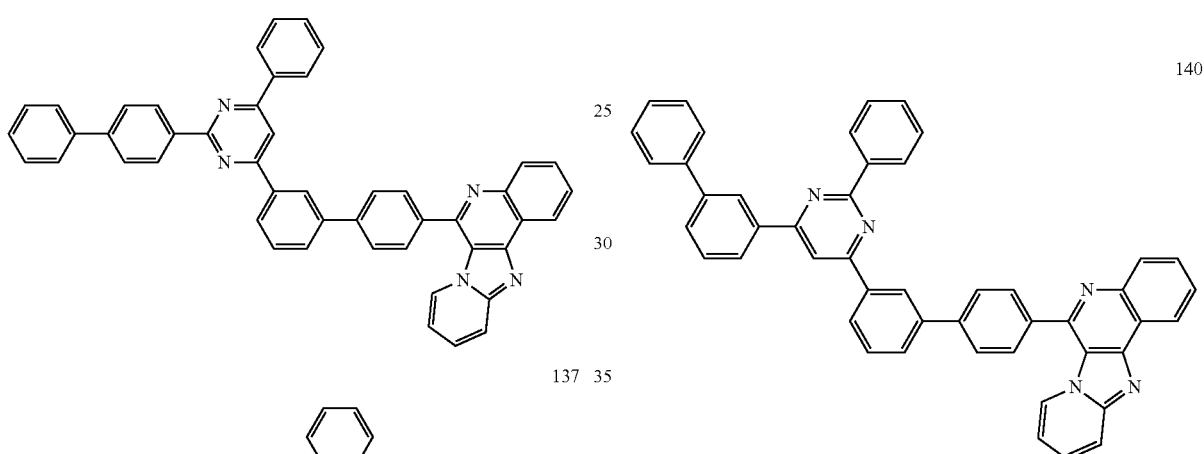
136
140
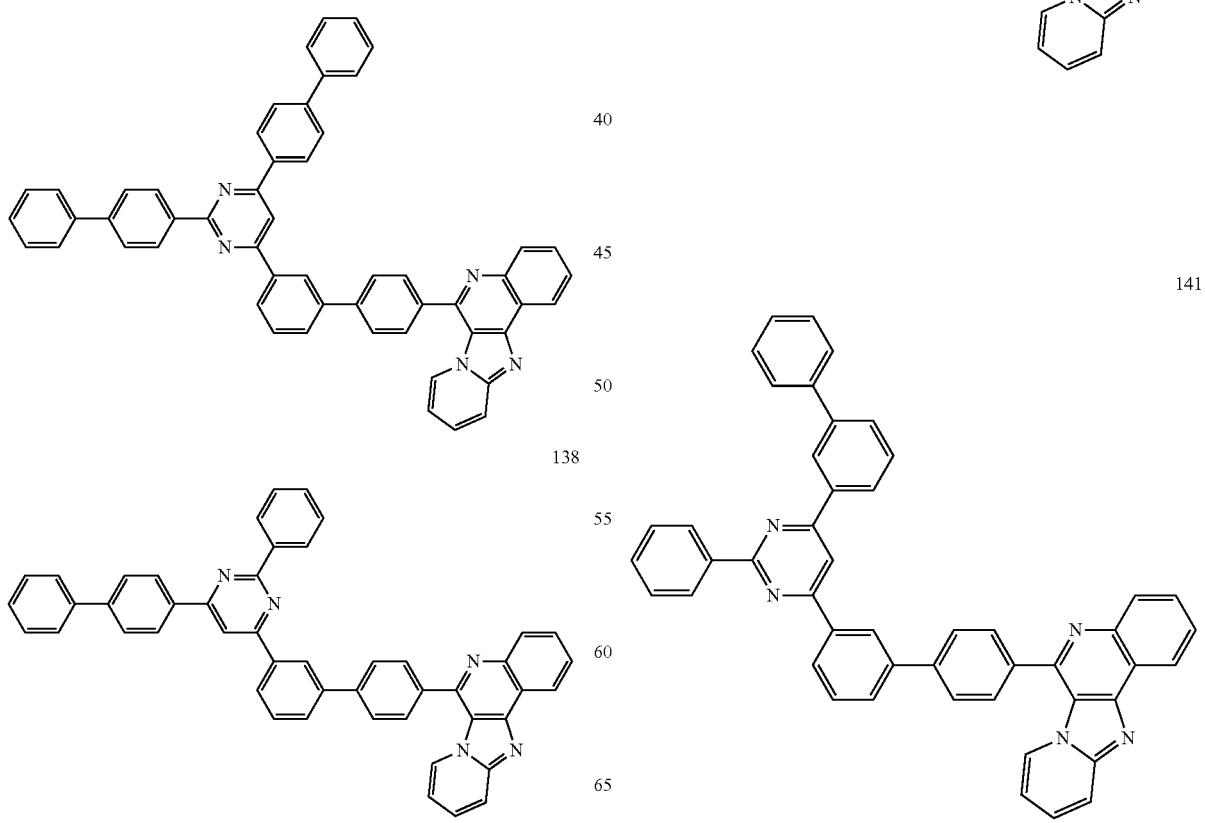
137
141
138

142
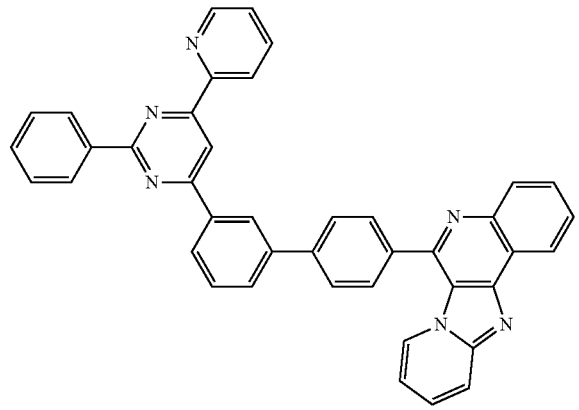
143
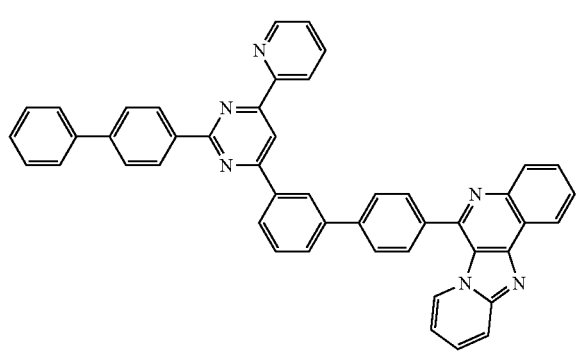
144
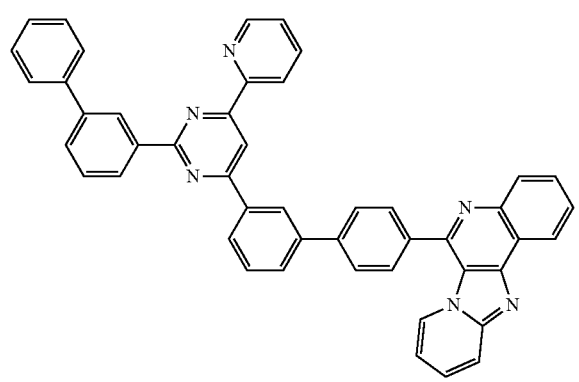
145
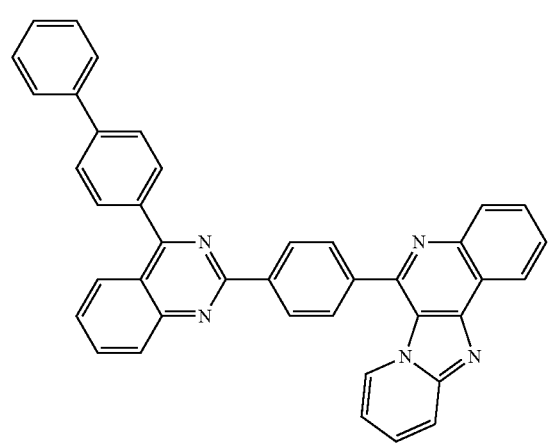
146
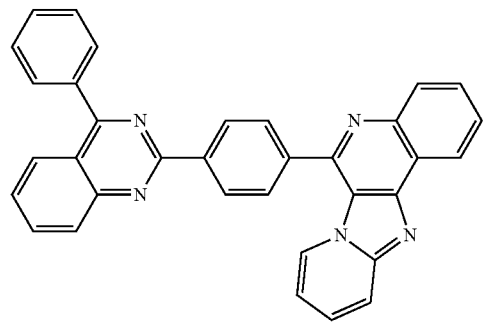
147
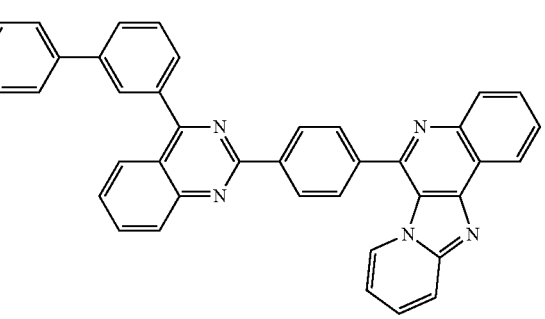
148
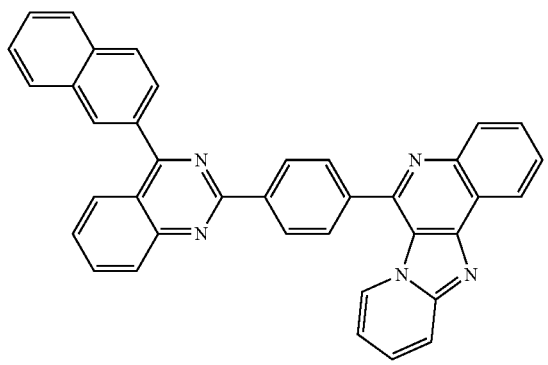
149
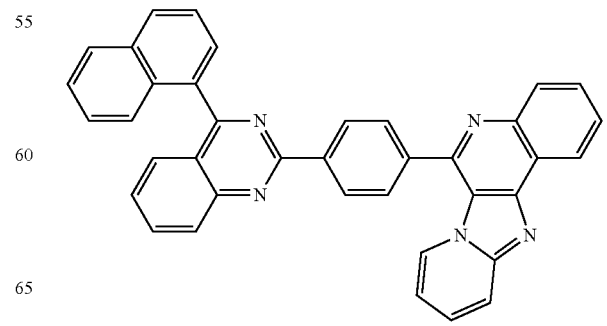

150
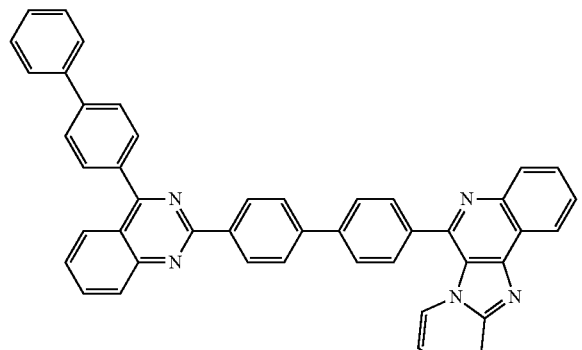
151
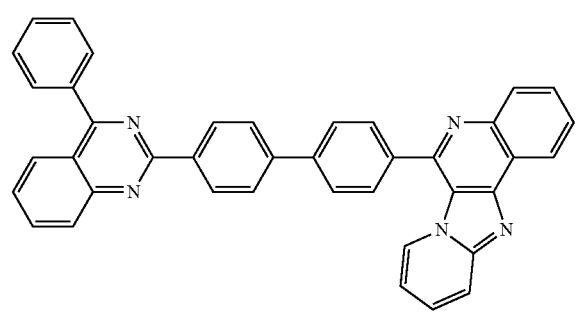
152
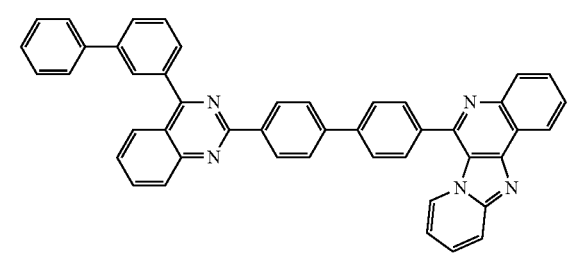
153
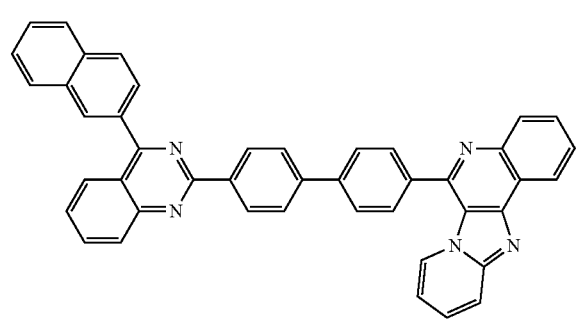
154
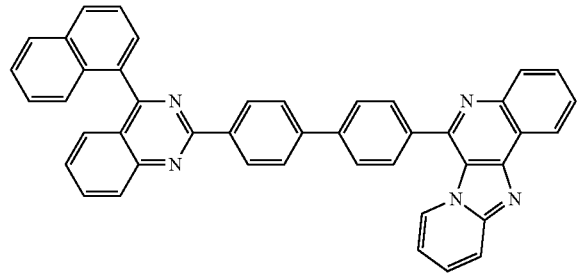
155
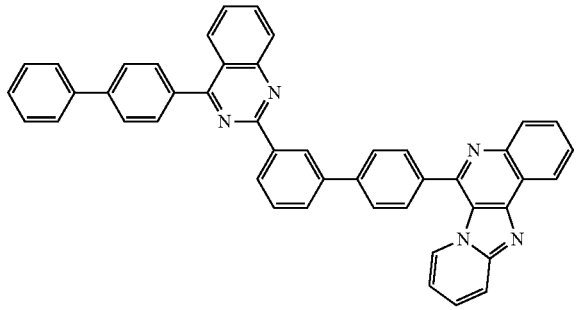
156
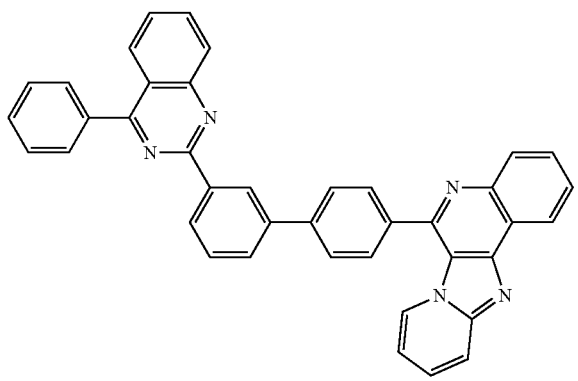
157
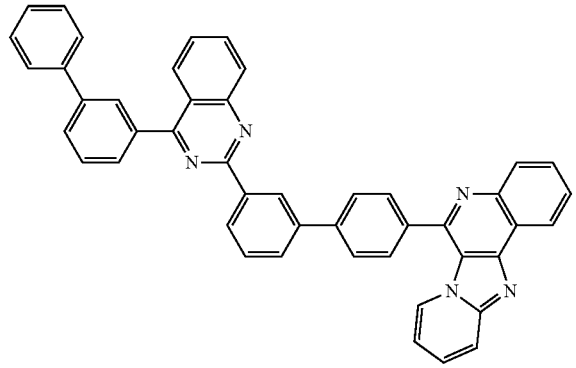
158
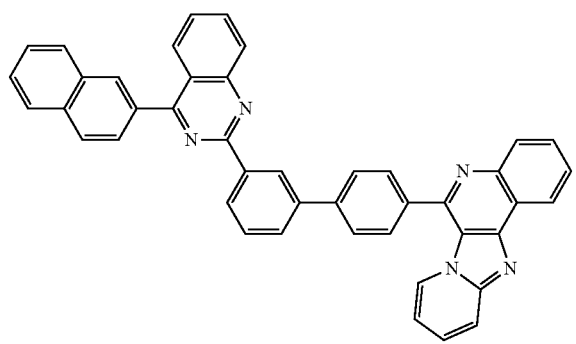

-continued
159
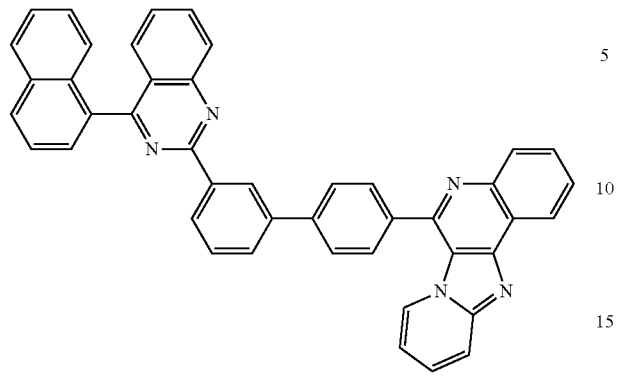
160
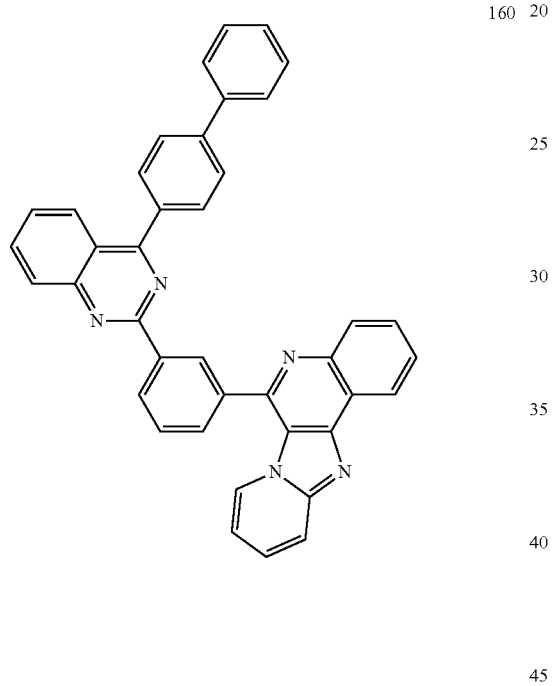
161
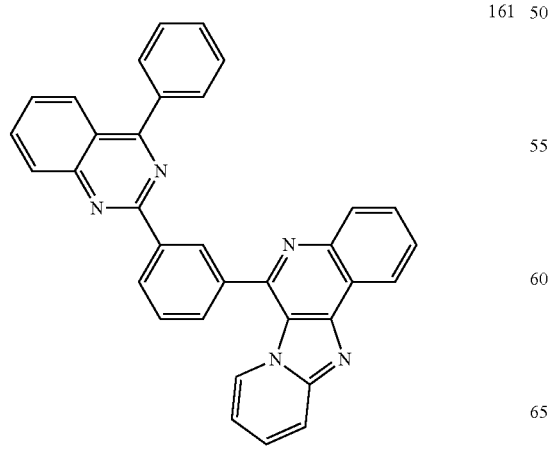
-continued
162
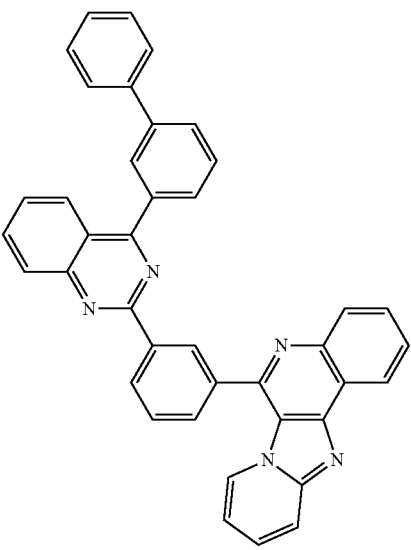
163
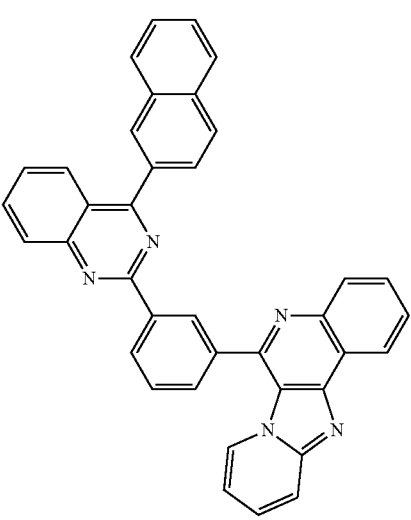
164
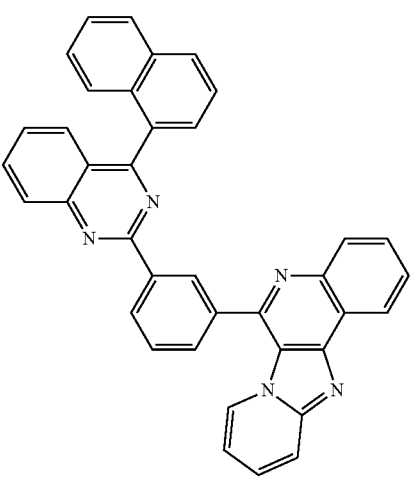

381
-continued
165
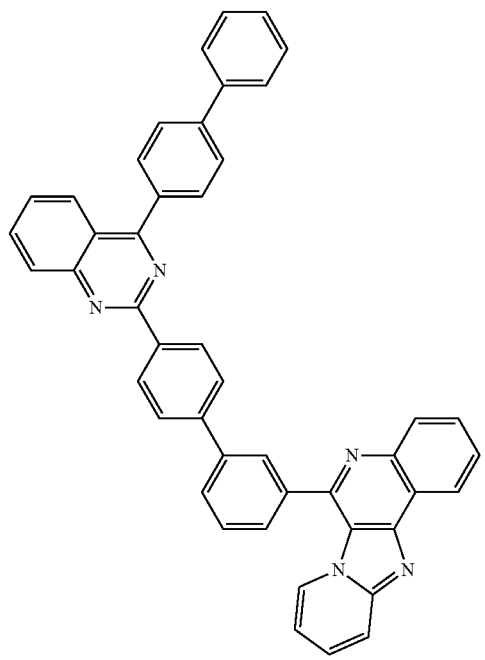
166
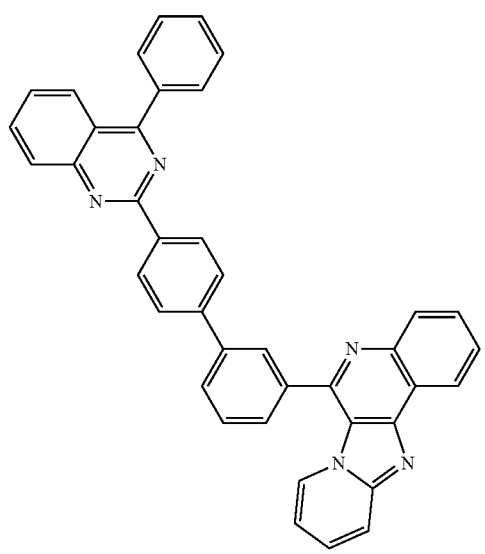
382
-continued
167
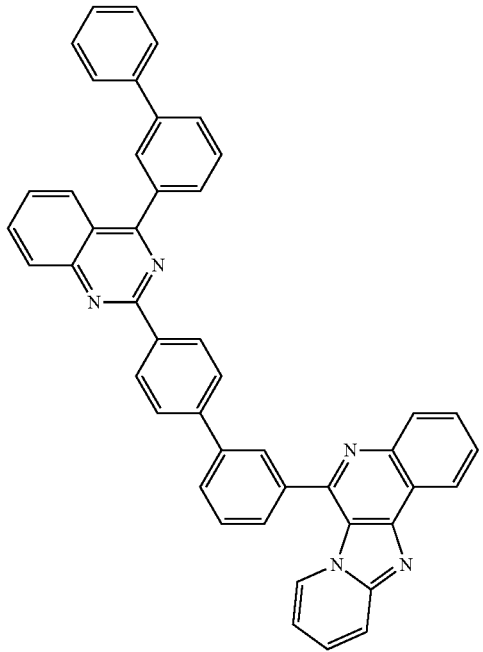
168
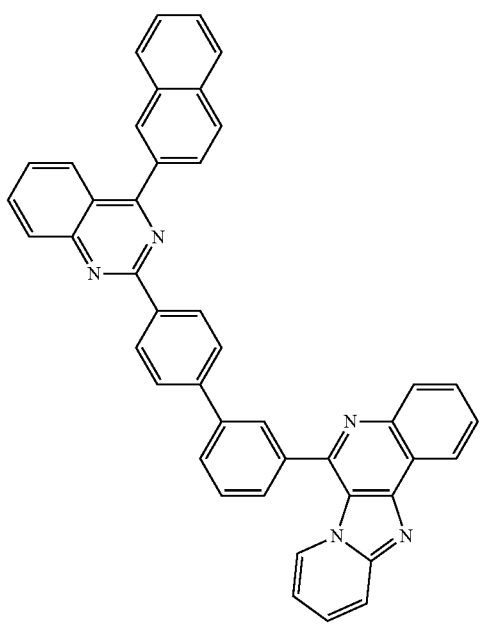

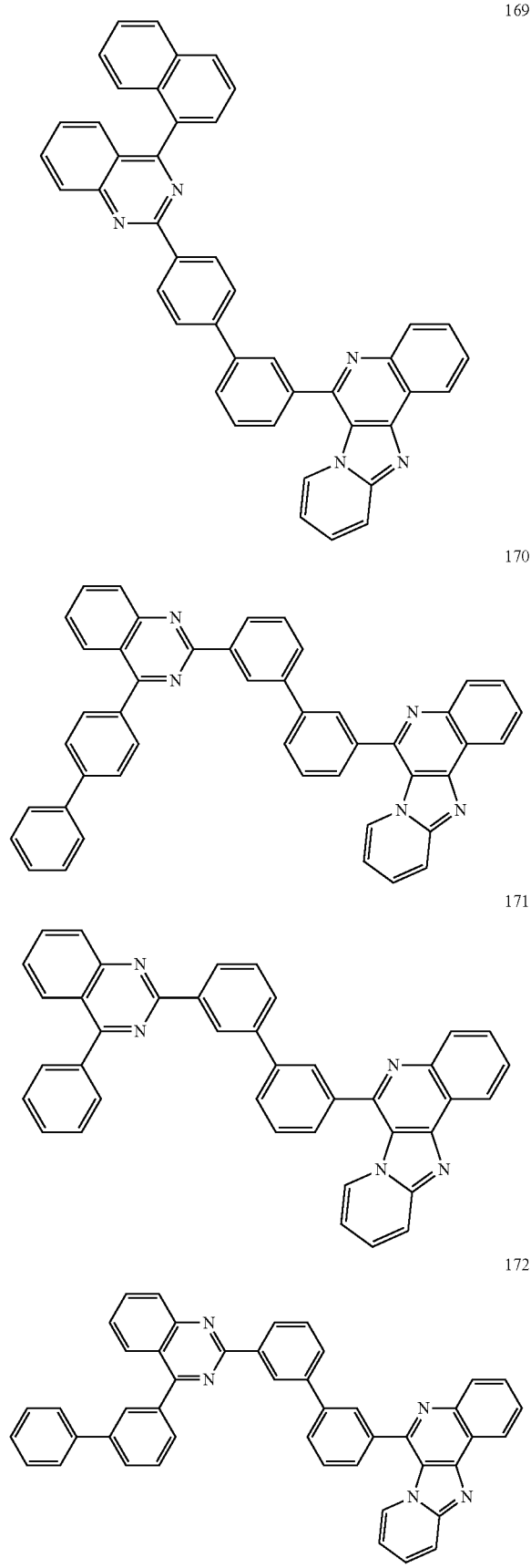
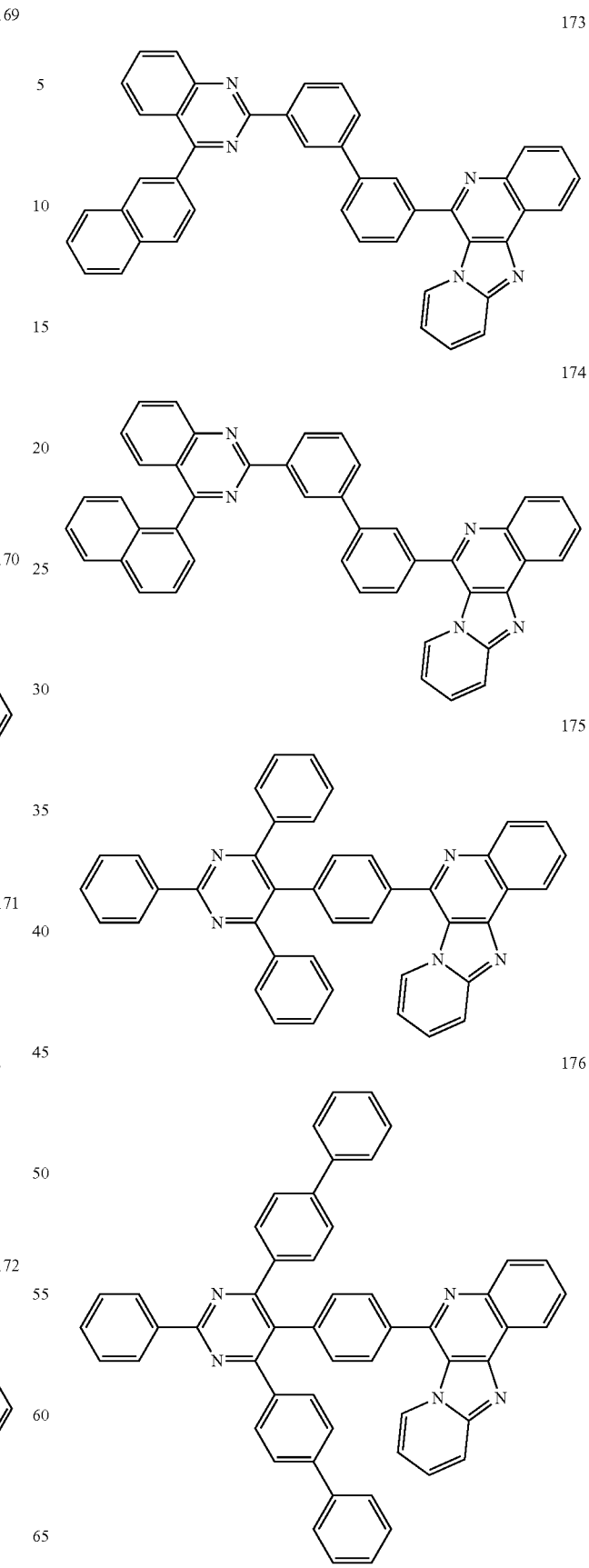

177
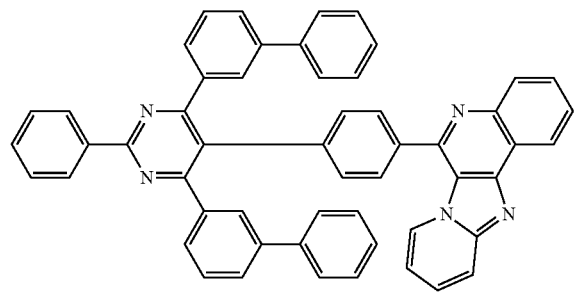
178
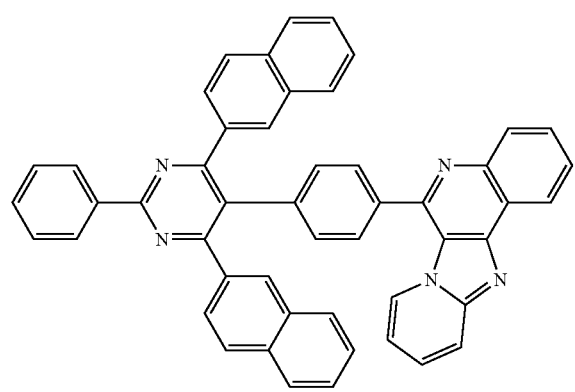
179
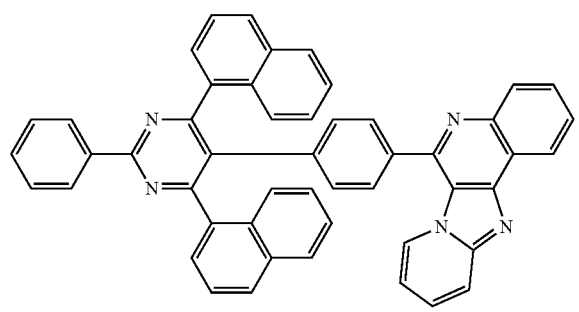
180
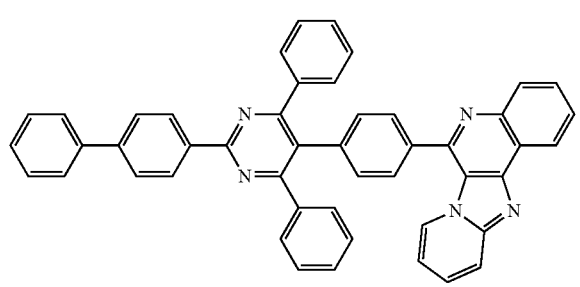
181
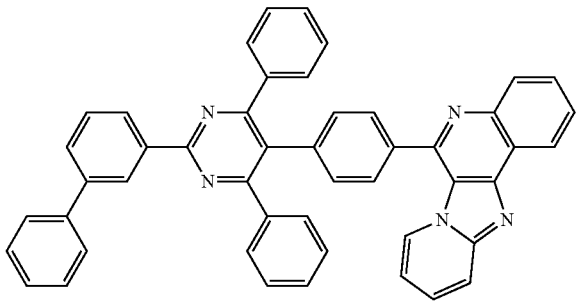
182
183
184
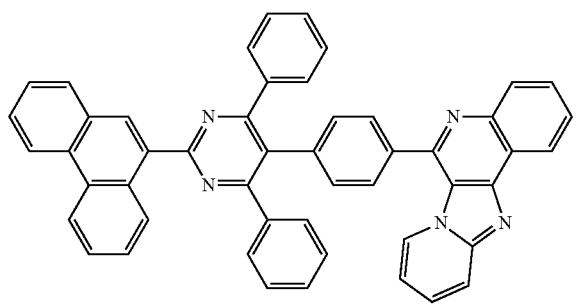

185
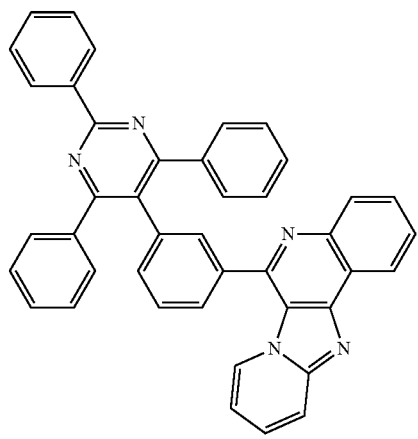
186
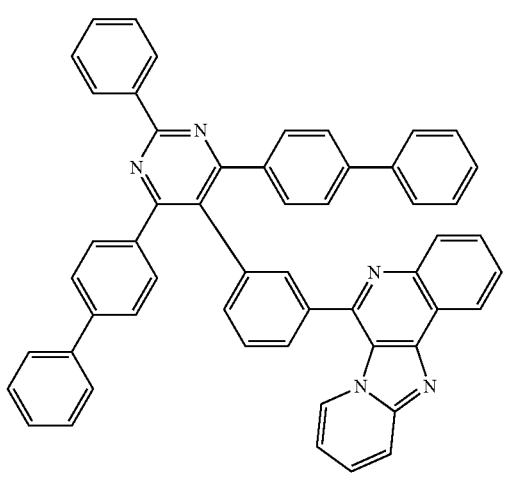
187
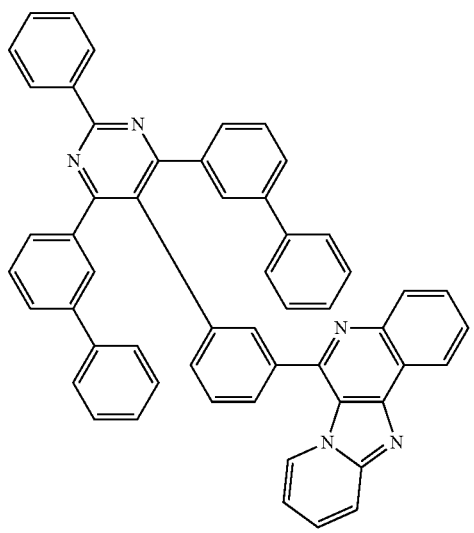
188
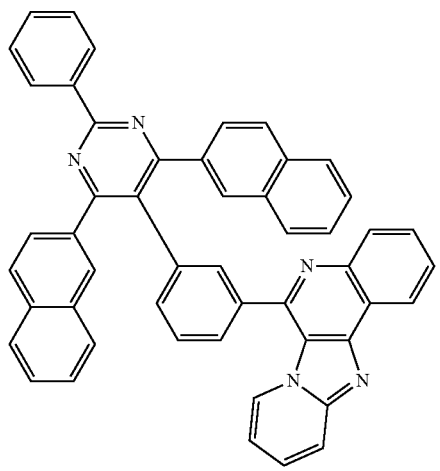
189
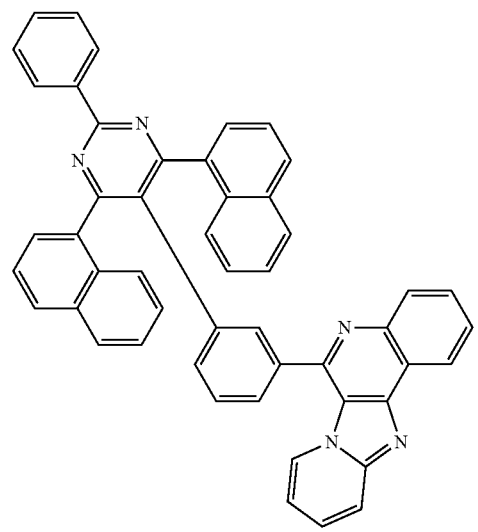
190
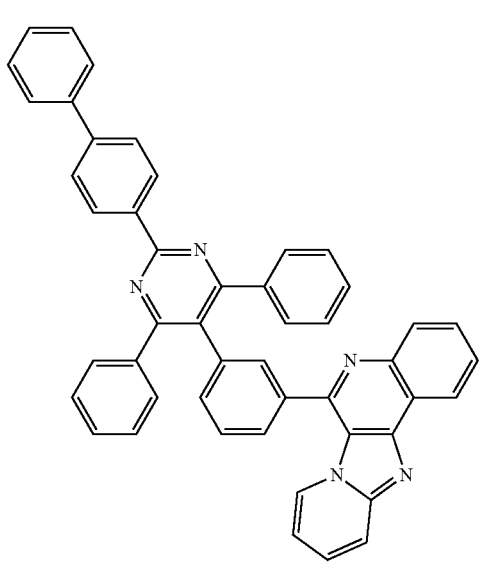

389
-continued
191
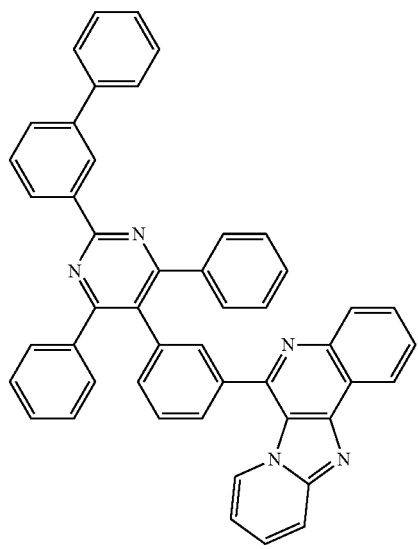
192
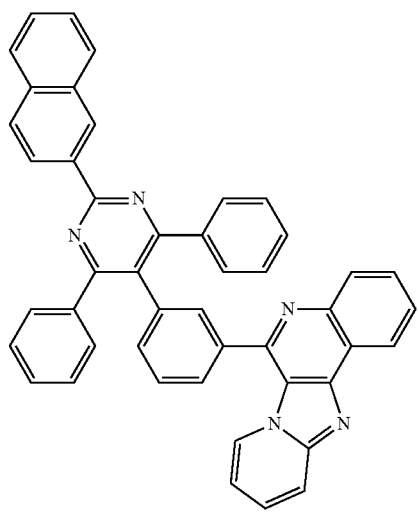
193
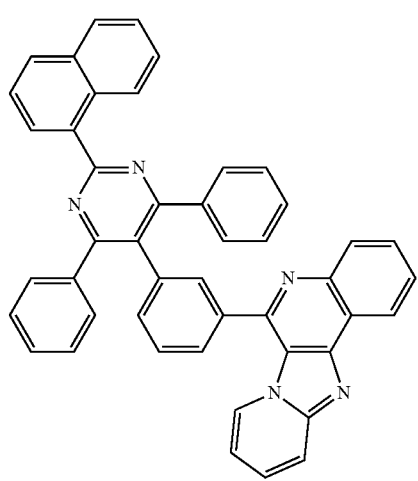
390
-continued
194
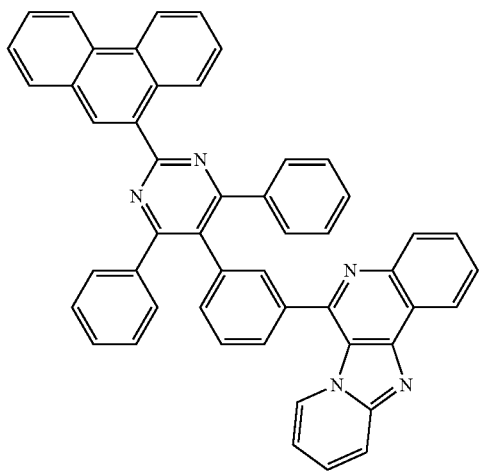
195
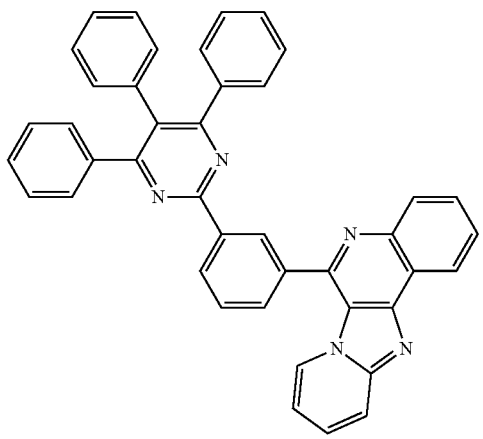
196
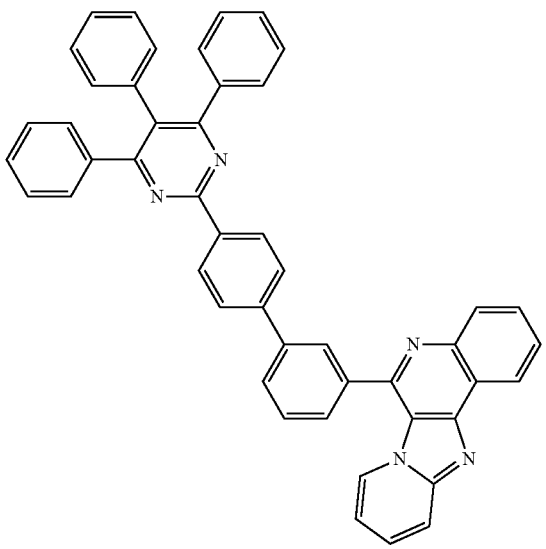

197
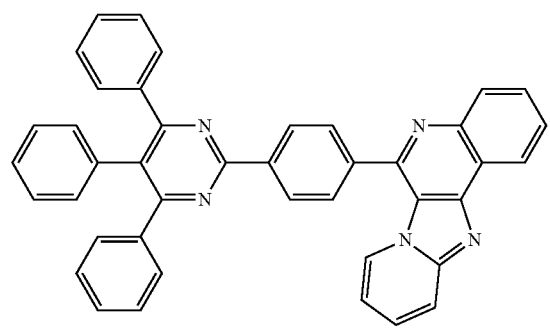
198
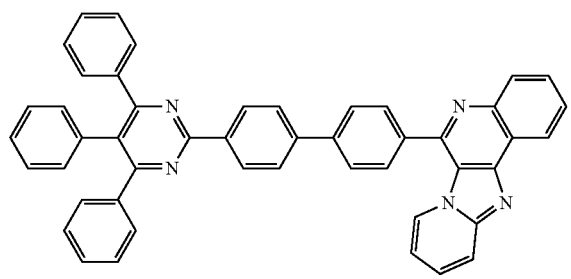
199
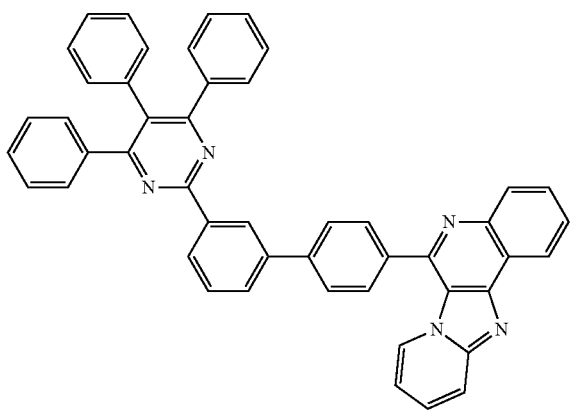
200
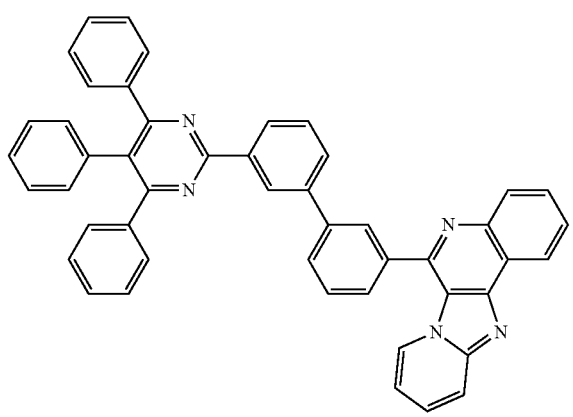
201
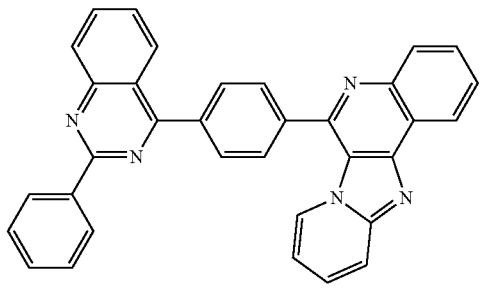
202
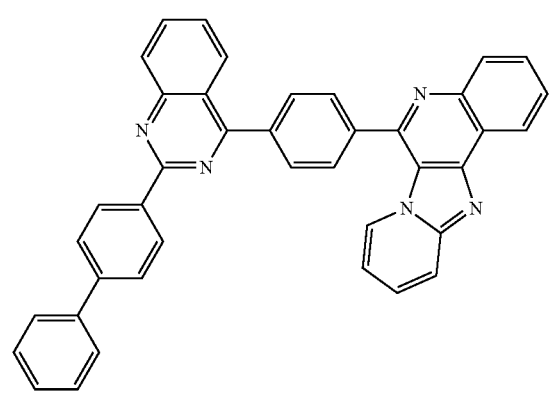
203
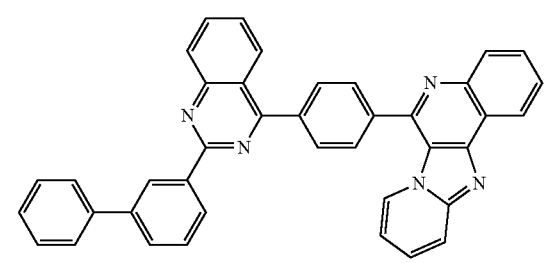
204
205
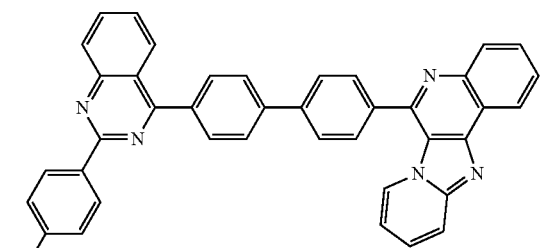

-continued
206
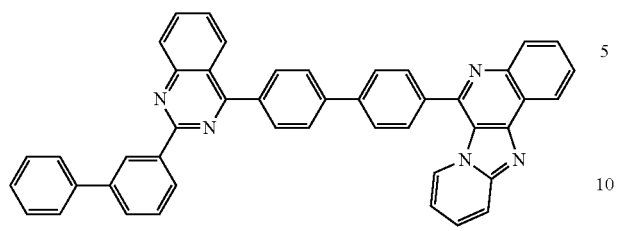
207
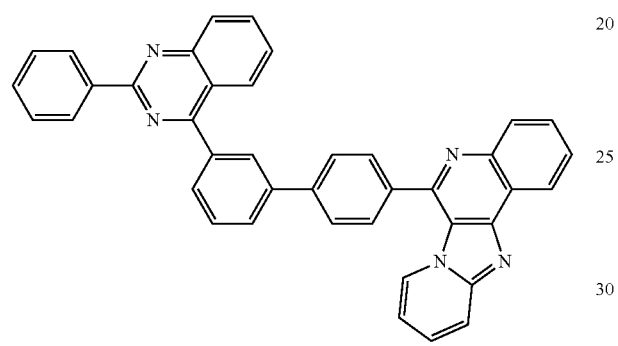
208
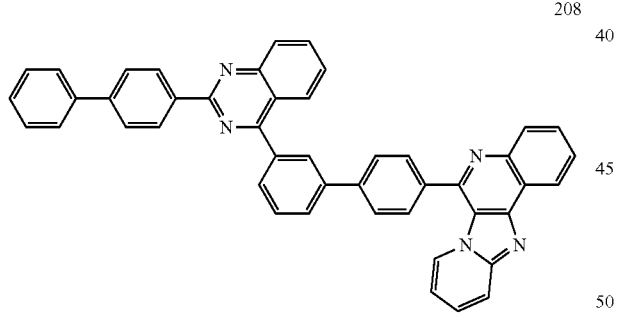
209
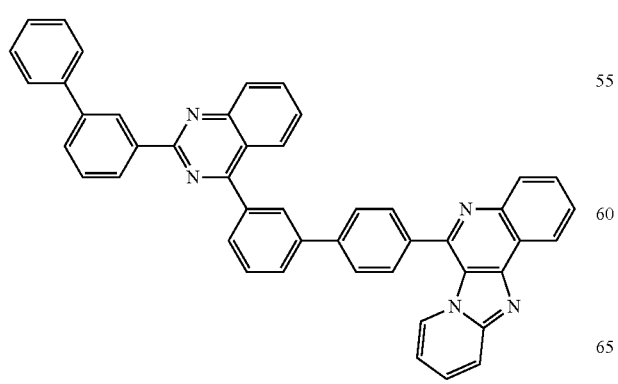
-continued
210
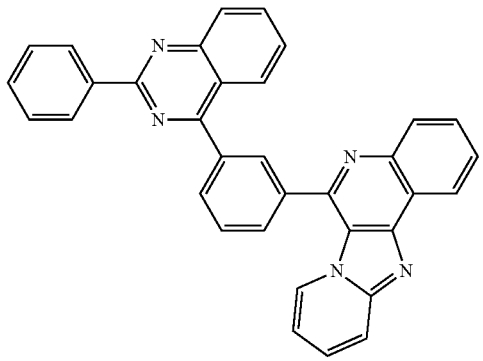
211
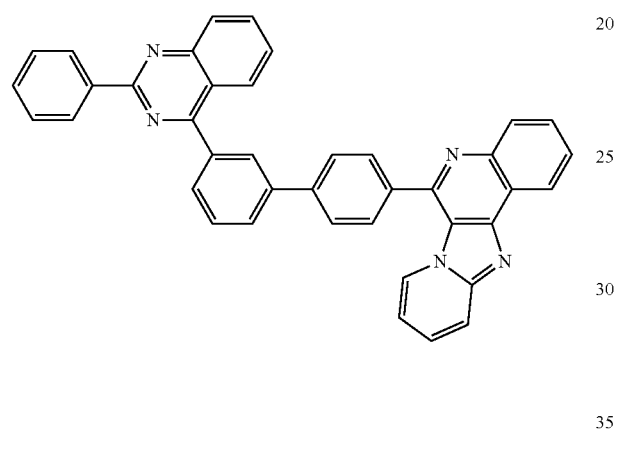
212
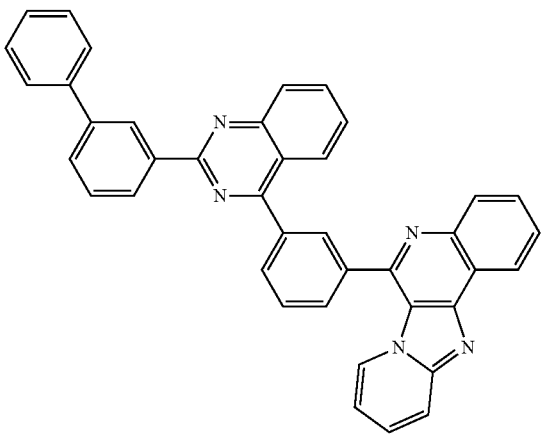

213
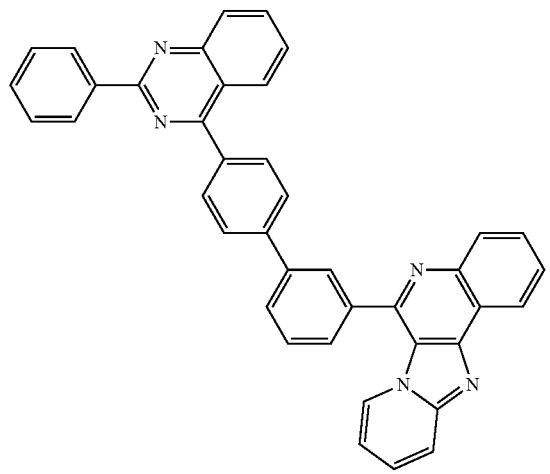
214
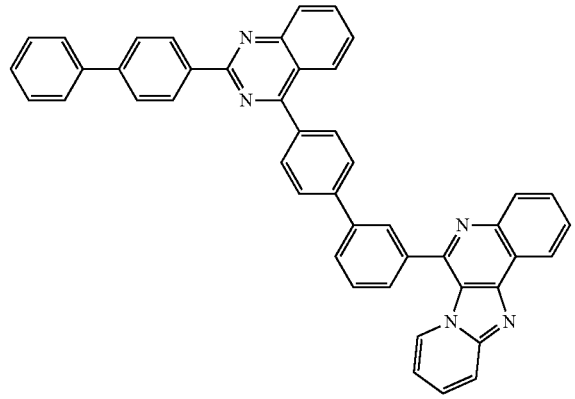
215
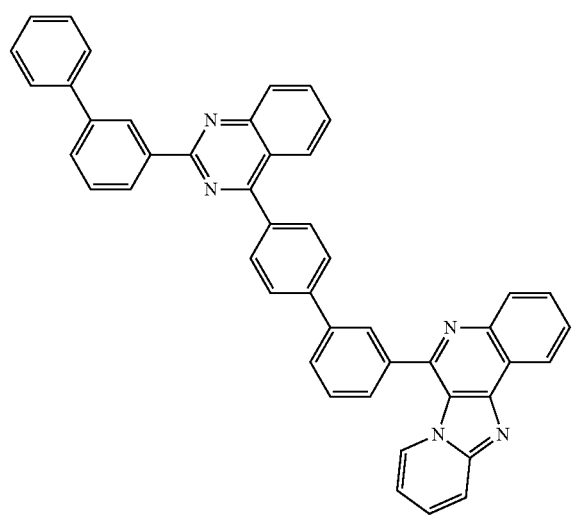
216
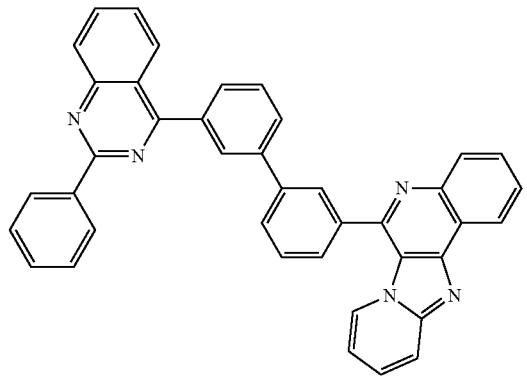
217
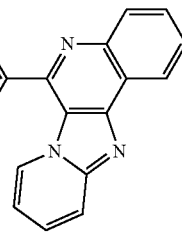
218
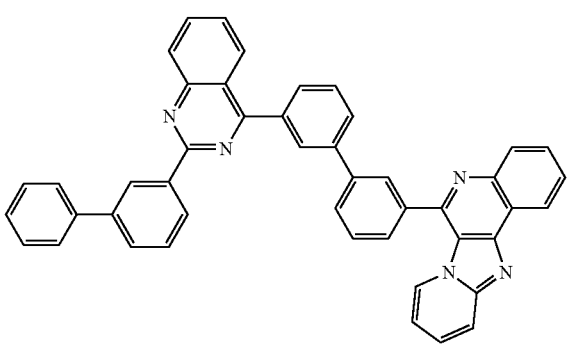
219
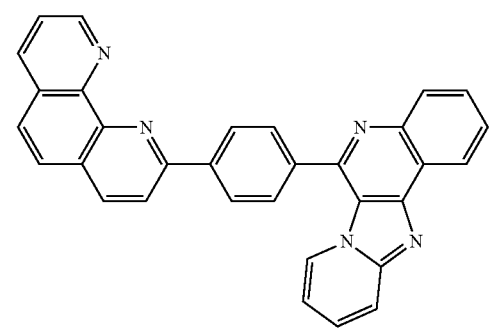

220
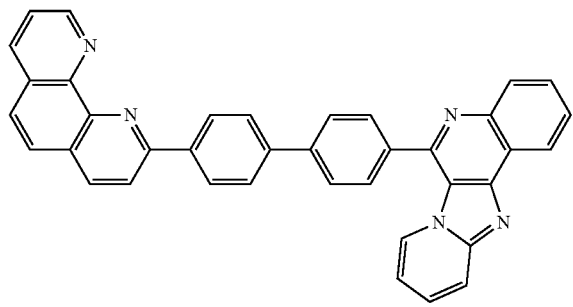
221
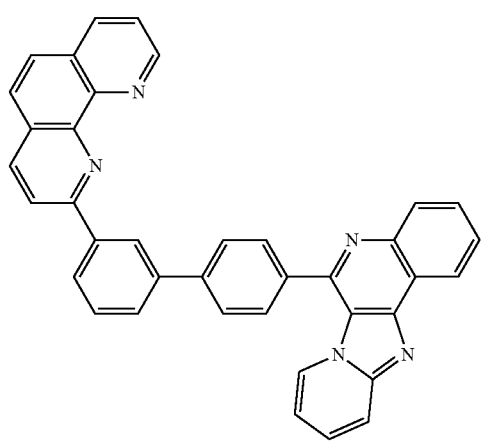
222
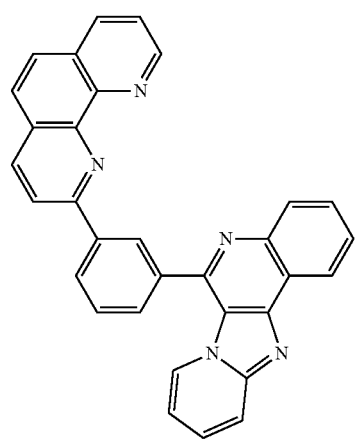
223
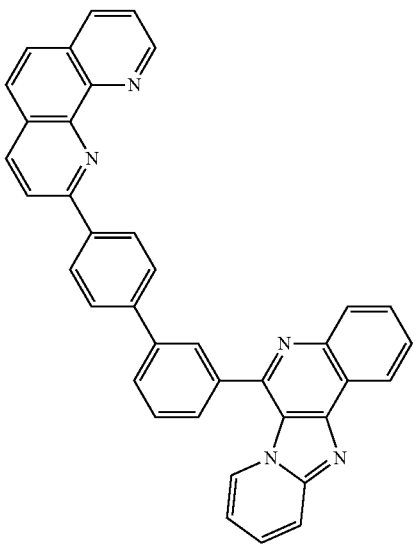
224
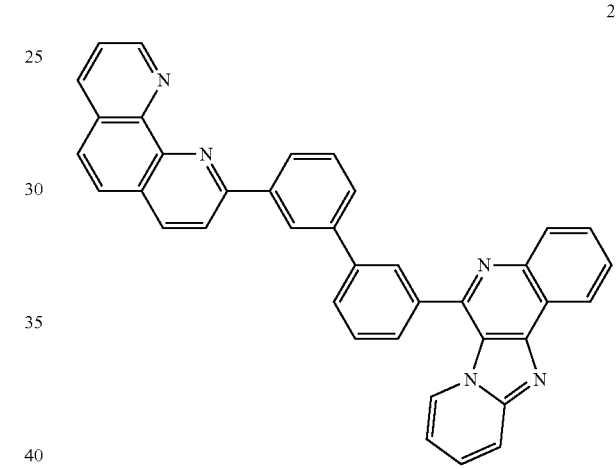
225
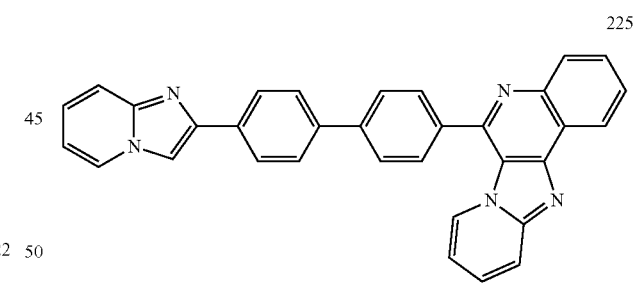
226
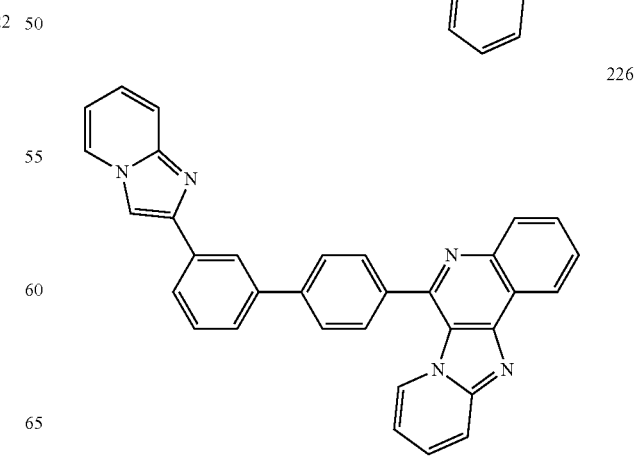

-continued
227
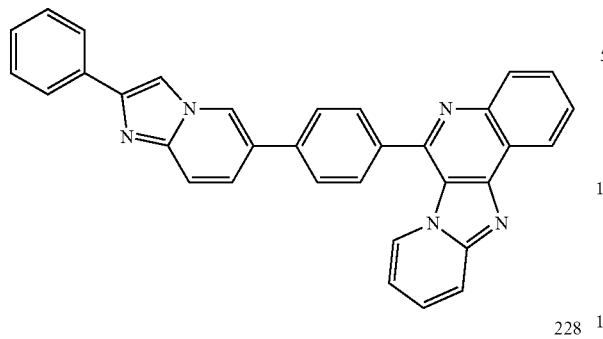
228
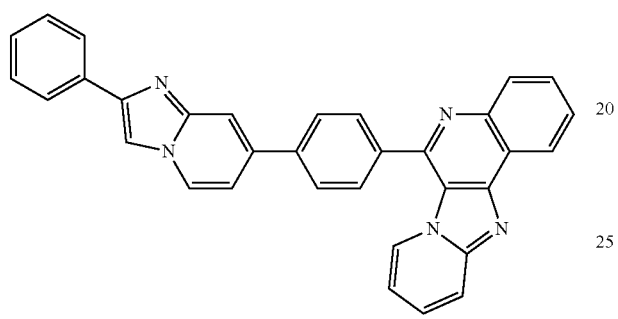
229
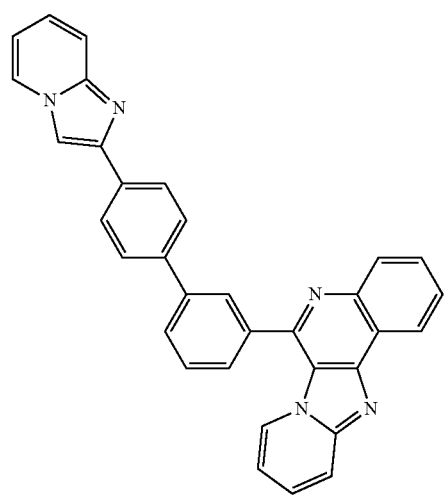
230
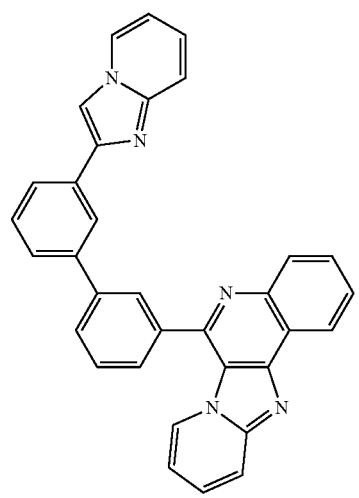
-continued
231
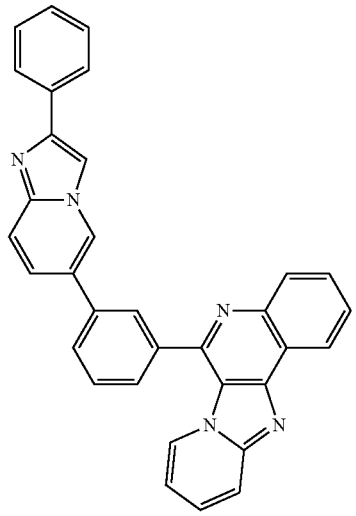
232
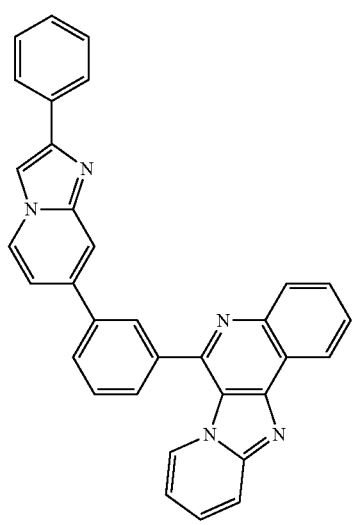
233
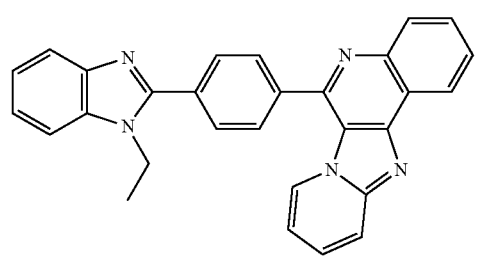
234
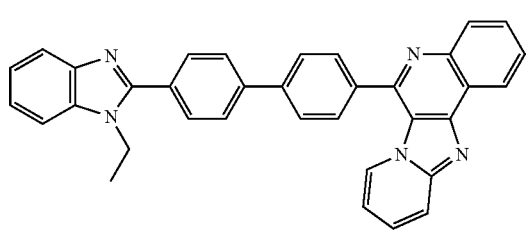

401
-continued
235
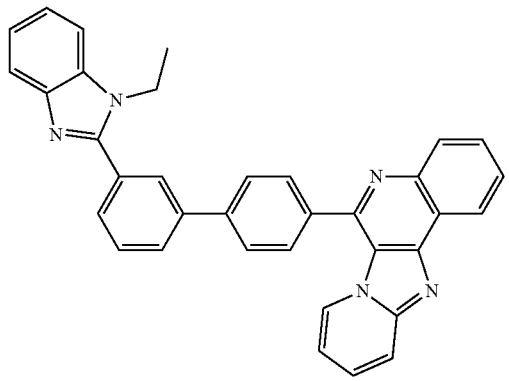
236
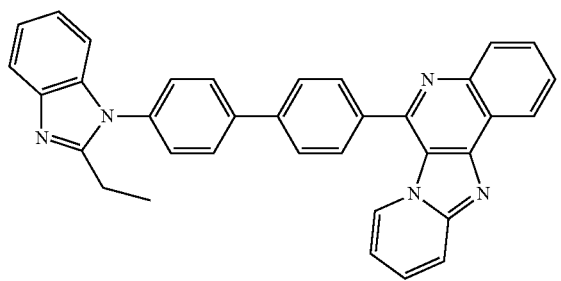
237
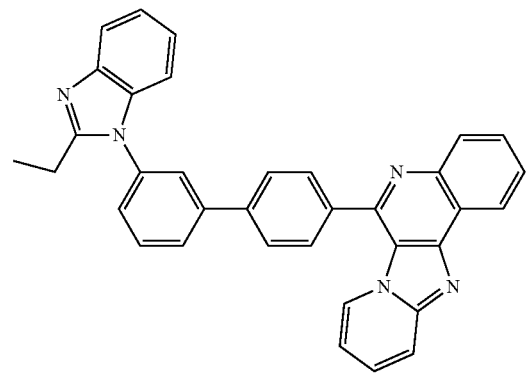
238
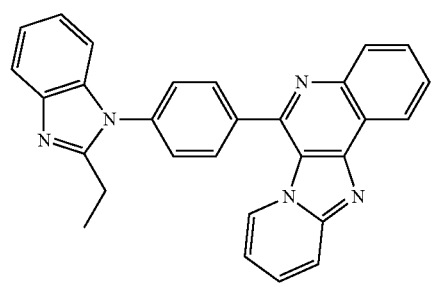
402
-continued
239
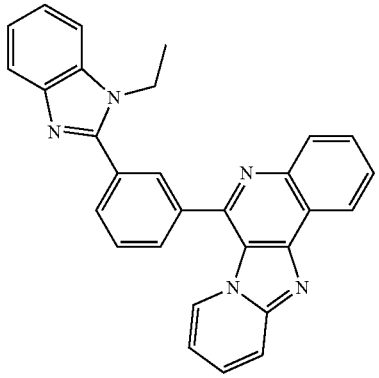
240
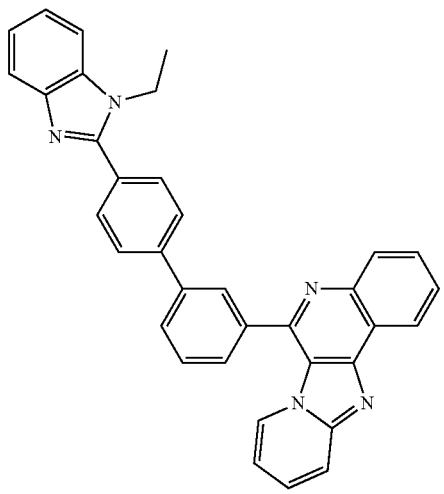
241
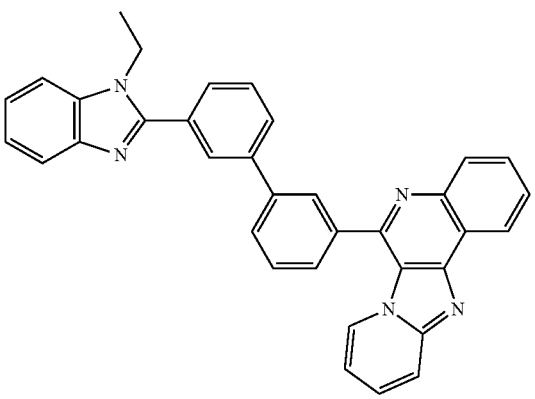

242
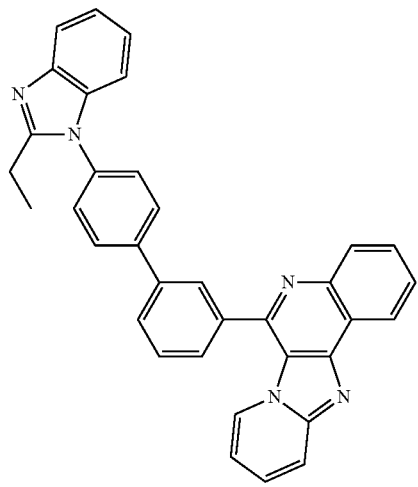
243
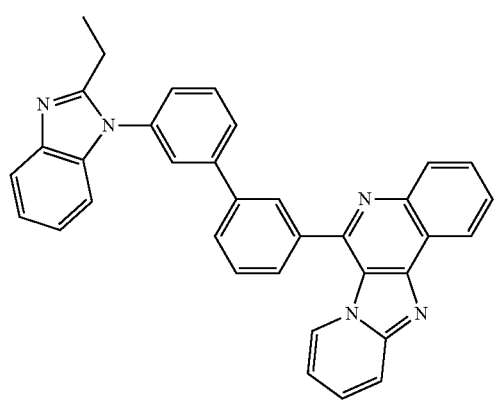
244
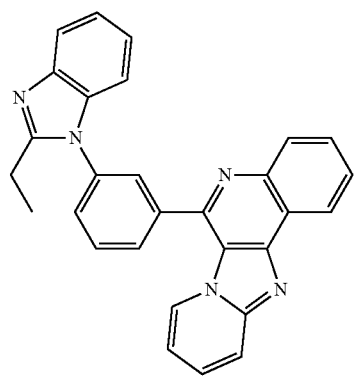
245
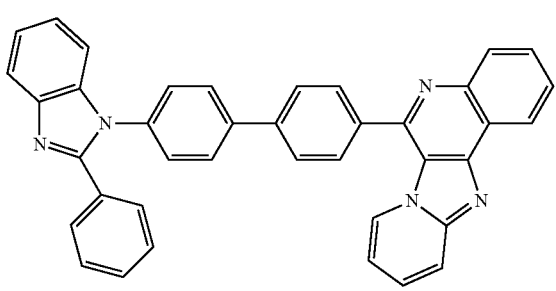
246
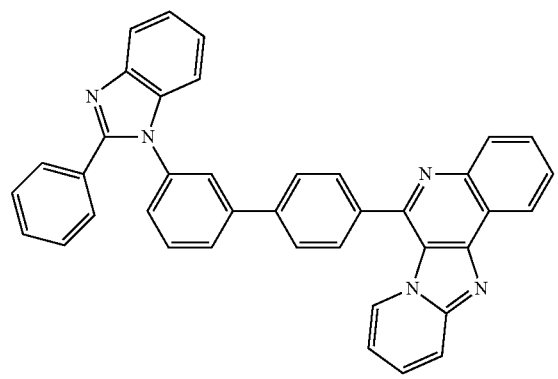
247
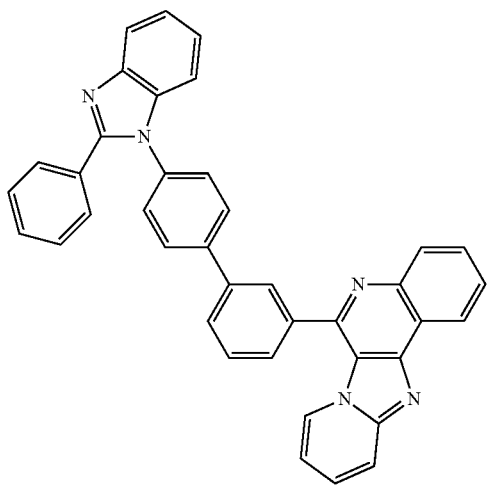
248
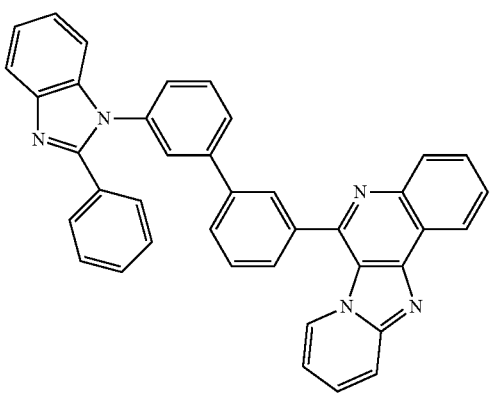
249
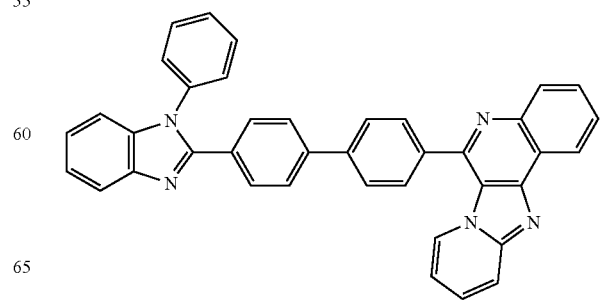

250
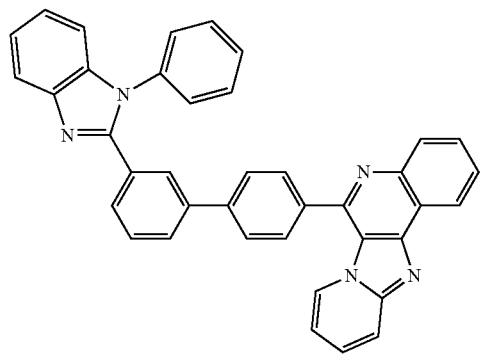
251
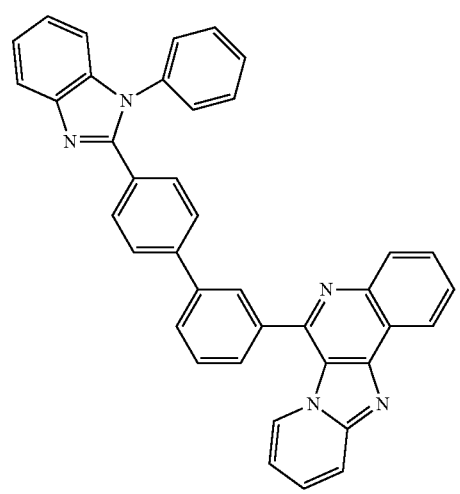
252
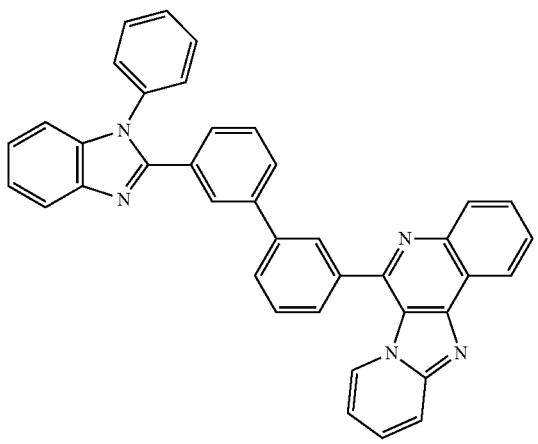
253
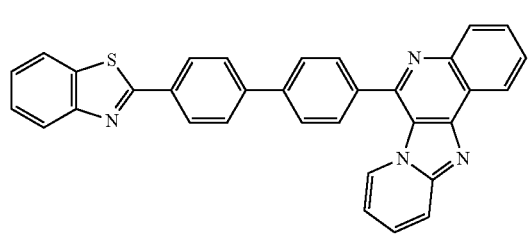
254
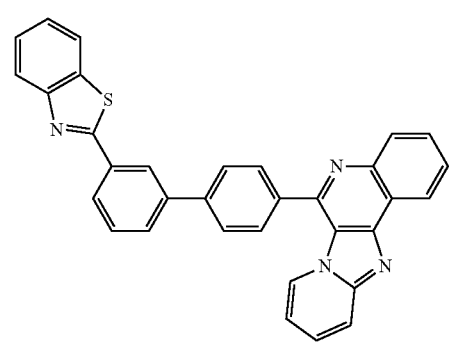
255
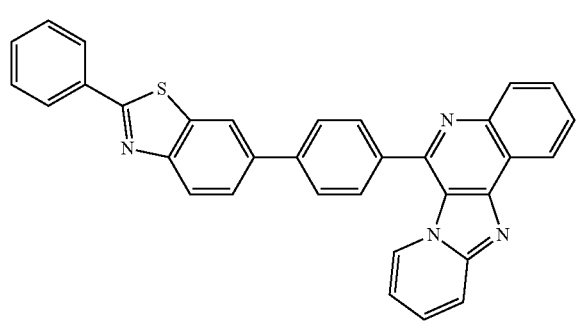
256
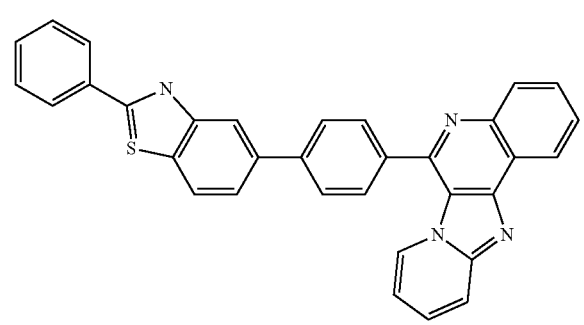

-continued
| 257 | 258 |
|---|---|
| 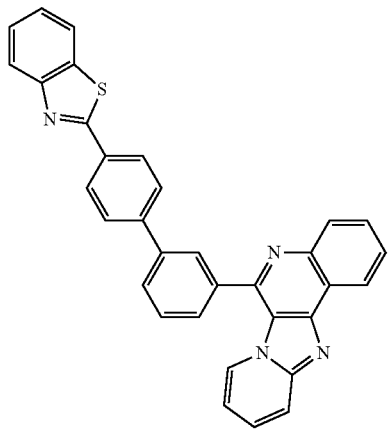 | 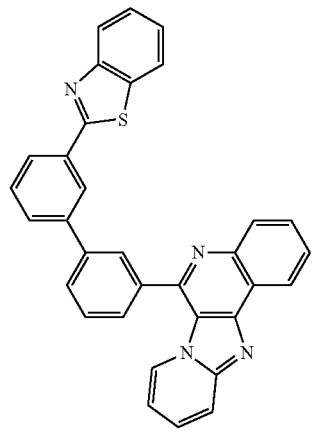 |
| 259 | 260 |
| 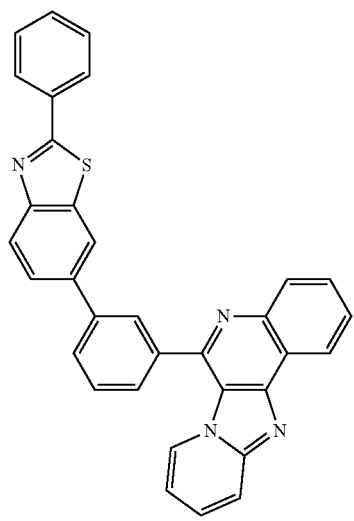 | 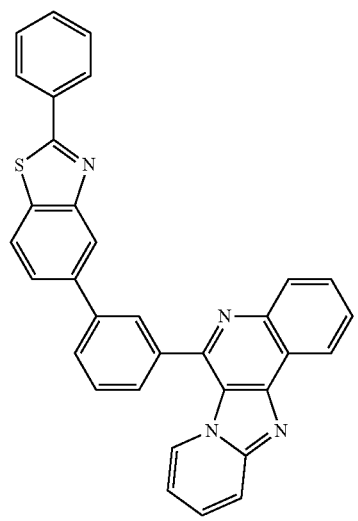 |
| 261 | 262 |
| 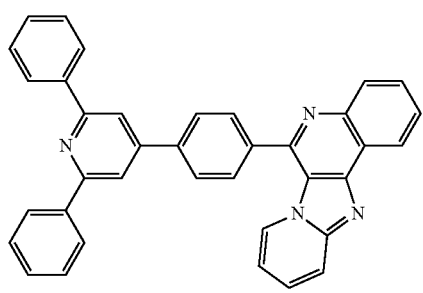 | 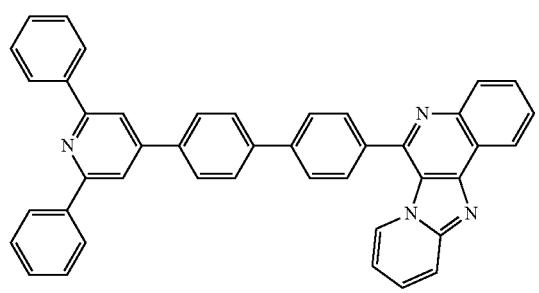 |
| 263 | 264 |
| 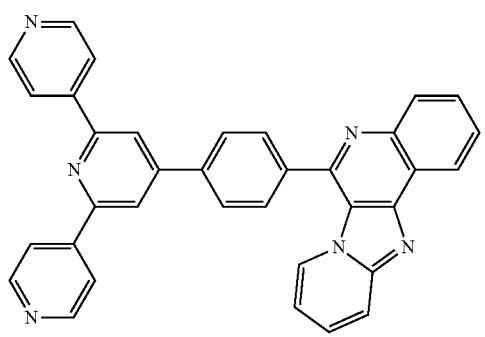 | 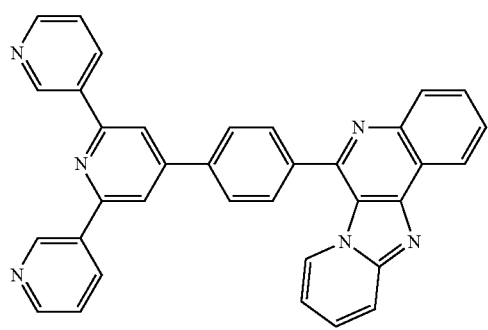 |

-continued
265
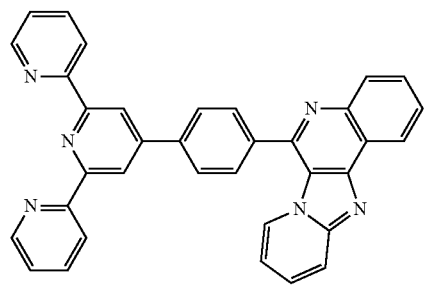
266
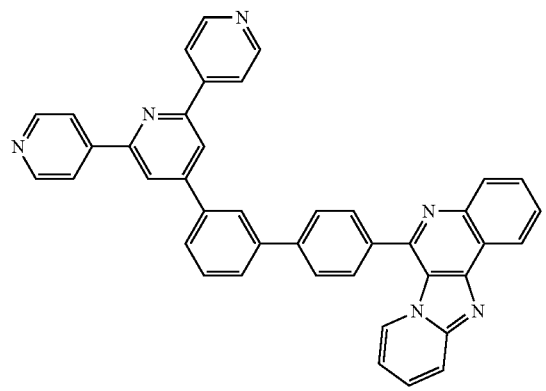
267
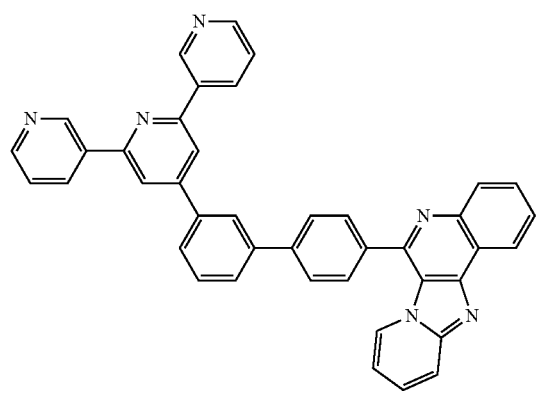
268
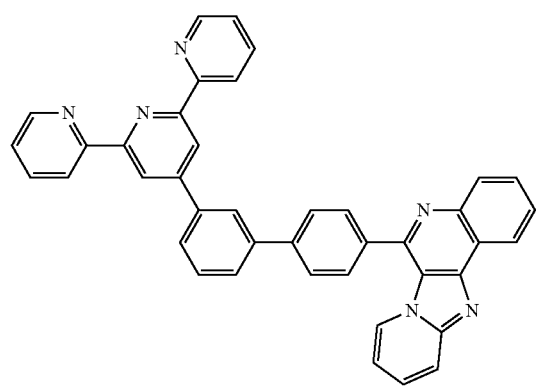
269
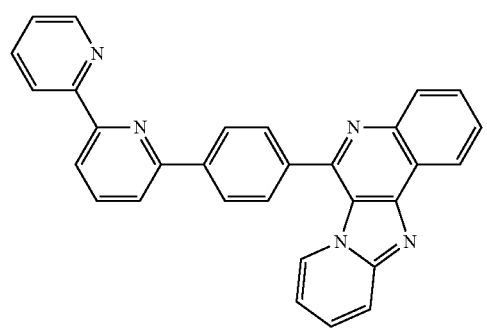
270
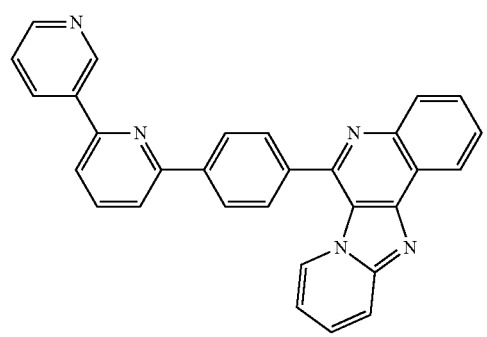
271
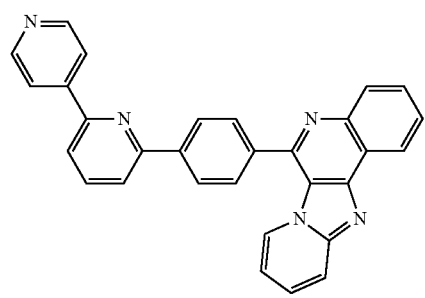
272
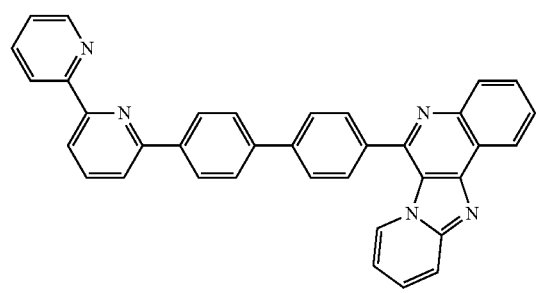

-continued
| 273 | 274 |
|---|---|
| 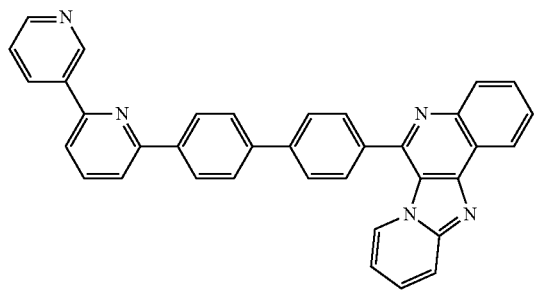 | 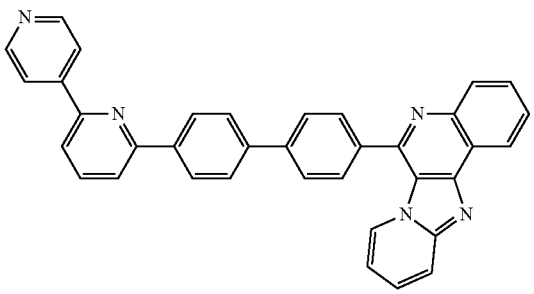 |
| 275 | 276 |
| 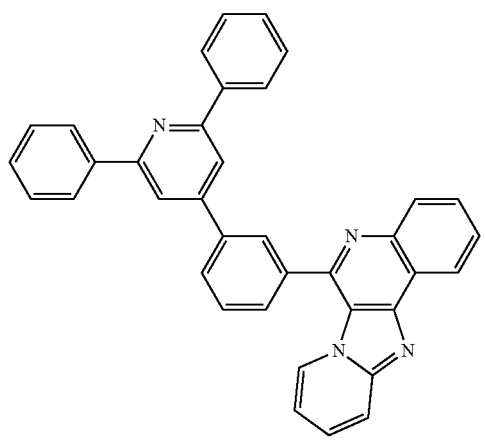 | 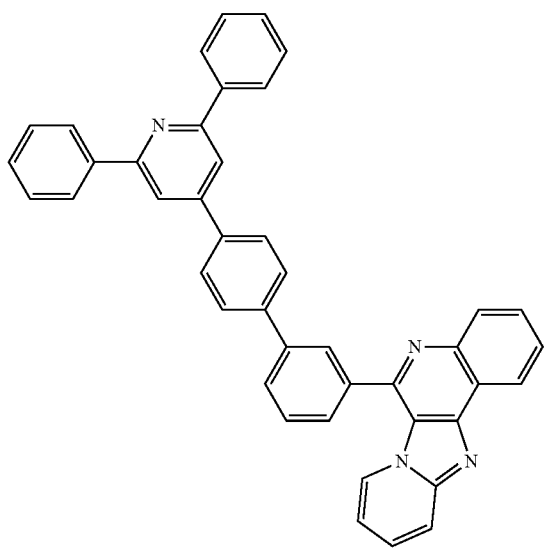 |
| 277 | 278 |
| 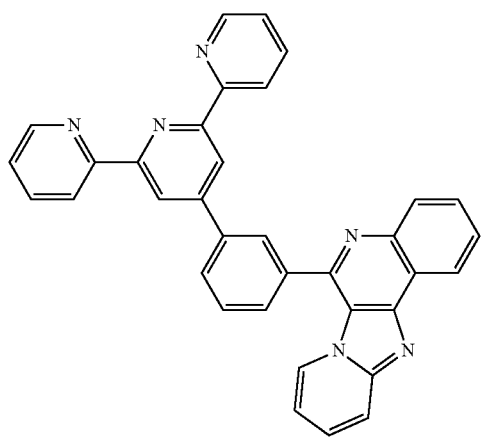 | 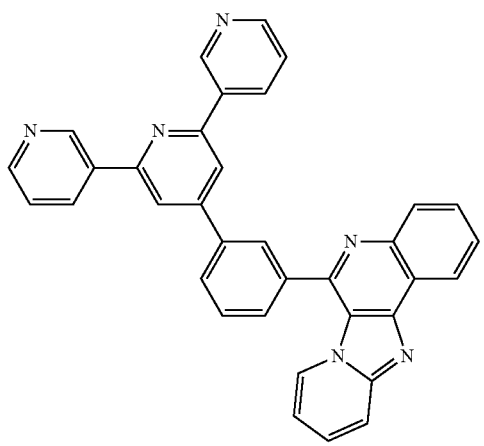 |

-continued
279
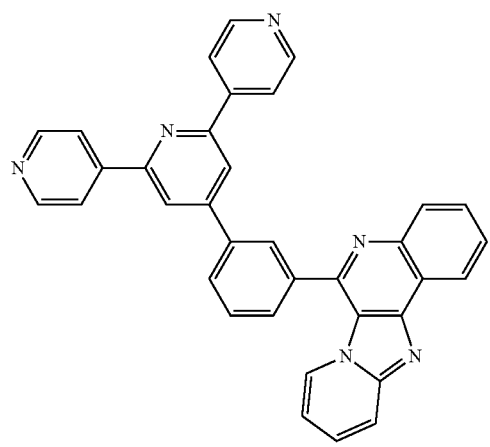
280
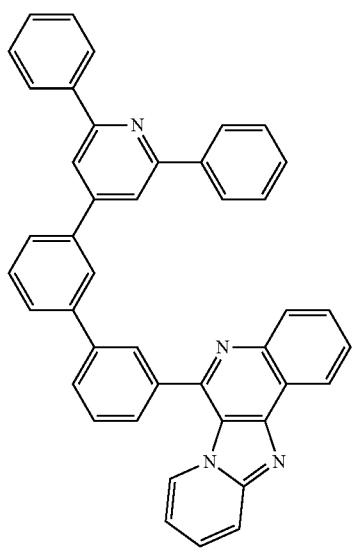
281
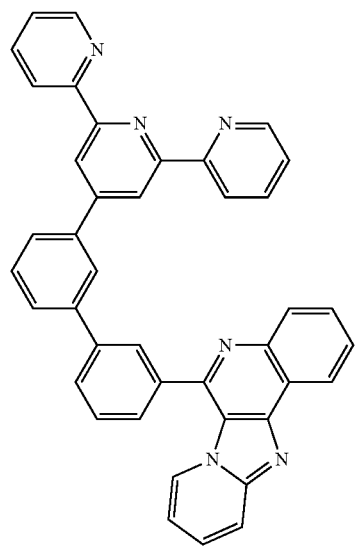
282
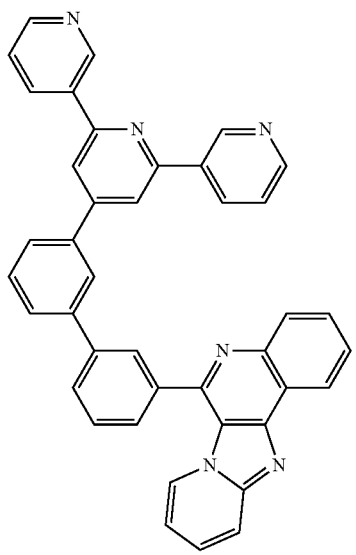
283
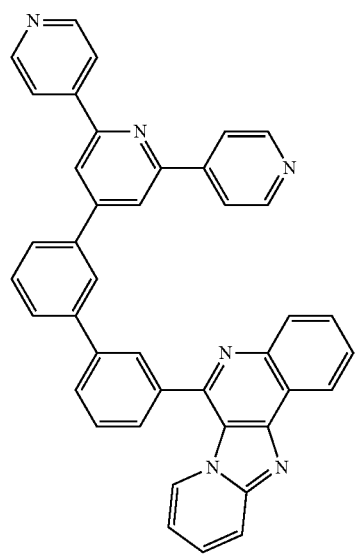
284
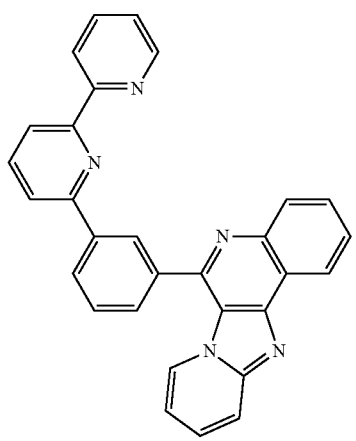

285 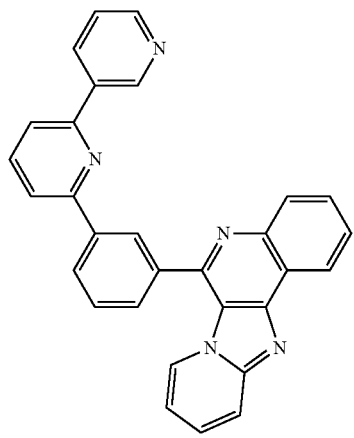 286 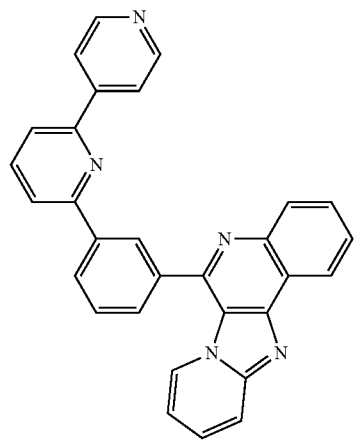
287 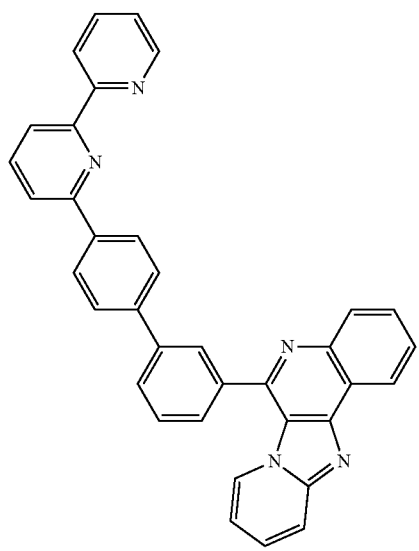 288 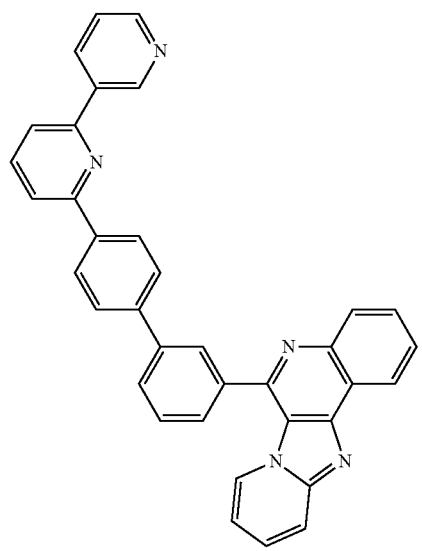
289 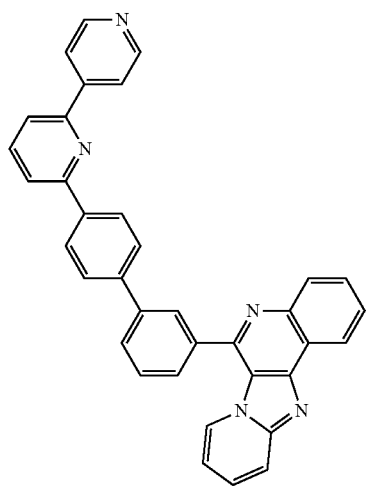 290 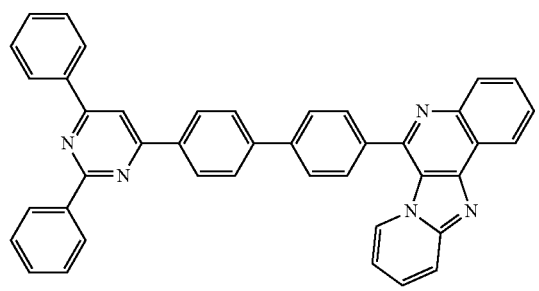

-continued
291 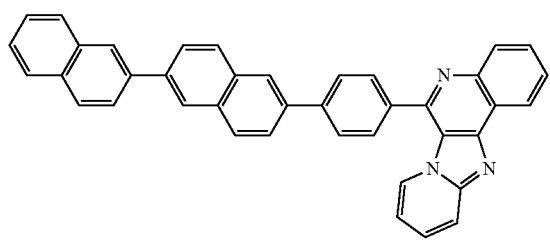
292 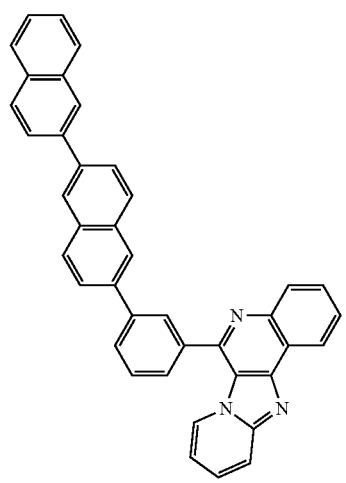
293 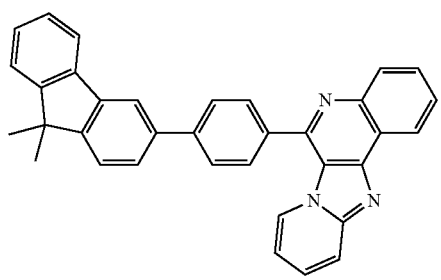
294 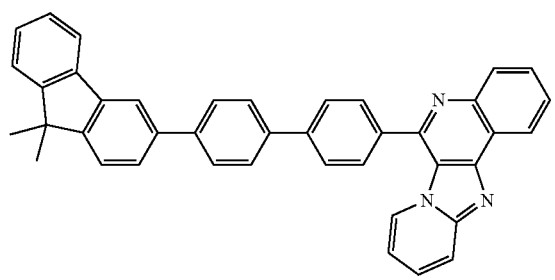
295 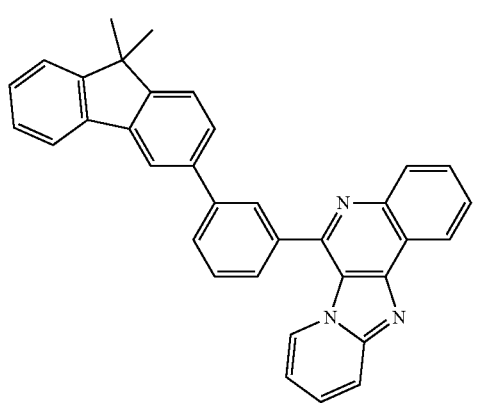
296 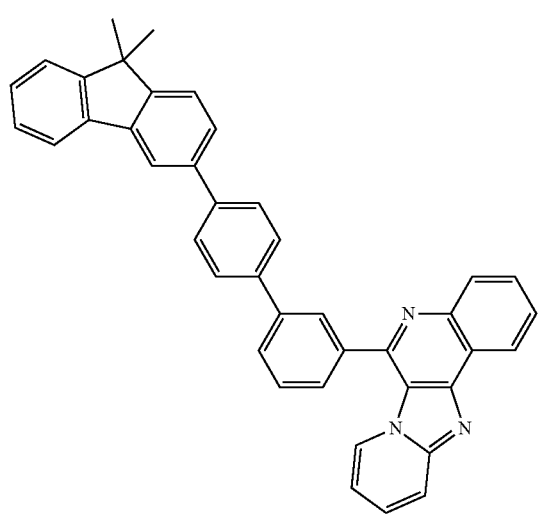

-continued
297
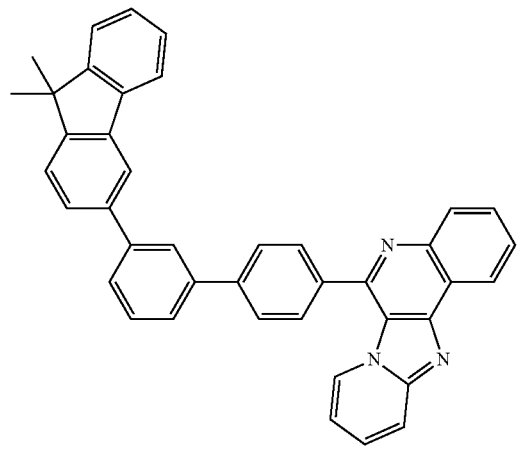
298
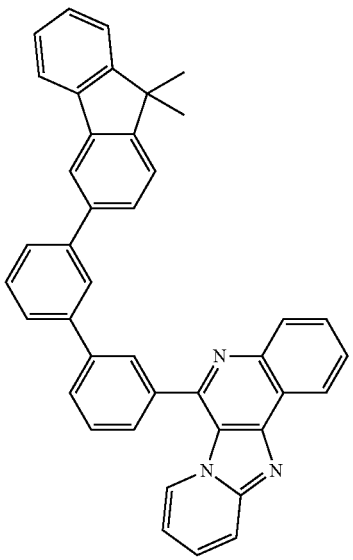
299
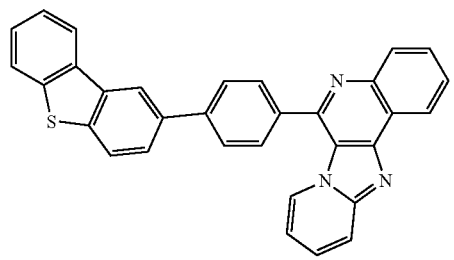
300
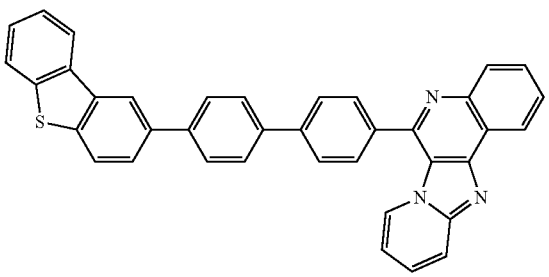
301
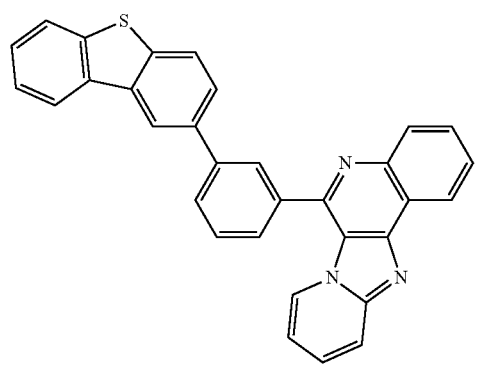
302
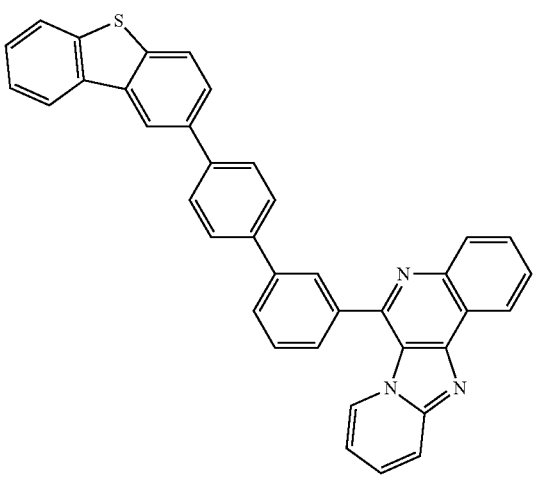

-continued
303 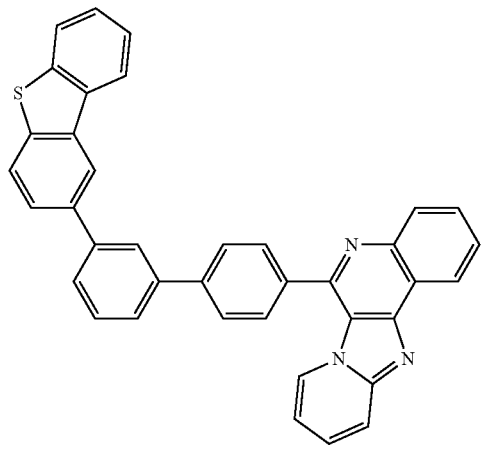
304 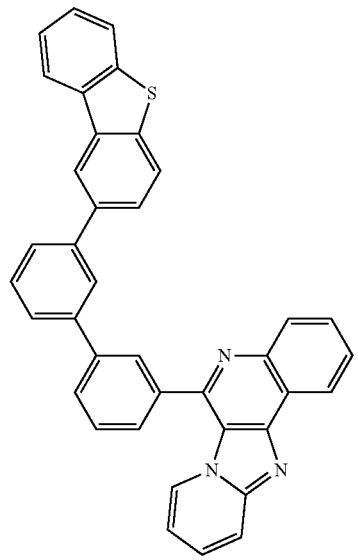
305 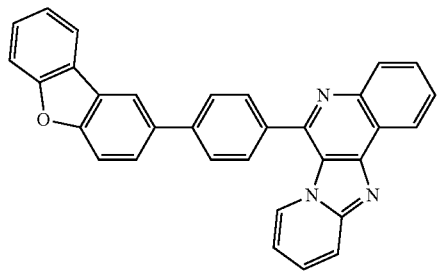
306 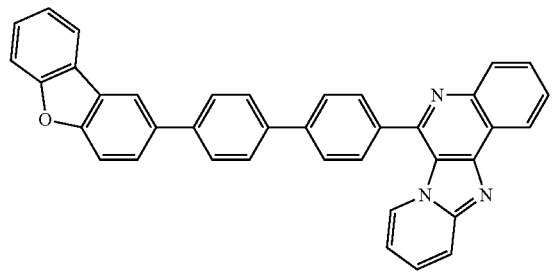
307 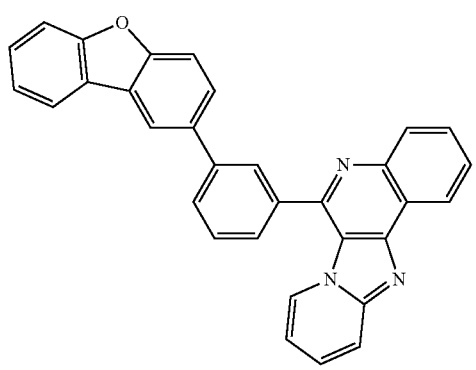
308 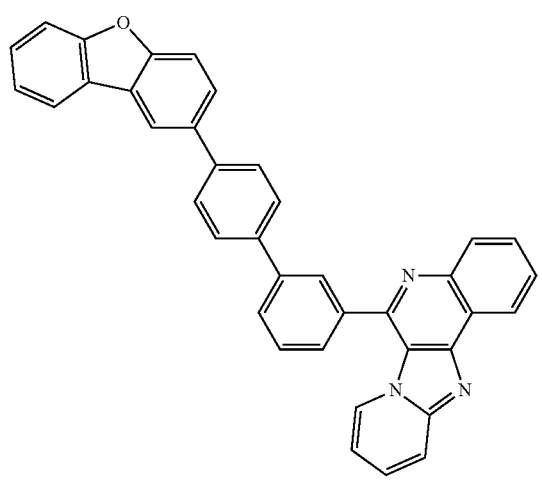

-continued
309
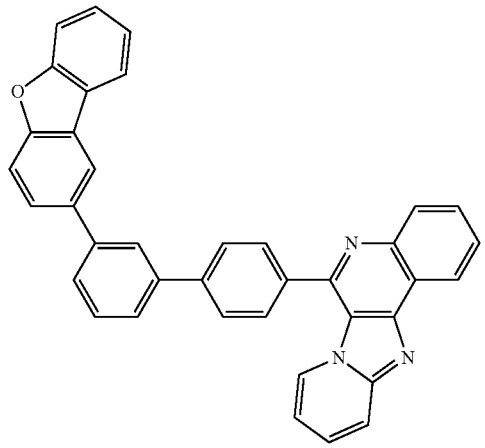
310
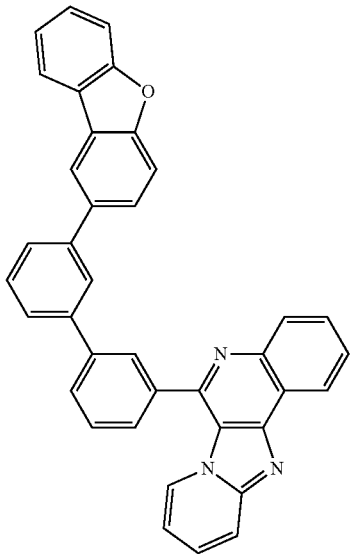
311
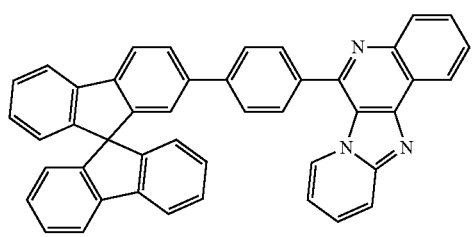
312
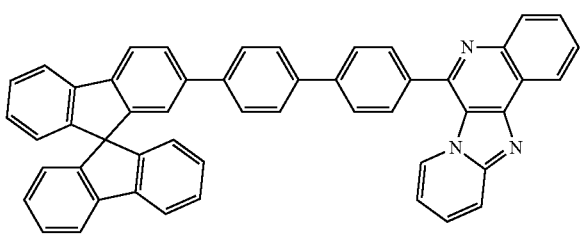
313
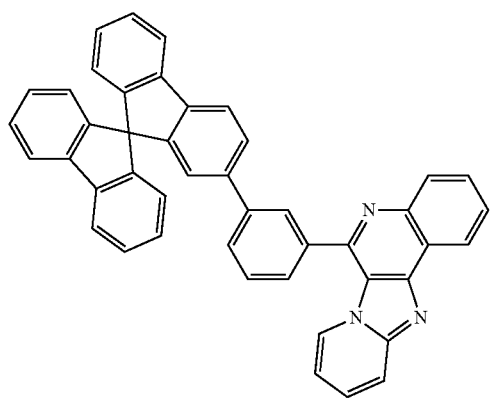
314
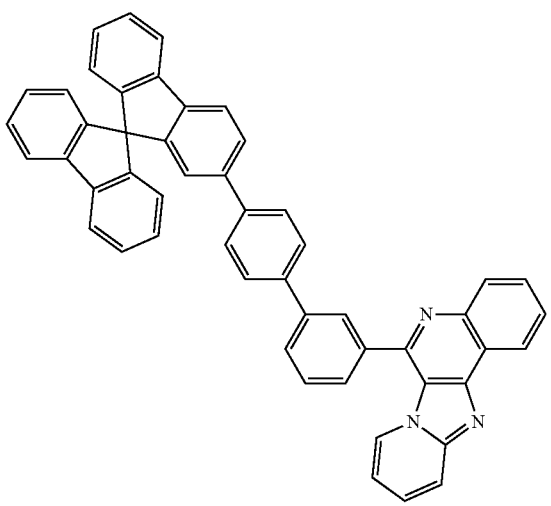

-continued
315
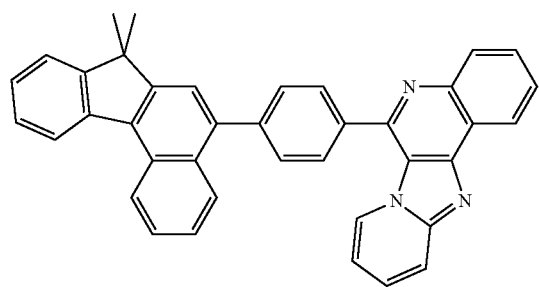
316
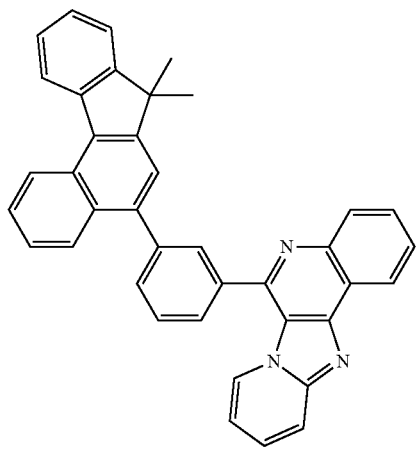
317
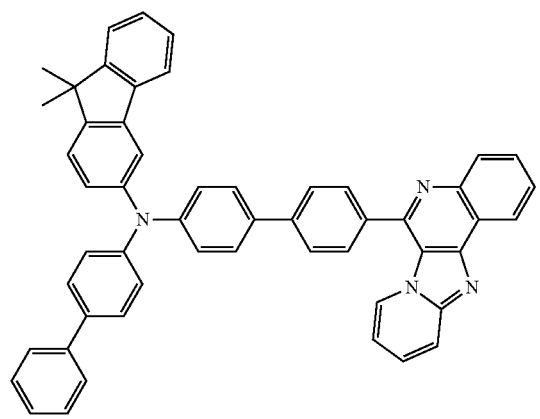
318
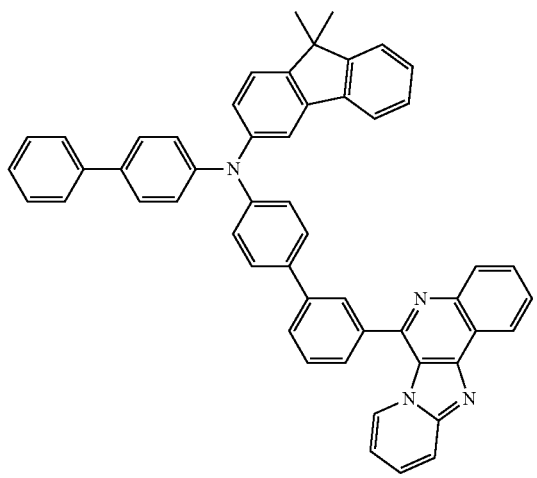
319
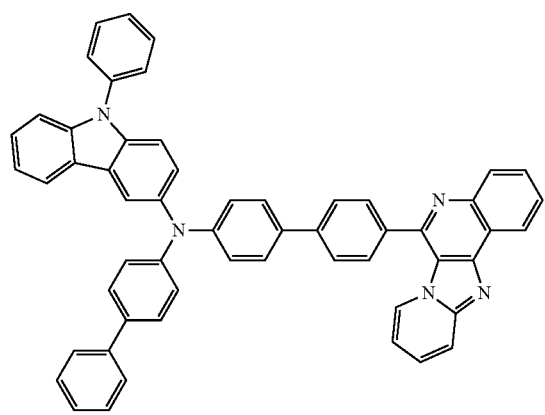
320
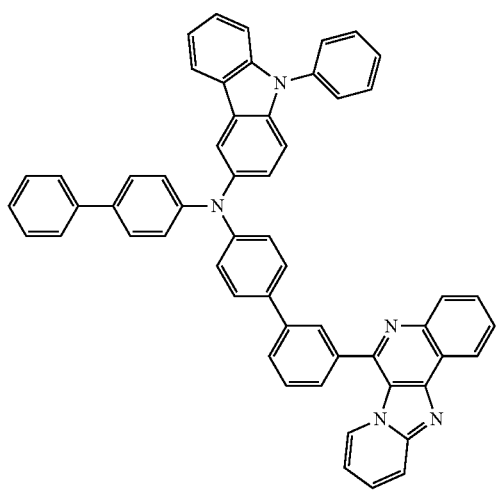

-continued
| 321 | 322 |
|---|---|
| 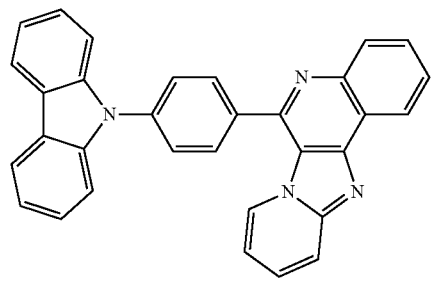 | 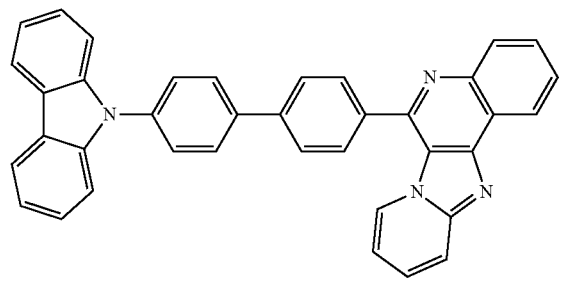 |
| 323 | 324 |
| 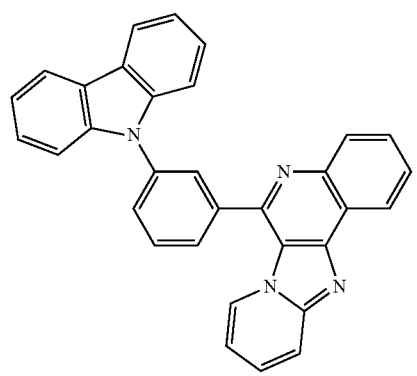 | 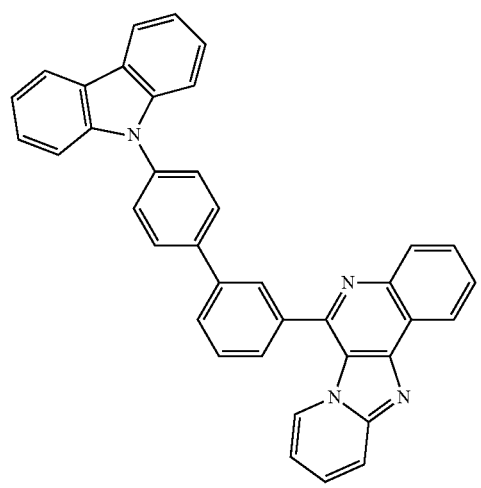 |
| 325 | 326 |
| 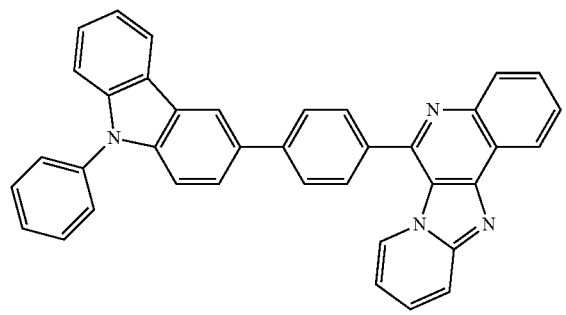 | 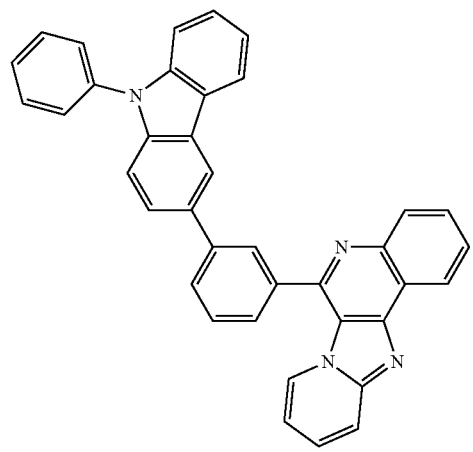 |
| 327 | 328 |
| 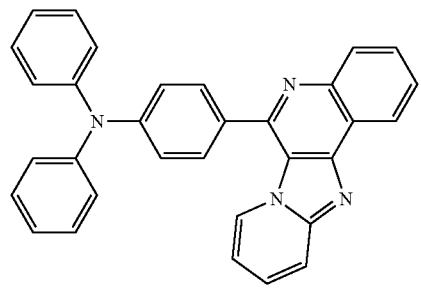 | 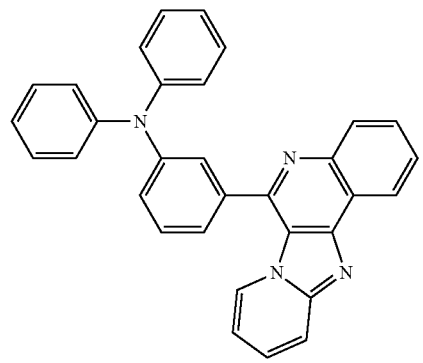 |

-continued
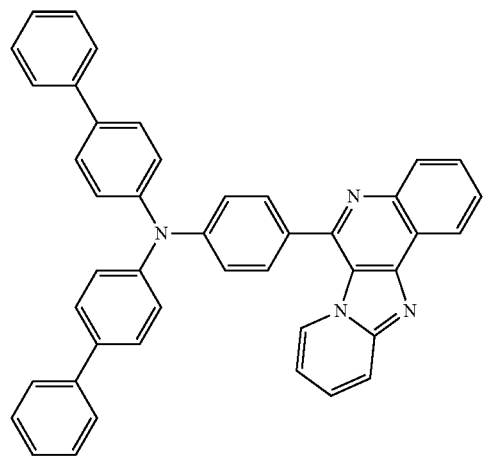
329
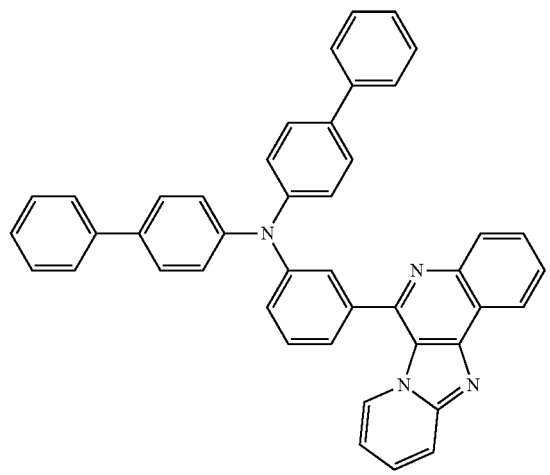
330
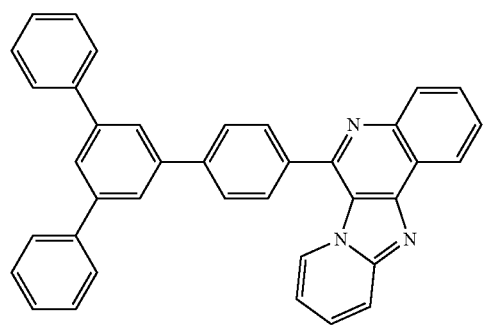
331
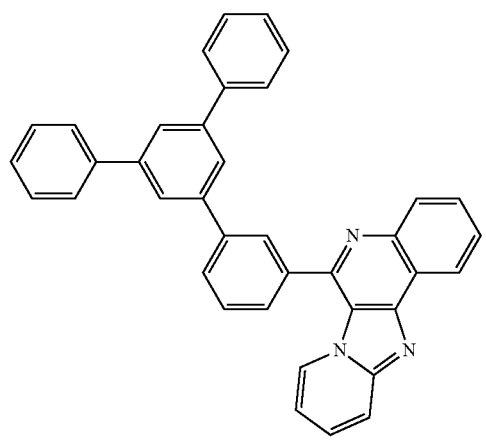
332
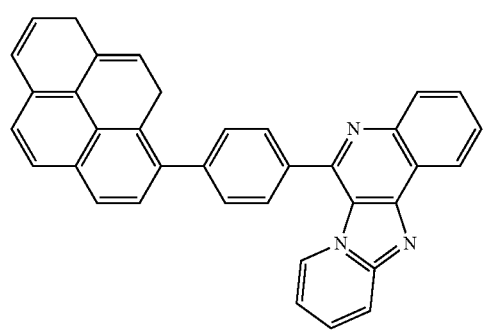
333

-continued
334
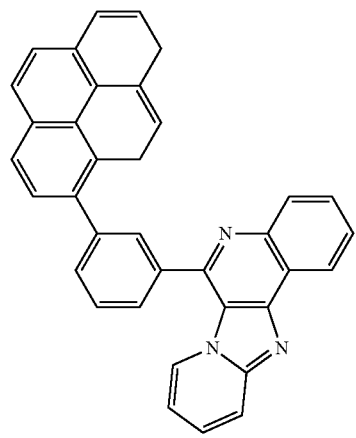
335
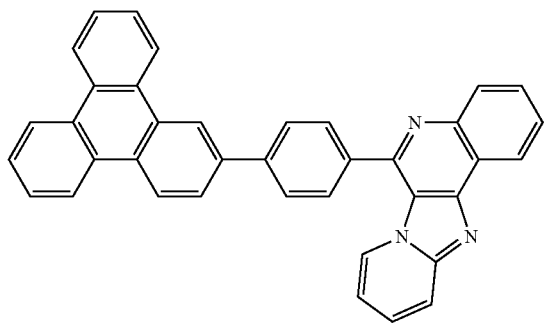
336
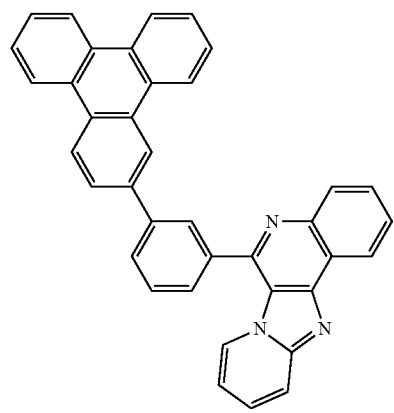
337
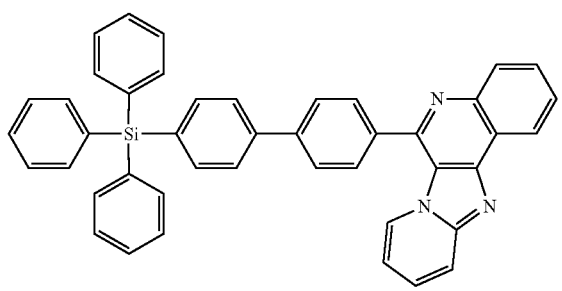
338
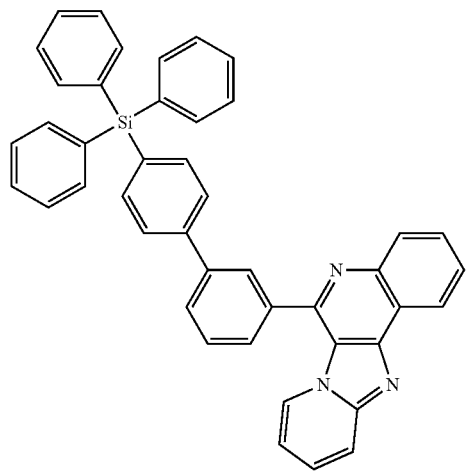
339
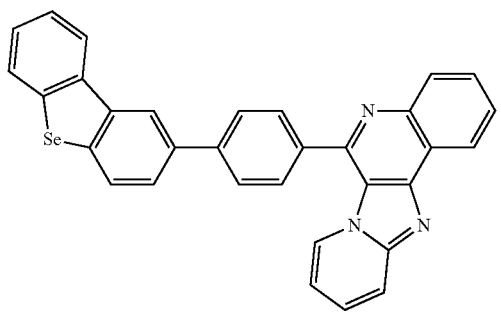
340
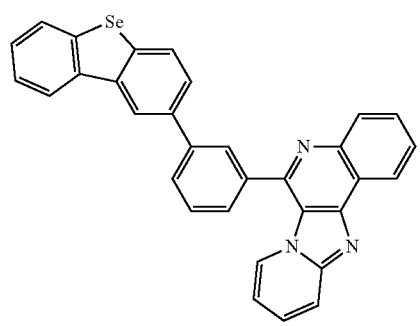
341
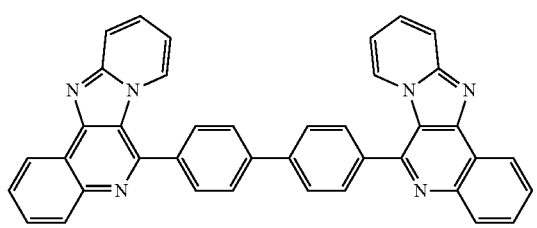

-continued
342
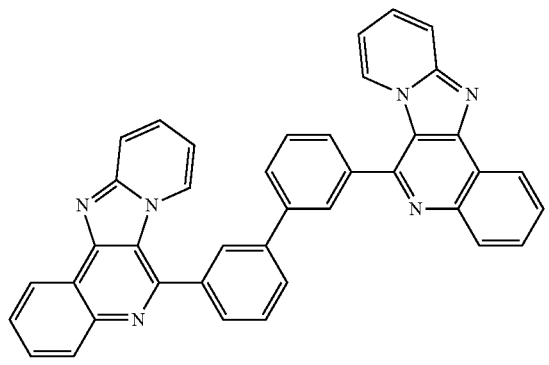
343
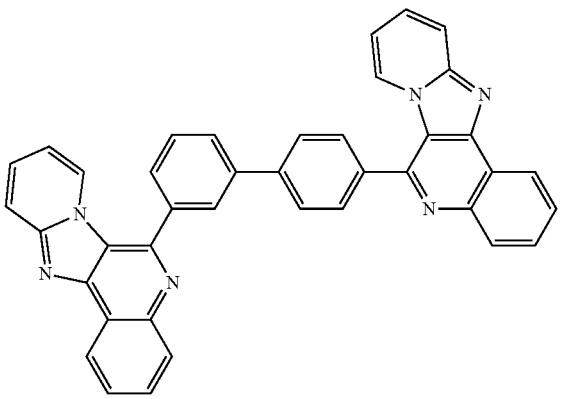
344
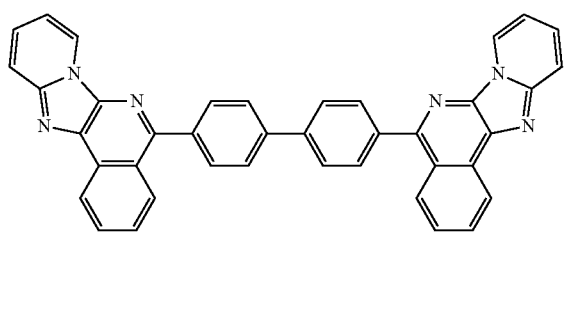
345
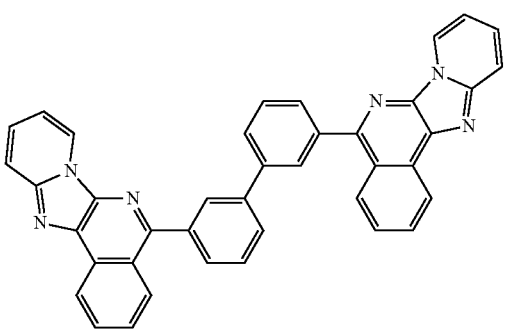
346
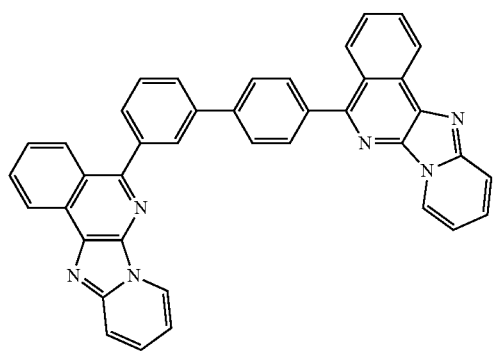
347
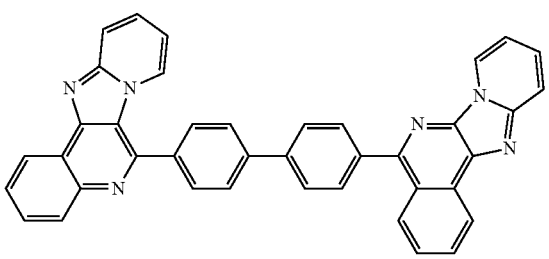
348
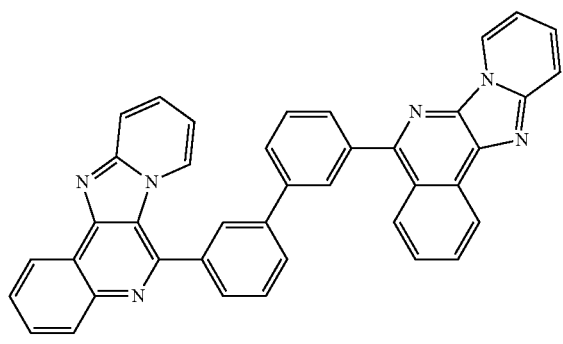
349
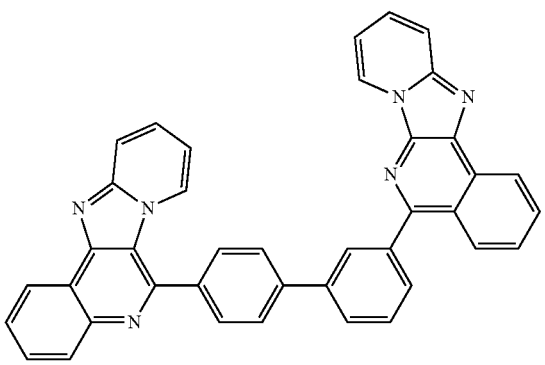

-continued
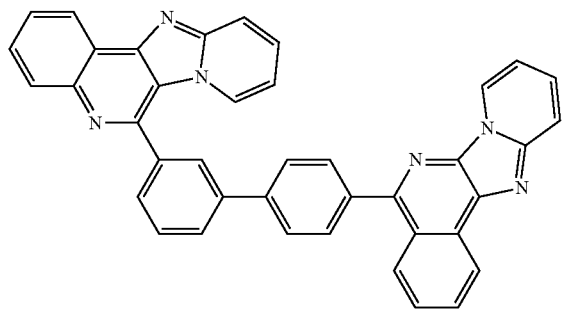
350
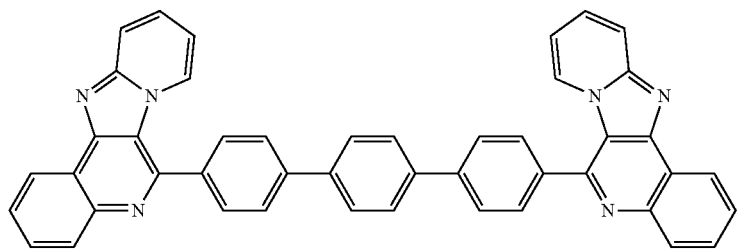
351
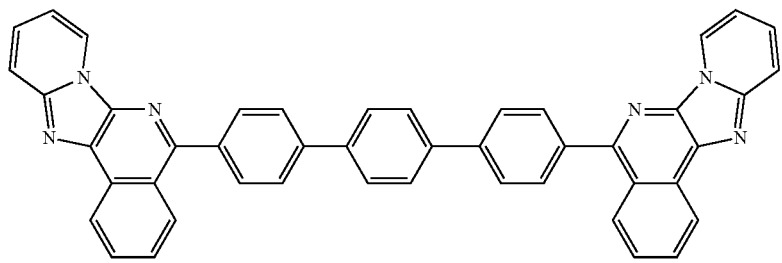
352
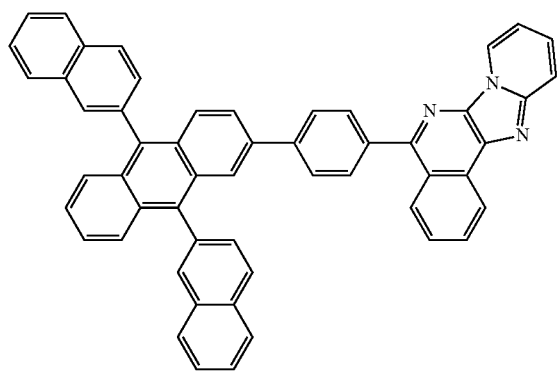
353
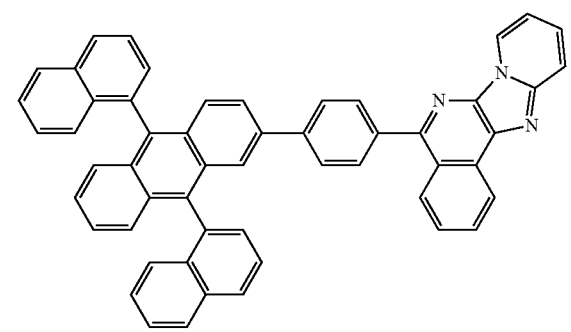
354
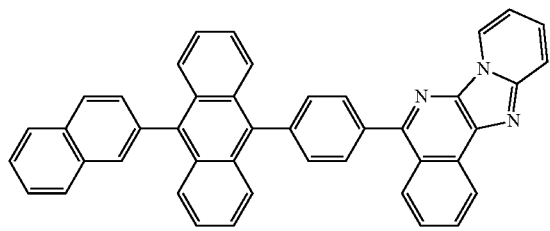
355
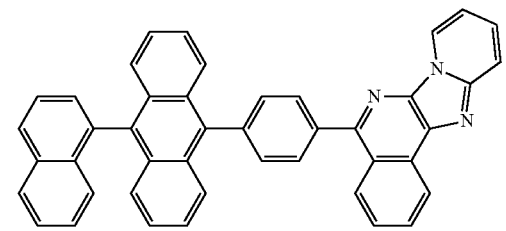
356

-continued
357
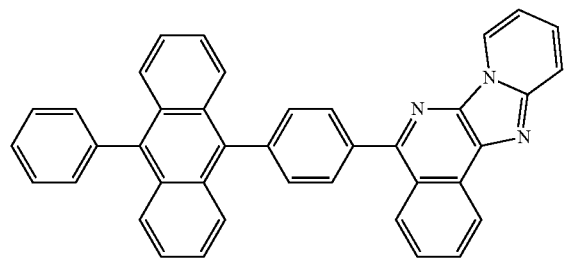
358
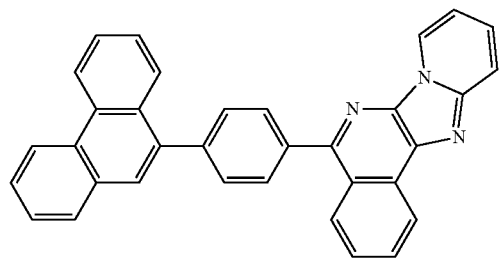
359
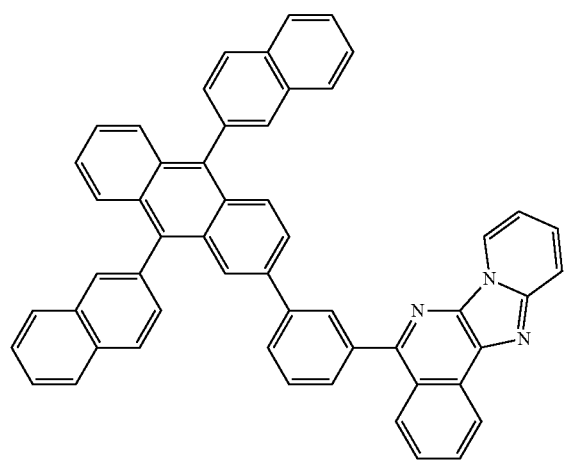
360
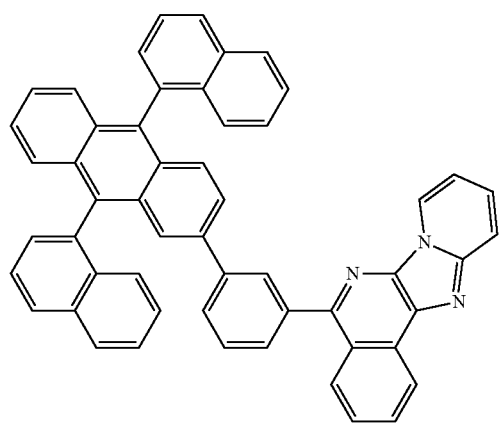
361
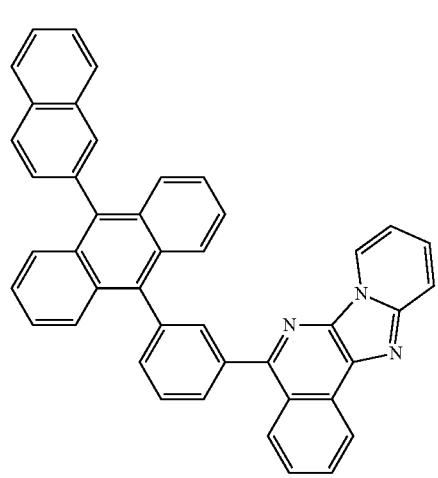
362
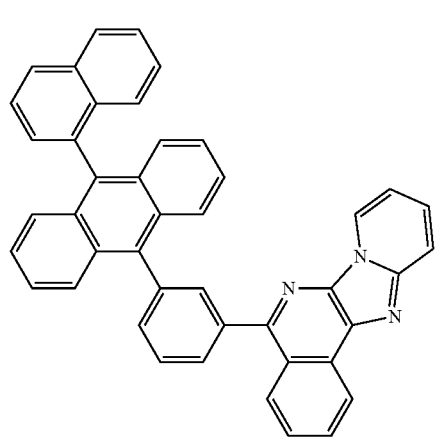
363
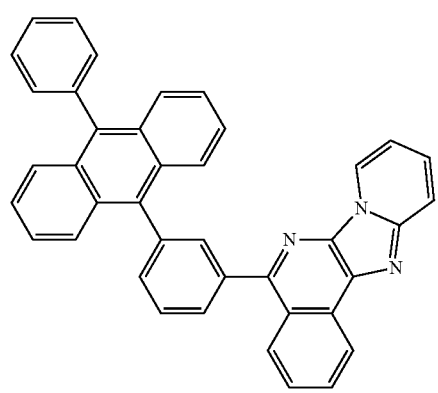
364
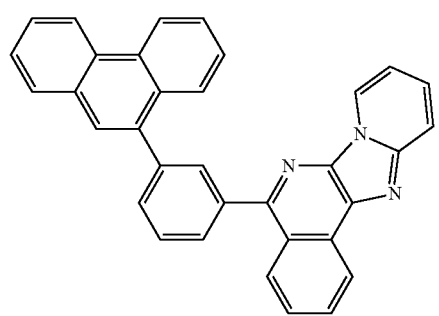

-continued
365
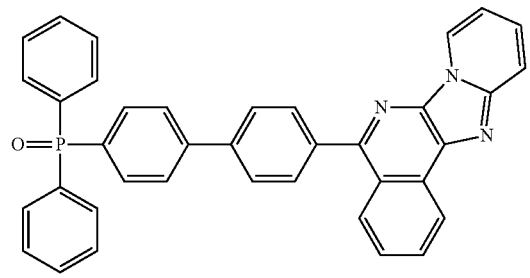
366
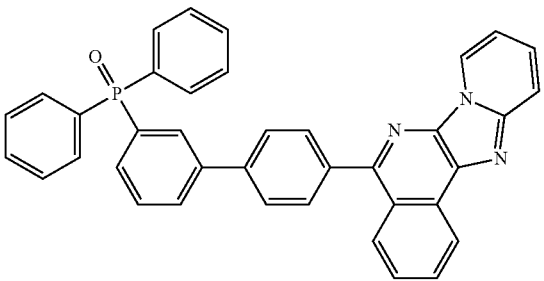
367
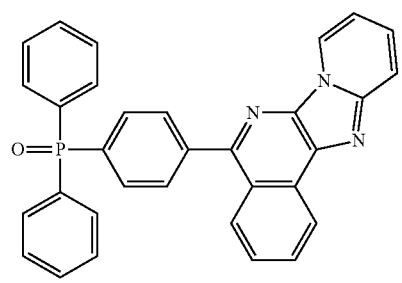
368
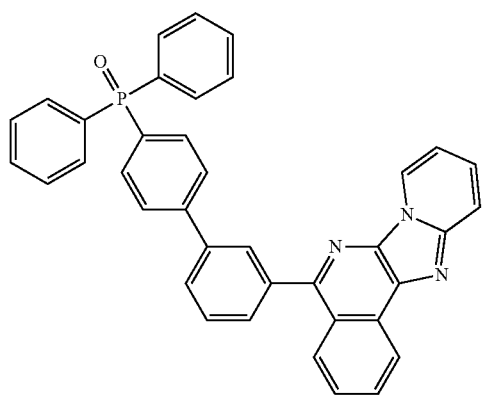
369
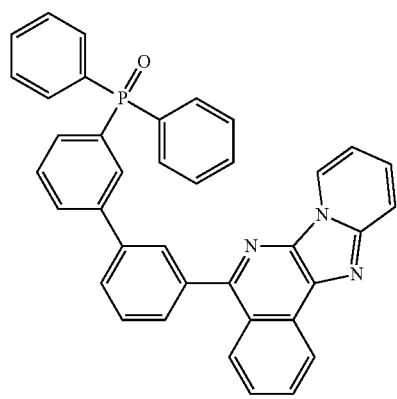
370
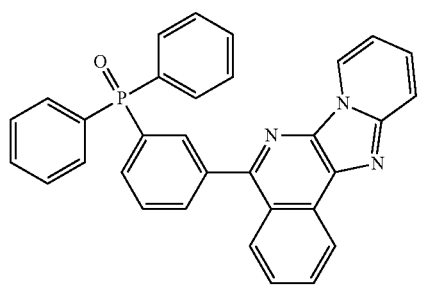
371
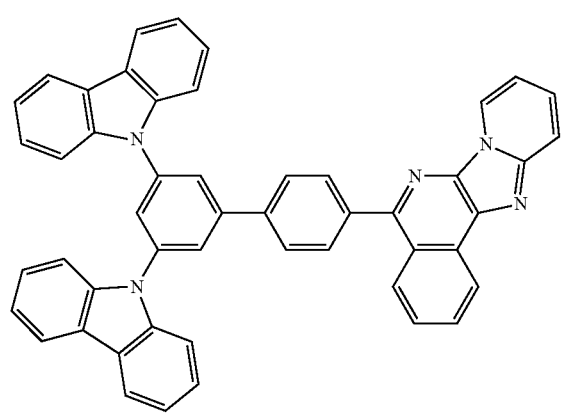
372
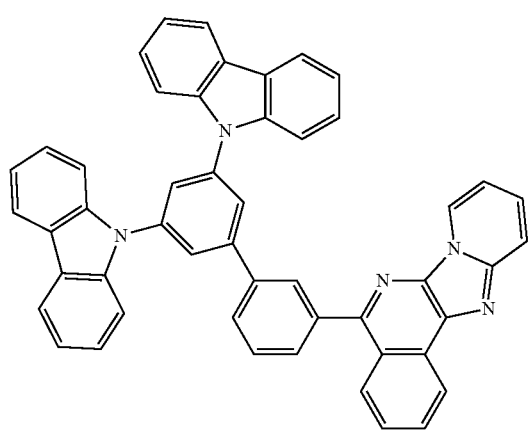

-continued
373
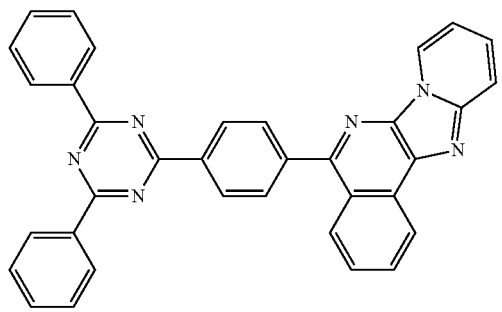
374
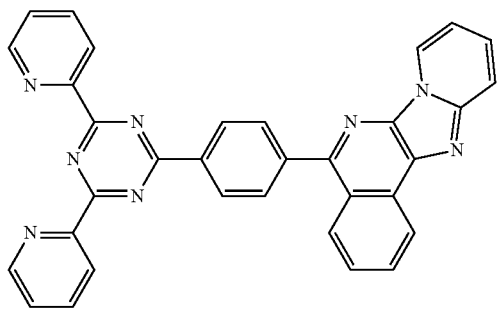
375
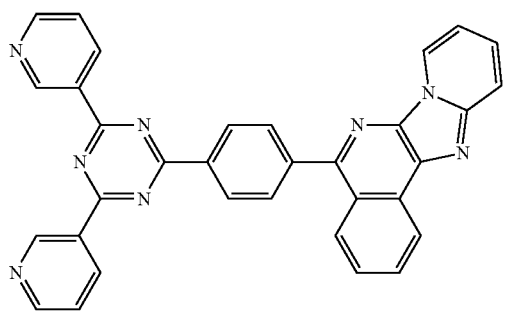
376
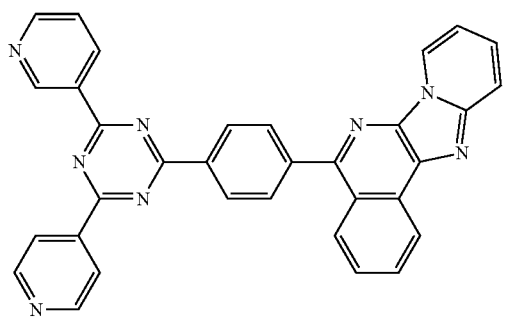
377
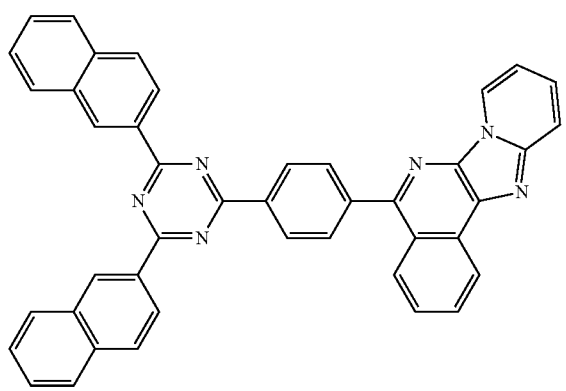
378
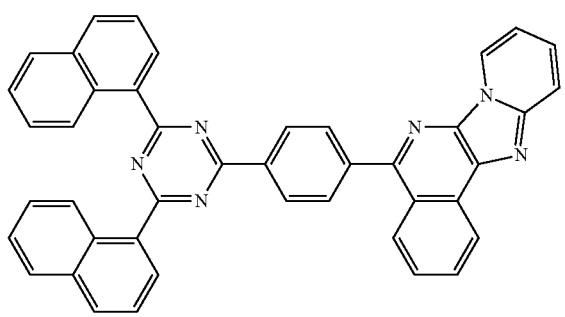
379
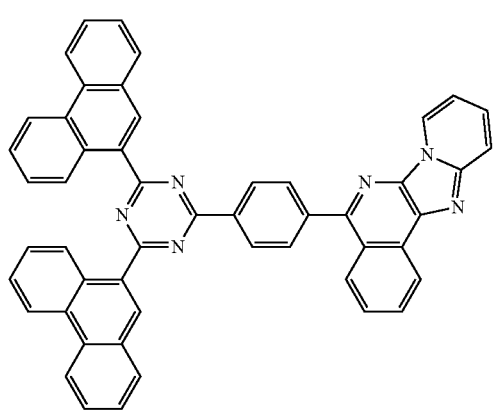
380
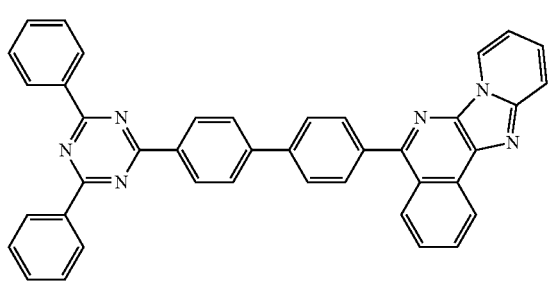

-continued
381
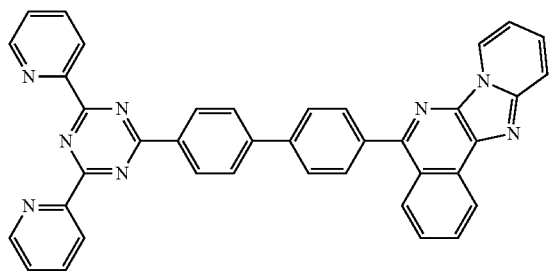
382
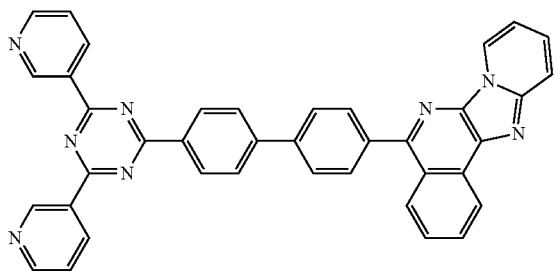
383
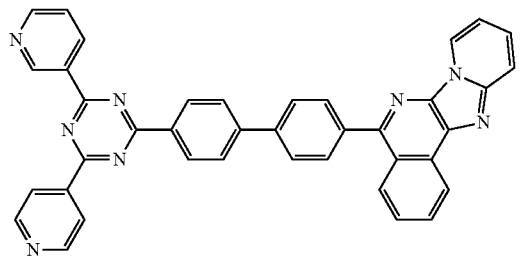
384
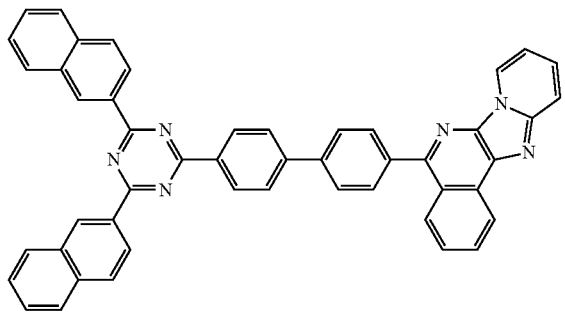
385
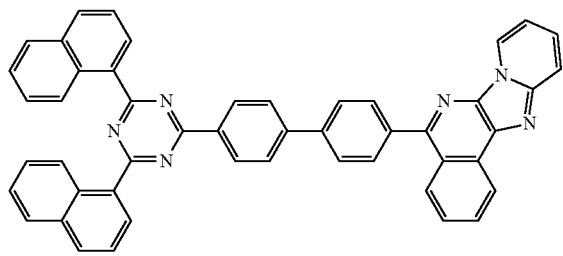
386
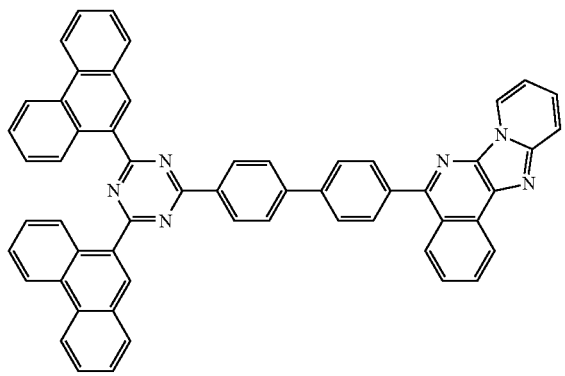
387
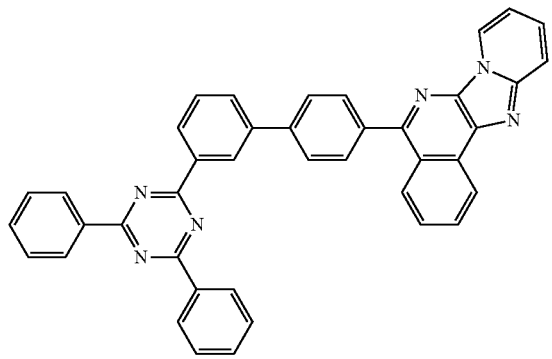
388
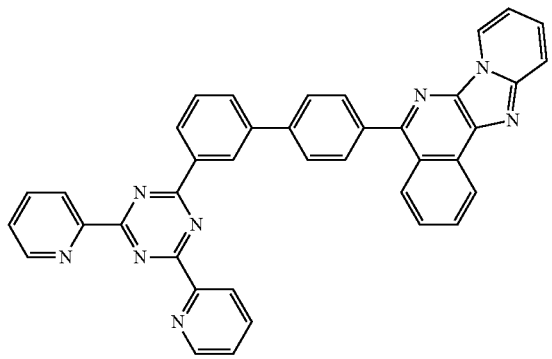

-continued
389
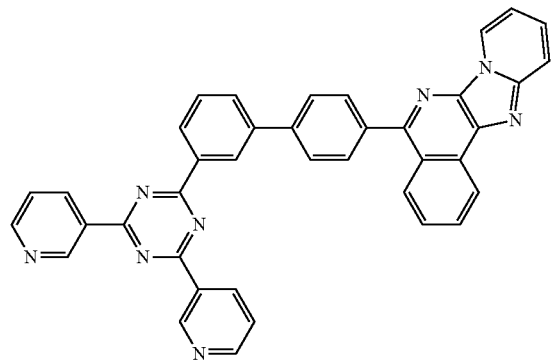
390
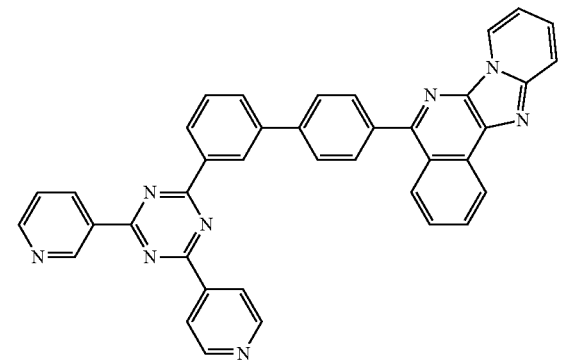
391
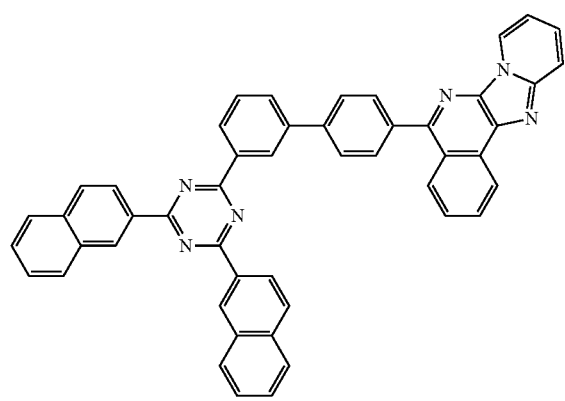
392
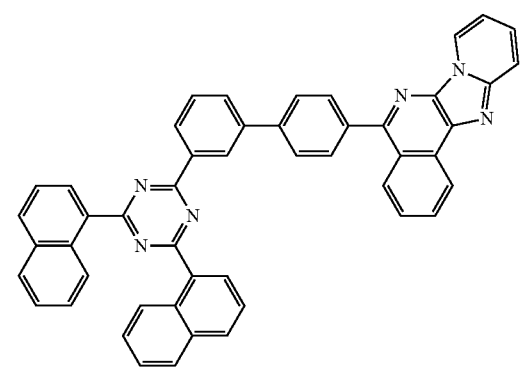
393
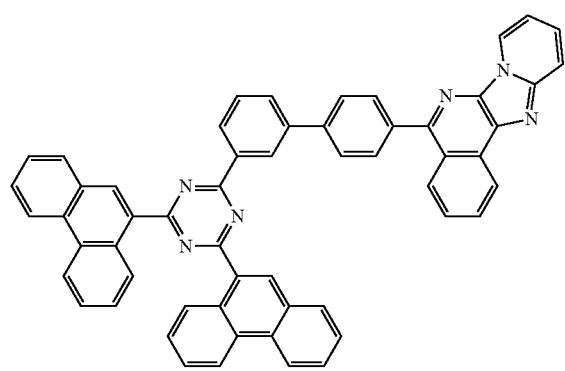
394
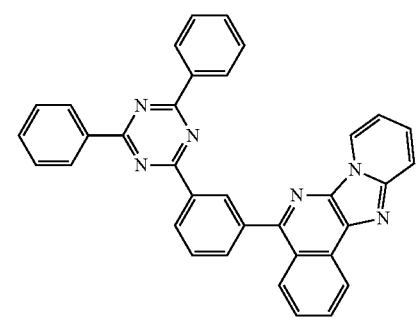
395
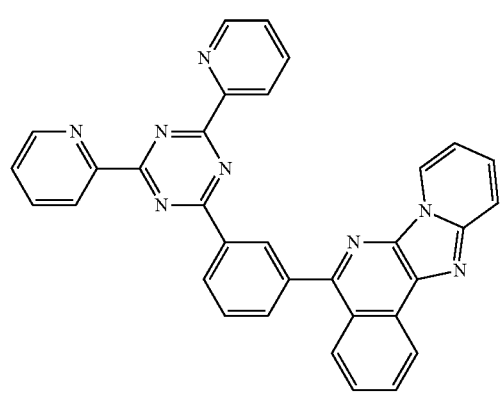
396
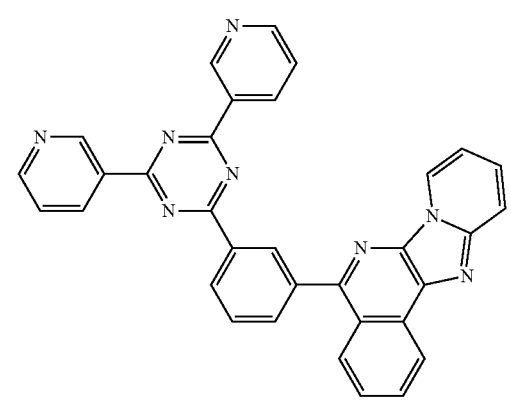

-continued
397
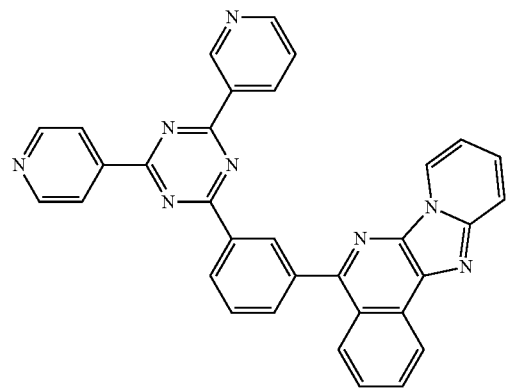
398
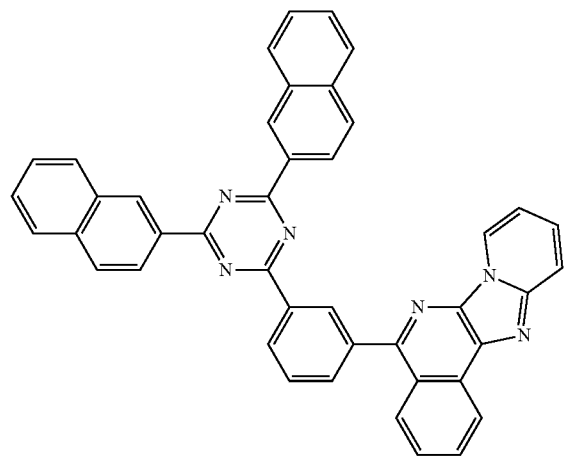
399
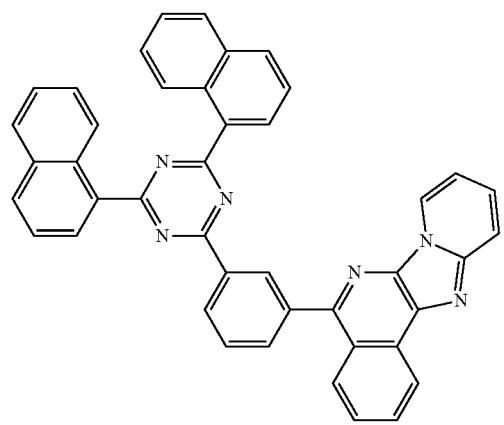
400
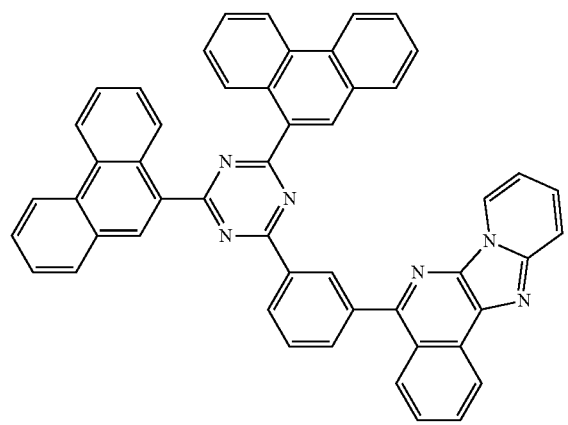
401
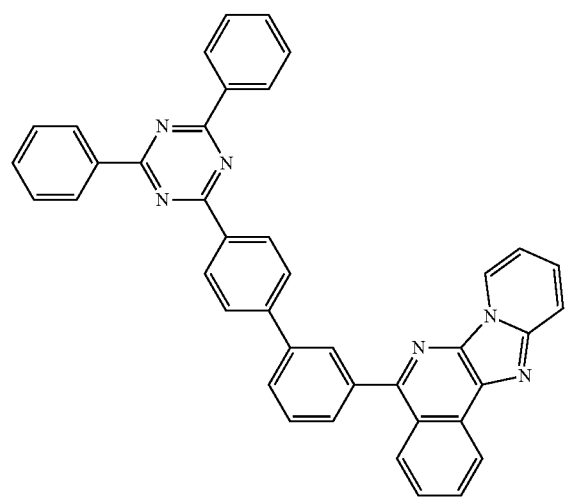
402
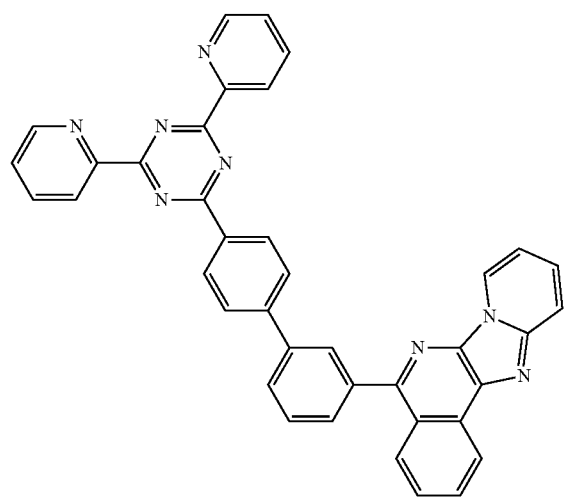

-continued
403
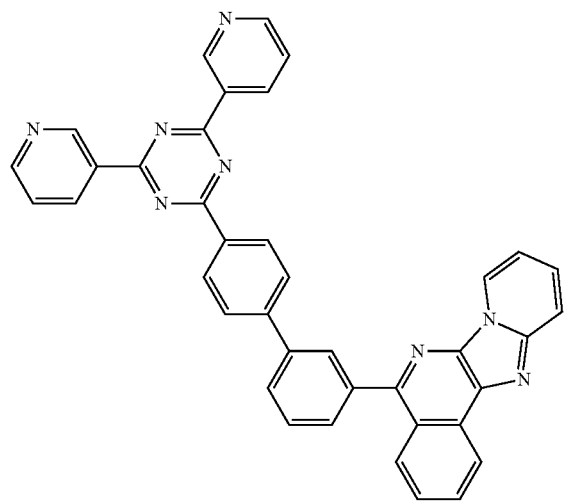
404
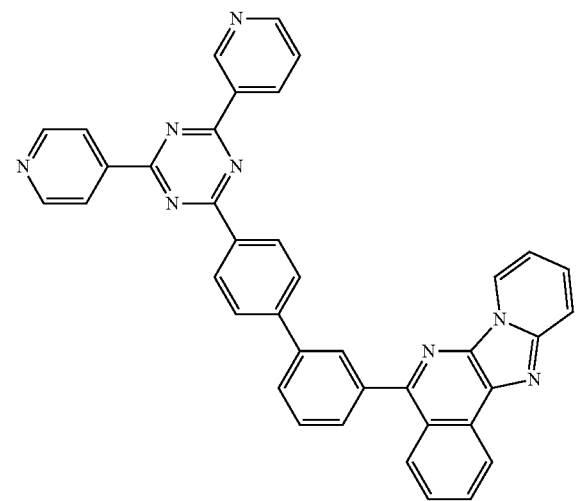
405
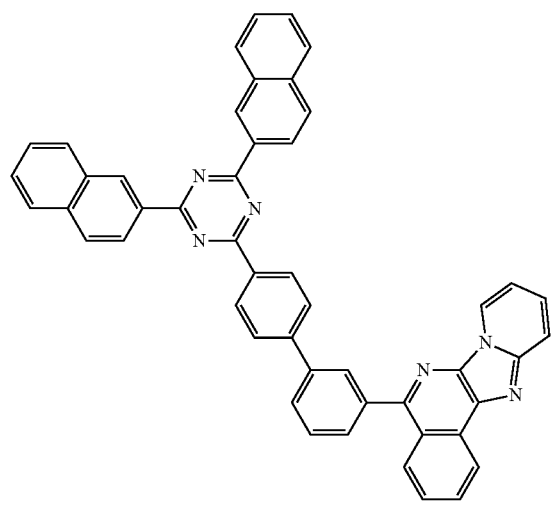
406
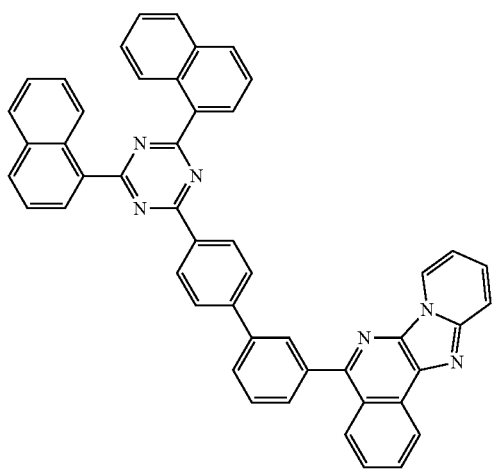
407
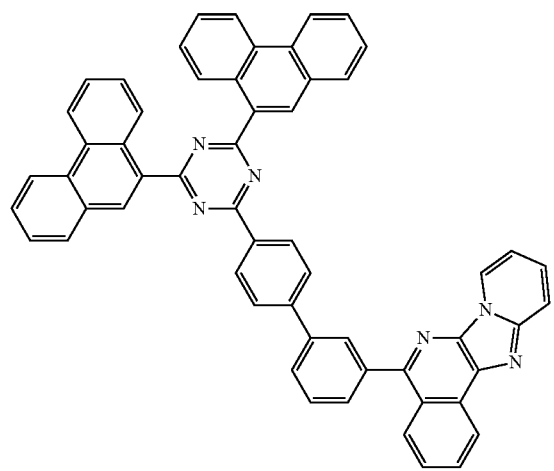
408
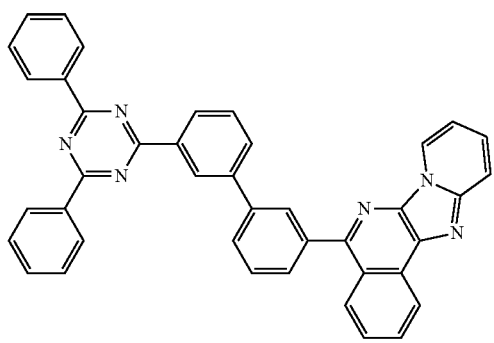

-continued
409
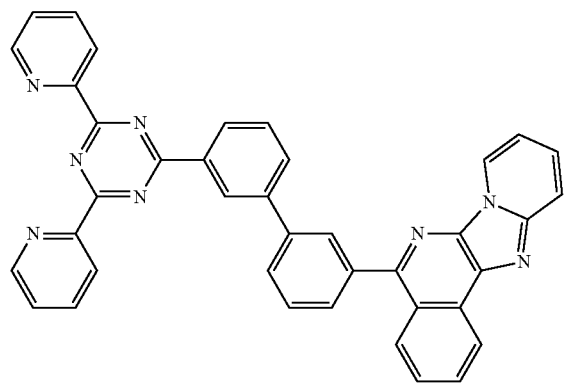
410
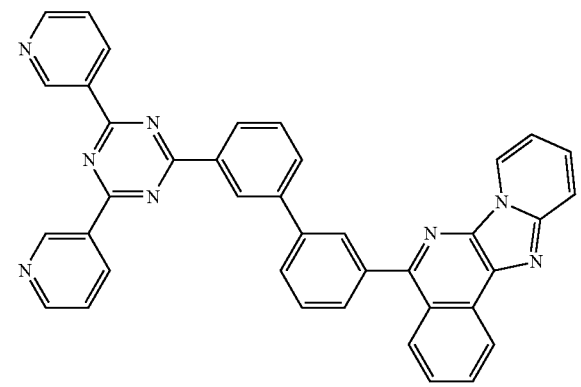
411
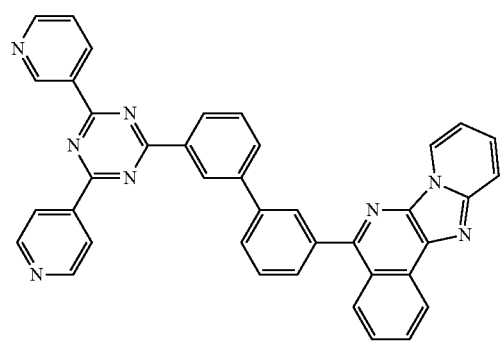
412
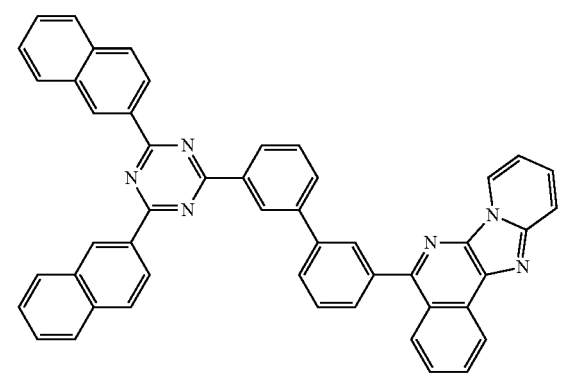
413
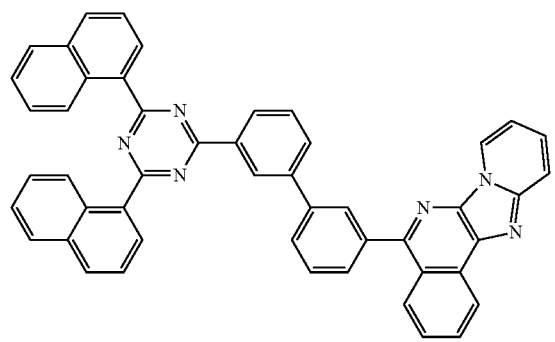
414
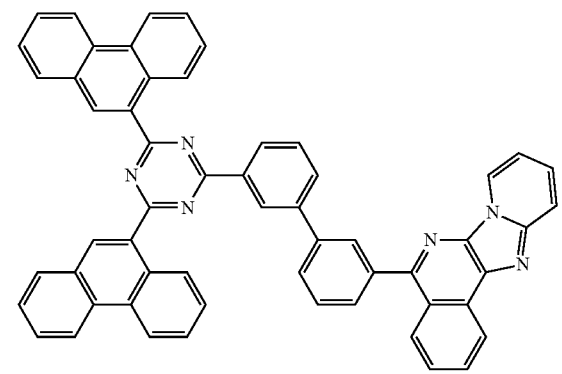
415
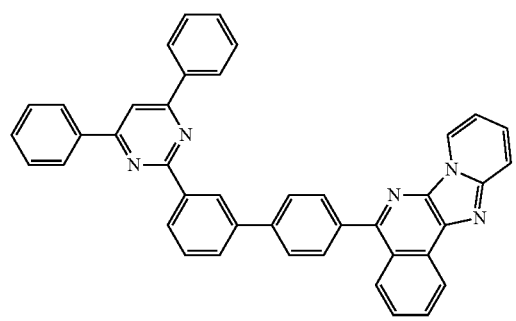
416
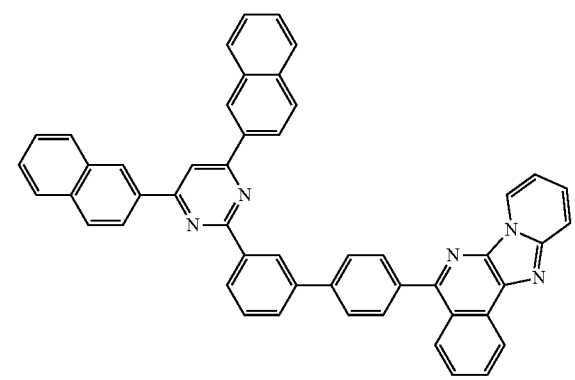

-continued
417
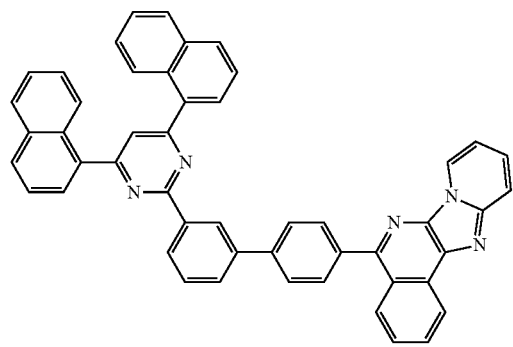
418
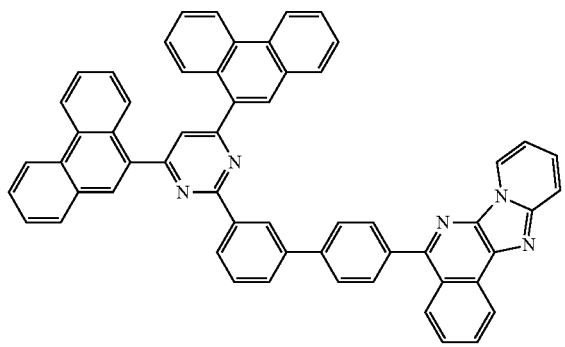
419
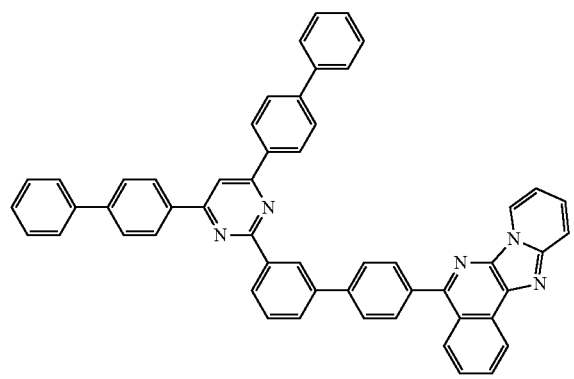
420
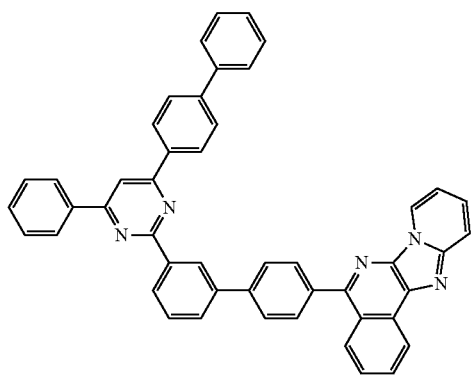
421
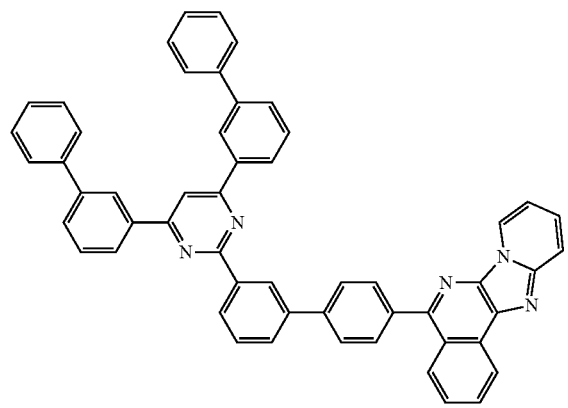
422
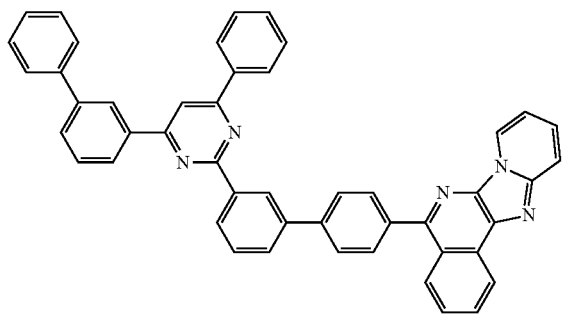
423
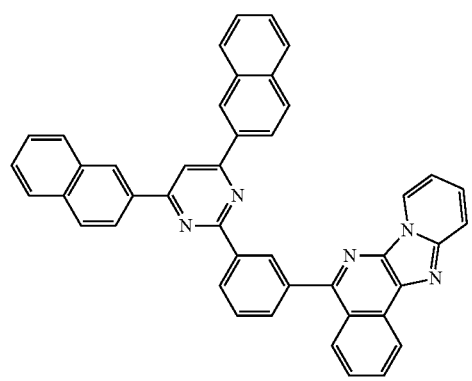
424
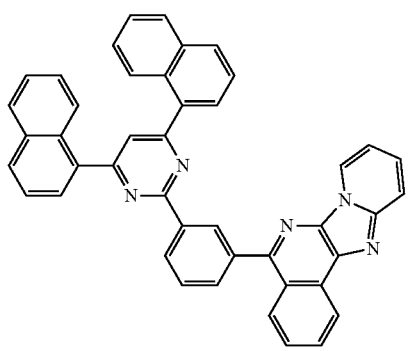

-continued
455 425
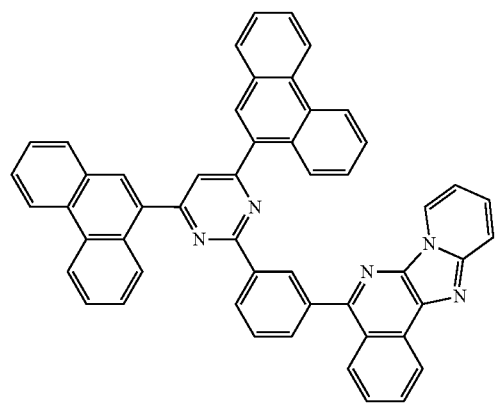
456 426
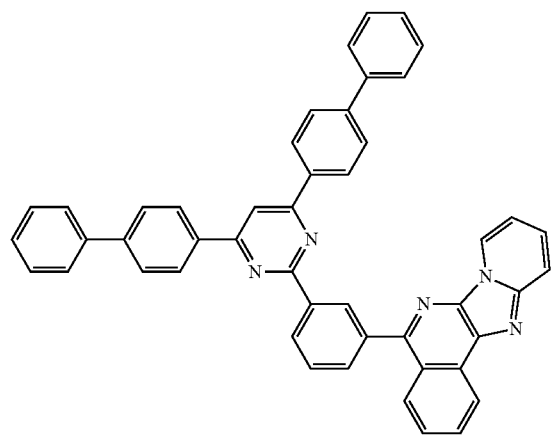
427
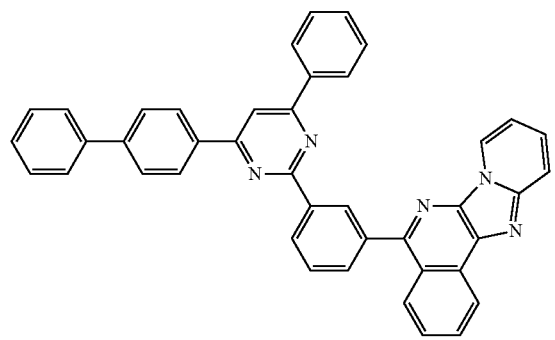
428
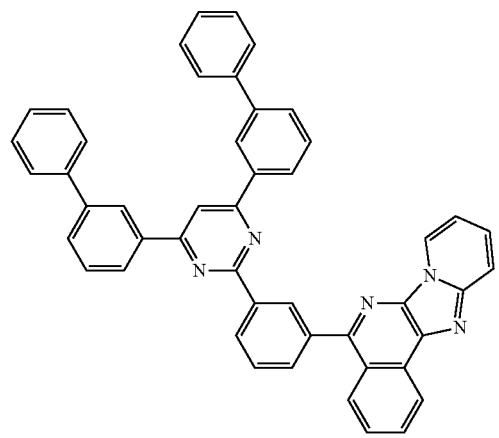
429
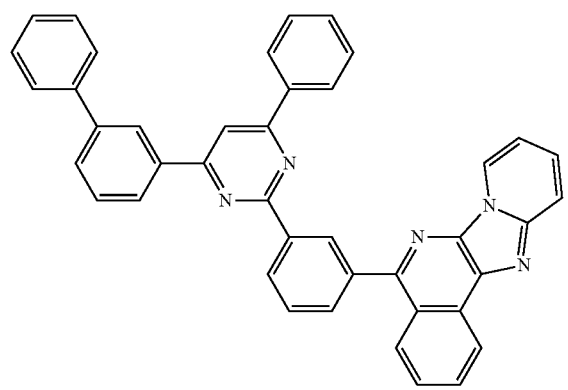
430
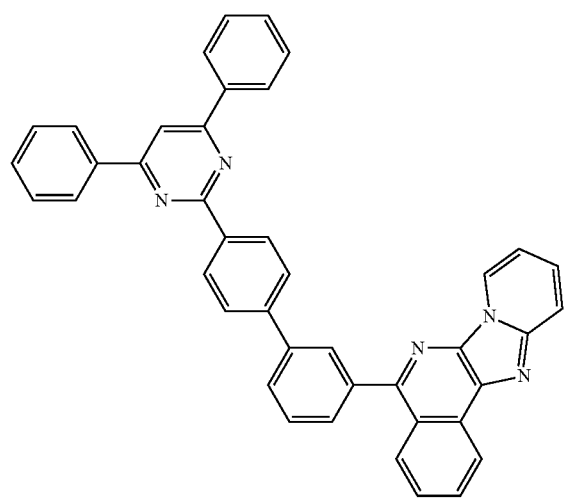

-continued
431
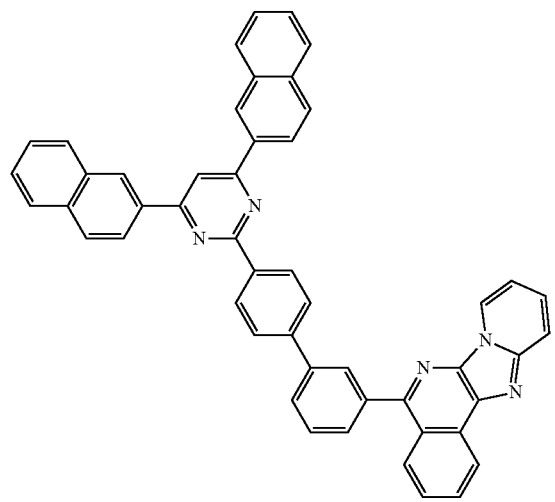
432
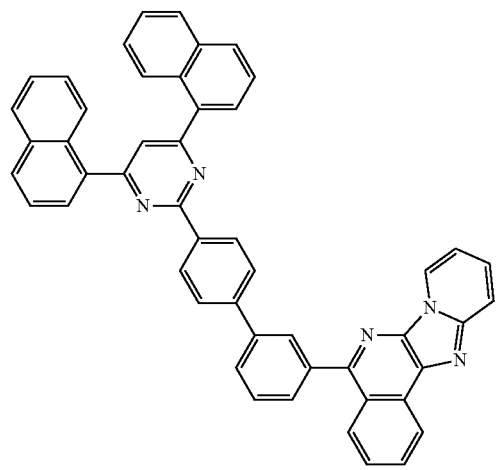
433
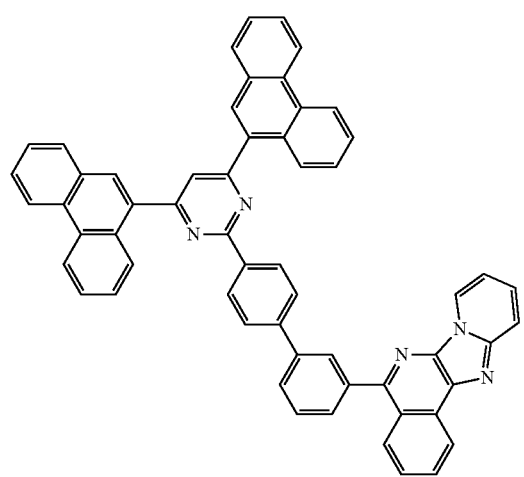
434
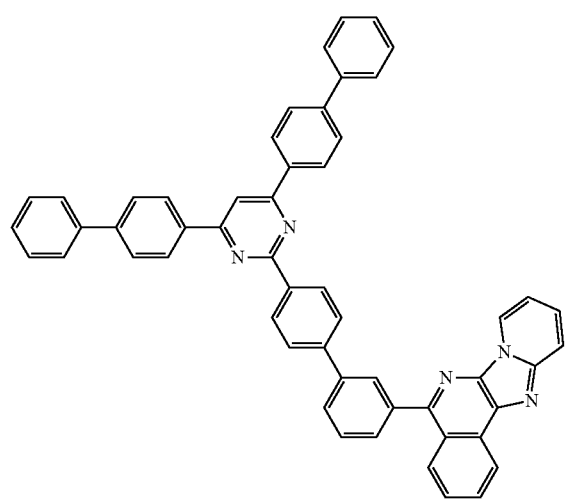
435
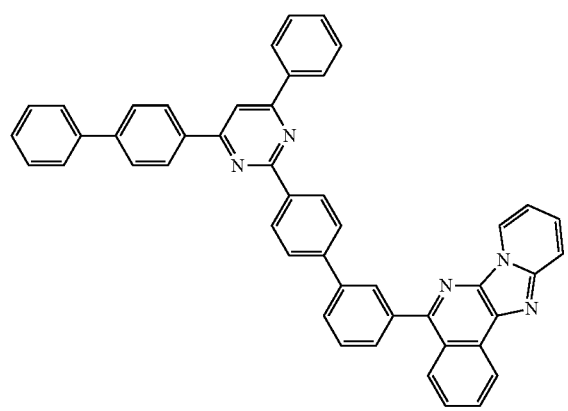
436
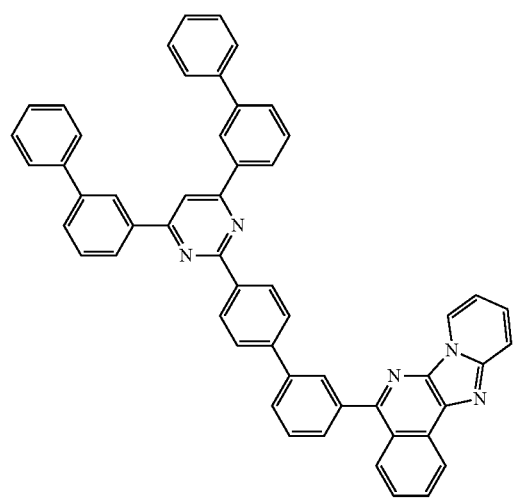

-continued
437
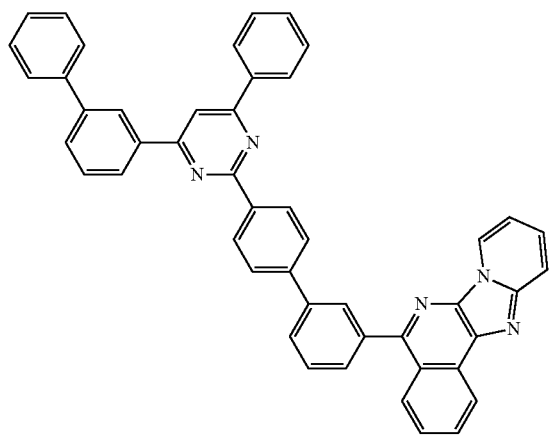
438
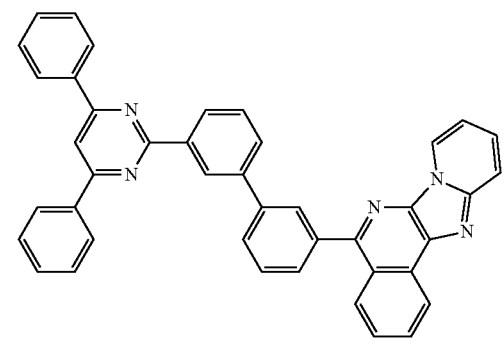
439
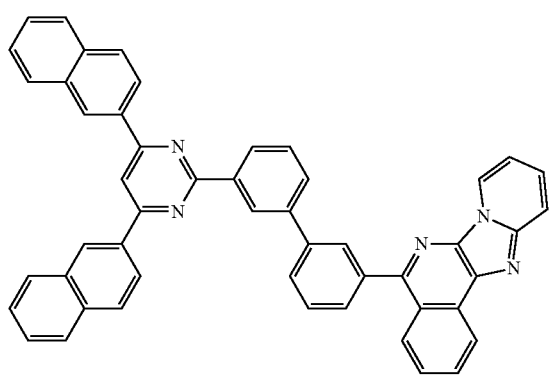
440
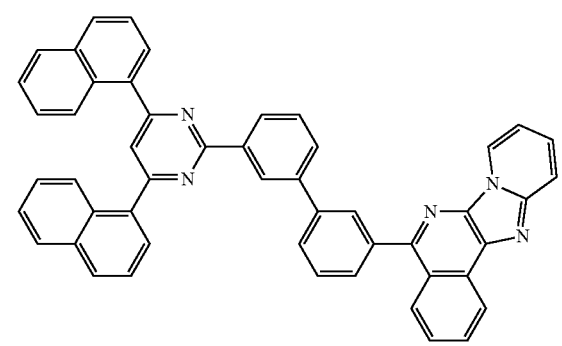
441
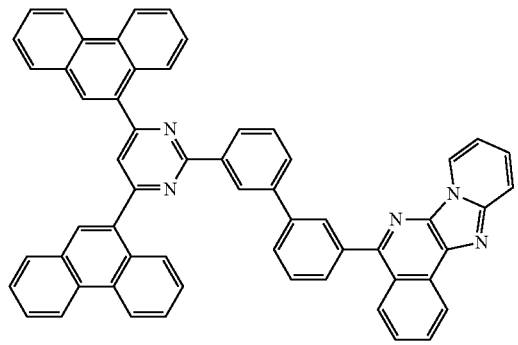
442
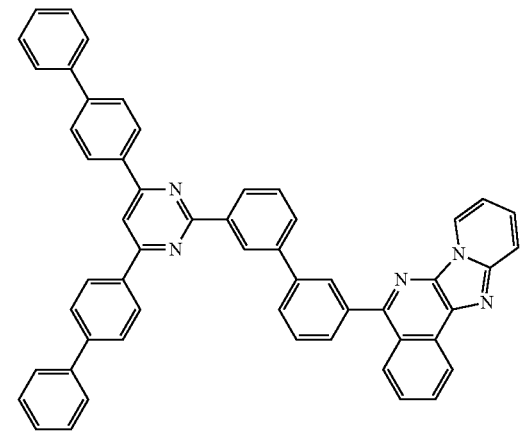
443
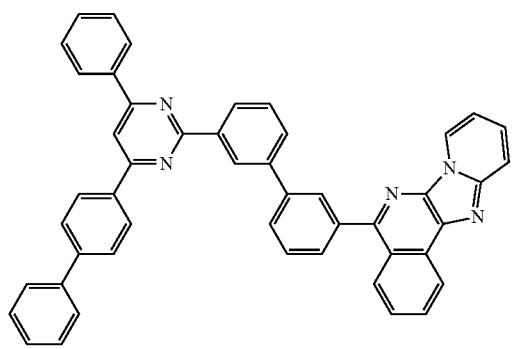
444
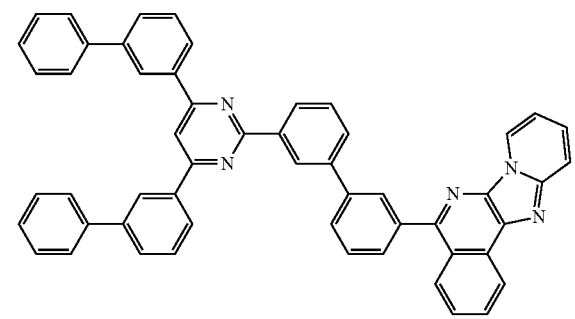

-continued
445
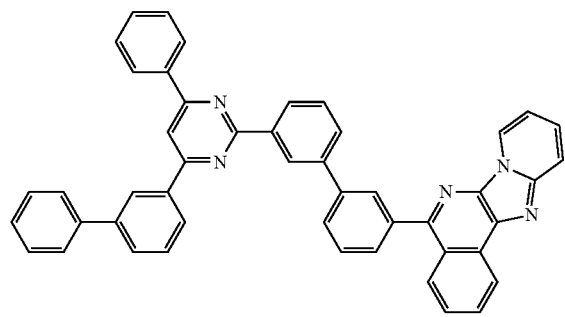
446
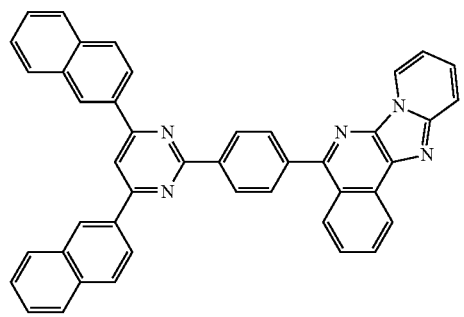
447
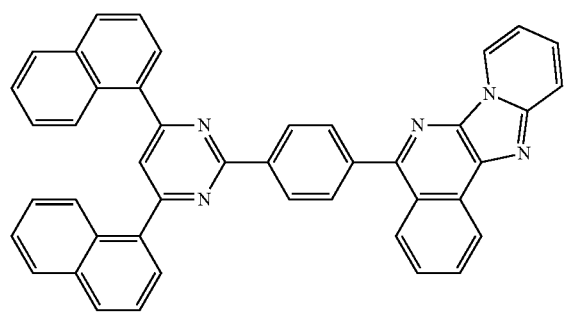
448
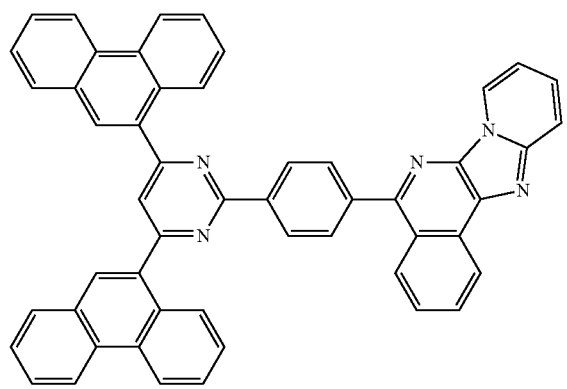
449
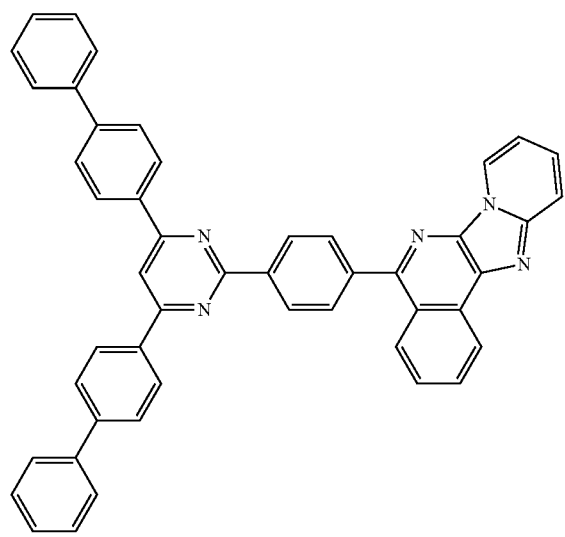
450
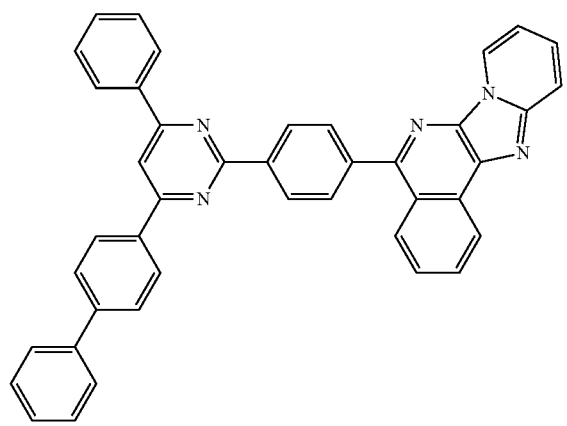
451
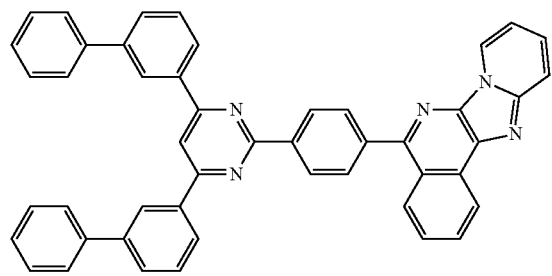
452
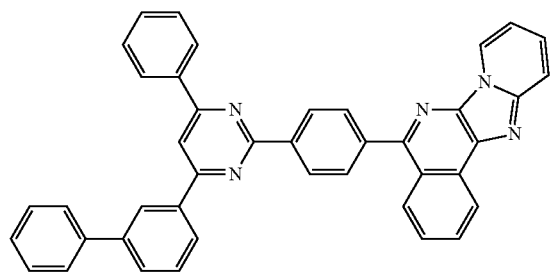

453
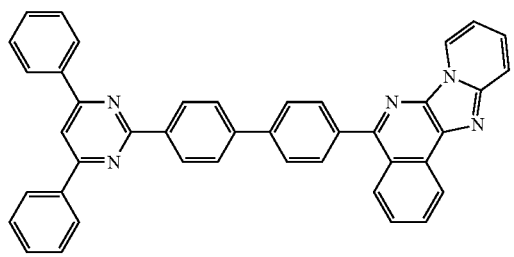
454
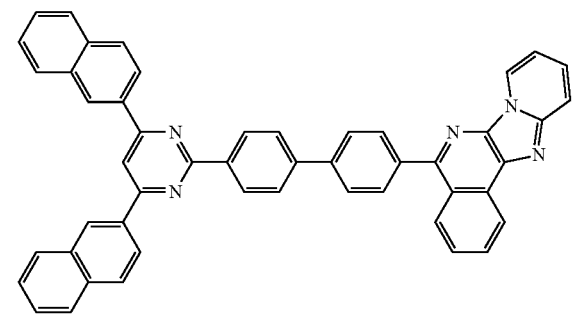
455
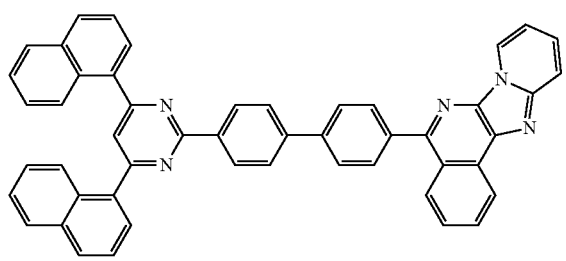
456
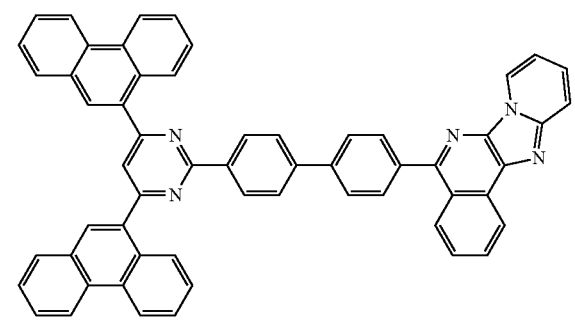
457
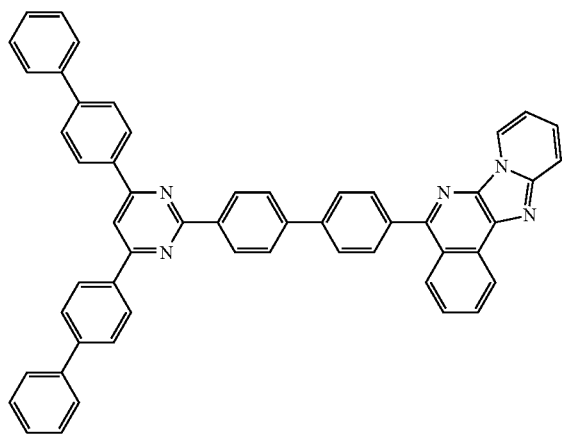
458
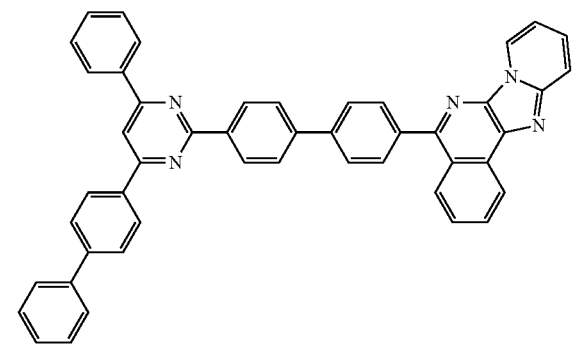
459
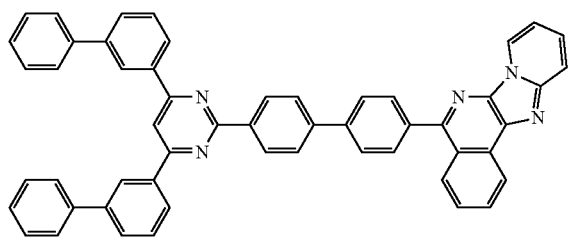
460
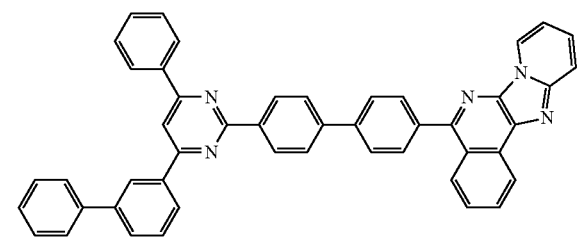

-continued
461
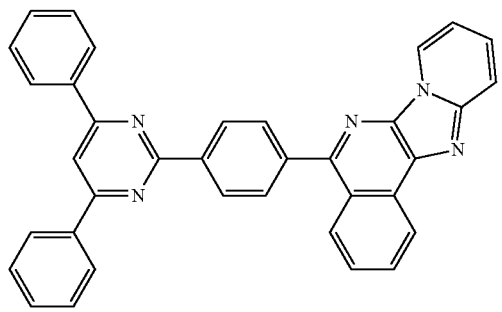
462
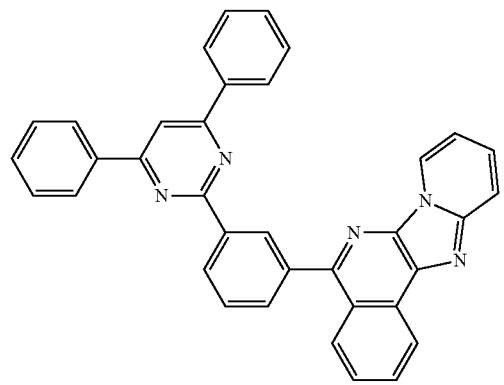
463
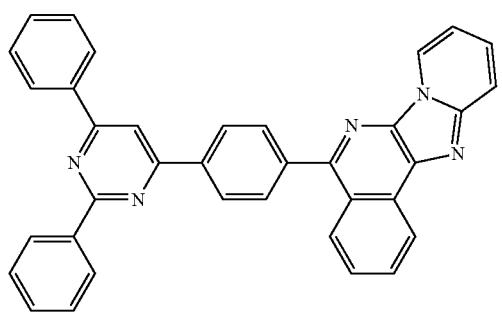
464
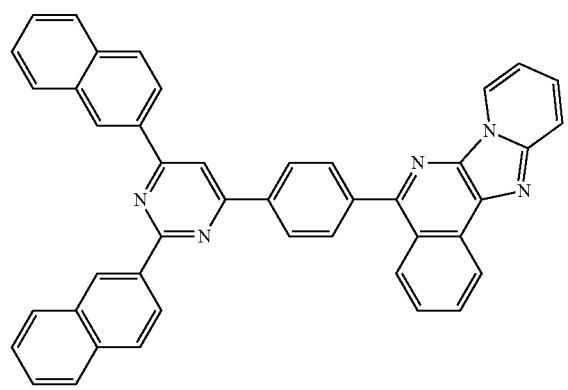
465
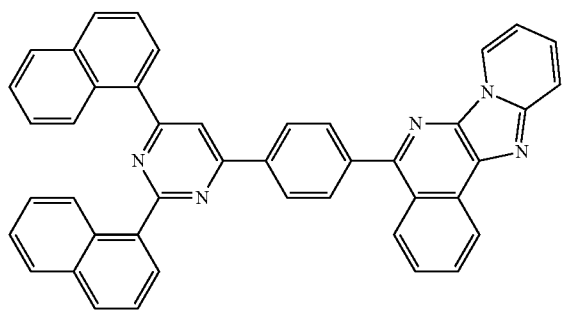
466
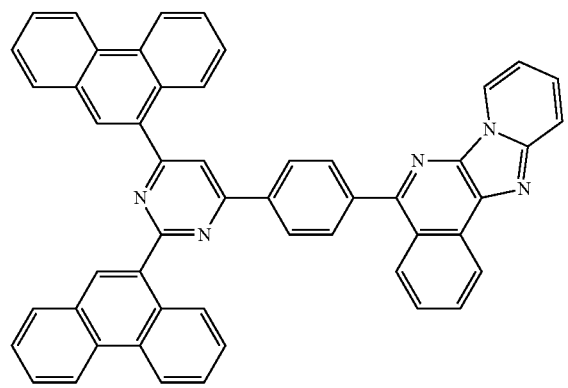

-continued
467
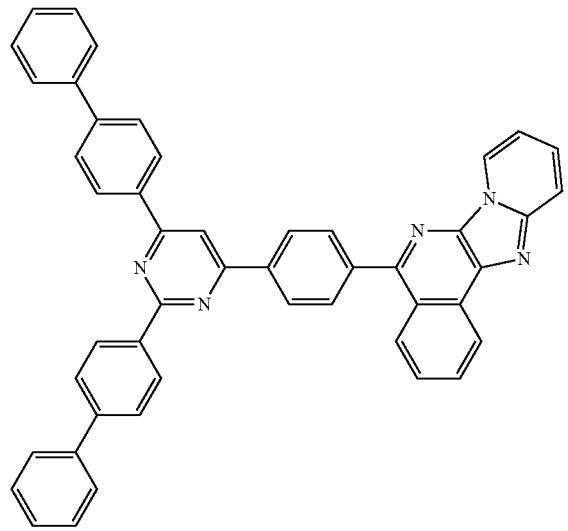
468
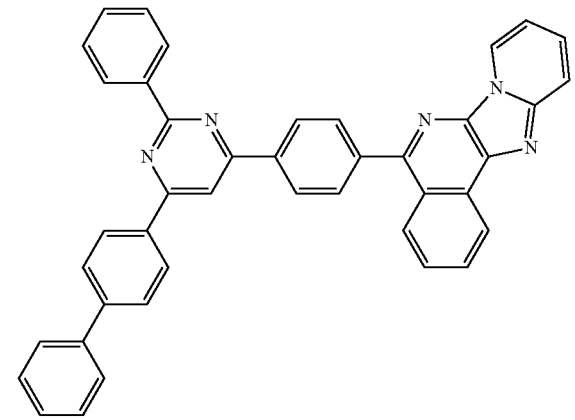
469
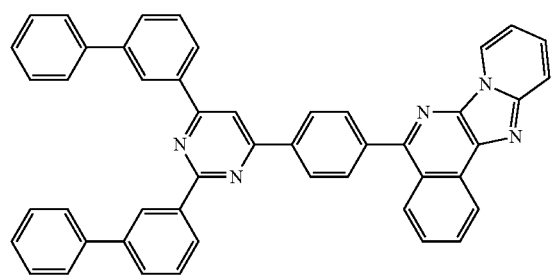
470
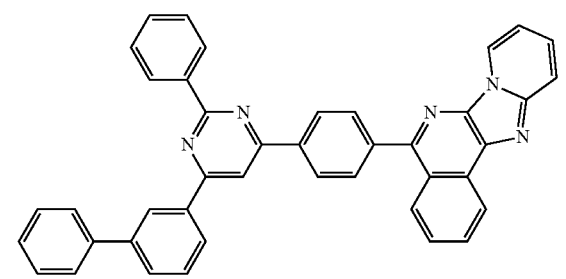
471
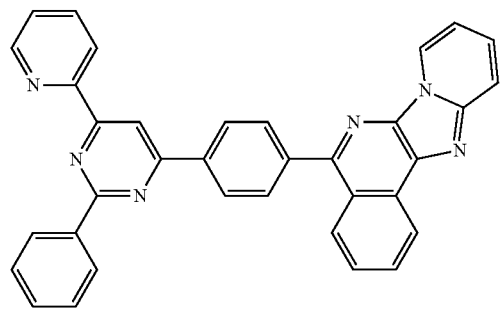
472
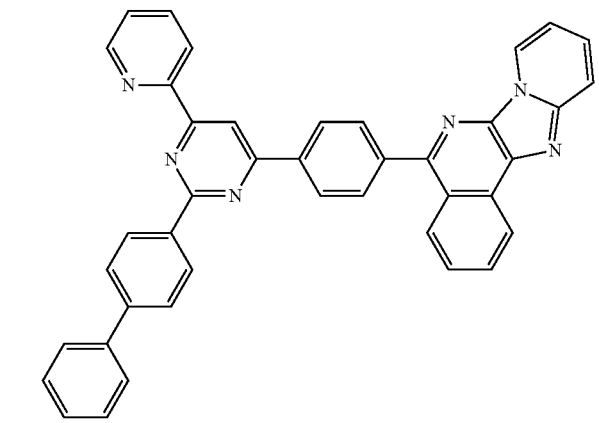
473
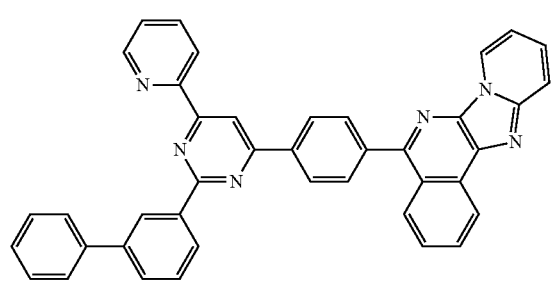
474
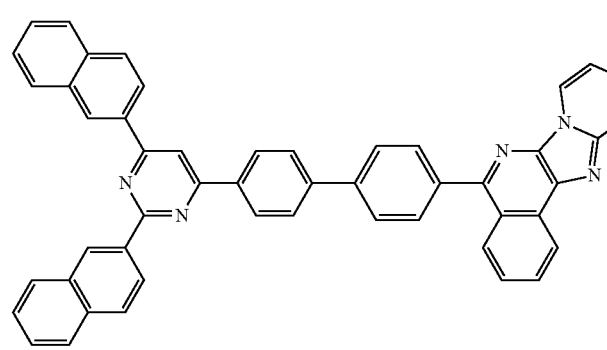

-continued
469
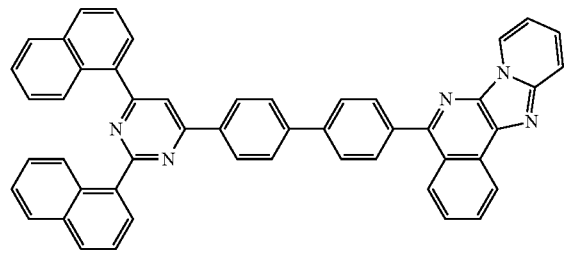
475
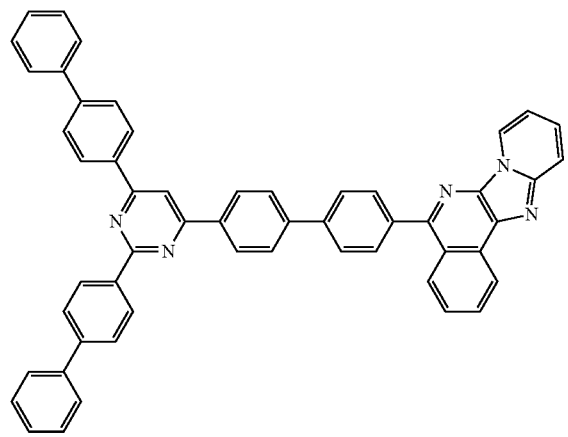
477
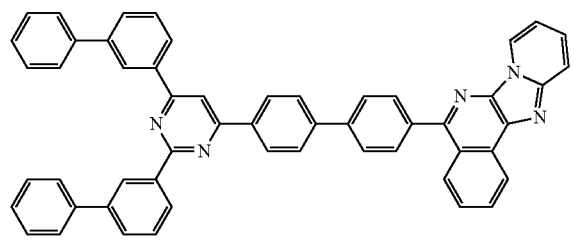
479
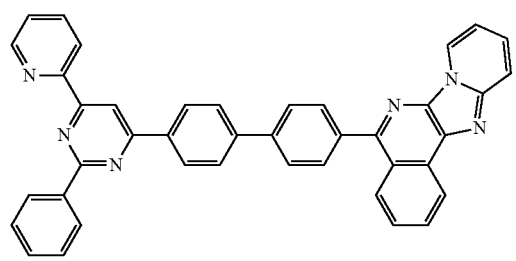
481
470
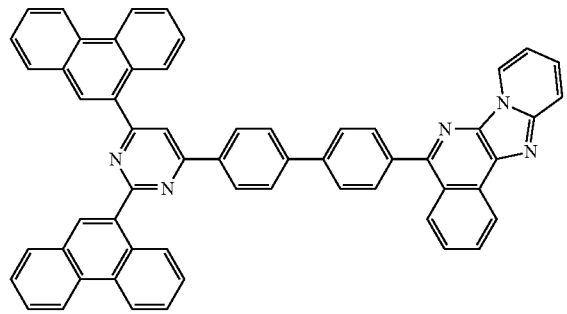
476
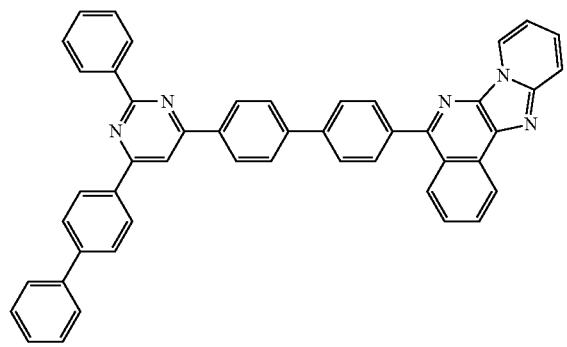
478
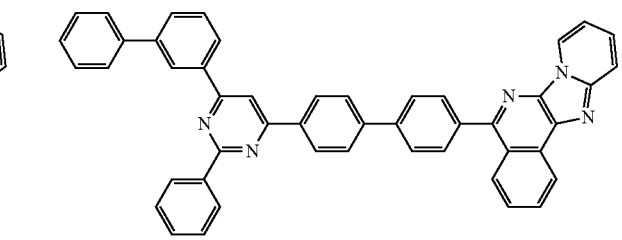
480
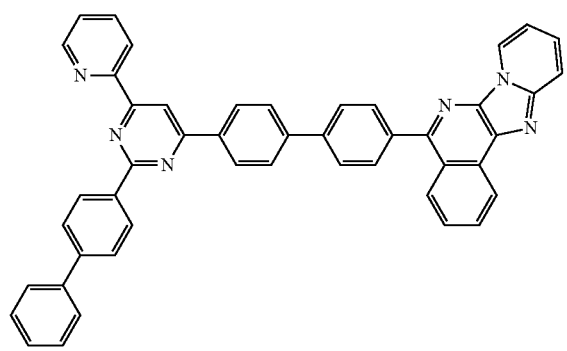
482

483
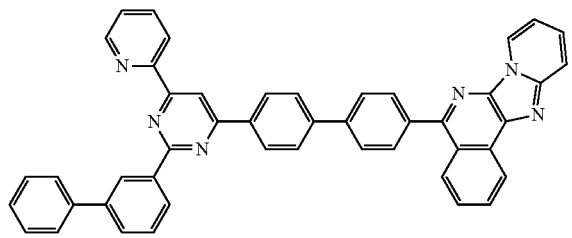
484
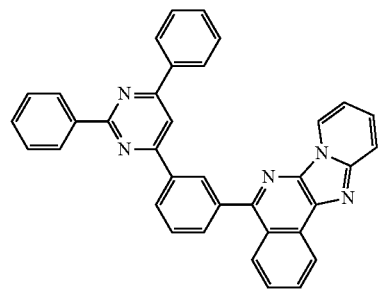
485
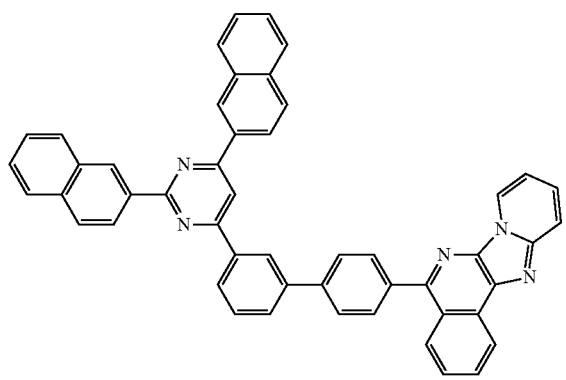
486
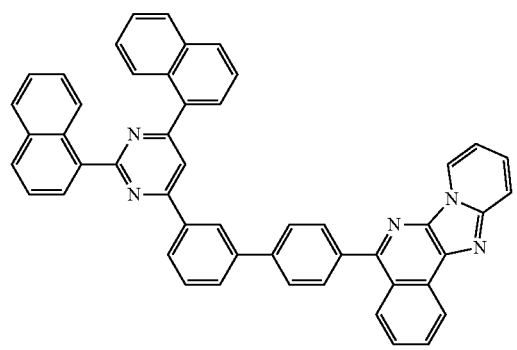
487
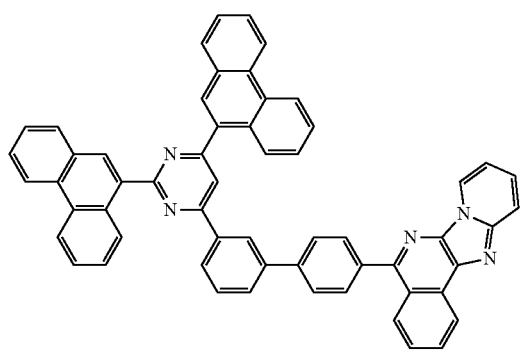
488
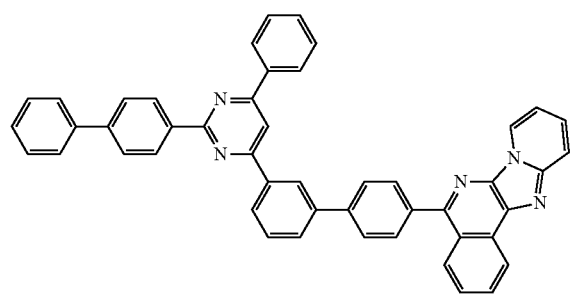
489
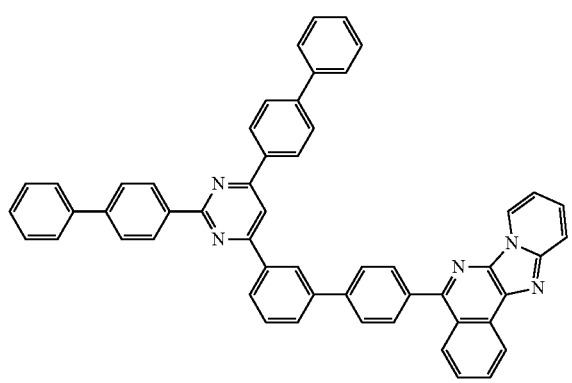
490
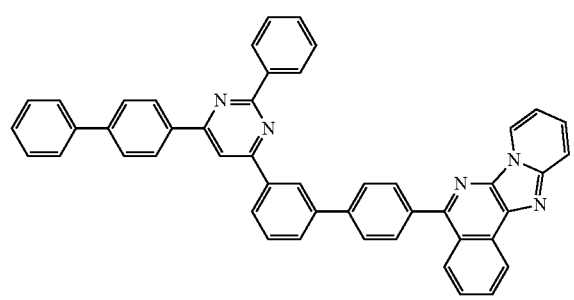

-continued
491
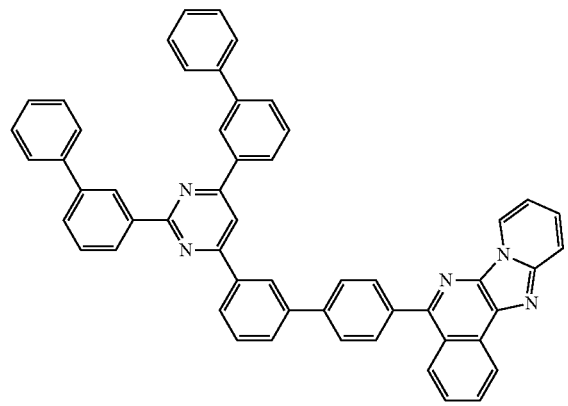
492
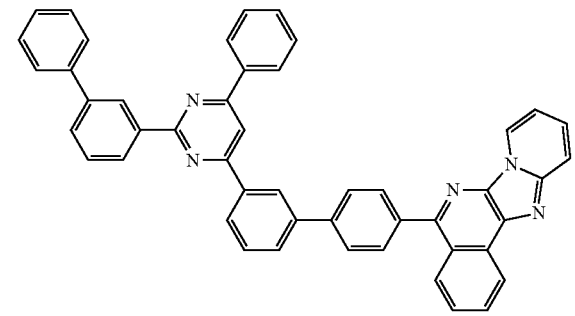
493
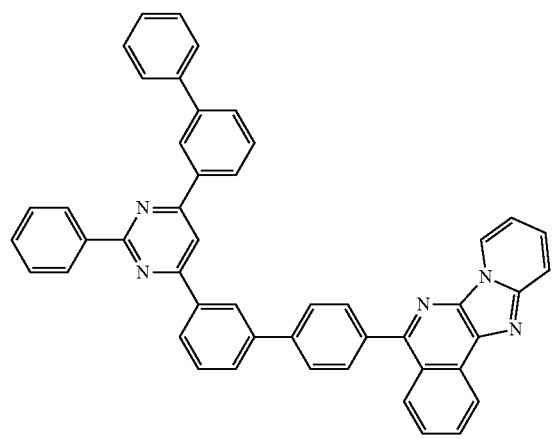
494
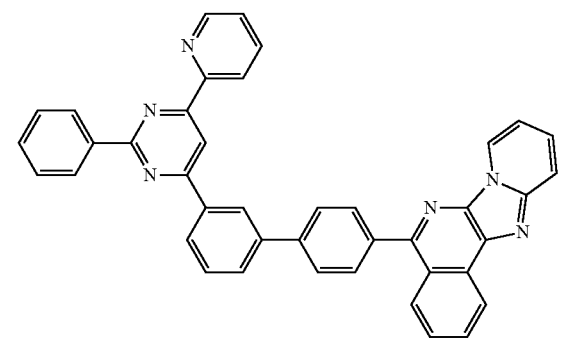
495
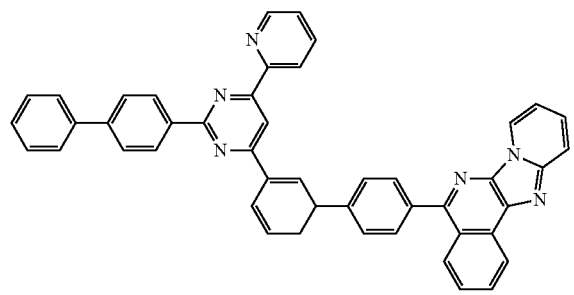
496
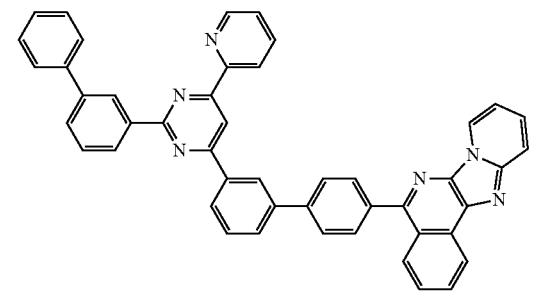
497
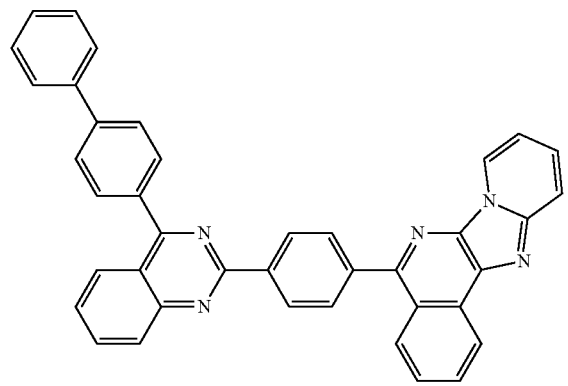
498
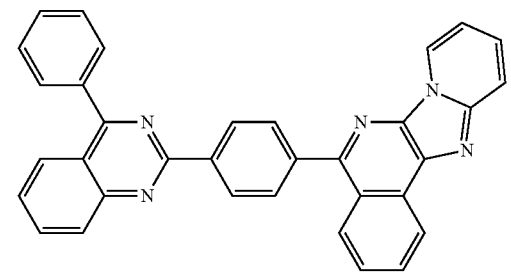

-continued
499
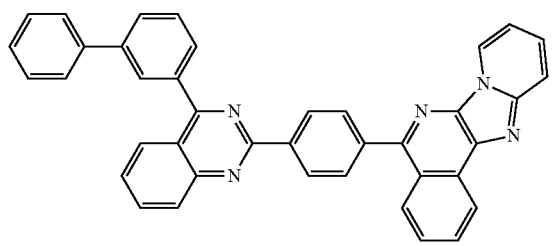
500
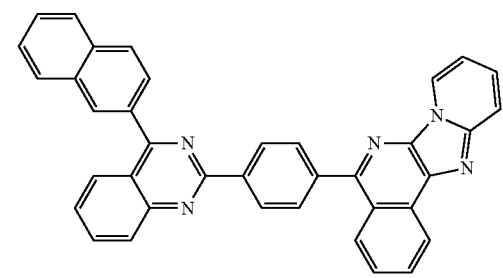
501
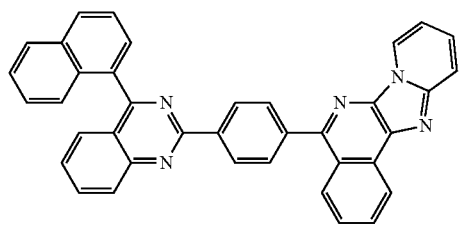
502
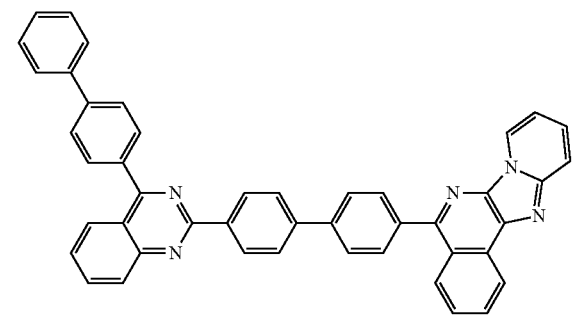
503
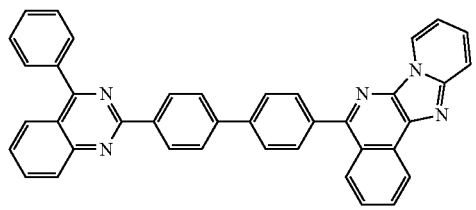
504
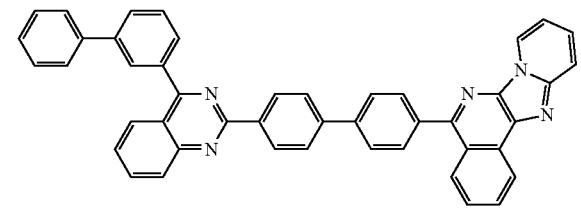
-continued
505
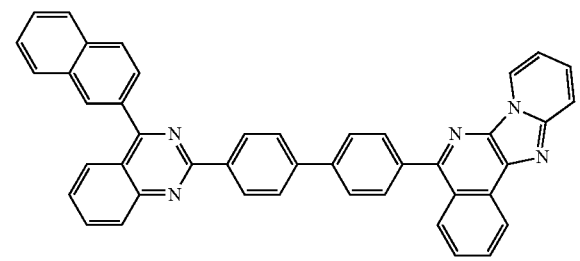
507
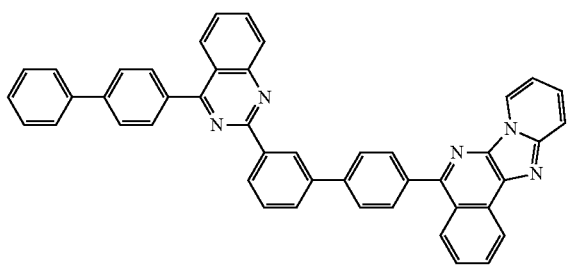
506
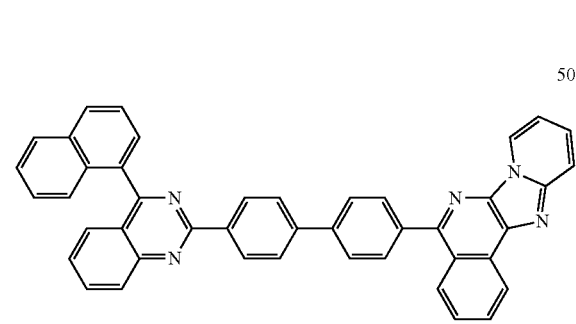
508
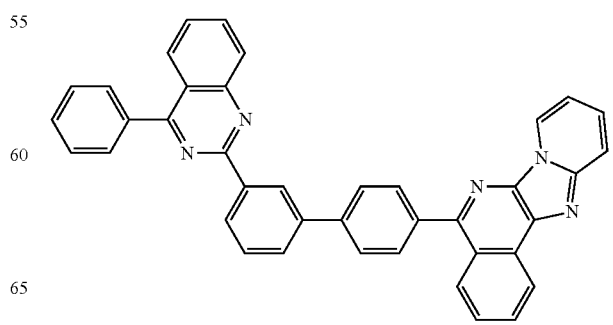

509
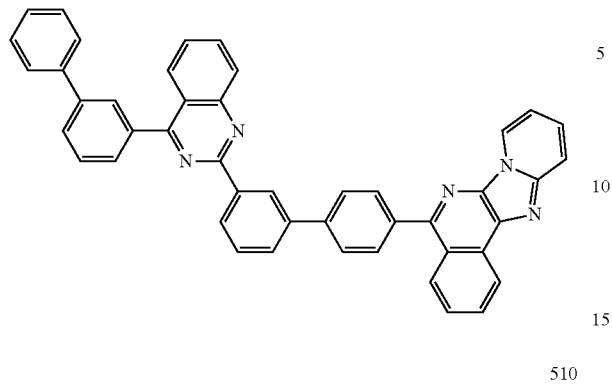
510
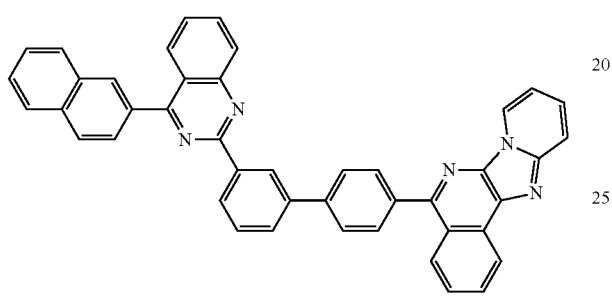
511
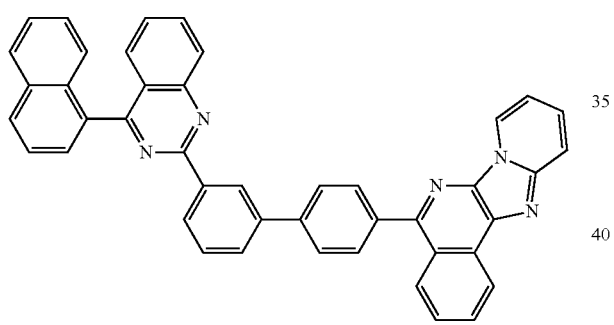
512
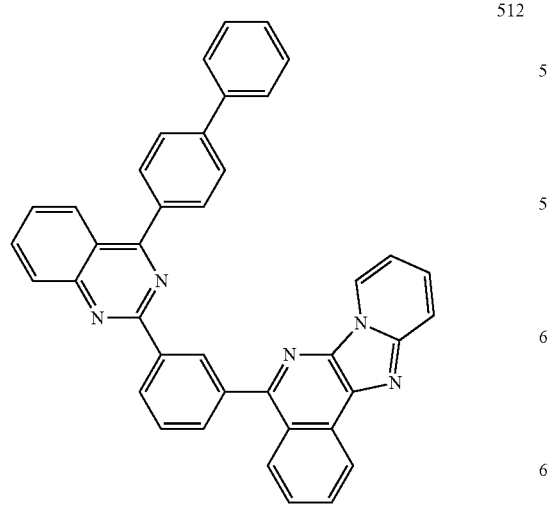
513
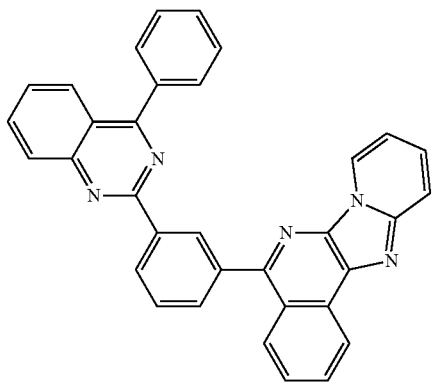
514
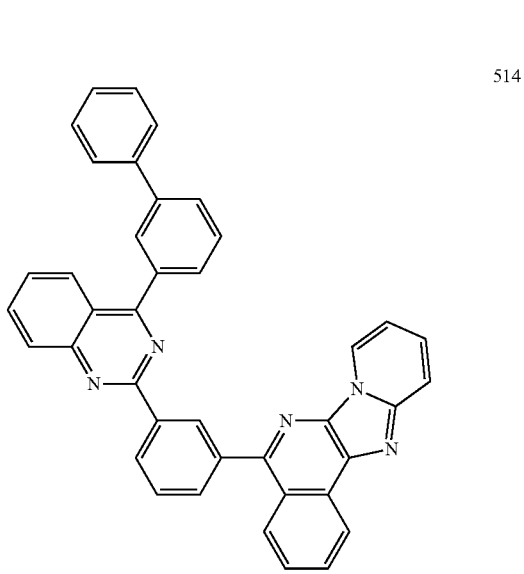
515
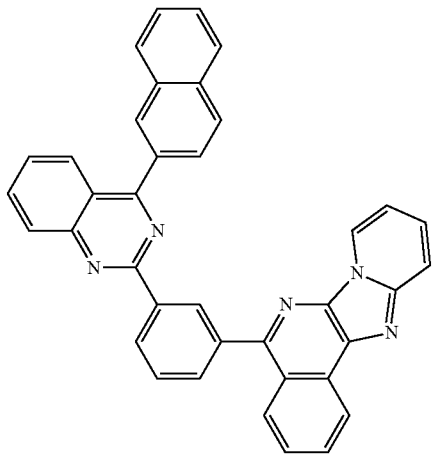

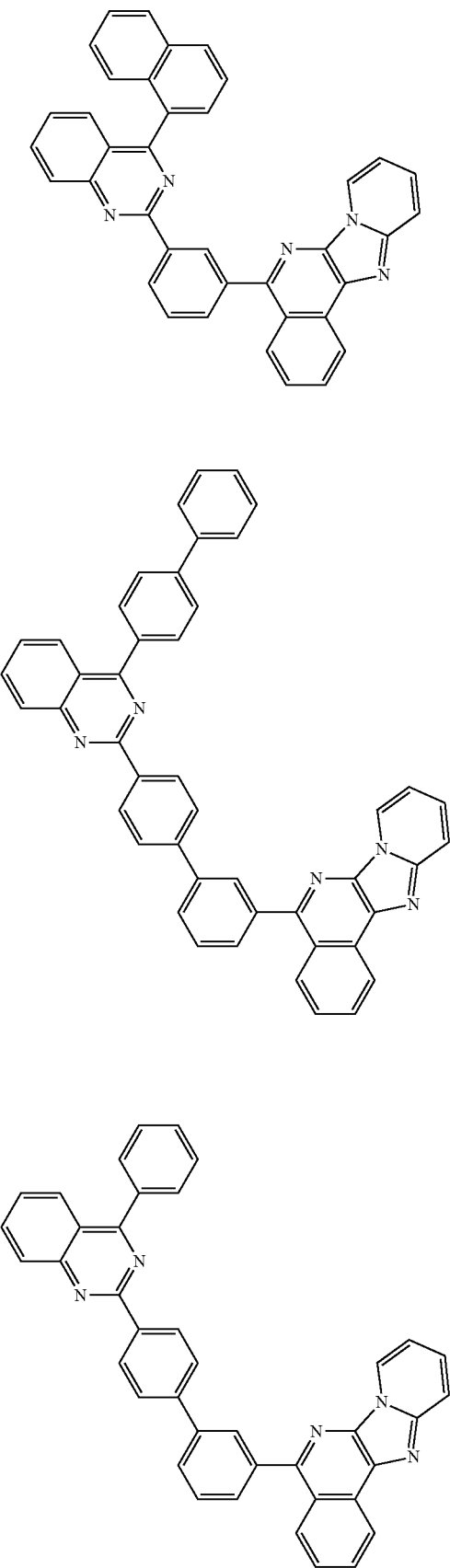
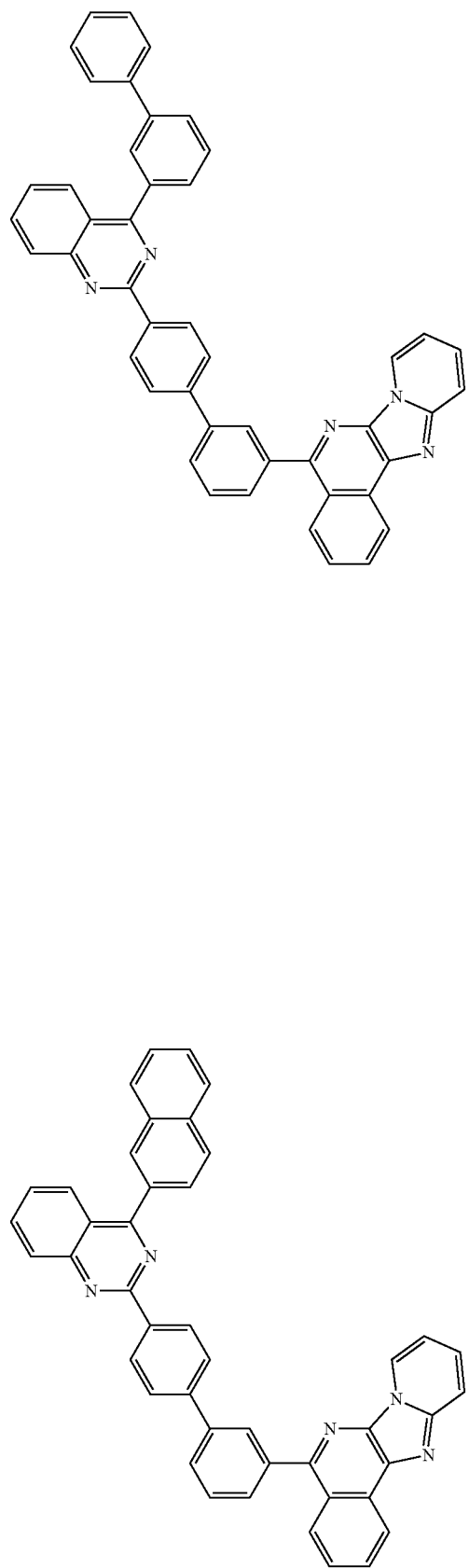

-continued
521
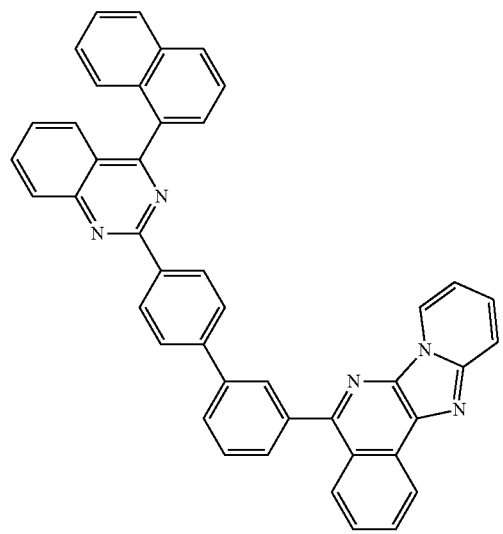
522
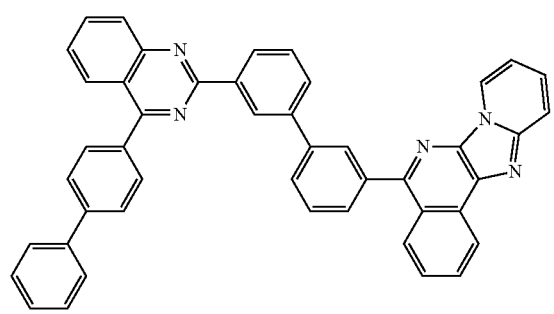
523
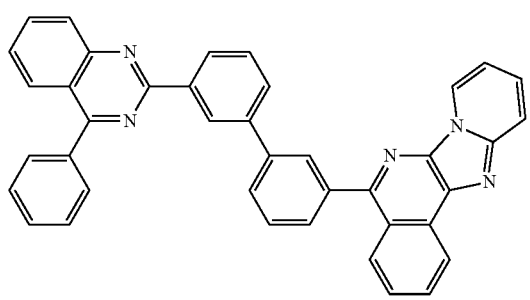
524
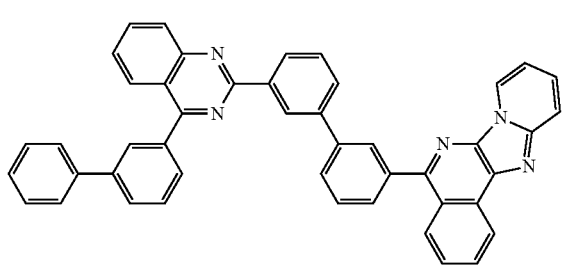
-continued
525
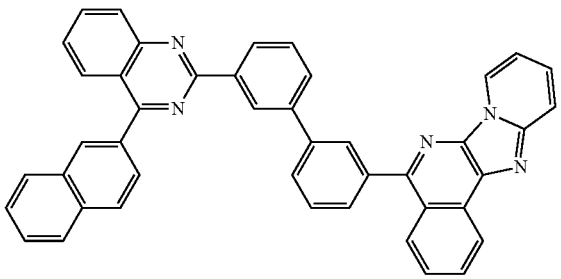
526
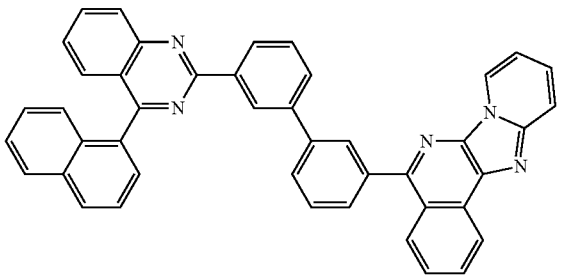
527
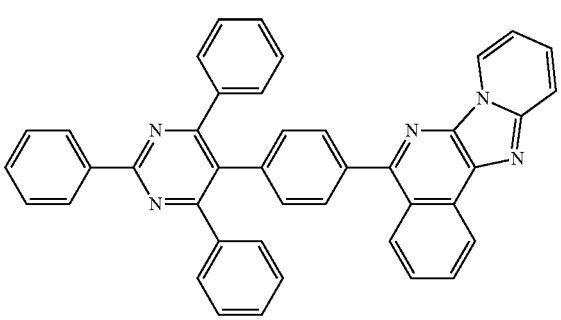
528
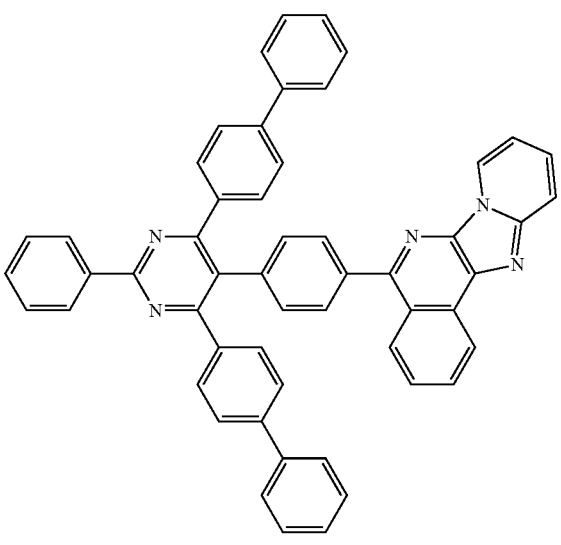

529
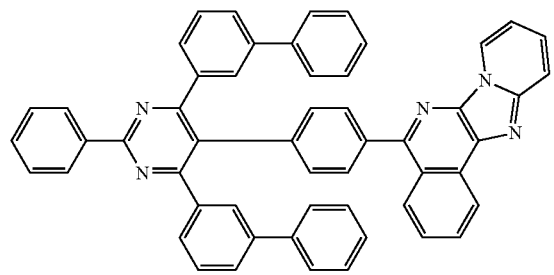
530
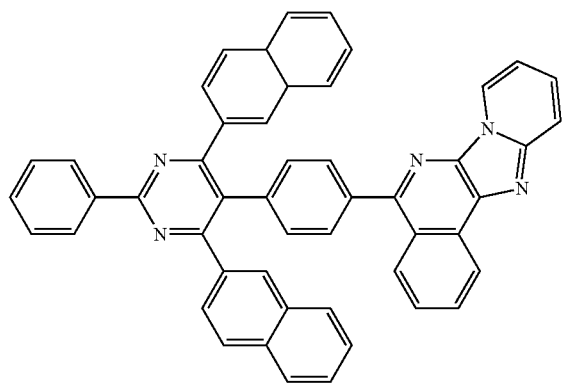
531
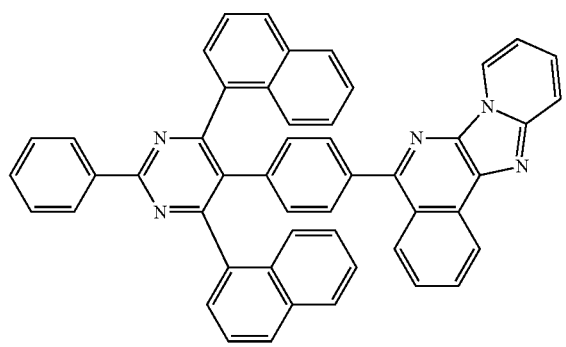
532
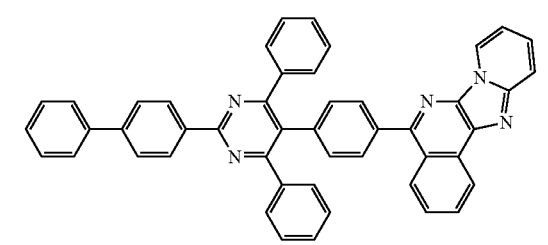
533
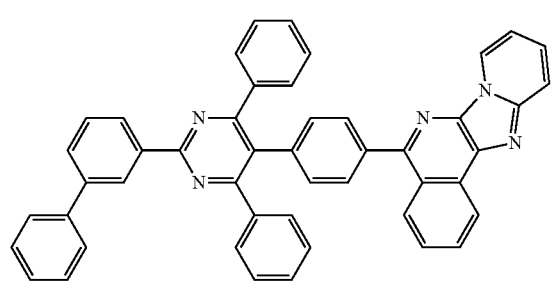
534
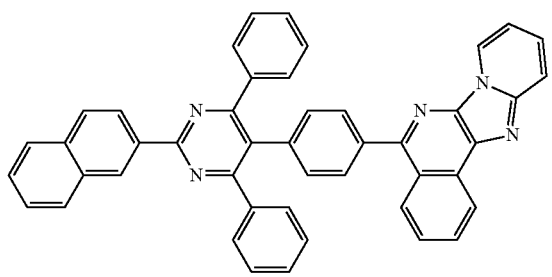
535
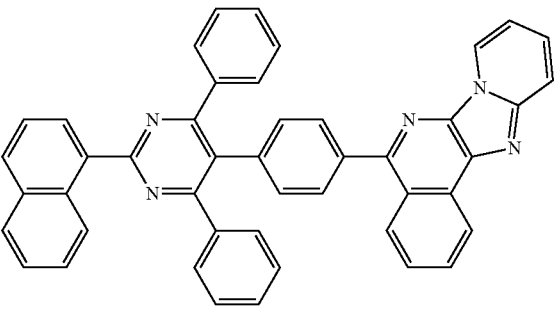
536
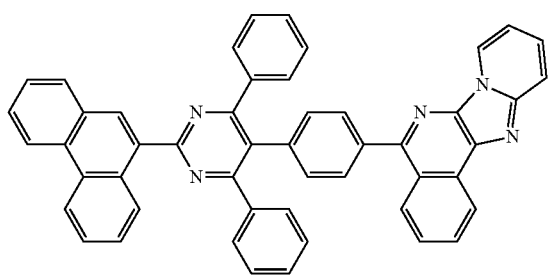
537
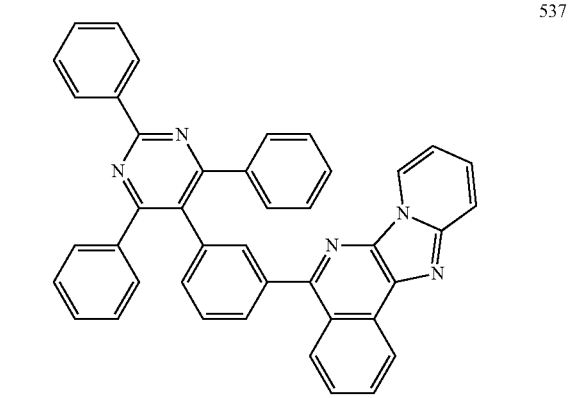

538
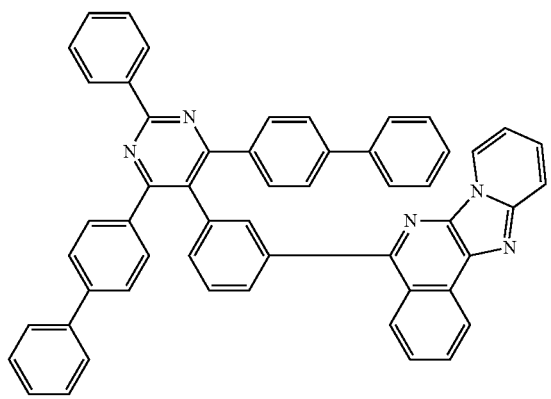
541
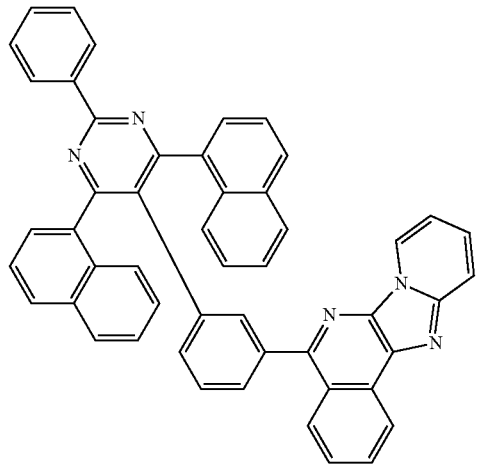
539
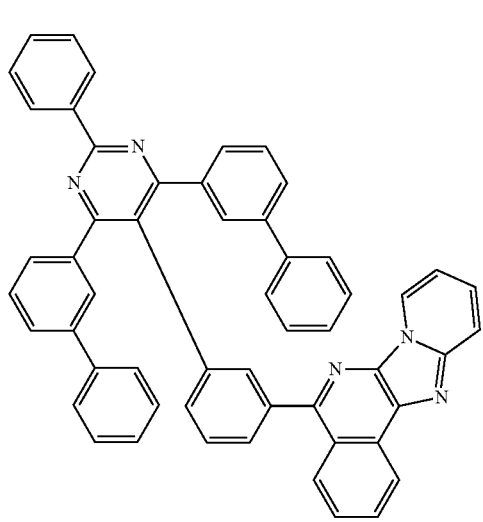
542
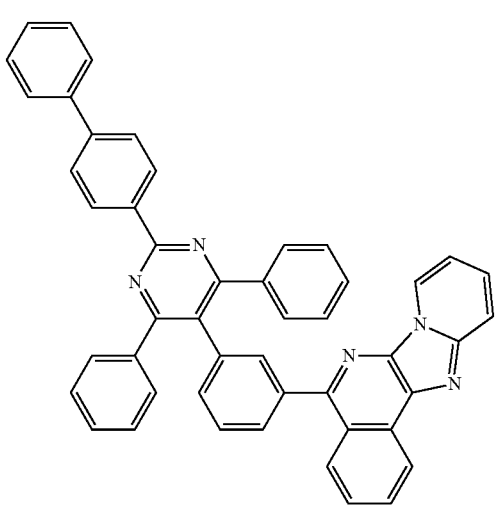
540
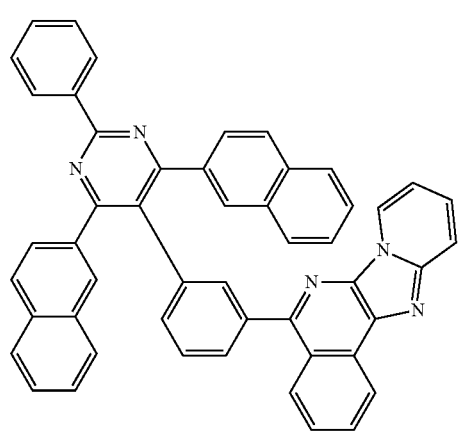
543
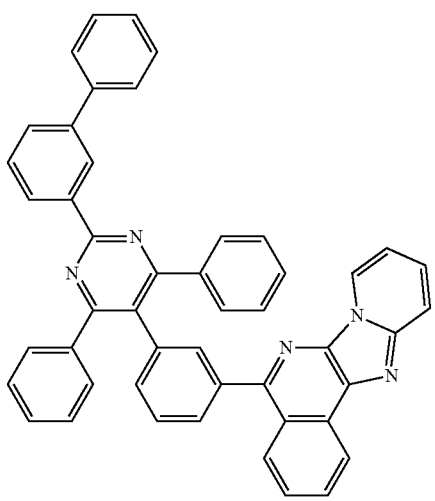

487
-continued
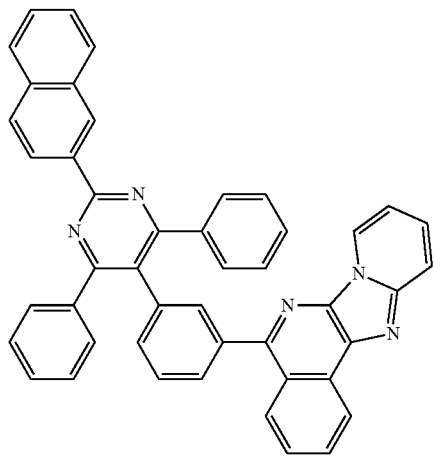
544
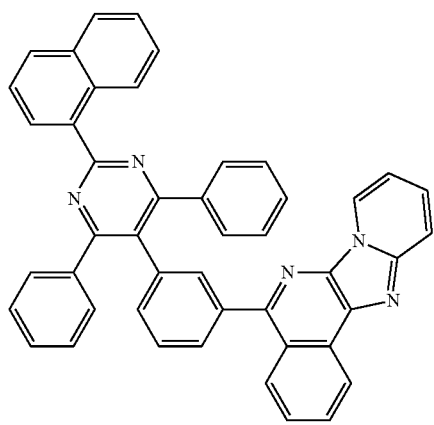
545
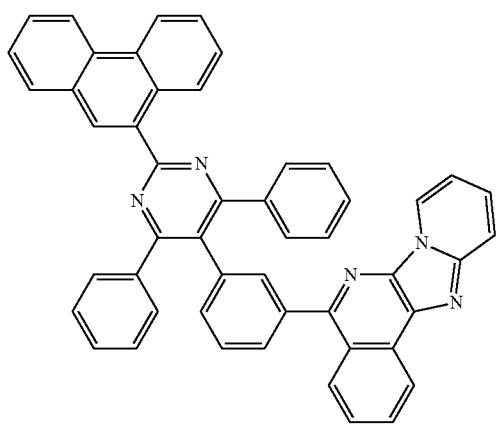
546
488
-continued
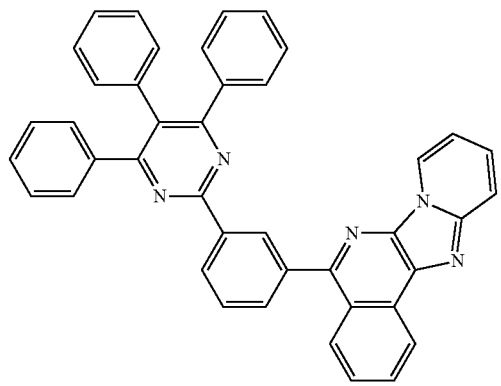
547
548
549
550

-continued
551
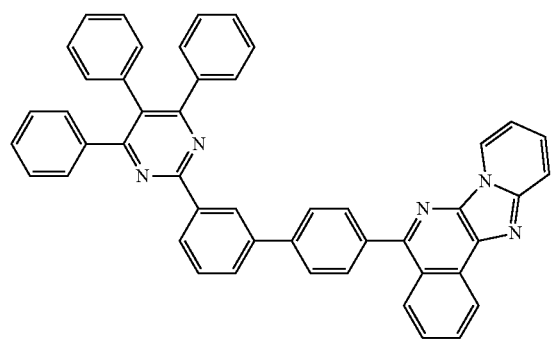
552
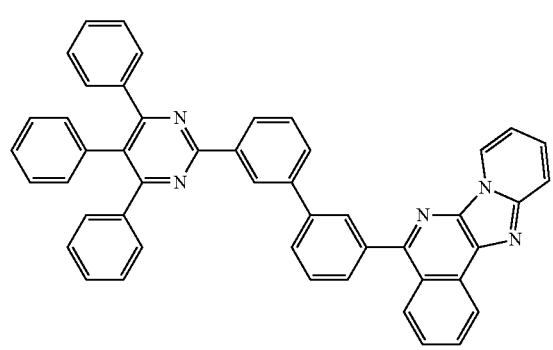
553
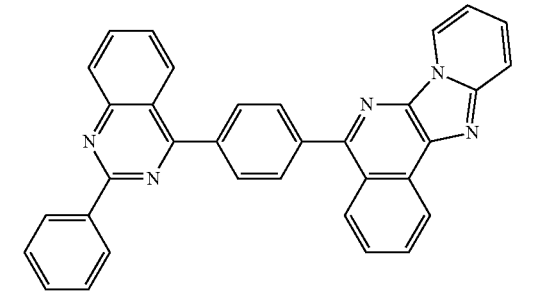
554
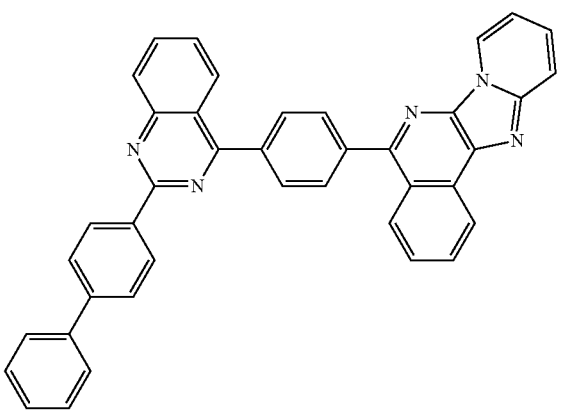
-continued
555
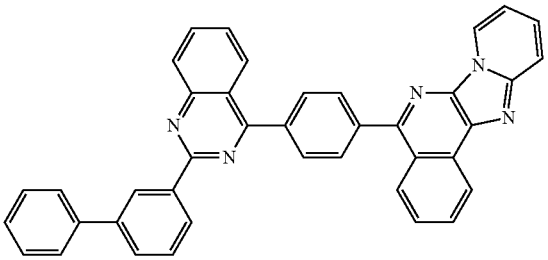
556
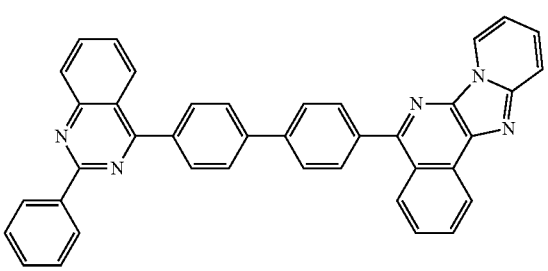
557
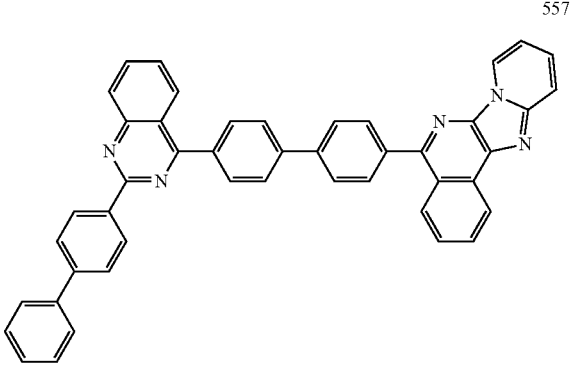
558
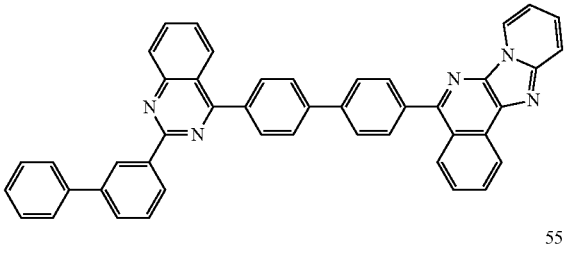
559
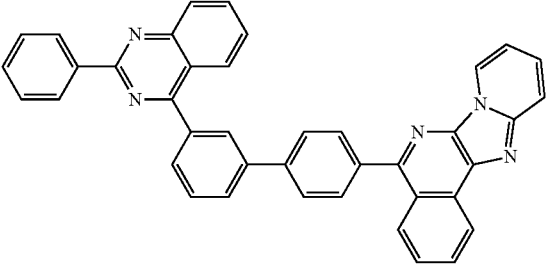

560
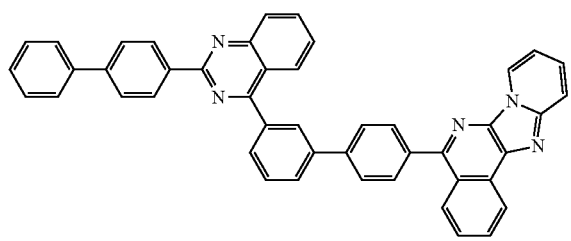
561
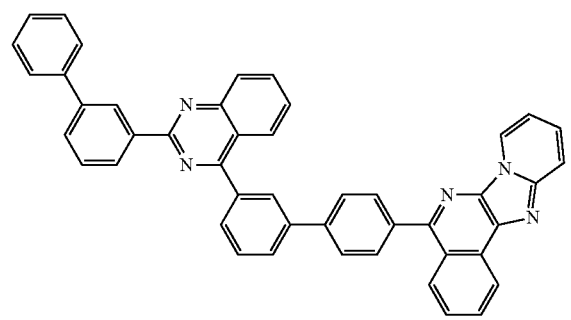
562
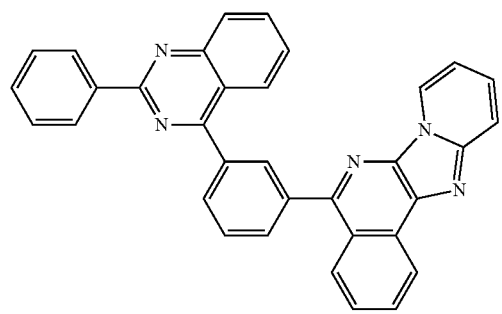
563
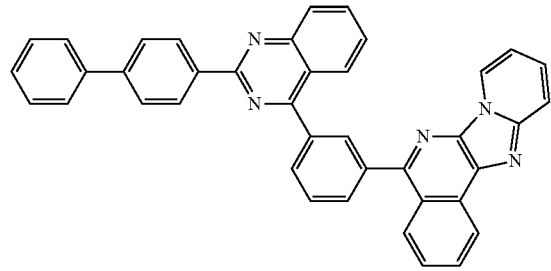
564
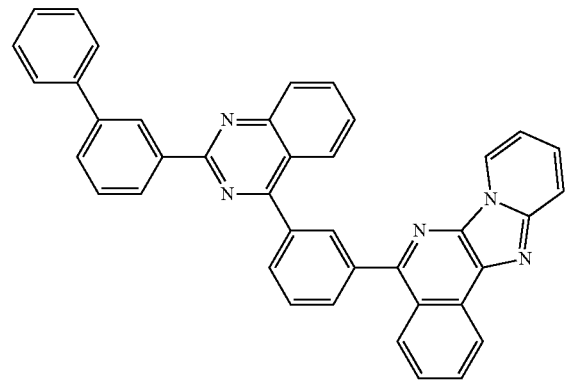
565
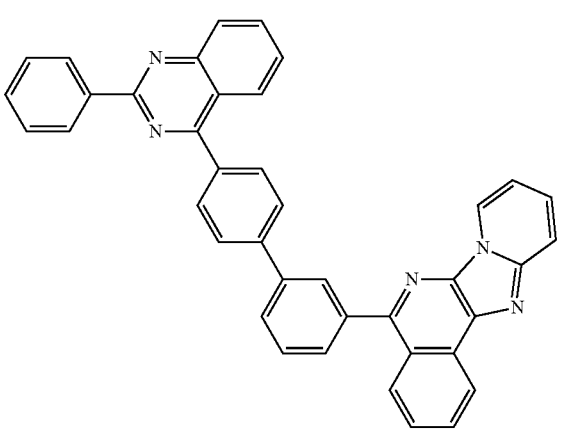
566
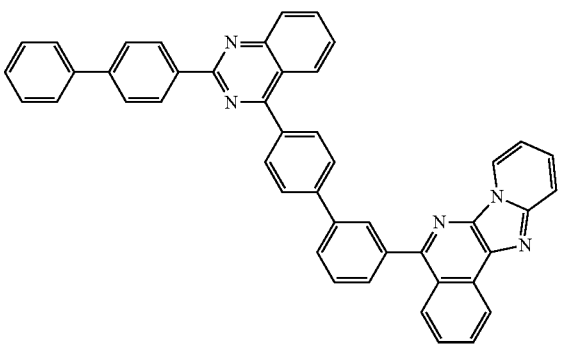
567
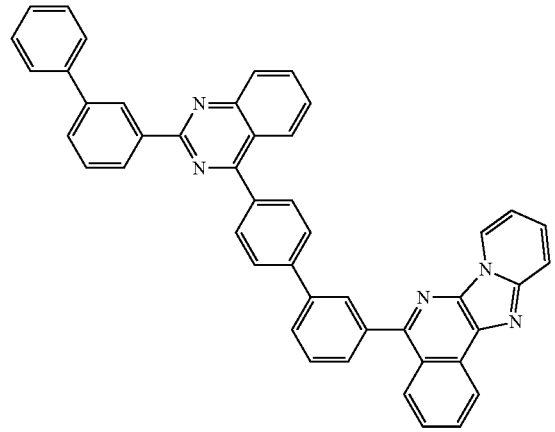
568
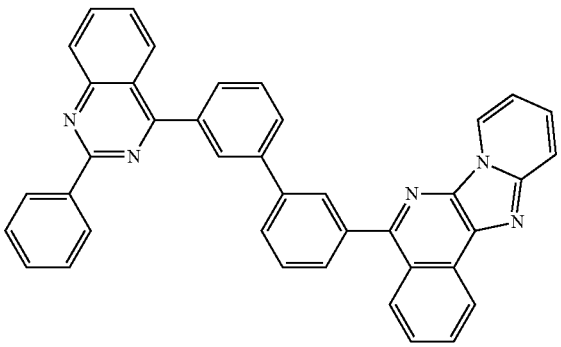

493
-continued
569
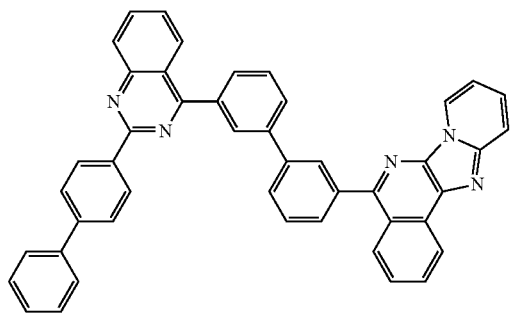
570
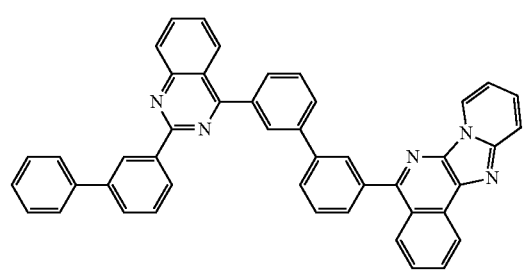
571
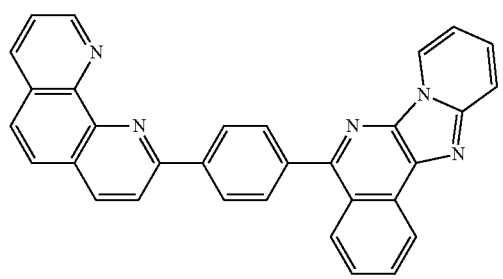
572
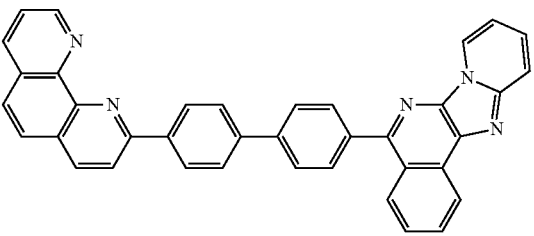
573
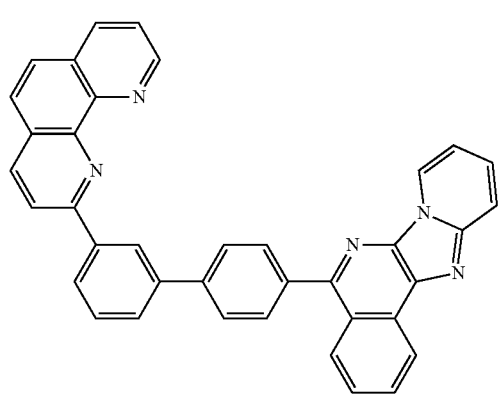
494
-continued
574
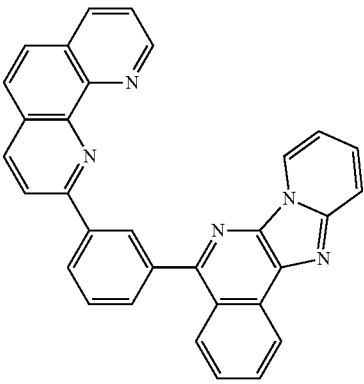
575
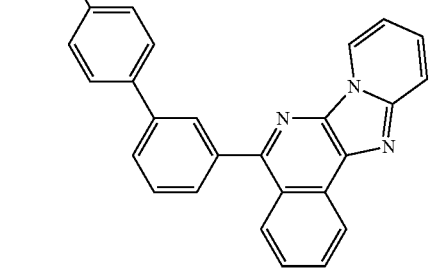
576
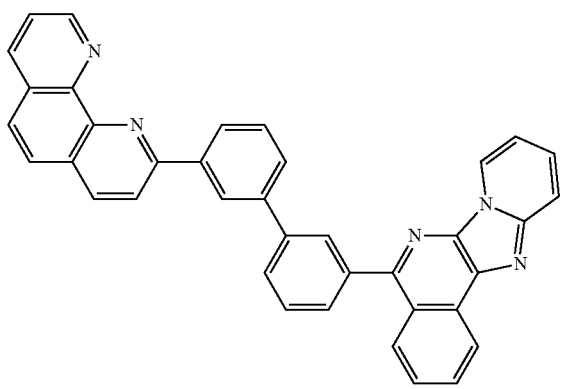
577
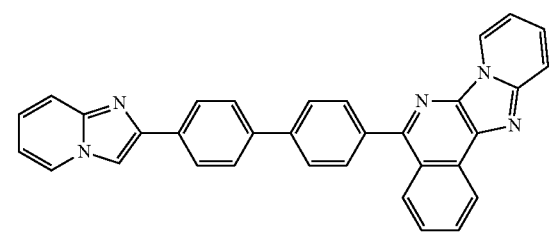

| 495 | 496 |
|---|---|
| 578 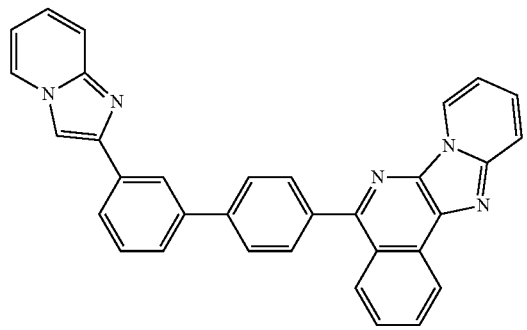 | 582 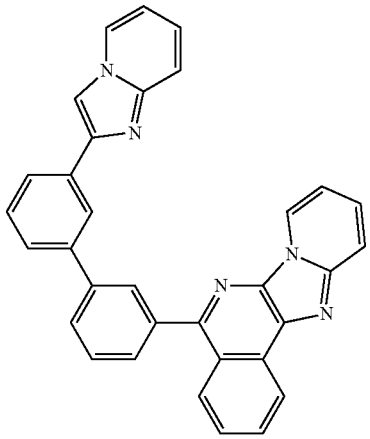 |
| 579 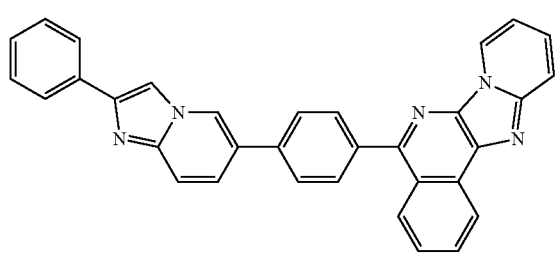 | 583 |
| 580 | 584 |
| 581 | 585 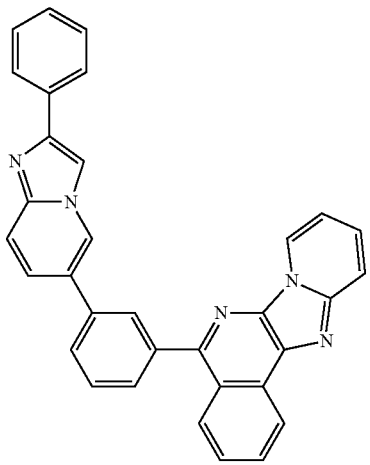 |

497
-continued
586
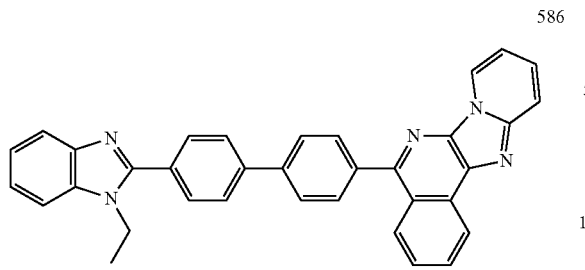
587
588
589
590
498
-continued
591
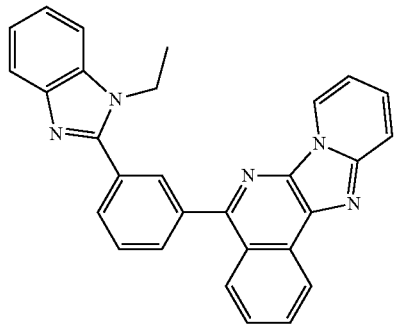
592
593
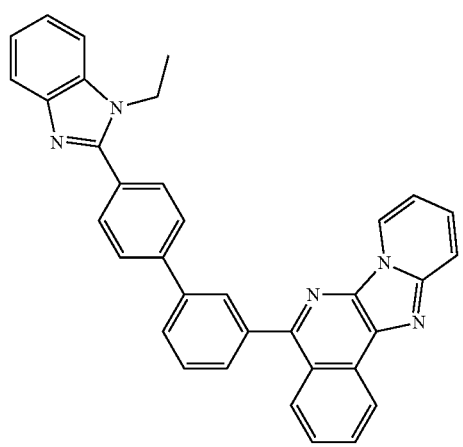
594

499
-continued
595
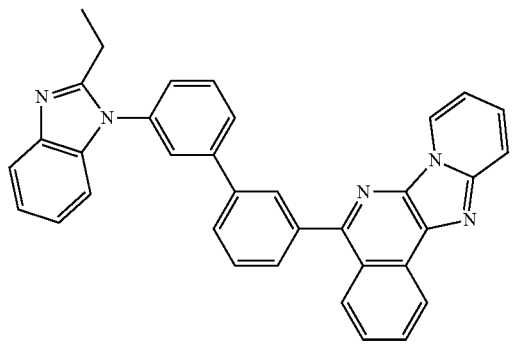
596
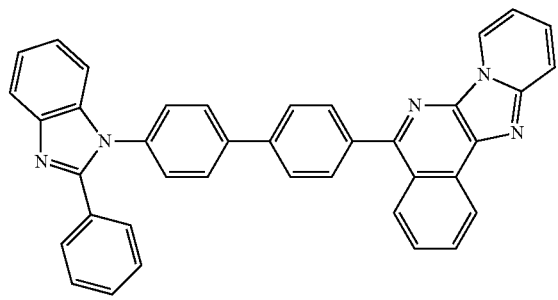
597
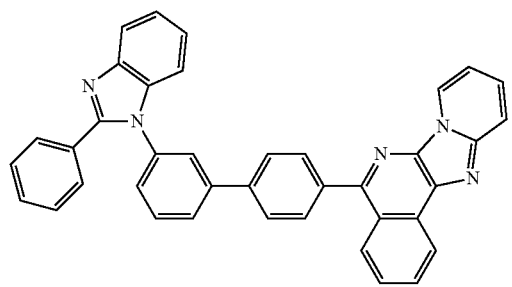
598
500
-continued
599
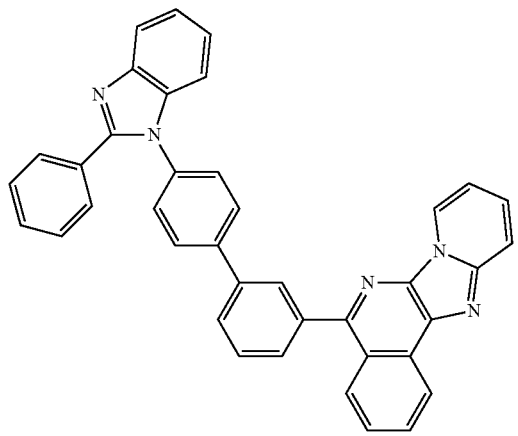
600
601
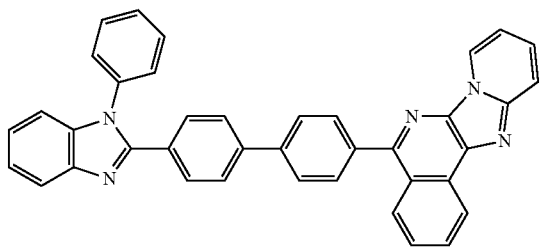
602
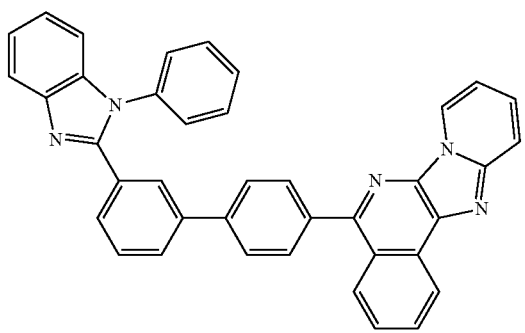

501
-continued
603
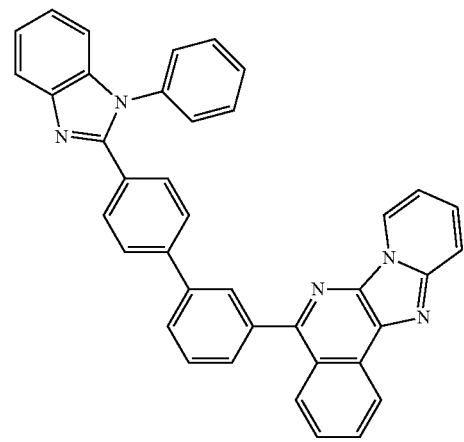
604
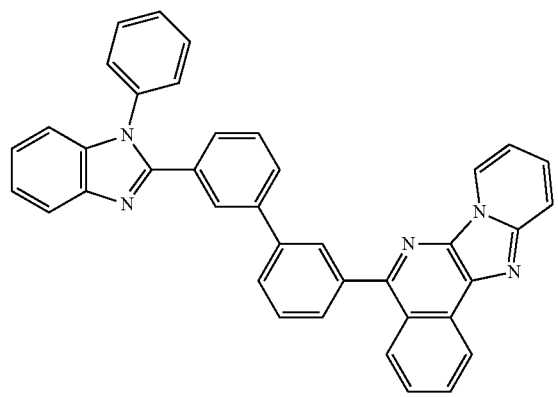
605
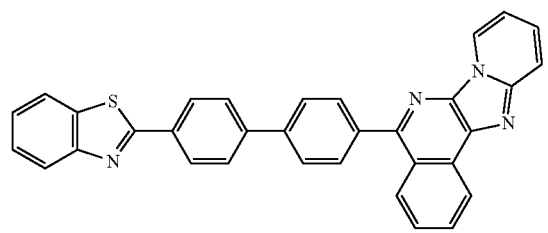
606
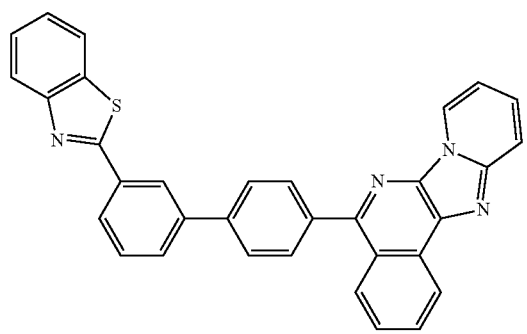
502
-continued
607
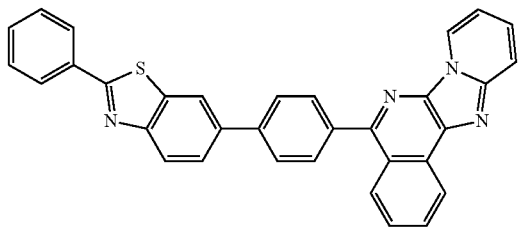
608
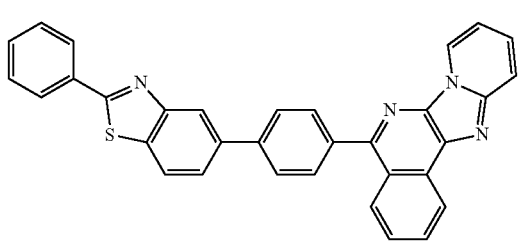
609
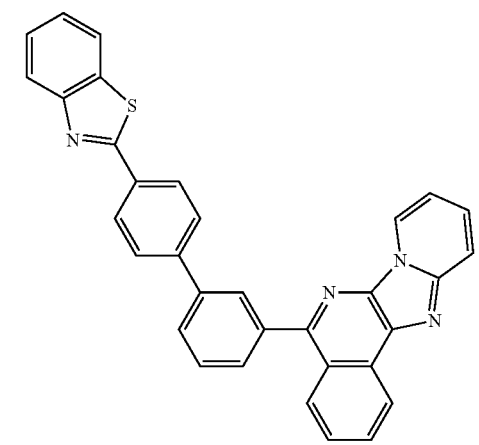
610
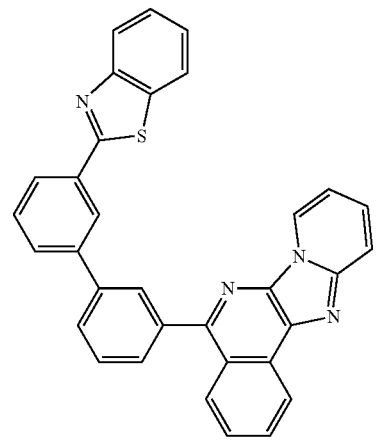

611
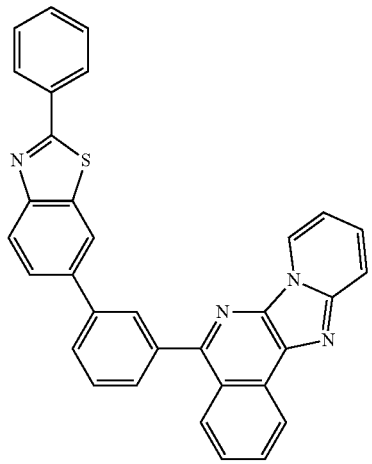
612
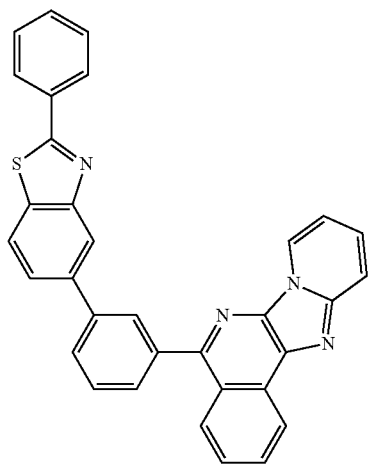
613
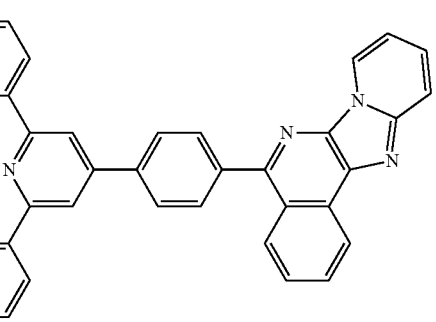
614
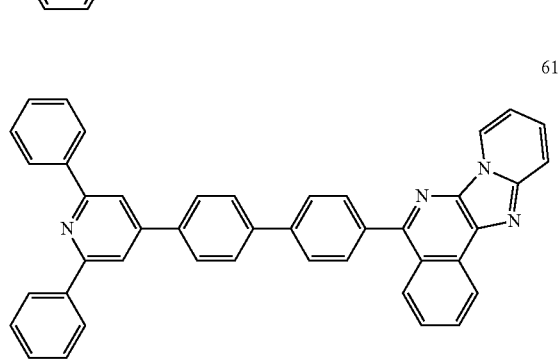
615
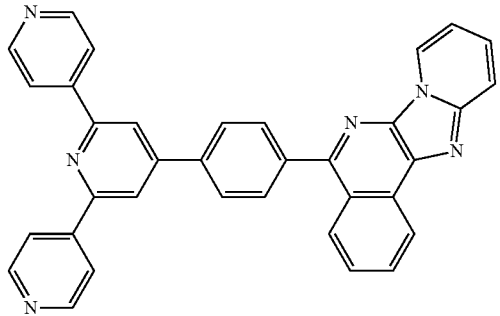
616
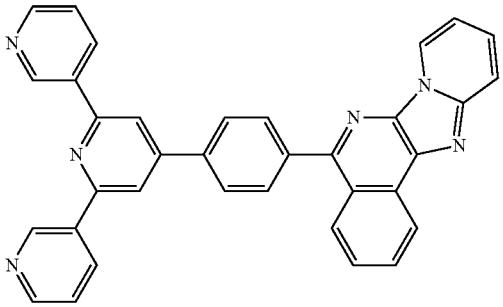
617
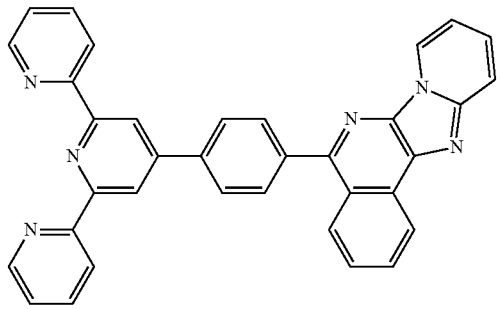
618
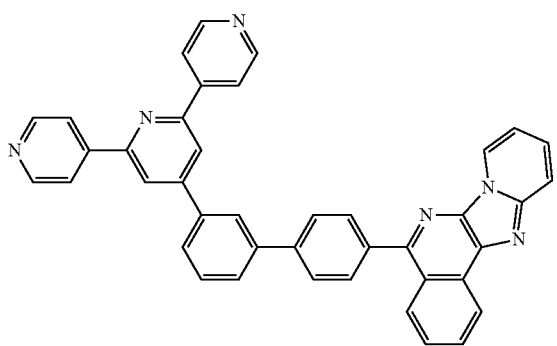

619
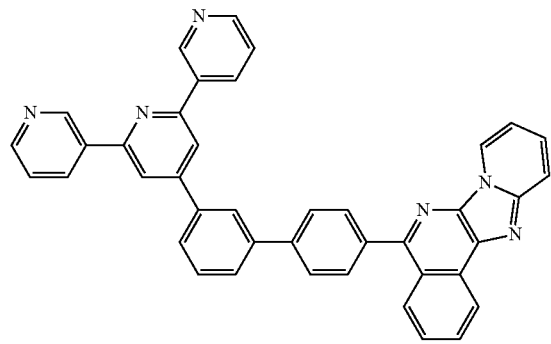
620
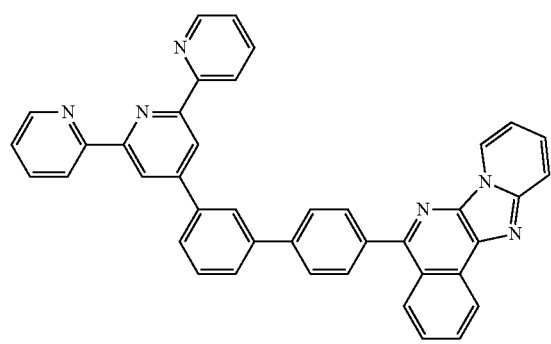
621
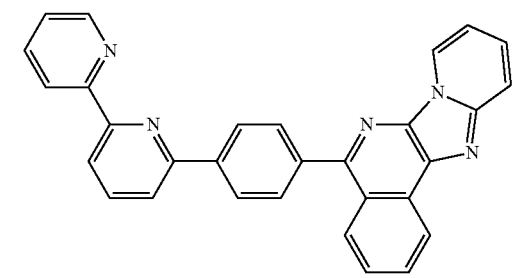
622
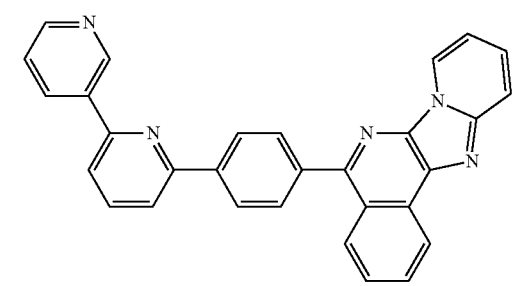
623
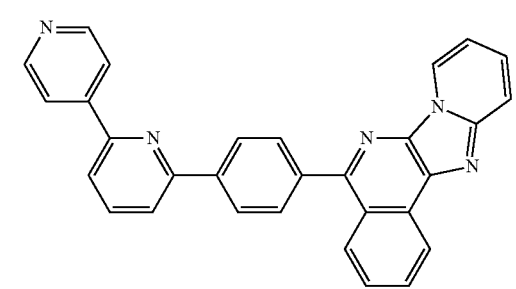
624
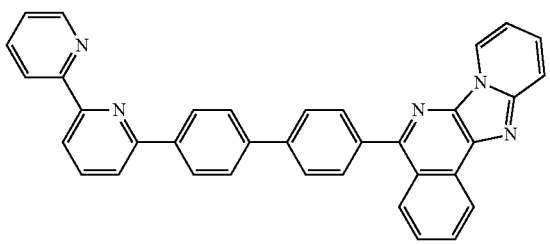
625
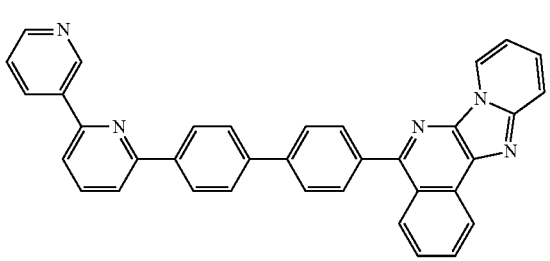
626
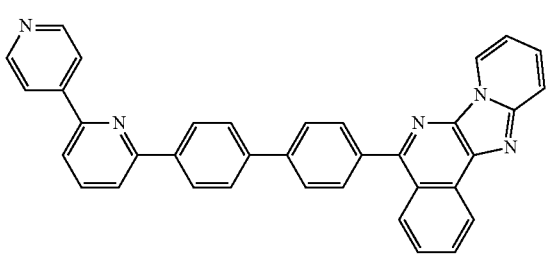
627
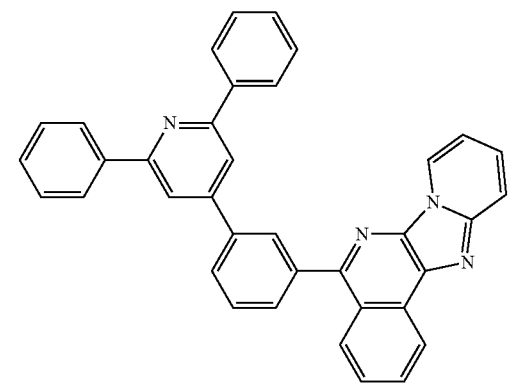

-continued
628
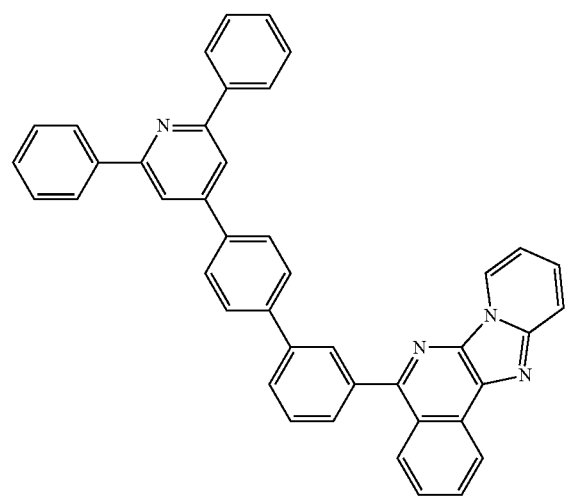
629
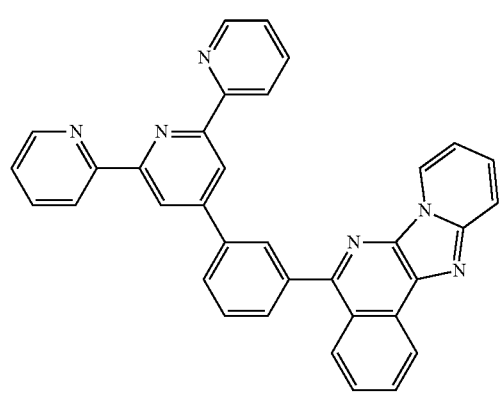
630
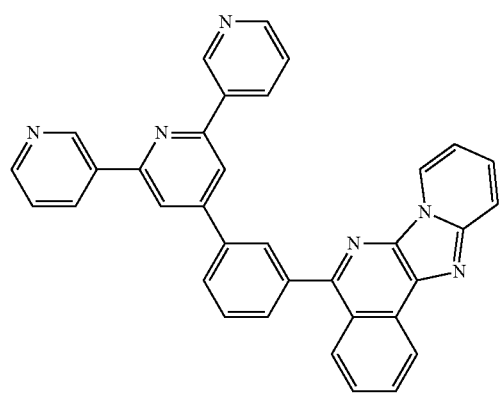
-continued
631
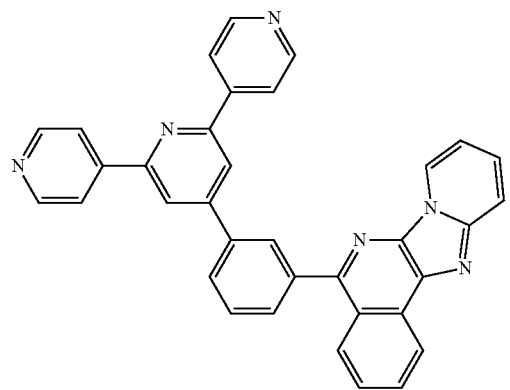
632
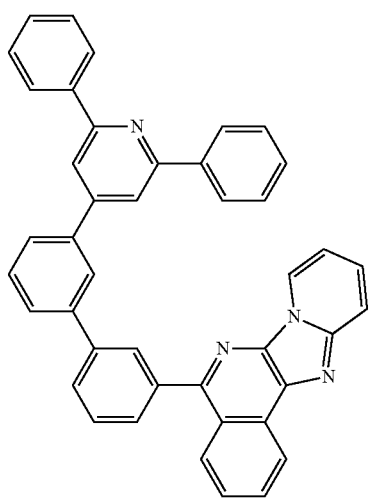
633
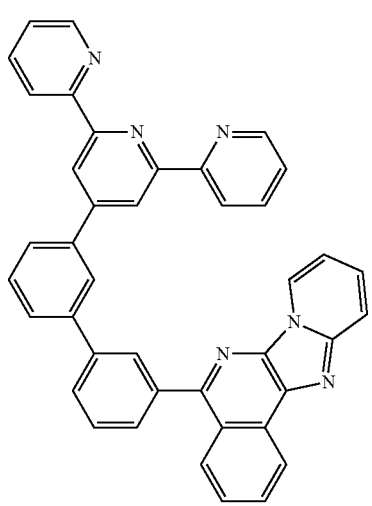

509
-continued
634
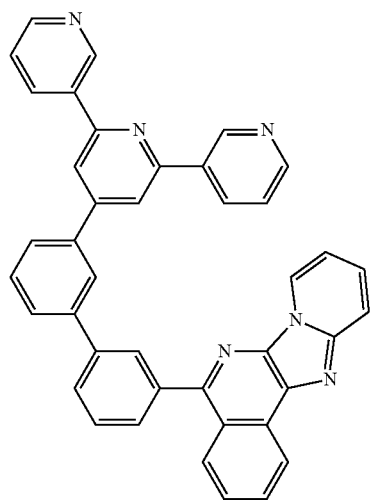
635
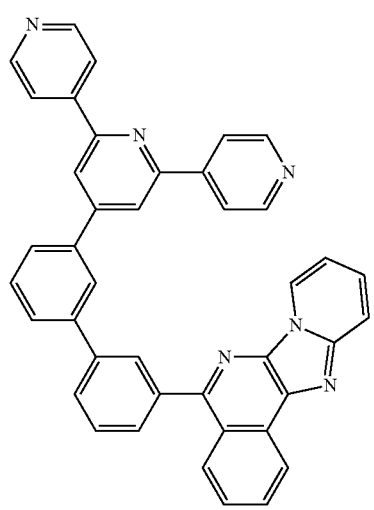
636
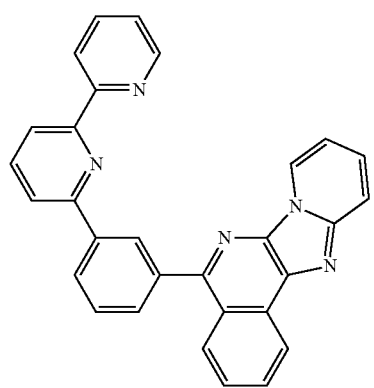
510
-continued
637
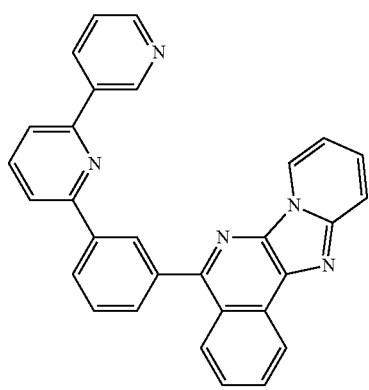
638
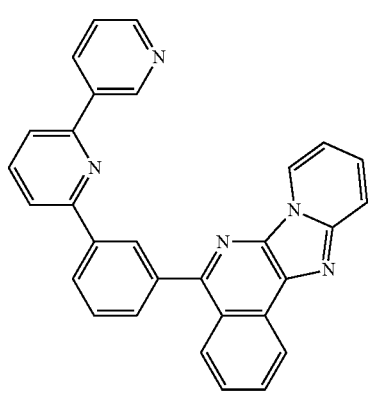
639
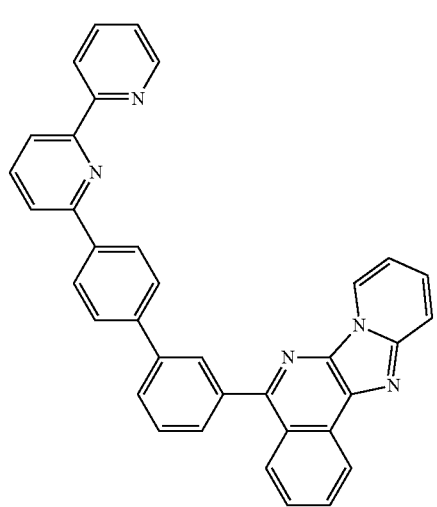

511
-continued
640
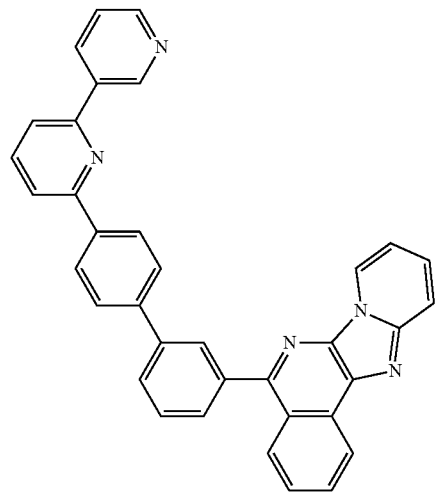
641
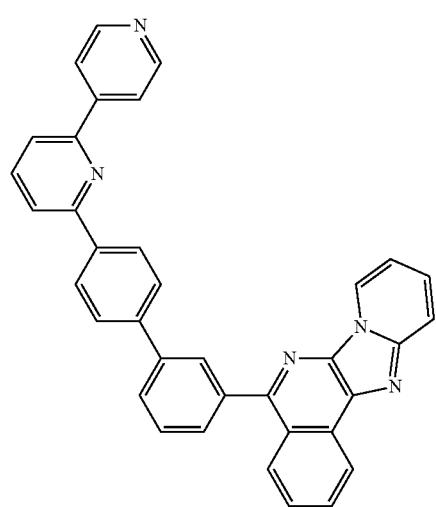
642
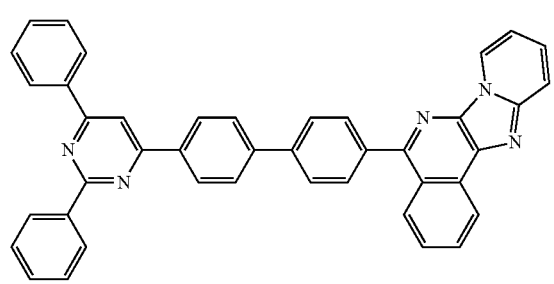
643
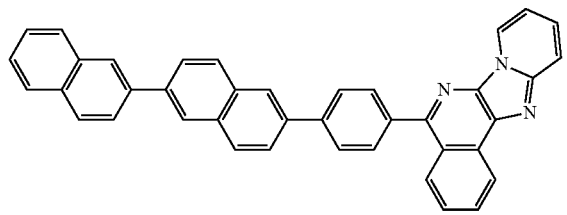
512
-continued
644
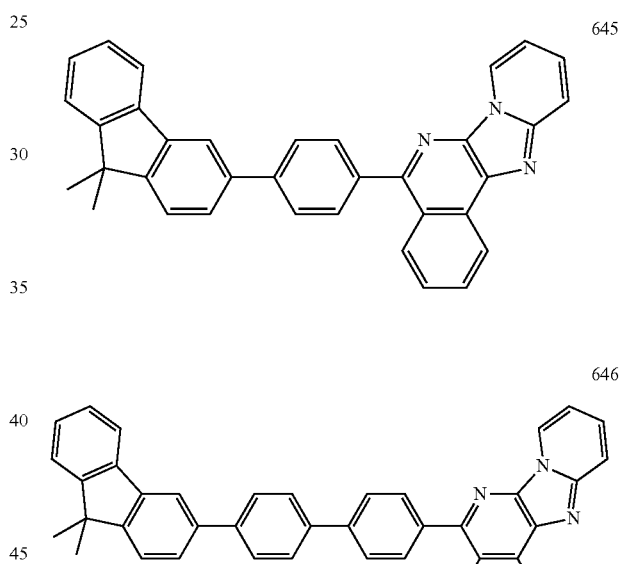
645
646
647
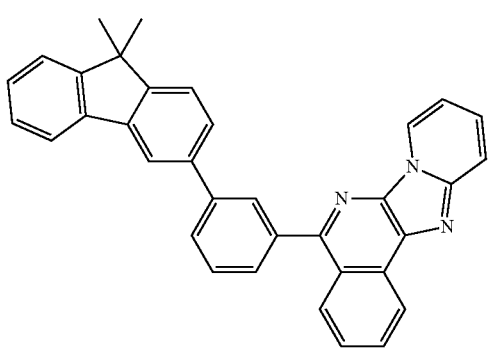

513
-continued
648
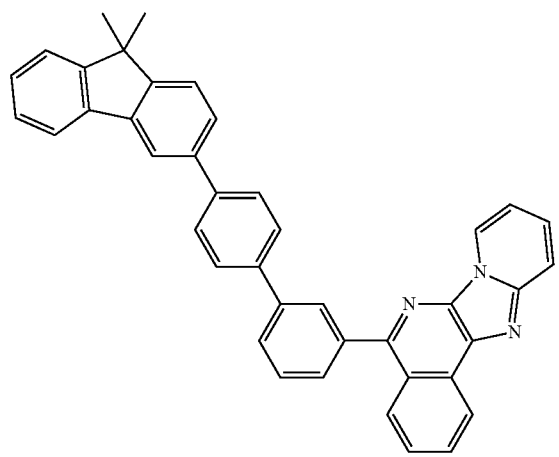
649
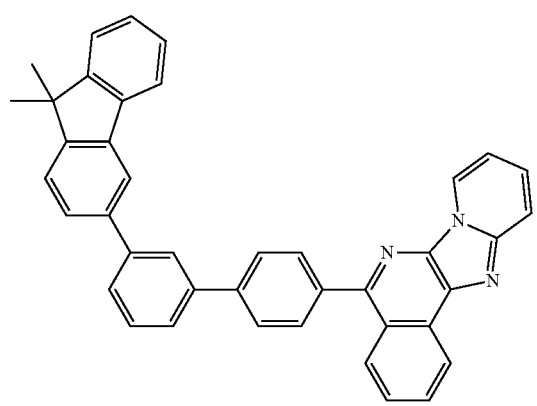
650
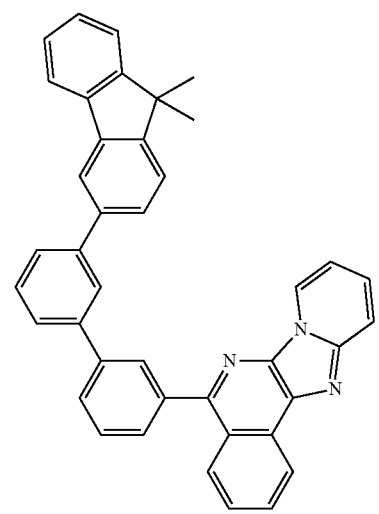
514
-continued
651
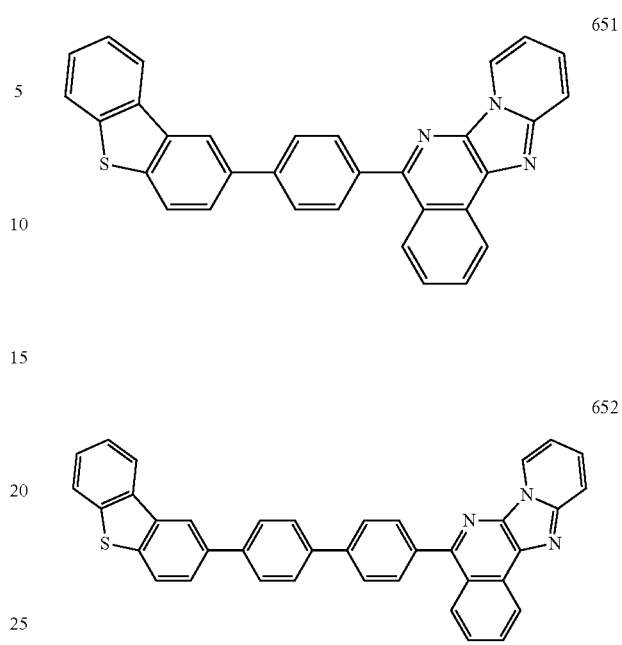
652
653
654
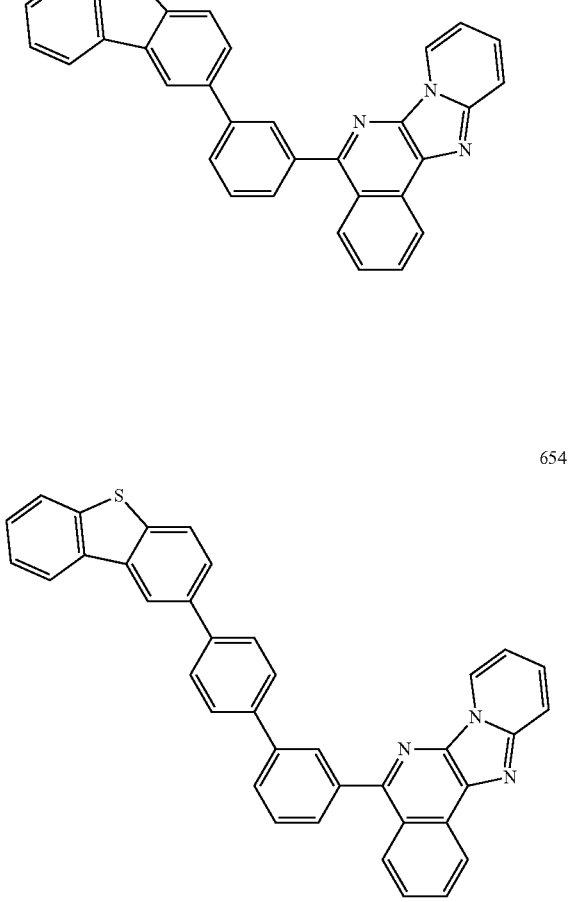

515
-continued
655
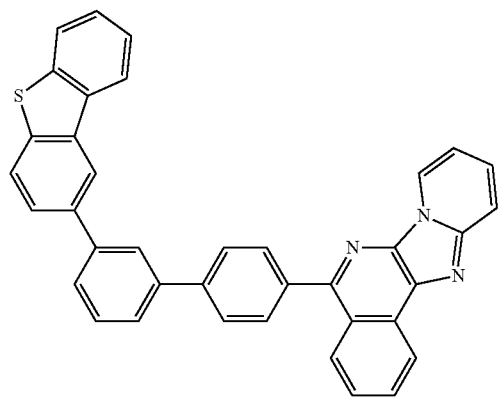
656
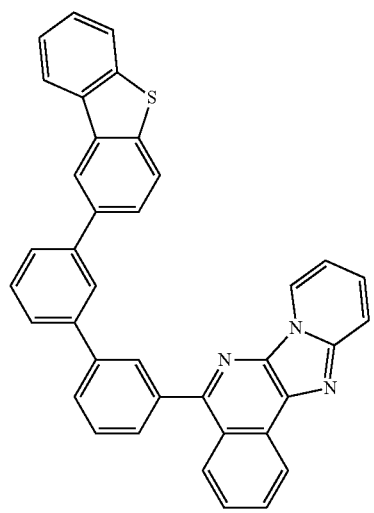
657
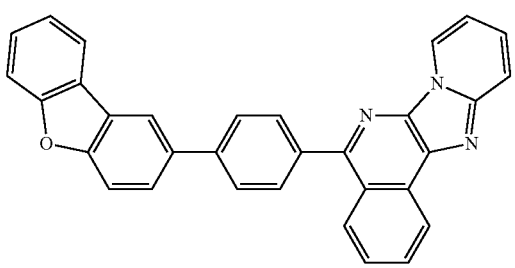
658
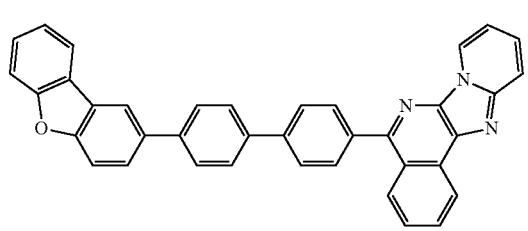
516
-continued
659
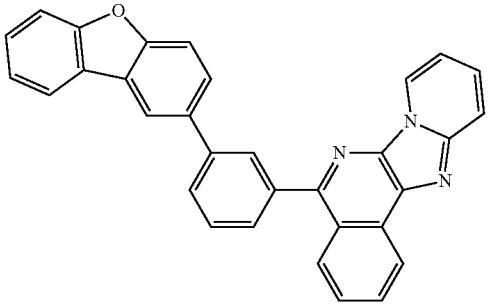
660
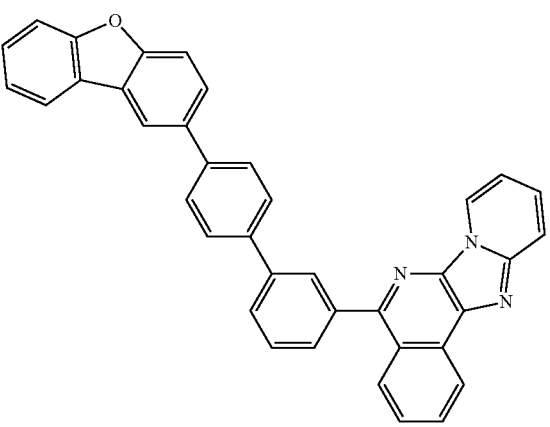
661
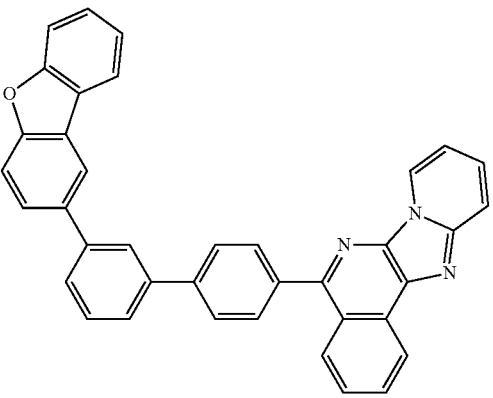

662
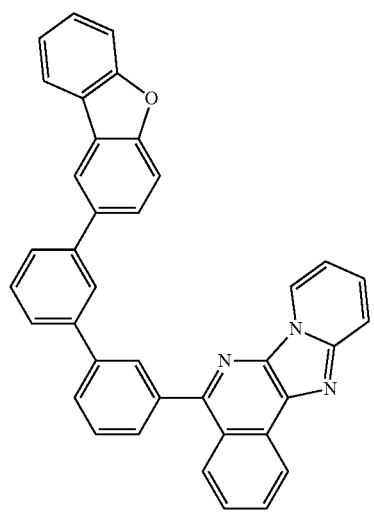
663
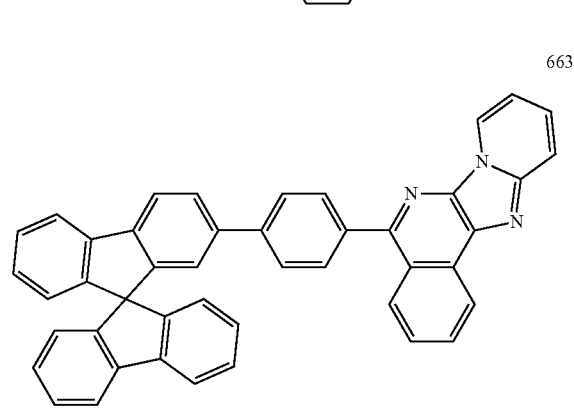
664
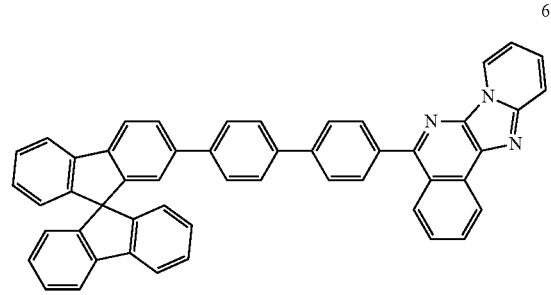
665
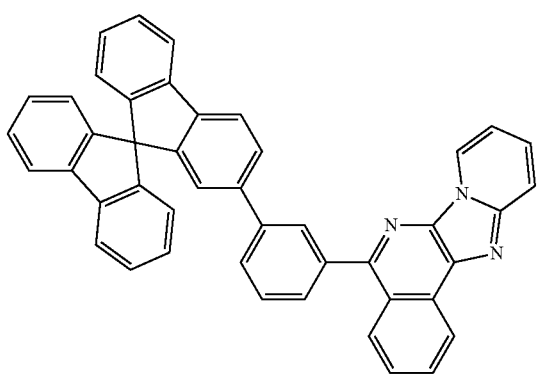
666
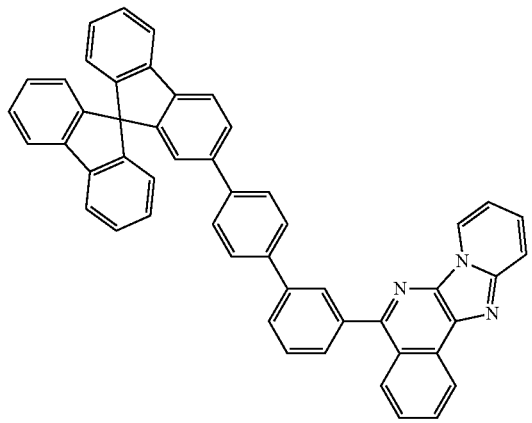
667
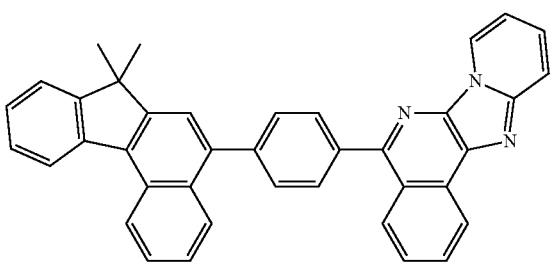
668
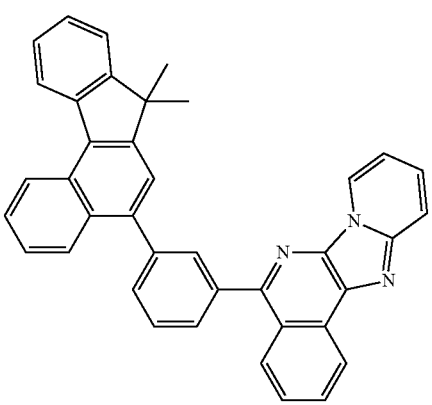
669
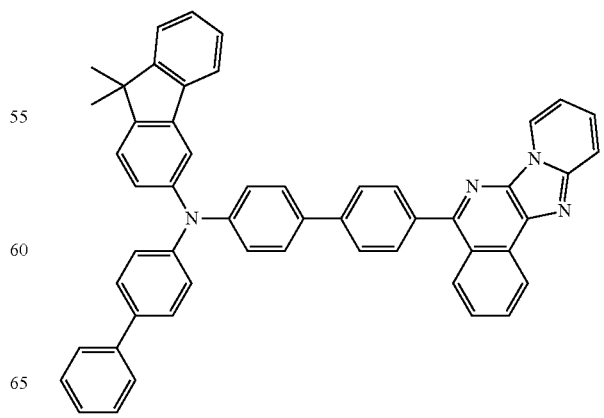

519
-continued
670
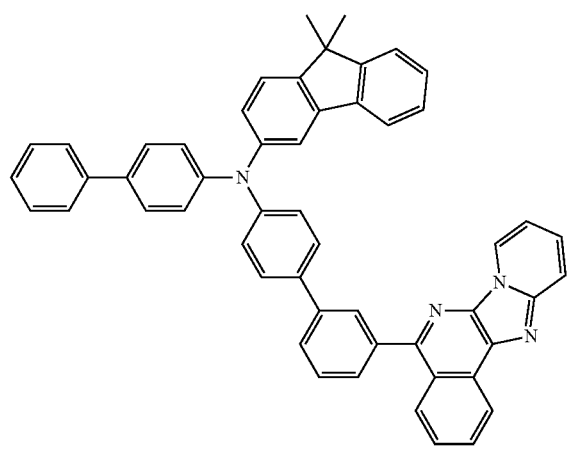
671
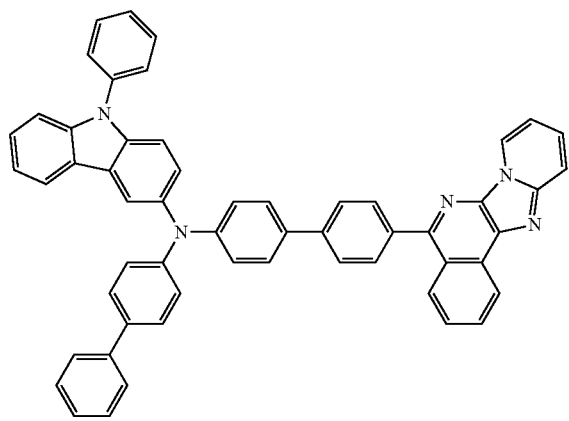
672
520
-continued
673
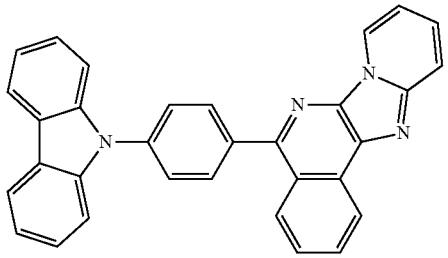
674
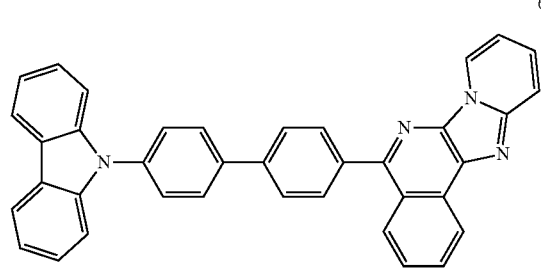
675
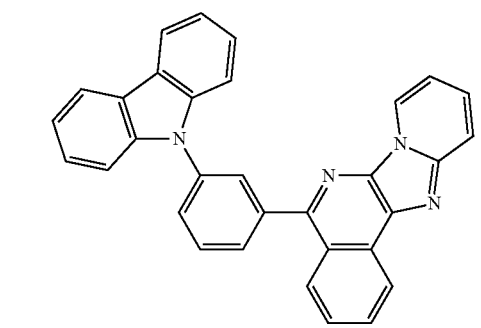
676
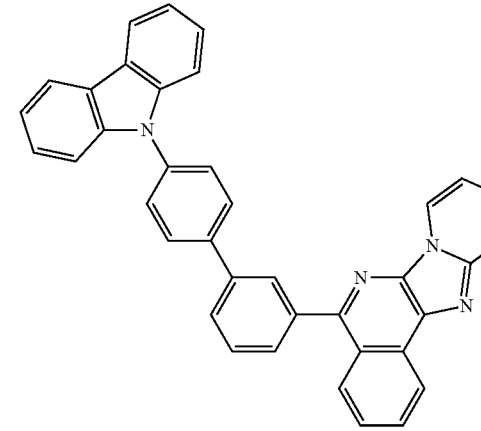
677
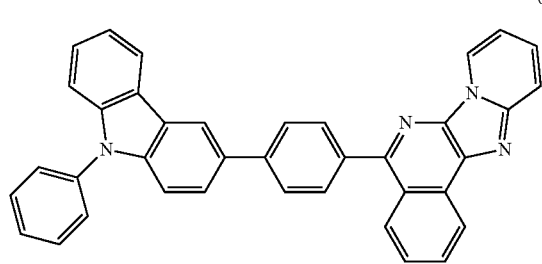

-continued
678
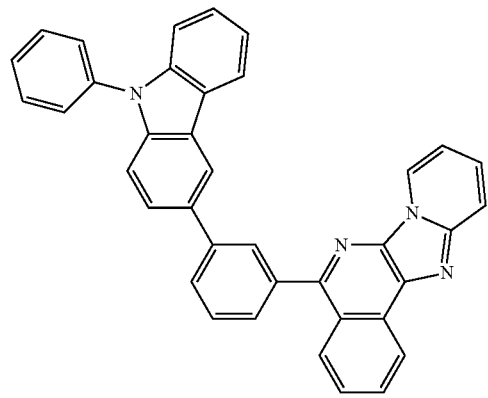
679
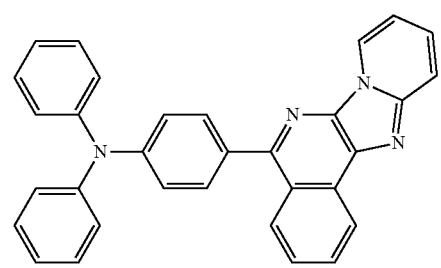
680
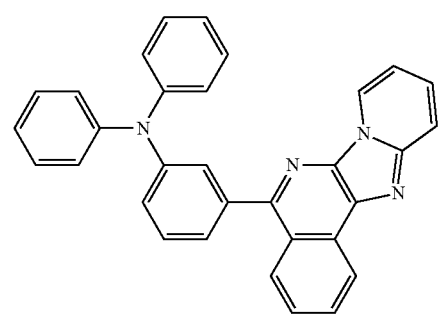
681
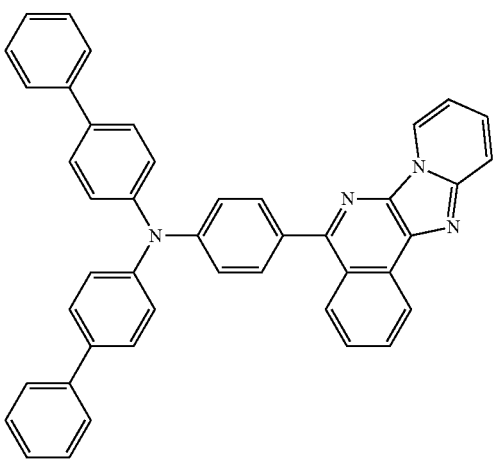
-continued
682
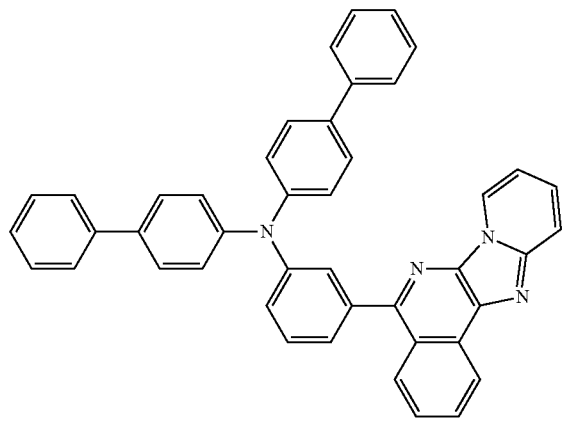
683
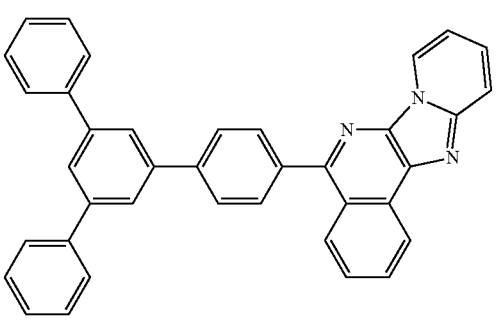
684
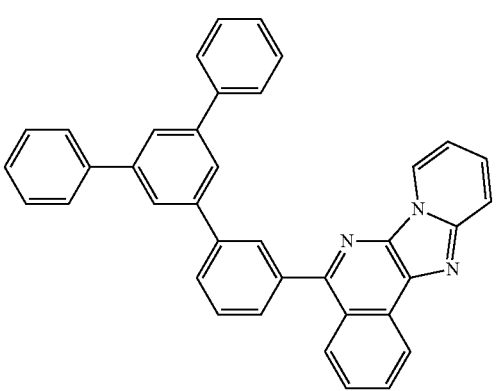
685
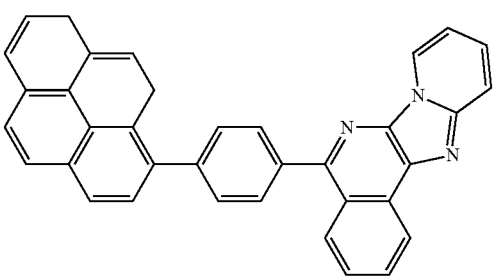

523
-continued
686
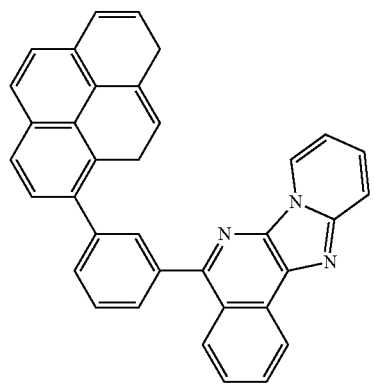
687
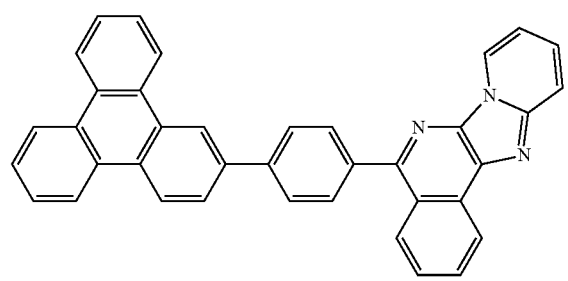
688
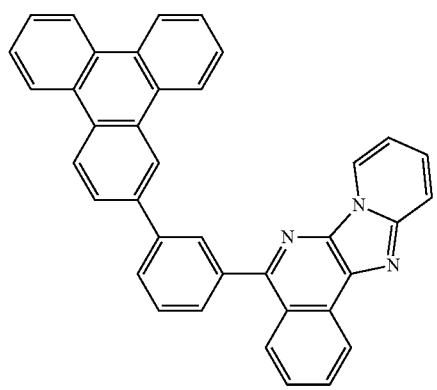
689
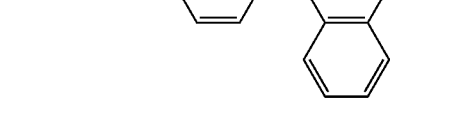
524
-continued
690
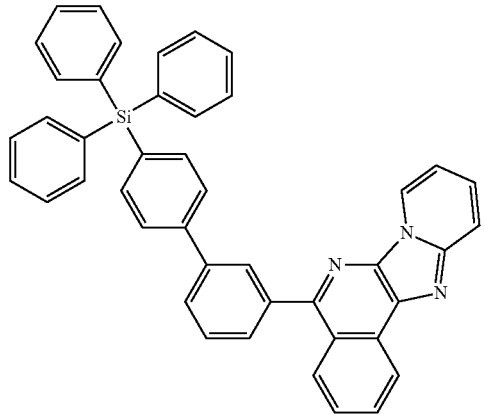
691
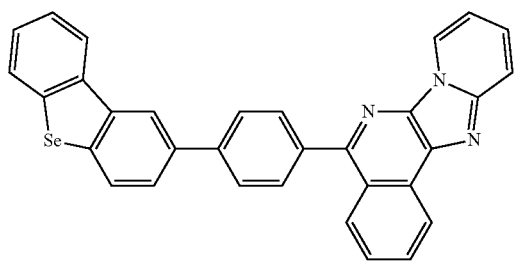
692
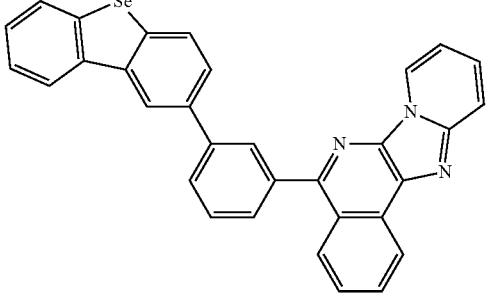
693
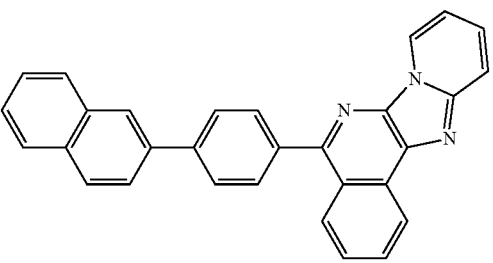
694
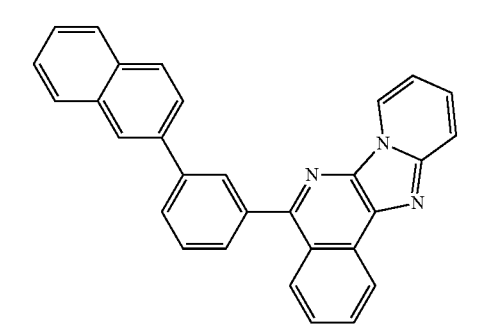

| 525 -continued | 526 -continued |
|---|---|
| 695 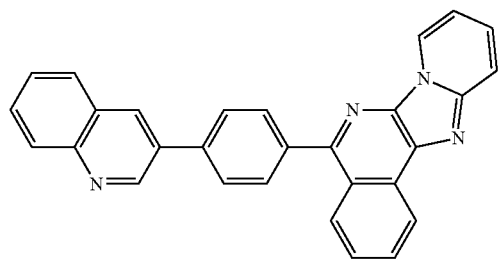 | 700 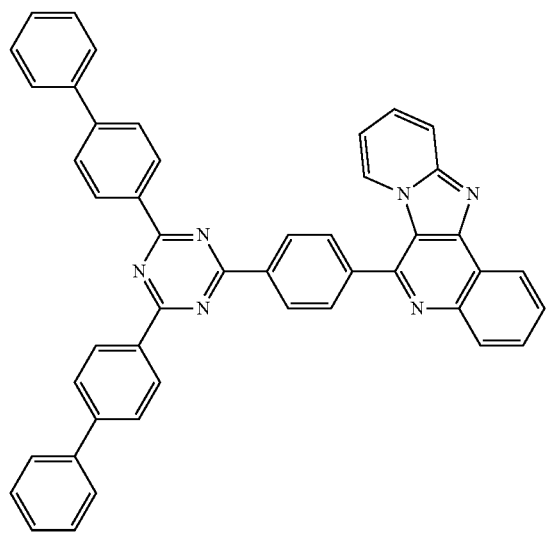 |
| 696 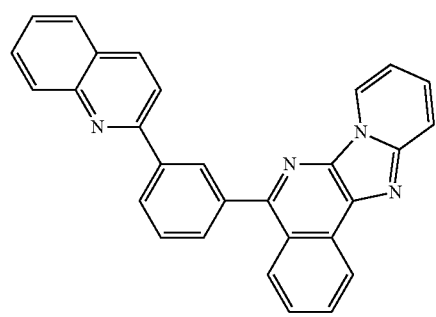 | |
| 697 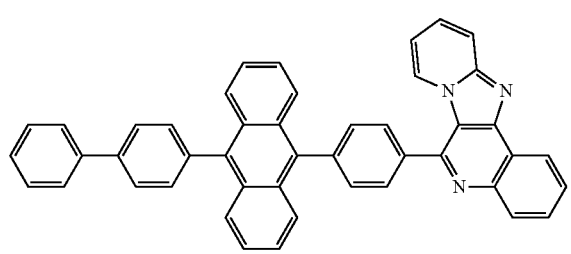 | 701 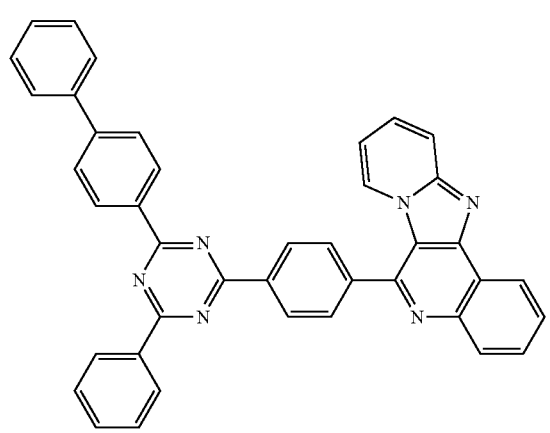 |
| 698 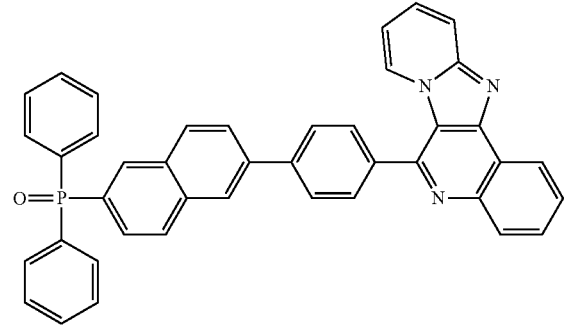 | |
| 699 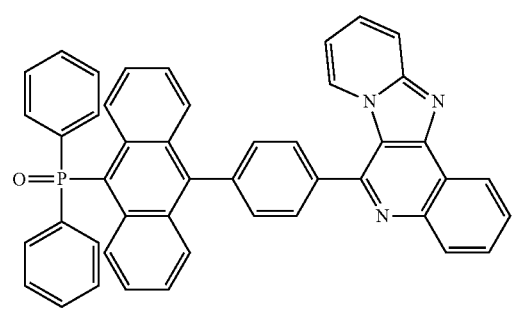 | 702 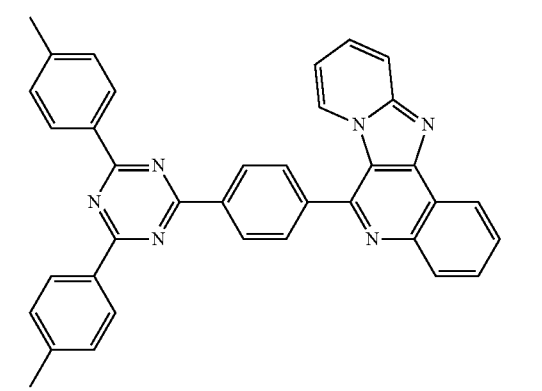 |

527
-continued
703
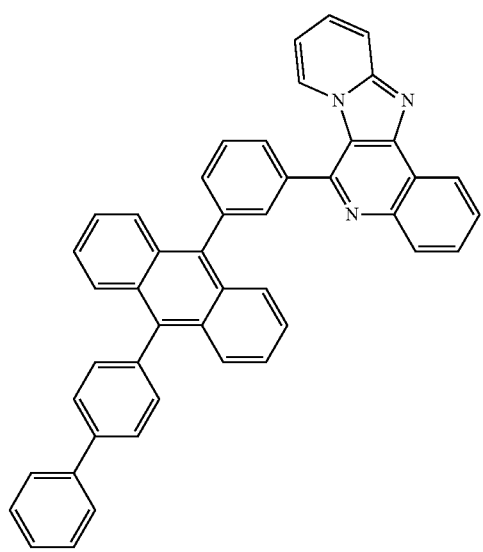
704
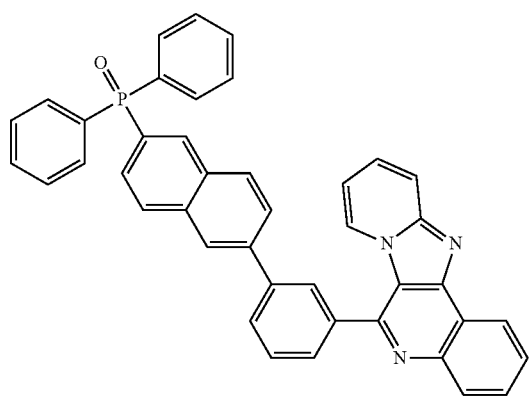
705
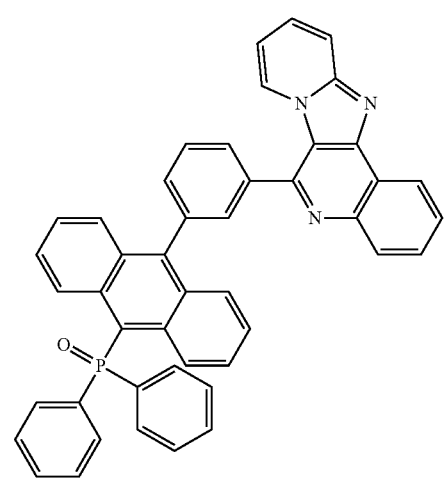
528
-continued
706
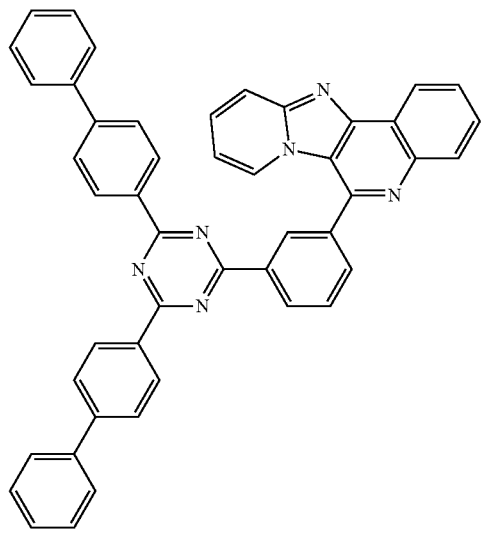
707
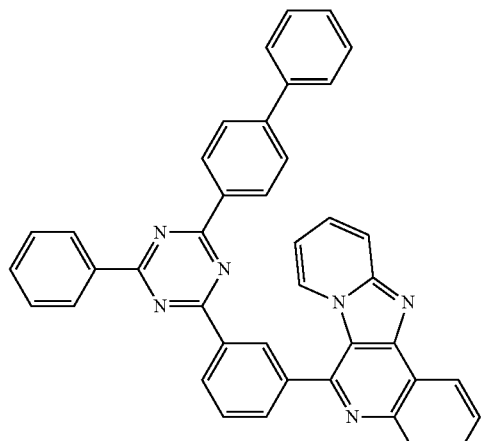
708
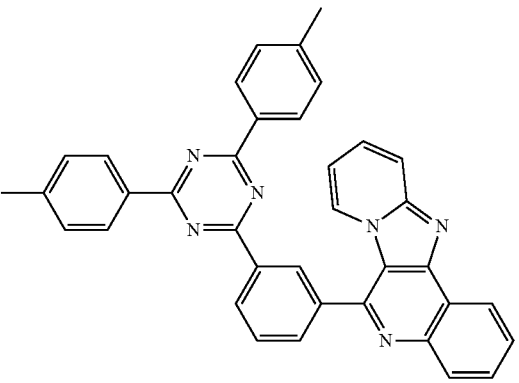
709
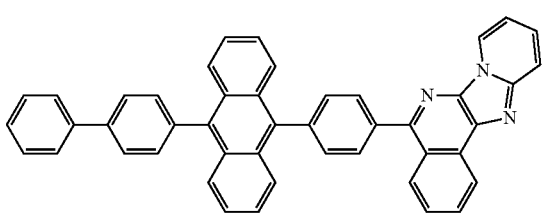

529
-continued
710
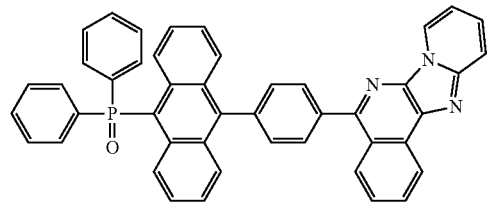
711
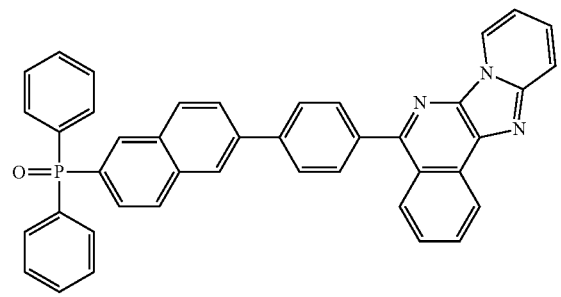
712
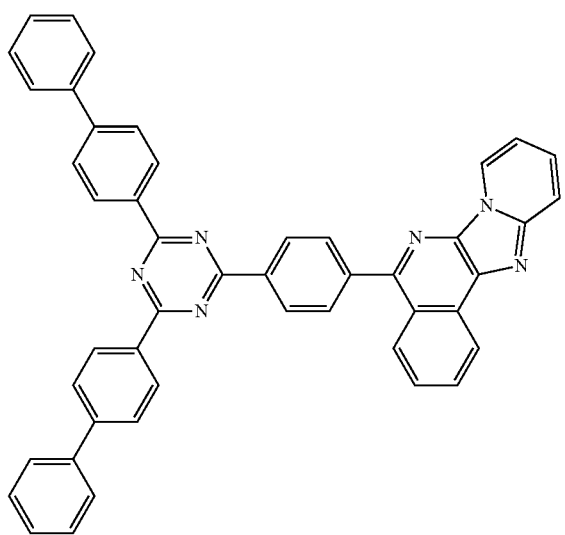
713
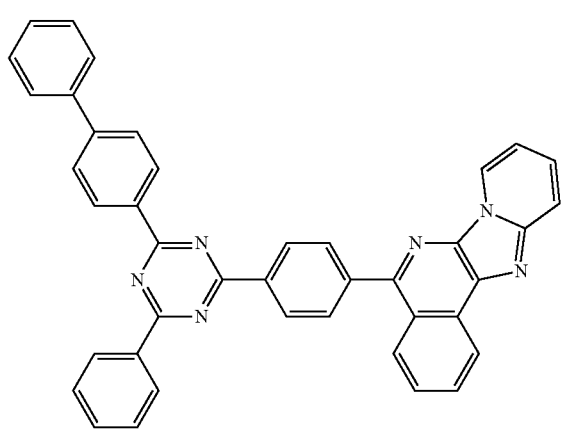
530
-continued
714
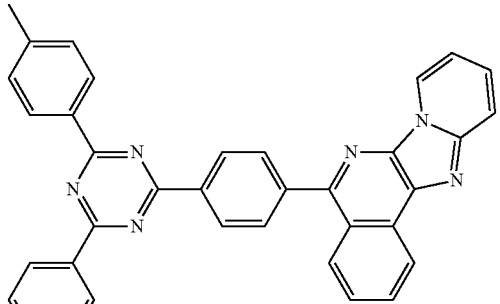
715
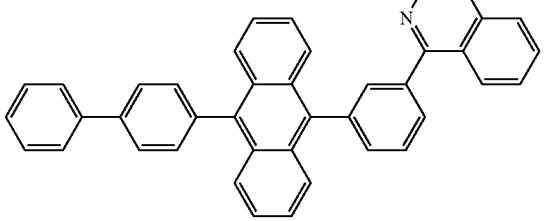
716
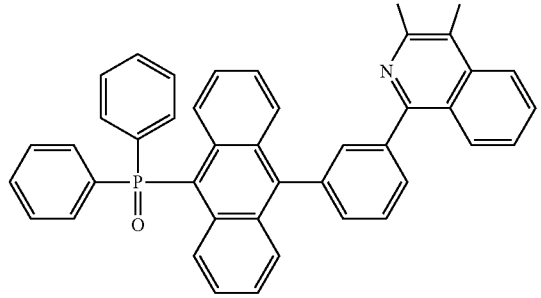
717
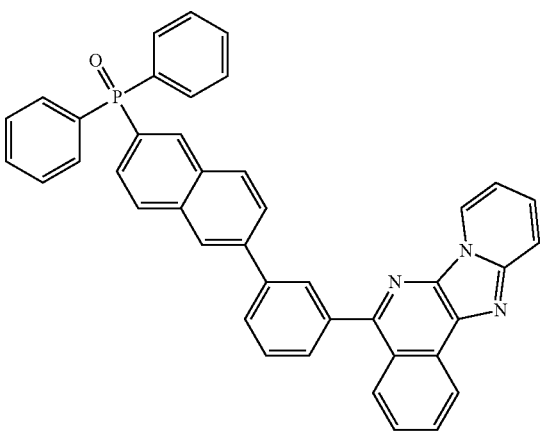

-continued
718
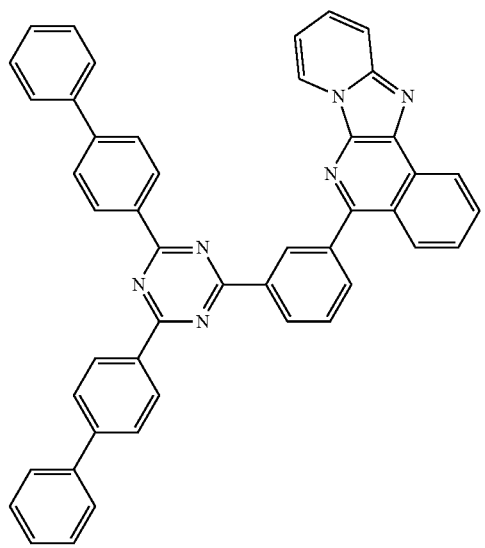
719
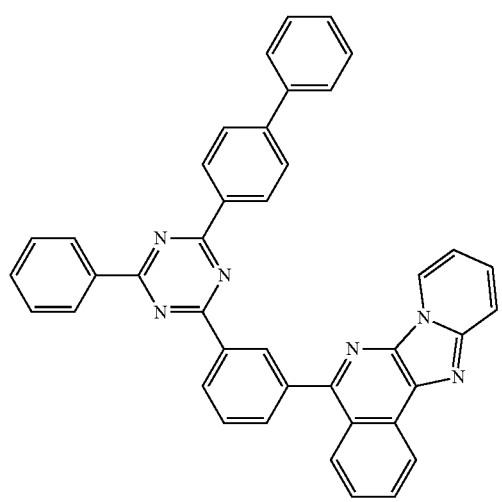
720
721
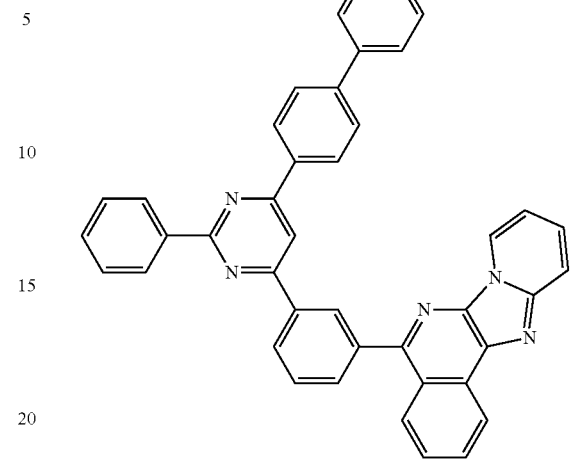
722
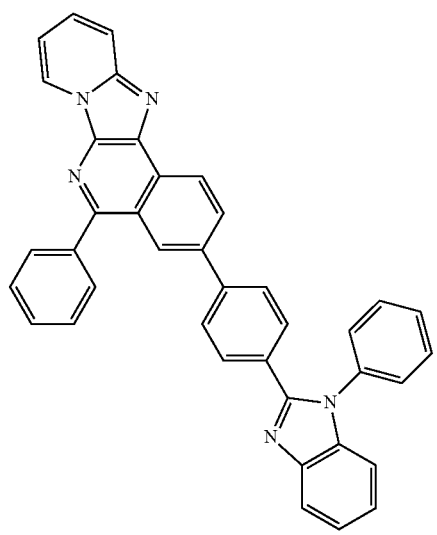
723
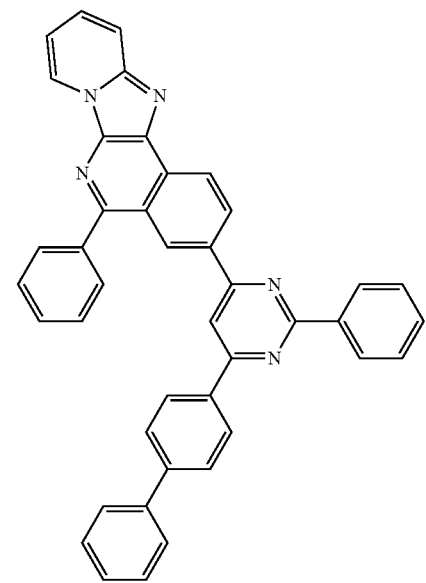

724
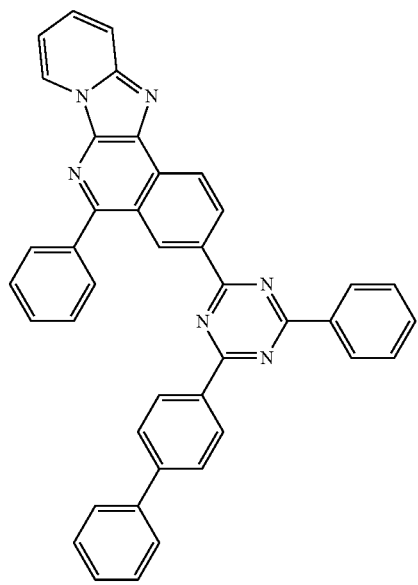
725
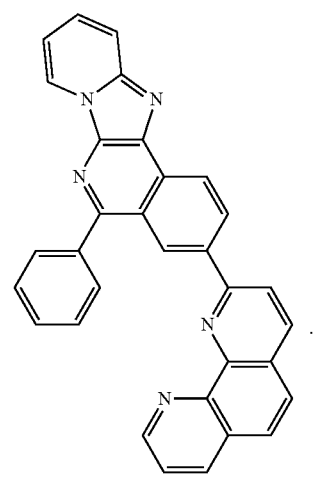
726
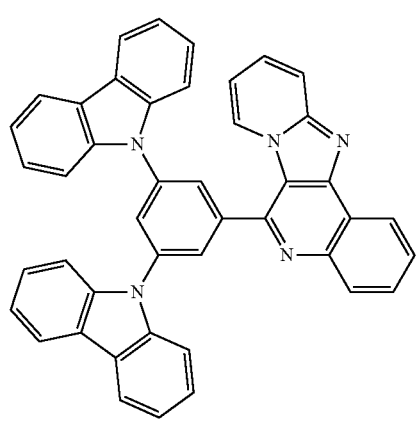
727
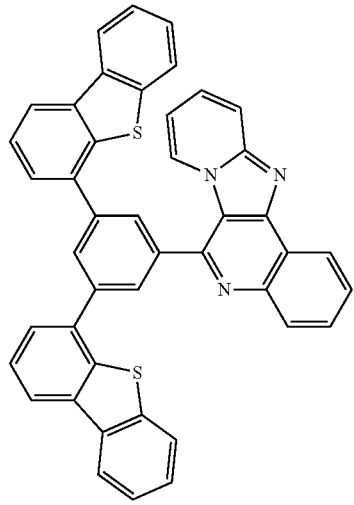
728
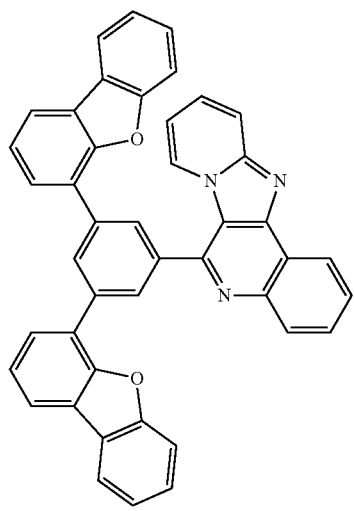
729
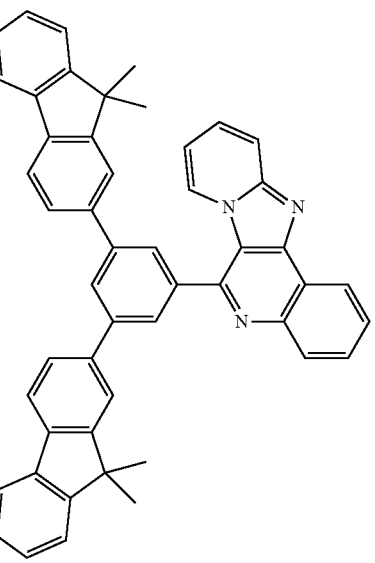

535
-continued

730
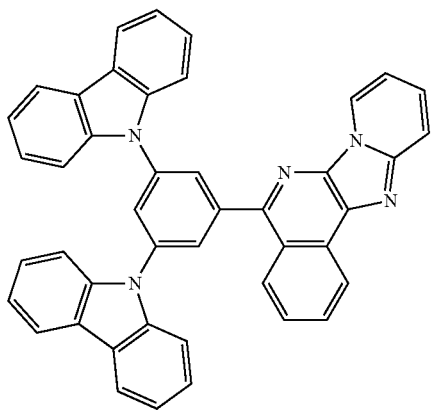

731
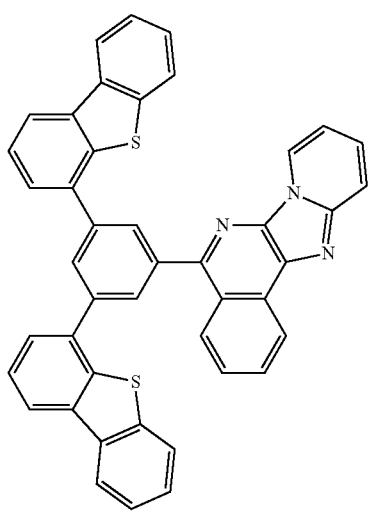

536
-continued

732
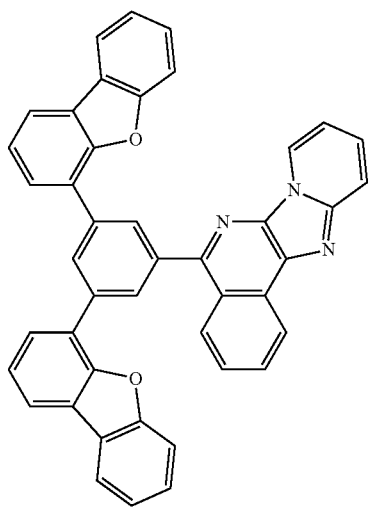

733
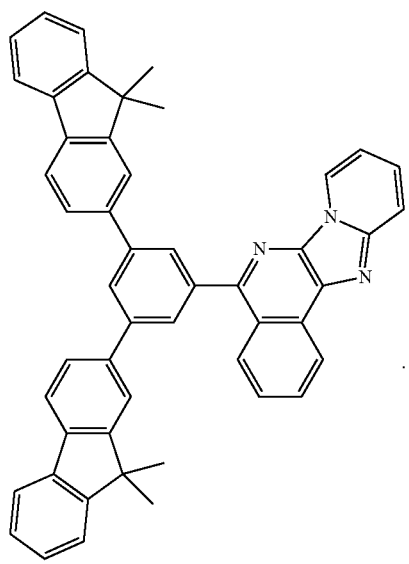

4. An organic light emitting device comprising:
a positive electrode;
a negative electrode; and
one or more organic material layers provided between the positive electrode and the negative electrode,
wherein one or more layers of the organic material layers comprise the hetero-cyclic compound of claim 1.

5. The organic light emitting device of claim 4, wherein the organic material layer comprising the hetero-cyclic compound is at least one layer selected from a hole injection layer, a hole transporting layer, a light emitting layer, an electron transporting layer, and an electron injection layer.

6. The organic light emitting device of claim 4, wherein the organic material layer comprising the hetero-cyclic compound is an electron transporting layer.

* * * * *